United States Patent
Klausen et al.

(10) Patent No.: US 11,896,033 B2
(45) Date of Patent: *Feb. 13, 2024

(54) POLYPEPTIDES HAVING LYSOZYME ACTIVITY, POLYNUCLEOTIDES ENCODING SAME AND USES AND COMPOSITIONS THEREOF

(71) Applicant: Novozymes A/S, Bagsvaerd (DK)

(72) Inventors: Mikkel Klausen, Copenhagen (DK); Kirk Matthew Schnorr, Holte (DK); Soeren Nymand-Grarup, Copenhagen (DK); Peter Bjarke Olsen, Copenhagen (DK); Marianne Thorup Cohn, Copenhagen (DK); Robert Piotr Olinski, Vaerloese (DK); Marc Dominique Morant, Frederiksberg (DK); Ming Li, Beijing (CN); Ye Liu, Beijing (CN); Lars Kobbeeroee Skov, Ballerup (DK); Dominique Aubert Skovlund, Vaerloese (DK); Han Bucong, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 1166 days.

This patent is subject to a terminal disclaimer.

(21) Appl. No.: 16/462,764

(22) PCT Filed: Dec. 21, 2017

(86) PCT No.: PCT/CN2017/117765
§ 371 (c)(1),
(2) Date: May 21, 2019

(87) PCT Pub. No.: WO2018/113745
PCT Pub. Date: Jun. 28, 2018

(65) Prior Publication Data
US 2021/0274810 A1    Sep. 9, 2021

(30) Foreign Application Priority Data

Dec. 21, 2016  (WO) ............... PCT/CN2016/111317
Mar. 8, 2017   (WO) ............... PCT/CN2017/075978

(51) Int. Cl.
| A23K 20/147 | (2016.01) |
| A23K 50/30  | (2016.01) |
| A23K 50/75  | (2016.01) |
| A23K 10/30  | (2016.01) |
| C12N 9/36   | (2006.01) |
| C12N 15/81  | (2006.01) |

(52) U.S. Cl.
CPC ............ *A23K 20/147* (2016.05); *A23K 10/30* (2016.05); *A23K 50/30* (2016.05); *A23K 50/75* (2016.05); *C12N 9/2462* (2013.01); *C12N 15/815* (2013.01); *C12Y 302/01017* (2013.01)

(58) Field of Classification Search
None
See application file for complete search history.

(56) References Cited

U.S. PATENT DOCUMENTS

| 2016/0030528 A1 | 2/2016  | Metcalf   |
| 2019/0351032 A1 | 11/2019 | Kjaerulff |
| 2020/0305465 A1 | 10/2020 | Aureli    |

FOREIGN PATENT DOCUMENTS

| EP | 2904912 A1     | 8/2015  |
| WO | 2005/011587 A2 | 2/2005  |
| WO | 2005/080559 A1 | 9/2005  |
| WO | 2009/102755 A1 | 8/2009  |
| WO | 2011/104339 A1 | 9/2011  |
| WO | 2012/027374 A2 | 3/2012  |
| WO | 2012/035103 A1 | 3/2012  |
| WO | 2013/076253 A1 | 5/2013  |
| WO | 2013/076259 A2 | 5/2013  |
| WO | 2013/110627 A1 | 8/2013  |
| WO | 2016/210238 A1 | 12/2016 |
| WO | 2017/001701 A1 | 1/2017  |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Baroncelli et al., NCBI Reference No. XP_018657583.1 (2016).
Berka et al., NCBI Reference No. XP_003650266.1 (2012).
Berka et al., NCBI Reference No. XP_003662567.1 (2012).
Berka et al., UniProt Accession No. G2QWF5 (2016).
Birren et al., NCBI Reference No. XP_001215317.1 (2008).
Corrochano et al., NCBI Reference No. XP_018287694.1 (2016).
Galagan et al., NCBI Reference No. XP_964535.1 (2015).
Jimenez et al., GenBank Accession No. OIW26653.1 (2016).
Kanematsu et al., GenBank Accession No. GAP89829.1 (2015).
Kohler et al., GenBank Accession No. KIJ42223.1 (2015).
Kohler et al., GenBank Accession No. KIN06446.1 (2015).
Kohler et al., GenBank Accession No. KIN08373.1 (2015).
Korczynska et al., Acta Crystallographica Section F, vol. F66, pp. 973-977 (2010).
Kubicek et al., NCBI Reference No. XP_013942670.1 (2015).
Li et al., UniProt Accession No. A0A0A2VUR3 (2015).
Linde et al., GenBank Accession No. CDS02619 (2015).
Masschalck et al., Journal of Food Protection, vol. 65, No. 12, pp. 1916-1923 (2002).
Meinhardt et al., NCBI Reference No. XP_007849295.1 (2014).
Morin et al., NCBI Reference No. XP_006463298.1 (2014).
Nierman, NCBI Reference No. XP_001276751.1 (2008).
Nowrousian et al., NCBI Reference No. XP_003352547.1 (2011).

(Continued)

*Primary Examiner* — Christian L Fronda
(74) *Attorney, Agent, or Firm* — Adam Rucker

(57) ABSTRACT

Provided are animal feed or animal feed additives comprising one or more polypeptides having lysozyme activity. Provided are polypeptides having lysozyme activity, polynucleotides encoding the polypeptides nucleic acid constructs, vectors, and host cells comprising the polynucleotides as well as methods of producing and using the polypeptides.

20 Claims, 6 Drawing Sheets

Specification includes a Sequence Listing.

(56) References Cited

OTHER PUBLICATIONS

Peter et al., GenBank Accession No. OCK75562.1 (2016).
Priebe et al., GenBank Accession No. CEJ53659.1 (2015).
Priebe et al., GenBank Accession No. CEL10138.1 (2016).
Riley et al., GenBank Accession No. KDQ07276.1 (2014).
Shang et al., GenBank Accession No. OAA73042.1 (2016).
Shang et al., GenBank Accession No. OAA81279.1 (2016).
Shang et al., UniProt Accession No. A0A162JSB9 (2016).
Sun et al., Nature Communications, vol. 8322, No. 6, pp. 1-12 (2015).
Terfehr et al., GenBank Accession No. KFH43569.1 (2014).
Wang et al., NCBI Reference No. XP_018138018.1 (2016).
Wang et al., NCBI Reference No. XP_018142497.1 (2016).
Wang et al., NCBI Reference No. XP_018175238.1 (2016).
Wang et al., UniProt Accession No. A0A179GAU8 (2017).
Zeiner et al., NCBI Reference No. XP_018032810.1 (2016).
Schnorr et al., EBI Accession No. BAP10817 (2013).
Visser et al., EBI Accession No. AZT73868 (2012).
Mondo et al., EBI Accession No. A0A1Y1Z9R4 (2017).

\* cited by examiner

SEQUENCE LISTING

<160> NUMBER OF SEQ ID NOS: 235

<210> SEQ ID NO 1
<211> LENGTH: 858
<212> TYPE: DNA
<213> ORGANISM: Sporormia fimetaria
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(855)
<220> FEATURE:
<221> NAME/KEY: CDS
<222> LOCATION: (267)..(751)
<220> FEATURE:
<221> NAME/KEY: CDS
<222> LOCATION: (810)..(855)

<400> SEQUENCE: 1

```
atg aag tcc gca ttc gtc ttt cta gct gca gta gca cag cta gcc agc          48
Met Lys Ser Ala Phe Val Phe Leu Ala Ala Val Ala Gln Leu Ala Ser
    -15                 -10                 -5 gct gct gtt cct ggc ttt gac atc tcc cac tac caa agc tcg gtg aat          96
Ala Ala Val Pro Gly Phe Asp Ile Ser His Tyr Gln Ser Ser Val Asn
-1  1               5                   10                  15 tac gcc ggt gcc tac tcc agc ggt gct cgc ttt gtc ata ata aag              141
Tyr Ala Gly Ala Tyr Ser Ser Gly Ala Arg Phe Val Ile Ile Lys
                20                  25                  30 gtacgcccct tctaattcct tccctcgtcg cggacccgta ttgtatacgt tatttctcca        201
agccgtctcc cttcccgctc aatcaatgaa agtgacataa aaccgtcagt ggctgacatt        261 tccag gcc act gaa gga aca acc tac atc gac cca aaa ttc tct gac cat       311
      Ala Thr Glu Gly Thr Thr Tyr Ile Asp Pro Lys Phe Ser Asp His
                  35                  40                  45 tac att ggc gcc aca aat gcc gga ctg att cgc ggc gcg tac cat ttt          359
Tyr Ile Gly Ala Thr Asn Ala Gly Leu Ile Arg Gly Ala Tyr His Phe
            50                  55                  60 gcg cga ccc gcc gcc tct act ggc gcc gct cag gct aat tac ttc gtc          407
Ala Arg Pro Ala Ala Ser Thr Gly Ala Ala Gln Ala Asn Tyr Phe Val
        65                  70                  75 tcc cac ggc gga ggt tgg tct gcc gac ggc atc act ctg ccc gga atg          455
Ser His Gly Gly Gly Trp Ser Ala Asp Gly Ile Thr Leu Pro Gly Met
    80                  85                  90 ctc gac atg gag tat ggg tcg aca tcg gcc tgc cac ggg ctc tcc cag          503
Leu Asp Met Glu Tyr Gly Ser Thr Ser Ala Cys His Gly Leu Ser Gln
95                  100                 105 tcc gca atg gtt acc tgg atc acg agc ttt gtg aac cag tac aac agc          551
Ser Ala Met Val Thr Trp Ile Thr Ser Phe Val Asn Gln Tyr Asn Ser
110                 115                 120                 125 ctg aca ggt cgg tat ccg atg att tac acc acg gca gat tgg tgg caa          599
Leu Thr Gly Arg Tyr Pro Met Ile Tyr Thr Thr Ala Asp Trp Trp Gln
                130                 135                 140 act tgc acg gga aat agc gcg gct ttc aac acc aaa tct cct ctg gta          647
Thr Cys Thr Gly Asn Ser Ala Ala Phe Asn Thr Lys Ser Pro Leu Val
            145                 150                 155 ctg gcg aga tac tcg agt tct gcg ggt acg gtc cct gga ggc tgg cca          695
Leu Ala Arg Tyr Ser Ser Ser Ala Gly Thr Val Pro Gly Gly Trp Pro
        160                 165                 170 tat tac acg att tgg caa ttt aat gat gca tat gct tat gga ggg gat          743
Tyr Tyr Thr Ile Trp Gln Phe Asn Asp Ala Tyr Ala Tyr Gly Gly Asp
```

```
                 175                 180                 185
tca gat ac   gtaagtgctt ttccatgcgc aattgatagt atgtattagg           791
Ser Asp Thr
190 gactaacagg acctatag t ttt aac ggc gac ctg gcc ggc tta aag agg ctc  843
                      Phe Asn Gly Asp Leu Ala Gly Leu Lys Arg Leu
                            195                 200 gcg aag ggc tcg tag                                                858
Ala Lys Gly Ser
    205

<210> SEQ ID NO 2
<211> LENGTH: 224
<212> TYPE: PRT
<213> ORGANISM: Sporormia fimetaria

<400> SEQUENCE: 2

Met Lys Ser Ala Phe Val Phe Leu Ala Val Ala Gln Leu Ala Ser
        -15                 -10                  -5

Ala Ala Val Pro Gly Phe Asp Ile Ser His Tyr Gln Ser Ser Val Asn
 -1   1               5                  10                  15

Tyr Ala Gly Ala Tyr Ser Ser Gly Ala Arg Phe Val Ile Ile Lys Ala
                20                  25                  30

Thr Glu Gly Thr Thr Tyr Ile Asp Pro Lys Phe Ser Asp His Tyr Ile
                35                  40                  45

Gly Ala Thr Asn Ala Gly Leu Ile Arg Gly Ala Tyr His Phe Ala Arg
                50                  55                  60

Pro Ala Ser Thr Gly Ala Ala Gln Ala Asn Tyr Phe Val Ser His
 65                  70                  75

Gly Gly Gly Trp Ser Ala Asp Gly Ile Thr Leu Pro Gly Met Leu Asp
 80                  85                  90                  95

Met Glu Tyr Gly Ser Thr Ser Ala Cys His Gly Leu Ser Gln Ser Ala
                100                 105                 110

Met Val Thr Trp Ile Thr Ser Phe Val Asn Gln Tyr Asn Ser Leu Thr
                115                 120                 125

Gly Arg Tyr Pro Met Ile Tyr Thr Thr Ala Asp Trp Trp Gln Thr Cys
                130                 135                 140

Thr Gly Asn Ser Ala Ala Phe Asn Thr Lys Ser Pro Leu Val Leu Ala
145                 150                 155

Arg Tyr Ser Ser Ser Ala Gly Thr Val Pro Gly Gly Trp Pro Tyr Tyr
160                 165                 170                 175

Thr Ile Trp Gln Phe Asn Asp Ala Tyr Ala Tyr Gly Gly Asp Ser Asp
                180                 185                 190

Thr Phe Asn Gly Asp Leu Ala Gly Leu Lys Arg Leu Ala Lys Gly Ser
                195                 200                 205

<210> SEQ ID NO 3
<211> LENGTH: 207
<212> TYPE: PRT
<213> ORGANISM: Sporormia fimetaria
<220> FEATURE:
<221> NAME/KEY: mat_peptide
<222> LOCATION: (1)..(207)

<400> SEQUENCE: 3

Ala Val Pro Gly Phe Asp Ile Ser His Tyr Gln Ser Ser Val Asn Tyr
 1               5                  10                  15

Ala Gly Ala Tyr Ser Ser Gly Ala Arg Phe Val Ile Ile Lys Ala Thr
```

```
                 20                  25                  30
Glu Gly Thr Thr Tyr Ile Asp Pro Lys Phe Ser Asp His Tyr Ile Gly
             35                  40                  45

Ala Thr Asn Ala Gly Leu Ile Arg Gly Ala Tyr His Phe Ala Arg Pro
         50                  55                  60

Ala Ala Ser Thr Gly Ala Ala Gln Ala Asn Tyr Phe Val Ser His Gly
 65                  70                  75                  80

Gly Gly Trp Ser Ala Asp Gly Ile Thr Leu Pro Gly Met Leu Asp Met
                 85                  90                  95

Glu Tyr Gly Ser Thr Ser Ala Cys His Gly Leu Ser Gln Ser Ala Met
             100                 105                 110

Val Thr Trp Ile Thr Ser Phe Val Asn Gln Tyr Asn Ser Leu Thr Gly
         115                 120                 125

Arg Tyr Pro Met Ile Tyr Thr Thr Ala Asp Trp Gln Thr Cys Thr
 130                 135                 140

Gly Asn Ser Ala Ala Phe Asn Thr Lys Ser Pro Leu Val Leu Ala Arg
145                 150                 155                 160

Tyr Ser Ser Ser Ala Gly Thr Val Pro Gly Gly Trp Pro Tyr Tyr Thr
                 165                 170                 175

Ile Trp Gln Phe Asn Asp Ala Tyr Ala Tyr Gly Gly Asp Ser Asp Thr
             180                 185                 190

Phe Asn Gly Asp Leu Ala Gly Leu Lys Arg Leu Ala Lys Gly Ser
         195                 200                 205

<210> SEQ ID NO 4
<211> LENGTH: 716
<212> TYPE: DNA
<213> ORGANISM: Poronia punctata
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(713)
<220> FEATURE:
<221> NAME/KEY: CDS
<222> LOCATION: (201)..(713)

<400> SEQUENCE: 4 atg aag tct tac atc gcc ccc ctc ctc ggc ctc gcc caa ggc gcg ctc      48
Met Lys Ser Tyr Ile Ala Pro Leu Leu Gly Leu Ala Gln Gly Ala Leu
        -15                 -10                  -5 gcc gcc gtc cag ggc ttc gac att tcg cac tat cag tcg agc gtc aac      96
Ala Ala Val Gln Gly Phe Asp Ile Ser His Tyr Gln Ser Ser Val Asn
 -1   1               5                  10                  15 ttt ggc gcc gcc aag agc tcc ggt gct cag ttt gtc atc atc aag           141
Phe Gly Ala Ala Lys Ser Ser Gly Ala Gln Phe Val Ile Ile Lys
                 20                  25                  30 gtgagaagga caagccataa aatgagggga aagtcgtgtg taactgacgt gaccaacag     200 gcg act gag ggt acc tcc tat acc gac ccc agt ttc agc tct cac tat     248
Ala Thr Glu Gly Thr Ser Tyr Thr Asp Pro Ser Phe Ser Ser His Tyr
             35                  40                  45 acc ggc gcc acc aat gct ggc ttg atc cgt ggc ggt tac cac ttc gcc     296
Thr Gly Ala Thr Asn Ala Gly Leu Ile Arg Gly Gly Tyr His Phe Ala
         50                  55                  60 cac ctc gat tcc agc tct ggt gct gcg cag gcc aag tac ttc ctc gcc     344
His Leu Asp Ser Ser Ser Gly Ala Ala Gln Ala Lys Tyr Phe Leu Ala
```

```
                65                  70                  75
cat ggt ggt ggc tgg tct gga gac ggc atc acc ctg ccc ggt atg ctg    392
His Gly Gly Gly Trp Ser Gly Asp Gly Ile Thr Leu Pro Gly Met Leu
    80                  85                  90 gat ctt gag ggc agc tgc gtc ctc tcg gct agc gct acc gtg tct tgg    440
Asp Leu Glu Gly Ser Cys Val Leu Ser Ala Ser Ala Thr Val Ser Trp
 95                 100                 105                 110 atc aag gac ttt agc aac acc tac cac tcg tcc acg ggc gtg tac cct    488
Ile Lys Asp Phe Ser Asn Thr Tyr His Ser Ser Thr Gly Val Tyr Pro
                115                 120                 125 cta att tac aca aac ccc tcg tgg tgg tct agc tgc acc ggt aac tcc    536
Leu Ile Tyr Thr Asn Pro Ser Trp Trp Ser Ser Cys Thr Gly Asn Ser
            130                 135                 140 aag gcc ttt atc gac acc aat cct ctc gta ctt gca cgg tac gcg tca    584
Lys Ala Phe Ile Asp Thr Asn Pro Leu Val Leu Ala Arg Tyr Ala Ser
        145                 150                 155 agc gct ggc acc cct ccc ggt ggc tgg cct tac tat acc atc tgg cag    632
Ser Ala Gly Thr Pro Pro Gly Gly Trp Pro Tyr Tyr Thr Ile Trp Gln
    160                 165                 170 tac aac gat gcc tac aag tac gga ggt gac tcg gac gtc ttc aac gga    680
Tyr Asn Asp Ala Tyr Lys Tyr Gly Gly Asp Ser Asp Val Phe Asn Gly
175                 180                 185                 190 gac ctt gcc ggc ctc aag aga ctg gct aag ggc taa                    716
Asp Leu Ala Gly Leu Lys Arg Leu Ala Lys Gly
                195                 200

<210> SEQ ID NO 5
<211> LENGTH: 218
<212> TYPE: PRT
<213> ORGANISM: Poronia punctata

<400> SEQUENCE: 5

Met Lys Ser Tyr Ile Ala Pro Leu Leu Gly Leu Ala Gln Gly Ala Leu
        -15                 -10                  -5

Ala Ala Val Gln Gly Phe Asp Ile Ser His Tyr Gln Ser Ser Val Asn
 -1  1               5                  10                  15

Phe Gly Ala Ala Lys Ser Ser Gly Ala Gln Phe Val Ile Ile Lys Ala
                20                  25                  30

Thr Glu Gly Thr Ser Tyr Thr Asp Pro Ser Phe Ser Ser His Tyr Thr
                35                  40                  45

Gly Ala Thr Asn Ala Gly Leu Ile Arg Gly Gly Tyr His Phe Ala His
            50                  55                  60

Leu Asp Ser Ser Ser Gly Ala Ala Gln Ala Lys Tyr Phe Leu Ala His
 65                  70                  75

Gly Gly Gly Trp Ser Gly Asp Gly Ile Thr Leu Pro Gly Met Leu Asp
 80                  85                  90                  95

Leu Glu Gly Ser Cys Val Leu Ser Ala Ser Ala Thr Val Ser Trp Ile
                100                 105                 110

Lys Asp Phe Ser Asn Thr Tyr His Ser Ser Thr Gly Val Tyr Pro Leu
                115                 120                 125

Ile Tyr Thr Asn Pro Ser Trp Trp Ser Ser Cys Thr Gly Asn Ser Lys
            130                 135                 140

Ala Phe Ile Asp Thr Asn Pro Leu Val Leu Ala Arg Tyr Ala Ser Ser
        145                 150                 155

Ala Gly Thr Pro Pro Gly Gly Trp Pro Tyr Tyr Thr Ile Trp Gln Tyr
160                 165                 170                 175

Asn Asp Ala Tyr Lys Tyr Gly Gly Asp Ser Asp Val Phe Asn Gly Asp
```

```
                    180                 185                 190
Leu Ala Gly Leu Lys Arg Leu Ala Lys Gly
            195                 200

<210> SEQ ID NO 6
<211> LENGTH: 201
<212> TYPE: PRT
<213> ORGANISM: Poronia punctata
<220> FEATURE:
<221> NAME/KEY: mat_peptide
<222> LOCATION: (1)..(201)

<400> SEQUENCE: 6

Ala Val Gln Gly Phe Asp Ile Ser His Tyr Gln Ser Ser Val Asn Phe
1               5                   10                  15

Gly Ala Ala Lys Ser Ser Gly Ala Gln Phe Val Ile Ile Lys Ala Thr
            20                  25                  30

Glu Gly Thr Ser Tyr Thr Asp Pro Ser Phe Ser Ser His Tyr Thr Gly
        35                  40                  45

Ala Thr Asn Ala Gly Leu Ile Arg Gly Gly Tyr His Phe Ala His Leu
    50                  55                  60

Asp Ser Ser Gly Ala Ala Gln Ala Lys Tyr Phe Leu Ala His Gly
65                  70                  75                  80

Gly Gly Trp Ser Gly Asp Gly Ile Thr Leu Pro Gly Met Leu Asp Leu
                85                  90                  95

Glu Gly Ser Cys Val Leu Ser Ala Ser Ala Thr Val Ser Trp Ile Lys
            100                 105                 110

Asp Phe Ser Asn Thr Tyr His Ser Ser Thr Gly Val Tyr Pro Leu Ile
        115                 120                 125

Tyr Thr Asn Pro Ser Trp Trp Ser Ser Cys Thr Gly Asn Ser Lys Ala
    130                 135                 140

Phe Ile Asp Thr Asn Pro Leu Val Leu Ala Arg Tyr Ala Ser Ser Ala
145                 150                 155                 160

Gly Thr Pro Pro Gly Gly Trp Pro Tyr Tyr Thr Ile Trp Gln Tyr Asn
                165                 170                 175

Asp Ala Tyr Lys Tyr Gly Gly Asp Ser Asp Val Phe Asn Gly Asp Leu
            180                 185                 190

Ala Gly Leu Lys Arg Leu Ala Lys Gly
        195                 200

<210> SEQ ID NO 7
<211> LENGTH: 771
<212> TYPE: DNA
<213> ORGANISM: Poronia punctata
<220> FEATURE:
<221> NAME/KEY: CDS
<222> LOCATION: (1)..(138)
<220> FEATURE:
<221> NAME/KEY: sig_peptide
<222> LOCATION: (1)..(48)
<220> FEATURE:
<221> NAME/KEY: mat_peptide
<222> LOCATION: (49)..(768)
<220> FEATURE:
<221> NAME/KEY: CDS
<222> LOCATION: (256)..(768)

<400> SEQUENCE: 7 atg aag tat ctc gtt ccc ctt ttg ggc ttc gcc cac ggc gcc ctg gcc    48
Met Lys Tyr Leu Val Pro Leu Leu Gly Phe Ala His Gly Ala Leu Ala
    -15                 -10                 -5                  -1
```

```
cag gtt caa ggc ttc gat atc tcg agc tac cag ccc agc gta gac ttt     96
Gln Val Gln Gly Phe Asp Ile Ser Ser Tyr Gln Pro Ser Val Asp Phe
 1               5                  10                  15 gcc ggt gct tat gct gat ggc gcc cga ttc gtc atc atc aag            138
Ala Gly Ala Tyr Ala Asp Gly Ala Arg Phe Val Ile Ile Lys
             20                  25                  30 gtaagaaaaa tactacaatc aagcccata accataacca aaaccccccg cccccattg    198 gattagatgg atgatggact aggtaaccta acctgctcta acacaaaata atcatag     255 gcc acc gaa gga act ggc tac atc gac ccc acc ttc agc gac cac tac   303
Ala Thr Glu Gly Thr Gly Tyr Ile Asp Pro Thr Phe Ser Asp His Tyr
                 35                  40                  45 gta ggc gca acc aac gcc ggc ctg ctc cgc ggc ggt tac cac tac gcc   351
Val Gly Ala Thr Asn Ala Gly Leu Leu Arg Gly Gly Tyr His Tyr Ala
             50                  55                  60 cac ctg gac tcg acc tcg ggc gct acc cag gcc cag tac ttc ctc gcc   399
His Leu Asp Ser Thr Ser Gly Ala Thr Gln Ala Gln Tyr Phe Leu Ala
             65                  70                  75 aac ggc ggt ggc tgg tcc ggc gac gga atc acc ctc ccc ggc atg ctt   447
Asn Gly Gly Gly Trp Ser Gly Asp Gly Ile Thr Leu Pro Gly Met Leu
 80                  85                  90 gat ctc gag ggt gac tgc gtg ctc tcg gcc gcc gac gcc gtc gcc tgg   495
Asp Leu Glu Gly Asp Cys Val Leu Ser Ala Ala Asp Ala Val Ala Trp
 95                 100                 105                 110 atc aag gac ttc agc gac acc tac cac gcc agc acg ggc gtc tac ccc   543
Ile Lys Asp Phe Ser Asp Thr Tyr His Ala Ser Thr Gly Val Tyr Pro
                115                 120                 125 ctg ctg tac acc aac cct tcg tgg tgg gcc tct tgc acc ggc gac tcc   591
Leu Leu Tyr Thr Asn Pro Ser Trp Trp Ala Ser Cys Thr Gly Asp Ser
            130                 135                 140 agc gcc ttc atc gac acc aac ccc ctc gtc ctc gcc cac tac gcc gac   639
Ser Ala Phe Ile Asp Thr Asn Pro Leu Val Leu Ala His Tyr Ala Asp
        145                 150                 155 gcc gcc ggc acc ccc cct ggt ggc tgg ccc ttc tac tcc ttc tgg cag   687
Ala Ala Gly Thr Pro Pro Gly Gly Trp Pro Phe Tyr Ser Phe Trp Gln
        160                 165                 170 tac aac gat gcc tac ccc tac ggt ggc gac tcc gag gtc tgg aac ggt   735
Tyr Asn Asp Ala Tyr Pro Tyr Gly Gly Asp Ser Glu Val Trp Asn Gly
175                 180                 185                 190 gat atg gac ggt ctt ctc cgc ctt gct tcg ggc taa                   771
Asp Met Asp Gly Leu Leu Arg Leu Ala Ser Gly
                195                 200

<210> SEQ ID NO 8
<211> LENGTH: 217
<212> TYPE: PRT
<213> ORGANISM: Poronia punctata

<400> SEQUENCE: 8

Met Lys Tyr Leu Val Pro Leu Leu Gly Phe Ala His Gly Ala Leu Ala
        -15                 -10                  -5              -1

Gln Val Gln Gly Phe Asp Ile Ser Ser Tyr Gln Pro Ser Val Asp Phe
 1               5                  10                  15

Ala Gly Ala Tyr Ala Asp Gly Ala Arg Phe Val Ile Ile Lys Ala Thr
             20                  25                  30

Glu Gly Thr Gly Tyr Ile Asp Pro Thr Phe Ser Asp His Tyr Val Gly
         35                  40                  45

Ala Thr Asn Ala Gly Leu Leu Arg Gly Gly Tyr His Tyr Ala His Leu
     50                  55                  60
```

```
Asp Ser Thr Ser Gly Ala Thr Gln Ala Gln Tyr Phe Leu Ala Asn Gly
 65                  70                  75                  80

Gly Gly Trp Ser Gly Asp Gly Ile Thr Leu Pro Gly Met Leu Asp Leu
                 85                  90                  95

Glu Gly Asp Cys Val Leu Ser Ala Ala Asp Ala Val Ala Trp Ile Lys
            100                 105                 110

Asp Phe Ser Asp Thr Tyr His Ala Ser Thr Gly Val Tyr Pro Leu Leu
        115                 120                 125

Tyr Thr Asn Pro Ser Trp Trp Ala Ser Cys Thr Gly Asp Ser Ser Ala
    130                 135                 140

Phe Ile Asp Thr Asn Pro Leu Val Leu Ala His Tyr Ala Asp Ala Ala
145                 150                 155                 160

Gly Thr Pro Pro Gly Gly Trp Pro Phe Tyr Ser Phe Trp Gln Tyr Asn
                165                 170                 175

Asp Ala Tyr Pro Tyr Gly Gly Asp Ser Glu Val Trp Asn Gly Asp Met
            180                 185                 190

Asp Gly Leu Leu Arg Leu Ala Ser Gly
        195                 200
```

```
<210> SEQ ID NO 9
<211> LENGTH: 201
<212> TYPE: PRT
<213> ORGANISM: Poronia punctata
<220> FEATURE:
<221> NAME/KEY: mat_peptide
<222> LOCATION: (1)..(201)

<400> SEQUENCE: 9
```

```
Gln Val Gln Gly Phe Asp Ile Ser Ser Tyr Gln Pro Ser Val Asp Phe
 1               5                  10                  15

Ala Gly Ala Tyr Ala Asp Gly Ala Arg Phe Val Ile Ile Lys Ala Thr
             20                  25                  30

Glu Gly Thr Gly Tyr Ile Asp Pro Thr Phe Ser Asp His Tyr Val Gly
         35                  40                  45

Ala Thr Asn Ala Gly Leu Leu Arg Gly Gly Tyr His Tyr Ala His Leu
     50                  55                  60

Asp Ser Thr Ser Gly Ala Thr Gln Ala Gln Tyr Phe Leu Ala Asn Gly
 65                  70                  75                  80

Gly Gly Trp Ser Gly Asp Gly Ile Thr Leu Pro Gly Met Leu Asp Leu
                 85                  90                  95

Glu Gly Asp Cys Val Leu Ser Ala Ala Asp Ala Val Ala Trp Ile Lys
            100                 105                 110

Asp Phe Ser Asp Thr Tyr His Ala Ser Thr Gly Val Tyr Pro Leu Leu
        115                 120                 125

Tyr Thr Asn Pro Ser Trp Trp Ala Ser Cys Thr Gly Asp Ser Ser Ala
    130                 135                 140

Phe Ile Asp Thr Asn Pro Leu Val Leu Ala His Tyr Ala Asp Ala Ala
145                 150                 155                 160

Gly Thr Pro Pro Gly Gly Trp Pro Phe Tyr Ser Phe Trp Gln Tyr Asn
                165                 170                 175

Asp Ala Tyr Pro Tyr Gly Gly Asp Ser Glu Val Trp Asn Gly Asp Met
            180                 185                 190

Asp Gly Leu Leu Arg Leu Ala Ser Gly
        195                 200
```

```
<210> SEQ ID NO 10
```

<211> LENGTH: 675
<212> TYPE: DNA
<213> ORGANISM: Lecanicillium sp. WMM742
<220> FEATURE:
<221> NAME/KEY: CDS
<222> LOCATION: (1)..(672)
<220> FEATURE:
<221> NAME/KEY: sig_peptide
<222> LOCATION: (1)..(63)
<220> FEATURE:
<221> NAME/KEY: mat_peptide
<222> LOCATION: (64)..(672)

<400> SEQUENCE: 10

```
atg cga cca ttt act gcc ctc ttt gtc gcc ttc gtc agc gcc gcc agt        48
Met Arg Pro Phe Thr Ala Leu Phe Val Ala Phe Val Ser Ala Ala Ser
    -20                 -15                 -10 gcg ctg acc cac gcc gtc gac agc tcc tcc gag gtg agc gtc gcc att        96
Ala Leu Thr His Ala Val Asp Ser Ser Ser Glu Val Ser Val Ala Ile
 -5              -1   1               5                  10 tac aaa aag gcc ctc ggc cag ggc ttc acc cgc gcc atc ttc cgc ggc       144
Tyr Lys Lys Ala Leu Gly Gln Gly Phe Thr Arg Ala Ile Phe Arg Gly
             15                  20                  25 tac caa gag gcc tgc tcg cag ggc ggc cgc gtc gac ccg acc ttt gtg       192
Tyr Gln Glu Ala Cys Ser Gln Gly Gly Arg Val Asp Pro Thr Phe Val
         30                  35                  40 ccg agc tac aag aat gcc gtc gcg gcc ggc tac aag gac ttt gac gcc       240
Pro Ser Tyr Lys Asn Ala Val Ala Ala Gly Tyr Lys Asp Phe Asp Ala
     45                  50                  55 tac ttc ttc ccc tgc acc ggc aag acc aac aag tgc aag ccc tac gcc       288
Tyr Phe Phe Pro Cys Thr Gly Lys Thr Asn Lys Cys Lys Pro Tyr Ala
 60                  65                  70                  75 gcg cag ctc gcc gag ctc ctc gac acc atc aag ggc cag aag ctg gcg       336
Ala Gln Leu Ala Glu Leu Leu Asp Thr Ile Lys Gly Gln Lys Leu Ala
                 80                  85                  90 att cgc cgc atc tgg ctc gac att gag acg gac agg gtg tgc aac ccg       384
Ile Arg Arg Ile Trp Leu Asp Ile Glu Thr Asp Arg Val Cys Asn Pro
             95                 100                 105 ttt gac tat ggc gca cag ggc aac ctt gcc gag gcc aag aag ctc gtg       432
Phe Asp Tyr Gly Ala Gln Gly Asn Leu Ala Glu Ala Lys Lys Leu Val
        110                 115                 120 gcc gcg ttt cgc gac gcc aag ctt gac tgg ggc atc tac acg tcg ccg       480
Ala Ala Phe Arg Asp Ala Lys Leu Asp Trp Gly Ile Tyr Thr Ser Pro
    125                 130                 135 acg cag tgg gag acc atc ttt ggc gcc aag acc gtc gag ctg gcc aag       528
Thr Gln Trp Glu Thr Ile Phe Gly Ala Lys Thr Val Glu Leu Ala Lys
140                 145                 150                 155 gac gtg ccg cta tgg ttt gcc aag ttt gac aat gtc gag acg ctg gag       576
Asp Val Pro Leu Trp Phe Ala Lys Phe Asp Asn Val Glu Thr Leu Glu
                160                 165                 170 ctc aag acg ccg ttt ggt ggc tgg aca aag gcg gat gcg aag cag tat       624
Leu Lys Thr Pro Phe Gly Gly Trp Thr Lys Ala Asp Ala Lys Gln Tyr
            175                 180                 185 act gac cag tcg gcc agc aac aag ttt gac ttg aac gtc ttt tct gcc       672
Thr Asp Gln Ser Ala Ser Asn Lys Phe Asp Leu Asn Val Phe Ser Ala
        190                 195                 200 taa                                                                    675
```

<210> SEQ ID NO 11
<211> LENGTH: 224
<212> TYPE: PRT
<213> ORGANISM: Lecanicillium sp. WMM742

```
<400> SEQUENCE: 11

Met Arg Pro Phe Thr Ala Leu Phe Val Ala Phe Val Ser Ala Ala Ser
    -20                 -15                 -10

Ala Leu Thr His Ala Val Asp Ser Ser Glu Val Ser Val Ala Ile
 -5              -1   1               5                  10

Tyr Lys Lys Ala Leu Gly Gln Gly Phe Thr Arg Ala Ile Phe Arg Gly
                 15                  20                  25

Tyr Gln Glu Ala Cys Ser Gln Gly Gly Arg Val Asp Pro Thr Phe Val
             30                  35                  40

Pro Ser Tyr Lys Asn Ala Val Ala Ala Gly Tyr Lys Asp Phe Asp Ala
         45                  50                  55

Tyr Phe Phe Pro Cys Thr Gly Lys Thr Asn Lys Cys Lys Pro Tyr Ala
 60              65                  70                  75

Ala Gln Leu Ala Glu Leu Leu Asp Thr Ile Lys Gly Gln Lys Leu Ala
                 80                  85                  90

Ile Arg Arg Ile Trp Leu Asp Ile Glu Thr Asp Arg Val Cys Asn Pro
             95                 100                 105

Phe Asp Tyr Gly Ala Gln Gly Asn Leu Ala Glu Ala Lys Lys Leu Val
         110                 115                 120

Ala Ala Phe Arg Asp Ala Lys Leu Asp Trp Gly Ile Tyr Thr Ser Pro
 125                 130                 135

Thr Gln Trp Glu Thr Ile Phe Gly Ala Lys Thr Val Glu Leu Ala Lys
 140                 145                 150                 155

Asp Val Pro Leu Trp Phe Ala Lys Phe Asp Asn Val Glu Thr Leu Glu
                 160                 165                 170

Leu Lys Thr Pro Phe Gly Gly Trp Thr Lys Ala Asp Ala Lys Gln Tyr
                 175                 180                 185

Thr Asp Gln Ser Ala Ser Asn Lys Phe Asp Leu Asn Val Phe Ser Ala
             190                 195                 200

<210> SEQ ID NO 12
<211> LENGTH: 203
<212> TYPE: PRT
<213> ORGANISM: Lecanicillium sp. WMM742
<220> FEATURE:
<221> NAME/KEY: mat_peptide
<222> LOCATION: (1)..(203)

<400> SEQUENCE: 12

Val Asp Ser Ser Glu Val Ser Val Ala Ile Tyr Lys Lys Ala Leu
 1               5                  10                  15

Gly Gln Gly Phe Thr Arg Ala Ile Phe Arg Gly Tyr Gln Glu Ala Cys
                 20                  25                  30

Ser Gln Gly Gly Arg Val Asp Pro Thr Phe Val Pro Ser Tyr Lys Asn
             35                  40                  45

Ala Val Ala Ala Gly Tyr Lys Asp Phe Asp Ala Tyr Phe Phe Pro Cys
         50                  55                  60

Thr Gly Lys Thr Asn Lys Cys Lys Pro Tyr Ala Ala Gln Leu Ala Glu
 65                  70                  75                  80

Leu Leu Asp Thr Ile Lys Gly Gln Lys Leu Ala Ile Arg Arg Ile Trp
                 85                  90                  95

Leu Asp Ile Glu Thr Asp Arg Val Cys Asn Pro Phe Asp Tyr Gly Ala
             100                 105                 110

Gln Gly Asn Leu Ala Glu Ala Lys Lys Leu Val Ala Ala Phe Arg Asp
         115                 120                 125
```

```
Ala Lys Leu Asp Trp Gly Ile Tyr Thr Ser Pro Thr Gln Trp Glu Thr
    130                 135                 140

Ile Phe Gly Ala Lys Thr Val Glu Leu Ala Lys Asp Val Pro Leu Trp
145                 150                 155                 160

Phe Ala Lys Phe Asp Asn Val Glu Thr Leu Glu Leu Lys Thr Pro Phe
                165                 170                 175

Gly Gly Trp Thr Lys Ala Asp Ala Lys Gln Tyr Thr Asp Gln Ser Ala
            180                 185                 190

Ser Asn Lys Phe Asp Leu Asn Val Phe Ser Ala
        195                 200

<210> SEQ ID NO 13
<211> LENGTH: 796
<212> TYPE: DNA
<213> ORGANISM: Lecanicillium sp. WMM742
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(793)
<220> FEATURE:
<221> NAME/KEY: CDS
<222> LOCATION: (199)..(381)
<220> FEATURE:
<221> NAME/KEY: CDS
<222> LOCATION: (443)..(793)

<400> SEQUENCE: 13 atg aag tca ttc tca tcc att atc gcc ggc atc gcc ggc ctt gcc tct         48
Met Lys Ser Phe Ser Ser Ile Ile Ala Gly Ile Ala Gly Leu Ala Ser
-20             -15                 -10                 -5 gtc gct tct gcc acg gtg cag ggc ttc gat gtc tct ggc tac cag ccc         96
Val Ala Ser Ala Thr Val Gln Gly Phe Asp Val Ser Gly Tyr Gln Pro
            -1  1                   5                   10 act gtc aac tgg ggt gcg gcc tac agc agc ggt gct cgc ttc gtc atg        144
Thr Val Asn Trp Gly Ala Ala Tyr Ser Ser Gly Ala Arg Phe Val Met
        15                  20                  25 atc aag gtatgctgca gcggacggtt cgaatcacag atgatgctga caggctag gcc       201
Ile Lys                                                         Ala
    30 acc gag gga act ggt tac atc tcg tcc agc ttc ggc tcg cag tac cct        249
Thr Glu Gly Thr Gly Tyr Ile Ser Ser Ser Phe Gly Ser Gln Tyr Pro
            35                  40                  45 ggt gcc acc aat gcg ggc ttt atc cgc ggc ggc tac cac ttt gcg ctg        297
Gly Ala Thr Asn Ala Gly Phe Ile Arg Gly Gly Tyr His Phe Ala Leu
        50                  55                  60 ccc gac cgg tcc tct ggc tcc gca cag gcc gac tac ttt ctg gcc cac        345
Pro Asp Arg Ser Ser Gly Ser Ala Gln Ala Asp Tyr Phe Leu Ala His
    65                  70                  75 ggc ggc ggc tgg agc ggc gat ggc atc act cta ccg gtaagtccca            391
Gly Gly Gly Trp Ser Gly Asp Gly Ile Thr Leu Pro
80                  85                  90 tcaccttcct tgaatcgaag cgccatggta gtgctagtct gacgcatcca g ggc atg      448
                                                        Gly Met ctg gac att gag tat aac ccg tac ggc gcc acc tgc tac ggc ctc tcg       496
Leu Asp Ile Glu Tyr Asn Pro Tyr Gly Ala Thr Cys Tyr Gly Leu Ser
            95                  100                 105 cag ggc gcc atg gtc aac tgg atc agc gac ttt gtc gag cac tac aag       544
Gln Gly Ala Met Val Asn Trp Ile Ser Asp Phe Val Glu His Tyr Lys
```

```
             110                 115                 120                 125
gcc agg acg acg cag tac ccc atc atc tac acg acg acc gac tgg tgg              592
Ala Arg Thr Thr Gln Tyr Pro Ile Ile Tyr Thr Thr Thr Asp Trp Trp
            130                 135                 140 aag acg tgc acg ggc aac agc cct gcc ttt ggc caa aag tgc ccg ctg              640
Lys Thr Cys Thr Gly Asn Ser Pro Ala Phe Gly Gln Lys Cys Pro Leu
            145                 150                 155 agc ctg gcc cgg tac tcg agc agc gtg ggc gag atc ccc aac ggc tgg              688
Ser Leu Ala Arg Tyr Ser Ser Ser Val Gly Glu Ile Pro Asn Gly Trp
            160                 165                 170 ccg ttc cag act ttc tgg cag aac agc gac aag tat gcg tac ggt ggc              736
Pro Phe Gln Thr Phe Trp Gln Asn Ser Asp Lys Tyr Ala Tyr Gly Gly
            175                 180                 185 gat tcg cag att ttc aac ggc gcg tac tct cag ctg cag aag att gct              784
Asp Ser Gln Ile Phe Asn Gly Ala Tyr Ser Gln Leu Gln Lys Ile Ala
190                 195                 200                 205 cgc ggt ggt tag                                                              796
Arg Gly Gly <210> SEQ ID NO 14
<211> LENGTH: 228
<212> TYPE: PRT
<213> ORGANISM: Lecanicillium sp. WMM742

<400> SEQUENCE: 14

Met Lys Ser Phe Ser Ser Ile Ile Ala Gly Ile Ala Gly Leu Ala Ser
 -20                 -15                 -10                  -5

Val Ala Ser Ala Thr Val Gln Gly Phe Asp Val Ser Gly Tyr Gln Pro
             -1  1                   5                  10

Thr Val Asn Trp Gly Ala Ala Tyr Ser Ser Gly Ala Arg Phe Val Met
             15                  20                  25

Ile Lys Ala Thr Glu Gly Thr Gly Tyr Ile Ser Ser Ser Phe Gly Ser
 30                  35                  40

Gln Tyr Pro Gly Ala Thr Asn Ala Gly Phe Ile Arg Gly Gly Tyr His
 45                  50                  55                  60

Phe Ala Leu Pro Asp Arg Ser Ser Gly Ser Ala Gln Ala Asp Tyr Phe
             65                  70                  75

Leu Ala His Gly Gly Gly Trp Ser Gly Asp Gly Ile Thr Leu Pro Gly
             80                  85                  90

Met Leu Asp Ile Glu Tyr Asn Pro Tyr Gly Ala Thr Cys Tyr Gly Leu
             95                 100                 105

Ser Gln Gly Ala Met Val Asn Trp Ile Ser Asp Phe Val Glu His Tyr
            110                 115                 120

Lys Ala Arg Thr Thr Gln Tyr Pro Ile Ile Tyr Thr Thr Thr Asp Trp
125                 130                 135                 140

Trp Lys Thr Cys Thr Gly Asn Ser Pro Ala Phe Gly Gln Lys Cys Pro
                145                 150                 155

Leu Ser Leu Ala Arg Tyr Ser Ser Ser Val Gly Glu Ile Pro Asn Gly
            160                 165                 170

Trp Pro Phe Gln Thr Phe Trp Gln Asn Ser Asp Lys Tyr Ala Tyr Gly
            175                 180                 185

Gly Asp Ser Gln Ile Phe Asn Gly Ala Tyr Ser Gln Leu Gln Lys Ile
            190                 195                 200

Ala Arg Gly Gly
205
```

```
<210> SEQ ID NO 15
<211> LENGTH: 208
<212> TYPE: PRT
<213> ORGANISM: Lecanicillium sp. WMM742
<220> FEATURE:
<221> NAME/KEY: mat_peptide
<222> LOCATION: (1)..(208)

<400> SEQUENCE: 15

Thr Val Gln Gly Phe Asp Val Ser Gly Tyr Gln Pro Thr Val Asn Trp
1               5                   10                  15

Gly Ala Ala Tyr Ser Ser Gly Ala Arg Phe Val Met Ile Lys Ala Thr
            20                  25                  30

Glu Gly Thr Gly Tyr Ile Ser Ser Phe Gly Ser Gln Tyr Pro Gly
        35                  40                  45

Ala Thr Asn Ala Gly Phe Ile Arg Gly Gly Tyr His Phe Ala Leu Pro
    50                  55                  60

Asp Arg Ser Ser Gly Ser Ala Gln Ala Asp Tyr Phe Leu Ala His Gly
65                  70                  75                  80

Gly Gly Trp Ser Gly Asp Gly Ile Thr Leu Pro Gly Met Leu Asp Ile
                85                  90                  95

Glu Tyr Asn Pro Tyr Gly Ala Thr Cys Tyr Gly Leu Ser Gln Gly Ala
            100                 105                 110

Met Val Asn Trp Ile Ser Asp Phe Val Glu His Tyr Lys Ala Arg Thr
        115                 120                 125

Thr Gln Tyr Pro Ile Ile Tyr Thr Thr Thr Asp Trp Trp Lys Thr Cys
    130                 135                 140

Thr Gly Asn Ser Pro Ala Phe Gly Gln Lys Cys Pro Leu Ser Leu Ala
145                 150                 155                 160

Arg Tyr Ser Ser Ser Val Gly Glu Ile Pro Asn Gly Trp Pro Phe Gln
                165                 170                 175

Thr Phe Trp Gln Asn Ser Asp Lys Tyr Ala Tyr Gly Gly Asp Ser Gln
            180                 185                 190

Ile Phe Asn Gly Ala Tyr Ser Gln Leu Gln Lys Ile Ala Arg Gly Gly
        195                 200                 205

<210> SEQ ID NO 16
<211> LENGTH: 734
<212> TYPE: DNA
<213> ORGANISM: Onygena equina
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(731)
<220> FEATURE:
<221> NAME/KEY: CDS
<222> LOCATION: (201)..(731)

<400> SEQUENCE: 16 atg ttg aaa aca att atc tat acc acc ctt gcc gtc gct agc ctg gcg      48
Met Leu Lys Thr Ile Ile Tyr Thr Thr Leu Ala Val Ala Ser Leu Ala
            -15                 -10                 -5 tca gca gcc gtt ccc ggt atc gac gtg tcg ggc tac caa ggc aac gtg      96
Ser Ala Ala Val Pro Gly Ile Asp Val Ser Gly Tyr Gln Gly Asn Val
    -1  1               5                   10 aac tgg gcg aac gtc gcc aac gct gga aag aag ttt gcc tac gtc aag     144
Asn Trp Ala Asn Val Ala Asn Ala Gly Lys Lys Phe Ala Tyr Val Lys
```

```
                15                  20                  25                  30
gtatgcgtct ccgtaatgag ttatgaattg gaactaatca aatcaatcgg gcatag gcc           203
                                                                       Ala acg gaa cat acc aac tac atc aac cct tac ttc gcc cag cag tac aat           251
Thr Glu His Thr Asn Tyr Ile Asn Pro Tyr Phe Ala Gln Gln Tyr Asn
             35                  40                  45 ggc gcc tac aac cag ggc att att cga ggt gca tac cac tac gcc cac           299
Gly Ala Tyr Asn Gln Gly Ile Ile Arg Gly Ala Tyr His Tyr Ala His
         50                  55                  60 ccc aac ggc gca agc gga gct tct cag gcc aac tac ttc ctt gct cac           347
Pro Asn Gly Ala Ser Gly Ala Ser Gln Ala Asn Tyr Phe Leu Ala His
 65                  70                  75 ggt ggc ggc tgg tct gct gat ggg aaa acc ctt cct ggt gcc gtc gac           395
Gly Gly Gly Trp Ser Ala Asp Gly Lys Thr Leu Pro Gly Ala Val Asp
80                  85                  90                  95 ctc gag tac gga ccc aat ggc agc act tgc tgg ggt atc agt caa tcg           443
Leu Glu Tyr Gly Pro Asn Gly Ser Thr Cys Trp Gly Ile Ser Gln Ser
                100                 105                 110 gcg atg atc gct tgg atc cgt gac ttc tcc aac acc tac cgt gcc aag           491
Ala Met Ile Ala Trp Ile Arg Asp Phe Ser Asn Thr Tyr Arg Ala Lys
            115                 120                 125 acc ggc cgg cct cca gtc atc tac acc agc acc tct tgg tgg aag acc           539
Thr Gly Arg Pro Pro Val Ile Tyr Thr Ser Thr Ser Trp Trp Lys Thr
        130                 135                 140 tgc acc ggt aac tat ggc ggt ttc gga aac gat aat ccc ctt tgg att           587
Cys Thr Gly Asn Tyr Gly Gly Phe Gly Asn Asp Asn Pro Leu Trp Ile
    145                 150                 155 gct cgt tat tca agc act gtc ggc gaa ctt cct gct ggc tgg cct ttc           635
Ala Arg Tyr Ser Ser Thr Val Gly Glu Leu Pro Ala Gly Trp Pro Phe
160                 165                 170                 175 cac agc atc tgg cag aac aac gat aac agc ggt gtt gga ggg gac ggt           683
His Ser Ile Trp Gln Asn Asn Asp Asn Ser Gly Val Gly Gly Asp Gly
                180                 185                 190 gat atc tgg aac ggt gac ctg gct gga ttg caa cga ttt gca aag ggc           731
Asp Ile Trp Asn Gly Asp Leu Ala Gly Leu Gln Arg Phe Ala Lys Gly
            195                 200                 205 taa                                                                        734
```

<210> SEQ ID NO 17
<211> LENGTH: 225
<212> TYPE: PRT
<213> ORGANISM: Onygena equina

<400> SEQUENCE: 17

```
Met Leu Lys Thr Ile Ile Tyr Thr Thr Leu Ala Val Ala Ser Leu Ala
             -15                 -10                  -5

Ser Ala Ala Val Pro Gly Ile Asp Val Ser Gly Tyr Gln Gly Asn Val
     -1  1               5                  10

Asn Trp Ala Asn Val Ala Asn Ala Gly Lys Lys Phe Ala Tyr Val Lys
 15                  20                  25                  30

Ala Thr Glu His Thr Asn Tyr Ile Asn Pro Tyr Phe Ala Gln Gln Tyr
                 35                  40                  45

Asn Gly Ala Tyr Asn Gln Gly Ile Ile Arg Gly Ala Tyr His Tyr Ala
             50                  55                  60

His Pro Asn Gly Ala Ser Gly Ala Ser Gln Ala Asn Tyr Phe Leu Ala
         65                  70                  75

His Gly Gly Gly Trp Ser Ala Asp Gly Lys Thr Leu Pro Gly Ala Val
     80                  85                  90
```

```
Asp Leu Glu Tyr Gly Pro Asn Gly Ser Thr Cys Trp Gly Ile Ser Gln
 95                 100                 105                 110

Ser Ala Met Ile Ala Trp Ile Arg Asp Phe Ser Asn Thr Tyr Arg Ala
                115                 120                 125

Lys Thr Gly Arg Pro Pro Val Ile Tyr Thr Ser Thr Ser Trp Trp Lys
            130                 135                 140

Thr Cys Thr Gly Asn Tyr Gly Gly Phe Gly Asn Asp Asn Pro Leu Trp
        145                 150                 155

Ile Ala Arg Tyr Ser Ser Thr Val Gly Glu Leu Pro Ala Gly Trp Pro
    160                 165                 170

Phe His Ser Ile Trp Gln Asn Asn Asp Asn Ser Gly Val Gly Gly Asp
175                 180                 185                 190

Gly Asp Ile Trp Asn Gly Asp Leu Ala Gly Leu Gln Arg Phe Ala Lys
                195                 200                 205

Gly

<210> SEQ ID NO 18
<211> LENGTH: 207
<212> TYPE: PRT
<213> ORGANISM: Onygena equina
<220> FEATURE:
<221> NAME/KEY: mat_peptide
<222> LOCATION: (1)..(207)

<400> SEQUENCE: 18

Ala Val Pro Gly Ile Asp Val Ser Gly Tyr Gln Gly Asn Val Asn Trp
  1               5                  10                  15

Ala Asn Val Ala Asn Ala Gly Lys Lys Phe Ala Tyr Val Lys Ala Thr
                 20                  25                  30

Glu His Thr Asn Tyr Ile Asn Pro Tyr Phe Ala Gln Gln Tyr Asn Gly
             35                  40                  45

Ala Tyr Asn Gln Gly Ile Ile Arg Gly Ala Tyr His Tyr Ala His Pro
         50                  55                  60

Asn Gly Ala Ser Gly Ala Ser Gln Ala Asn Tyr Phe Leu Ala His Gly
 65                  70                  75                  80

Gly Gly Trp Ser Ala Asp Gly Lys Thr Leu Pro Gly Ala Val Asp Leu
                 85                  90                  95

Glu Tyr Gly Pro Asn Gly Ser Thr Cys Trp Gly Ile Ser Gln Ser Ala
            100                 105                 110

Met Ile Ala Trp Ile Arg Asp Phe Ser Asn Thr Tyr Arg Ala Lys Thr
        115                 120                 125

Gly Arg Pro Pro Val Ile Tyr Thr Ser Thr Ser Trp Trp Lys Thr Cys
    130                 135                 140

Thr Gly Asn Tyr Gly Gly Phe Gly Asn Asp Asn Pro Leu Trp Ile Ala
145                 150                 155                 160

Arg Tyr Ser Ser Thr Val Gly Glu Leu Pro Ala Gly Trp Pro Phe His
                165                 170                 175

Ser Ile Trp Gln Asn Asn Asp Asn Ser Gly Val Gly Gly Asp Gly Asp
            180                 185                 190

Ile Trp Asn Gly Asp Leu Ala Gly Leu Gln Arg Phe Ala Lys Gly
        195                 200                 205

<210> SEQ ID NO 19
<211> LENGTH: 742
<212> TYPE: DNA
<213> ORGANISM: Purpureocillium lilacinum
```

```
<220> FEATURE:
<221> NAME/KEY: CDS
<222> LOCATION: (1)..(147)
<220> FEATURE:
<221> NAME/KEY: sig_peptide
<222> LOCATION: (1)..(57)
<223> OTHER INFORMATION: 739
<220> FEATURE:
<221> NAME/KEY: mat_peptide
<222> LOCATION: (58)..(739)
<223> OTHER INFORMATION: 739
<220> FEATURE:
<221> NAME/KEY: CDS
<222> LOCATION: (206)..(739)
<223> OTHER INFORMATION: 739

<400> SEQUENCE: 19
```

| | | | | | | | | | | | | | | | | |
|---|---|---|---|---|---|---|---|---|---|---|---|---|---|---|---|---|
| atg | aag | ttc | gca | tcc | gtc | gcc | gcc | tct | gtg | tcc | gcc | ctc | tgc | ggc | gtg | 48 |
| Met | Lys | Phe | Ala | Ser | Val | Ala | Ala | Ser | Val | Ser | Ala | Leu | Cys | Gly | Val | |
| | | | | -15 | | | | | -10 | | | | | -5 | | |
| gcc | tct | gcc | gct | gtc | aag | ggc | ttt | gac | att | tcc | cac | tac | cag | ccc | aac | 96 |
| Ala | Ser | Ala | Ala | Val | Lys | Gly | Phe | Asp | Ile | Ser | His | Tyr | Gln | Pro | Asn | |
| | | -1 | 1 | | | 5 | | | | | 10 | | | | | |
| gtc | gac | ttt | gcc | aag | gcc | tat | gcc | gat | ggc | gcc | cgc | ttc | gtg | atg | atc | 144 |
| Val | Asp | Phe | Ala | Lys | Ala | Tyr | Ala | Asp | Gly | Ala | Arg | Phe | Val | Met | Ile | |
| | 15 | | | | 20 | | | | | 25 | | | | | | |

```
aag gtgcgttcac ccagatgaag agcttccccc gaattccatc taacgttcac        197
Lys
 30 gtcggcag gcc acg gag ggc acc acg tac acg gac ccc agc ttc agc tcg   247
         Ala Thr Glu Gly Thr Thr Tyr Thr Asp Pro Ser Phe Ser Ser
                         35                  40
```

| | | | | | | | | | | | | | | | | |
|---|---|---|---|---|---|---|---|---|---|---|---|---|---|---|---|---|
| cac | tac | acg | ggc | gcc | acc | aag | gcg | ggc | ttc | atc | cgc | ggc | ggc | tac | cac | 295 |
| His | Tyr | Thr | Gly | Ala | Thr | Lys | Ala | Gly | Phe | Ile | Arg | Gly | Gly | Tyr | His | |
| 45 | | | | | 50 | | | | | 55 | | | | | 60 | |
| ttt | gcc | cgc | ccg | gcg | tcc | tcg | tcc | ggt | gcc | gcg | cag | gcc | aag | tac | ttt | 343 |
| Phe | Ala | Arg | Pro | Ala | Ser | Ser | Ser | Gly | Ala | Ala | Gln | Ala | Lys | Tyr | Phe | |
| | | | | | 65 | | | | | 70 | | | | | 75 | |
| atc | gcg | cac | ggc | ggc | ggc | tgg | tcc | aag | gac | ggc | atc | acg | ctg | cct | ggc | 391 |
| Ile | Ala | His | Gly | Gly | Gly | Trp | Ser | Lys | Asp | Gly | Ile | Thr | Leu | Pro | Gly | |
| | | | 80 | | | | | 85 | | | | | 90 | | | |
| atg | ctc | gac | atg | gag | tac | cag | tcg | tcg | agc | agc | gcg | tgc | ggc | ggg | ctc | 439 |
| Met | Leu | Asp | Met | Glu | Tyr | Gln | Ser | Ser | Ser | Ser | Ala | Cys | Gly | Gly | Leu | |
| | | | | 95 | | | | | 100 | | | | | 105 | | |
| tca | cag | agc | gcc | atg | gtc | agc | tgg | atc | aac | gac | ttt | gtc | aac | acg | tac | 487 |
| Ser | Gln | Ser | Ala | Met | Val | Ser | Trp | Ile | Asn | Asp | Phe | Val | Asn | Thr | Tyr | |
| | | | | 110 | | | | | 115 | | | | | 120 | | |
| cac | gcc | gcc | acg | ggc | gtc | tac | ccg | ctc | atc | tac | acc | tcg | acc | agc | tgg | 535 |
| His | Ala | Ala | Thr | Gly | Val | Tyr | Pro | Leu | Ile | Tyr | Thr | Ser | Thr | Ser | Trp | |
| 125 | | | | | 130 | | | | | 135 | | | | | 140 | |
| tgg | acg | cag | tgc | acg | ggc | aac | agc | gcc | gcc | ttt | ggc | agc | aag | tgc | cct | 583 |
| Trp | Thr | Gln | Cys | Thr | Gly | Asn | Ser | Ala | Ala | Phe | Gly | Ser | Lys | Cys | Pro | |
| | | | | 145 | | | | | 150 | | | | | 155 | | |
| ctc | gtc | gtc | gcg | cgc | tat | gct | agc | tcc | gtc | ggc | acg | ctc | cct | gct | ggc | 631 |
| Leu | Val | Val | Ala | Arg | Tyr | Ala | Ser | Ser | Val | Gly | Thr | Leu | Pro | Ala | Gly | |
| | | | | 160 | | | | | 165 | | | | | 170 | | |
| tgg | ggc | ttc | tac | acc | ttc | tgg | cag | tac | tcg | gac | gcg | gcg | ccc | tgg | ggt | 679 |
| Trp | Gly | Phe | Tyr | Thr | Phe | Trp | Gln | Tyr | Ser | Asp | Ala | Ala | Pro | Trp | Gly | |
| | | | 175 | | | | | 180 | | | | | 185 | | | |
| ggt | gat | gcg | gat | acc | ttt | aac | ggc | gac | att | act | gct | ctc | aag | aag | att | 727 |
| Gly | Asp | Ala | Asp | Thr | Phe | Asn | Gly | Asp | Ile | Thr | Ala | Leu | Lys | Lys | Ile | |
| | | | 190 | | | | | 195 | | | | | 200 | | | |
| gcc | aac | gcc | ggt | taa | | | | | | | | | | | | 742 |

Ala Asn Ala Gly
205

<210> SEQ ID NO 20
<211> LENGTH: 227
<212> TYPE: PRT
<213> ORGANISM: Purpureocillium lilacinum

<400> SEQUENCE: 20

Met Lys Phe Ala Ser Val Ala Ala Ser Val Ser Ala Leu Cys Gly Val
                -15                 -10                  -5
Ala Ser Ala Ala Val Lys Gly Phe Asp Ile Ser His Tyr Gln Pro Asn
            -1   1               5                  10
Val Asp Phe Ala Lys Ala Tyr Ala Asp Gly Ala Arg Phe Val Met Ile
            15                  20                  25
Lys Ala Thr Glu Gly Thr Thr Tyr Thr Asp Pro Ser Phe Ser Ser His
 30                  35                  40                  45
Tyr Thr Gly Ala Thr Lys Ala Gly Phe Ile Arg Gly Gly Tyr His Phe
                 50                  55                  60
Ala Arg Pro Ala Ser Ser Gly Ala Ala Gln Ala Lys Tyr Phe Ile
                 65                  70                  75
Ala His Gly Gly Gly Trp Ser Lys Asp Gly Ile Thr Leu Pro Gly Met
             80                  85                  90
Leu Asp Met Glu Tyr Gln Ser Ser Ser Ala Cys Gly Gly Leu Ser
 95                 100                 105
Gln Ser Ala Met Val Ser Trp Ile Asn Asp Phe Val Asn Thr Tyr His
110                 115                 120                 125
Ala Ala Thr Gly Val Tyr Pro Leu Ile Tyr Thr Ser Thr Ser Trp Trp
                130                 135                 140
Thr Gln Cys Thr Gly Asn Ser Ala Ala Phe Gly Ser Lys Cys Pro Leu
            145                 150                 155
Val Val Ala Arg Tyr Ala Ser Ser Val Gly Thr Leu Pro Ala Gly Trp
            160                 165                 170
Gly Phe Tyr Thr Phe Trp Gln Tyr Ser Asp Ala Ala Pro Trp Gly Gly
        175                 180                 185
Asp Ala Asp Thr Phe Asn Gly Asp Ile Thr Ala Leu Lys Lys Ile Ala
190                 195                 200                 205
Asn Ala Gly

<210> SEQ ID NO 21
<211> LENGTH: 208
<212> TYPE: PRT
<213> ORGANISM: Purpureocillium lilacinum
<220> FEATURE:
<221> NAME/KEY: mat_peptide
<222> LOCATION: (1)..(208)

<400> SEQUENCE: 21

Ala Val Lys Gly Phe Asp Ile Ser His Tyr Gln Pro Asn Val Asp Phe
  1               5                  10                  15
Ala Lys Ala Tyr Ala Asp Gly Ala Arg Phe Val Met Ile Lys Ala Thr
                 20                  25                  30
Glu Gly Thr Thr Tyr Thr Asp Pro Ser Phe Ser Ser His Tyr Thr Gly
             35                  40                  45
Ala Thr Lys Ala Gly Phe Ile Arg Gly Gly Tyr His Phe Ala Arg Pro
         50                  55                  60
Ala Ser Ser Ser Gly Ala Ala Gln Ala Lys Tyr Phe Ile Ala His Gly

```
                65                  70                  75                  80
Gly Gly Trp Ser Lys Asp Gly Ile Thr Leu Pro Gly Met Leu Asp Met
                    85                  90                  95

Glu Tyr Gln Ser Ser Ser Ala Cys Gly Gly Leu Ser Gln Ser Ala
                100                 105                 110

Met Val Ser Trp Ile Asn Asp Phe Val Asn Thr Tyr His Ala Ala Thr
                115                 120                 125

Gly Val Tyr Pro Leu Ile Tyr Thr Ser Thr Ser Trp Trp Thr Gln Cys
    130                 135                 140

Thr Gly Asn Ser Ala Ala Phe Gly Ser Lys Cys Pro Leu Val Val Ala
145                 150                 155                 160

Arg Tyr Ala Ser Ser Val Gly Thr Leu Pro Ala Gly Trp Gly Phe Tyr
                165                 170                 175

Thr Phe Trp Gln Tyr Ser Asp Ala Ala Pro Trp Gly Gly Asp Ala Asp
                180                 185                 190

Thr Phe Asn Gly Asp Ile Thr Ala Leu Lys Lys Ile Ala Asn Ala Gly
                195                 200                 205

<210> SEQ ID NO 22
<211> LENGTH: 895
<212> TYPE: DNA
<213> ORGANISM: Trichobolus zukalii
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(876)
<220> FEATURE:
<221> NAME/KEY: CDS
<222> LOCATION: (293)..(750)
<220> FEATURE:
<221> NAME/KEY: CDS
<222> LOCATION: (820)..(892)

<400> SEQUENCE: 22 atg aag ctc acc act ttt atc acg ggc ctt gta tcg gcc agc acc gct        48
Met Lys Leu Thr Thr Phe Ile Thr Gly Leu Val Ser Ala Ser Thr Ala
            -15                 -10                  -5 ctt gct gcc gtt cca gga ttc gat atc tcc cac tac caa ccg tcc gtt       96
Leu Ala Ala Val Pro Gly Phe Asp Ile Ser His Tyr Gln Pro Ser Val
    -1   1               5                  10 aac tac gcc ggc gcc tac aac tcc ggc gct cgt ttc gtc atc atc aaa      144
Asn Tyr Ala Gly Ala Tyr Asn Ser Gly Ala Arg Phe Val Ile Ile Lys
15                  20                  25                  30 gtcctcttcc ttactctcc cttctcccct tctcccttc tcccttctc ccttctccc        204 cttctcccct tctcccttc tccccttct cccttctccc cttctcccct tctcctctca      264
acatcccatc ctaactccct tctcctag gcg acc gaa ggt aca acc tac act       316
                              Ala Thr Glu Gly Thr Thr Tyr Thr
                                                    35 gac ccc gta ttc tcc act cac tat acc gga gct acc aaa gct ggc tta      364
Asp Pro Val Phe Ser Thr His Tyr Thr Gly Ala Thr Lys Ala Gly Leu
    40                  45                  50 atc cgg gga ggc tac cac ttc gct cgt ccc gcc tcg tcg tcc ggc tcc      412
Ile Arg Gly Gly Tyr His Phe Ala Arg Pro Ala Ser Ser Ser Gly Ser
55                  60                  65                  70 gcc caa gcc gat ttc ttc ttc aaa aac gga ggc ggg tgg tct gct gac      460
Ala Gln Ala Asp Phe Phe Phe Lys Asn Gly Gly Gly Trp Ser Ala Asp
```

```
                75                  80                  85
ggt atc aca ctt cct ggt atg ctc gat atg gaa tat ggc agc act tca    508
Gly Ile Thr Leu Pro Gly Met Leu Asp Met Glu Tyr Gly Ser Thr Ser
         90                  95                 100 tca tgc cat gga ctt tct caa act gct atg gtg aat tgg atc agc gat    556
Ser Cys His Gly Leu Ser Gln Thr Ala Met Val Asn Trp Ile Ser Asp
            105                 110                 115 ttc gtg aac cgg tat aaa acg ttg agt ggg agg tat ccg atg att tat    604
Phe Val Asn Arg Tyr Lys Thr Leu Ser Gly Arg Tyr Pro Met Ile Tyr
        120                 125                 130 act ggt tac tat tgg tgg gtg gag tgt aca ggg aac tct aac aag ttt    652
Thr Gly Tyr Tyr Trp Trp Val Glu Cys Thr Gly Asn Ser Asn Lys Phe
135                 140                 145                 150 gca acg act tgt cct ttg gtg ctt gca agg tat tcg agt tcc gtg gga    700
Ala Thr Thr Cys Pro Leu Val Leu Ala Arg Tyr Ser Ser Ser Val Gly
                155                 160                 165 gag att ccg gga ggc tgg ggg tat caa acg att tgg cag ttt aat gat    748
Glu Ile Pro Gly Gly Trp Gly Tyr Gln Thr Ile Trp Gln Phe Asn Asp
            170                 175                 180 aa  gtaagtggtt ttccgaaggt gagatgaagt gaggacggga ggatgtaggc         800
Lys taattagaca ccgctgcag g tac gct tat ggc ggt gac tcg gat agt ttc     850
                       Tyr Ala Tyr Gly Gly Asp Ser Asp Ser Phe
                                   185                 190 aat ggc tcg ctc gat cgc ctt aag gcg ctt gcc aag ggg act taa        895
Asn Gly Ser Leu Asp Arg Leu Lys Ala Leu Ala Lys Gly Thr
195                 200                 205

<210> SEQ ID NO 23
<211> LENGTH: 225
<212> TYPE: PRT
<213> ORGANISM: Trichobolus zukalii

<400> SEQUENCE: 23

Met Lys Leu Thr Thr Phe Ile Thr Gly Leu Val Ser Ala Ser Thr Ala
            -15                 -10                  -5

Leu Ala Ala Val Pro Gly Phe Asp Ile Ser His Tyr Gln Pro Ser Val
 -1   1               5                  10

Asn Tyr Ala Gly Ala Tyr Asn Ser Gly Ala Arg Phe Val Ile Ile Lys
 15                 20                  25                  30

Ala Thr Glu Gly Thr Thr Tyr Thr Asp Pro Val Phe Ser Thr His Tyr
                 35                  40                  45

Thr Gly Ala Thr Lys Ala Gly Leu Ile Arg Gly Gly Tyr His Phe Ala
             50                  55                  60

Arg Pro Ala Ser Ser Ser Gly Ser Ala Gln Ala Asp Phe Phe Phe Lys
         65                  70                  75

Asn Gly Gly Gly Trp Ser Ala Asp Gly Ile Thr Leu Pro Gly Met Leu
 80                  85                  90

Asp Met Glu Tyr Gly Ser Thr Ser Ser Cys His Gly Leu Ser Gln Thr
 95                 100                 105                 110

Ala Met Val Asn Trp Ile Ser Asp Phe Val Asn Arg Tyr Lys Thr Leu
                115                 120                 125

Ser Gly Arg Tyr Pro Met Ile Tyr Thr Gly Tyr Tyr Trp Trp Val Glu
            130                 135                 140

Cys Thr Gly Asn Ser Asn Lys Phe Ala Thr Thr Cys Pro Leu Val Leu
        145                 150                 155

Ala Arg Tyr Ser Ser Ser Val Gly Glu Ile Pro Gly Gly Trp Gly Tyr
```

Gln Thr Ile Trp Gln Phe Asn Asp Lys Tyr Ala Tyr Gly Gly Asp Ser
175                 180                 185                 190

Asp Ser Phe Asn Gly Ser Leu Asp Arg Leu Lys Ala Leu Ala Lys Gly
                195                 200                 205

Thr

<210> SEQ ID NO 24
<211> LENGTH: 207
<212> TYPE: PRT
<213> ORGANISM: Trichobolus zukalii
<220> FEATURE:
<221> NAME/KEY: mat_peptide
<222> LOCATION: (1)..(207)

<400> SEQUENCE: 24

Ala Val Pro Gly Phe Asp Ile Ser His Tyr Gln Pro Ser Val Asn Tyr
1               5                   10                  15

Ala Gly Ala Tyr Asn Ser Gly Ala Arg Phe Val Ile Ile Lys Ala Thr
            20                  25                  30

Glu Gly Thr Thr Tyr Thr Asp Pro Val Phe Ser Thr His Tyr Thr Gly
        35                  40                  45

Ala Thr Lys Ala Gly Leu Ile Arg Gly Gly Tyr His Phe Ala Arg Pro
    50                  55                  60

Ala Ser Ser Ser Gly Ser Ala Gln Ala Asp Phe Phe Lys Asn Gly
65                  70                  75                  80

Gly Gly Trp Ser Ala Asp Gly Ile Thr Leu Pro Gly Met Leu Asp Met
                85                  90                  95

Glu Tyr Gly Ser Thr Ser Ser Cys His Gly Leu Ser Gln Thr Ala Met
            100                 105                 110

Val Asn Trp Ile Ser Asp Phe Val Asn Arg Tyr Lys Thr Leu Ser Gly
        115                 120                 125

Arg Tyr Pro Met Ile Tyr Thr Gly Tyr Tyr Trp Trp Val Glu Cys Thr
    130                 135                 140

Gly Asn Ser Asn Lys Phe Ala Thr Thr Cys Pro Leu Val Leu Ala Arg
145                 150                 155                 160

Tyr Ser Ser Ser Val Gly Glu Ile Pro Gly Gly Trp Gly Tyr Gln Thr
                165                 170                 175

Ile Trp Gln Phe Asn Asp Lys Tyr Ala Tyr Gly Gly Asp Ser Asp Ser
            180                 185                 190

Phe Asn Gly Ser Leu Asp Arg Leu Lys Ala Leu Ala Lys Gly Thr
        195                 200                 205

<210> SEQ ID NO 25
<211> LENGTH: 672
<212> TYPE: DNA
<213> ORGANISM: Penicillium citrinum
<220> FEATURE:
<221> NAME/KEY: CDS
<222> LOCATION: (1)..(669)
<220> FEATURE:
<221> NAME/KEY: sig_peptide
<222> LOCATION: (1)..(48)
<220> FEATURE:
<221> NAME/KEY: mat_peptide
<222> LOCATION: (49)..(669)

<400> SEQUENCE: 25 atg cgc ccc tcc gtc ata ttg ctc gct ttt gcc agc gca gcc agc gct    48
Met Arg Pro Ser Val Ile Leu Leu Ala Phe Ala Ser Ala Ala Ser Ala

|   |   |   |   |   |   |   |   |   |   |   |   |   |   |   |   |     |
|---|---|---|---|---|---|---|---|---|---|---|---|---|---|---|---|-----|
| -15 | | | | | -10 | | | | | -5 | | | | | -1 | |
| ctc | atc | cac | gct | gtc | gac | agc | tcc | tcc | gaa | gta | tcc | gtc | gac | att | tac | 96 |
| Leu | Ile | His | Ala | Val | Asp | Ser | Ser | Ser | Glu | Val | Ser | Val | Asp | Ile | Tyr | |
| 1 | | | | 5 | | | | | 10 | | | | | 15 | | |
| aaa | aag | gcc | ttg | agc | gag | ggc | ttc | tcg | cgc | gca | atc | ttc | cgc | ggt | tac | 144 |
| Lys | Lys | Ala | Leu | Ser | Glu | Gly | Phe | Ser | Arg | Ala | Ile | Phe | Arg | Gly | Tyr | |
| | | | 20 | | | | | 25 | | | | | 30 | | | |
| cag | gag | gcc | tgc | tcc | cag | ggc | ggc | cgc | gtc | gac | cca | acc | ttt | ttg | ccc | 192 |
| Gln | Glu | Ala | Cys | Ser | Gln | Gly | Gly | Arg | Val | Asp | Pro | Thr | Phe | Leu | Pro | |
| | | 35 | | | | | 40 | | | | | 45 | | | | |
| agc | tac | aag | aat | gcg | caa | aca | gcc | ggc | tac | aaa | gac | ttt | gac | gcc | tat | 240 |
| Ser | Tyr | Lys | Asn | Ala | Gln | Thr | Ala | Gly | Tyr | Lys | Asp | Phe | Asp | Ala | Tyr | |
| | 50 | | | | | 55 | | | | | 60 | | | | | |
| ttc | ttc | ccc | tgc | acg | ggc | tcc | gga | aac | aaa | tgc | aag | cca | tac | gac | gtg | 288 |
| Phe | Phe | Pro | Cys | Thr | Gly | Ser | Gly | Asn | Lys | Cys | Lys | Pro | Tyr | Asp | Val | |
| 65 | | | | | 70 | | | | | 75 | | | | | 80 | |
| cag | att | ggc | gag | ctc | gtc | gac | gct | att | aaa | aag | aac | aac | atg | gcc | att | 336 |
| Gln | Ile | Gly | Glu | Leu | Val | Asp | Ala | Ile | Lys | Lys | Asn | Asn | Met | Ala | Ile | |
| | | | | 85 | | | | | 90 | | | | | 95 | | |
| cgc | cgc | atc | tgg | gtc | gac | ttt | gaa | aag | gac | aag | acc | tgc | aac | ccg | ttt | 384 |
| Arg | Arg | Ile | Trp | Val | Asp | Phe | Glu | Lys | Asp | Lys | Thr | Cys | Asn | Pro | Phe | |
| | | | 100 | | | | | 105 | | | | | 110 | | | |
| aac | tgg | gac | cct | aaa | cgc | aac | att | gat | gag | gcc | aag | agg | att | ata | ggt | 432 |
| Asn | Trp | Asp | Pro | Lys | Arg | Asn | Ile | Asp | Glu | Ala | Lys | Arg | Ile | Ile | Gly | |
| | | 115 | | | | | 120 | | | | | 125 | | | | |
| gca | gtg | cgc | aag | aca | aag | ttc | gat | ttt | ggc | gtg | tac | acc | tca | gca | aca | 480 |
| Ala | Val | Arg | Lys | Thr | Lys | Phe | Asp | Phe | Gly | Val | Tyr | Thr | Ser | Ala | Thr | |
| | 130 | | | | | 135 | | | | | 140 | | | | | |
| cag | tgg | act | tcc | atc | ttt | ggc | tcc | aag | gac | gta | gtc | ctg | gct | aat | gat | 528 |
| Gln | Trp | Thr | Ser | Ile | Phe | Gly | Ser | Lys | Asp | Val | Val | Leu | Ala | Asn | Asp | |
| 145 | | | | | 150 | | | | | 155 | | | | | 160 | |
| gtg | ccg | ctt | tgg | ttt | gcc | aag | ttt | gat | aat | gtc | gag | aac | ctt | gac | ctg | 576 |
| Val | Pro | Leu | Trp | Phe | Ala | Lys | Phe | Asp | Asn | Val | Glu | Asn | Leu | Asp | Leu | |
| | | | 165 | | | | | 170 | | | | | 175 | | | |
| gcg | cag | cct | ttt | gga | ggc | tgg | aca | aag | gcg | gac | gga | aag | caa | tac | acc | 624 |
| Ala | Gln | Pro | Phe | Gly | Gly | Trp | Thr | Lys | Ala | Asp | Gly | Lys | Gln | Tyr | Thr | |
| | | 180 | | | | | 185 | | | | | 190 | | | | |
| gac | aag | tca | gct | agt | aag | aag | ttt | gat | ttg | aac | gtg | ttt | tct | gct | taa | 672 |
| Asp | Lys | Ser | Ala | Ser | Lys | Lys | Phe | Asp | Leu | Asn | Val | Phe | Ser | Ala | | |
| | 195 | | | | | 200 | | | | | 205 | | | | | |

<210> SEQ ID NO 26
<211> LENGTH: 223
<212> TYPE: PRT
<213> ORGANISM: Penicillium citrinum

<400> SEQUENCE: 26

Met Arg Pro Ser Val Ile Leu Leu Ala Phe Ala Ser Ala Ala Ser Ala
        -15                 -10                 -5              -1

Leu Ile His Ala Val Asp Ser Ser Ser Glu Val Ser Val Asp Ile Tyr
1               5                   10                  15

Lys Lys Ala Leu Ser Glu Gly Phe Ser Arg Ala Ile Phe Arg Gly Tyr
                20                  25                  30

Gln Glu Ala Cys Ser Gln Gly Gly Arg Val Asp Pro Thr Phe Leu Pro
            35                  40                  45

Ser Tyr Lys Asn Ala Gln Thr Ala Gly Tyr Lys Asp Phe Asp Ala Tyr
        50                  55                  60

Phe Phe Pro Cys Thr Gly Ser Gly Asn Lys Cys Lys Pro Tyr Asp Val
65                  70                  75                  80

```
Gln Ile Gly Glu Leu Val Asp Ala Ile Lys Lys Asn Asn Met Ala Ile
                 85                  90                  95

Arg Arg Ile Trp Val Asp Phe Glu Lys Asp Lys Thr Cys Asn Pro Phe
            100                 105                 110

Asn Trp Asp Pro Lys Arg Asn Ile Asp Glu Ala Lys Arg Ile Ile Gly
            115                 120                 125

Ala Val Arg Lys Thr Lys Phe Asp Phe Gly Val Tyr Thr Ser Ala Thr
            130                 135                 140

Gln Trp Thr Ser Ile Phe Gly Ser Lys Asp Val Val Leu Ala Asn Asp
145                 150                 155                 160

Val Pro Leu Trp Phe Ala Lys Phe Asp Asn Val Glu Asn Leu Asp Leu
                165                 170                 175

Ala Gln Pro Phe Gly Gly Trp Thr Lys Ala Asp Gly Lys Gln Tyr Thr
            180                 185                 190

Asp Lys Ser Ala Ser Lys Lys Phe Asp Leu Asn Val Phe Ser Ala
            195                 200                 205

<210> SEQ ID NO 27
<211> LENGTH: 207
<212> TYPE: PRT
<213> ORGANISM: Penicillium citrinum
<220> FEATURE:
<221> NAME/KEY: mat_peptide
<222> LOCATION: (1)..(207)

<400> SEQUENCE: 27

Leu Ile His Ala Val Asp Ser Ser Glu Val Ser Val Asp Ile Tyr
1               5                   10                  15

Lys Lys Ala Leu Ser Glu Gly Phe Ser Arg Ala Ile Phe Arg Gly Tyr
                20                  25                  30

Gln Glu Ala Cys Ser Gln Gly Gly Arg Val Asp Pro Thr Phe Leu Pro
            35                  40                  45

Ser Tyr Lys Asn Ala Gln Thr Ala Gly Tyr Lys Asp Phe Asp Ala Tyr
        50                  55                  60

Phe Phe Pro Cys Thr Gly Ser Gly Asn Lys Cys Lys Pro Tyr Asp Val
65                  70                  75                  80

Gln Ile Gly Glu Leu Val Asp Ala Ile Lys Lys Asn Asn Met Ala Ile
                85                  90                  95

Arg Arg Ile Trp Val Asp Phe Glu Lys Asp Lys Thr Cys Asn Pro Phe
            100                 105                 110

Asn Trp Asp Pro Lys Arg Asn Ile Asp Glu Ala Lys Arg Ile Ile Gly
            115                 120                 125

Ala Val Arg Lys Thr Lys Phe Asp Phe Gly Val Tyr Thr Ser Ala Thr
            130                 135                 140

Gln Trp Thr Ser Ile Phe Gly Ser Lys Asp Val Val Leu Ala Asn Asp
145                 150                 155                 160

Val Pro Leu Trp Phe Ala Lys Phe Asp Asn Val Glu Asn Leu Asp Leu
                165                 170                 175

Ala Gln Pro Phe Gly Gly Trp Thr Lys Ala Asp Gly Lys Gln Tyr Thr
            180                 185                 190

Asp Lys Ser Ala Ser Lys Lys Phe Asp Leu Asn Val Phe Ser Ala
            195                 200                 205

<210> SEQ ID NO 28
<211> LENGTH: 690
<212> TYPE: DNA
```

<213> ORGANISM: Cladorrhinum bulbillosum
<220> FEATURE:
<221> NAME/KEY: CDS
<222> LOCATION: (1)..(687)
<220> FEATURE:
<221> NAME/KEY: sig_peptide
<222> LOCATION: (1)..(66)
<220> FEATURE:
<221> NAME/KEY: mat_peptide
<222> LOCATION: (67)..(687)

<400> SEQUENCE: 28

| | | | | | | | | | | | | | | | | |
|---|---|---|---|---|---|---|---|---|---|---|---|---|---|---|---|---|
| atg | aag | ctc | ctc | ccc | ctt | tcc | acc | acc | tta | ttg | ccc | gtg | gcc | ctc | ctc | 48 |
| Met | Lys | Leu | Leu | Pro | Leu | Ser | Thr | Thr | Leu | Leu | Pro | Val | Ala | Leu | Leu | |
| | | -20 | | | | -15 | | | | -10 | | | | | | |
| gcc | acc | gag | gcc | tcg | gcg | gca | gtc | caa | ggc | ttc | gac | atc | tcg | cac | tac | 96 |
| Ala | Thr | Glu | Ala | Ser | Ala | Ala | Val | Gln | Gly | Phe | Asp | Ile | Ser | His | Tyr | |
| | -5 | | | | -1 | 1 | | | 5 | | | | | | 10 | |
| caa | tcc | tca | gtc | aac | ttc | cag | gcg | gcc | tac | aac | tcg | ggc | gcc | cgc | ttc | 144 |
| Gln | Ser | Ser | Val | Asn | Phe | Gln | Ala | Ala | Tyr | Asn | Ser | Gly | Ala | Arg | Phe | |
| | | | | 15 | | | | | 20 | | | | | 25 | | |
| gtc | atc | atc | aag | gcg | aca | gag | ggc | acg | acc | tac | atc | gac | ccc | aag | ttt | 192 |
| Val | Ile | Ile | Lys | Ala | Thr | Glu | Gly | Thr | Thr | Tyr | Ile | Asp | Pro | Lys | Phe | |
| | | | 30 | | | | | 35 | | | | | 40 | | | |
| tcg | tct | cac | tac | acg | gga | gcc | acc | aac | gcc | ggg | cta | atc | cgg | ggc | ggg | 240 |
| Ser | Ser | His | Tyr | Thr | Gly | Ala | Thr | Asn | Ala | Gly | Leu | Ile | Arg | Gly | Gly | |
| | | 45 | | | | | 50 | | | | | 55 | | | | |
| tac | cac | ttt | gcc | cat | ccg | gac | tcg | tcg | acc | ggc | gcc | gcg | cag | gca | gat | 288 |
| Tyr | His | Phe | Ala | His | Pro | Asp | Ser | Ser | Thr | Gly | Ala | Ala | Gln | Ala | Asp | |
| | 60 | | | | | 65 | | | | | 70 | | | | | |
| ttt | ttc | ctc | gcc | cac | ggc | ggc | ggc | tgg | tcc | ggc | gac | ggc | atc | acc | ctg | 336 |
| Phe | Phe | Leu | Ala | His | Gly | Gly | Gly | Trp | Ser | Gly | Asp | Gly | Ile | Thr | Leu | |
| 75 | | | | | 80 | | | | | 85 | | | | | 90 | |
| ccc | ggg | atg | ctc | gac | ctc | gaa | tcc | gtc | tcc | gga | aag | gcg | acc | tgc | ttc | 384 |
| Pro | Gly | Met | Leu | Asp | Leu | Glu | Ser | Val | Ser | Gly | Lys | Ala | Thr | Cys | Phe | |
| | | | | 95 | | | | | 100 | | | | | 105 | | |
| ggg | ctc | tcg | gcc | tcg | tcc | atg | gtc | gcc | tgg | atc | aag | tcg | ttc | tct | gac | 432 |
| Gly | Leu | Ser | Ala | Ser | Ser | Met | Val | Ala | Trp | Ile | Lys | Ser | Phe | Ser | Asp | |
| | | | 110 | | | | | 115 | | | | | 120 | | | |
| cgg | tac | cac | acc | cgg | acc | gga | cgg | tac | ccg | atg | ctg | tac | acc | aac | ccg | 480 |
| Arg | Tyr | His | Thr | Arg | Thr | Gly | Arg | Tyr | Pro | Met | Leu | Tyr | Thr | Asn | Pro | |
| | | 125 | | | | | 130 | | | | | 135 | | | | |
| tct | tgg | tgg | acc | acc | tgc | acc | gga | aac | agc | aac | gcg | ttc | gtc | aac | acg | 528 |
| Ser | Trp | Trp | Thr | Thr | Cys | Thr | Gly | Asn | Ser | Asn | Ala | Phe | Val | Asn | Thr | |
| | 140 | | | | | 145 | | | | | 150 | | | | | |
| aac | ccg | ctc | gtt | ctg | gct | cgg | tac | gcc | agc | gcg | ccc | ggg | acc | atc | ccc | 576 |
| Asn | Pro | Leu | Val | Leu | Ala | Arg | Tyr | Ala | Ser | Ala | Pro | Gly | Thr | Ile | Pro | |
| 155 | | | | | 160 | | | | | 165 | | | | | 170 | |
| ggt | gga | tgg | ccg | tat | cag | acc | atc | tgg | cag | aat | tcg | gac | tcg | tat | acc | 624 |
| Gly | Gly | Trp | Pro | Tyr | Gln | Thr | Ile | Trp | Gln | Asn | Ser | Asp | Ser | Tyr | Thr | |
| | | | 175 | | | | | 180 | | | | | 185 | | | |
| tac | gga | ggg | gat | tcg | gat | att | ttt | aac | ggc | gcg | ctg | agt | ggg | ttg | caa | 672 |
| Tyr | Gly | Gly | Asp | Ser | Asp | Ile | Phe | Asn | Gly | Ala | Leu | Ser | Gly | Leu | Gln | |
| | | | 190 | | | | | 195 | | | | | 200 | | | |
| aag | ttg | gcc | agc | ggt | taa | | | | | | | | | | | 690 |
| Lys | Leu | Ala | Ser | Gly | | | | | | | | | | | | |
| | | 205 | | | | | | | | | | | | | | |

<210> SEQ ID NO 29
<211> LENGTH: 229
<212> TYPE: PRT
<213> ORGANISM: Cladorrhinum bulbillosum

```
<400> SEQUENCE: 29

Met Lys Leu Leu Pro Leu Ser Thr Thr Leu Leu Pro Val Ala Leu Leu
        -20                 -15                 -10

Ala Thr Glu Ala Ser Ala Ala Val Gln Gly Phe Asp Ile Ser His Tyr
         -5              -1   1               5                 10

Gln Ser Ser Val Asn Phe Gln Ala Ala Tyr Asn Ser Gly Ala Arg Phe
                 15                  20                  25

Val Ile Ile Lys Ala Thr Glu Gly Thr Thr Tyr Ile Asp Pro Lys Phe
                 30                  35                  40

Ser Ser His Tyr Thr Gly Ala Thr Asn Ala Gly Leu Ile Arg Gly Gly
                 45                  50                  55

Tyr His Phe Ala His Pro Asp Ser Ser Thr Gly Ala Ala Gln Ala Asp
         60                  65                  70

Phe Phe Leu Ala His Gly Gly Gly Trp Ser Gly Asp Gly Ile Thr Leu
75                   80                  85                  90

Pro Gly Met Leu Asp Leu Glu Ser Val Ser Gly Lys Ala Thr Cys Phe
                 95                 100                 105

Gly Leu Ser Ala Ser Ser Met Val Ala Trp Ile Lys Ser Phe Ser Asp
                110                 115                 120

Arg Tyr His Thr Arg Thr Gly Arg Tyr Pro Met Leu Tyr Thr Asn Pro
                125                 130                 135

Ser Trp Trp Thr Thr Cys Thr Gly Asn Ser Asn Ala Phe Val Asn Thr
140                 145                 150

Asn Pro Leu Val Leu Ala Arg Tyr Ala Ser Ala Pro Gly Thr Ile Pro
155                 160                 165                 170

Gly Gly Trp Pro Tyr Gln Thr Ile Trp Gln Asn Ser Asp Ser Tyr Thr
                175                 180                 185

Tyr Gly Gly Asp Ser Asp Ile Phe Asn Gly Ala Leu Ser Gly Leu Gln
                190                 195                 200

Lys Leu Ala Ser Gly
        205

<210> SEQ ID NO 30
<211> LENGTH: 207
<212> TYPE: PRT
<213> ORGANISM: Cladorrhinum bulbillosum
<220> FEATURE:
<221> NAME/KEY: mat_peptide
<222> LOCATION: (1)..(207)

<400> SEQUENCE: 30

Ala Val Gln Gly Phe Asp Ile Ser His Tyr Gln Ser Ser Val Asn Phe
1               5                  10                  15

Gln Ala Ala Tyr Asn Ser Gly Ala Arg Phe Val Ile Ile Lys Ala Thr
                20                  25                  30

Glu Gly Thr Thr Tyr Ile Asp Pro Lys Phe Ser Ser His Tyr Thr Gly
                35                  40                  45

Ala Thr Asn Ala Gly Leu Ile Arg Gly Gly Tyr His Phe Ala His Pro
                50                  55                  60

Asp Ser Ser Thr Gly Ala Ala Gln Ala Asp Phe Phe Leu Ala His Gly
65                  70                  75                  80

Gly Gly Trp Ser Gly Asp Gly Ile Thr Leu Pro Gly Met Leu Asp Leu
                85                  90                  95

Glu Ser Val Ser Gly Lys Ala Thr Cys Phe Gly Leu Ser Ala Ser Ser
                100                 105                 110
```

```
Met Val Ala Trp Ile Lys Ser Phe Ser Asp Arg Tyr His Thr Arg Thr
            115                 120                 125

Gly Arg Tyr Pro Met Leu Tyr Thr Asn Pro Ser Trp Trp Thr Thr Cys
    130                 135                 140

Thr Gly Asn Ser Asn Ala Phe Val Asn Thr Asn Pro Leu Val Leu Ala
145                 150                 155                 160

Arg Tyr Ala Ser Ala Pro Gly Thr Ile Pro Gly Trp Pro Tyr Gln
                165                 170                 175

Thr Ile Trp Gln Asn Ser Asp Ser Tyr Thr Tyr Gly Gly Asp Ser Asp
            180                 185                 190

Ile Phe Asn Gly Ala Leu Ser Gly Leu Gln Lys Leu Ala Ser Gly
            195                 200                 205
```

<210> SEQ ID NO 31
<211> LENGTH: 687
<212> TYPE: DNA
<213> ORGANISM: Umbelopsis westeae
<220> FEATURE:
<221> NAME/KEY: CDS
<222> LOCATION: (1)..(684)
<220> FEATURE:
<221> NAME/KEY: sig_peptide
<222> LOCATION: (1)..(60)
<220> FEATURE:
<221> NAME/KEY: mat_peptide
<222> LOCATION: (61)..(684)

<400> SEQUENCE: 31

```
atg aag ctc acc ttt gcc tct cta act ctc cta tct tcc gct ctt gtt      48
Met Lys Leu Thr Phe Ala Ser Leu Thr Leu Leu Ser Ser Ala Leu Val
-20                 -15                 -10                  -5 gga gtg tca gct aaa ttg aaa gga ttg gat gtt agc ggt tac caa cca      96
Gly Val Ser Ala Lys Leu Lys Gly Leu Asp Val Ser Gly Tyr Gln Pro
        -1  1                   5                      10 aat gta gct tgg tca acc gtc aag gcc aat ggt gca tcc ttt gct tat     144
Asn Val Ala Trp Ser Thr Val Lys Ala Asn Gly Ala Ser Phe Ala Tyr
            15                  20                  25 atc aaa gct act gaa ggc act aat tat aaa aac cca tcg ttt gct caa     192
Ile Lys Ala Thr Glu Gly Thr Asn Tyr Lys Asn Pro Ser Phe Ala Gln
        30                  35                  40 cag tac aac gga gca tat aat gct ggc ttg att cgc ggc tcg tac cat     240
Gln Tyr Asn Gly Ala Tyr Asn Ala Gly Leu Ile Arg Gly Ser Tyr His
45                  50                  55                  60 ttt gct cag cct tcc tcc tct acc ggt gct gct caa gcc aac tac ttc     288
Phe Ala Gln Pro Ser Ser Ser Thr Gly Ala Ala Gln Ala Asn Tyr Phe
                65                  70                  75 ctt gcg cac gga ggt ggc tgg tct cct gat ggc aag act ctt ccc ggt     336
Leu Ala His Gly Gly Gly Trp Ser Pro Asp Gly Lys Thr Leu Pro Gly
            80                  85                  90 gct ttg gat atg gaa tat aac cct cat ggc tct aca tgc tat ggc tta     384
Ala Leu Asp Met Glu Tyr Asn Pro His Gly Ser Thr Cys Tyr Gly Leu
        95                  100                 105 tcc aag gat gct atg gta aag tgg att aag gat ttc agt aat acc tac     432
Ser Lys Asp Ala Met Val Lys Trp Ile Lys Asp Phe Ser Asn Thr Tyr
    110                 115                 120 cac tct gcc act ggc cgt tat ccc gta att tac act acc act agt tgg     480
His Ser Ala Thr Gly Arg Tyr Pro Val Ile Tyr Thr Thr Thr Ser Trp
125                 130                 135                 140 tgg acg act tgc acc ggt aac agt gct gca ttt ggc gct acc aac cct     528
Trp Thr Thr Cys Thr Gly Asn Ser Ala Ala Phe Gly Ala Thr Asn Pro
                145                 150                 155
```

```
ctt tgg atc gct aga tac tcc tct acg gct ggg aac ttg ccc aat ggt    576
Leu Trp Ile Ala Arg Tyr Ser Ser Thr Ala Gly Asn Leu Pro Asn Gly
        160                 165                 170 tgg gca ttc tac tct ttc tgg caa aat gcc gac agt ggc atc ttc cct    624
Trp Ala Phe Tyr Ser Phe Trp Gln Asn Ala Asp Ser Gly Ile Phe Pro
    175                 180                 185 ggt gat caa gat att tgg aac ggt gat gct gct gct ttg tct agg atg    672
Gly Asp Gln Asp Ile Trp Asn Gly Asp Ala Ala Ala Leu Ser Arg Met
190                 195                 200 gcc aaa gga gcc taa                                                687
Ala Lys Gly Ala
205
```

<210> SEQ ID NO 32
<211> LENGTH: 228
<212> TYPE: PRT
<213> ORGANISM: Umbelopsis westeae

<400> SEQUENCE: 32

```
Met Lys Leu Thr Phe Ala Ser Leu Thr Leu Leu Ser Ala Leu Val
-20             -15                 -10                 -5

Gly Val Ser Ala Lys Leu Lys Gly Leu Asp Val Ser Gly Tyr Gln Pro
        -1  1               5                   10

Asn Val Ala Trp Ser Thr Val Lys Ala Asn Gly Ala Ser Phe Ala Tyr
            15                  20                  25

Ile Lys Ala Thr Glu Gly Thr Asn Tyr Lys Asn Pro Ser Phe Ala Gln
        30                  35                  40

Gln Tyr Asn Gly Ala Tyr Asn Ala Gly Leu Ile Arg Gly Ser Tyr His
45                  50                  55                  60

Phe Ala Gln Pro Ser Ser Thr Gly Ala Ala Gln Ala Asn Tyr Phe
            65                  70                  75

Leu Ala His Gly Gly Trp Ser Pro Asp Gly Lys Thr Leu Pro Gly
        80                  85                  90

Ala Leu Asp Met Glu Tyr Asn Pro His Gly Ser Thr Cys Tyr Gly Leu
        95                  100                 105

Ser Lys Asp Ala Met Val Lys Trp Ile Lys Asp Phe Ser Asn Thr Tyr
110                 115                 120

His Ser Ala Thr Gly Arg Tyr Pro Val Ile Tyr Thr Thr Ser Trp
125             130                 135                 140

Trp Thr Thr Cys Thr Gly Asn Ser Ala Ala Phe Gly Ala Thr Asn Pro
                145                 150                 155

Leu Trp Ile Ala Arg Tyr Ser Ser Thr Ala Gly Asn Leu Pro Asn Gly
        160                 165                 170

Trp Ala Phe Tyr Ser Phe Trp Gln Asn Ala Asp Ser Gly Ile Phe Pro
    175                 180                 185

Gly Asp Gln Asp Ile Trp Asn Gly Asp Ala Ala Ala Leu Ser Arg Met
190                 195                 200

Ala Lys Gly Ala
205
```

<210> SEQ ID NO 33
<211> LENGTH: 208
<212> TYPE: PRT
<213> ORGANISM: Umbelopsis westeae
<220> FEATURE:
<221> NAME/KEY: mat_peptide
<222> LOCATION: (1)..(208)

<400> SEQUENCE: 33

```
Lys Leu Lys Gly Leu Asp Val Ser Gly Tyr Gln Pro Asn Val Ala Trp
1               5                   10                  15

Ser Thr Val Lys Ala Asn Gly Ala Ser Phe Ala Tyr Ile Lys Ala Thr
            20                  25                  30

Glu Gly Thr Asn Tyr Lys Asn Pro Ser Phe Ala Gln Gln Tyr Asn Gly
            35                  40                  45

Ala Tyr Asn Ala Gly Leu Ile Arg Gly Ser Tyr His Phe Ala Gln Pro
    50                  55                  60

Ser Ser Ser Thr Gly Ala Ala Gln Ala Asn Tyr Phe Leu Ala His Gly
65              70                  75                  80

Gly Gly Trp Ser Pro Asp Gly Lys Thr Leu Pro Gly Ala Leu Asp Met
                85                  90                  95

Glu Tyr Asn Pro His Gly Ser Thr Cys Tyr Gly Leu Ser Lys Asp Ala
                100                 105                 110

Met Val Lys Trp Ile Lys Asp Phe Ser Asn Thr Tyr His Ser Ala Thr
            115                 120                 125

Gly Arg Tyr Pro Val Ile Tyr Thr Thr Thr Ser Trp Trp Thr Thr Cys
130                 135                 140

Thr Gly Asn Ser Ala Ala Phe Gly Ala Thr Asn Pro Leu Trp Ile Ala
145                 150                 155                 160

Arg Tyr Ser Ser Thr Ala Gly Asn Leu Pro Asn Gly Trp Ala Phe Tyr
                165                 170                 175

Ser Phe Trp Gln Asn Ala Asp Ser Gly Ile Phe Pro Gly Asp Gln Asp
                180                 185                 190

Ile Trp Asn Gly Asp Ala Ala Leu Ser Arg Met Ala Lys Gly Ala
                195                 200                 205

<210> SEQ ID NO 34
<211> LENGTH: 684
<212> TYPE: DNA
<213> ORGANISM: Zygomycetes sp. XZ2655
<220> FEATURE:
<221> NAME/KEY: CDS
<222> LOCATION: (1)..(681)
<220> FEATURE:
<221> NAME/KEY: sig_peptide
<222> LOCATION: (1)..(57)
<220> FEATURE:
<221> NAME/KEY: mat_peptide
<222> LOCATION: (58)..(681)

<400> SEQUENCE: 34 atg aaa gca atc gta aca gca tta gca tta tcc ttg tta tgg gcg ggt    48
Met Lys Ala Ile Val Thr Ala Leu Ala Leu Ser Leu Leu Trp Ala Gly
                -15                 -10                 -5 gcc cat gca act ttg ccc ggc tta gac gtc agc agc tac caa ggt aac    96
Ala His Ala Thr Leu Pro Gly Leu Asp Val Ser Ser Tyr Gln Gly Asn
        -1  1               5                   10 gtc aat tgg gga aca gtg gcg agt caa gga gca aaa ttt gct tac gtc   144
Val Asn Trp Gly Thr Val Ala Ser Gln Gly Ala Lys Phe Ala Tyr Val
        15                  20                  25 aag gct acc gag ggt acg acc tac acg aat ccc tat ttt gcg tcc caa   192
Lys Ala Thr Glu Gly Thr Thr Tyr Thr Asn Pro Tyr Phe Ala Ser Gln
30                  35                  40                  45 tac gac gga tcc tac aac gcg ggc cta att cgc ggt gcc tat cac ttt   240
Tyr Asp Gly Ser Tyr Asn Ala Gly Leu Ile Arg Gly Ala Tyr His Phe
                50                  55                  60 gcc cat ccc gat tct tcc tct gga gct acc caa gca aac tat ttc ctt   288
Ala His Pro Asp Ser Ser Ser Gly Ala Thr Gln Ala Asn Tyr Phe Leu
```

```
                  65                  70                  75
gct cat ggt ggc ggc tgg tcc gct gac gga aag acc tta cct ggt gcg      336
Ala His Gly Gly Gly Trp Ser Ala Asp Gly Lys Thr Leu Pro Gly Ala
         80                  85                  90 cta gat att gag tac aat cct aac ggc gct gaa tgc tac ggc ttg tct      384
Leu Asp Ile Glu Tyr Asn Pro Asn Gly Ala Glu Cys Tyr Gly Leu Ser
     95                 100                 105 caa ttg gcc atg att agc tgg att caa gac ttc agc aac acc tat cac      432
Gln Leu Ala Met Ile Ser Trp Ile Gln Asp Phe Ser Asn Thr Tyr His
110                 115                 120                 125 tcc cac acg ggc aga tat ccg gtc att tac acg act acg gac tgg tgg      480
Ser His Thr Gly Arg Tyr Pro Val Ile Tyr Thr Thr Thr Asp Trp Trp
                130                 135                 140 acc acc tgc acg ggt aac agc gca gcc ttt gga acc aac aac cct ctc      528
Thr Thr Cys Thr Gly Asn Ser Ala Ala Phe Gly Thr Asn Asn Pro Leu
            145                 150                 155 tgg att gct cgg tat tcg tct tcg gtg ggc acc ctg cct gca ggt tgg      576
Trp Ile Ala Arg Tyr Ser Ser Ser Val Gly Thr Leu Pro Ala Gly Trp
        160                 165                 170 ggc tac gag agc ttc tgg cag aag gca tct tcg ggt acg ttc cct gga      624
Gly Tyr Glu Ser Phe Trp Gln Lys Ala Ser Ser Gly Thr Phe Pro Gly
    175                 180                 185 gac caa gat atc tgg aat ggc gat gct gct gga ctc tcc aga ttc gcc      672
Asp Gln Asp Ile Trp Asn Gly Asp Ala Ala Gly Leu Ser Arg Phe Ala
190                 195                 200                 205 acc ggc aaa tga                                                      684
Thr Gly Lys <210> SEQ ID NO 35
<211> LENGTH: 227
<212> TYPE: PRT
<213> ORGANISM: Zygomycetes sp. XZ2655

<400> SEQUENCE: 35

Met Lys Ala Ile Val Thr Ala Leu Ala Leu Ser Leu Leu Trp Ala Gly
                -15                 -10                  -5

Ala His Ala Thr Leu Pro Gly Leu Asp Val Ser Ser Tyr Gln Gly Asn
         -1  1                   5                  10

Val Asn Trp Gly Thr Val Ala Ser Gln Gly Ala Lys Phe Ala Tyr Val
     15                  20                  25

Lys Ala Thr Glu Gly Thr Thr Tyr Thr Asn Pro Tyr Phe Ala Ser Gln
 30                  35                  40                  45

Tyr Asp Gly Ser Tyr Asn Ala Gly Leu Ile Arg Gly Ala Tyr His Phe
                 50                  55                  60

Ala His Pro Asp Ser Ser Gly Ala Thr Gln Ala Asn Tyr Phe Leu
             65                  70                  75

Ala His Gly Gly Gly Trp Ser Ala Asp Gly Lys Thr Leu Pro Gly Ala
         80                  85                  90

Leu Asp Ile Glu Tyr Asn Pro Asn Gly Ala Glu Cys Tyr Gly Leu Ser
     95                 100                 105

Gln Leu Ala Met Ile Ser Trp Ile Gln Asp Phe Ser Asn Thr Tyr His
110                 115                 120                 125

Ser His Thr Gly Arg Tyr Pro Val Ile Tyr Thr Thr Thr Asp Trp Trp
                130                 135                 140

Thr Thr Cys Thr Gly Asn Ser Ala Ala Phe Gly Thr Asn Asn Pro Leu
            145                 150                 155

Trp Ile Ala Arg Tyr Ser Ser Ser Val Gly Thr Leu Pro Ala Gly Trp
```

-continued

```
            160                 165                 170
Gly Tyr Glu Ser Phe Trp Gln Lys Ala Ser Ser Gly Thr Phe Pro Gly
        175                 180                 185

Asp Gln Asp Ile Trp Asn Gly Asp Ala Ala Gly Leu Ser Arg Phe Ala
190                 195                 200                 205

Thr Gly Lys

<210> SEQ ID NO 36
<211> LENGTH: 208
<212> TYPE: PRT
<213> ORGANISM: Zygomycetes sp. XZ2655
<220> FEATURE:
<221> NAME/KEY: mat_peptide
<222> LOCATION: (1)..(208)

<400> SEQUENCE: 36

Thr Leu Pro Gly Leu Asp Val Ser Ser Tyr Gln Gly Asn Val Asn Trp
1               5                   10                  15

Gly Thr Val Ala Ser Gln Gly Ala Lys Phe Ala Tyr Val Lys Ala Thr
            20                  25                  30

Glu Gly Thr Thr Tyr Thr Asn Pro Tyr Phe Ala Ser Gln Tyr Asp Gly
        35                  40                  45

Ser Tyr Asn Ala Gly Leu Ile Arg Gly Ala Tyr His Phe Ala His Pro
    50                  55                  60

Asp Ser Ser Ser Gly Ala Thr Gln Ala Asn Tyr Phe Leu Ala His Gly
65                  70                  75                  80

Gly Gly Trp Ser Ala Asp Gly Lys Thr Leu Pro Gly Ala Leu Asp Ile
                85                  90                  95

Glu Tyr Asn Pro Asn Gly Ala Glu Cys Tyr Gly Leu Ser Gln Leu Ala
            100                 105                 110

Met Ile Ser Trp Ile Gln Asp Phe Ser Asn Thr Tyr His Ser His Thr
        115                 120                 125

Gly Arg Tyr Pro Val Ile Tyr Thr Thr Thr Asp Trp Trp Thr Thr Cys
    130                 135                 140

Thr Gly Asn Ser Ala Ala Phe Gly Thr Asn Asn Pro Leu Trp Ile Ala
145                 150                 155                 160

Arg Tyr Ser Ser Val Gly Thr Leu Pro Ala Gly Trp Gly Tyr Glu
                165                 170                 175

Ser Phe Trp Gln Lys Ala Ser Ser Gly Thr Phe Pro Gly Asp Gln Asp
            180                 185                 190

Ile Trp Asn Gly Asp Ala Ala Gly Leu Ser Arg Phe Ala Thr Gly Lys
        195                 200                 205

<210> SEQ ID NO 37
<211> LENGTH: 747
<212> TYPE: DNA
<213> ORGANISM: Chaetomium cupreum
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(744)
<220> FEATURE:
<221> NAME/KEY: CDS
<222> LOCATION: (217)..(744)

<400> SEQUENCE: 37
```

```
atg aaa tcc gcc atc ctc gcc tgt gtc ggt ttt gct gcc gcg gtg caa        48
Met Lys Ser Ala Ile Leu Ala Cys Val Gly Phe Ala Ala Ala Val Gln
        -15                 -10                 -5 gcc acg gtc cag ggc ttt gac atc tcc ggc tat cag cca aat gtc aac        96
Ala Thr Val Gln Gly Phe Asp Ile Ser Gly Tyr Gln Pro Asn Val Asn
-1  1                   5                   10                  15 ttt gcc gcc gcc tat gcc gca ggc gcc cgc ttc gtc atc atc aag           141
Phe Ala Ala Ala Tyr Ala Ala Gly Ala Arg Phe Val Ile Ile Lys
                    20                  25                  30 gtgagcagcc caagtcatca cagtcaccca ctacctgagg tacggtagtc aaggcaatca    201
gctaacctct gccag gcc acc gag ggc acc agc tac atc agc ccc tcc ttc    252
                Ala Thr Glu Gly Thr Ser Tyr Ile Ser Pro Ser Phe
                                35                  40 tcc tcg cag tac acg ggc gcc acc aac gcc ggc ttc atc cgc ggc ggc      300
Ser Ser Gln Tyr Thr Gly Ala Thr Asn Ala Gly Phe Ile Arg Gly Gly
                45                  50                  55 tac cac ttc gcc cac ccg ggc gcg tcg tcc ggc acc acc cag gcc gac      348
Tyr His Phe Ala His Pro Gly Ala Ser Ser Gly Thr Thr Gln Ala Asp
        60                  65                  70 tac ttc atc gcg cac ggc ggc ggc tgg act cct gac ggc atc acg ctg      396
Tyr Phe Ile Ala His Gly Gly Gly Trp Thr Pro Asp Gly Ile Thr Leu
75                  80                  85                  90 ccg ggc atg ctg gac ctc gag tcc gag tcg agt ggc acg tgc tgg ggc      444
Pro Gly Met Leu Asp Leu Glu Ser Glu Ser Ser Gly Thr Cys Trp Gly
                95                  100                 105 ctg tcg gcg agc gcc atg gtg gcc tgg atc aag gac ttc agc gac cac      492
Leu Ser Ala Ser Ala Met Val Ala Trp Ile Lys Asp Phe Ser Asp His
                110                 115                 120 tac cac tcg cgg atg ggc gtc tac ccg ctg ctg tac acg aac ccg tcg      540
Tyr His Ser Arg Met Gly Val Tyr Pro Leu Leu Tyr Thr Asn Pro Ser
                125                 130                 135 tgg tgg gag gag tgc acg ggc aac tcc aac gcc ttc gtc gac acc aac      588
Trp Trp Glu Glu Cys Thr Gly Asn Ser Asn Ala Phe Val Asp Thr Asn
140                 145                 150 ccg ctc gtg ctg gcg cac tac agc agc agc gtc ggg acg atc ccc ggc      636
Pro Leu Val Leu Ala His Tyr Ser Ser Ser Val Gly Thr Ile Pro Gly
155                 160                 165                 170 ggg tgg ccg tat gag acg atc tgg cag aac tcg gac tcg tat gcg tac      684
Gly Trp Pro Tyr Glu Thr Ile Trp Gln Asn Ser Asp Ser Tyr Ala Tyr
                175                 180                 185 ggc ggt gac tcg gat gtg ttt aat ggg gat ctg gct ggg ctg cag aga      732
Gly Gly Asp Ser Asp Val Phe Asn Gly Asp Leu Ala Gly Leu Gln Arg
                190                 195                 200 ctt gcg agg ggt taa                                                  747
Leu Ala Arg Gly
        205
```

<210> SEQ ID NO 38
<211> LENGTH: 223
<212> TYPE: PRT
<213> ORGANISM: Chaetomium cupreum

<400> SEQUENCE: 38

```
Met Lys Ser Ala Ile Leu Ala Cys Val Gly Phe Ala Ala Ala Val Gln
        -15                 -10                 -5

Ala Thr Val Gln Gly Phe Asp Ile Ser Gly Tyr Gln Pro Asn Val Asn
-1  1                   5                   10                  15

Phe Ala Ala Ala Tyr Ala Ala Gly Ala Arg Phe Val Ile Ile Lys Ala
                    20                  25                  30
```

Thr Glu Gly Thr Ser Tyr Ile Ser Pro Ser Phe Ser Ser Gln Tyr Thr
                35                  40                  45

Gly Ala Thr Asn Ala Gly Phe Ile Arg Gly Gly Tyr His Phe Ala His
            50                  55                  60

Pro Gly Ala Ser Ser Gly Thr Thr Gln Ala Asp Tyr Phe Ile Ala His
65                  70                  75

Gly Gly Gly Trp Thr Pro Asp Gly Ile Thr Leu Pro Gly Met Leu Asp
80                  85                  90                  95

Leu Glu Ser Glu Ser Ser Gly Thr Cys Trp Gly Leu Ser Ala Ser Ala
                100                 105                 110

Met Val Ala Trp Ile Lys Asp Phe Ser Asp His Tyr His Ser Arg Met
            115                 120                 125

Gly Val Tyr Pro Leu Leu Tyr Thr Asn Pro Ser Trp Trp Glu Glu Cys
        130                 135                 140

Thr Gly Asn Ser Asn Ala Phe Val Asp Thr Asn Pro Leu Val Leu Ala
        145                 150                 155

His Tyr Ser Ser Ser Val Gly Thr Ile Pro Gly Gly Trp Pro Tyr Glu
160                 165                 170                 175

Thr Ile Trp Gln Asn Ser Asp Ser Tyr Ala Tyr Gly Gly Asp Ser Asp
                180                 185                 190

Val Phe Asn Gly Asp Leu Ala Gly Leu Gln Arg Leu Ala Arg Gly
            195                 200                 205

<210> SEQ ID NO 39
<211> LENGTH: 206
<212> TYPE: PRT
<213> ORGANISM: Chaetomium cupreum
<220> FEATURE:
<221> NAME/KEY: mat_peptide
<222> LOCATION: (1)..(206)

<400> SEQUENCE: 39

Thr Val Gln Gly Phe Asp Ile Ser Gly Tyr Gln Pro Asn Val Asn Phe
1               5                   10                  15

Ala Ala Ala Tyr Ala Ala Gly Ala Arg Phe Val Ile Ile Lys Ala Thr
            20                  25                  30

Glu Gly Thr Ser Tyr Ile Ser Pro Ser Phe Ser Ser Gln Tyr Thr Gly
        35                  40                  45

Ala Thr Asn Ala Gly Phe Ile Arg Gly Gly Tyr His Phe Ala His Pro
    50                  55                  60

Gly Ala Ser Ser Gly Thr Thr Gln Ala Asp Tyr Phe Ile Ala His Gly
65                  70                  75                  80

Gly Gly Trp Thr Pro Asp Gly Ile Thr Leu Pro Gly Met Leu Asp Leu
                85                  90                  95

Glu Ser Glu Ser Ser Gly Thr Cys Trp Gly Leu Ser Ala Ser Ala Met
            100                 105                 110

Val Ala Trp Ile Lys Asp Phe Ser Asp His Tyr His Ser Arg Met Gly
        115                 120                 125

Val Tyr Pro Leu Leu Tyr Thr Asn Pro Ser Trp Trp Glu Glu Cys Thr
    130                 135                 140

Gly Asn Ser Asn Ala Phe Val Asp Thr Asn Pro Leu Val Leu Ala His
145                 150                 155                 160

Tyr Ser Ser Ser Val Gly Thr Ile Pro Gly Gly Trp Pro Tyr Glu Thr
                165                 170                 175

Ile Trp Gln Asn Ser Asp Ser Tyr Ala Tyr Gly Gly Asp Ser Asp Val

```
                    180              185              190
Phe Asn Gly Asp Leu Ala Gly Leu Gln Arg Leu Ala Arg Gly
        195              200              205

<210> SEQ ID NO 40
<211> LENGTH: 675
<212> TYPE: DNA
<213> ORGANISM: Cordyceps cardinalis
<220> FEATURE:
<221> NAME/KEY: CDS
<222> LOCATION: (1)..(672)
<220> FEATURE:
<221> NAME/KEY: sig_peptide
<222> LOCATION: (1)..(51)
<220> FEATURE:
<221> NAME/KEY: mat_peptide
<222> LOCATION: (52)..(672)

<400> SEQUENCE: 40 atg cgc gcc ttt att cca gtc ttt ctc gcc cta gcc ggc gca gcc aac      48
Met Arg Ala Phe Ile Pro Val Phe Leu Ala Leu Ala Gly Ala Ala Asn
        -15              -10              -5 gcc ctc att cac gcc gtc gac agc tcc tcc gag gtg tcc gtc gac gtc      96
Ala Leu Ile His Ala Val Asp Ser Ser Ser Glu Val Ser Val Asp Val
-1   1               5                10                   15 tac aaa aag gcc ctc gcc gag ggc ttc aca cgc gcc atc ttc cgc ggc     144
Tyr Lys Lys Ala Leu Ala Glu Gly Phe Thr Arg Ala Ile Phe Arg Gly
              20               25               30 tac cag gag gcc tgc tcg cag ggc ggc cgc gtc gac cct acc ttc ctg     192
Tyr Gln Glu Ala Cys Ser Gln Gly Gly Arg Val Asp Pro Thr Phe Leu
          35               40               45 ccc agc tac aag aac gcc cag aag gcg ggc tac aag gac ttt gac gcc     240
Pro Ser Tyr Lys Asn Ala Gln Lys Ala Gly Tyr Lys Asp Phe Asp Ala
      50               55               60 tac ttc ttc ccg tgc acc ggc tcc ggc aac aag tgc aag ccc tac gcg     288
Tyr Phe Phe Pro Cys Thr Gly Ser Gly Asn Lys Cys Lys Pro Tyr Ala
  65               70               75 aag cag att ggc gag ctc gtc gac gcc atc gag ggc aat cag ctg gcc     336
Lys Gln Ile Gly Glu Leu Val Asp Ala Ile Glu Gly Asn Gln Leu Ala
80               85               90               95 atc cgc cgc atc tgg atc gac atc gag acg gac aag gtc tgc aac gcg     384
Ile Arg Arg Ile Trp Ile Asp Ile Glu Thr Asp Lys Val Cys Asn Ala
                 100              105              110 ttt aac tgg ggc gcc gag ggc aac atc caa gag gcc aag aag ctc atc     432
Phe Asn Trp Gly Ala Glu Gly Asn Ile Gln Glu Ala Lys Lys Leu Ile
             115              120              125 gcc gcc gtg cga ggc aca aag cgc gac ttt ggc atc tac acg tcg gcg     480
Ala Ala Val Arg Gly Thr Lys Arg Asp Phe Gly Ile Tyr Thr Ser Ala
         130              135              140 acg caa tgg gag aac atc ttt ggc tcc agg act gtg gaa ctg gcc aag     528
Thr Gln Trp Glu Asn Ile Phe Gly Ser Arg Thr Val Glu Leu Ala Lys
     145              150              155 gac gtg ccg ctg tgg ttt gcc aag ttt gac aat gtt gag acg ctg gag     576
Asp Val Pro Leu Trp Phe Ala Lys Phe Asp Asn Val Glu Thr Leu Glu
160              165              170              175 ctg aag acg cct ttt ggc ggc tgg aca aag gcc gac gcg aag cag tat     624
Leu Lys Thr Pro Phe Gly Gly Trp Thr Lys Ala Asp Ala Lys Gln Tyr
                 180              185              190 act gac aag tcg gct agc aag aaa ttt gat ctc aac gtt ttc tct gcc     672
Thr Asp Lys Ser Ala Ser Lys Lys Phe Asp Leu Asn Val Phe Ser Ala
             195              200              205 taa                                                                  675
```

<210> SEQ ID NO 41
<211> LENGTH: 224
<212> TYPE: PRT
<213> ORGANISM: Cordyceps cardinalis

<400> SEQUENCE: 41

```
Met Arg Ala Phe Ile Pro Val Phe Leu Ala Leu Ala Gly Ala Ala Asn
            -15              -10               -5
Ala Leu Ile His Ala Val Asp Ser Ser Glu Val Ser Val Asp Val
 -1  1           5                   10                  15
Tyr Lys Lys Ala Leu Ala Glu Gly Phe Thr Arg Ala Ile Phe Arg Gly
                 20                  25                  30
Tyr Gln Glu Ala Cys Ser Gln Gly Gly Arg Val Asp Pro Thr Phe Leu
             35                  40                  45
Pro Ser Tyr Lys Asn Ala Gln Lys Ala Gly Tyr Lys Asp Phe Asp Ala
         50                  55                  60
Tyr Phe Phe Pro Cys Thr Gly Ser Gly Asn Lys Cys Lys Pro Tyr Ala
 65                  70                  75
Lys Gln Ile Gly Glu Leu Val Asp Ala Ile Glu Gly Asn Gln Leu Ala
 80                  85                  90                  95
Ile Arg Arg Ile Trp Ile Asp Ile Glu Thr Asp Lys Val Cys Asn Ala
                100                 105                 110
Phe Asn Trp Gly Ala Glu Gly Asn Ile Gln Glu Ala Lys Lys Leu Ile
                115                 120                 125
Ala Ala Val Arg Gly Thr Lys Arg Asp Phe Gly Ile Tyr Thr Ser Ala
            130                 135                 140
Thr Gln Trp Glu Asn Ile Phe Gly Ser Arg Thr Val Glu Leu Ala Lys
        145                 150                 155
Asp Val Pro Leu Trp Phe Ala Lys Phe Asp Asn Val Glu Thr Leu Glu
160                 165                 170                 175
Leu Lys Thr Pro Phe Gly Gly Trp Thr Lys Ala Asp Ala Lys Gln Tyr
                180                 185                 190
Thr Asp Lys Ser Ala Ser Lys Lys Phe Asp Leu Asn Val Phe Ser Ala
            195                 200                 205
```

<210> SEQ ID NO 42
<211> LENGTH: 207
<212> TYPE: PRT
<213> ORGANISM: Cordyceps cardinalis
<220> FEATURE:
<221> NAME/KEY: mat_peptide
<222> LOCATION: (1)..(207)

<400> SEQUENCE: 42

```
Leu Ile His Ala Val Asp Ser Ser Glu Val Ser Val Asp Val Tyr
 1               5                  10                  15
Lys Lys Ala Leu Ala Glu Gly Phe Thr Arg Ala Ile Phe Arg Gly Tyr
             20                  25                  30
Gln Glu Ala Cys Ser Gln Gly Gly Arg Val Asp Pro Thr Phe Leu Pro
         35                  40                  45
Ser Tyr Lys Asn Ala Gln Lys Ala Gly Tyr Lys Asp Phe Asp Ala Tyr
     50                  55                  60
Phe Phe Pro Cys Thr Gly Ser Gly Asn Lys Cys Lys Pro Tyr Ala Lys
 65                  70                  75                  80
Gln Ile Gly Glu Leu Val Asp Ala Ile Glu Gly Asn Gln Leu Ala Ile
                 85                  90                  95
```

```
Arg Arg Ile Trp Ile Asp Ile Glu Thr Asp Lys Val Cys Asn Ala Phe
            100                 105                 110

Asn Trp Gly Ala Glu Gly Asn Ile Gln Glu Ala Lys Lys Leu Ile Ala
            115                 120                 125

Ala Val Arg Gly Thr Lys Arg Asp Phe Gly Ile Tyr Thr Ser Ala Thr
            130                 135                 140

Gln Trp Glu Asn Ile Phe Gly Ser Arg Thr Val Glu Leu Ala Lys Asp
145                 150                 155                 160

Val Pro Leu Trp Phe Ala Lys Phe Asp Asn Val Glu Thr Leu Glu Leu
                165                 170                 175

Lys Thr Pro Phe Gly Gly Trp Thr Lys Ala Asp Ala Lys Gln Tyr Thr
                180                 185                 190

Asp Lys Ser Ala Ser Lys Lys Phe Asp Leu Asn Val Phe Ser Ala
            195                 200                 205

<210> SEQ ID NO 43
<211> LENGTH: 761
<212> TYPE: DNA
<213> ORGANISM: Penicillium sp. 'qii'
<220> FEATURE:
<221> NAME/KEY: CDS
<222> LOCATION: (1)..(165)
<220> FEATURE:
<221> NAME/KEY: sig_peptide
<222> LOCATION: (1)..(51)
<220> FEATURE:
<221> NAME/KEY: mat_peptide
<222> LOCATION: (52)..(758)
<220> FEATURE:
<221> NAME/KEY: CDS
<222> LOCATION: (225)..(758)

<400> SEQUENCE: 43 atg aag act acg ggt gtc tct ctt ctg ctt gca gca ggt act gcc tac        48
Met Lys Thr Thr Gly Val Ser Leu Leu Leu Ala Ala Gly Thr Ala Tyr
        -15                 -10                  -5 gca tcg aca atc cag cct cgg gca agc ggc gtc cag gga ttc gat atc       96
Ala Ser Thr Ile Gln Pro Arg Ala Ser Gly Val Gln Gly Phe Asp Ile
 -1   1               5                  10                  15 tca agc tac caa ggc acc gtc aac ttt gcc ggc gcc tac gga gcc ggt      144
Ser Ser Tyr Gln Gly Thr Val Asn Phe Ala Gly Ala Tyr Gly Ala Gly
                 20                  25                  30 gca cga ttc gtc atg atc aag gtgagcctcg gcataaactt gtgaccggcg         195
Ala Arg Phe Val Met Ile Lys
                 35 agttgtttgg actaactgaa acgcgctag gcg act gaa ggc acc acc tac ata      248
                                Ala Thr Glu Gly Thr Thr Tyr Ile
                                     40                  45 gat tcc acc ttc tcc agc cac tat gac ggt gct acc agc gcc ggc ttg      296
Asp Ser Thr Phe Ser Ser His Tyr Asp Gly Ala Thr Ser Ala Gly Leu
         50                  55                  60 atc cgc ggg gct tac cac ttc gcc cac ccg gac tcc agc tct ggc gct      344
Ile Arg Gly Ala Tyr His Phe Ala His Pro Asp Ser Ser Ser Gly Ala
             65                  70                  75 acc cag gcc gag tac ttc ctg gct cac gga ggt ggc tgg acc aac gat      392
Thr Gln Ala Glu Tyr Phe Leu Ala His Gly Gly Gly Trp Thr Asn Asp
 80                  85                  90 ggc atc acc ttg ccc ggc atg ctg gac atc gaa tac aac ccc tcg ggc      440
Gly Ile Thr Leu Pro Gly Met Leu Asp Ile Glu Tyr Asn Pro Ser Gly
 95                 100                 105                 110 tct acc tgc tac ggt ctg agt gct tcc gcc atg gtc tcc tgg atc aag      488
Ser Thr Cys Tyr Gly Leu Ser Ala Ser Ala Met Val Ser Trp Ile Lys
```

```
Ser Thr Cys Tyr Gly Leu Ser Ala Ser Ala Met Val Ser Trp Ile Lys
            115                 120                 125 gac ttc gga gag acc tac aac agc aag act ggt cgg tac cct atg atc      536
Asp Phe Gly Glu Thr Tyr Asn Ser Lys Thr Gly Arg Tyr Pro Met Ile
            130                 135                 140 tac agc acg gcc gat tgg tgg agc acc tgc aca gga gac agc aca tcc      584
Tyr Ser Thr Ala Asp Trp Trp Ser Thr Cys Thr Gly Asp Ser Thr Ser
            145                 150                 155 ttc agt agt gac tac cct ctg gtg ctt gct cag tat gct agc tcc att      632
Phe Ser Ser Asp Tyr Pro Leu Val Leu Ala Gln Tyr Ala Ser Ser Ile
        160                 165                 170 agc acc gtc ccc gga ggc tgg cct tac cag agc ttc tgg cag aac gcg      680
Ser Thr Val Pro Gly Gly Trp Pro Tyr Gln Ser Phe Trp Gln Asn Ala
175                 180                 185                 190 gac tca tac agc tat ggc ggt gat tct gat ctg tgg aat ggt agc gag      728
Asp Ser Tyr Ser Tyr Gly Gly Asp Ser Asp Leu Trp Asn Gly Ser Glu
                195                 200                 205 gac tct ctg aag acc ttt gcc aag ggt tct taa                          761
Asp Ser Leu Lys Thr Phe Ala Lys Gly Ser
            210                 215

<210> SEQ ID NO 44
<211> LENGTH: 233
<212> TYPE: PRT
<213> ORGANISM: Penicillium sp. 'qii'

<400> SEQUENCE: 44

Met Lys Thr Thr Gly Val Ser Leu Leu Ala Ala Gly Thr Ala Tyr
        -15                 -10                  -5

Ala Ser Thr Ile Gln Pro Arg Ala Ser Gly Val Gln Gly Phe Asp Ile
-1   1               5                  10                  15

Ser Ser Tyr Gln Gly Thr Val Asn Phe Ala Gly Ala Tyr Gly Ala Gly
                 20                  25                  30

Ala Arg Phe Val Met Ile Lys Ala Thr Glu Gly Thr Thr Tyr Ile Asp
             35                  40                  45

Ser Thr Phe Ser Ser His Tyr Asp Gly Ala Thr Ser Ala Gly Leu Ile
         50                  55                  60

Arg Gly Ala Tyr His Phe Ala His Pro Asp Ser Ser Ser Gly Ala Thr
 65                  70                  75

Gln Ala Glu Tyr Phe Leu Ala His Gly Gly Gly Trp Thr Asn Asp Gly
 80                  85                  90                  95

Ile Thr Leu Pro Gly Met Leu Asp Ile Glu Tyr Asn Pro Ser Gly Ser
                100                 105                 110

Thr Cys Tyr Gly Leu Ser Ala Ser Ala Met Val Ser Trp Ile Lys Asp
            115                 120                 125

Phe Gly Glu Thr Tyr Asn Ser Lys Thr Gly Arg Tyr Pro Met Ile Tyr
            130                 135                 140

Ser Thr Ala Asp Trp Trp Ser Thr Cys Thr Gly Asp Ser Thr Ser Phe
            145                 150                 155

Ser Ser Asp Tyr Pro Leu Val Leu Ala Gln Tyr Ala Ser Ser Ile Ser
160                 165                 170                 175

Thr Val Pro Gly Gly Trp Pro Tyr Gln Ser Phe Trp Gln Asn Ala Asp
                180                 185                 190

Ser Tyr Ser Tyr Gly Gly Asp Ser Asp Leu Trp Asn Gly Ser Glu Asp
            195                 200                 205

Ser Leu Lys Thr Phe Ala Lys Gly Ser
            210                 215
```

<210> SEQ ID NO 45
<211> LENGTH: 216
<212> TYPE: PRT
<213> ORGANISM: Penicillium sp. 'qii'
<220> FEATURE:
<221> NAME/KEY: mat_peptide
<222> LOCATION: (1)..(216)

<400> SEQUENCE: 45

Ser Thr Ile Gln Pro Arg Ala Ser Gly Val Gln Gly Phe Asp Ile Ser
1               5                   10                  15

Ser Tyr Gln Gly Thr Val Asn Phe Ala Gly Ala Tyr Gly Ala Gly Ala
            20                  25                  30

Arg Phe Val Met Ile Lys Ala Thr Glu Gly Thr Thr Tyr Ile Asp Ser
        35                  40                  45

Thr Phe Ser Ser His Tyr Asp Gly Ala Thr Ser Ala Gly Leu Ile Arg
    50                  55                  60

Gly Ala Tyr His Phe Ala His Pro Asp Ser Ser Gly Ala Thr Gln
65                  70                  75                  80

Ala Glu Tyr Phe Leu Ala His Gly Gly Gly Trp Thr Asn Asp Gly Ile
                85                  90                  95

Thr Leu Pro Gly Met Leu Asp Ile Glu Tyr Asn Pro Ser Gly Ser Thr
            100                 105                 110

Cys Tyr Gly Leu Ser Ala Ser Ala Met Val Ser Trp Ile Lys Asp Phe
        115                 120                 125

Gly Glu Thr Tyr Asn Ser Lys Thr Gly Arg Tyr Pro Met Ile Tyr Ser
130                 135                 140

Thr Ala Asp Trp Trp Ser Thr Cys Thr Gly Asp Ser Thr Ser Phe Ser
145                 150                 155                 160

Ser Asp Tyr Pro Leu Val Leu Ala Gln Tyr Ala Ser Ser Ile Ser Thr
                165                 170                 175

Val Pro Gly Gly Trp Pro Tyr Gln Ser Phe Trp Gln Asn Ala Asp Ser
            180                 185                 190

Tyr Ser Tyr Gly Gly Asp Ser Asp Leu Trp Asn Gly Ser Glu Asp Ser
        195                 200                 205

Leu Lys Thr Phe Ala Lys Gly Ser
    210                 215

<210> SEQ ID NO 46
<211> LENGTH: 781
<212> TYPE: DNA
<213> ORGANISM: Aspergillus sp. nov. XZ2609
<220> FEATURE:
<221> NAME/KEY: CDS
<222> LOCATION: (1)..(174)
<220> FEATURE:
<221> NAME/KEY: sig_peptide
<222> LOCATION: (1)..(54)
<220> FEATURE:
<221> NAME/KEY: mat_peptide
<222> LOCATION: (55)..(778)
<220> FEATURE:
<221> NAME/KEY: CDS
<222> LOCATION: (245)..(778)

<400> SEQUENCE: 46 atg aag ttc act acc att gcc act acc gcg gcc atc tct ggc ctt gcc      48
Met Lys Phe Thr Thr Ile Ala Thr Thr Ala Ala Ile Ser Gly Leu Ala
        -15                 -10                 -5 aca gcc ttg cct acc aaa ctg gct gct cga tat agc act gtg caa gga      96

```
Thr Ala Leu Pro Thr Lys Leu Ala Ala Arg Tyr Ser Thr Val Gln Gly
 -1   1               5                      10 ttt gat gtg tcc aat tac caa ccg aac gtg gac ttc tct gcc gca aag      144
Phe Asp Val Ser Asn Tyr Gln Pro Asn Val Asp Phe Ser Ala Ala Lys
 15              20                  25                  30 agt gct ggt gcc gaa ttt gtc att atc aag gtacatccag ctttatccct        194
Ser Ala Gly Ala Glu Phe Val Ile Ile Lys
                 35                  40 tttctaccca gtaacatggt acagataagt taacaagtca ttcataacag gcc acc       250
                                                      Ala Thr gaa gga acc gat tac aaa gac acc tat ttc aac tcc cac tac acc ggc      298
Glu Gly Thr Asp Tyr Lys Asp Thr Tyr Phe Asn Ser His Tyr Thr Gly
             45                  50                  55 gcc acc aac gct ggc ctc atc cgc ggt ggc tat cat ttc gcg cgc cct      346
Ala Thr Asn Ala Gly Leu Ile Arg Gly Gly Tyr His Phe Ala Arg Pro
 60                  65                  70 gat aaa tct tcc ggt acc gcg caa gcc gag tat ttc ctc gcg cac ggt      394
Asp Lys Ser Ser Gly Thr Ala Gln Ala Glu Tyr Phe Leu Ala His Gly
 75                  80                  85                  90 ggc ggc tgg agc aaa gat ggc aga acc ctc cct ggc atg cta gac atc      442
Gly Gly Trp Ser Lys Asp Gly Arg Thr Leu Pro Gly Met Leu Asp Ile
                 95                 100                 105 gag tat aac ccg tac ggc gcc acc tgc tac ggt ctc agt cac tcc gcg      490
Glu Tyr Asn Pro Tyr Gly Ala Thr Cys Tyr Gly Leu Ser His Ser Ala
            110                 115                 120 atg gtc tca tgg gtc aac gaa ttc ctc aac gaa tat cac agc aag acg      538
Met Val Ser Trp Val Asn Glu Phe Leu Asn Glu Tyr His Ser Lys Thr
            125                 130                 135 ggt gtt tat ccg ttg ctc tat acc acg gca gat tgg tgg aat cag tgc      586
Gly Val Tyr Pro Leu Leu Tyr Thr Thr Ala Asp Trp Trp Asn Gln Cys
140                 145                 150 aca ggg aat gct cat gga ttt ggt aac aag agc cct ctt gtt ctg gct      634
Thr Gly Asn Ala His Gly Phe Gly Asn Lys Ser Pro Leu Val Leu Ala
155                 160                 165                 170 tca tat agc agt gag tca cct cgg act gtg cct gga gat tgg cag acg      682
Ser Tyr Ser Ser Glu Ser Pro Arg Thr Val Pro Gly Asp Trp Gln Thr
                175                 180                 185 tgg act atc tgg cag aac gcg gat aag tat aag tat ggg ggt gat tcc      730
Trp Thr Ile Trp Gln Asn Ala Asp Lys Tyr Lys Tyr Gly Gly Asp Ser
            190                 195                 200 gat att ttc aat ggc gat ctc acg cag ttg aag aag att gtc gag ggg      778
Asp Ile Phe Asn Gly Asp Leu Thr Gln Leu Lys Lys Ile Val Glu Gly
            205                 210                 215 tag                                                                   781

<210> SEQ ID NO 47
<211> LENGTH: 236
<212> TYPE: PRT
<213> ORGANISM: Aspergillus sp. nov. XZ2609

<400> SEQUENCE: 47

Met Lys Phe Thr Thr Ile Ala Thr Thr Ala Ala Ile Ser Gly Leu Ala
            -15                 -10                  -5

Thr Ala Leu Pro Thr Lys Leu Ala Ala Arg Tyr Ser Thr Val Gln Gly
 -1   1               5                      10

Phe Asp Val Ser Asn Tyr Gln Pro Asn Val Asp Phe Ser Ala Ala Lys
 15              20                  25                  30

Ser Ala Gly Ala Glu Phe Val Ile Ile Lys Ala Thr Glu Gly Thr Asp
                 35                  40                  45
```

```
Tyr Lys Asp Thr Tyr Phe Asn Ser His Tyr Thr Gly Ala Thr Asn Ala
             50                  55                  60

Gly Leu Ile Arg Gly Gly Tyr His Phe Ala Arg Pro Asp Lys Ser Ser
         65                  70                  75

Gly Thr Ala Gln Ala Glu Tyr Phe Leu Ala His Gly Gly Trp Ser
     80                  85                  90

Lys Asp Gly Arg Thr Leu Pro Gly Met Leu Asp Ile Glu Tyr Asn Pro
 95                 100                 105                 110

Tyr Gly Ala Thr Cys Tyr Gly Leu Ser His Ser Ala Met Val Ser Trp
                115                 120                 125

Val Asn Glu Phe Leu Asn Glu Tyr His Ser Lys Thr Gly Val Tyr Pro
            130                 135                 140

Leu Leu Tyr Thr Thr Ala Asp Trp Trp Asn Gln Cys Thr Gly Asn Ala
            145                 150                 155

His Gly Phe Gly Asn Lys Ser Pro Leu Val Leu Ala Ser Tyr Ser Ser
            160                 165                 170

Glu Ser Pro Arg Thr Val Pro Gly Asp Trp Gln Thr Trp Thr Ile Trp
175                 180                 185                 190

Gln Asn Ala Asp Lys Tyr Lys Tyr Gly Gly Asp Ser Asp Ile Phe Asn
                195                 200                 205

Gly Asp Leu Thr Gln Leu Lys Lys Ile Val Glu Gly
            210                 215

<210> SEQ ID NO 48
<211> LENGTH: 218
<212> TYPE: PRT
<213> ORGANISM: Aspergillus sp. nov. XZ2609
<220> FEATURE:
<221> NAME/KEY: mat_peptide
<222> LOCATION: (1)..(218)

<400> SEQUENCE: 48

Leu Pro Thr Lys Leu Ala Ala Arg Tyr Ser Thr Val Gln Gly Phe Asp
 1               5                  10                  15

Val Ser Asn Tyr Gln Pro Asn Val Asp Phe Ser Ala Ala Lys Ser Ala
            20                  25                  30

Gly Ala Glu Phe Val Ile Ile Lys Ala Thr Glu Gly Thr Asp Tyr Lys
        35                  40                  45

Asp Thr Tyr Phe Asn Ser His Tyr Thr Gly Ala Thr Asn Ala Gly Leu
     50                 55                  60

Ile Arg Gly Gly Tyr His Phe Ala Arg Pro Asp Lys Ser Ser Gly Thr
 65                 70                  75                  80

Ala Gln Ala Glu Tyr Phe Leu Ala His Gly Gly Trp Ser Lys Asp
                85                  90                  95

Gly Arg Thr Leu Pro Gly Met Leu Asp Ile Glu Tyr Asn Pro Tyr Gly
            100                 105                 110

Ala Thr Cys Tyr Gly Leu Ser His Ser Ala Met Val Ser Trp Val Asn
        115                 120                 125

Glu Phe Leu Asn Glu Tyr His Ser Lys Thr Gly Val Tyr Pro Leu Leu
    130                 135                 140

Tyr Thr Thr Ala Asp Trp Trp Asn Gln Cys Thr Gly Asn Ala His Gly
145                 150                 155                 160

Phe Gly Asn Lys Ser Pro Leu Val Leu Ala Ser Tyr Ser Ser Glu Ser
                165                 170                 175

Pro Arg Thr Val Pro Gly Asp Trp Gln Thr Trp Thr Ile Trp Gln Asn
```

```
                180                 185                 190
Ala Asp Lys Tyr Lys Tyr Gly Gly Asp Ser Asp Ile Phe Asn Gly Asp
        195                 200                 205

Leu Thr Gln Leu Lys Lys Ile Val Glu Gly
        210                 215

<210> SEQ ID NO 49
<211> LENGTH: 747
<212> TYPE: DNA
<213> ORGANISM: Paecilomyces sp. XZ2658
<220> FEATURE:
<221> NAME/KEY: CDS
<222> LOCATION: (1)..(135)
<220> FEATURE:
<221> NAME/KEY: sig_peptide
<222> LOCATION: (1)..(57)
<220> FEATURE:
<221> NAME/KEY: mat_peptide
<222> LOCATION: (58)..(744)
<220> FEATURE:
<221> NAME/KEY: CDS
<222> LOCATION: (211)..(744)

<400> SEQUENCE: 49 atg aag tct gtt gct gtc ttt gcc ggt ctg gcc tcc atg gtc agc att      48
Met Lys Ser Val Ala Val Phe Ala Gly Leu Ala Ser Met Val Ser Ile
            -15                 -10                  -5 gcc aca gcc acc gtt gca ggc ttc gat att tcc aac tac caa cct tcg     96
Ala Thr Ala Thr Val Ala Gly Phe Asp Ile Ser Asn Tyr Gln Pro Ser
        -1   1               5                  10 gtc aac ttt gca aaa gca tac gcg gac ggt gca cgc ttc gtcattatca     145
Val Asn Phe Ala Lys Ala Tyr Ala Asp Gly Ala Arg Phe
        15                  20                  25 aggcaagcag gccagaccag cgcctgccag ctcaaacaag accagattgc taactctctt   205 ctcag gcc acc gaa ggc acc acc tac atc gac ccc agt ttc agc tcc cat  255
      Ala Thr Glu Gly Thr Thr Tyr Ile Asp Pro Ser Phe Ser Ser His
              30                  35                  40 tac acc ggg gcc act aac gcc ggt ctc atc cgc gga ggc tac cat ttt    303
Tyr Thr Gly Ala Thr Asn Ala Gly Leu Ile Arg Gly Gly Tyr His Phe
            45                  50                  55 gcc cat ccg gga tcc agc acc ggc gcc gct cag gcc acc tac ttc ctt    351
Ala His Pro Gly Ser Ser Thr Gly Ala Ala Gln Ala Thr Tyr Phe Leu
        60                  65                  70 gcc cac ggc ggc ggc tgg tcc aag gac ggc atc acg ctc cct ggc atg    399
Ala His Gly Gly Gly Trp Ser Lys Asp Gly Ile Thr Leu Pro Gly Met
    75                  80                  85 atc gac ctc gag tac aac ccc agt ggc gcg acc tgc tat ggc ctc tcg    447
Ile Asp Leu Glu Tyr Asn Pro Ser Gly Ala Thr Cys Tyr Gly Leu Ser
90                  95                 100                 105 acc agc gcc atg gtc agc tgg atc tcc gac ttt gtc gag acg tac cac    495
Thr Ser Ala Met Val Ser Trp Ile Ser Asp Phe Val Glu Thr Tyr His
                110                 115                 120 agc aag acg ggc gtc tac ccg ctc att tat acc tcg aca agc tgg tgg    543
Ser Lys Thr Gly Val Tyr Pro Leu Ile Tyr Thr Ser Thr Ser Trp Trp
            125                 130                 135 aac cag tgt acc ggc agc agc acc gcc ttt gcc agc aag tgt cct ctt    591
Asn Gln Cys Thr Gly Ser Ser Thr Ala Phe Ala Ser Lys Cys Pro Leu
        140                 145                 150 gtg gtt gct cgc tac gcc agc agc gtt ggc act ctt cct gcc ggt tgg    639
Val Val Ala Arg Tyr Ala Ser Ser Val Gly Thr Leu Pro Ala Gly Trp
    155                 160                 165 ggc tac cag acc atc tgg cag aat agc gat agc tcg ccc tgg ggc ggt    687
```

-continued

```
Gly Tyr Gln Thr Ile Trp Gln Asn Ser Asp Ser Ser Pro Trp Gly Gly
170                 175                 180                 185 gac aat gat att ttc aac ggc agt ctg gac cag ctc aag cgc att gcg    735
Asp Asn Asp Ile Phe Asn Gly Ser Leu Asp Gln Leu Lys Arg Ile Ala
                190                 195                 200 aat gct tct tag                                                    747
Asn Ala Ser <210> SEQ ID NO 50
<211> LENGTH: 223
<212> TYPE: PRT
<213> ORGANISM: Paecilomyces sp. XZ2658

<400> SEQUENCE: 50

Met Lys Ser Val Ala Val Phe Ala Gly Leu Ala Ser Met Val Ser Ile
                -15                 -10                  -5

Ala Thr Ala Thr Val Ala Gly Phe Asp Ile Ser Asn Tyr Gln Pro Ser
         -1  1                  5                  10

Val Asn Phe Ala Lys Ala Tyr Ala Asp Gly Ala Arg Phe Ala Thr Glu
 15                  20                 25

Gly Thr Thr Tyr Ile Asp Pro Ser Phe Ser Ser His Tyr Thr Gly Ala
 30                 35                  40                  45

Thr Asn Ala Gly Leu Ile Arg Gly Gly Tyr His Phe Ala His Pro Gly
                 50                  55                  60

Ser Ser Thr Gly Ala Ala Gln Ala Thr Tyr Phe Leu Ala His Gly Gly
                 65                  70                  75

Gly Trp Ser Lys Asp Gly Ile Thr Leu Pro Gly Met Ile Asp Leu Glu
                 80                  85                  90

Tyr Asn Pro Ser Gly Ala Thr Cys Tyr Gly Leu Ser Thr Ser Ala Met
 95                 100                 105

Val Ser Trp Ile Ser Asp Phe Val Glu Thr Tyr His Ser Lys Thr Gly
110                 115                 120                 125

Val Tyr Pro Leu Ile Tyr Thr Ser Thr Ser Trp Trp Asn Gln Cys Thr
                130                 135                 140

Gly Ser Ser Thr Ala Phe Ala Ser Lys Cys Pro Leu Val Val Ala Arg
                145                 150                 155

Tyr Ala Ser Ser Val Gly Thr Leu Pro Ala Gly Trp Gly Tyr Gln Thr
                160                 165                 170

Ile Trp Gln Asn Ser Asp Ser Ser Pro Trp Gly Gly Asp Asn Asp Ile
                175                 180                 185

Phe Asn Gly Ser Leu Asp Gln Leu Lys Arg Ile Ala Asn Ala Ser
190                 195                 200

<210> SEQ ID NO 51
<211> LENGTH: 204
<212> TYPE: PRT
<213> ORGANISM: Paecilomyces sp. XZ2658
<220> FEATURE:
<221> NAME/KEY: mat_peptide
<222> LOCATION: (1)..(204)

<400> SEQUENCE: 51

Thr Val Ala Gly Phe Asp Ile Ser Asn Tyr Gln Pro Ser Val Asn Phe
  1               5                  10                  15

Ala Lys Ala Tyr Ala Asp Gly Ala Arg Phe Ala Thr Glu Gly Thr Thr
                 20                  25                  30

Tyr Ile Asp Pro Ser Phe Ser Ser His Tyr Thr Gly Ala Thr Asn Ala
                 35                  40                  45
```

```
Gly Leu Ile Arg Gly Gly Tyr His Phe Ala His Pro Gly Ser Ser Thr
 50                  55                  60
Gly Ala Ala Gln Ala Thr Tyr Phe Leu Ala His Gly Gly Gly Trp Ser
 65                  70                  75                  80
Lys Asp Gly Ile Thr Leu Pro Gly Met Ile Asp Leu Glu Tyr Asn Pro
                 85                  90                  95
Ser Gly Ala Thr Cys Tyr Gly Leu Ser Thr Ser Ala Met Val Ser Trp
                100                 105                 110
Ile Ser Asp Phe Val Glu Thr Tyr His Ser Lys Thr Gly Val Tyr Pro
            115                 120                 125
Leu Ile Tyr Thr Ser Thr Ser Trp Trp Asn Gln Cys Thr Gly Ser Ser
130                 135                 140
Thr Ala Phe Ala Ser Lys Cys Pro Leu Val Val Ala Arg Tyr Ala Ser
145                 150                 155                 160
Ser Val Gly Thr Leu Pro Ala Gly Trp Gly Tyr Gln Thr Ile Trp Gln
                165                 170                 175
Asn Ser Asp Ser Ser Pro Trp Gly Gly Asp Asn Asp Ile Phe Asn Gly
            180                 185                 190
Ser Leu Asp Gln Leu Lys Arg Ile Ala Asn Ala Ser
            195                 200

<210> SEQ ID NO 52
<211> LENGTH: 669
<212> TYPE: DNA
<213> ORGANISM: Paecilomyces sp. XZ2658
<220> FEATURE:
<221> NAME/KEY: CDS
<222> LOCATION: (1)..(666)
<220> FEATURE:
<221> NAME/KEY: sig_peptide
<222> LOCATION: (1)..(57)
<220> FEATURE:
<221> NAME/KEY: mat_peptide
<222> LOCATION: (58)..(666)

<400> SEQUENCE: 52 atg aag ctc acg agt gtg ttg acc ctg gtt ggc tgt gcc gtc aca ggc      48
Met Lys Leu Thr Ser Val Leu Thr Leu Val Gly Cys Ala Val Thr Gly
             -15                 -10                  -5 aca tct gcc gcc gtg caa gga cac gac gtc agc cat tgg cag ggt aac      96
Thr Ser Ala Ala Val Gln Gly His Asp Val Ser His Trp Gln Gly Asn
         -1  1                   5                  10 atc aac tgg ggc gcg gtc aag gca gcc ggc gtc aag ttt aca tac att     144
Ile Asn Trp Gly Ala Val Lys Ala Ala Gly Val Lys Phe Thr Tyr Ile
 15                  20                  25 aaa gca aca gag tca acc aac tac atc gac ccc agc ttc aac gca aat     192
Lys Ala Thr Glu Ser Thr Asn Tyr Ile Asp Pro Ser Phe Asn Ala Asn
 30                  35                  40                  45 tat gtc ggc gcc acc aat acc gga ctg ata cgc ggc gca tac cac ttt     240
Tyr Val Gly Ala Thr Asn Thr Gly Leu Ile Arg Gly Ala Tyr His Phe
                 50                  55                  60 gcc cgg cca ggg gat tca tca ggt gcc gcg cag gca aat tat ttt gtc     288
Ala Arg Pro Gly Asp Ser Ser Gly Ala Ala Gln Ala Asn Tyr Phe Val
             65                  70                  75 agc cat ggt ggt ggg tgg tcc gca gac ggg aga act ttg cct ggc gct     336
Ser His Gly Gly Gly Trp Ser Ala Asp Gly Arg Thr Leu Pro Gly Ala
         80                  85                  90 ctt gat ctt gag gcg ggc tgt agc gga ttg tcg caa tca gca atg acg     384
Leu Asp Leu Glu Ala Gly Cys Ser Gly Leu Ser Gln Ser Ala Met Thr
 95                 100                 105
```

```
gcc tgg atc cgg gac ttc agc aac acc tat cac gcg cgg act ggt cgg      432
Ala Trp Ile Arg Asp Phe Ser Asn Thr Tyr His Ala Arg Thr Gly Arg
110             115                 120                 125 ttc ccc gtc att tac aca act acc agc tgg tgg aag act tgc acc ggc      480
Phe Pro Val Ile Tyr Thr Thr Thr Ser Trp Trp Lys Thr Cys Thr Gly
                130                 135                 140 aat gcg tcc gga ttt cag aac gac cat ccg ctt tgg att gcg cga tgg      528
Asn Ala Ser Gly Phe Gln Asn Asp His Pro Leu Trp Ile Ala Arg Trp
            145                 150                 155 ggc cct tca cct ggg gag ttg ccg gca gga tat ggc ttt cac acc ttt      576
Gly Pro Ser Pro Gly Glu Leu Pro Ala Gly Tyr Gly Phe His Thr Phe
        160                 165                 170 tgg cag tat gcg gac aag gga cct ctt cca ggc gac cag gac aac ttt      624
Trp Gln Tyr Ala Asp Lys Gly Pro Leu Pro Gly Asp Gln Asp Asn Phe
    175                 180                 185 aat ggc gat gag gcc ggt ctt gca agg ctt gct aga ggt tcg taa          669
Asn Gly Asp Glu Ala Gly Leu Ala Arg Leu Ala Arg Gly Ser
190                 195                 200

<210> SEQ ID NO 53
<211> LENGTH: 222
<212> TYPE: PRT
<213> ORGANISM: Paecilomyces sp. XZ2658

<400> SEQUENCE: 53

Met Lys Leu Thr Ser Val Leu Thr Leu Val Gly Cys Ala Val Thr Gly
                -15                 -10                  -5

Thr Ser Ala Ala Val Gln Gly His Asp Val Ser His Trp Gln Gly Asn
        -1  1                  5                  10

Ile Asn Trp Gly Ala Val Lys Ala Ala Gly Val Lys Phe Thr Tyr Ile
 15                  20                  25

Lys Ala Thr Glu Ser Thr Asn Tyr Ile Asp Pro Ser Phe Asn Ala Asn
 30                  35                  40                  45

Tyr Val Gly Ala Thr Asn Thr Gly Leu Ile Arg Gly Ala Tyr His Phe
                 50                  55                  60

Ala Arg Pro Gly Asp Ser Ser Gly Ala Ala Gln Ala Asn Tyr Phe Val
             65                  70                  75

Ser His Gly Gly Gly Trp Ser Ala Asp Gly Arg Thr Leu Pro Gly Ala
         80                  85                  90

Leu Asp Leu Glu Ala Gly Cys Ser Gly Leu Ser Gln Ser Ala Met Thr
     95                 100                 105

Ala Trp Ile Arg Asp Phe Ser Asn Thr Tyr His Ala Arg Thr Gly Arg
110                 115                 120                 125

Phe Pro Val Ile Tyr Thr Thr Thr Ser Trp Trp Lys Thr Cys Thr Gly
                130                 135                 140

Asn Ala Ser Gly Phe Gln Asn Asp His Pro Leu Trp Ile Ala Arg Trp
            145                 150                 155

Gly Pro Ser Pro Gly Glu Leu Pro Ala Gly Tyr Gly Phe His Thr Phe
        160                 165                 170

Trp Gln Tyr Ala Asp Lys Gly Pro Leu Pro Gly Asp Gln Asp Asn Phe
    175                 180                 185

Asn Gly Asp Glu Ala Gly Leu Ala Arg Leu Ala Arg Gly Ser
190                 195                 200

<210> SEQ ID NO 54
<211> LENGTH: 203
<212> TYPE: PRT
```

<213> ORGANISM: Paecilomyces sp. XZ2658
<220> FEATURE:
<221> NAME/KEY: mat_peptide
<222> LOCATION: (1)..(203)

<400> SEQUENCE: 54

Ala Val Gln Gly His Asp Val Ser His Trp Gln Gly Asn Ile Asn Trp
1               5                   10                  15
Gly Ala Val Lys Ala Ala Gly Val Lys Phe Thr Tyr Ile Lys Ala Thr
            20                  25                  30
Glu Ser Thr Asn Tyr Ile Asp Pro Ser Phe Asn Ala Asn Tyr Val Gly
        35                  40                  45
Ala Thr Asn Thr Gly Leu Ile Arg Gly Ala Tyr His Phe Ala Arg Pro
    50                  55                  60
Gly Asp Ser Ser Gly Ala Ala Gln Ala Asn Tyr Phe Val Ser His Gly
65                  70                  75                  80
Gly Gly Trp Ser Ala Asp Gly Arg Thr Leu Pro Gly Ala Leu Asp Leu
                85                  90                  95
Glu Ala Gly Cys Ser Gly Leu Ser Gln Ser Ala Met Thr Ala Trp Ile
            100                 105                 110
Arg Asp Phe Ser Asn Thr Tyr His Ala Arg Thr Gly Arg Phe Pro Val
        115                 120                 125
Ile Tyr Thr Thr Thr Ser Trp Trp Lys Thr Cys Thr Gly Asn Ala Ser
    130                 135                 140
Gly Phe Gln Asn Asp His Pro Leu Trp Ile Ala Arg Trp Gly Pro Ser
145                 150                 155                 160
Pro Gly Glu Leu Pro Ala Gly Tyr Gly Phe His Thr Phe Trp Gln Tyr
                165                 170                 175
Ala Asp Lys Gly Pro Leu Pro Gly Asp Gln Asp Asn Phe Asn Gly Asp
            180                 185                 190
Glu Ala Gly Leu Ala Arg Leu Ala Arg Gly Ser
        195                 200

<210> SEQ ID NO 55
<211> LENGTH: 944
<212> TYPE: DNA
<213> ORGANISM: Rhizomucor pusillus
<220> FEATURE:
<221> NAME/KEY: CDS
<222> LOCATION: (1)..(184)
<220> FEATURE:
<221> NAME/KEY: sig_peptide
<222> LOCATION: (1)..(60)
<220> FEATURE:
<221> NAME/KEY: mat_peptide
<222> LOCATION: (61)..(941)
<220> FEATURE:
<221> NAME/KEY: CDS
<222> LOCATION: (241)..(242)
<220> FEATURE:
<221> NAME/KEY: CDS
<222> LOCATION: (244)..(484)
<220> FEATURE:
<221> NAME/KEY: CDS
<222> LOCATION: (555)..(688)
<220> FEATURE:
<221> NAME/KEY: CDS
<222> LOCATION: (757)..(825)
<220> FEATURE:
<221> NAME/KEY: CDS
<222> LOCATION: (885)..(941)

<400> SEQUENCE: 55 atg aag ttt gca ctc cta gta tct gct atc gca ggc ctt gca gca acc    48

```
                Met Lys Phe Ala Leu Leu Val Ser Ala Ile Ala Gly Leu Ala Ala Thr
                    -20             -15                 -10                  -5 gcc gtc caa gcc tac gaa act ggc gtt gat gtc tct gcc ttg act tcc              96
Ala Val Gln Ala Tyr Glu Thr Gly Val Asp Val Ser Ala Leu Thr Ser
        -1  1                   5                      10 acc tcc gcc tgg agc tgt gca aag aaa ctc ggt tac gat cac gct att             144
Thr Ser Ala Trp Ser Cys Ala Lys Lys Leu Gly Tyr Asp His Ala Ile
         15                  20                  25 gtc cgc tgc tac att gag gca tac gga ggc aac cct gca a gtatcatgca            194
Val Arg Cys Tyr Ile Glu Ala Tyr Gly Gly Asn Pro Ala
     30                  35                  40 tcagagaaga cgactactac gttctagcgt gctaacaatg tactag gg  t ggt aaa            249
                                                       Arg Gly Lys att gac agc aac tgc ttc cag aac tac aag aac gcc aaa gca ggt gga             297
Ile Asp Ser Asn Cys Phe Gln Asn Tyr Lys Asn Ala Lys Ala Gly Gly
 45              50                  55                   60 ttc acc agc gtt gac att tac atg ttc ccc tgc act ggc cgc tcc aca             345
Phe Thr Ser Val Asp Ile Tyr Met Phe Pro Cys Thr Gly Arg Ser Thr
             65                  70                  75 tgc aag tcg ccc gct gct cag gtc aag gag gtc gtt gac tac gtt ggc             393
Cys Lys Ser Pro Ala Ala Gln Val Lys Glu Val Val Asp Tyr Val Gly
         80                  85                  90 tcc aac aag atg act gtt gga cgt ctc tgg ctc gac gtc gaa atc gat             441
Ser Asn Lys Met Thr Val Gly Arg Leu Trp Leu Asp Val Glu Ile Asp
     95                 100                 105 cct tct gct aac aac tgg cca tcc gcc agt agc gct cgc agc a                   484
Pro Ser Ala Asn Asn Trp Pro Ser Ala Ser Ser Ala Arg Ser
110                 115                 120 gtaagaaaga ggacaagaaa ccaattcagg atgctcacaa tgttgctaac attttttatt           544
acttgttaag cc  ttg aag tcc ttc aag tct gct ctt gac tcg act ggc              592
                Thr Leu Lys Ser Phe Lys Ser Ala Leu Asp Ser Thr Gly
                         125                 130                 135 tgg aaa tac ggt atc tat tct tct gct tcc caa tgg tcg cag att acc             640
Trp Lys Tyr Gly Ile Tyr Ser Ser Ala Ser Gln Trp Ser Gln Ile Thr
             140                 145                 150 gga tcc tcc tcc tgg gag ctt gat tcc tcg ttg cca ctt tgg tac gct             688
Gly Ser Ser Ser Trp Glu Leu Asp Ser Ser Leu Pro Leu Trp Tyr Ala
         155                 160                 165 gtaagtagct ctcacgttat tccgtatatt gtgggagaac gtggctgatc tgaatttatt           748 accacaag cac tac gac gct tct ctc agc ttc agc gac ttt tcg cca ttt            798
         His Tyr Asp Ala Ser Leu Ser Phe Ser Asp Phe Ser Pro Phe
                 170                 175                 180 ggt ggc tgg act aag cct acc atc aag gtaaatattc aggtcatccg                   845
Gly Gly Trp Thr Lys Pro Thr Ile Lys
         185                 190 gtgcttgacg catatgtact caattaaatc gccatttag caa tat gct ggc tct              899
                                           Gln Tyr Ala Gly Ser
                                                           195 gta agc ttc tgc tcc gct ggc tgg gac aag aac tac tat ggc taa                 944
Val Ser Phe Cys Ser Ala Gly Trp Asp Lys Asn Tyr Tyr Gly
             200                 205

<210> SEQ ID NO 56
<211> LENGTH: 229
<212> TYPE: PRT
<213> ORGANISM: Rhizomucor pusillus

<400> SEQUENCE: 56

Met Lys Phe Ala Leu Leu Val Ser Ala Ile Ala Gly Leu Ala Ala Thr
```

```
            -20             -15             -10             -5
    Ala Val Gln Ala Tyr Glu Thr Gly Val Asp Val Ser Ala Leu Thr Ser
                     -1  1               5                  10

Thr Ser Ala Trp Ser Cys Ala Lys Lys Leu Gly Tyr Asp His Ala Ile
                15                  20                  25

Val Arg Cys Tyr Ile Glu Ala Tyr Gly Gly Asn Pro Ala Arg Gly Lys
            30                  35                  40

Ile Asp Ser Asn Cys Phe Gln Asn Tyr Lys Asn Ala Lys Ala Gly Gly
    45                  50                  55                  60

Phe Thr Ser Val Asp Ile Tyr Met Phe Pro Cys Thr Gly Arg Ser Thr
                    65                  70                  75

Cys Lys Ser Pro Ala Ala Gln Val Lys Glu Val Val Asp Tyr Val Gly
                80                  85                  90

Ser Asn Lys Met Thr Val Gly Arg Leu Trp Leu Asp Val Glu Ile Asp
                95                  100                 105

Pro Ser Ala Asn Asn Trp Pro Ser Ala Ser Ser Ala Arg Ser Thr Leu
    110                 115                 120

Lys Ser Phe Lys Ser Ala Leu Asp Ser Thr Gly Trp Lys Tyr Gly Ile
    125                 130                 135                 140

Tyr Ser Ser Ala Ser Gln Trp Ser Gln Ile Thr Gly Ser Ser Ser Trp
                    145                 150                 155

Glu Leu Asp Ser Ser Leu Pro Leu Trp Tyr Ala His Tyr Asp Ala Ser
                160                 165                 170

Leu Ser Phe Ser Asp Phe Ser Pro Phe Gly Gly Trp Thr Lys Pro Thr
                175                 180                 185

Ile Lys Gln Tyr Ala Gly Ser Val Ser Phe Cys Ser Ala Gly Trp Asp
        190                 195                 200

Lys Asn Tyr Tyr Gly
    205

<210> SEQ ID NO 57
    <211> LENGTH: 209
    <212> TYPE: PRT
    <213> ORGANISM: Rhizomucor pusillus
    <220> FEATURE:
    <221> NAME/KEY: mat_peptide
    <222> LOCATION: (1)..(209)

<400> SEQUENCE: 57

Tyr Glu Thr Gly Val Asp Val Ser Ala Leu Thr Ser Thr Ser Ala Trp
    1               5                   10                  15

Ser Cys Ala Lys Lys Leu Gly Tyr Asp His Ala Ile Val Arg Cys Tyr
                    20                  25                  30

Ile Glu Ala Tyr Gly Gly Asn Pro Ala Arg Gly Lys Ile Asp Ser Asn
                35                  40                  45

Cys Phe Gln Asn Tyr Lys Asn Ala Lys Ala Gly Gly Phe Thr Ser Val
        50                  55                  60

Asp Ile Tyr Met Phe Pro Cys Thr Gly Arg Ser Thr Cys Lys Ser Pro
    65                  70                  75                  80

Ala Ala Gln Val Lys Glu Val Val Asp Tyr Val Gly Ser Asn Lys Met
                    85                  90                  95

Thr Val Gly Arg Leu Trp Leu Asp Val Glu Ile Asp Pro Ser Ala Asn
                100                 105                 110

Asn Trp Pro Ser Ala Ser Ser Ala Arg Ser Thr Leu Lys Ser Phe Lys
                115                 120                 125
```

-continued

```
Ser Ala Leu Asp Ser Thr Gly Trp Lys Tyr Gly Ile Tyr Ser Ser Ala
    130                 135                 140

Ser Gln Trp Ser Gln Ile Thr Gly Ser Ser Trp Glu Leu Asp Ser
145                 150                 155                 160

Ser Leu Pro Leu Trp Tyr Ala His Tyr Asp Ala Ser Leu Ser Phe Ser
                165                 170                 175

Asp Phe Ser Pro Phe Gly Gly Trp Thr Lys Pro Thr Ile Lys Gln Tyr
            180                 185                 190

Ala Gly Ser Val Ser Phe Cys Ser Ala Gly Trp Asp Lys Asn Tyr Tyr
            195                 200                 205

Gly

<210> SEQ ID NO 58
<211> LENGTH: 887
<212> TYPE: DNA
<213> ORGANISM: Pycnidiophora cf. dispera
<220> FEATURE:
<221> NAME/KEY: CDS
<222> LOCATION: (1)..(144)
<220> FEATURE:
<221> NAME/KEY: sig_peptide
<222> LOCATION: (1)..(51)
<220> FEATURE:
<221> NAME/KEY: mat_peptide
<222> LOCATION: (52)..(884)
<220> FEATURE:
<221> NAME/KEY: CDS
<222> LOCATION: (205)..(265)
<220> FEATURE:
<221> NAME/KEY: CDS
<222> LOCATION: (358)..(781)
<220> FEATURE:
<221> NAME/KEY: CDS
<222> LOCATION: (839)..(884)

<400> SEQUENCE: 58 atg aag tcc gta ctc gcc ctg ctc gcc gct ggc gcc caa ctt gcc agt      48
Met Lys Ser Val Leu Ala Leu Leu Ala Ala Gly Ala Gln Leu Ala Ser
        -15                 -10                  -5 gcg gcc gtc tcc ggc atg gat atc tcc cac tac caa ggg aca aac tac      96
Ala Ala Val Ser Gly Met Asp Ile Ser His Tyr Gln Gly Thr Asn Tyr
 -1   1               5                  10                  15 aac ttt gcc ggc gca tac tcc tct ggt gct cgc ttt gtc atc atc aag     144
Asn Phe Ala Gly Ala Tyr Ser Ser Gly Ala Arg Phe Val Ile Ile Lys
                 20                  25                  30 gtacatgccc attctagctt aaggatttga ccccaatgtt cggcctttaa cgcatcctag    204 gcc acc gaa gga acc aca tat acc gat cct cag ttc tcc gct aac tac     252
Ala Thr Glu Gly Thr Thr Tyr Thr Asp Pro Gln Phe Ser Ala Asn Tyr
             35                  40                  45 att ggt gcc acg a gtaagtagat ttccccatga ggtagctggt cgttagtctt       305
Ile Gly Ala Thr
             50 ctcctctcct accacactgt ccatgctggg gagacccatt aacactgagt ag at  gct   362
                                                            Asn Ala ggt ttt atc cgc ggc gcg tac cat ttc gcc cgc cct gcc gcc tct act     410
Gly Phe Ile Arg Gly Ala Tyr His Phe Ala Arg Pro Ala Ala Ser Thr
         55                  60                  65 ggg gcc gtc caa gcc tcc tac ttc gtc tcc cat ggc ggt ggg tgg tca     458
Gly Ala Val Gln Ala Ser Tyr Phe Val Ser His Gly Gly Gly Trp Ser
70                  75                  80                  85 tcg gat ggc atc aca ctc ccc ggc atg ctt gac atg gaa tat ggc tct     506
Ser Asp Gly Ile Thr Leu Pro Gly Met Leu Asp Met Glu Tyr Gly Ser
                 90                  95                 100
```

```
acc tcc act tgc cac ggc ctt tct gtc tcc gcc atg aac acg tgg atc      554
Thr Ser Thr Cys His Gly Leu Ser Val Ser Ala Met Asn Thr Trp Ile
            105                 110                 115 gcc tcc ttc gtg aac cag tac aag agt ttg acg ggc gca tac ccc atg      602
Ala Ser Phe Val Asn Gln Tyr Lys Ser Leu Thr Gly Ala Tyr Pro Met
        120                 125                 130 att tac acc aca gcc gat tgg tgg aag act tgc aca gga gac agc acg      650
Ile Tyr Thr Thr Ala Asp Trp Trp Lys Thr Cys Thr Gly Asp Ser Thr
    135                 140                 145 gct tgg aac acc aag tgc cct ttg gta ttg gcc agg tac tct agt tct      698
Ala Trp Asn Thr Lys Cys Pro Leu Val Leu Ala Arg Tyr Ser Ser Ser
150                 155                 160                 165 gtg ggg acg att cct gga ggt tgg ccg tat cat acc att tgg caa tat      746
Val Gly Thr Ile Pro Gly Gly Trp Pro Tyr His Thr Ile Trp Gln Tyr
                170                 175                 180 tcc gat tcc tat gcg tac ggt ggg gat tcg gat ac  gtaagttcga           791
Ser Asp Ser Tyr Ala Tyr Gly Gly Asp Ser Asp Thr
            185                 190 catgctcaag cgaatggaac ggatggagtg gctaacggga tggacag a ttc aat ggc    848
                                                    Phe Asn Gly
                                                        195 gac ttg gct ggc tta aag agg ctt gcg aag ggc agc taa                  887
Asp Leu Ala Gly Leu Lys Arg Leu Ala Lys Gly Ser
            200                 205
```

<210> SEQ ID NO 59
<211> LENGTH: 225
<212> TYPE: PRT
<213> ORGANISM: Pycnidiophora cf. dispera

<400> SEQUENCE: 59

```
Met Lys Ser Val Leu Ala Leu Leu Ala Ala Gly Ala Gln Leu Ala Ser
        -15                 -10                  -5

Ala Ala Val Ser Gly Met Asp Ile Ser His Tyr Gln Gly Thr Asn Tyr
 -1  1               5                  10                  15

Asn Phe Ala Gly Ala Tyr Ser Ser Gly Ala Arg Phe Val Ile Ile Lys
                20                  25                  30

Ala Thr Glu Gly Thr Thr Tyr Thr Asp Pro Gln Phe Ser Ala Asn Tyr
            35                  40                  45

Ile Gly Ala Thr Asn Ala Gly Phe Ile Arg Gly Ala Tyr His Phe Ala
        50                  55                  60

Arg Pro Ala Ala Ser Thr Gly Ala Val Gln Ala Ser Tyr Phe Val Ser
    65                  70                  75

His Gly Gly Gly Trp Ser Ser Asp Gly Ile Thr Leu Pro Gly Met Leu
80                  85                  90                  95

Asp Met Glu Tyr Gly Ser Thr Ser Thr Cys His Gly Leu Ser Val Ser
                100                 105                 110

Ala Met Asn Thr Trp Ile Ala Ser Phe Val Asn Gln Tyr Lys Ser Leu
            115                 120                 125

Thr Gly Ala Tyr Pro Met Ile Tyr Thr Thr Ala Asp Trp Trp Lys Thr
        130                 135                 140

Cys Thr Gly Asp Ser Thr Ala Trp Asn Thr Lys Cys Pro Leu Val Leu
    145                 150                 155

Ala Arg Tyr Ser Ser Ser Val Gly Thr Ile Pro Gly Gly Trp Pro Tyr
160                 165                 170                 175

His Thr Ile Trp Gln Tyr Ser Asp Ser Tyr Ala Tyr Gly Gly Asp Ser
                180                 185                 190
```

Asp Thr Phe Asn Gly Asp Leu Ala Gly Leu Lys Arg Leu Ala Lys Gly
            195                 200                 205

Ser

<210> SEQ ID NO 60
<211> LENGTH: 208
<212> TYPE: PRT
<213> ORGANISM: Pycnidiophora cf. dispera
<220> FEATURE:
<221> NAME/KEY: mat_peptide
<222> LOCATION: (1)..(208)

<400> SEQUENCE: 60

Ala Val Ser Gly Met Asp Ile Ser His Tyr Gln Gly Thr Asn Tyr Asn
1               5                   10                  15

Phe Ala Gly Ala Tyr Ser Ser Gly Ala Arg Phe Val Ile Ile Lys Ala
            20                  25                  30

Thr Glu Gly Thr Thr Tyr Thr Asp Pro Gln Phe Ser Ala Asn Tyr Ile
        35                  40                  45

Gly Ala Thr Asn Ala Gly Phe Ile Arg Gly Ala Tyr His Phe Ala Arg
    50                  55                  60

Pro Ala Ala Ser Thr Gly Ala Val Gln Ala Ser Tyr Phe Val Ser His
65                  70                  75                  80

Gly Gly Gly Trp Ser Ser Asp Gly Ile Thr Leu Pro Gly Met Leu Asp
                85                  90                  95

Met Glu Tyr Gly Ser Thr Ser Thr Cys His Gly Leu Ser Val Ser Ala
            100                 105                 110

Met Asn Thr Trp Ile Ala Ser Phe Val Asn Gln Tyr Lys Ser Leu Thr
        115                 120                 125

Gly Ala Tyr Pro Met Ile Tyr Thr Thr Ala Asp Trp Trp Lys Thr Cys
    130                 135                 140

Thr Gly Asp Ser Thr Ala Trp Asn Thr Lys Cys Pro Leu Val Leu Ala
145                 150                 155                 160

Arg Tyr Ser Ser Val Gly Thr Ile Pro Gly Gly Trp Pro Tyr His
                165                 170                 175

Thr Ile Trp Gln Tyr Ser Asp Ser Tyr Ala Tyr Gly Gly Asp Ser Asp
            180                 185                 190

Thr Phe Asn Gly Asp Leu Ala Gly Leu Lys Arg Leu Ala Lys Gly Ser
        195                 200                 205

<210> SEQ ID NO 61
<211> LENGTH: 974
<212> TYPE: DNA
<213> ORGANISM: Thermomucor indicae-seudaticae
<220> FEATURE:
<221> NAME/KEY: CDS
<222> LOCATION: (1)..(186)
<220> FEATURE:
<221> NAME/KEY: sig_peptide
<222> LOCATION: (1)..(66)
<220> FEATURE:
<221> NAME/KEY: mat_peptide
<222> LOCATION: (67)..(971)
<220> FEATURE:
<221> NAME/KEY: CDS
<222> LOCATION: (250)..(493)
<220> FEATURE:
<221> NAME/KEY: CDS
<222> LOCATION: (579)..(712)
<220> FEATURE:
<221> NAME/KEY: CDS
<222> LOCATION: (777)..(851)

<220> FEATURE:
<221> NAME/KEY: CDS
<222> LOCATION: (915)..(971)

<400> SEQUENCE: 61

```
atg aag ttt tca atc ttt gct att gct gct gct gct gcc gcc gtg          48
Met Lys Phe Ser Ile Phe Ala Ile Ala Ala Ala Ala Ala Ala Val
        -20             -15                 -10 gcc acc ttg gtt caa ggc tac caa acc ggt ctg gat gta tct gcc ttg      96
Ala Thr Leu Val Gln Gly Tyr Gln Thr Gly Leu Asp Val Ser Ala Leu
     -5              -1  1               5                  10 acc tcg aca tcg tcc ttt agc tgt gcg aaa aac ctt gga tat gac cat     144
Thr Ser Thr Ser Ser Phe Ser Cys Ala Lys Asn Leu Gly Tyr Asp His
                 15                  20                  25 gtg att gct cga tgc tac atg gaa gcc tac ggc aac aac ccg             186
Val Ile Ala Arg Cys Tyr Met Glu Ala Tyr Gly Asn Asn Pro
                 30                  35              40 gtaaaaccaa catcgaactc aaaggaagat ggaaatgaaa taacaaaaaa gggttatacg   246 cag ggt ggc aaa gtg gat ccc aac tgt tat agc aat tac aag aac gcc    294
    Gly Gly Lys Val Asp Pro Asn Cys Tyr Ser Asn Tyr Lys Asn Ala
                     45                  50                  55 aag gca gct gga ttc acg tcg gtg gat atc tac atg ttc cca tgt acc    342
Lys Ala Ala Gly Phe Thr Ser Val Asp Ile Tyr Met Phe Pro Cys Thr
                     60                  65                  70 ggc cga tcc acc tgc aag tcg cca gcg act caa gtc caa gaa atc gtg    390
Gly Arg Ser Thr Cys Lys Ser Pro Ala Thr Gln Val Gln Glu Ile Val
                75                  80                  85 gat tac gtc ggg gcc cac aag atg att gtc gga act ttg tgg ttg gat    438
Asp Tyr Val Gly Ala His Lys Met Ile Val Gly Thr Leu Trp Leu Asp
            90                  95                  100 gtc gag gtc gat tcg gct gct aat aac tgg ccg tcc acg tcc gaa gcc    486
Val Glu Val Asp Ser Ala Ala Asn Asn Trp Pro Ser Thr Ser Glu Ala
        105                 110                 115 cgg tcc a gtaagttccc ccgtccagag ctgtctatct atctatctat caattgtatg   543
Arg Ser
120 aaccgttcgt cataactcac ggtgcgcatc gttag ca   ctc cga gct ttc aag    595
                                           Thr Leu Arg Ala Phe Lys
                                                           125 acg gcg ttg gat aag tcc gga tgg aaa tgg ggc gtt tat tcc agc aag    643
Thr Ala Leu Asp Lys Ser Gly Trp Lys Trp Gly Val Tyr Ser Ser Lys
                130                 135                 140 tcg caa tgg acg cgt atc acc gga tca gct tca tgg gtt tta gac ccg    691
Ser Gln Trp Thr Arg Ile Thr Gly Ser Ala Ser Trp Val Leu Asp Pro
    145                 150                 155 tcg gtg cct ttg tgg tat tcg gtaagttgtt acataacagc tgcgatttcc      742
Ser Val Pro Leu Trp Tyr Ser
160                 165 gtgccatgat ctttcttatc tgtttcatac gtag cac tac gac gat acc ctt agt  797
                                     His Tyr Asp Asp Thr Leu Ser
                                                         170 ttc agt gac tat cca tcg cac gct ttc ggt ggc tgg tcc aaa cca aca    845
Phe Ser Asp Tyr Pro Ser His Ala Phe Gly Gly Trp Ser Lys Pro Thr
                175                 180                 185 atc aag gtacgttagc attttttttca aaataaaata gttctctgcc gtattaatcc    901
Ile Lys
190 tctccatgct cag caa tat acg gga gat gct tcc ttt tgc tct gcc agt     950
                Gln Tyr Thr Gly Asp Ala Ser Phe Cys Ser Ala Ser
                                195                 200
```

```
tgg gac aag aac tac tat ggt tag                                    974
Trp Asp Lys Asn Tyr Tyr Gly
    205             210

<210> SEQ ID NO 62
<211> LENGTH: 232
<212> TYPE: PRT
<213> ORGANISM: Thermomucor indicae-seudaticae

<400> SEQUENCE: 62

Met Lys Phe Ser Ile Phe Ala Ile Ala Ala Ala Ala Ala Val
        -20             -15             -10

Ala Thr Leu Val Gln Gly Tyr Gln Thr Gly Leu Asp Val Ser Ala Leu
     -5              -1   1               5                  10

Thr Ser Thr Ser Ser Phe Ser Cys Ala Lys Asn Leu Gly Tyr Asp His
                 15                  20                  25

Val Ile Ala Arg Cys Tyr Met Glu Ala Tyr Gly Asn Asn Pro Gly Gly
             30                  35                  40

Lys Val Asp Pro Asn Cys Tyr Ser Asn Tyr Lys Asn Ala Lys Ala Ala
             45                  50                  55

Gly Phe Thr Ser Val Asp Ile Tyr Met Phe Pro Cys Thr Gly Arg Ser
 60                  65                  70

Thr Cys Lys Ser Pro Ala Thr Gln Val Gln Glu Ile Val Asp Tyr Val
 75              80                  85                      90

Gly Ala His Lys Met Ile Val Gly Thr Leu Trp Leu Asp Val Glu Val
                 95                  100                 105

Asp Ser Ala Ala Asn Asn Trp Pro Ser Thr Ser Glu Ala Arg Ser Thr
             110                 115                 120

Leu Arg Ala Phe Lys Thr Ala Leu Asp Lys Ser Gly Trp Lys Trp Gly
             125                 130                 135

Val Tyr Ser Ser Lys Ser Gln Trp Thr Arg Ile Thr Gly Ser Ala Ser
     140                 145                 150

Trp Val Leu Asp Pro Ser Val Pro Leu Trp Tyr Ser His Tyr Asp Asp
155                 160                 165                 170

Thr Leu Ser Phe Ser Asp Tyr Pro Ser His Ala Phe Gly Gly Trp Ser
                 175                 180                 185

Lys Pro Thr Ile Lys Gln Tyr Thr Gly Asp Ala Ser Phe Cys Ser Ala
             190                 195                 200

Ser Trp Asp Lys Asn Tyr Tyr Gly
    205             210

<210> SEQ ID NO 63
<211> LENGTH: 210
<212> TYPE: PRT
<213> ORGANISM: Thermomucor indicae-seudaticae
<220> FEATURE:
<221> NAME/KEY: mat_peptide
<222> LOCATION: (1)..(210)

<400> SEQUENCE: 63

Tyr Gln Thr Gly Leu Asp Val Ser Ala Leu Thr Ser Thr Ser Ser Phe
 1               5                   10                  15

Ser Cys Ala Lys Asn Leu Gly Tyr Asp His Val Ile Ala Arg Cys Tyr
                 20                  25                  30

Met Glu Ala Tyr Gly Asn Asn Pro Gly Gly Lys Val Asp Pro Asn Cys
             35                  40                  45

Tyr Ser Asn Tyr Lys Asn Ala Lys Ala Ala Gly Phe Thr Ser Val Asp
```

```
                50                  55                  60
Ile Tyr Met Phe Pro Cys Thr Gly Arg Ser Thr Cys Lys Ser Pro Ala
 65                  70                  75                  80

Thr Gln Val Gln Glu Ile Val Asp Tyr Val Gly Ala His Lys Met Ile
                 85                  90                  95

Val Gly Thr Leu Trp Leu Asp Val Glu Val Asp Ser Ala Ala Asn Asn
            100                 105                 110

Trp Pro Ser Thr Ser Glu Ala Arg Ser Thr Leu Arg Ala Phe Lys Thr
            115                 120                 125

Ala Leu Asp Lys Ser Gly Trp Lys Trp Gly Val Tyr Ser Ser Lys Ser
            130                 135                 140

Gln Trp Thr Arg Ile Thr Gly Ser Ala Ser Trp Val Leu Asp Pro Ser
145                 150                 155                 160

Val Pro Leu Trp Tyr Ser His Tyr Asp Asp Thr Leu Ser Phe Ser Asp
                165                 170                 175

Tyr Pro Ser His Ala Phe Gly Gly Trp Ser Lys Pro Thr Ile Lys Gln
                180                 185                 190

Tyr Thr Gly Asp Ala Ser Phe Cys Ser Ala Ser Trp Asp Lys Asn Tyr
            195                 200                 205

Tyr Gly
    210

<210> SEQ ID NO 64
<211> LENGTH: 675
<212> TYPE: DNA
<213> ORGANISM: Isaria farinosa
<220> FEATURE:
<221> NAME/KEY: CDS
<222> LOCATION: (1)..(672)
<220> FEATURE:
<221> NAME/KEY: sig_peptide
<222> LOCATION: (1)..(51)
<220> FEATURE:
<221> NAME/KEY: mat_peptide
<222> LOCATION: (52)..(672)

<400> SEQUENCE: 64 atg cgc gcc tct aca gcc ctc ttt atc gcc ttt gcc ggc gtg gcc act        48
Met Arg Ala Ser Thr Ala Leu Phe Ile Ala Phe Ala Gly Val Ala Thr
        -15                 -10                  -5 gcc ctg acc cac gcc gtc gac agc tcc tcc gag gtg agc gtc gac att       96
Ala Leu Thr His Ala Val Asp Ser Ser Ser Glu Val Ser Val Asp Ile
 -1   1               5                  10                  15 tac aaa aag gcg ctc ggc cag ggc ttc acg cgc gcc atc ttc cgc ggc      144
Tyr Lys Lys Ala Leu Gly Gln Gly Phe Thr Arg Ala Ile Phe Arg Gly
                 20                  25                  30 tac cag gag gcg tgc tcg ctc ggc ggc cgc gtc gac ccg acc ttt gtg      192
Tyr Gln Glu Ala Cys Ser Leu Gly Gly Arg Val Asp Pro Thr Phe Val
             35                  40                  45 ccc agc tac aaa aac gcc gtc gcg gcc ggc tac aag gac ttt gac gcc      240
Pro Ser Tyr Lys Asn Ala Val Ala Ala Gly Tyr Lys Asp Phe Asp Ala
         50                  55                  60 tac ttc ttc ccc tgc acc ggc acg acc aac aag tgc aag ccg tac gcg      288
Tyr Phe Phe Pro Cys Thr Gly Thr Thr Asn Lys Cys Lys Pro Tyr Ala
     65                  70                  75 acg cag ctc gcc gag ctg ctc gac acc atc agc agc cag aag ctg gcg      336
Thr Gln Leu Ala Glu Leu Leu Asp Thr Ile Ser Ser Gln Lys Leu Ala
 80                  85                  90                  95 atc cgc cgc atc tgg ctc gac att gag acg gac cag gtc tgc agc ccg      384
Ile Arg Arg Ile Trp Leu Asp Ile Glu Thr Asp Gln Val Cys Ser Pro
```

| | | | | |
|---|---|---|---|---|
| ttc gac tat ggc gcg cag ggc aac att gcc gag gcc aag aag ctc gtc<br>Phe Asp Tyr Gly Ala Gln Gly Asn Ile Ala Glu Ala Lys Lys Leu Val<br>115                               120                           125 | | | | 432 |
| gcc gcg ttt cgc gcc gca aag cac gac tgg ggc atc tac acg tcg ccg<br>Ala Ala Phe Arg Ala Ala Lys His Asp Trp Gly Ile Tyr Thr Ser Pro<br>130                               135                           140 | | | | 480 |
| acg cag tgg gag act atc ttt ggc tcc aag aca ttc gtg ctg gcc aat<br>Thr Gln Trp Glu Thr Ile Phe Gly Ser Lys Thr Phe Val Leu Ala Asn<br>145                               150                           155 | | | | 528 |
| gat gtg ccg ctc tgg ttt gcc aag ttt gac aat gtc gag acg ctg gac<br>Asp Val Pro Leu Trp Phe Ala Lys Phe Asp Asn Val Glu Thr Leu Asp<br>160                               165                           170                           175 | | | | 576 |
| ctg aag acg ccg ttt ggc ggc tgg aca aag gcc gac gca aaa cag tac<br>Leu Lys Thr Pro Phe Gly Gly Trp Thr Lys Ala Asp Ala Lys Gln Tyr<br>                    180                           185                           190 | | | | 624 |
| acg gac cag tcg gct agc aag aag ttt gac ttg aac gtc ttc tct gca<br>Thr Asp Gln Ser Ala Ser Lys Lys Phe Asp Leu Asn Val Phe Ser Ala<br>                    195                           200                           205 | | | | 672 |
| taa | | | | 675 |

<210> SEQ ID NO 65
<211> LENGTH: 224
<212> TYPE: PRT
<213> ORGANISM: Isaria farinosa

<400> SEQUENCE: 65

Met Arg Ala Ser Thr Ala Leu Phe Ile Ala Phe Ala Gly Val Ala Thr
        -15                  -10                     -5

Ala Leu Thr His Ala Val Asp Ser Ser Glu Val Ser Val Asp Ile
-1  1               5                   10                  15

Tyr Lys Lys Ala Leu Gly Gln Gly Phe Thr Arg Ala Ile Phe Arg Gly
         20                       25                     30

Tyr Gln Glu Ala Cys Ser Leu Gly Gly Arg Val Asp Pro Thr Phe Val
         35                       40                     45

Pro Ser Tyr Lys Asn Ala Val Ala Ala Gly Tyr Lys Asp Phe Asp Ala
         50                       55                     60

Tyr Phe Phe Pro Cys Thr Gly Thr Thr Asn Lys Cys Lys Pro Tyr Ala
 65                        70                       75

Thr Gln Leu Ala Glu Leu Leu Asp Thr Ile Ser Ser Gln Lys Leu Ala
 80                    85                      90                     95

Ile Arg Arg Ile Trp Leu Asp Ile Glu Thr Asp Gln Val Cys Ser Pro
         100                     105                    110

Phe Asp Tyr Gly Ala Gln Gly Asn Ile Ala Glu Ala Lys Lys Leu Val
         115                     120                    125

Ala Ala Phe Arg Ala Ala Lys His Asp Trp Gly Ile Tyr Thr Ser Pro
         130                     135                    140

Thr Gln Trp Glu Thr Ile Phe Gly Ser Lys Thr Phe Val Leu Ala Asn
         145                     150                    155

Asp Val Pro Leu Trp Phe Ala Lys Phe Asp Asn Val Glu Thr Leu Asp
160                      165                         170                    175

Leu Lys Thr Pro Phe Gly Gly Trp Thr Lys Ala Asp Ala Lys Gln Tyr
                    180                           185                           190

Thr Asp Gln Ser Ala Ser Lys Lys Phe Asp Leu Asn Val Phe Ser Ala
                    195                           200                           205

```
<210> SEQ ID NO 66
<211> LENGTH: 207
<212> TYPE: PRT
<213> ORGANISM: Isaria farinosa
<220> FEATURE:
<221> NAME/KEY: mat_peptide
<222> LOCATION: (1)..(207)

<400> SEQUENCE: 66
```

Leu Thr His Ala Val Asp Ser Ser Glu Val Ser Val Asp Ile Tyr
1               5                  10                  15

Lys Lys Ala Leu Gly Gln Gly Phe Thr Arg Ala Ile Phe Arg Gly Tyr
            20                  25                  30

Gln Glu Ala Cys Ser Leu Gly Gly Arg Val Asp Pro Thr Phe Val Pro
            35                  40                  45

Ser Tyr Lys Asn Ala Val Ala Ala Gly Tyr Lys Asp Phe Asp Ala Tyr
    50                  55                  60

Phe Phe Pro Cys Thr Gly Thr Thr Asn Lys Cys Lys Pro Tyr Ala Thr
65              70                  75                  80

Gln Leu Ala Glu Leu Leu Asp Thr Ile Ser Ser Gln Lys Leu Ala Ile
                85                  90                  95

Arg Arg Ile Trp Leu Asp Ile Glu Thr Asp Gln Val Cys Ser Pro Phe
            100                 105                 110

Asp Tyr Gly Ala Gln Gly Asn Ile Ala Glu Ala Lys Lys Leu Val Ala
        115                 120                 125

Ala Phe Arg Ala Ala Lys His Asp Trp Gly Ile Tyr Thr Ser Pro Thr
    130                 135                 140

Gln Trp Glu Thr Ile Phe Gly Ser Lys Thr Phe Val Leu Ala Asn Asp
145                 150                 155                 160

Val Pro Leu Trp Phe Ala Lys Phe Asp Asn Val Glu Thr Leu Asp Leu
                165                 170                 175

Lys Thr Pro Phe Gly Gly Trp Thr Lys Ala Asp Ala Lys Gln Tyr Thr
            180                 185                 190

Asp Gln Ser Ala Ser Lys Lys Phe Asp Leu Asn Val Phe Ser Ala
        195                 200                 205

```
<210> SEQ ID NO 67
<211> LENGTH: 829
<212> TYPE: DNA
<213> ORGANISM: Lecanicillium sp. WMM742
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: mat_peptide
<222> LOCATION: (58)..(826)
<220> FEATURE:
<221> NAME/KEY: CDS
<222> LOCATION: (210)..(393)
<220> FEATURE:
<221> NAME/KEY: CDS
<222> LOCATION: (480)..(826)

<400> SEQUENCE: 67
``` atg aag tct ttt ggc ctg ttc gcc tca ctc gcc tct ctg gct ggc atc       48
Met Lys Ser Phe Gly Leu Phe Ala Ser Leu Ala Ser Leu Ala Gly Ile
                -15                 -10                 -5 gcc agc gcc tcg gtc cag ggt ttt gac att tcc cac tac cag agc tct       96
Ala Ser Ala Ser Val Gln Gly Phe Asp Ile Ser His Tyr Gln Ser Ser
        -1  1               5                   10

```
gtc aac ttt ggc gcg gcc tac gct gac ggc gct cgc ttc gtc att atc      144
Val Asn Phe Gly Ala Ala Tyr Ala Asp Gly Ala Arg Phe Val Ile Ile
        15                  20                  25 aag gtgcgatttt gtcgcctggc gttttctcaa ccctggctac ctactcacaa           197
Lys
30 ccttatcatt ag gca acc gag gga acg acg tac cgc gac ccc aag ttc agc   248
              Ala Thr Glu Gly Thr Thr Tyr Arg Asp Pro Lys Phe Ser
                                  35                  40 gag cac tac ggc ggc gcc acc aag gcc ggc ttc atc cgc ggc ggc tat     296
Glu His Tyr Gly Gly Ala Thr Lys Ala Gly Phe Ile Arg Gly Gly Tyr
    45                  50                  55 cac ttt gcc cag cct gcc tca tcc tct ggc gcc gcg cag gcc aac ttt     344
His Phe Ala Gln Pro Ala Ser Ser Ser Gly Ala Ala Gln Ala Asn Phe
60                  65                  70                  75 ttc ctc gct cac ggc ggc ggc tgg agc ggc gac ggc atc acc ctg ccc g   393
Phe Leu Ala His Gly Gly Gly Trp Ser Gly Asp Gly Ile Thr Leu Pro
                80                  85                  90 gtaagcctcg cgcttataca cgcatgcttt tcacacccca gctcgacaaa gaaccctcat   453
ttctgattaa acttttgtg gcttag gt  atg ctg gat ctc gag tat ggc ccg     505
                              Gly Met Leu Asp Leu Glu Tyr Gly Pro
                                              95                  100 aac ggg aac acc tgc tac ggc ctc ggc ccg gcg tcc atg cgg agc tgg     553
Asn Gly Asn Thr Cys Tyr Gly Leu Gly Pro Ala Ser Met Arg Ser Trp
                105                 110                 115 atc agc gac ttt gtc gag acg tac cac gcc aag acg ggc cgc tac ccc     601
Ile Ser Asp Phe Val Glu Thr Tyr His Ala Lys Thr Gly Arg Tyr Pro
        120                 125                 130 ctc atc tac acg tcg acg agc tgg tgg aag acg tgc acg ggc aac acg     649
Leu Ile Tyr Thr Ser Thr Ser Trp Trp Lys Thr Cys Thr Gly Asn Thr
            135                 140                 145 tcc ctc ttt gcc gac aag tgc ccg ctg gtc gtc gcg cgc tat aac agc     697
Ser Leu Phe Ala Asp Lys Cys Pro Leu Val Val Ala Arg Tyr Asn Ser
150                 155                 160 cag gtc ggc gag ctc cct gcc ggc tgg ggc ttc tac act ttc tgg cag     745
Gln Val Gly Glu Leu Pro Ala Gly Trp Gly Phe Tyr Thr Phe Trp Gln
165                 170                 175                 180 ttc aac gat cac tac aag cat ggc ggc gac tcg gac gtg ttc aac ggc     793
Phe Asn Asp His Tyr Lys His Gly Gly Asp Ser Asp Val Phe Asn Gly
                185                 190                 195 gcc tac tct cag ctt cag aag att gcc act ggt tag                     829
Ala Tyr Ser Gln Leu Gln Lys Ile Ala Thr Gly
            200                 205

<210> SEQ ID NO 68
<211> LENGTH: 226
<212> TYPE: PRT
<213> ORGANISM: Lecanicillium sp. WMM742

<400> SEQUENCE: 68

Met Lys Ser Phe Gly Leu Phe Ala Ser Leu Ala Ser Leu Ala Gly Ile
                -15                 -10                 -5

Ala Ser Ala Ser Val Gln Gly Phe Asp Ile Ser His Tyr Gln Ser Ser
        -1  1                   5                   10

Val Asn Phe Gly Ala Ala Tyr Ala Asp Gly Ala Arg Phe Val Ile Ile
        15                  20                  25

Lys Ala Thr Glu Gly Thr Thr Tyr Arg Asp Pro Lys Phe Ser Glu His
30                  35                  40                  45
```

Tyr Gly Gly Ala Thr Lys Ala Gly Phe Ile Arg Gly Gly Tyr His Phe
                    50                  55                  60

Ala Gln Pro Ala Ser Ser Gly Ala Ala Gln Ala Asn Phe Phe Leu
            65                  70                  75

Ala His Gly Gly Gly Trp Ser Gly Asp Gly Ile Thr Leu Pro Gly Met
        80                  85                  90

Leu Asp Leu Glu Tyr Gly Pro Asn Gly Asn Thr Cys Tyr Gly Leu Gly
 95                 100                 105

Pro Ala Ser Met Arg Ser Trp Ile Ser Asp Phe Val Glu Thr Tyr His
110                 115                 120                 125

Ala Lys Thr Gly Arg Tyr Pro Leu Ile Tyr Thr Ser Thr Ser Trp Trp
            130                 135                 140

Lys Thr Cys Thr Gly Asn Thr Ser Leu Phe Ala Asp Lys Cys Pro Leu
            145                 150                 155

Val Val Ala Arg Tyr Asn Ser Gln Val Gly Glu Leu Pro Ala Gly Trp
            160                 165                 170

Gly Phe Tyr Thr Phe Trp Gln Phe Asn Asp His Tyr Lys His Gly Gly
        175                 180                 185

Asp Ser Asp Val Phe Asn Gly Ala Tyr Ser Gln Leu Gln Lys Ile Ala
190                 195                 200                 205

Thr Gly

<210> SEQ ID NO 69
<211> LENGTH: 207
<212> TYPE: PRT
<213> ORGANISM: Lecanicillium sp. WMM742
<220> FEATURE:
<221> NAME/KEY: mat_peptide
<222> LOCATION: (1)..(207)

<400> SEQUENCE: 69

Ser Val Gln Gly Phe Asp Ile Ser His Tyr Gln Ser Ser Val Asn Phe
1               5                   10                  15

Gly Ala Ala Tyr Ala Asp Gly Ala Arg Phe Val Ile Ile Lys Ala Thr
            20                  25                  30

Glu Gly Thr Thr Tyr Arg Asp Pro Lys Phe Ser Glu His Tyr Gly Gly
        35                  40                  45

Ala Thr Lys Ala Gly Phe Ile Arg Gly Gly Tyr His Phe Ala Gln Pro
    50                  55                  60

Ala Ser Ser Gly Ala Ala Gln Ala Asn Phe Phe Leu Ala His Gly
65              70                  75                  80

Gly Gly Trp Ser Gly Asp Gly Ile Thr Leu Pro Gly Met Leu Asp Leu
            85                  90                  95

Glu Tyr Gly Pro Asn Gly Asn Thr Cys Tyr Gly Leu Gly Pro Ala Ser
        100                 105                 110

Met Arg Ser Trp Ile Ser Asp Phe Val Glu Thr Tyr His Ala Lys Thr
    115                 120                 125

Gly Arg Tyr Pro Leu Ile Tyr Thr Ser Thr Ser Trp Trp Lys Thr Cys
130                 135                 140

Thr Gly Asn Thr Ser Leu Phe Ala Asp Lys Cys Pro Leu Val Val Ala
145                 150                 155                 160

Arg Tyr Asn Ser Gln Val Gly Glu Leu Pro Ala Gly Trp Gly Phe Tyr
            165                 170                 175

Thr Phe Trp Gln Phe Asn Asp His Tyr Lys His Gly Gly Asp Ser Asp
        180                 185                 190

```
<210> SEQ ID NO 70
<211> LENGTH: 742
<212> TYPE: DNA
<213> ORGANISM: Zopfiella sp. t180-6
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(739)
<220> FEATURE:
<221> NAME/KEY: CDS
<222> LOCATION: (206)..(739)

<400> SEQUENCE: 70
```

| | | | | | | | | | | | | | | | | |
|---|---|---|---|---|---|---|---|---|---|---|---|---|---|---|---|---|
| atg | aaa | tcc | atc | ctc | ctc | tca | gct | gct | tcc | ctc | atc | ggg | gcc | gcc | caa | 48 |
| Met | Lys | Ser | Ile | Leu | Leu | Ser | Ala | Ala | Ser | Leu | Ile | Gly | Ala | Ala | Gln | |
| | -15 | | | | -10 | | | | | -5 | | | | | | |
| gcc | gcg | gtc | cag | gga | ttc | gac | gtc | tcc | cat | tgg | cag | tcc | agc | gtc | aac | 96 |
| Ala | Ala | Val | Gln | Gly | Phe | Asp | Val | Ser | His | Trp | Gln | Ser | Ser | Val | Asn | |
| -1 | 1 | | | | 5 | | | | | 10 | | | | | 15 | |
| ttt | gcc | gcc | gcc | tac | aac | tcg | ggg | gct | cgg | ttt | gtg | atc | atc | aag | | 141 |
| Phe | Ala | Ala | Ala | Tyr | Asn | Ser | Gly | Ala | Arg | Phe | Val | Ile | Ile | Lys | | |
| | | 20 | | | | | 25 | | | | | 30 | | | | | gtctttttttt ttccttcatt cattcaccaa taactaccta ctgacccgtg agatgtcatg    201

| | | | | | | | | | | | | | | | | |
|---|---|---|---|---|---|---|---|---|---|---|---|---|---|---|---|---|
| acag | gcc | acc | gag | agc | aac | aac | tac | atc | gac | ccc | aag | ttc | aac | acg | tac | 250 |
| | Ala | Thr | Glu | Ser | Asn | Asn | Tyr | Ile | Asp | Pro | Lys | Phe | Asn | Thr | Tyr | |
| | | 35 | | | | | 40 | | | | | 45 | | | | |
| tat | ccg | gcc | gcc | acc | agc | gcc | ggt | ctg | atc | cgg | ggc | ggg | tac | cac | ttc | 298 |
| Tyr | Pro | Ala | Ala | Thr | Ser | Ala | Gly | Leu | Ile | Arg | Gly | Gly | Tyr | His | Phe | |
| | | 50 | | | | | 55 | | | | | 60 | | | | |
| gcc | cac | ccg | ggg | gag | acc | acg | ggc | gcc | gtg | cag | gcg | gac | tac | ttc | atc | 346 |
| Ala | His | Pro | Gly | Glu | Thr | Thr | Gly | Ala | Val | Gln | Ala | Asp | Tyr | Phe | Ile | |
| | | 65 | | | | | 70 | | | | | 75 | | | | |
| gcg | cac | ggc | ggg | ggt | tgg | tcc | agc | gac | ggc | atc | act | ctc | ccg | gga | atg | 394 |
| Ala | His | Gly | Gly | Gly | Trp | Ser | Ser | Asp | Gly | Ile | Thr | Leu | Pro | Gly | Met | |
| | 80 | | | | | 85 | | | | | 90 | | | | | |
| ctc | gac | ctg | gag | aac | gca | agc | ggc | tac | ccg | gcc | tgc | tgg | ggc | ctg | tcg | 442 |
| Leu | Asp | Leu | Glu | Asn | Ala | Ser | Gly | Tyr | Pro | Ala | Cys | Trp | Gly | Leu | Ser | |
| | 95 | | | | | 100 | | | | | 105 | | | | | |
| cag | agc | gcc | atg | gtc | tcg | tgg | atc | aag | gcc | ttc | agc | gac | cgg | tac | aag | 490 |
| Gln | Ser | Ala | Met | Val | Ser | Trp | Ile | Lys | Ala | Phe | Ser | Asp | Arg | Tyr | Lys | |
| 110 | | | | | 115 | | | | | 120 | | | | | 125 | |
| gcc | cgc | acc | ggc | gtc | tac | ccc | atg | ctc | tac | acc | aac | ccg | tcc | tgg | tgg | 538 |
| Ala | Arg | Thr | Gly | Val | Tyr | Pro | Met | Leu | Tyr | Thr | Asn | Pro | Ser | Trp | Trp | |
| | | | 130 | | | | | 135 | | | | | 140 | | | |
| acc | agc | tgc | acc | ggc | aac | tcc | aac | gcc | ttc | gtc | aac | acc | aac | ccc | ctc | 586 |
| Thr | Ser | Cys | Thr | Gly | Asn | Ser | Asn | Ala | Phe | Val | Asn | Thr | Asn | Pro | Leu | |
| | | | 145 | | | | | 150 | | | | | 155 | | | |
| gtc | ctg | gcc | cgc | tac | gcc | agc | tcc | ccc | ggc | acc | atc | ccc | ggc | ggc | tgg | 634 |
| Val | Leu | Ala | Arg | Tyr | Ala | Ser | Ser | Pro | Gly | Thr | Ile | Pro | Gly | Gly | Trp | |
| | | | 160 | | | | | 165 | | | | | 170 | | | |
| ccc | tac | cag | acc | atc | tgg | cag | aac | tcg | gac | tcg | tat | acc | tac | ggc | ggc | 682 |
| Pro | Tyr | Gln | Thr | Ile | Trp | Gln | Asn | Ser | Asp | Ser | Tyr | Thr | Tyr | Gly | Gly | |
| | 175 | | | | | 180 | | | | | 185 | | | | | |
| gac | tcg | gac | atc | ttt | aat | ggg | gat | ctg | gct | ggt | ctc | aag | agg | ttg | gcc | 730 |
| Asp | Ser | Asp | Ile | Phe | Asn | Gly | Asp | Leu | Ala | Gly | Leu | Lys | Arg | Leu | Ala | |

Val Phe Asn Gly Ala Tyr Ser Gln Leu Gln Lys Ile Ala Thr Gly
        195                 200                 205

```
                190              195             200              205
aag ggt tct taa                                                                742
Lys Gly Ser
```

<210> SEQ ID NO 71
<211> LENGTH: 225
<212> TYPE: PRT
<213> ORGANISM: Zopfiella sp. t180-6

<400> SEQUENCE: 71

```
Met Lys Ser Ile Leu Leu Ser Ala Ala Ser Leu Ile Gly Ala Ala Gln
        -15             -10                 -5

Ala Ala Val Gln Gly Phe Asp Val Ser His Trp Gln Ser Ser Val Asn
-1   1           5                   10                  15

Phe Ala Ala Ala Tyr Asn Ser Gly Ala Arg Phe Val Ile Ile Lys Ala
                20                  25                  30

Thr Glu Ser Asn Asn Tyr Ile Asp Pro Lys Phe Asn Thr Tyr Tyr Pro
            35                  40                  45

Ala Ala Thr Ser Ala Gly Leu Ile Arg Gly Gly Tyr His Phe Ala His
            50                  55                  60

Pro Gly Glu Thr Thr Gly Ala Val Gln Ala Asp Tyr Phe Ile Ala His
65                  70                  75

Gly Gly Gly Trp Ser Ser Asp Gly Ile Thr Leu Pro Gly Met Leu Asp
80                  85                  90                  95

Leu Glu Asn Ala Ser Gly Tyr Pro Ala Cys Trp Gly Leu Ser Gln Ser
                100                 105                 110

Ala Met Val Ser Trp Ile Lys Ala Phe Ser Asp Arg Tyr Lys Ala Arg
            115                 120                 125

Thr Gly Val Tyr Pro Met Leu Tyr Thr Asn Pro Ser Trp Trp Thr Ser
        130                 135                 140

Cys Thr Gly Asn Ser Asn Ala Phe Val Asn Thr Asn Pro Leu Val Leu
    145                 150                 155

Ala Arg Tyr Ala Ser Ser Pro Gly Thr Ile Pro Gly Gly Trp Pro Tyr
160                 165                 170                 175

Gln Thr Ile Trp Gln Asn Ser Asp Ser Tyr Thr Tyr Gly Gly Asp Ser
                180                 185                 190

Asp Ile Phe Asn Gly Asp Leu Ala Gly Leu Lys Arg Leu Ala Lys Gly
            195                 200                 205

Ser
```

<210> SEQ ID NO 72
<211> LENGTH: 208
<212> TYPE: PRT
<213> ORGANISM: Zopfiella sp. t180-6
<220> FEATURE:
<221> NAME/KEY: mat_peptide
<222> LOCATION: (1)..(208)

<400> SEQUENCE: 72

```
Ala Val Gln Gly Phe Asp Val Ser His Trp Gln Ser Ser Val Asn Phe
1               5                   10                  15

Ala Ala Ala Tyr Asn Ser Gly Ala Arg Phe Val Ile Ile Lys Ala Thr
                20                  25                  30

Glu Ser Asn Asn Tyr Ile Asp Pro Lys Phe Asn Thr Tyr Tyr Pro Ala
            35                  40                  45

Ala Thr Ser Ala Gly Leu Ile Arg Gly Gly Tyr His Phe Ala His Pro
        50                  55                  60
```

```
Gly Glu Thr Thr Gly Ala Val Gln Ala Asp Tyr Phe Ile Ala His Gly
 65                  70                  75                  80

Gly Gly Trp Ser Ser Asp Gly Ile Thr Leu Pro Gly Met Leu Asp Leu
                 85                  90                  95

Glu Asn Ala Ser Gly Tyr Pro Ala Cys Trp Gly Leu Ser Gln Ser Ala
            100                 105                 110

Met Val Ser Trp Ile Lys Ala Phe Ser Asp Arg Tyr Lys Ala Arg Thr
        115                 120                 125

Gly Val Tyr Pro Met Leu Tyr Thr Asn Pro Ser Trp Trp Thr Ser Cys
    130                 135                 140

Thr Gly Asn Ser Asn Ala Phe Val Asn Thr Asn Pro Leu Val Leu Ala
145                 150                 155                 160

Arg Tyr Ala Ser Ser Pro Gly Thr Ile Pro Gly Gly Trp Pro Tyr Gln
                165                 170                 175

Thr Ile Trp Gln Asn Ser Asp Ser Tyr Thr Tyr Gly Gly Asp Ser Asp
            180                 185                 190

Ile Phe Asn Gly Asp Leu Ala Gly Leu Lys Arg Leu Ala Lys Gly Ser
        195                 200                 205

<210> SEQ ID NO 73
<211> LENGTH: 767
<212> TYPE: DNA
<213> ORGANISM: Malbranchea flava
<220> FEATURE:
<221> NAME/KEY: CDS
<222> LOCATION: (1)..(174)
<220> FEATURE:
<221> NAME/KEY: sig_peptide
<222> LOCATION: (1)..(54)
<220> FEATURE:
<221> NAME/KEY: mat_peptide
<222> LOCATION: (55)..(764)
<220> FEATURE:
<221> NAME/KEY: CDS
<222> LOCATION: (234)..(764)

<400> SEQUENCE: 73 atg aag ctg tct ctc ctc ctt att gtt gct gca tca ctg gcc gtg gcc    48
Met Lys Leu Ser Leu Leu Leu Ile Val Ala Ala Ser Leu Ala Val Ala
        -15                 -10                  -5 agt gca ggc ccc aag gag ttc gag tca cgc gcg tcg ggc gtc cag ggc    96
Ser Ala Gly Pro Lys Glu Phe Glu Ser Arg Ala Ser Gly Val Gln Gly
     -1   1               5                  10 ttt gac atc tct ggt tgg cag tcc aac gtc aat ttt gca ggt gca tac   144
Phe Asp Ile Ser Gly Trp Gln Ser Asn Val Asn Phe Ala Gly Ala Tyr
 15                  20                  25                  30 aat tct ggc gca cgc ttc gtc atg atc aag gtacatttga gtgaattcgt     194
Asn Ser Gly Ala Arg Phe Val Met Ile Lys
                 35                  40 ttctcctggt ataataccct gactaatgta aagatccag gct agc gag ggt acc    248
                                           Ala Ser Glu Gly Thr
                                                            45 acc ttc aag gac cgt caa ttc agc aat cat tac att ggc gcc acc aag   296
Thr Phe Lys Asp Arg Gln Phe Ser Asn His Tyr Ile Gly Ala Thr Lys
                 50                  55                  60 gct ggc ttt atc cgt ggc ggc tac cac ttt gcg ttg cca gac gtc agc   344
Ala Gly Phe Ile Arg Gly Gly Tyr His Phe Ala Leu Pro Asp Val Ser
             65                  70                  75 agc gcc act gcc caa gtg aac cat ttc ctg gcc agc ggt ggt ggc tgg   392
Ser Ala Thr Ala Gln Val Asn His Phe Leu Ala Ser Gly Gly Gly Trp
         80                  85                  90
```

```
agc aga gac ggc atc acg ctg ccg ggc atg ctg gac atc gag agc aac      440
Ser Arg Asp Gly Ile Thr Leu Pro Gly Met Leu Asp Ile Glu Ser Asn
    95              100                 105 ccg tat ggc gcc cag tgc tac ggc ctt gac gct ggt cgt atg gtt gcc      488
Pro Tyr Gly Ala Gln Cys Tyr Gly Leu Asp Ala Gly Arg Met Val Ala
110             115                 120                 125 tgg atc cgg gag ttt gtt gac gcg tac aag cgc gca act gga cgg tat      536
Trp Ile Arg Glu Phe Val Asp Ala Tyr Lys Arg Ala Thr Gly Arg Tyr
                130                 135                 140 cct ctg atc tac acg tct ccc agc tgg tgg cag act tgc acg ggc aat      584
Pro Leu Ile Tyr Thr Ser Pro Ser Trp Trp Gln Thr Cys Thr Gly Asn
            145                 150                 155 agc aat gcc ttt ata gac aag tgc ccg ctt gtg ttg gca cgg tgg gcg      632
Ser Asn Ala Phe Ile Asp Lys Cys Pro Leu Val Leu Ala Arg Trp Ala
        160                 165                 170 agt agc cct ggc act ccg cct ggt ggg tgg ccg ttc cac agt ttt tgg      680
Ser Ser Pro Gly Thr Pro Pro Gly Gly Trp Pro Phe His Ser Phe Trp
    175                 180                 185 cag tac gcc gat tcc tat caa ttc ggt ggt gac gcc cag gta ttc aat      728
Gln Tyr Ala Asp Ser Tyr Gln Phe Gly Gly Asp Ala Gln Val Phe Asn
190                 195                 200                 205 ggc gat gag gct ggg ttg aag aga atg gcc cta ggt taa                  767
Gly Asp Glu Ala Gly Leu Lys Arg Met Ala Leu Gly
                210                 215

<210> SEQ ID NO 74
<211> LENGTH: 235
<212> TYPE: PRT
<213> ORGANISM: Malbranchea flava

<400> SEQUENCE: 74

Met Lys Leu Ser Leu Leu Leu Ile Val Ala Ala Ser Leu Ala Val Ala
            -15                 -10                  -5

Ser Ala Gly Pro Lys Glu Phe Glu Ser Arg Ala Ser Gly Val Gln Gly
        -1  1               5                  10

Phe Asp Ile Ser Gly Trp Gln Ser Asn Val Asn Phe Ala Gly Ala Tyr
15                  20                  25                  30

Asn Ser Gly Ala Arg Phe Val Met Ile Lys Ala Ser Glu Gly Thr Thr
                35                  40                  45

Phe Lys Asp Arg Gln Phe Ser Asn His Tyr Ile Gly Ala Thr Lys Ala
            50                  55                  60

Gly Phe Ile Arg Gly Gly Tyr His Phe Ala Leu Pro Asp Val Ser Ser
        65                  70                  75

Ala Thr Ala Gln Val Asn His Phe Leu Ala Ser Gly Gly Trp Ser
    80                  85                  90

Arg Asp Gly Ile Thr Leu Pro Gly Met Leu Asp Ile Glu Ser Asn Pro
95                  100                 105                 110

Tyr Gly Ala Gln Cys Tyr Gly Leu Asp Ala Gly Arg Met Val Ala Trp
                115                 120                 125

Ile Arg Glu Phe Val Asp Ala Tyr Lys Arg Ala Thr Gly Arg Tyr Pro
            130                 135                 140

Leu Ile Tyr Thr Ser Pro Ser Trp Trp Gln Thr Cys Thr Gly Asn Ser
        145                 150                 155

Asn Ala Phe Ile Asp Lys Cys Pro Leu Val Leu Ala Arg Trp Ala Ser
    160                 165                 170

Ser Pro Gly Thr Pro Pro Gly Gly Trp Pro Phe His Ser Phe Trp Gln
175                 180                 185                 190
```

```
Tyr Ala Asp Ser Tyr Gln Phe Gly Gly Asp Ala Gln Val Phe Asn Gly
            195                 200                 205

Asp Glu Ala Gly Leu Lys Arg Met Ala Leu Gly
        210                 215
```

<210> SEQ ID NO 75
<211> LENGTH: 217
<212> TYPE: PRT
<213> ORGANISM: Malbranchea flava
<220> FEATURE:
<221> NAME/KEY: mat_peptide
<222> LOCATION: (1)..(217)

<400> SEQUENCE: 75

```
Gly Pro Lys Glu Phe Glu Ser Arg Ala Ser Gly Val Gln Gly Phe Asp
1               5                   10                  15

Ile Ser Gly Trp Gln Ser Asn Val Asn Phe Ala Gly Ala Tyr Asn Ser
            20                  25                  30

Gly Ala Arg Phe Val Met Ile Lys Ala Ser Glu Gly Thr Thr Phe Lys
        35                  40                  45

Asp Arg Gln Phe Ser Asn His Tyr Ile Gly Ala Thr Lys Ala Gly Phe
50                  55                  60

Ile Arg Gly Gly Tyr His Phe Ala Leu Pro Asp Val Ser Ser Ala Thr
65                  70                  75                  80

Ala Gln Val Asn His Phe Leu Ala Ser Gly Gly Trp Ser Arg Asp
            85                  90                  95

Gly Ile Thr Leu Pro Gly Met Leu Asp Ile Glu Ser Asn Pro Tyr Gly
            100                 105                 110

Ala Gln Cys Tyr Gly Leu Asp Ala Gly Arg Met Val Ala Trp Ile Arg
            115                 120                 125

Glu Phe Val Asp Ala Tyr Lys Arg Ala Thr Gly Arg Tyr Pro Leu Ile
            130                 135                 140

Tyr Thr Ser Pro Ser Trp Trp Gln Thr Cys Thr Gly Asn Ser Asn Ala
145                 150                 155                 160

Phe Ile Asp Lys Cys Pro Leu Val Leu Ala Arg Trp Ala Ser Ser Pro
            165                 170                 175

Gly Thr Pro Pro Gly Gly Trp Pro Phe His Ser Phe Trp Gln Tyr Ala
            180                 185                 190

Asp Ser Tyr Gln Phe Gly Gly Asp Ala Gln Val Phe Asn Gly Asp Glu
            195                 200                 205

Ala Gly Leu Lys Arg Met Ala Leu Gly
        210                 215
```

<210> SEQ ID NO 76
<211> LENGTH: 935
<212> TYPE: DNA
<213> ORGANISM: Hypholoma polytrichi
<220> FEATURE:
<221> NAME/KEY: CDS
<222> LOCATION: (1)..(396)
<220> FEATURE:
<221> NAME/KEY: sig_peptide
<222> LOCATION: (1)..(60)
<220> FEATURE:
<221> NAME/KEY: mat_peptide
<222> LOCATION: (61)..(932)
<220> FEATURE:
<221> NAME/KEY: CDS
<222> LOCATION: (454)..(552)
<220> FEATURE:
<221> NAME/KEY: CDS

```
<222> LOCATION: (620)..(703)
<220> FEATURE:
<221> NAME/KEY: CDS
<222> LOCATION: (770)..(798)
<220> FEATURE:
<221> NAME/KEY: CDS
<222> LOCATION: (857)..(932)

<400> SEQUENCE: 76 atg gct aag ctc ttg aaa caa ctc gtg ctc ctt cct ttc ctc gcg ctc        48
Met Ala Lys Leu Leu Lys Gln Leu Val Leu Leu Pro Phe Leu Ala Leu
-20              -15                 -10                 -5 gcg gcg cac gcg ctc gtc tac ggc gtg gac tcc tcc agc ctc gtc ccc        96
Ala Ala His Ala Leu Val Tyr Gly Val Asp Ser Ser Ser Leu Val Pro
        -1  1                 5                  10 gtc gcg acg tac cag aag gcg ctc ggc gag ggc ttc acg aag gcg gtt       144
Val Ala Thr Tyr Gln Lys Ala Leu Gly Glu Gly Phe Thr Lys Ala Val
        15                  20                  25 atc cgc ggg tac gag gag gcg tgc ggc gtg ggg ggc gag gtc gac ccc       192
Ile Arg Gly Tyr Glu Glu Ala Cys Gly Val Gly Gly Glu Val Asp Pro
    30                  35                  40 aac ttc gtc ccg tcg tac aag aac gcg cgc gcg ggg tac acg gac           240
Asn Phe Val Pro Ser Tyr Lys Asn Ala Arg Ala Ala Gly Tyr Thr Asp
45                  50                  55                  60 att gac atg tac tgg ttc ccg tgc aac ggc tcg acg cac agc tgc aag       288
Ile Asp Met Tyr Trp Phe Pro Cys Asn Gly Ser Thr His Ser Cys Lys
                65                  70                  75 tcg tat gcg gcg cag ctc gcc gcg atc gcg gcc gcg ttc tct gcg aat       336
Ser Tyr Ala Ala Gln Leu Ala Ala Ile Ala Ala Ala Phe Ser Ala Asn
            80                  85                  90 gcg atg aag atc ggc acg atc tgg atc gac atc gag aag gac gcg gcg       384
Ala Met Lys Ile Gly Thr Ile Trp Ile Asp Ile Glu Lys Asp Ala Ala
        95                  100                 105 atc tgc aac aac gtgagtggtc cgtcgtgttg tgcggcgcac ggcgtgagtt           436
Ile Cys Asn Asn
        110 gaccgtttgg cacacag tgg gac tat ggc acg gcg ggg aac ctc gcg cag        486
                   Trp Asp Tyr Gly Thr Ala Gly Asn Leu Ala Gln
                                   115                 120 gcg aaa gcg ctg atc gcg gct gcg aag gcg tcg gga ttc aat ttt ggc       534
Ala Lys Ala Leu Ile Ala Ala Ala Lys Ala Ser Gly Phe Asn Phe Gly
        125                 130                 135 atc tac agt agc cct ggg gtatgtgtgg tgctgcatta gcctgccaat              582
Ile Tyr Ser Ser Pro Gly
140             145 ggatcttcac tgaaaatttg gattctcgta tacacag gag tgg agc aca att ttc      637
                                           Glu Trp Ser Thr Ile Phe
                                                               150 ggc tcg acg agt gtc gtc gtc gac aac tcg gca ccg ctc tgg ttt gct       685
Gly Ser Thr Ser Val Val Val Asp Asn Ser Ala Pro Leu Trp Phe Ala
            155                 160                 165 act tac aac aac gtc caa gtacgtgctc acattaattg actgctatct              733
Thr Tyr Asn Asn Val Gln
            170 gctgcttttc gttgcttacc tctcacttcg tggcag acc ctt act ttg gga aca       787
                                       Thr Leu Thr Leu Gly Thr
                                                       175 ccg ttc ggc gg  gtaagtcatg cgcccaacgt caattctgat tctgtgattc           838
Pro Phe Gly Gly
180 tcaaattgtg cgccttag c tgg agt acg gct gtg ggc cac caa tat act gac     890
```

```
                        Trp Ser Thr Ala Val Gly His Gln Tyr Thr Asp
                                    185                 190 gtc tcg gcg tcg ggg tta ttc gat ctc aac gtt ttt gcc cac taa          935
Val Ser Ala Ser Gly Leu Phe Asp Leu Asn Val Phe Ala His
195             200                 205

<210> SEQ ID NO 77
<211> LENGTH: 228
<212> TYPE: PRT
<213> ORGANISM: Hypholoma polytrichi

<400> SEQUENCE: 77

Met Ala Lys Leu Leu Lys Gln Leu Val Leu Leu Pro Phe Leu Ala Leu
-20                 -15                 -10                 -5

Ala Ala His Ala Leu Val Tyr Gly Val Asp Ser Ser Ser Leu Val Pro
            -1  1                   5                   10

Val Ala Thr Tyr Gln Lys Ala Leu Gly Glu Gly Phe Thr Lys Ala Val
                15                  20                  25

Ile Arg Gly Tyr Glu Glu Ala Cys Gly Val Gly Glu Val Asp Pro
 30                  35                  40

Asn Phe Val Pro Ser Tyr Lys Asn Ala Arg Ala Ala Gly Tyr Thr Asp
 45                  50                  55                  60

Ile Asp Met Tyr Trp Phe Pro Cys Asn Gly Ser Thr His Ser Cys Lys
                 65                  70                  75

Ser Tyr Ala Ala Gln Leu Ala Ala Ile Ala Ala Ala Phe Ser Ala Asn
                 80                  85                  90

Ala Met Lys Ile Gly Thr Ile Trp Ile Asp Ile Glu Lys Asp Ala Ala
                 95                 100                 105

Ile Cys Asn Asn Trp Asp Tyr Gly Thr Ala Gly Asn Leu Ala Gln Ala
            110                 115                 120

Lys Ala Leu Ile Ala Ala Ala Lys Ala Ser Gly Phe Asn Phe Gly Ile
125                 130                 135                 140

Tyr Ser Ser Pro Gly Glu Trp Ser Thr Ile Phe Gly Ser Thr Ser Val
                145                 150                 155

Val Val Asp Asn Ser Ala Pro Leu Trp Phe Ala Thr Tyr Asn Asn Val
                160                 165                 170

Gln Thr Leu Thr Leu Gly Thr Pro Phe Gly Gly Trp Ser Thr Ala Val
                175                 180                 185

Gly His Gln Tyr Thr Asp Val Ser Ala Ser Gly Leu Phe Asp Leu Asn
        190                 195                 200

Val Phe Ala His
205

<210> SEQ ID NO 78
<211> LENGTH: 687
<212> TYPE: DNA
<213> ORGANISM: Artificial Sequence
<220> FEATURE:
<223> OTHER INFORMATION: Codon optimised DNA sequence
<220> FEATURE:
<221> NAME/KEY: CDS
<222> LOCATION: (1)..(684)
<220> FEATURE:
<221> NAME/KEY: sig_peptide
<222> LOCATION: (1)..(60)
<220> FEATURE:
<221> NAME/KEY: mat_peptide
<222> LOCATION: (61)..(694)

<400> SEQUENCE: 78
```

| | | |
|---|---|---|
| atg gca aag ctc ctc aag cag ttg gtg ttg ctc ccg ttc ctc gcg ttg<br>Met Ala Lys Leu Leu Lys Gln Leu Val Leu Leu Pro Phe Leu Ala Leu<br>-20                          -15                         -10                        -5 | 48 | |
| gca gca cac gca ttg gtc tac gga gtc gat tcg tcc tcg ttg gtc cct<br>Ala Ala His Ala Leu Val Tyr Gly Val Asp Ser Ser Ser Leu Val Pro<br>            -1  1                     5                           10 | 96 | |
| gtg gcg acg tat cag aag gca ttg gga gaa ggc ttc aca aag gcc gtc<br>Val Ala Thr Tyr Gln Lys Ala Leu Gly Glu Gly Phe Thr Lys Ala Val<br>            15                    20                    25 | 144 | |
| att agg ggc tac gaa gag gcc tgt gga gtc gga gag gtc gat ccc<br>Ile Arg Gly Tyr Glu Glu Ala Cys Gly Val Gly Glu Val Asp Pro<br>30                         35                      40 | 192 | |
| aac ttc gtc ccc tcc tac aaa aac gca cga gcg gca gga tac aca gac<br>Asn Phe Val Pro Ser Tyr Lys Asn Ala Arg Ala Ala Gly Tyr Thr Asp<br>45                         50                      55                    60 | 240 | |
| atc gat atg tac tgg ttc ccc tgt aac ggc tcc act cat tcg tgt aaa<br>Ile Asp Met Tyr Trp Phe Pro Cys Asn Gly Ser Thr His Ser Cys Lys<br>                         65                      70                    75 | 288 | |
| tcg tat gcc gca cag ttg gca gcc att gcc gca gcc ttc tcg gcg aac<br>Ser Tyr Ala Ala Gln Leu Ala Ala Ile Ala Ala Ala Phe Ser Ala Asn<br>               80                        85                     90 | 336 | |
| gcc atg aag atc ggt act att tgg atc gac atc gaa aaa gat gca gcc<br>Ala Met Lys Ile Gly Thr Ile Trp Ile Asp Ile Glu Lys Asp Ala Ala<br>          95                     100                     105 | 384 | |
| atc tgt aac aac tgg gat tac ggc act gca ggt aac ttg gcc cag gcg<br>Ile Cys Asn Asn Trp Asp Tyr Gly Thr Ala Gly Asn Leu Ala Gln Ala<br>       110                     115                     120 | 432 | |
| aag gca ttg att gcc gca gcg aag gca tcc ggt ttc aac ttc ggc atc<br>Lys Ala Leu Ile Ala Ala Ala Lys Ala Ser Gly Phe Asn Phe Gly Ile<br>125                       130                     135                   140 | 480 | |
| tac tcg tcg cct gga gag tgg tcg acc atc ttc ggc tcg acc tcg gtc<br>Tyr Ser Ser Pro Gly Glu Trp Ser Thr Ile Phe Gly Ser Thr Ser Val<br>                     145                     150                     155 | 528 | |
| gtc gtc gac aac tcc gca ccg ctc tgg ttc gcg acc tat aac aac gtc<br>Val Val Asp Asn Ser Ala Pro Leu Trp Phe Ala Thr Tyr Asn Asn Val<br>                 160                     165                     170 | 576 | |
| cag acc ctc acg ctc ggc act cct ttc gga ggc tgg tcg aca gcc gtc<br>Gln Thr Leu Thr Leu Gly Thr Pro Phe Gly Gly Trp Ser Thr Ala Val<br>             175                     180                     185 | 624 | |
| ggt cat cag tat acc gat gtg tcc gcc tcc gga ctc ttc gac ctc aac<br>Gly His Gln Tyr Thr Asp Val Ser Ala Ser Gly Leu Phe Asp Leu Asn<br>         190                     195                     200 | 672 | |
| gtc ttc gcc cac taa<br>Val Phe Ala His<br>205 | 687 | |

<210> SEQ ID NO 79
<211> LENGTH: 228
<212> TYPE: PRT
<213> ORGANISM: Artificial Sequence
<220> FEATURE:
<223> OTHER INFORMATION: Synthetic Construct

<400> SEQUENCE: 79

Met Ala Lys Leu Leu Lys Gln Leu Val Leu Leu Pro Phe Leu Ala Leu
-20                       -15                      -10                     -5

Ala Ala His Ala Leu Val Tyr Gly Val Asp Ser Ser Ser Leu Val Pro
        -1  1                   5                         10

Val Ala Thr Tyr Gln Lys Ala Leu Gly Glu Gly Phe Thr Lys Ala Val
        15                    20                    25

```
Ile Arg Gly Tyr Glu Glu Ala Cys Gly Val Gly Gly Glu Val Asp Pro
    30                  35                  40

Asn Phe Val Pro Ser Tyr Lys Asn Ala Arg Ala Ala Gly Tyr Thr Asp
 45                  50                  55                  60

Ile Asp Met Tyr Trp Phe Pro Cys Asn Gly Ser Thr His Ser Cys Lys
                 65                  70                  75

Ser Tyr Ala Ala Gln Leu Ala Ala Ile Ala Ala Ala Phe Ser Ala Asn
             80                  85                  90

Ala Met Lys Ile Gly Thr Ile Trp Ile Asp Ile Glu Lys Asp Ala Ala
         95                 100                 105

Ile Cys Asn Asn Trp Asp Tyr Gly Thr Ala Gly Asn Leu Ala Gln Ala
110                 115                 120

Lys Ala Leu Ile Ala Ala Lys Ala Ser Gly Phe Asn Phe Gly Ile
125                 130                 135                 140

Tyr Ser Ser Pro Gly Glu Trp Ser Thr Ile Phe Gly Ser Thr Ser Val
                145                 150                 155

Val Val Asp Asn Ser Ala Pro Leu Trp Phe Ala Thr Tyr Asn Asn Val
            160                 165                 170

Gln Thr Leu Thr Leu Gly Thr Pro Phe Gly Gly Trp Ser Thr Ala Val
        175                 180                 185

Gly His Gln Tyr Thr Asp Val Ser Ala Ser Gly Leu Phe Asp Leu Asn
    190                 195                 200

Val Phe Ala His
205

<210> SEQ ID NO 80
<211> LENGTH: 208
<212> TYPE: PRT
<213> ORGANISM: Hypholoma polytrichi
<220> FEATURE:
<221> NAME/KEY: mat_peptide
<222> LOCATION: (1)..(208)

<400> SEQUENCE: 80

Leu Val Tyr Gly Val Asp Ser Ser Leu Val Pro Val Ala Thr Tyr
 1               5                  10                  15

Gln Lys Ala Leu Gly Glu Gly Phe Thr Lys Ala Val Ile Arg Gly Tyr
             20                  25                  30

Glu Glu Ala Cys Gly Val Gly Gly Glu Val Asp Pro Asn Phe Val Pro
         35                  40                  45

Ser Tyr Lys Asn Ala Arg Ala Ala Gly Tyr Thr Asp Ile Asp Met Tyr
     50                  55                  60

Trp Phe Pro Cys Asn Gly Ser Thr His Ser Cys Lys Ser Tyr Ala Ala
 65                  70                  75                  80

Gln Leu Ala Ala Ile Ala Ala Ala Phe Ser Ala Asn Ala Met Lys Ile
             85                  90                  95

Gly Thr Ile Trp Ile Asp Ile Glu Lys Asp Ala Ala Ile Cys Asn Asn
            100                 105                 110

Trp Asp Tyr Gly Thr Ala Gly Asn Leu Ala Gln Ala Lys Ala Leu Ile
        115                 120                 125

Ala Ala Ala Lys Ala Ser Gly Phe Asn Phe Gly Ile Tyr Ser Ser Pro
    130                 135                 140

Gly Glu Trp Ser Thr Ile Phe Gly Ser Thr Ser Val Val Val Asp Asn
145                 150                 155                 160

Ser Ala Pro Leu Trp Phe Ala Thr Tyr Asn Asn Val Gln Thr Leu Thr
                165                 170                 175
```

```
Leu Gly Thr Pro Phe Gly Gly Trp Ser Thr Ala Val Gly His Gln Tyr
            180                 185                 190

Thr Asp Val Ser Ala Ser Gly Leu Phe Asp Leu Asn Val Phe Ala His
        195                 200                 205

<210> SEQ ID NO 81
<211> LENGTH: 701
<212> TYPE: DNA
<213> ORGANISM: Aspergillus deflectus
<220> FEATURE:
<221> NAME/KEY: CDS
<222> LOCATION: (1)..(135)
<220> FEATURE:
<221> NAME/KEY: sig_peptide
<222> LOCATION: (1)..(45)
<220> FEATURE:
<221> NAME/KEY: mat_peptide
<222> LOCATION: (46)..(698)
<220> FEATURE:
<221> NAME/KEY: CDS
<222> LOCATION: (186)..(698)

<400> SEQUENCE: 81 atg aag ctt ctt tcc gcc ctt gcg ctc cct ggt ctg gcc tac gcc gca    48
Met Lys Leu Leu Ser Ala Leu Ala Leu Pro Gly Leu Ala Tyr Ala Ala
-15             -10                 -5                  -1  1 gtc caa ggc ttc gac att tcg cac tac cag tcg agt gtc gac tat gcc    96
Val Gln Gly Phe Asp Ile Ser His Tyr Gln Ser Ser Val Asp Tyr Ala
            5                   10                  15 ggc gcc tac tcc tcg ggt gcc cgc ttc gtc atg atc aag gtaccctcct   145
Gly Ala Tyr Ser Ser Gly Ala Arg Phe Val Met Ile Lys
            20                  25                  30 agcctctacc agcagaaaca agggactaag agagagaaag gcc acc gaa gga acg   200
                                            Ala Thr Glu Gly Thr
                                                            35 acg tat acg gac ccg gct ttt agt act cac tat acg ggt gct aca aac   248
Thr Tyr Thr Asp Pro Ala Phe Ser Thr His Tyr Thr Gly Ala Thr Asn
                40                  45                  50 gct ggc ctg atc cgt ggc ggt tat cac ttt gct cgc ccc ggt tct agt   296
Ala Gly Leu Ile Arg Gly Gly Tyr His Phe Ala Arg Pro Gly Ser Ser
            55                  60                  65 tct ggt gcc gcc caa gca gaa tat ttc ctt gcc cat ggc ggt ggg tgg   344
Ser Gly Ala Ala Gln Ala Glu Tyr Phe Leu Ala His Gly Gly Gly Trp
        70                  75                  80 act ggt gat gga atc acc ctt cct ggt atg ttg gac ctt gag gct gga   392
Thr Gly Asp Gly Ile Thr Leu Pro Gly Met Leu Asp Leu Glu Ala Gly
    85                  90                  95 tgc tct ggt ctg tcg gcc tca gcc atg gtc tcc tgg atc cag gac ttt   440
Cys Ser Gly Leu Ser Ala Ser Ala Met Val Ser Trp Ile Gln Asp Phe
100                 105                 110                 115 ggc gag acc tac aag gca agc acg gga cgg tat cca atg atc tat acc   488
Gly Glu Thr Tyr Lys Ala Ser Thr Gly Arg Tyr Pro Met Ile Tyr Thr
                120                 125                 130 aca aca agc tgg tgg agt tcc tgt aca ggc aac aat ggt ggc ttt ggc   536
Thr Thr Ser Trp Trp Ser Ser Cys Thr Gly Asn Asn Gly Gly Phe Gly
            135                 140                 145 gat tat cct ctg gtc ctt gcg aga tgg gct tca tcg cca ggc gag ctt   584
Asp Tyr Pro Leu Val Leu Ala Arg Trp Ala Ser Ser Pro Gly Glu Leu
        150                 155                 160 ccg aac ggc tgg tcg gtg cac tct ttc tgg caa aat gcc gat act tat   632
Pro Asn Gly Trp Ser Val His Ser Phe Trp Gln Asn Ala Asp Thr Tyr
    165                 170                 175
```

```
gag tat ggg ggt gat tcc gag att tgg aac gga agt caa gaa aat ctt      680
Glu Tyr Gly Gly Asp Ser Glu Ile Trp Asn Gly Ser Gln Glu Asn Leu
180             185                 190                 195 gtc aag ttt gcc tct cag tga                                          701
Val Lys Phe Ala Ser Gln
            200
```

<210> SEQ ID NO 82
<211> LENGTH: 216
<212> TYPE: PRT
<213> ORGANISM: Aspergillus deflectus

<400> SEQUENCE: 82

```
Met Lys Leu Leu Ser Ala Leu Ala Leu Pro Gly Leu Ala Tyr Ala Ala
-15                 -10                 -5                  -1  1

Val Gln Gly Phe Asp Ile Ser His Tyr Gln Ser Ser Val Asp Tyr Ala
                5                   10                  15

Gly Ala Tyr Ser Ser Gly Ala Arg Phe Val Met Ile Lys Ala Thr Glu
            20                  25                  30

Gly Thr Thr Tyr Thr Asp Pro Ala Phe Ser Thr His Tyr Thr Gly Ala
        35                  40                  45

Thr Asn Ala Gly Leu Ile Arg Gly Gly Tyr His Phe Ala Arg Pro Gly
50                  55                  60                  65

Ser Ser Ser Gly Ala Ala Gln Ala Glu Tyr Phe Leu Ala His Gly Gly
                70                  75                  80

Gly Trp Thr Gly Asp Gly Ile Thr Leu Pro Gly Met Leu Asp Leu Glu
            85                  90                  95

Ala Gly Cys Ser Gly Leu Ser Ala Ser Ala Met Val Ser Trp Ile Gln
        100                 105                 110

Asp Phe Gly Glu Thr Tyr Lys Ala Ser Thr Gly Arg Tyr Pro Met Ile
    115                 120                 125

Tyr Thr Thr Thr Ser Trp Trp Ser Ser Cys Thr Gly Asn Asn Gly Gly
130                 135                 140                 145

Phe Gly Asp Tyr Pro Leu Val Leu Ala Arg Trp Ala Ser Ser Pro Gly
                150                 155                 160

Glu Leu Pro Asn Gly Trp Ser Val His Ser Phe Trp Gln Asn Ala Asp
            165                 170                 175

Thr Tyr Glu Tyr Gly Gly Asp Ser Glu Ile Trp Asn Gly Ser Gln Glu
        180                 185                 190

Asn Leu Val Lys Phe Ala Ser Gln
    195                 200
```

<210> SEQ ID NO 83
<211> LENGTH: 201
<212> TYPE: PRT
<213> ORGANISM: Aspergillus deflectus
<220> FEATURE:
<221> NAME/KEY: mat_peptide
<222> LOCATION: (1)..(201)

<400> SEQUENCE: 83

```
Ala Val Gln Gly Phe Asp Ile Ser His Tyr Gln Ser Ser Val Asp Tyr
1               5                   10                  15

Ala Gly Ala Tyr Ser Ser Gly Ala Arg Phe Val Met Ile Lys Ala Thr
            20                  25                  30

Glu Gly Thr Thr Tyr Thr Asp Pro Ala Phe Ser Thr His Tyr Thr Gly
        35                  40                  45

Ala Thr Asn Ala Gly Leu Ile Arg Gly Gly Tyr His Phe Ala Arg Pro
```

```
                  50                  55                  60
Gly Ser Ser Gly Ala Ala Gln Ala Glu Tyr Phe Leu Ala His Gly
 65                  70                  75                  80

Gly Gly Trp Thr Gly Asp Gly Ile Thr Leu Pro Gly Met Leu Asp Leu
                 85                  90                  95

Glu Ala Gly Cys Ser Gly Leu Ser Ala Ser Ala Met Val Ser Trp Ile
             100                 105                 110

Gln Asp Phe Gly Glu Thr Tyr Lys Ala Ser Thr Gly Arg Tyr Pro Met
         115                 120                 125

Ile Tyr Thr Thr Thr Ser Trp Trp Ser Ser Cys Thr Gly Asn Asn Gly
    130                 135                 140

Gly Phe Gly Asp Tyr Pro Leu Val Leu Ala Arg Trp Ala Ser Ser Pro
145                 150                 155                 160

Gly Glu Leu Pro Asn Gly Trp Ser Val His Ser Phe Trp Gln Asn Ala
                165                 170                 175

Asp Thr Tyr Glu Tyr Gly Gly Asp Ser Glu Ile Trp Asn Gly Ser Gln
            180                 185                 190

Glu Asn Leu Val Lys Phe Ala Ser Gln
        195                 200

<210> SEQ ID NO 84
<211> LENGTH: 820
<212> TYPE: DNA
<213> ORGANISM: Ascobolus stictoideus
<220> FEATURE:
<221> NAME/KEY: CDS
<222> LOCATION: (1)..(138)
<220> FEATURE:
<221> NAME/KEY: sig_peptide
<222> LOCATION: (1)..(48)
<220> FEATURE:
<221> NAME/KEY: mat_peptide
<222> LOCATION: (49)..(817)
<220> FEATURE:
<221> NAME/KEY: CDS
<222> LOCATION: (230)..(675)
<220> FEATURE:
<221> NAME/KEY: CDS
<222> LOCATION: (748)..(817)

<400> SEQUENCE: 84 atg aag tgg ctt ggt ctc atc acc ctc ctc gtc gga aca gcc tcg gct      48
Met Lys Trp Leu Gly Leu Ile Thr Leu Leu Val Gly Thr Ala Ser Ala
    -15                 -10                  -5                  -1 gca gtc cct ggc ttc gac atc tcc cac tac caa agc acc gtc aat ttc      96
Ala Val Pro Gly Phe Asp Ile Ser His Tyr Gln Ser Thr Val Asn Phe
  1               5                  10                  15 gcc gat gcc tac tcc tca gga gct cga ttc gtc atc atc aag              138
Ala Asp Ala Tyr Ser Ser Gly Ala Arg Phe Val Ile Ile Lys
                 20                  25                  30 gtaatattcc tcctcttacc ccttcctcct atcgacctca agccattatc aattccatca    198
tgatcgatca gtgctaacct tctctctcca g gcc acc gaa ggc aca acc tac       250
                                   Ala Thr Glu Gly Thr Thr Tyr
                                                       35 aaa gac cca aaa ttc tcc tcc cac tac acc ggc gca acc aac gcc ggt      298
Lys Asp Pro Lys Phe Ser Ser His Tyr Thr Gly Ala Thr Asn Ala Gly
         40                  45                  50 cta att cgc ggc ggc tac cat ttc gcc cgt ccc gcc tcc agc acc ggc      346
Leu Ile Arg Gly Gly Tyr His Phe Ala Arg Pro Ala Ser Ser Thr Gly
     55                  60                  65 gcc gtg caa gcc caa tac ttt gtc agt aac ggt ggt ggt tgg tcc ggc      394
```

```
Ala Val Gln Ala Gln Tyr Phe Val Ser Asn Gly Gly Gly Trp Ser Gly
70              75                  80                  85 gat ggc ctt act ctc ccc ggc atg ctt gat ctt gag gga gat tgt gcc      442
Asp Gly Leu Thr Leu Pro Gly Met Leu Asp Leu Glu Gly Asp Cys Ala
        90                  95                  100 gga tta tca caa gcc ggt atg gta tca tgg att aca tca ttc gtc aac      490
Gly Leu Ser Gln Ala Gly Met Val Ser Trp Ile Thr Ser Phe Val Asn
            105                 110                 115 aag tac aag gct ttg act aca aga tat cca atg att tat act acc aat      538
Lys Tyr Lys Ala Leu Thr Thr Arg Tyr Pro Met Ile Tyr Thr Thr Asn
                120                 125                 130 tct tgg tgg aat act tgt acg ggg aat agt cag gct ttt agt gcg aat      586
Ser Trp Trp Asn Thr Cys Thr Gly Asn Ser Gln Ala Phe Ser Ala Asn
        135                 140                 145 tgt ccc ttg gtt att gcg agg tat aat tcg gtt gtt gga act att cct      634
Cys Pro Leu Val Ile Ala Arg Tyr Asn Ser Val Val Gly Thr Ile Pro
150                 155                 160                 165 gga ggc tgg cct tat tat act att tgg cag ttt aat gat gc               675
Gly Gly Trp Pro Tyr Tyr Thr Ile Trp Gln Phe Asn Asp Ala
            170                 175 gtaagttact ccccatgagc ctgttttgg atgaggggg agtagagttt ggctaactag     735
gtggctttat ag g tac tcc tat ggt ggt gat tct gat acc ttc aat ggg      784
              Tyr Ser Tyr Gly Gly Asp Ser Asp Thr Phe Asn Gly
              180                 185                 190 gct tac tcg cag ctt gtt aag ctc gct act ggt taa                      820
Ala Tyr Ser Gln Leu Val Lys Leu Ala Thr Gly
            195                 200
```

<210> SEQ ID NO 85
<211> LENGTH: 218
<212> TYPE: PRT
<213> ORGANISM: Ascobolus stictoideus

<400> SEQUENCE: 85

```
Met Lys Trp Leu Gly Leu Ile Thr Leu Leu Val Gly Thr Ala Ser Ala
    -15                 -10                 -5                  -1

Ala Val Pro Gly Phe Asp Ile Ser His Tyr Gln Ser Thr Val Asn Phe
1               5                   10                  15

Ala Asp Ala Tyr Ser Ser Gly Ala Arg Phe Val Ile Ile Lys Ala Thr
            20                  25                  30

Glu Gly Thr Thr Tyr Lys Asp Pro Lys Phe Ser Ser His Tyr Thr Gly
        35                  40                  45

Ala Thr Asn Ala Gly Leu Ile Arg Gly Gly Tyr His Phe Ala Arg Pro
50                  55                  60

Ala Ser Ser Thr Gly Ala Val Gln Ala Gln Tyr Phe Val Ser Asn Gly
65                  70                  75                  80

Gly Gly Trp Ser Gly Asp Gly Leu Thr Leu Pro Gly Met Leu Asp Leu
                85                  90                  95

Glu Gly Asp Cys Ala Gly Leu Ser Gln Ala Gly Met Val Ser Trp Ile
            100                 105                 110

Thr Ser Phe Val Asn Lys Tyr Lys Ala Leu Thr Thr Arg Tyr Pro Met
        115                 120                 125

Ile Tyr Thr Thr Asn Ser Trp Trp Asn Thr Cys Thr Gly Asn Ser Gln
    130                 135                 140

Ala Phe Ser Ala Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Phe
```

```
                      165                 170                 175

Asn Asp Ala Tyr Ser Tyr Gly Gly Asp Ser Asp Thr Phe Asn Gly Ala
            180                 185                 190

Tyr Ser Gln Leu Val Lys Leu Ala Thr Gly
            195                 200

<210> SEQ ID NO 86
<211> LENGTH: 202
<212> TYPE: PRT
<213> ORGANISM: Ascobolus stictoideus
<220> FEATURE:
<221> NAME/KEY: mat_peptide
<222> LOCATION: (1)..(202)

<400> SEQUENCE: 86

Ala Val Pro Gly Phe Asp Ile Ser His Tyr Gln Ser Thr Val Asn Phe
1               5                   10                  15

Ala Asp Ala Tyr Ser Ser Gly Ala Arg Phe Val Ile Ile Lys Ala Thr
            20                  25                  30

Glu Gly Thr Thr Tyr Lys Asp Pro Lys Phe Ser Ser His Tyr Thr Gly
        35                  40                  45

Ala Thr Asn Ala Gly Leu Ile Arg Gly Gly Tyr His Phe Ala Arg Pro
    50                  55                  60

Ala Ser Ser Thr Gly Ala Val Gln Ala Gln Tyr Phe Val Ser Asn Gly
65                  70                  75                  80

Gly Gly Trp Ser Gly Asp Gly Leu Thr Leu Pro Gly Met Leu Asp Leu
                85                  90                  95

Glu Gly Asp Cys Ala Gly Leu Ser Gln Ala Gly Met Val Ser Trp Ile
            100                 105                 110

Thr Ser Phe Val Asn Lys Tyr Lys Ala Leu Thr Thr Arg Tyr Pro Met
        115                 120                 125

Ile Tyr Thr Thr Asn Ser Trp Trp Asn Thr Cys Thr Gly Asn Ser Gln
    130                 135                 140

Ala Phe Ser Ala Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Phe
                165                 170                 175

Asn Asp Ala Tyr Ser Tyr Gly Gly Asp Ser Asp Thr Phe Asn Gly Ala
            180                 185                 190

Tyr Ser Gln Leu Val Lys Leu Ala Thr Gly
            195                 200

<210> SEQ ID NO 87
<211> LENGTH: 734
<212> TYPE: DNA
<213> ORGANISM: Coniochaeta sp.
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(731)
<220> FEATURE:
<221> NAME/KEY: CDS
<222> LOCATION: (201)..(731)

<400> SEQUENCE: 87 atg aag tcc aca ttc atc acc gct cta ggc cta gca ggc gtc gcg cag     48
```

```
                Met Lys Ser Thr Phe Ile Thr Ala Leu Gly Leu Ala Gly Val Ala Gln
                    -15                 -10                  -5 gcg act gtc cag ggc ttc gac atc tcg cac tac cag ccc acg gtc aac          96
Ala Thr Val Gln Gly Phe Asp Ile Ser His Tyr Gln Pro Thr Val Asn
-1  1               5                  10                  15 tat gcc ggt gct tat aac gca ggt gca cgc ttc gtc atc atc aag              141
Tyr Ala Gly Ala Tyr Asn Ala Gly Ala Arg Phe Val Ile Ile Lys
                    20                  25                  30 gtcagtcacc tcggttgaac cttctgcttc acacatgtca aagattaaca tcaagccag         200 gcc acc gag gga aca act tac acc gac cct tcc ttc agc acc cac tac         248
Ala Thr Glu Gly Thr Thr Tyr Thr Asp Pro Ser Phe Ser Thr His Tyr
                        35                  40                  45 aac ggc gca acc aag gcc ggt ctc atc cgc ggc ggc tac cac ttc gcc         296
Asn Gly Ala Thr Lys Ala Gly Leu Ile Arg Gly Gly Tyr His Phe Ala
                50                  55                  60 cac ccc ggc gtc acc acc ggc gcc gcg gag gcc aac ttc ttc ctc gcc         344
His Pro Gly Val Thr Thr Gly Ala Ala Glu Ala Asn Phe Phe Leu Ala
            65                  70                  75 cac ggc ggc ggc tgg tcg ggc gac ggc atc acc ctc ccc ggc atg ctc         392
His Gly Gly Gly Trp Ser Gly Asp Gly Ile Thr Leu Pro Gly Met Leu
        80                  85                  90 gac ctc gag tcc gag ggc tcc aac ccg cag tgc tgg ggc ctg tcc acc         440
Asp Leu Glu Ser Glu Gly Ser Asn Pro Gln Cys Trp Gly Leu Ser Thr
95                  100                 105                 110 tcc ggc atg gtc gcg tgg atc aag tcc ttc agc gac cgg tac cac acc         488
Ser Gly Met Val Ala Trp Ile Lys Ser Phe Ser Asp Arg Tyr His Thr
                115                 120                 125 gtc acc ggc cgg tat ccc atg ctc tac acc aac ccg tcc tgg tgg agc         536
Val Thr Gly Arg Tyr Pro Met Leu Tyr Thr Asn Pro Ser Trp Trp Ser
            130                 135                 140 acc tgc acc ggc aac agc aac gct ttc gtc aac acc aac ccg ctc gtc         584
Thr Cys Thr Gly Asn Ser Asn Ala Phe Val Asn Thr Asn Pro Leu Val
        145                 150                 155 ctg gcg cgg tat gct tcc gcg ccc ggc acc atc ccc ggc ggc tgg ccg         632
Leu Ala Arg Tyr Ala Ser Ala Pro Gly Thr Ile Pro Gly Gly Trp Pro
    160                 165                 170 tat cag acc atc tgg cag aac agc gac tcg tac tct tat ggc ggt gat         680
Tyr Gln Thr Ile Trp Gln Asn Ser Asp Ser Tyr Ser Tyr Gly Gly Asp
175                 180                 185                 190 tcg gac atc ttc aac ggg aac ttg gct agc ttg cag aag ttg gct act         728
Ser Asp Ile Phe Asn Gly Asn Leu Ala Ser Leu Gln Lys Leu Ala Thr
                195                 200                 205 ggt tag                                                                  734
Gly <210> SEQ ID NO 88
<211> LENGTH: 224
<212> TYPE: PRT
<213> ORGANISM: Coniochaeta sp.

<400> SEQUENCE: 88

Met Lys Ser Thr Phe Ile Thr Ala Leu Gly Leu Ala Gly Val Ala Gln
    -15                 -10                  -5

Ala Thr Val Gln Gly Phe Asp Ile Ser His Tyr Gln Pro Thr Val Asn
-1  1               5                  10                  15

Tyr Ala Gly Ala Tyr Asn Ala Gly Ala Arg Phe Val Ile Ile Lys Ala
                    20                  25                  30

Thr Glu Gly Thr Thr Tyr Thr Asp Pro Ser Phe Ser Thr His Tyr Asn
                35                  40                  45
```

```
Gly Ala Thr Lys Ala Gly Leu Ile Arg Gly Gly Tyr His Phe Ala His
             50                  55                  60

Pro Gly Val Thr Thr Gly Ala Ala Glu Ala Asn Phe Phe Leu Ala His
 65                  70                  75

Gly Gly Gly Trp Ser Gly Asp Gly Ile Thr Leu Pro Gly Met Leu Asp
 80                  85                  90                  95

Leu Glu Ser Glu Gly Ser Asn Pro Gln Cys Trp Gly Leu Ser Thr Ser
                100                 105                 110

Gly Met Val Ala Trp Ile Lys Ser Phe Ser Asp Arg Tyr His Thr Val
                115                 120                 125

Thr Gly Arg Tyr Pro Met Leu Tyr Thr Asn Pro Ser Trp Trp Ser Thr
            130                 135                 140

Cys Thr Gly Asn Ser Asn Ala Phe Val Asn Thr Asn Pro Leu Val Leu
        145                 150                 155

Ala Arg Tyr Ala Ser Ala Pro Gly Thr Ile Pro Gly Gly Trp Pro Tyr
160                 165                 170                 175

Gln Thr Ile Trp Gln Asn Ser Asp Ser Tyr Ser Tyr Gly Gly Asp Ser
                180                 185                 190

Asp Ile Phe Asn Gly Asn Leu Ala Ser Leu Gln Lys Leu Ala Thr Gly
            195                 200                 205

<210> SEQ ID NO 89
<211> LENGTH: 207
<212> TYPE: PRT
<213> ORGANISM: Coniochaeta sp.
<220> FEATURE:
<221> NAME/KEY: mat_peptide
<222> LOCATION: (1)..(207)

<400> SEQUENCE: 89

Thr Val Gln Gly Phe Asp Ile Ser His Tyr Gln Pro Thr Val Asn Tyr
 1               5                  10                  15

Ala Gly Ala Tyr Asn Ala Gly Ala Arg Phe Val Ile Ile Lys Ala Thr
             20                  25                  30

Glu Gly Thr Thr Tyr Thr Asp Pro Ser Phe Ser Thr His Tyr Asn Gly
         35                  40                  45

Ala Thr Lys Ala Gly Leu Ile Arg Gly Gly Tyr His Phe Ala His Pro
     50                  55                  60

Gly Val Thr Thr Gly Ala Ala Glu Ala Asn Phe Phe Leu Ala His Gly
 65                  70                  75                  80

Gly Gly Trp Ser Gly Asp Gly Ile Thr Leu Pro Gly Met Leu Asp Leu
             85                  90                  95

Glu Ser Glu Gly Ser Asn Pro Gln Cys Trp Gly Leu Ser Thr Ser Gly
            100                 105                 110

Met Val Ala Trp Ile Lys Ser Phe Ser Asp Arg Tyr His Thr Val Thr
        115                 120                 125

Gly Arg Tyr Pro Met Leu Tyr Thr Asn Pro Ser Trp Trp Ser Thr Cys
    130                 135                 140

Thr Gly Asn Ser Asn Ala Phe Val Asn Thr Asn Pro Leu Val Leu Ala
145                 150                 155                 160

Arg Tyr Ala Ser Ala Pro Gly Thr Ile Pro Gly Gly Trp Pro Tyr Gln
                165                 170                 175

Thr Ile Trp Gln Asn Ser Asp Ser Tyr Ser Tyr Gly Gly Asp Ser Asp
            180                 185                 190

Ile Phe Asn Gly Asn Leu Ala Ser Leu Gln Lys Leu Ala Thr Gly
```

<210> SEQ ID NO 90
<211> LENGTH: 815
<212> TYPE: DNA
<213> ORGANISM: Daldinia fissa
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(812)
<220> FEATURE:
<221> NAME/KEY: CDS
<222> LOCATION: (226)..(712)
<220> FEATURE:
<221> NAME/KEY: CDS
<222> LOCATION: (784)..(812)

<400> SEQUENCE: 90

| | | | | | | | | | | | | | | | | |
|---|---|---|---|---|---|---|---|---|---|---|---|---|---|---|---|---|
| atg | aag | acc | ttc | att | aca | agt | tgt | cta | ggc | ctc | gct | ggc | ctc | gct | agc | 48 |
| Met | Lys | Thr | Phe | Ile | Thr | Ser | Cys | Leu | Gly | Leu | Ala | Gly | Leu | Ala | Ser | |
| -20 | | | | -15 | | | | | -10 | | | | | -5 | | |

| | | | | | | | | | | | | | | | | |
|---|---|---|---|---|---|---|---|---|---|---|---|---|---|---|---|---|
| ctt | gcc | ctc | gct | gct | gtc | cca | ggc | ttc | gac | att | tcc | cat | tat | cag | tcg | 96 |
| Leu | Ala | Leu | Ala | Ala | Val | Pro | Gly | Phe | Asp | Ile | Ser | His | Tyr | Gln | Ser | |
| | | | -1 | 1 | | | | 5 | | | | | 10 | | | |

| | | | | | | | | | | | | | | | | |
|---|---|---|---|---|---|---|---|---|---|---|---|---|---|---|---|---|
| agc | gta | gac | ttt | ggg | gca | gca | tat | agt | tct | gga | gcc | cgt | ttc | gtt | atc | 144 |
| Ser | Val | Asp | Phe | Gly | Ala | Ala | Tyr | Ser | Ser | Gly | Ala | Arg | Phe | Val | Ile | |
| | | 15 | | | | | 20 | | | | | 25 | | | | |

| | | | | | |
|---|---|---|---|---|---|
| atc | aaa | gtgagtccta cctaggtacc tacctatatc taccaaccaa atacgtcccc | | | 200 |
| Ile | Lys | | | | |
| | 30 | | | | |

| | | | | | | | | | | | | |
|---|---|---|---|---|---|---|---|---|---|---|---|---|
| ctcgaaactt accatatgag accag | gct | aca | gag | ggc | acc | acc | tac | cag | gac | 252 |
| | Ala | Thr | Glu | Gly | Thr | Thr | Tyr | Gln | Asp | |
| | | | | 35 | | | | | | |

| | | | | | | | | | | | | | | | | |
|---|---|---|---|---|---|---|---|---|---|---|---|---|---|---|---|---|
| ccc | aaa | ttc | agc | agc | cac | tac | gcc | ggc | gct | acc | aac | gcc | ggc | ctc | atc | 300 |
| Pro | Lys | Phe | Ser | Ser | His | Tyr | Ala | Gly | Ala | Thr | Asn | Ala | Gly | Leu | Ile | |
| 40 | | | | | 45 | | | | | 50 | | | | | 55 | |

| | | | | | | | | | | | | | | | | |
|---|---|---|---|---|---|---|---|---|---|---|---|---|---|---|---|---|
| cgc | ggc | ggc | tac | cac | ttc | gcg | cgc | ccc | gcg | tcg | tcc | tcc | ggc | gcc | gcc | 348 |
| Arg | Gly | Gly | Tyr | His | Phe | Ala | Arg | Pro | Ala | Ser | Ser | Ser | Gly | Ala | Ala | |
| | | | | 60 | | | | | 65 | | | | | 70 | | |

| | | | | | | | | | | | | | | | | |
|---|---|---|---|---|---|---|---|---|---|---|---|---|---|---|---|---|
| caa | gca | acg | ttc | ttc | ctc | gcg | cac | ggt | ggc | ggg | tgg | tcg | ggc | gat | ggg | 396 |
| Gln | Ala | Thr | Phe | Phe | Leu | Ala | His | Gly | Gly | Gly | Trp | Ser | Gly | Asp | Gly | |
| | | | 75 | | | | | 80 | | | | | 85 | | | |

| | | | | | | | | | | | | | | | | |
|---|---|---|---|---|---|---|---|---|---|---|---|---|---|---|---|---|
| atc | acg | ctg | ccg | gga | atg | ctg | gac | tta | gaa | ggt | gat | tgt | gcg | ggc | ttg | 444 |
| Ile | Thr | Leu | Pro | Gly | Met | Leu | Asp | Leu | Glu | Gly | Asp | Cys | Ala | Gly | Leu | |
| | | 90 | | | | | 95 | | | | | 100 | | | | |

| | | | | | | | | | | | | | | | | |
|---|---|---|---|---|---|---|---|---|---|---|---|---|---|---|---|---|
| tcg | acc | agc | gcc | atg | gtc | tcg | tgg | atc | agg | gac | ttt | agc | gat | acg | tat | 492 |
| Ser | Thr | Ser | Ala | Met | Val | Ser | Trp | Ile | Arg | Asp | Phe | Ser | Asp | Thr | Tyr | |
| 105 | | | | | 110 | | | | | 115 | | | | | | |

| | | | | | | | | | | | | | | | | |
|---|---|---|---|---|---|---|---|---|---|---|---|---|---|---|---|---|
| cac | ggc | aag | acg | ggg | cgg | tat | ccc | ctg | ctg | tac | acg | aat | ccg | tcg | tgg | 540 |
| His | Gly | Lys | Thr | Gly | Arg | Tyr | Pro | Leu | Leu | Tyr | Thr | Asn | Pro | Ser | Trp | |
| 120 | | | | 125 | | | | | 130 | | | | | 135 | | |

| | | | | | | | | | | | | | | | | |
|---|---|---|---|---|---|---|---|---|---|---|---|---|---|---|---|---|
| tgg | tcg | agt | tgt | acg | ggc | ggg | tcg | agc | gcg | ttc | gtg | aat | acg | aat | ccg | 588 |
| Trp | Ser | Ser | Cys | Thr | Gly | Gly | Ser | Ser | Ala | Phe | Val | Asn | Thr | Asn | Pro | |
| | | | 140 | | | | | 145 | | | | | 150 | | | |

| | | | | | | | | | | | | | | | | |
|---|---|---|---|---|---|---|---|---|---|---|---|---|---|---|---|---|
| ctc | gtg | ctt | gcg | cgg | tat | gct | agt | agc | ccg | ggg | gcg | ttg | ccg | ggg | ggc | 636 |
| Leu | Val | Leu | Ala | Arg | Tyr | Ala | Ser | Ser | Pro | Gly | Ala | Leu | Pro | Gly | Gly | |
| | | | 155 | | | | | 160 | | | | | 165 | | | |

| | | | | | | | | | | | | | | | | |
|---|---|---|---|---|---|---|---|---|---|---|---|---|---|---|---|---|
| tgg | ccg | tat | tat | acc | att | tgg | cag | ttt | aat | gat | gcg | tat | aag | tat | ggg | 684 |
| Trp | Pro | Tyr | Tyr | Thr | Ile | Trp | Gln | Phe | Asn | Asp | Ala | Tyr | Lys | Tyr | Gly | |

```
              170                 175                 180
ggc gac tcg gat acg ttt aat ggc gat c gtgagtaacc tagttttact         732
Gly Asp Ser Asp Thr Phe Asn Gly Asp
    185                 190 tgtctttctc tgttcctttt tttgtccccct tttgctaacg tagtgttgca g tc  acg   788
                                                         Leu Thr cag ttg aag aaa ttg gct tcg ggg taa                                 815
Gln Leu Lys Lys Leu Ala Ser Gly
195                 200

<210> SEQ ID NO 91
<211> LENGTH: 222
<212> TYPE: PRT
<213> ORGANISM: Daldinia fissa

<400> SEQUENCE: 91

Met Lys Thr Phe Ile Thr Ser Cys Leu Gly Leu Ala Gly Leu Ala Ser
-20              -15              -10              -5

Leu Ala Leu Ala Ala Val Pro Gly Phe Asp Ile Ser His Tyr Gln Ser
             -1  1               5                  10

Ser Val Asp Phe Gly Ala Ala Tyr Ser Ser Gly Ala Arg Phe Val Ile
            15                  20                  25

Ile Lys Ala Thr Glu Gly Thr Thr Tyr Gln Asp Pro Lys Phe Ser Ser
        30                  35                  40

His Tyr Ala Gly Ala Thr Asn Ala Gly Leu Ile Arg Gly Gly Tyr His
45                  50                  55                  60

Phe Ala Arg Pro Ala Ser Ser Gly Ala Gln Ala Thr Phe Phe
                65                  70                  75

Leu Ala His Gly Gly Gly Trp Ser Gly Asp Gly Ile Thr Leu Pro Gly
            80                  85                  90

Met Leu Asp Leu Glu Gly Asp Cys Ala Gly Leu Ser Thr Ser Ala Met
        95                  100                 105

Val Ser Trp Ile Arg Asp Phe Ser Asp Thr Tyr His Gly Lys Thr Gly
    110                 115                 120

Arg Tyr Pro Leu Leu Tyr Thr Asn Pro Ser Trp Trp Ser Ser Cys Thr
125                 130                 135                 140

Gly Gly Ser Ser Ala Phe Val Asn Thr Asn Pro Leu Val Leu Ala Arg
                145                 150                 155

Tyr Ala Ser Ser Pro Gly Ala Leu Pro Gly Gly Trp Pro Tyr Tyr Thr
                160                 165                 170

Ile Trp Gln Phe Asn Asp Ala Tyr Lys Tyr Gly Gly Asp Ser Asp Thr
    175                 180                 185

Phe Asn Gly Asp Leu Thr Gln Leu Lys Lys Leu Ala Ser Gly
    190                 195                 200

<210> SEQ ID NO 92
<211> LENGTH: 202
<212> TYPE: PRT
<213> ORGANISM: Daldinia fissa
<220> FEATURE:
<221> NAME/KEY: mat_peptide
<222> LOCATION: (1)..(202)

<400> SEQUENCE: 92

Ala Val Pro Gly Phe Asp Ile Ser His Tyr Gln Ser Ser Val Asp Phe
1               5                   10                  15

Gly Ala Ala Tyr Ser Ser Gly Ala Arg Phe Val Ile Ile Lys Ala Thr
            20                  25                  30
```

```
Glu Gly Thr Thr Tyr Gln Asp Pro Lys Phe Ser Ser His Tyr Ala Gly
         35                  40                  45

Ala Thr Asn Ala Gly Leu Ile Arg Gly Gly Tyr His Phe Ala Arg Pro
 50                  55                  60

Ala Ser Ser Ser Gly Ala Ala Gln Ala Thr Phe Phe Leu Ala His Gly
 65                  70                  75                  80

Gly Gly Trp Ser Gly Asp Gly Ile Thr Leu Pro Gly Met Leu Asp Leu
                 85                  90                  95

Glu Gly Asp Cys Ala Gly Leu Ser Thr Ser Ala Met Val Ser Trp Ile
                100                 105                 110

Arg Asp Phe Ser Asp Thr Tyr His Gly Lys Thr Gly Arg Tyr Pro Leu
                115                 120                 125

Leu Tyr Thr Asn Pro Ser Trp Trp Ser Ser Cys Thr Gly Gly Ser Ser
        130                 135                 140

Ala Phe Val Asn Thr Asn Pro Leu Val Leu Ala Arg Tyr Ala Ser Ser
145                 150                 155                 160

Pro Gly Ala Leu Pro Gly Gly Trp Pro Tyr Tyr Thr Ile Trp Gln Phe
                165                 170                 175

Asn Asp Ala Tyr Lys Tyr Gly Gly Asp Ser Asp Ser Thr Phe Asn Gly Asp
            180                 185                 190

Leu Thr Gln Leu Lys Lys Leu Ala Ser Gly
        195                 200

<210> SEQ ID NO 93
<211> LENGTH: 732
<212> TYPE: DNA
<213> ORGANISM: Delitschia sp.
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(725)
<220> FEATURE:
<221> NAME/KEY: CDS
<222> LOCATION: (217)..(729)

<400> SEQUENCE: 93 atg aag gct act ctc gct tcc ctc ctc ggt ctt gcc aac ggc gcc ctc      48
Met Lys Ala Thr Leu Ala Ser Leu Leu Gly Leu Ala Asn Gly Ala Leu
            -15                 -10                  -5 gcg gct gtc cag ggc ttc gac atc tcc cac tac cag tcg agc gtc aac      96
Ala Ala Val Gln Gly Phe Asp Ile Ser His Tyr Gln Ser Ser Val Asn
 -1   1               5                  10                  15 ttc gcc ggt gcg tat agc gcc ggt gcc cgt ttc gtc atc atc aag           141
Phe Ala Gly Ala Tyr Ser Ala Gly Ala Arg Phe Val Ile Ile Lys
                 20                  25                  30 gtgagacccg tcgacgcaca tcagcccacg agaaagaaaa aaccagtcag agaactaac     201 ccggcgcgtg cacag gcg aca gag ggc acg tcc tac atc gac ccc aag ttc     252
              Ala Thr Glu Gly Thr Ser Tyr Ile Asp Pro Lys Phe
                                  35                  40 agc tcc cac tac atc ggt gcc acg aat gcc ggc ctg atc cgc ggt ggc      300
Ser Ser His Tyr Ile Gly Ala Thr Asn Ala Gly Leu Ile Arg Gly Gly
                45                  50                  55 tac cac ttc gcc cac ctg ggc tcg agc tcc ggt gcg gcc cag gct aac      348
Tyr His Phe Ala His Leu Gly Ser Ser Ser Gly Ala Ala Gln Ala Asn
        60                  65                  70
```

```
tac ttc ctc gcc cac ggc ggt ggc tgg tcc ggc gac ggc atc acc ctc      396
Tyr Phe Leu Ala His Gly Gly Gly Trp Ser Gly Asp Gly Ile Thr Leu
 75                  80                  85                  90 ccc ggc atg ctc gac ctc gag ggc gac tgc gtg ctc tcg gcc agc ggc      444
Pro Gly Met Leu Asp Leu Glu Gly Asp Cys Val Leu Ser Ala Ser Gly
                 95                 100                 105 gcc gtg gcc tgg atc aag gac ttc agc gac acc tac cac tcc aag acc      492
Ala Val Ala Trp Ile Lys Asp Phe Ser Asp Thr Tyr His Ser Lys Thr
            110                 115                 120 ggt gtg tac ccc ctg ctc tac acc aac ccc tcg tgg tgg tcg tcc tgc      540
Gly Val Tyr Pro Leu Leu Tyr Thr Asn Pro Ser Trp Trp Ser Ser Cys
        125                 130                 135 acg ggc aac tcc aac gcc ttc gtc aac acc aac ccc ctg gtg ctc gcc      588
Thr Gly Asn Ser Asn Ala Phe Val Asn Thr Asn Pro Leu Val Leu Ala
140                 145                 150 cgc tac agc tcc agc gcc ggc acc cct ccc ggt ggc tgg ccc tac tac      636
Arg Tyr Ser Ser Ser Ala Gly Thr Pro Pro Gly Gly Trp Pro Tyr Tyr
155                 160                 165                 170 acc atc tgg cag tac aac gac gcc tac gcg tac ggt ggt gac tcg gac      684
Thr Ile Trp Gln Tyr Asn Asp Ala Tyr Ala Tyr Gly Gly Asp Ser Asp
                175                 180                 185 gtg ttc aac ggc gac atg gct ggc ctc ctc cgc ctt gcc aag gga taa     732
Val Phe Asn Gly Asp Met Ala Gly Leu Leu Arg Leu Ala Lys Gly
            190                 195                 200

<210> SEQ ID NO 94
<211> LENGTH: 218
<212> TYPE: PRT
<213> ORGANISM: Delitschia sp.

<400> SEQUENCE: 94

Met Lys Ala Thr Leu Ala Ser Leu Leu Gly Leu Ala Asn Gly Ala Leu
        -15                 -10                  -5

Ala Ala Val Gln Gly Phe Asp Ile Ser His Tyr Gln Ser Ser Val Asn
 -1   1               5                  10                  15

Phe Ala Gly Ala Tyr Ser Ala Gly Ala Arg Phe Val Ile Ile Lys Ala
                 20                  25                  30

Thr Glu Gly Thr Ser Tyr Ile Asp Pro Lys Phe Ser Ser His Tyr Ile
             35                  40                  45

Gly Ala Thr Asn Ala Gly Leu Ile Arg Gly Tyr His Phe Ala His
 50                  55                  60

Leu Gly Ser Ser Gly Ala Ala Gln Ala Asn Tyr Phe Leu Ala His
 65                  70                  75

Gly Gly Gly Trp Ser Gly Asp Gly Ile Thr Leu Pro Gly Met Leu Asp
 80                  85                  90                  95

Leu Glu Gly Asp Cys Val Leu Ser Ala Ser Gly Ala Val Ala Trp Ile
                100                 105                 110

Lys Asp Phe Ser Asp Thr Tyr His Ser Lys Thr Gly Val Tyr Pro Leu
            115                 120                 125

Leu Tyr Thr Asn Pro Ser Trp Trp Ser Ser Cys Thr Gly Asn Ser Asn
        130                 135                 140

Ala Phe Val Asn Thr Asn Pro Leu Val Leu Ala Arg Tyr Ser Ser Ser
145                 150                 155

Ala Gly Thr Pro Pro Gly Gly Trp Pro Tyr Tyr Thr Ile Trp Gln Tyr
160                 165                 170                 175

Asn Asp Ala Tyr Ala Tyr Gly Gly Asp Ser Asp Val Phe Asn Gly Asp
                180                 185                 190
```

```
Met Ala Gly Leu Leu Arg Leu Ala Lys Gly
            195                 200
```

<210> SEQ ID NO 95
<211> LENGTH: 201
<212> TYPE: PRT
<213> ORGANISM: Rosellinia sp.
<220> FEATURE:
<221> NAME/KEY: mat_peptide
<222> LOCATION: (1)..(201)

<400> SEQUENCE: 95

```
Ala Val Gln Gly Phe Asp Ile Ser His Tyr Gln Ser Ser Val Asn Phe
1               5                   10                  15

Ala Gly Ala Tyr Ser Ala Gly Ala Arg Phe Val Ile Ile Lys Ala Thr
            20                  25                  30

Glu Gly Thr Ser Tyr Ile Asp Pro Lys Phe Ser Ser His Tyr Ile Gly
        35                  40                  45

Ala Thr Asn Ala Gly Leu Ile Arg Gly Gly Tyr His Phe Ala His Leu
    50                  55                  60

Gly Ser Ser Ser Gly Ala Ala Gln Ala Asn Tyr Phe Leu Ala His Gly
65                  70                  75                  80

Gly Gly Trp Ser Gly Asp Gly Ile Thr Leu Pro Gly Met Leu Asp Leu
                85                  90                  95

Glu Gly Asp Cys Val Leu Ser Ala Ser Gly Ala Val Ala Trp Ile Lys
            100                 105                 110

Asp Phe Ser Asp Thr Tyr His Ser Lys Thr Gly Val Tyr Pro Leu Leu
        115                 120                 125

Tyr Thr Asn Pro Ser Trp Trp Ser Ser Cys Thr Gly Asn Ser Asn Ala
    130                 135                 140

Phe Val Asn Thr Asn Pro Leu Val Leu Ala Arg Tyr Ser Ser Ser Ala
145                 150                 155                 160

Gly Thr Pro Pro Gly Gly Trp Pro Tyr Tyr Thr Ile Trp Gln Tyr Asn
                165                 170                 175

Asp Ala Tyr Ala Tyr Gly Gly Asp Ser Asp Val Phe Asn Gly Asp Met
            180                 185                 190

Ala Gly Leu Leu Arg Leu Ala Lys Gly
        195                 200
```

<210> SEQ ID NO 96
<211> LENGTH: 784
<212> TYPE: DNA
<213> ORGANISM: Ascobolus sp. ZY179
<220> FEATURE:
<221> NAME/KEY: CDS
<222> LOCATION: (1)..(138)
<220> FEATURE:
<221> NAME/KEY: sig_peptide
<222> LOCATION: (1)..(48)
<220> FEATURE:
<221> NAME/KEY: mat_peptide
<222> LOCATION: (49)..(781)
<220> FEATURE:
<221> NAME/KEY: CDS
<222> LOCATION: (195)..(640)
<220> FEATURE:
<221> NAME/KEY: CDS
<222> LOCATION: (712)..(781)

<400> SEQUENCE: 96

```
atg aag tgg ctc ggt ctc gtc acc ctc ctt gtc ggc gcg gcg caa gct    48
Met Lys Trp Leu Gly Leu Val Thr Leu Leu Val Gly Ala Ala Gln Ala
```

```
                -15                 -10                   -5                  -1
    gca gtc cct ggt ttc gac atc tcc cac tgg cag agc agt gtc aac ttt              96
    Ala Val Pro Gly Phe Asp Ile Ser His Trp Gln Ser Ser Val Asn Phe
    1               5                   10                  15 gcc tct gcc tac tcc tct ggt gcc cgt ttc gtc atc atc aag                     138
    Ala Ser Ala Tyr Ser Ser Gly Ala Arg Phe Val Ile Ile Lys
            20                  25                  30 gtagtccaac acctccatcc accctagagt ccgagtatta accaccttct ctccag gct           197
                                                                       Ala acc gaa ggc acg acc tac aag gac cca aag ttc tcc tcc cac tac act             245
    Thr Glu Gly Thr Thr Tyr Lys Asp Pro Lys Phe Ser Ser His Tyr Thr
                    35                  40                  45 ggc gcc acc aag gcc ggt ttc atc cgc gga ggc tac cac ttt gcc cgc             293
    Gly Ala Thr Lys Ala Gly Phe Ile Arg Gly Gly Tyr His Phe Ala Arg
    50                  55                  60 cct gcg tcc agc act ggc gcc gcg caa gcc caa ttc ttc gcc agt aac             341
    Pro Ala Ser Ser Thr Gly Ala Ala Gln Ala Gln Phe Phe Ala Ser Asn
            65                  70                  75 ggc ggc ggg tgg tcc ggc gat ggc atc acg ctc ccc ggc atg ttg gat             389
    Gly Gly Gly Trp Ser Gly Asp Gly Ile Thr Leu Pro Gly Met Leu Asp
    80                  85                  90                  95 ctt gag gga gac tgt gct ggt ctt tct cag tcc ggc atg gtg tca tgg             437
    Leu Glu Gly Asp Cys Ala Gly Leu Ser Gln Ser Gly Met Val Ser Trp
                    100                 105                 110 att agc tct ttc gtc aac aag tac agg tcg ctc aca ggc aga tac cca             485
    Ile Ser Ser Phe Val Asn Lys Tyr Arg Ser Leu Thr Gly Arg Tyr Pro
                115                 120                 125 atg atc tac acc acc aac tcg tgg tgg gtt acc tgc act ggt aac agc             533
    Met Ile Tyr Thr Thr Asn Ser Trp Trp Val Thr Cys Thr Gly Asn Ser
    130                 135                 140 aaa gct ttc agc tca aac tgc ccg ttg gtc att gct aga tac aac tcg             581
    Lys Ala Phe Ser Ser Asn Cys Pro Leu Val Ile Ala Arg Tyr Asn Ser
            145                 150                 155 gtg gtt gga act att ccg gga ggt tgg cct tat tat acc att tgg cag             629
    Val Val Gly Thr Ile Pro Gly Gly Trp Pro Tyr Tyr Thr Ile Trp Gln
    160                 165                 170                 175 tac aac gat gc  gtaagttttc ctccgtgctg ggtgtgtggg agacattggg                 680
    Tyr Asn Asp Ala aacattgact aactctggtt ttcctttta g c tat aag tat ggt ggt gat tcg            733
                                         Tyr Lys Tyr Gly Gly Asp Ser
                                                 180                 185 gat act ttc aac ggt gct tac tct cag ctc gtc aag ctc gcc act ggt             781
    Asp Thr Phe Asn Gly Ala Tyr Ser Gln Leu Val Lys Leu Ala Thr Gly
                    190                 195                 200 taa                                                                         784
```

<210> SEQ ID NO 97
<211> LENGTH: 218
<212> TYPE: PRT
<213> ORGANISM: Ascobolus sp. ZY179

<400> SEQUENCE: 97

```
Met Lys Trp Leu Gly Leu Val Thr Leu Leu Val Gly Ala Ala Gln Ala
        -15                 -10                  -5                  -1

Ala Val Pro Gly Phe Asp Ile Ser His Trp Gln Ser Ser Val Asn Phe
1               5                   10                  15

Ala Ser Ala Tyr Ser Ser Gly Ala Arg Phe Val Ile Ile Lys Ala Thr
            20                  25                  30
```

```
Glu Gly Thr Thr Tyr Lys Asp Pro Lys Phe Ser Ser His Tyr Thr Gly
            35                  40                  45

Ala Thr Lys Ala Gly Phe Ile Arg Gly Gly Tyr His Phe Ala Arg Pro
 50                  55                  60

Ala Ser Ser Thr Gly Ala Ala Gln Ala Gln Phe Phe Ala Ser Asn Gly
 65                  70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Gln Ser Gly Met Val Ser Trp Ile
                100                 105                 110

Ser Ser Phe Val Asn Lys Tyr Arg Ser Leu Thr Gly Arg Tyr Pro Met
            115                 120                 125

Ile Tyr Thr Thr Asn Ser Trp Trp Val Thr Cys Thr Gly Asn Ser Lys
            130                 135                 140

Ala Phe Ser Ser Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Tyr
                165                 170                 175

Asn Asp Ala Tyr Lys Tyr Gly Gly Asp Ser Asp Thr Phe Asn Gly Ala
                180                 185                 190

Tyr Ser Gln Leu Val Lys Leu Ala Thr Gly
            195                 200

<210> SEQ ID NO 98
<211> LENGTH: 202
<212> TYPE: PRT
<213> ORGANISM: Ascobolus sp. ZY179
<220> FEATURE:
<221> NAME/KEY: mat_peptide
<222> LOCATION: (1)..(202)

<400> SEQUENCE: 98

Ala Val Pro Gly Phe Asp Ile Ser His Trp Gln Ser Ser Val Asn Phe
1               5                   10                  15

Ala Ser Ala Tyr Ser Ser Gly Ala Arg Phe Val Ile Ile Lys Ala Thr
                20                  25                  30

Glu Gly Thr Thr Tyr Lys Asp Pro Lys Phe Ser Ser His Tyr Thr Gly
            35                  40                  45

Ala Thr Lys Ala Gly Phe Ile Arg Gly Gly Tyr His Phe Ala Arg Pro
 50                  55                  60

Ala Ser Ser Thr Gly Ala Ala Gln Ala Gln Phe Phe Ala Ser Asn Gly
 65                  70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Gln Ser Gly Met Val Ser Trp Ile
                100                 105                 110

Ser Ser Phe Val Asn Lys Tyr Arg Ser Leu Thr Gly Arg Tyr Pro Met
            115                 120                 125

Ile Tyr Thr Thr Asn Ser Trp Trp Val Thr Cys Thr Gly Asn Ser Lys
            130                 135                 140

Ala Phe Ser Ser Asn Cys Pro Leu Val Ile Ala Arg Tyr Asn Ser Val
145                 150                 155                 160

Val Gly Thr Ile Pro Gly Gly Trp Pro Tyr Tyr Thr Ile Trp Gln Tyr
                165                 170                 175

Asn Asp Ala Tyr Lys Tyr Gly Gly Asp Ser Asp Thr Phe Asn Gly Ala
                180                 185                 190
```

```
Tyr Ser Gln Leu Val Lys Leu Ala Thr Gly
        195                 200

<210> SEQ ID NO 99
<211> LENGTH: 956
<212> TYPE: DNA
<213> ORGANISM: Curreya sp. XZ2623
<220> FEATURE:
<221> NAME/KEY: CDS
<222> LOCATION: (1)..(214)
<220> FEATURE:
<221> NAME/KEY: sig_peptide
<222> LOCATION: (1)..(54)
<220> FEATURE:
<221> NAME/KEY: mat_peptide
<222> LOCATION: (55)..(953)
<220> FEATURE:
<221> NAME/KEY: CDS
<222> LOCATION: (275)..(331)
<220> FEATURE:
<221> NAME/KEY: CDS
<222> LOCATION: (385)..(450)
<220> FEATURE:
<221> NAME/KEY: CDS
<222> LOCATION: (506)..(648)
<220> FEATURE:
<221> NAME/KEY: CDS
<222> LOCATION: (700)..(821)
<220> FEATURE:
<221> NAME/KEY: CDS
<222> LOCATION: (884)..(953)

<400> SEQUENCE: 99 atg aat ctc tct ggt ctt ctc gca atc gcg tcc tac ctt gct ctt tcg      48
Met Asn Leu Ser Gly Leu Leu Ala Ile Ala Ser Tyr Leu Ala Leu Ser
        -15                 -10                 -5 gca gca acc gtg cct ggg ttc gac att tcc cac tac caa ggc act gtg      96
Ala Ala Thr Val Pro Gly Phe Asp Ile Ser His Tyr Gln Gly Thr Val
     -1  1               5                  10 aac ttc gct ggt gct tac tcc tca ggg gcg cgc ttt gtg atc atc aaa     144
Asn Phe Ala Gly Ala Tyr Ser Ser Gly Ala Arg Phe Val Ile Ile Lys
 15                  20                  25                  30 gca act gag ggc acc act tat acg gac cca aac ttc tcc aac aac tat     192
Ala Thr Glu Gly Thr Thr Tyr Thr Asp Pro Asn Phe Ser Asn Asn Tyr
                 35                  40                  45 gtt ggt gcg acg aat gct aaa t gtatgcaagc ccttcggcat aactccgata      244
Val Gly Ala Thr Asn Ala Lys
                 50 cctgcctgct aacggtgcat gcacatccag tt  att cgc ggt gct tat cat ttc    297
                                    Phe Ile Arg Gly Ala Tyr His Phe
                                         55                  60 gct cga cca gat ggc gga tcg ggc tcc acc caa g gttcgctatt            341
Ala Arg Pro Asp Gly Gly Ser Gly Ser Thr Gln
             65                  70 ctttggtcaa acttacattg agtcacccc taatgaagct cag ca  caa ttc ttt      395
                                                 Ala Gln Phe Phe
                                                              75 cat tct cat ggt ggt ggg tgg tct ggc gat ggc atc acc ctg cct ggg     443
His Ser His Gly Gly Gly Trp Ser Gly Asp Gly Ile Thr Leu Pro Gly
             80                  85                  90 atg ttg g gtaagtgtgc tcaagctcat gggattttcc cttgactaac gtcctgggta   500
Met Leu cgaag ac  atc gaa tat ggc cct aca tcg aca tgc tat ggc ctc tcc acg  549
      Asp Ile Glu Tyr Gly Pro Thr Ser Thr Cys Tyr Gly Leu Ser Thr
       95                 100                 105
```

| | | |
|---|---|---|
| tct gct atg gtc aca tgg att act gat ttt gtc aac gag tac cat gct<br>Ser Ala Met Val Thr Trp Ile Thr Asp Phe Val Asn Glu Tyr His Ala<br>110                        115                         120                       125 | | 597 |
| ttg aca ggt cgc tac cct ctc atc tac acc acc aat gac tgg tgg aac<br>Leu Thr Gly Arg Tyr Pro Leu Ile Tyr Thr Thr Asn Asp Trp Trp Asn<br>              130                         135                       140 | | 645 |
| act gtgagtatac tgtaccgtca ccgtctccgg agctctttct cacagtaata g tgc<br>Thr                                                                                                  Cys | | 702 |
| acc gga aac aca aac aag ttt agc act act tgc ccg ctt gtc ctc gca<br>Thr Gly Asn Thr Asn Lys Phe Ser Thr Thr Cys Pro Leu Val Leu Ala<br>     145                          150                       155 | | 750 |
| cgg tac agc agc tcc gtg ggg acc atc ccc gga ggt tgg ccg ttc cag<br>Arg Tyr Ser Ser Ser Val Gly Thr Ile Pro Gly Gly Trp Pro Phe Gln<br>160                        165                       170                       175 | | 798 |
| aca atc tgg caa ttc aat gac aa gtaagtgctt caccttagtt gtaacgaaga<br>Thr Ile Trp Gln Phe Asn Asp Asn<br>                      180 | | 851 |
| aattggactt cgctgatgca gttgtattgc ag t tac gct tat ggt ggc gac tct<br>                                                 Tyr Ala Tyr Gly Gly Asp Ser<br>                                                              185                       190 | | 905 |
| gat aca ttt aac gga gat ctg gcg gga ttg aag aag ctt gcg acc gga<br>Asp Thr Phe Asn Gly Asp Leu Ala Gly Leu Lys Lys Leu Ala Thr Gly<br>                195                         200                         205 | | 953 |
| taa | | 956 |

<210> SEQ ID NO 100
<211> LENGTH: 224
<212> TYPE: PRT
<213> ORGANISM: Curreya sp. XZ2623

<400> SEQUENCE: 100

Met Asn Leu Ser Gly Leu Leu Ala Ile Ala Ser Tyr Leu Ala Leu Ser
              -15                       -10                         -5

Ala Ala Thr Val Pro Gly Phe Asp Ile Ser His Tyr Gln Gly Thr Val
  -1  1                      5                           10

Asn Phe Ala Gly Ala Tyr Ser Ser Gly Ala Arg Phe Val Ile Ile Lys
15                    20                    25                    30

Ala Thr Glu Gly Thr Thr Tyr Thr Asp Pro Asn Phe Ser Asn Asn Tyr
                 35                       40                       45

Val Gly Ala Thr Asn Ala Lys Phe Ile Arg Gly Ala Tyr His Phe Ala
          50                         55                       60

Arg Pro Asp Gly Gly Ser Gly Ser Thr Gln Ala Gln Phe Phe His Ser
     65                       70                       75

His Gly Gly Gly Trp Ser Gly Asp Gly Ile Thr Leu Pro Gly Met Leu
80                    85                    90

Asp Ile Glu Tyr Gly Pro Thr Ser Thr Cys Tyr Gly Leu Ser Thr Ser
95                   100                  105                 110

Ala Met Val Thr Trp Ile Thr Asp Phe Val Asn Glu Tyr His Ala Leu
                115                       120                     125

Thr Gly Arg Tyr Pro Leu Ile Tyr Thr Thr Asn Asp Trp Trp Asn Thr
          130                       135                       140

Cys Thr Gly Asn Thr Asn Lys Phe Ser Thr Thr Cys Pro Leu Val Leu
                145                       150                       155

Ala Arg Tyr Ser Ser Ser Val Gly Thr Ile Pro Gly Gly Trp Pro Phe
          160                       165                       170

Gln Thr Ile Trp Gln Phe Asn Asp Asn Tyr Ala Tyr Gly Gly Asp Ser
175                    180                  185                 190

```
Asp Thr Phe Asn Gly Asp Leu Ala Gly Leu Lys Lys Leu Ala Thr Gly
            195                 200                 205
```

```
<210> SEQ ID NO 101
<211> LENGTH: 206
<212> TYPE: PRT
<213> ORGANISM: Curreya sp. XZ2623
<220> FEATURE:
<221> NAME/KEY: mat_peptide
<222> LOCATION: (1)..(206)

<400> SEQUENCE: 101
```

```
Thr Val Pro Gly Phe Asp Ile Ser His Tyr Gln Gly Thr Val Asn Phe
1               5                   10                  15

Ala Gly Ala Tyr Ser Ser Gly Ala Arg Phe Val Ile Ile Lys Ala Thr
            20                  25                  30

Glu Gly Thr Thr Tyr Thr Asp Pro Asn Phe Ser Asn Asn Tyr Val Gly
        35                  40                  45

Ala Thr Asn Ala Lys Phe Ile Arg Gly Ala Tyr His Phe Ala Arg Pro
    50                  55                  60

Asp Gly Gly Ser Gly Ser Thr Gln Ala Gln Phe Phe His Ser His Gly
65                  70                  75                  80

Gly Gly Trp Ser Gly Asp Gly Ile Thr Leu Pro Gly Met Leu Asp Ile
                85                  90                  95

Glu Tyr Gly Pro Thr Ser Thr Cys Tyr Gly Leu Ser Thr Ser Ala Met
            100                 105                 110

Val Thr Trp Ile Thr Asp Phe Val Asn Glu Tyr His Ala Leu Thr Gly
        115                 120                 125

Arg Tyr Pro Leu Ile Tyr Thr Thr Asn Asp Trp Trp Asn Thr Cys Thr
    130                 135                 140

Gly Asn Thr Asn Lys Phe Ser Thr Thr Cys Pro Leu Val Leu Ala Arg
145                 150                 155                 160

Tyr Ser Ser Ser Val Gly Thr Ile Pro Gly Gly Trp Pro Phe Gln Thr
                165                 170                 175

Ile Trp Gln Phe Asn Asp Asn Tyr Ala Tyr Gly Gly Asp Ser Asp Thr
            180                 185                 190

Phe Asn Gly Asp Leu Ala Gly Leu Lys Lys Leu Ala Thr Gly
        195                 200                 205
```

```
<210> SEQ ID NO 102
<211> LENGTH: 814
<212> TYPE: DNA
<213> ORGANISM: Coniothyrium sp
<220> FEATURE:
<221> NAME/KEY: CDS
<222> LOCATION: (1)..(231)
<220> FEATURE:
<221> NAME/KEY: sig_peptide
<222> LOCATION: (1)..(48)
<220> FEATURE:
<221> NAME/KEY: mat_peptide
<222> LOCATION: (49)..(811)
<220> FEATURE:
<221> NAME/KEY: CDS
<222> LOCATION: (389)..(811)

<400> SEQUENCE: 102
```

```
atg aag tgt ctt tca ttc ctt cca ttg ttg gct gca aca gct cat ggc      48
Met Lys Cys Leu Ser Phe Leu Pro Leu Leu Ala Ala Thr Ala His Gly
    -15                 -10                 -5                  -1 gcg gtc caa ggc ttc gac atc tcc cat tat caa gca tcc gtc aat ttc      96
```

```
Ala Val Gln Gly Phe Asp Ile Ser His Tyr Gln Ala Ser Val Asn Phe
1               5                   10                  15 gct gca gcc tac tcg ggc ggc cta cgc ttc gta tac atc aaa gct aca      144
Ala Ala Ala Tyr Ser Gly Gly Leu Arg Phe Val Tyr Ile Lys Ala Thr
            20                  25                  30 gaa ggc acg aca tac cag gat cca gcc ttc tcc tcg cat tac agt ggc      192
Glu Gly Thr Thr Tyr Gln Asp Pro Ala Phe Ser Ser His Tyr Ser Gly
            35                  40                  45 gcc acg tct gca ggg ttc atc cgc ggc ggc tac cac ttc gtaagctctc       241
Ala Thr Ser Ala Gly Phe Ile Arg Gly Gly Tyr His Phe
    50                  55                  60 cccatacaca attgccaatc gatgaagcat gagatgttcg agtccctgga gctcataaac    301
agaatgcaaa atttaccccc gatctttttcc gcaacgtttt catcctcatg cgaaagacaa   361
ccactaacct gtaccgcaca ctcacag gca cgc ccc gcc tcc tcc acc ggc gca    415
                              Ala Arg Pro Ala Ser Ser Thr Gly Ala
                                  65                  70 gcc caa gcc tcc tac ttc gtc gcg cac ggc ggc ggg tgg tcg aac gac      463
Ala Gln Ala Ser Tyr Phe Val Ala His Gly Gly Gly Trp Ser Asn Asp
            75                  80                  85 ggc ata acg ctc cca ggg atg ctc gac ctg gaa ggc gac tgc gcg ggc      511
Gly Ile Thr Leu Pro Gly Met Leu Asp Leu Glu Gly Asp Cys Ala Gly
            90                  95                  100 ctc tct acc gcc tcc atg gta tcc tgg atc agc agc ttc tcc aac cag      559
Leu Ser Thr Ala Ser Met Val Ser Trp Ile Ser Ser Phe Ser Asn Gln
            105                 110                 115 tac cac agc ctg acg ggc cgc tgg ccc gtc atc tac acg acg aac agc      607
Tyr His Ser Leu Thr Gly Arg Trp Pro Val Ile Tyr Thr Thr Asn Ser
        120                 125                 130 tgg tgg acg acg tgc acg ggg aac agc gcg gcg ttc aac gcg aac agc      655
Trp Trp Thr Thr Cys Thr Gly Asn Ser Ala Ala Phe Asn Ala Asn Ser
135             140                 145                 150 ccg ctg atg ctg gcg cgg tgg gga agc acg gcg ggc acg atc ccg ggg      703
Pro Leu Met Leu Ala Arg Trp Gly Ser Thr Ala Gly Thr Ile Pro Gly
                155                 160                 165 ggc tgg cct tat tat acg att tgg cag tac aag gat agc aat acg tat      751
Gly Trp Pro Tyr Tyr Thr Ile Trp Gln Tyr Lys Asp Ser Asn Thr Tyr
            170                 175                 180 ggg ggt gat agc gat gtg ttc aac ggt gat gcg acg cag ttg aag aaa      799
Gly Gly Asp Ser Asp Val Phe Asn Gly Asp Ala Thr Gln Leu Lys Lys
            185                 190                 195 ttg gcg aca ggt taa                                                   814
Leu Ala Thr Gly
    200

<210> SEQ ID NO 103
<211> LENGTH: 218
<212> TYPE: PRT
<213> ORGANISM: Coniothyrium sp

<400> SEQUENCE: 103

Met Lys Cys Leu Ser Phe Leu Pro Leu Leu Ala Ala Thr Ala His Gly
            -15                 -10                 -5              -1

Ala Val Gln Gly Phe Asp Ile Ser His Tyr Gln Ala Ser Val Asn Phe
1               5                   10                  15

Ala Ala Ala Tyr Ser Gly Gly Leu Arg Phe Val Tyr Ile Lys Ala Thr
            20                  25                  30

Glu Gly Thr Thr Tyr Gln Asp Pro Ala Phe Ser Ser His Tyr Ser Gly
            35                  40                  45
```

```
Ala Thr Ser Ala Gly Phe Ile Arg Gly Gly Tyr His Phe Ala Arg Pro
 50                  55                  60

Ala Ser Ser Thr Gly Ala Ala Gln Ala Ser Tyr Phe Val Ala His Gly
 65                  70                  75                  80

Gly Gly Trp Ser Asn Asp Gly Ile Thr Leu Pro Gly Met Leu Asp Leu
                 85                  90                  95

Glu Gly Asp Cys Ala Gly Leu Ser Thr Ala Ser Met Val Ser Trp Ile
                100                 105                 110

Ser Ser Phe Ser Asn Gln Tyr His Ser Leu Thr Gly Arg Trp Pro Val
                115                 120                 125

Ile Tyr Thr Thr Asn Ser Trp Trp Thr Thr Cys Thr Gly Asn Ser Ala
130                 135                 140

Ala Phe Asn Ala Asn Ser Pro Leu Met Leu Ala Arg Trp Gly Ser Thr
145                 150                 155                 160

Ala Gly Thr Ile Pro Gly Gly Trp Pro Tyr Tyr Thr Ile Trp Gln Tyr
                165                 170                 175

Lys Asp Ser Asn Thr Tyr Gly Gly Asp Ser Asp Val Phe Asn Gly Asp
                180                 185                 190

Ala Thr Gln Leu Lys Lys Leu Ala Thr Gly
                195                 200
```

<210> SEQ ID NO 104
<211> LENGTH: 202
<212> TYPE: PRT
<213> ORGANISM: Coniothyrium sp
<220> FEATURE:
<221> NAME/KEY: mat_peptide
<222> LOCATION: (1)..(202)

<400> SEQUENCE: 104

```
Ala Val Gln Gly Phe Asp Ile Ser His Tyr Gln Ala Ser Val Asn Phe
 1               5                  10                  15

Ala Ala Ala Tyr Ser Gly Gly Leu Arg Phe Val Tyr Ile Lys Ala Thr
                 20                  25                  30

Glu Gly Thr Thr Tyr Gln Asp Pro Ala Phe Ser Ser His Tyr Ser Gly
             35                  40                  45

Ala Thr Ser Ala Gly Phe Ile Arg Gly Gly Tyr His Phe Ala Arg Pro
 50                  55                  60

Ala Ser Ser Thr Gly Ala Ala Gln Ala Ser Tyr Phe Val Ala His Gly
 65                  70                  75                  80

Gly Gly Trp Ser Asn Asp Gly Ile Thr Leu Pro Gly Met Leu Asp Leu
                 85                  90                  95

Glu Gly Asp Cys Ala Gly Leu Ser Thr Ala Ser Met Val Ser Trp Ile
                100                 105                 110

Ser Ser Phe Ser Asn Gln Tyr His Ser Leu Thr Gly Arg Trp Pro Val
                115                 120                 125

Ile Tyr Thr Thr Asn Ser Trp Trp Thr Thr Cys Thr Gly Asn Ser Ala
130                 135                 140

Ala Phe Asn Ala Asn Ser Pro Leu Met Leu Ala Arg Trp Gly Ser Thr
145                 150                 155                 160

Ala Gly Thr Ile Pro Gly Gly Trp Pro Tyr Tyr Thr Ile Trp Gln Tyr
                165                 170                 175

Lys Asp Ser Asn Thr Tyr Gly Gly Asp Ser Asp Val Phe Asn Gly Asp
                180                 185                 190

Ala Thr Gln Leu Lys Lys Leu Ala Thr Gly
                195                 200
```

```
<210> SEQ ID NO 105
<211> LENGTH: 802
<212> TYPE: DNA
<213> ORGANISM: Hypoxylon sp.
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(799)
<220> FEATURE:
<221> NAME/KEY: CDS
<222> LOCATION: (210)..(696)
<220> FEATURE:
<221> NAME/KEY: CDS
<222> LOCATION: (771)..(799)

<400> SEQUENCE: 105
```

| | | | | | | | | | | | | | | | |
|---|---|---|---|---|---|---|---|---|---|---|---|---|---|---|---|
| atg | aaa | gct | ttc | att | act | acc | tgt | cta | agc | ttg | agc | agc | ctt | gcc | ctc | 48 |
| Met | Lys | Ala | Phe | Ile | Thr | Thr | Cys | Leu | Ser | Leu | Ser | Ser | Leu | Ala | Leu |
| | -15 | | | | -10 | | | | | -5 | | | | | |

| gct | gct | gtc | cct | ggc | ttt | gat | att | tct | cac | tac | cag | tcg | aac | gta | gac | 96 |
| Ala | Ala | Val | Pro | Gly | Phe | Asp | Ile | Ser | His | Tyr | Gln | Ser | Asn | Val | Asp |
| -1 | 1 | | | 5 | | | | | 10 | | | | | 15 | |

| ttc | ggg | gca | gca | tat | agt | tcc | ggg | gca | cga | ttc | gtt | atc | atc | aaa | | 141 |
| Phe | Gly | Ala | Ala | Tyr | Ser | Ser | Gly | Ala | Arg | Phe | Val | Ile | Ile | Lys |
| | | | | 20 | | | | | 25 | | | | | 30 | gtgagcttaa cctacctata tctataactc aaatatatcc cccgcgaaac tcaccagatg     201 aaaaacag gct aca gaa ggc acc act tac caa gac ccc agc ttc agc acc     251
         Ala Thr Glu Gly Thr Thr Tyr Gln Asp Pro Ser Phe Ser Thr
                         35                  40 cac tac acc ggc gcc acc aaa gcc ggc ctc atc cgc ggc agc tac cac     299
His Tyr Thr Gly Ala Thr Lys Ala Gly Leu Ile Arg Gly Ser Tyr His
45              50                  55                  60 ttc gcg cgc ccc gga tcg tcc tcc ggc gct gcc caa gcg acg tac ttc     347
Phe Ala Arg Pro Gly Ser Ser Ser Gly Ala Ala Gln Ala Thr Tyr Phe
                65                  70                  75 ctc gcg cac ggc ggc ggg tgg tcg ggc gac ggg atc acg ctg ccg ggg     395
Leu Ala His Gly Gly Gly Trp Ser Gly Asp Gly Ile Thr Leu Pro Gly
            80                  85                  90 atg ctg gac cta gaa ggc gat tgc gcg ggc ctg tcg acc aac gcc atg     443
Met Leu Asp Leu Glu Gly Asp Cys Ala Gly Leu Ser Thr Asn Ala Met
        95                  100                 105 gtc gcg tgg atc agg gac ttt agc gat acg tac cac ggc agg acg gga     491
Val Ala Trp Ile Arg Asp Phe Ser Asp Thr Tyr His Gly Arg Thr Gly
    110                 115                 120 cgg tat ccg ctg ctg tac acg aac ccg tcg tgg tgg tcg ggt tgc gcg     539
Arg Tyr Pro Leu Leu Tyr Thr Asn Pro Ser Trp Trp Ser Gly Cys Ala
125                 130                 135                 140 ggc ggg tcg gcc gcg ttc gtc ggt acg aat ccg ctt gtg ctt gcg cgg     587
Gly Gly Ser Ala Ala Phe Val Gly Thr Asn Pro Leu Val Leu Ala Arg
                145                 150                 155 tat gct ggg agc ccg ggg gcg ttg ccg gga ggg tgg ccg tat tat acg     635
Tyr Ala Gly Ser Pro Gly Ala Leu Pro Gly Gly Trp Pro Tyr Tyr Thr
            160                 165                 170 att tgg cag ttt gac gat gcg tat aag tat ggg ggc gat tcg gat acg     683
Ile Trp Gln Phe Asp Asp Ala Tyr Lys Tyr Gly Gly Asp Ser Asp Thr
        175                 180                 185 ttt aat ggc gat c gtgagtacct atcgttgctt aatttttctt ttctattatt        736
Phe Asn Gly Asp

```
                                                ttcttgtcct ttggctaacg tggtggtgtt gcag tc  acg cag tta aag aaa ttg    790
                                                                                         Leu Thr Gln Leu Lys Lys Leu
                                                                                                 195 gct tct ggc tag                                                                                                      802
Ala Ser Gly
200
```

```
<210> SEQ ID NO 106
<211> LENGTH: 219
<212> TYPE: PRT
<213> ORGANISM: Hypoxylon sp.

<400> SEQUENCE: 106
```

Phe Asn Gly Asp
    190

Met Lys Ala Phe Ile Thr Thr Cys Leu Ser Leu Ser Ser Leu Ala Leu
        -15                 -10                 -5

Ala Ala Val Pro Gly Phe Asp Ile Ser His Tyr Gln Ser Asn Val Asp
-1   1               5                   10                  15

Phe Gly Ala Ala Tyr Ser Ser Gly Ala Arg Phe Val Ile Ile Lys Ala
                20                  25                  30

Thr Glu Gly Thr Thr Tyr Gln Asp Pro Ser Phe Ser Thr His Tyr Thr
            35                  40                  45

Gly Ala Thr Lys Ala Gly Leu Ile Arg Gly Ser Tyr His Phe Ala Arg
        50                  55                  60

Pro Gly Ser Ser Ser Gly Ala Ala Gln Ala Thr Tyr Phe Leu Ala His
    65                  70                  75

Gly Gly Gly Trp Ser Asp Gly Ile Thr Leu Pro Gly Met Leu Asp
80                  85                  90                  95

Leu Glu Gly Asp Cys Ala Gly Leu Ser Thr Asn Ala Met Val Ala Trp
                100                 105                 110

Ile Arg Asp Phe Ser Asp Thr Tyr His Gly Arg Thr Gly Arg Tyr Pro
            115                 120                 125

Leu Leu Tyr Thr Asn Pro Ser Trp Trp Ser Gly Cys Ala Gly Gly Ser
        130                 135                 140

Ala Ala Phe Val Gly Thr Asn Pro Leu Val Leu Ala Arg Tyr Ala Gly
    145                 150                 155

Ser Pro Gly Ala Leu Pro Gly Gly Trp Pro Tyr Tyr Thr Ile Trp Gln
160                 165                 170                 175

Phe Asp Asp Ala Tyr Lys Tyr Gly Gly Asp Ser Asp Thr Phe Asn Gly
                180                 185                 190

Asp Leu Thr Gln Leu Lys Lys Leu Ala Ser Gly
            195                 200

```
<210> SEQ ID NO 107
<211> LENGTH: 202
<212> TYPE: PRT
<213> ORGANISM: Hypoxylon sp.
<220> FEATURE:
<221> NAME/KEY: mat_peptide
<222> LOCATION: (1)..(202)

<400> SEQUENCE: 107
```

Ala Val Pro Gly Phe Asp Ile Ser His Tyr Gln Ser Asn Val Asp Phe
1               5                   10                  15

Gly Ala Ala Tyr Ser Ser Gly Ala Arg Phe Val Ile Ile Lys Ala Thr
            20                  25                  30

Glu Gly Thr Thr Tyr Gln Asp Pro Ser Phe Ser Thr His Tyr Thr Gly

```
                35                  40                  45
Ala Thr Lys Ala Gly Leu Ile Arg Gly Ser Tyr His Phe Ala Arg Pro
 50                  55                  60

Gly Ser Ser Gly Ala Ala Gln Ala Thr Tyr Phe Leu Ala His Gly
 65                  70                  75                  80

Gly Gly Trp Ser Gly Asp Gly Ile Thr Leu Pro Gly Met Leu Asp Leu
                 85                  90                  95

Glu Gly Asp Cys Ala Gly Leu Ser Thr Asn Ala Met Val Ala Trp Ile
                100                 105                 110

Arg Asp Phe Ser Asp Thr Tyr His Gly Arg Thr Gly Arg Tyr Pro Leu
                115                 120                 125

Leu Tyr Thr Asn Pro Ser Trp Trp Ser Gly Cys Ala Gly Gly Ser Ala
                130                 135                 140

Ala Phe Val Gly Thr Asn Pro Leu Val Leu Ala Arg Tyr Ala Gly Ser
145                 150                 155                 160

Pro Gly Ala Leu Pro Gly Gly Trp Pro Tyr Tyr Thr Ile Trp Gln Phe
                165                 170                 175

Asp Asp Ala Tyr Lys Tyr Gly Gly Asp Ser Asp Thr Phe Asn Gly Asp
                180                 185                 190

Leu Thr Gln Leu Lys Lys Leu Ala Ser Gly
                195                 200

<210> SEQ ID NO 108
<211> LENGTH: 837
<212> TYPE: DNA
<213> ORGANISM: Xylariaceae sp. 1653h
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(834)
<220> FEATURE:
<221> NAME/KEY: CDS
<222> LOCATION: (199)..(685)
<220> FEATURE:
<221> NAME/KEY: CDS
<222> LOCATION: (806)..(834)

<400> SEQUENCE: 108
```

| | | | | | | | | | | | | | | | | |
|---|---|---|---|---|---|---|---|---|---|---|---|---|---|---|---|---|
| atg | aag | ctc | ttc | att | gcc | acg | tgt | ttg | ggc | ctg | ggt | agc | atc | gcc | ctc | 48 |
| Met | Lys | Leu | Phe | Ile | Ala | Thr | Cys | Leu | Gly | Leu | Gly | Ser | Ile | Ala | Leu | |
| | -15 | | | | | -10 | | | | | -5 | | | | | |

| | | | | | | | | | | | | | | | | |
|---|---|---|---|---|---|---|---|---|---|---|---|---|---|---|---|---|
| gca | gct | gtc | cca | gga | ttc | gat | atc | tcc | cac | tat | caa | tcg | agc | gtg | gat | 96 |
| Ala | Ala | Val | Pro | Gly | Phe | Asp | Ile | Ser | His | Tyr | Gln | Ser | Ser | Val | Asp | |
| -1 | 1 | | | 5 | | | | | 10 | | | | | 15 | | |

| | | | | | | | | | | | |
|---|---|---|---|---|---|---|---|---|---|---|---|
| ttt | gcg | gca | gct | tac | agt | gct | gga | gct | cgc | ttc | gtt | att | atc | aag | 141 |
| Phe | Ala | Ala | Ala | Tyr | Ser | Ala | Gly | Ala | Arg | Phe | Val | Ile | Ile | Lys | |
| | | | 20 | | | | | 25 | | | | | 30 | | | gtagcactaa accccaaaat tgaagccatt gaaaggagaa ctaacaagta atactag    198

| | | | | | | | | | | | | | | | | |
|---|---|---|---|---|---|---|---|---|---|---|---|---|---|---|---|---|
| gct | aca | gag | ggt | acc | acc | tac | att | gac | ccg | agt | ttc | agc | agt | cac | tac | 246 |
| Ala | Thr | Glu | Gly | Thr | Thr | Tyr | Ile | Asp | Pro | Ser | Phe | Ser | Ser | His | Tyr | |
| | | | | 35 | | | | | 40 | | | | | 45 | | |

| | | | | | | | | | | | | | | | | |
|---|---|---|---|---|---|---|---|---|---|---|---|---|---|---|---|---|
| acc | ggt | gcc | acc | aac | gcc | ggg | ctc | atc | cgc | ggc | ggc | tac | cac | ttc | gca | 294 |
| Thr | Gly | Ala | Thr | Asn | Ala | Gly | Leu | Ile | Arg | Gly | Gly | Tyr | His | Phe | Ala | |
| | | | 50 | | | | | 55 | | | | | 60 | | | |

| | | | | | | | | | | | | | | | | |
|---|---|---|---|---|---|---|---|---|---|---|---|---|---|---|---|---|
| cat | ccc | ggt | tcc | tct | tcg | ggt | gcc | acg | cag | gcc | aac | tat | ttc | cta | gca | 342 |
| His | Pro | Gly | Ser | Ser | Ser | Gly | Ala | Thr | Gln | Ala | Asn | Tyr | Phe | Leu | Ala | |

```
cat ggc gga ggc tgg tca gga gac gga att act ctc cca ggc atg ttg      390
His Gly Gly Gly Trp Ser Gly Asp Gly Ile Thr Leu Pro Gly Met Leu
    80                  85                  90 gac tta gag ggt gac tgc gca ggc ctc tca aca agc gcc atg gtc tcc      438
Asp Leu Glu Gly Asp Cys Ala Gly Leu Ser Thr Ser Ala Met Val Ser
95                  100                 105                 110 tgg atc aaa gac ttc agc aat gca tat cac agc aaa acg gga cgc tac      486
Trp Ile Lys Asp Phe Ser Asn Ala Tyr His Ser Lys Thr Gly Arg Tyr
                115                 120                 125 cca ctc ctc tac aca aac ccg tcg tgg tgg tcc agt tgc act ggt agc      534
Pro Leu Leu Tyr Thr Asn Pro Ser Trp Trp Ser Ser Cys Thr Gly Ser
            130                 135                 140 tca agt gct ttt gtc aat acg aac cct ctt gtc ctt gca cgg tat agc      582
Ser Ser Ala Phe Val Asn Thr Asn Pro Leu Val Leu Ala Arg Tyr Ser
        145                 150                 155 agc agt gct gga aca cct cct ggt ggc tgg ccg tac tac acg att tgg      630
Ser Ser Ala Gly Thr Pro Pro Gly Gly Trp Pro Tyr Tyr Thr Ile Trp
    160                 165                 170 cag ttc aat gat gcg tac aag tat ggt ggc gac tcg gat act ttc aat      678
Gln Phe Asn Asp Ala Tyr Lys Tyr Gly Gly Asp Ser Asp Thr Phe Asn
175                 180                 185                 190 gga gaa t gtaagtcaac ctaagtcatt tcctgcttct ttgtcttgat ctgcgagtgg     735
Gly Glu cagatccta atggcagtgc aaactttctc agtgctgagc aataactctg gctaatacac      795
ggtgttgtag at gct tca ttg caa aag ctg gct act ggt taa                 837
               Tyr Ala Ser Leu Gln Lys Leu Ala Thr Gly
                   195                 200

<210> SEQ ID NO 109
<211> LENGTH: 219
<212> TYPE: PRT
<213> ORGANISM: Xylariaceae sp. 1653h

<400> SEQUENCE: 109

Met Lys Leu Phe Ile Ala Thr Cys Leu Gly Leu Gly Ser Ile Ala Leu
        -15                 -10                 -5

Ala Ala Val Pro Gly Phe Asp Ile Ser His Tyr Gln Ser Ser Val Asp
-1   1               5                  10                  15

Phe Ala Ala Ala Tyr Ser Ala Gly Ala Arg Phe Val Ile Ile Lys Ala
                20                  25                  30

Thr Glu Gly Thr Thr Tyr Ile Asp Pro Ser Phe Ser Ser His Tyr Thr
            35                  40                  45

Gly Ala Thr Asn Ala Gly Leu Ile Arg Gly Gly Tyr His Phe Ala His
        50                  55                  60

Pro Gly Ser Ser Ser Gly Ala Thr Gln Ala Asn Tyr Phe Leu Ala His
    65                  70                  75

Gly Gly Gly Trp Ser Gly Asp Gly Ile Thr Leu Pro Gly Met Leu Asp
80                  85                  90                  95

Leu Glu Gly Asp Cys Ala Gly Leu Ser Thr Ser Ala Met Val Ser Trp
                100                 105                 110

Ile Lys Asp Phe Ser Asn Ala Tyr His Ser Lys Thr Gly Arg Tyr Pro
            115                 120                 125

Leu Leu Tyr Thr Asn Pro Ser Trp Trp Ser Ser Cys Thr Gly Ser Ser
        130                 135                 140

Ser Ala Phe Val Asn Thr Asn Pro Leu Val Leu Ala Arg Tyr Ser Ser
    145                 150                 155
```

```
Ser Ala Gly Thr Pro Pro Gly Gly Trp Pro Tyr Tyr Thr Ile Trp Gln
160                 165                 170                 175

Phe Asn Asp Ala Tyr Lys Tyr Gly Gly Asp Ser Asp Thr Phe Asn Gly
            180                 185                 190

Glu Tyr Ala Ser Leu Gln Lys Leu Ala Thr Gly
        195                 200
```

<210> SEQ ID NO 110
<211> LENGTH: 202
<212> TYPE: PRT
<213> ORGANISM: Xylariaceae sp. 1653h
<220> FEATURE:
<221> NAME/KEY: mat_peptide
<222> LOCATION: (1)..(202)

<400> SEQUENCE: 110

```
Ala Val Pro Gly Phe Asp Ile Ser His Tyr Gln Ser Ser Val Asp Phe
1               5                   10                  15

Ala Ala Ala Tyr Ser Ala Gly Ala Arg Phe Val Ile Ile Lys Ala Thr
            20                  25                  30

Glu Gly Thr Thr Tyr Ile Asp Pro Ser Phe Ser Ser His Tyr Thr Gly
        35                  40                  45

Ala Thr Asn Ala Gly Leu Ile Arg Gly Gly Tyr His Phe Ala His Pro
    50                  55                  60

Gly Ser Ser Ser Gly Ala Thr Gln Ala Asn Tyr Phe Leu Ala His Gly
65                  70                  75                  80

Gly Gly Trp Ser Gly Asp Gly Ile Thr Leu Pro Gly Met Leu Asp Leu
                85                  90                  95

Glu Gly Asp Cys Ala Gly Leu Ser Thr Ser Ala Met Val Ser Trp Ile
            100                 105                 110

Lys Asp Phe Ser Asn Ala Tyr His Ser Lys Thr Gly Arg Tyr Pro Leu
        115                 120                 125

Leu Tyr Thr Asn Pro Ser Trp Trp Ser Ser Cys Thr Gly Ser Ser Ser
    130                 135                 140

Ala Phe Val Asn Thr Asn Pro Leu Val Leu Ala Arg Tyr Ser Ser Ser
145                 150                 155                 160

Ala Gly Thr Pro Pro Gly Gly Trp Pro Tyr Tyr Thr Ile Trp Gln Phe
                165                 170                 175

Asn Asp Ala Tyr Lys Tyr Gly Gly Asp Ser Asp Thr Phe Asn Gly Glu
            180                 185                 190

Tyr Ala Ser Leu Gln Lys Leu Ala Thr Gly
        195                 200
```

<210> SEQ ID NO 111
<211> LENGTH: 835
<212> TYPE: DNA
<213> ORGANISM: Hypoxylon sp.
<220> FEATURE:
<221> NAME/KEY: CDS
<222> LOCATION: (1)..(141)
<220> FEATURE:
<221> NAME/KEY: sig_peptide
<222> LOCATION: (1)..(51)
<220> FEATURE:
<221> NAME/KEY: mat_peptide
<222> LOCATION: (52)..(832)
<220> FEATURE:
<221> NAME/KEY: CDS
<222> LOCATION: (201)..(687)
<220> FEATURE:
<221> NAME/KEY: CDS

<222> LOCATION: (804)..(832)

<400> SEQUENCE: 111

```
atg aag ttc ttc gtt gcc act ttc tta ggt cta agc agc gtt gcc ctc        48
Met Lys Phe Phe Val Ala Thr Phe Leu Gly Leu Ser Ser Val Ala Leu
        -15                 -10                 -5 gca gca gtg cca gga ttc gat att tct cac tac caa tcg agt gtg gat        96
Ala Ala Val Pro Gly Phe Asp Ile Ser His Tyr Gln Ser Ser Val Asp
-1  1               5                   10                  15 ttt gca gca gcc tac aat tcc ggg gcg cgc ttt gtt att atc aag            141
Phe Ala Ala Ala Tyr Asn Ser Gly Ala Arg Phe Val Ile Ile Lys
                20                  25                  30 gtaaccctga atcctaaaga gaaaagtcgt tcgaaataga tttaacccgt tccgaatag       200 gct act gag ggc acc acg tac atc gac cca agt ttc agt agt cac tat       248
Ala Thr Glu Gly Thr Thr Tyr Ile Asp Pro Ser Phe Ser Ser His Tyr
            35                  40                  45 acc ggt gct acc aag gct gga ttc atc cgc ggt ggc tat cat ttt gca       296
Thr Gly Ala Thr Lys Ala Gly Phe Ile Arg Gly Gly Tyr His Phe Ala
        50                  55                  60 cat ccc ggt tct tcg tcg gga gcg gcg caa gcc aac tat ttc cta gca       344
His Pro Gly Ser Ser Ser Gly Ala Ala Gln Ala Asn Tyr Phe Leu Ala
    65                  70                  75 cat ggc ggt ggc tgg tcg ggc gac gga atc act ttc cca ggc atg ttg       392
His Gly Gly Gly Trp Ser Gly Asp Gly Ile Thr Phe Pro Gly Met Leu
80                  85                  90 gat tta gag ggt gac tgc gcg ggc ctc tcg aca agt gct atg gtc tct       440
Asp Leu Glu Gly Asp Cys Ala Gly Leu Ser Thr Ser Ala Met Val Ser
95                  100                 105                 110 tgg atc aag gac ttc agc gat aca tat cac agt aag acg gga cgc tac       488
Trp Ile Lys Asp Phe Ser Asp Thr Tyr His Ser Lys Thr Gly Arg Tyr
                115                 120                 125 cct ctc ctc tac aca aac cct tcg tgg tgg tcg agc tgc acc ggt gat       536
Pro Leu Leu Tyr Thr Asn Pro Ser Trp Trp Ser Ser Cys Thr Gly Asp
            130                 135                 140 tcg agt gcc ttt gtc aat acg aac ccc ctc gtc ctc gca cga tat agc       584
Ser Ser Ala Phe Val Asn Thr Asn Pro Leu Val Leu Ala Arg Tyr Ser
        145                 150                 155 agc agc gct gga acg ccg ccc ggc ggc tgg ccg tat tac acg atc tgg       632
Ser Ser Ala Gly Thr Pro Pro Gly Gly Trp Pro Tyr Tyr Thr Ile Trp
    160                 165                 170 cag ttt aac gac gca tac aaa tat ggt ggt gac tcg gat act ttc aat       680
Gln Phe Asn Asp Ala Tyr Lys Tyr Gly Gly Asp Ser Asp Thr Phe Asn
175                 180                 185                 190 gga aac t gtaagtgaac ttgcgatcgt tttggccacc atcgaaacct ataaatgcga     737
Gly Asn ggtcgtcgat ggcagtgcaa actctaccta ctcttagcaa caatttcagc taatatgata    797 ttttag at  gct tcg ctg caa aag tta gct act ggt tag                    835
           Tyr Ala Ser Leu Gln Lys Leu Ala Thr Gly
               195                 200
```

<210> SEQ ID NO 112
<211> LENGTH: 219
<212> TYPE: PRT
<213> ORGANISM: Hypoxylon sp.

<400> SEQUENCE: 112

```
Met Lys Phe Phe Val Ala Thr Phe Leu Gly Leu Ser Ser Val Ala Leu
        -15                 -10                 -5

Ala Ala Val Pro Gly Phe Asp Ile Ser His Tyr Gln Ser Ser Val Asp
```

```
          -1   1                    5                        10                       15
          Phe  Ala  Ala  Ala  Tyr  Asn  Ser  Gly  Ala  Arg  Phe  Val  Ile  Ile  Lys  Ala
                              20                        25                       30
          Thr  Glu  Gly  Thr  Thr  Tyr  Ile  Asp  Pro  Ser  Phe  Ser  Ser  His  Tyr  Thr
                              35                        40                       45
          Gly  Ala  Thr  Lys  Ala  Gly  Phe  Ile  Arg  Gly  Gly  Tyr  His  Phe  Ala  His
                              50                        55                       60
          Pro  Gly  Ser  Ser  Ser  Gly  Ala  Ala  Gln  Ala  Asn  Tyr  Phe  Leu  Ala  His
               65                        70                       75
          Gly  Gly  Gly  Trp  Ser  Gly  Asp  Gly  Ile  Thr  Phe  Pro  Gly  Met  Leu  Asp
          80                        85                        90                       95
          Leu  Glu  Gly  Asp  Cys  Ala  Gly  Leu  Ser  Thr  Ser  Ala  Met  Val  Ser  Trp
                              100                       105                      110
          Ile  Lys  Asp  Phe  Ser  Asp  Thr  Tyr  His  Ser  Lys  Thr  Gly  Arg  Tyr  Pro
                              115                       120                      125
          Leu  Leu  Tyr  Thr  Asn  Pro  Ser  Trp  Trp  Ser  Ser  Cys  Thr  Gly  Asp  Ser
                              130                       135                      140
          Ser  Ala  Phe  Val  Asn  Thr  Asn  Pro  Leu  Val  Leu  Ala  Arg  Tyr  Ser  Ser
               145                       150                      155
          Ser  Ala  Gly  Thr  Pro  Pro  Gly  Gly  Trp  Pro  Tyr  Tyr  Thr  Ile  Trp  Gln
          160                       165                       170                      175
          Phe  Asn  Asp  Ala  Tyr  Lys  Tyr  Gly  Gly  Asp  Ser  Asp  Thr  Phe  Asn  Gly
                              180                       185                      190
          Asn  Tyr  Ala  Ser  Leu  Gln  Lys  Leu  Ala  Thr  Gly
                    195                       200

<210> SEQ ID NO 113
<211> LENGTH: 202
<212> TYPE: PRT
<213> ORGANISM: Hypoxylon sp.
<220> FEATURE:
<221> NAME/KEY: mat_peptide
<222> LOCATION: (1)..(202)

<400> SEQUENCE: 113

Ala  Val  Pro  Gly  Phe  Asp  Ile  Ser  His  Tyr  Gln  Ser  Ser  Val  Asp  Phe
1                   5                        10                       15
Ala  Ala  Ala  Tyr  Asn  Ser  Gly  Ala  Arg  Phe  Val  Ile  Ile  Lys  Ala  Thr
                    20                       25                       30
Glu  Gly  Thr  Thr  Tyr  Ile  Asp  Pro  Ser  Phe  Ser  Ser  His  Tyr  Thr  Gly
               35                       40                       45
Ala  Thr  Lys  Ala  Gly  Phe  Ile  Arg  Gly  Gly  Tyr  His  Phe  Ala  His  Pro
     50                       55                       60
Gly  Ser  Ser  Ser  Gly  Ala  Ala  Gln  Ala  Asn  Tyr  Phe  Leu  Ala  His  Gly
65                       70                       75                       80
Gly  Gly  Trp  Ser  Gly  Asp  Gly  Ile  Thr  Phe  Pro  Gly  Met  Leu  Asp  Leu
                    85                       90                       95
Glu  Gly  Asp  Cys  Ala  Gly  Leu  Ser  Thr  Ser  Ala  Met  Val  Ser  Trp  Ile
               100                      105                      110
Lys  Asp  Phe  Ser  Asp  Thr  Tyr  His  Ser  Lys  Thr  Gly  Arg  Tyr  Pro  Leu
          115                      120                      125
Leu  Tyr  Thr  Asn  Pro  Ser  Trp  Trp  Ser  Ser  Cys  Thr  Gly  Asp  Ser  Ser
     130                      135                      140
Ala  Phe  Val  Asn  Thr  Asn  Pro  Leu  Val  Leu  Ala  Arg  Tyr  Ser  Ser  Ser
145                      150                      155                      160
```

```
Ala Gly Thr Pro Pro Gly Gly Trp Pro Tyr Tyr Thr Ile Trp Gln Phe
            165                 170                 175

Asn Asp Ala Tyr Lys Tyr Gly Asp Ser Asp Thr Phe Asn Gly Asn
            180                 185                 190

Tyr Ala Ser Leu Gln Lys Leu Ala Thr Gly
        195                 200

<210> SEQ ID NO 114
<211> LENGTH: 748
<212> TYPE: DNA
<213> ORGANISM: Yunnania penicillata
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(743)
<220> FEATURE:
<221> NAME/KEY: CDS
<222> LOCATION: (218)..(745)

<400> SEQUENCE: 114 atg aag tcc att acc gcc gcc gct ctt ctg ggc ctc gcc gcc act gtc      48
Met Lys Ser Ile Thr Ala Ala Ala Leu Leu Gly Leu Ala Ala Thr Val
            -15                 -10                  -5 cag gcc gat gtc gac ggc ttt gac atc tcc cac tac cag gag act gtc      96
Gln Ala Asp Val Asp Gly Phe Asp Ile Ser His Tyr Gln Glu Thr Val
    -1   1               5                  10 gac tat gcc ggt gcc tac ggc gct ggt gcc cgc ttc gtc atc atc aag     144
Asp Tyr Ala Gly Ala Tyr Gly Ala Gly Ala Arg Phe Val Ile Ile Lys
 15          20                  25                  30 gtgagcacac cacatcacca aacagtggat gtgtcttatc gagacaagtg acagtgacta    204
accccgtcca cag gcg act gag ggc acg aac tac atc gac tcc tct ttc       253
               Ala Thr Glu Gly Thr Asn Tyr Ile Asp Ser Ser Phe
                            35                  40 aac acg cac tac gct ggt gcc acc gac gcg ggc ctc atc cgc ggc ggc      301
Asn Thr His Tyr Ala Gly Ala Thr Asp Ala Gly Leu Ile Arg Gly Gly
            45                  50                  55 tac cac ttc gcg cac ccg ggc gag acg acg ggc gcg gag cag gcc gac      349
Tyr His Phe Ala His Pro Gly Glu Thr Thr Gly Ala Glu Gln Ala Asp
        60                  65                  70 tac ttc atc gcg cac ggc ggc aac tgg tcc aac gac ggc atc acg ctg      397
Tyr Phe Ile Ala His Gly Gly Asn Trp Ser Asn Asp Gly Ile Thr Leu
 75              80                  85                  90 ccg ggc atg ctg gac ctc gag ggc gag ggc agc acc acg tgc tgg gac      445
Pro Gly Met Leu Asp Leu Glu Gly Glu Gly Ser Thr Thr Cys Trp Asp
                 95                 100                 105 ctg agc gcc gcc gac atg gtc gcc tgg atc aag gcc ttc agc gac cgg      493
Leu Ser Ala Ala Asp Met Val Ala Trp Ile Lys Ala Phe Ser Asp Arg
             110                 115                 120 tac cag gag gtc acg agc cgg tac ccc ctc ctc tac acc aac ccg tcg      541
Tyr Gln Glu Val Thr Ser Arg Tyr Pro Leu Leu Tyr Thr Asn Pro Ser
         125                 130                 135 tgg tgg tcc gag tgc acg ggc aac tcg gac gcc ttc gtg gac acc aac      589
Trp Trp Ser Glu Cys Thr Gly Asn Ser Asp Ala Phe Val Asp Thr Asn
     140                 145                 150 ccg ctg gtg ctt gcg cgg tac gcg agc tcg cct ggc gag atc ccc ggc      637
Pro Leu Val Leu Ala Arg Tyr Ala Ser Ser Pro Gly Glu Ile Pro Gly
155                 160                 165                 170
```

```
ggc tgg ccg gcg cag acc atc tgg cag aac tcg gac agc tac tcg ttc       685
Gly Trp Pro Ala Gln Thr Ile Trp Gln Asn Ser Asp Ser Tyr Ser Phe
            175                 180                 185 ggt gga gac tcg gac atc ttc aac ggc gac gag gcc ggc ctg aag aag       733
Gly Gly Asp Ser Asp Ile Phe Asn Gly Asp Glu Ala Gly Leu Lys Lys
            190                 195                 200 ctt gcg agc ggt taa                                                   748
Leu Ala Ser Gly
        205
```

<210> SEQ ID NO 115
<211> LENGTH: 224
<212> TYPE: PRT
<213> ORGANISM: Yunnania penicillata

<400> SEQUENCE: 115

```
Met Lys Ser Ile Thr Ala Ala Leu Leu Gly Leu Ala Ala Thr Val
            -15                 -10                 -5

Gln Ala Asp Val Asp Gly Phe Asp Ile Ser His Tyr Gln Glu Thr Val
        -1  1               5                   10

Asp Tyr Ala Gly Ala Tyr Gly Ala Gly Ala Arg Phe Val Ile Ile Lys
15                  20                  25                  30

Ala Thr Glu Gly Thr Asn Tyr Ile Asp Ser Ser Phe Asn Thr His Tyr
                35                  40                  45

Ala Gly Ala Thr Asp Ala Gly Leu Ile Arg Gly Gly Tyr His Phe Ala
            50                  55                  60

His Pro Gly Glu Thr Thr Gly Ala Glu Gln Ala Asp Tyr Phe Ile Ala
        65                  70                  75

His Gly Gly Asn Trp Ser Asn Asp Gly Ile Thr Leu Pro Gly Met Leu
    80                  85                  90

Asp Leu Glu Gly Glu Gly Ser Thr Thr Cys Trp Asp Leu Ser Ala Ala
95                  100                 105                 110

Asp Met Val Ala Trp Ile Lys Ala Phe Ser Asp Arg Tyr Gln Glu Val
                115                 120                 125

Thr Ser Arg Tyr Pro Leu Leu Tyr Thr Asn Pro Ser Trp Trp Ser Glu
            130                 135                 140

Cys Thr Gly Asn Ser Asp Ala Phe Val Asp Thr Asn Pro Leu Val Leu
        145                 150                 155

Ala Arg Tyr Ala Ser Ser Pro Gly Glu Ile Pro Gly Gly Trp Pro Ala
    160                 165                 170

Gln Thr Ile Trp Gln Asn Ser Asp Ser Tyr Ser Phe Gly Gly Asp Ser
175                 180                 185                 190

Asp Ile Phe Asn Gly Asp Glu Ala Gly Leu Lys Lys Leu Ala Ser Gly
                195                 200                 205
```

<210> SEQ ID NO 116
<211> LENGTH: 206
<212> TYPE: PRT
<213> ORGANISM: Yunnania penicillata
<220> FEATURE:
<221> NAME/KEY: mat_peptide
<222> LOCATION: (1)..(206)

<400> SEQUENCE: 116

```
Asp Val Asp Gly Phe Asp Ile Ser His Tyr Gln Glu Thr Val Asp Tyr
1               5                   10                  15

Ala Gly Ala Tyr Gly Ala Gly Ala Arg Phe Val Ile Ile Lys Ala Thr
            20                  25                  30
```

```
Glu Gly Thr Asn Tyr Ile Asp Ser Phe Asn Thr His Tyr Ala Gly
            35                  40                  45

Ala Thr Asp Ala Gly Leu Ile Arg Gly Tyr His Phe Ala His Pro
 50                  55                  60

Gly Glu Thr Thr Gly Ala Glu Gln Ala Asp Tyr Phe Ile Ala His Gly
 65                  70                  75                  80

Gly Asn Trp Ser Asn Asp Gly Ile Thr Leu Pro Gly Met Leu Asp Leu
                 85                  90                  95

Glu Gly Glu Gly Ser Thr Thr Cys Trp Asp Leu Ser Ala Ala Asp Met
100                 105                 110

Val Ala Trp Ile Lys Ala Phe Ser Asp Arg Tyr Gln Glu Val Thr Ser
            115                 120                 125

Arg Tyr Pro Leu Leu Tyr Thr Asn Pro Ser Trp Trp Ser Glu Cys Thr
130                 135                 140

Gly Asn Ser Asp Ala Phe Val Asp Thr Asn Pro Leu Val Leu Ala Arg
145                 150                 155                 160

Tyr Ala Ser Ser Pro Gly Glu Ile Pro Gly Gly Trp Pro Ala Gln Thr
                165                 170                 175

Ile Trp Gln Asn Ser Asp Ser Tyr Ser Phe Gly Gly Asp Ser Asp Ile
            180                 185                 190

Phe Asn Gly Asp Glu Ala Gly Leu Lys Lys Leu Ala Ser Gly
            195                 200                 205

<210> SEQ ID NO 117
<211> LENGTH: 782
<212> TYPE: DNA
<213> ORGANISM: Engyodontium album
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(779)
<220> FEATURE:
<221> NAME/KEY: CDS
<222> LOCATION: (200)..(383)
<220> FEATURE:
<221> NAME/KEY: CDS
<222> LOCATION: (433)..(779)

<400> SEQUENCE: 117 atg aag tct ttt ggt gtt att gct acc ggt ttg gcc acc ctt gtg ggt      48
Met Lys Ser Phe Gly Val Ile Ala Thr Gly Leu Ala Thr Leu Val Gly
-20                 -15                 -10                  -5 gtt gcc tct gcc aga gtc caa ggt ttc gac atc tcc cac tat cag ccc      96
Val Ala Ser Ala Arg Val Gln Gly Phe Asp Ile Ser His Tyr Gln Pro
            -1   1               5                  10 agc gtc gac ttc aat gcg gcc tat gct gac gga gct cgc ttt gtg atc     144
Ser Val Asp Phe Asn Ala Ala Tyr Ala Asp Gly Ala Arg Phe Val Ile
         15                  20                  25 atc aag gtataacaaa ccataacttg gcttatgaac accatctaat gtattgcag gca   202
Ile Lys                                                         Ala
    30 acc gag ggt acc acc tac aaa gat ccc aag ttc agc cag cac tac atc     250
Thr Glu Gly Thr Thr Tyr Lys Asp Pro Lys Phe Ser Gln His Tyr Ile
            35                  40                  45 ggt gct acc aac gcc gga ttc atc cgc ggt ggc tac cac ttt gct cag     298
Gly Ala Thr Asn Ala Gly Phe Ile Arg Gly Gly Tyr His Phe Ala Gln
 50                  55                  60
```

```
cct gct tcc tct tct ggt gca gcg cag gca gac tat ttc ctc aag aac    346
Pro Ala Ser Ser Ser Gly Ala Ala Gln Ala Asp Tyr Phe Leu Lys Asn
65                  70                  75 gga ggt ggt tgg tct agc gat gga att act ctc cca g gtgagcaaag       393
Gly Gly Gly Trp Ser Ser Asp Gly Ile Thr Leu Pro
80              85                  90 tcacaaacgt tcgagggcag ttcactaata tcgtggcag gt atg ctt gat atg      446
                                              Gly Met Leu Asp Met
                                                          95 gag tac aac ccc aat ggc agt gct tgc tac ggt ctt tcc cag gct tcc    494
Glu Tyr Asn Pro Asn Gly Ser Ala Cys Tyr Gly Leu Ser Gln Ala Ser
            100                 105                 110 atg cgc aac tgg atc aac gac ttt gtc aac acc tac cac tcc cgc acg    542
Met Arg Asn Trp Ile Asn Asp Phe Val Asn Thr Tyr His Ser Arg Thr
        115                 120                 125 ggt gtc tac cct ctc ctt tac acc acc acc agc tgg tgg aaa acc tgc    590
Gly Val Tyr Pro Leu Leu Tyr Thr Thr Thr Ser Trp Trp Lys Thr Cys
130                 135                 140 acg ggt aac act gcc atg ttt gcc gac aag tgc cct ctc gtc atc gct    638
Thr Gly Asn Thr Ala Met Phe Ala Asp Lys Cys Pro Leu Val Ile Ala
145                 150                 155                 160 cgc tac aac agc gta gtc gga gag ctc ccc gct ggt tgg tct ttc tgg    686
Arg Tyr Asn Ser Val Val Gly Glu Leu Pro Ala Gly Trp Ser Phe Trp
                165                 170                 175 aca att tgg cag tac aac gac cac tac aag cat ggt ggt gac tca gac    734
Thr Ile Trp Gln Tyr Asn Asp His Tyr Lys His Gly Gly Asp Ser Asp
            180                 185                 190 gct ttt aac gga gac tac tct cag ctt cag aga atc gcc aga ggc taa    782
Ala Phe Asn Gly Asp Tyr Ser Gln Leu Gln Arg Ile Ala Arg Gly
        195                 200                 205

<210> SEQ ID NO 118
<211> LENGTH: 227
<212> TYPE: PRT
<213> ORGANISM: Engyodontium album

<400> SEQUENCE: 118

Met Lys Ser Phe Gly Val Ile Ala Thr Gly Leu Ala Thr Leu Val Gly
-20                 -15                 -10                 -5

Val Ala Ser Ala Arg Val Gln Gly Phe Asp Ile Ser His Tyr Gln Pro
            -1  1               5                   10

Ser Val Asp Phe Asn Ala Ala Tyr Ala Asp Gly Ala Arg Phe Val Ile
            15                  20                  25

Ile Lys Ala Thr Glu Gly Thr Thr Tyr Lys Asp Pro Lys Phe Ser Gln
        30                  35                  40

His Tyr Ile Gly Ala Thr Asn Ala Gly Phe Ile Arg Gly Gly Tyr His
45                  50                  55                  60

Phe Ala Gln Pro Ala Ser Ser Ser Gly Ala Ala Gln Ala Asp Tyr Phe
            65                  70                  75

Leu Lys Asn Gly Gly Gly Trp Ser Ser Asp Gly Ile Thr Leu Pro Gly
        80                  85                  90

Met Leu Asp Met Glu Tyr Asn Pro Asn Gly Ser Ala Cys Tyr Gly Leu
    95                  100                 105

Ser Gln Ala Ser Met Arg Asn Trp Ile Asn Asp Phe Val Asn Thr Tyr
            110                 115                 120

His Ser Arg Thr Gly Val Tyr Pro Leu Leu Tyr Thr Thr Thr Ser Trp
125                 130                 135                 140
```

```
Trp Lys Thr Cys Thr Gly Asn Thr Ala Met Phe Ala Asp Lys Cys Pro
            145                 150                 155

Leu Val Ile Ala Arg Tyr Asn Ser Val Val Gly Glu Leu Pro Ala Gly
        160                 165                 170

Trp Ser Phe Trp Thr Ile Trp Gln Tyr Asn Asp His Tyr Lys His Gly
    175                 180                 185

Gly Asp Ser Asp Ala Phe Asn Gly Asp Tyr Ser Gln Leu Gln Arg Ile
190                 195                 200

Ala Arg Gly
205

<210> SEQ ID NO 119
<211> LENGTH: 207
<212> TYPE: PRT
<213> ORGANISM: Engyodontium album
<220> FEATURE:
<221> NAME/KEY: mat_peptide
<222> LOCATION: (1)..(207)

<400> SEQUENCE: 119

Arg Val Gln Gly Phe Asp Ile Ser His Tyr Gln Pro Ser Val Asp Phe
1               5                   10                  15

Asn Ala Ala Tyr Ala Asp Gly Ala Arg Phe Val Ile Ile Lys Ala Thr
            20                  25                  30

Glu Gly Thr Thr Tyr Lys Asp Pro Lys Phe Ser Gln His Tyr Ile Gly
        35                  40                  45

Ala Thr Asn Ala Gly Phe Ile Arg Gly Gly Tyr His Phe Ala Gln Pro
    50                  55                  60

Ala Ser Ser Ser Gly Ala Ala Gln Ala Asp Tyr Phe Leu Lys Asn Gly
65                  70                  75                  80

Gly Gly Trp Ser Ser Asp Gly Ile Thr Leu Pro Gly Met Leu Asp Met
                85                  90                  95

Glu Tyr Asn Pro Asn Gly Ser Ala Cys Tyr Gly Leu Ser Gln Ala Ser
            100                 105                 110

Met Arg Asn Trp Ile Asn Asp Phe Val Asn Thr Tyr His Ser Arg Thr
        115                 120                 125

Gly Val Tyr Pro Leu Leu Tyr Thr Thr Thr Ser Trp Trp Lys Thr Cys
    130                 135                 140

Thr Gly Asn Thr Ala Met Phe Asp Lys Cys Pro Leu Val Ile Ala
145                 150                 155                 160

Arg Tyr Asn Ser Val Val Gly Glu Leu Pro Ala Gly Trp Ser Phe Trp
                165                 170                 175

Thr Ile Trp Gln Tyr Asn Asp His Tyr Lys His Gly Gly Asp Ser Asp
            180                 185                 190

Ala Phe Asn Gly Asp Tyr Ser Gln Leu Gln Arg Ile Ala Arg Gly
        195                 200                 205

<210> SEQ ID NO 120
<211> LENGTH: 741
<212> TYPE: DNA
<213> ORGANISM: Metapochonia bulbillosa
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: mat_peptide
<222> LOCATION: (58)..(738)
```

```
<220> FEATURE:
<221> NAME/KEY: CDS
<222> LOCATION: (205)..(738)

<400> SEQUENCE: 120 atg aag tct gtt act ttc atc gcc agt ctc gcc tcc att gtg agc gta       48
Met Lys Ser Val Thr Phe Ile Ala Ser Leu Ala Ser Ile Val Ser Val
        -15                 -10                  -5 gcc acc gcc acc gtt gct ggg ttt gac att tca aac tac caa ccc acc       96
Ala Thr Ala Thr Val Ala Gly Phe Asp Ile Ser Asn Tyr Gln Pro Thr
        -1   1               5                  10 gtt gac ttt aaa aag gcc tac gca gac ggt gct cgc ttc gtc att atc      144
Val Asp Phe Lys Lys Ala Tyr Ala Asp Gly Ala Arg Phe Val Ile Ile
     15                 20                  25 aaa gtaagacaaa tagcacagtg tacaaaagtg aaacaatac tctaacaaaa            197
Lys
30 ccaccag gcc acc gaa ggc aca aca tac acc gat ccc agc ttc agc tcc      246
        Ala Thr Glu Gly Thr Thr Tyr Thr Asp Pro Ser Phe Ser Ser
                         35                  40 cac tac act ggc gcc acg cag gcc ggc ctc atc cgg gga ggc tac cac      294
His Tyr Thr Gly Ala Thr Gln Ala Gly Leu Ile Arg Gly Gly Tyr His
45                  50                  55                  60 ttc gca cac ccc gga tca ggc acc ggc gcc gcc cag gcg aat tac ttc      342
Phe Ala His Pro Gly Ser Gly Thr Gly Ala Ala Gln Ala Asn Tyr Phe
                 65                  70                  75 ctc gcc cac ggc ggc ggc tgg tcc aag gat ggc atc acg ctc ccg ggc      390
Leu Ala His Gly Gly Gly Trp Ser Lys Asp Gly Ile Thr Leu Pro Gly
             80                  85                  90 atg att gat ctc gag tac aac ccc agc ggt gct acg tgc tac ggt ctc      438
Met Ile Asp Leu Glu Tyr Asn Pro Ser Gly Ala Thr Cys Tyr Gly Leu
         95                 100                 105 tcg gcc agc ggc atg gtc agc tgg atc tct gac ttt gtc gag acg tac      486
Ser Ala Ser Gly Met Val Ser Trp Ile Ser Asp Phe Val Glu Thr Tyr
    110                 115                 120 cat agc aag act ggg gtt tat cct ctt att tac acg tcg acg agc tgg      534
His Ser Lys Thr Gly Val Tyr Pro Leu Ile Tyr Thr Ser Thr Ser Trp
125                 130                 135                 140 tgg aac cag tgt acg ggt agc agt act gcc ttt ggt aat aag tgc ccg      582
Trp Asn Gln Cys Thr Gly Ser Ser Thr Ala Phe Gly Asn Lys Cys Pro
                145                 150                 155 ctt gtg gtt gcg cgg tat gct agc tct gtt ggg gcg ttg cct gct ggt      630
Leu Val Val Ala Arg Tyr Ala Ser Ser Val Gly Ala Leu Pro Ala Gly
            160                 165                 170 tgg gga ttt cag act att tgg cag aat agc gat aag tcg cct tgg ggt      678
Trp Gly Phe Gln Thr Ile Trp Gln Asn Ser Asp Lys Ser Pro Trp Gly
        175                 180                 185 ggt gac aat gat att ttc aac ggt agc ctt gat cag ctt aag cgt att      726
Gly Asp Asn Asp Ile Phe Asn Gly Ser Leu Asp Gln Leu Lys Arg Ile
    190                 195                 200 gct aac gct tcg taa                                                  741
Ala Asn Ala Ser
205

<210> SEQ ID NO 121
<211> LENGTH: 227
<212> TYPE: PRT
<213> ORGANISM: Metapochonia bulbillosa

<400> SEQUENCE: 121

Met Lys Ser Val Thr Phe Ile Ala Ser Leu Ala Ser Ile Val Ser Val
```

```
                -15             -10              -5
Ala Thr Ala Thr Val Ala Gly Phe Asp Ile Ser Asn Tyr Gln Pro Thr
           -1   1           5                  10

Val Asp Phe Lys Lys Ala Tyr Ala Asp Gly Ala Arg Phe Val Ile Ile
 15                  20                  25

Lys Ala Thr Glu Gly Thr Thr Tyr Thr Asp Pro Ser Phe Ser Ser His
 30                  35                  40                  45

Tyr Thr Gly Ala Thr Gln Ala Gly Leu Ile Arg Gly Gly Tyr His Phe
                 50                  55                  60

Ala His Pro Gly Ser Gly Thr Gly Ala Ala Gln Ala Asn Tyr Phe Leu
             65                  70                  75

Ala His Gly Gly Gly Trp Ser Lys Asp Gly Ile Thr Leu Pro Gly Met
         80                  85                  90

Ile Asp Leu Glu Tyr Asn Pro Ser Gly Ala Thr Cys Tyr Gly Leu Ser
     95                 100                 105

Ala Ser Gly Met Val Ser Trp Ile Ser Asp Phe Val Glu Thr Tyr His
110                 115                 120                 125

Ser Lys Thr Gly Val Tyr Pro Leu Ile Tyr Thr Ser Thr Ser Trp Trp
                130                 135                 140

Asn Gln Cys Thr Gly Ser Ser Thr Ala Phe Gly Asn Lys Cys Pro Leu
            145                 150                 155

Val Val Ala Arg Tyr Ala Ser Ser Val Gly Ala Leu Pro Ala Gly Trp
        160                 165                 170

Gly Phe Gln Thr Ile Trp Gln Asn Ser Asp Lys Ser Pro Trp Gly Gly
    175                 180                 185

Asp Asn Asp Ile Phe Asn Gly Ser Leu Asp Gln Leu Lys Arg Ile Ala
190                 195                 200                 205

Asn Ala Ser
```

<210> SEQ ID NO 122
<211> LENGTH: 208
<212> TYPE: PRT
<213> ORGANISM: Metapochonia bulbillosa
<220> FEATURE:
<221> NAME/KEY: mat_peptide
<222> LOCATION: (1)..(208)

<400> SEQUENCE: 122

```
Thr Val Ala Gly Phe Asp Ile Ser Asn Tyr Gln Pro Thr Val Asp Phe
 1               5                  10                  15

Lys Lys Ala Tyr Ala Asp Gly Ala Arg Phe Val Ile Ile Lys Ala Thr
                 20                  25                  30

Glu Gly Thr Thr Tyr Thr Asp Pro Ser Phe Ser Ser His Tyr Thr Gly
             35                  40                  45

Ala Thr Gln Ala Gly Leu Ile Arg Gly Gly Tyr His Phe Ala His Pro
         50                  55                  60

Gly Ser Gly Thr Gly Ala Ala Gln Ala Asn Tyr Phe Leu Ala His Gly
 65                  70                  75                  80

Gly Gly Trp Ser Lys Asp Gly Ile Thr Leu Pro Gly Met Ile Asp Leu
                 85                  90                  95

Glu Tyr Asn Pro Ser Gly Ala Thr Cys Tyr Gly Leu Ser Ala Ser Gly
            100                 105                 110

Met Val Ser Trp Ile Ser Asp Phe Val Glu Thr Tyr His Ser Lys Thr
        115                 120                 125

Gly Val Tyr Pro Leu Ile Tyr Thr Ser Thr Ser Trp Trp Asn Gln Cys
    130                 135                 140
```

```
Thr Gly Ser Ser Thr Ala Phe Gly Asn Lys Cys Pro Leu Val Val Ala
145                 150                 155                 160

Arg Tyr Ala Ser Ser Val Gly Ala Leu Pro Ala Gly Trp Gly Phe Gln
            165                 170                 175

Thr Ile Trp Gln Asn Ser Asp Lys Ser Pro Trp Gly Gly Asp Asn Asp
        180                 185                 190

Ile Phe Asn Gly Ser Leu Asp Gln Leu Lys Arg Ile Ala Asn Ala Ser
        195                 200                 205

<210> SEQ ID NO 123
<211> LENGTH: 756
<212> TYPE: DNA
<213> ORGANISM: Hamigera paravellanea
<220> FEATURE:
<221> NAME/KEY: CDS
<222> LOCATION: (1)..(168)
<220> FEATURE:
<221> NAME/KEY: sig_peptide
<222> LOCATION: (1)..(54)
<220> FEATURE:
<221> NAME/KEY: mat_peptide
<222> LOCATION: (55)..(753)
<220> FEATURE:
<221> NAME/KEY: CDS
<222> LOCATION: (223)..(753)

<400> SEQUENCE: 123 atg aag gct tct tcc atc ctc tcc ctg ctg gcc tcc ctg gcc ctc acc        48
Met Lys Ala Ser Ser Ile Leu Ser Leu Leu Ala Ser Leu Ala Leu Thr
            -15                 -10                  -5 agc gca gct cct ctc gag gcg cgc gcc ggc agc gtg caa ggc ttc gac        96
Ser Ala Ala Pro Leu Glu Ala Arg Ala Gly Ser Val Gln Gly Phe Asp
    -1   1               5                  10 atc tcg cac tac caa gcg aag gtc gac ttc gcc gcc gca tac cgc agc       144
Ile Ser His Tyr Gln Ala Lys Val Asp Phe Ala Ala Ala Tyr Arg Ser
 15                  20                  25                  30 ggt gct cgc ttc gtc atc atc aag gtacttactc ctcgtgctcg tcctcacaga      198
Gly Ala Arg Phe Val Ile Ile Lys
                35 cacagacact gaccacagaa caag gcc acc gaa gga acc acg tac acc gac        249
                          Ala Thr Glu Gly Thr Thr Tyr Thr Asp
                                       40                  45 ccg gcc ttc tcc tcg cac tac acc tcc gcc acc aac gcc ggc ttc atc       297
Pro Ala Phe Ser Ser His Tyr Thr Ser Ala Thr Asn Ala Gly Phe Ile
            50                  55                  60 cgg ggc ggc tac cac ttc gca cac ccg gac tcc agc tcg ggc gca gcg       345
Arg Gly Gly Tyr His Phe Ala His Pro Asp Ser Ser Ser Gly Ala Ala
 65                  70                  75 caa gcc acc tac ttc ctt gcc cac ggc ggc tgg tcc ggc gac ggc           393
Gln Ala Thr Tyr Phe Leu Ala His Gly Gly Trp Ser Gly Asp Gly
 80                  85                  90                  95 atc acg ctg ccc gga atg ctg gac ctc gag tac aac ccc tcg ggg gcg       441
Ile Thr Leu Pro Gly Met Leu Asp Leu Glu Tyr Asn Pro Ser Gly Ala
            100                 105                 110 acg tgc tac ggg ctc agc gat gcg gcc atg gtc gcc tgg atc cag gac       489
Thr Cys Tyr Gly Leu Ser Asp Ala Ala Met Val Ala Trp Ile Gln Asp
            115                 120                 125 ttc gtg gac acg tac cac gcc cgc acg ggg cgc tac ccg atg atc tac       537
Phe Val Asp Thr Tyr His Ala Arg Thr Gly Arg Tyr Pro Met Ile Tyr
            130                 135                 140 acc acg gcc gac tgg tgg aac acc tgc acg ggc aac agc agc aag ttc       585
Thr Thr Ala Asp Trp Trp Asn Thr Cys Thr Gly Asn Ser Ser Lys Phe
```

```
                    145                 150                 155
agc cag acg tgt ccg ttg gtg ctg gcc cgg tac gcc agc agc gtc ggc       633
Ser Gln Thr Cys Pro Leu Val Leu Ala Arg Tyr Ala Ser Ser Val Gly
160                 165                 170                 175 acc gtt ccc ggc ggc tgg ggg tat cag acc atc tgg cag aat tcg gat       681
Thr Val Pro Gly Gly Trp Gly Tyr Gln Thr Ile Trp Gln Asn Ser Asp
                    180                 185                 190 agc tat gcg tat ggc ggg gat tcg gat att ttt aac ggg gat gag acg       729
Ser Tyr Ala Tyr Gly Gly Asp Ser Asp Ile Phe Asn Gly Asp Glu Thr
                195                 200                 205 cag ttg aag aag ttg gcg agt gga tga                                   756
Gln Leu Lys Lys Leu Ala Ser Gly
            210                 215

<210> SEQ ID NO 124
<211> LENGTH: 233
<212> TYPE: PRT
<213> ORGANISM: Hamigera paravellanea

<400> SEQUENCE: 124

Met Lys Ala Ser Ser Ile Leu Ser Leu Leu Ala Ser Leu Ala Leu Thr
            -15                 -10                  -5

Ser Ala Ala Pro Leu Glu Ala Arg Ala Gly Ser Val Gln Gly Phe Asp
     -1  1               5                  10

Ile Ser His Tyr Gln Ala Lys Val Asp Phe Ala Ala Tyr Arg Ser
 15                  20                  25                  30

Gly Ala Arg Phe Val Ile Ile Lys Ala Thr Glu Gly Thr Thr Tyr Thr
                 35                  40                  45

Asp Pro Ala Phe Ser Ser His Tyr Thr Ser Ala Thr Asn Ala Gly Phe
             50                  55                  60

Ile Arg Gly Gly Tyr His Phe Ala His Pro Asp Ser Ser Gly Ala
         65                  70                  75

Ala Gln Ala Thr Tyr Phe Leu Ala His Gly Gly Trp Ser Gly Asp
     80                  85                  90

Gly Ile Thr Leu Pro Gly Met Leu Asp Leu Glu Tyr Asn Pro Ser Gly
 95                 100                 105                 110

Ala Thr Cys Tyr Gly Leu Ser Asp Ala Ala Met Val Ala Trp Ile Gln
                115                 120                 125

Asp Phe Val Asp Thr Tyr His Ala Arg Thr Gly Arg Tyr Pro Met Ile
            130                 135                 140

Tyr Thr Thr Ala Asp Trp Trp Asn Thr Cys Thr Gly Asn Ser Ser Lys
                145                 150                 155

Phe Ser Gln Thr Cys Pro Leu Val Leu Ala Arg Tyr Ala Ser Ser Val
            160                 165                 170

Gly Thr Val Pro Gly Gly Trp Gly Tyr Gln Thr Ile Trp Gln Asn Ser
175                 180                 185                 190

Asp Ser Tyr Ala Tyr Gly Gly Asp Ser Asp Ile Phe Asn Gly Asp Glu
                195                 200                 205

Thr Gln Leu Lys Lys Leu Ala Ser Gly
                210                 215

<210> SEQ ID NO 125
<211> LENGTH: 215
<212> TYPE: PRT
<213> ORGANISM: Hamigera paravellanea
<220> FEATURE:
<221> NAME/KEY: mat_peptide
<222> LOCATION: (1)..(215)
```

<400> SEQUENCE: 125

Ala Pro Leu Glu Ala Arg Ala Gly Ser Val Gln Gly Phe Asp Ile Ser
1               5                   10                  15

His Tyr Gln Ala Lys Val Asp Phe Ala Ala Tyr Arg Ser Gly Ala
            20                  25                  30

Arg Phe Val Ile Ile Lys Ala Thr Glu Gly Thr Thr Tyr Thr Asp Pro
            35                  40                  45

Ala Phe Ser Ser His Tyr Thr Ser Ala Thr Asn Ala Gly Phe Ile Arg
        50                  55                  60

Gly Gly Tyr His Phe Ala His Pro Asp Ser Ser Gly Ala Ala Gln
65              70                  75                  80

Ala Thr Tyr Phe Leu Ala His Gly Gly Trp Ser Gly Asp Gly Ile
            85                  90                  95

Thr Leu Pro Gly Met Leu Asp Leu Glu Tyr Asn Pro Ser Gly Ala Thr
                100                 105                 110

Cys Tyr Gly Leu Ser Asp Ala Ala Met Val Ala Trp Ile Gln Asp Phe
            115                 120                 125

Val Asp Thr Tyr His Ala Arg Thr Gly Arg Tyr Pro Met Ile Tyr Thr
130                 135                 140

Thr Ala Asp Trp Trp Asn Thr Cys Thr Gly Asn Ser Ser Lys Phe Ser
145                 150                 155                 160

Gln Thr Cys Pro Leu Val Leu Ala Arg Tyr Ala Ser Ser Val Gly Thr
                165                 170                 175

Val Pro Gly Gly Trp Gly Tyr Gln Thr Ile Trp Gln Asn Ser Asp Ser
            180                 185                 190

Tyr Ala Tyr Gly Gly Asp Ser Asp Ile Phe Asn Gly Asp Glu Thr Gln
            195                 200                 205

Leu Lys Lys Leu Ala Ser Gly
            210                 215

<210> SEQ ID NO 126
<211> LENGTH: 774
<212> TYPE: DNA
<213> ORGANISM: Metarhizium iadini
<220> FEATURE:
<221> NAME/KEY: CDS
<222> LOCATION: (1)..(180)
<220> FEATURE:
<221> NAME/KEY: sig_peptide
<222> LOCATION: (1)..(60)
<220> FEATURE:
<221> NAME/KEY: mat_peptide
<222> LOCATION: (61)..(771)
<220> FEATURE:
<221> NAME/KEY: CDS
<222> LOCATION: (241)..(771)

<400> SEQUENCE: 126

```
atg aag act tca ggc gcc att tcc ctt ggc ctc gcc gct ctc gtc agc      48
Met Lys Thr Ser Gly Ala Ile Ser Leu Gly Leu Ala Ala Leu Val Ser
-20             -15                 -10                 -5 tca gca gcc gcc tcc ccc gtg gag ctc gag cag cgc gcc

```
                  30                  35                   40
acctggacac atgtctgacc ttggcagcac agccgtctaa ccacgtcaag gcc acc         246
                                                        Ala Thr gag gga acc acc tac atc gac aag acc ttc tcc aag cac tac acg ggc        294
Glu Gly Thr Thr Tyr Ile Asp Lys Thr Phe Ser Lys His Tyr Thr Gly
            45                  50                  55 gca acc aag gcc aag ctc atc cgc ggc gcg tac cac ttc gcc cac ccg        342
Ala Thr Lys Ala Lys Leu Ile Arg Gly Ala Tyr His Phe Ala His Pro
        60                  65                  70 ggg cag aac aag gcc tcg gcc gag gct gac ttc ttc gtc cag cac ggc        390
Gly Gln Asn Lys Ala Ser Ala Glu Ala Asp Phe Phe Val Gln His Gly
75                  80                  85                  90 ggc aac tgg tcc aag gac gcc atc acc ctg ccc ggc atg gtc gat cta        438
Gly Asn Trp Ser Lys Asp Ala Ile Thr Leu Pro Gly Met Val Asp Leu
                95                  100                 105 gag tcc gaa aag ggc cac ccc ccg tgc tgg ggg ttg tcg cat tcc gca        486
Glu Ser Glu Lys Gly His Pro Pro Cys Trp Gly Leu Ser His Ser Ala
            110                 115                 120 atg gtc gct tgg atc agc gag ttt gtc gcc gct tac cac aag aaa acg        534
Met Val Ala Trp Ile Ser Glu Phe Val Ala Ala Tyr His Lys Lys Thr
        125                 130                 135 acc cga tat ccc atg ctg tac acc aac ccg tcg tgg tgg tcc gct tgc        582
Thr Arg Tyr Pro Met Leu Tyr Thr Asn Pro Ser Trp Trp Ser Ala Cys
140                 145                 150 acc ggc aac agc aag gcc ttc aag gat acc tgc cct ctg gtc ctg gcc        630
Thr Gly Asn Ser Lys Ala Phe Lys Asp Thr Cys Pro Leu Val Leu Ala
155                 160                 165                 170 aga tac gcc agc tcg ccc ggc gcc att cct ggt ggc tgg cct gct cag        678
Arg Tyr Ala Ser Ser Pro Gly Ala Ile Pro Gly Gly Trp Pro Ala Gln
                175                 180                 185 acc atc tgg caa aac agc gat aag agc ccg tgg ggt ggt gac tct gac        726
Thr Ile Trp Gln Asn Ser Asp Lys Ser Pro Trp Gly Gly Asp Ser Asp
            190                 195                 200 atg ttc aac ggc gac ttg gcc cag ttg aag aag ctt gct acc ggt tag        774
Met Phe Asn Gly Asp Leu Ala Gln Leu Lys Lys Leu Ala Thr Gly
        205                 210                 215
```

<210> SEQ ID NO 127
<211> LENGTH: 237
<212> TYPE: PRT
<213> ORGANISM: Metarhizium iadini

<400> SEQUENCE: 127

```
Met Lys Thr Ser Gly Ala Ile Ser Leu Gly Leu Ala Ala Leu Val Ser
-20                 -15                 -10                  -5

Ser Ala Ala Ala Ser Pro Val Glu Leu Glu Gln Arg Ala Ala Ser Val
            -1   1               5                   10

Lys Gly Phe Asp Ile Ser Gly Tyr Gln Pro Asn Val Asp Phe Asn Lys
        15                  20                  25

Ala Tyr Ala Asp Gly Ala Arg Phe Val Ile Ile Lys Ala Thr Glu Gly
    30                  35                  40

Thr Thr Tyr Ile Asp Lys Thr Phe Ser Lys His Tyr Thr Gly Ala Thr
45                  50                  55                  60

Lys Ala Lys Leu Ile Arg Gly Ala Tyr His Phe Ala His Pro Gly Gln
            65                  70                  75

Asn Lys Ala Ser Ala Glu Ala Asp Phe Phe Val Gln His Gly Gly Asn
        80                  85                  90

Trp Ser Lys Asp Ala Ile Thr Leu Pro Gly Met Val Asp Leu Glu Ser
```

```
              95                  100                 105
Glu Lys Gly His Pro Cys Trp Gly Leu Ser His Ser Ala Met Val
110                 115                 120

Ala Trp Ile Ser Glu Phe Val Ala Ala Tyr His Lys Lys Thr Thr Arg
125                 130                 135                 140

Tyr Pro Met Leu Tyr Thr Asn Pro Ser Trp Trp Ser Ala Cys Thr Gly
                    145                 150                 155

Asn Ser Lys Ala Phe Lys Asp Thr Cys Pro Leu Val Leu Ala Arg Tyr
                160                 165                 170

Ala Ser Ser Pro Gly Ala Ile Pro Gly Gly Trp Pro Ala Gln Thr Ile
                175                 180                 185

Trp Gln Asn Ser Asp Lys Ser Pro Trp Gly Gly Asp Ser Asp Met Phe
190                 195                 200

Asn Gly Asp Leu Ala Gln Leu Lys Lys Leu Ala Thr Gly
205                 210                 215

<210> SEQ ID NO 128
<211> LENGTH: 217
<212> TYPE: PRT
<213> ORGANISM: Metarhizium iadini
<220> FEATURE:
<221> NAME/KEY: mat_peptide
<222> LOCATION: (1)..(217)

<400> SEQUENCE: 128

Ser Pro Val Glu Leu Glu Gln Arg Ala Ala Ser Val Lys Gly Phe Asp
1               5                   10                  15

Ile Ser Gly Tyr Gln Pro Asn Val Asp Phe Asn Lys Ala Tyr Ala Asp
                20                  25                  30

Gly Ala Arg Phe Val Ile Ile Lys Ala Thr Glu Gly Thr Thr Tyr Ile
            35                  40                  45

Asp Lys Thr Phe Ser Lys His Tyr Thr Gly Ala Thr Lys Ala Lys Leu
        50                  55                  60

Ile Arg Gly Ala Tyr His Phe Ala His Pro Gly Gln Asn Lys Ala Ser
65                  70                  75                  80

Ala Glu Ala Asp Phe Phe Val Gln His Gly Gly Asn Trp Ser Lys Asp
                85                  90                  95

Ala Ile Thr Leu Pro Gly Met Val Asp Leu Glu Ser Glu Lys Gly His
                100                 105                 110

Pro Pro Cys Trp Gly Leu Ser His Ser Ala Met Val Ala Trp Ile Ser
            115                 120                 125

Glu Phe Val Ala Ala Tyr His Lys Lys Thr Thr Arg Tyr Pro Met Leu
130                 135                 140

Tyr Thr Asn Pro Ser Trp Trp Ser Ala Cys Thr Gly Asn Ser Lys Ala
145                 150                 155                 160

Phe Lys Asp Thr Cys Pro Leu Val Leu Ala Arg Tyr Ala Ser Ser Pro
                165                 170                 175

Gly Ala Ile Pro Gly Gly Trp Pro Ala Gln Thr Ile Trp Gln Asn Ser
            180                 185                 190

Asp Lys Ser Pro Trp Gly Gly Asp Ser Asp Met Phe Asn Gly Asp Leu
        195                 200                 205

Ala Gln Leu Lys Lys Leu Ala Thr Gly
    210                 215

<210> SEQ ID NO 129
<211> LENGTH: 747
```

```
<212> TYPE: DNA
<213> ORGANISM: Thermoascus aurantiacus
<220> FEATURE:
<221> NAME/KEY: CDS
<222> LOCATION: (1)..(159)
<220> FEATURE:
<221> NAME/KEY: sig_peptide
<222> LOCATION: (1)..(48)
<220> FEATURE:
<221> NAME/KEY: mat_peptide
<222> LOCATION: (49)..(746)
<220> FEATURE:
<221> NAME/KEY: CDS
<222> LOCATION: (214)..(744)

<400> SEQUENCE: 129
```

| | | | | | | | | | | | | | | | | |
|---|---|---|---|---|---|---|---|---|---|---|---|---|---|---|---|---|
| atg | aag | atc | gct | cct | ctc | ctc | ctc | gcc | ggc | ctc | gcc | gcc | gcc | gcc | ccc | 48 |
| Met | Lys | Ile | Ala | Pro | Leu | Leu | Leu | Ala | Gly | Leu | Ala | Ala | Ala | Ala | Pro | |
| | -15 | | | | -10 | | | | | -5 | | | | | -1 | |

| | | | | | | | | | | | | | | | | |
|---|---|---|---|---|---|---|---|---|---|---|---|---|---|---|---|---|
| gag | ctc | gac | aag | cgc | gcc | cgc | ggc | gtc | cag | ggc | ttt | gat | atc | tcg | cac | 96 |
| Glu | Leu | Asp | Lys | Arg | Ala | Arg | Gly | Val | Gln | Gly | Phe | Asp | Ile | Ser | His | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tac | cag | ccc | aac | gtc | gac | ttc | aag | ggc | gcg | tac | aac | agc | ggc | gcc | cgc | 144 |
| Tyr | Gln | Pro | Asn | Val | Asp | Phe | Lys | Gly | Ala | Tyr | Asn | Ser | Gly | Ala | Arg | |
| | | | 20 | | | | | 25 | | | | | 30 | | | |

```
ttc gtc atc atc aag gtatgcctct ctctctctct ctatcttctt cgcacctcta    199
Phe Val Ile Ile Lys
              35
```

```
ctgatgcagg ccag gcc acc gag ggc acg acg tac aag gac ccg gcc ttc    249
               Ala Thr Glu Gly Thr Thr Tyr Lys Asp Pro Ala Phe
                                40                  45
```

| | | | | | | | | | | | | | | | | |
|---|---|---|---|---|---|---|---|---|---|---|---|---|---|---|---|---|
| tcc | aag | cac | tac | atc | ggc | gcc | acc | gag | gcc | ggc | ctc | atc | cgc | ggc | gga | 297 |
| Ser | Lys | His | Tyr | Ile | Gly | Ala | Thr | Glu | Ala | Gly | Leu | Ile | Arg | Gly | Gly | |
| 50 | | | | | 55 | | | | | 60 | | | | | 65 | |

| | | | | | | | | | | | | | | | | |
|---|---|---|---|---|---|---|---|---|---|---|---|---|---|---|---|---|
| tac | cac | ttc | gcc | cac | ccg | gac | aag | agc | agc | ggc | gcg | gcg | cag | gcc | aac | 345 |
| Tyr | His | Phe | Ala | His | Pro | Asp | Lys | Ser | Ser | Gly | Ala | Ala | Gln | Ala | Asn | |
| | | | | 70 | | | | | 75 | | | | | 80 | | |

| | | | | | | | | | | | | | | | | |
|---|---|---|---|---|---|---|---|---|---|---|---|---|---|---|---|---|
| ttc | ttc | ctc | gcc | cac | ggc | ggc | ggc | tgg | tcc | ggc | gac | ggc | atc | acg | ctg | 393 |
| Phe | Phe | Leu | Ala | His | Gly | Gly | Gly | Trp | Ser | Gly | Asp | Gly | Ile | Thr | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ccc | ggc | atg | gtc | gac | ctc | gag | tac | aac | ccc | tcg | ggc | gac | gcc | tgc | tac | 441 |
| Pro | Gly | Met | Val | Asp | Leu | Glu | Tyr | Asn | Pro | Ser | Gly | Asp | Ala | Cys | Tyr | |
| | | 100 | | | | | 105 | | | | | 110 | | | | |

| | | | | | | | | | | | | | | | | |
|---|---|---|---|---|---|---|---|---|---|---|---|---|---|---|---|---|
| ggc | ctg | tcc | gac | tcg | cag | atg | gtc | tcc | tgg | atc | cgg | gac | ttt | gtc | aac | 489 |
| Gly | Leu | Ser | Asp | Ser | Gln | Met | Val | Ser | Trp | Ile | Arg | Asp | Phe | Val | Asn | |
| | 115 | | | | | 120 | | | | | 125 | | | | | |

| | | | | | | | | | | | | | | | | |
|---|---|---|---|---|---|---|---|---|---|---|---|---|---|---|---|---|
| acc | tac | cac | gcg | cac | acg | gga | cgc | tac | ccc | atg | atc | tac | acc | acg | gcc | 537 |
| Thr | Tyr | His | Ala | His | Thr | Gly | Arg | Tyr | Pro | Met | Ile | Tyr | Thr | Thr | Ala | |
| 130 | | | | | 135 | | | | | 140 | | | | | 145 | |

| | | | | | | | | | | | | | | | | |
|---|---|---|---|---|---|---|---|---|---|---|---|---|---|---|---|---|
| gac | tgg | tgg | aag | agg | tgc | acc | ggc | gac | agc | cac | gcc | ttc | tcg | acc | acc | 585 |
| Asp | Trp | Trp | Lys | Arg | Cys | Thr | Gly | Asp | Ser | His | Ala | Phe | Ser | Thr | Thr | |
| | | | 150 | | | | | 155 | | | | | 160 | | | |

| | | | | | | | | | | | | | | | | |
|---|---|---|---|---|---|---|---|---|---|---|---|---|---|---|---|---|
| tgc | ccg | ctc | gtc | ctg | gcg | cgg | tac | aac | agc | tca | ccg | ggc | acg | gtg | ccc | 633 |
| Cys | Pro | Leu | Val | Leu | Ala | Arg | Tyr | Asn | Ser | Ser | Pro | Gly | Thr | Val | Pro | |
| | | | 165 | | | | | 170 | | | | | 175 | | | |

| | | | | | | | | | | | | | | | | |
|---|---|---|---|---|---|---|---|---|---|---|---|---|---|---|---|---|
| ggc | ggc | tgg | ccc | tac | cac | acc | atc | tgg | cag | aac | tcg | gac | aag | tac | cgc | 681 |
| Gly | Gly | Trp | Pro | Tyr | His | Thr | Ile | Trp | Gln | Asn | Ser | Asp | Lys | Tyr | Arg | |
| | | 180 | | | | | 185 | | | | | 190 | | | | |

| | | | | | | | | | | | | | | | | |
|---|---|---|---|---|---|---|---|---|---|---|---|---|---|---|---|---|
| ttc | ggc | ggc | gac | tcg | gac | atc | ttc | aac | ggc | gac | ctg | gcg | ggg | ctg | aag | 729 |
| Phe | Gly | Gly | Asp | Ser | Asp | Ile | Phe | Asn | Gly | Asp | Leu | Ala | Gly | Leu | Lys | |
| | 195 | | | | | 200 | | | | | 205 | | | | | |

| | | | | | |
|---|---|---|---|---|---|
| agg | ctg | gcc | aag | ggc | tga | 747 |
| Arg | Leu | Ala | Lys | Gly | | |

-continued

```
<210> SEQ ID NO 130
<211> LENGTH: 230
<212> TYPE: PRT
<213> ORGANISM: Thermoascus aurantiacus

<400> SEQUENCE: 130

Met Lys Ile Ala Pro Leu Leu Leu Ala Gly Leu Ala Ala Ala Pro
    -15                 -10                 -5                  -1

Glu Leu Asp Lys Arg Ala Arg Gly Val Gln Gly Phe Asp Ile Ser His
1               5                   10                  15

Tyr Gln Pro Asn Val Asp Phe Lys Gly Ala Tyr Asn Ser Gly Ala Arg
                20                  25                  30

Phe Val Ile Ile Lys Ala Thr Glu Gly Thr Thr Tyr Lys Asp Pro Ala
            35                  40                  45

Phe Ser Lys His Tyr Ile Gly Ala Thr Glu Ala Gly Leu Ile Arg Gly
        50                  55                  60

Gly Tyr His Phe Ala His Pro Asp Lys Ser Ser Gly Ala Ala Gln Ala
65                  70                  75                  80

Asn Phe Phe Leu Ala His Gly Gly Gly Trp Ser Gly Asp Gly Ile Thr
                85                  90                  95

Leu Pro Gly Met Val Asp Leu Glu Tyr Asn Pro Ser Gly Asp Ala Cys
            100                 105                 110

Tyr Gly Leu Ser Asp Ser Gln Met Val Ser Trp Ile Arg Asp Phe Val
        115                 120                 125

Asn Thr Tyr His Ala His Thr Gly Arg Tyr Pro Met Ile Tyr Thr Thr
130                 135                 140

Ala Asp Trp Trp Lys Arg Cys Thr Gly Asp Ser His Ala Phe Ser Thr
145                 150                 155                 160

Thr Cys Pro Leu Val Leu Ala Arg Tyr Asn Ser Ser Pro Gly Thr Val
                165                 170                 175

Pro Gly Gly Trp Pro Tyr His Thr Ile Trp Gln Asn Ser Asp Lys Tyr
            180                 185                 190

Arg Phe Gly Gly Asp Ser Asp Ile Phe Asn Gly Asp Leu Ala Gly Leu
        195                 200                 205

Lys Arg Leu Ala Lys Gly
    210

<210> SEQ ID NO 131
<211> LENGTH: 214
<212> TYPE: PRT
<213> ORGANISM: Thermoascus aurantiacus
<220> FEATURE:
<221> NAME/KEY: mat_peptide
<222> LOCATION: (1)..(214)

<400> SEQUENCE: 131

Glu Leu Asp Lys Arg Ala Arg Gly Val Gln Gly Phe Asp Ile Ser His
1               5                   10                  15

Tyr Gln Pro Asn Val Asp Phe Lys Gly Ala Tyr Asn Ser Gly Ala Arg
                20                  25                  30

Phe Val Ile Ile Lys Ala Thr Glu Gly Thr Thr Tyr Lys Asp Pro Ala
            35                  40                  45

Phe Ser Lys His Tyr Ile Gly Ala Thr Glu Ala Gly Leu Ile Arg Gly
        50                  55                  60

Gly Tyr His Phe Ala His Pro Asp Lys Ser Ser Gly Ala Ala Gln Ala
```

```
                65                  70                  75                  80
Asn Phe Phe Leu Ala His Gly Gly Trp Ser Gly Asp Gly Ile Thr
                    85                  90                  95

Leu Pro Gly Met Val Asp Leu Glu Tyr Asn Pro Ser Gly Asp Ala Cys
                100                 105                 110

Tyr Gly Leu Ser Asp Ser Gln Met Val Ser Trp Ile Arg Asp Phe Val
            115                 120                 125

Asn Thr Tyr His Ala His Thr Gly Arg Tyr Pro Met Ile Tyr Thr Thr
130                 135                 140

Ala Asp Trp Trp Lys Arg Cys Thr Gly Asp Ser His Ala Phe Ser Thr
145                 150                 155                 160

Thr Cys Pro Leu Val Leu Ala Arg Tyr Asn Ser Ser Pro Gly Thr Val
                165                 170                 175

Pro Gly Gly Trp Pro Tyr His Thr Ile Trp Gln Asn Ser Asp Lys Tyr
                180                 185                 190

Arg Phe Gly Gly Asp Ser Asp Ile Phe Asn Gly Asp Leu Ala Gly Leu
            195                 200                 205

Lys Arg Leu Ala Lys Gly
210

<210> SEQ ID NO 132
<211> LENGTH: 753
<212> TYPE: DNA
<213> ORGANISM: Clonostachys rossmaniae
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(750)
<220> FEATURE:
<221> NAME/KEY: CDS
<222> LOCATION: (217)..(750)

<400> SEQUENCE: 132 atg aag agt tct ctg tac ctt gct ttt gtt gca ctt gcg acg gtg gcc      48
Met Lys Ser Ser Leu Tyr Leu Ala Phe Val Ala Leu Ala Thr Val Ala
            -15                 -10                  -5 gta gca gca gtg cca gga ttt gat ata tcc ggg tgg cag aaa tcc act      96
Val Ala Ala Val Pro Gly Phe Asp Ile Ser Gly Trp Gln Lys Ser Thr
 -1  1               5                  10 gac ttt gct aag tca tac gca aac gga gat cgt ttt gtg tac atc aag     144
Asp Phe Ala Lys Ser Tyr Ala Asn Gly Asp Arg Phe Val Tyr Ile Lys
 15                  20                  25                  30 gtaaaaccca agtcatattt ttcactggaa cattccccgt ttagttcaac tgagcaggct    204
aacaccttgt ag gct aca gag ggt aca acc ttt aag aat cct ctt ttc tcg   255
              Ala Thr Glu Gly Thr Thr Phe Lys Asn Pro Leu Phe Ser
                                 35                  40 aag cag tat acc ggt gct aca aat gcc cgt ctc att cgt ggt gcc tat     303
Lys Gln Tyr Thr Gly Ala Thr Asn Ala Arg Leu Ile Arg Gly Ala Tyr
         45                  50                  55 cac ttt gcc cag ccg gca tct tca tcc ggg gcc tca cag gct cgt ttc     351
His Phe Ala Gln Pro Ala Ser Ser Ser Gly Ala Ser Gln Ala Arg Phe
 60                  65                  70                  75 ttt gtt gca aat ggc gga ggt tgg tcc aac gat ggc atc acc ttg cct     399
Phe Val Ala Asn Gly Gly Gly Trp Ser Asn Asp Gly Ile Thr Leu Pro
                 80                  85                  90
```

-continued

| | | | | | | | | | | | | | | | | |
|---|---|---|---|---|---|---|---|---|---|---|---|---|---|---|---|---|
| ggt | gcg | gtg | gat | atg | gag | tac | aac | ccc | agt | ggc | gcc | aca | tgc | tac | ggg | 447 |
| Gly | Ala | Val | Asp | Met | Glu | Tyr | Asn | Pro | Ser | Gly | Ala | Thr | Cys | Tyr | Gly | |
| | | | 95 | | | | | 100 | | | | | 105 | | | |
| ctg | tcc | aaa | acc | gcc | atg | gtg | aac | tgg | atc | gag | gac | ttt | gtg | tca | aca | 495 |
| Leu | Ser | Lys | Thr | Ala | Met | Val | Asn | Trp | Ile | Glu | Asp | Phe | Val | Ser | Thr | |
| | | 110 | | | | | 115 | | | | | 120 | | | | |
| tac | cag | gct | ttg | acc | ggg | cgc | tgg | cct | gtc | gtt | tat | acc | acg | ctt | gac | 543 |
| Tyr | Gln | Ala | Leu | Thr | Gly | Arg | Trp | Pro | Val | Val | Tyr | Thr | Thr | Leu | Asp | |
| | 125 | | | | | 130 | | | | | 135 | | | | | |
| tgg | tgg | acc | caa | tgc | act | ggc | aac | agc | gcc | aag | ttt | ggg | gat | cgg | tgc | 591 |
| Trp | Trp | Thr | Gln | Cys | Thr | Gly | Asn | Ser | Ala | Lys | Phe | Gly | Asp | Arg | Cys | |
| 140 | | | | 145 | | | | | 150 | | | | | 155 | | |
| ccg | ctg | tgg | gtg | gca | cga | tat | gca | agt | gct | gtc | ggc | caa | atc | ccc | gca | 639 |
| Pro | Leu | Trp | Val | Ala | Arg | Tyr | Ala | Ser | Ala | Val | Gly | Gln | Ile | Pro | Ala | |
| | | | 160 | | | | | 165 | | | | | 170 | | | |
| ggt | tgg | agc | ttt | cac | act | ata | tgg | caa | tat | aac | gcg | aaa | tac | cct | gaa | 687 |
| Gly | Trp | Ser | Phe | His | Thr | Ile | Trp | Gln | Tyr | Asn | Ala | Lys | Tyr | Pro | Glu | |
| | | 175 | | | | | 180 | | | | | 185 | | | | |
| ggt | gga | gac | tct | gat | ata | ttc | aat | ggc | gac | gag | act | cgc | ctt | aaa | gct | 735 |
| Gly | Gly | Asp | Ser | Asp | Ile | Phe | Asn | Gly | Asp | Glu | Thr | Arg | Leu | Lys | Ala | |
| | 190 | | | | | 195 | | | | | 200 | | | | | |
| tta | gct | tcc | ggg | gcc | tga | | | | | | | | | | | 753 |
| Leu | Ala | Ser | Gly | Ala | | | | | | | | | | | | |
| 205 | | | | | | | | | | | | | | | | |

<210> SEQ ID NO 133
<211> LENGTH: 226
<212> TYPE: PRT
<213> ORGANISM: Clonostachys rossmaniae

<400> SEQUENCE: 133

Met Lys Ser Ser Leu Tyr Leu Ala Phe Val Ala Leu Ala Thr Val Ala
            -15                 -10                    -5

Val Ala Ala Val Pro Gly Phe Asp Ile Ser Gly Trp Gln Lys Ser Thr
 -1  1              5                     10

Asp Phe Ala Lys Ser Tyr Ala Asn Gly Asp Arg Phe Val Tyr Ile Lys
15                  20                 25                 30

Ala Thr Glu Gly Thr Thr Phe Lys Asn Pro Leu Phe Ser Lys Gln Tyr
               35                 40                45

Thr Gly Ala Thr Asn Ala Arg Leu Ile Arg Gly Ala Tyr His Phe Ala
          50                 55                60

Gln Pro Ala Ser Ser Gly Ala Ser Gln Ala Arg Phe Phe Val Ala
       65               70               75

Asn Gly Gly Gly Trp Ser Asn Asp Gly Ile Thr Leu Pro Gly Ala Val
80                  85                 90

Asp Met Glu Tyr Asn Pro Ser Gly Ala Thr Cys Tyr Gly Leu Ser Lys
95                  100               105             110

Thr Ala Met Val Asn Trp Ile Glu Asp Phe Val Ser Thr Tyr Gln Ala
               115               120              125

Leu Thr Gly Arg Trp Pro Val Val Tyr Thr Thr Leu Asp Trp Trp Thr
          130               135              140

Gln Cys Thr Gly Asn Ser Ala Lys Phe Gly Asp Arg Cys Pro Leu Trp
       145               150               155

Val Ala Arg Tyr Ala Ser Ala Val Gly Gln Ile Pro Ala Gly Trp Ser
          160               165              170

Phe His Thr Ile Trp Gln Tyr Asn Ala Lys Tyr Pro Glu Gly Gly Asp
175                 180               185             190

Ser Asp Ile Phe Asn Gly Asp Glu Thr Arg Leu Lys Ala Leu Ala Ser
             195                 200                 205

Gly Ala

<210> SEQ ID NO 134
<211> LENGTH: 208
<212> TYPE: PRT
<213> ORGANISM: Clonostachys rossmaniae
<220> FEATURE:
<221> NAME/KEY: mat_peptide
<222> LOCATION: (1)..(208)

<400> SEQUENCE: 134

Ala Val Pro Gly Phe Asp Ile Ser Gly Trp Gln Lys Ser Thr Asp Phe
1               5                   10                  15

Ala Lys Ser Tyr Ala Asn Gly Asp Arg Phe Val Tyr Ile Lys Ala Thr
            20                  25                  30

Glu Gly Thr Thr Phe Lys Asn Pro Leu Phe Ser Lys Gln Tyr Thr Gly
        35                  40                  45

Ala Thr Asn Ala Arg Leu Ile Arg Gly Ala Tyr His Phe Ala Gln Pro
    50                  55                  60

Ala Ser Ser Ser Gly Ala Ser Gln Ala Arg Phe Phe Val Ala Asn Gly
65                  70                  75                  80

Gly Gly Trp Ser Asn Asp Gly Ile Thr Leu Pro Gly Ala Val Asp Met
                85                  90                  95

Glu Tyr Asn Pro Ser Gly Ala Thr Cys Tyr Gly Leu Ser Lys Thr Ala
            100                 105                 110

Met Val Asn Trp Ile Glu Asp Phe Val Ser Thr Tyr Gln Ala Leu Thr
        115                 120                 125

Gly Arg Trp Pro Val Val Tyr Thr Thr Leu Asp Trp Trp Thr Gln Cys
    130                 135                 140

Thr Gly Asn Ser Ala Lys Phe Gly Asp Arg Cys Pro Leu Trp Val Ala
145                 150                 155                 160

Arg Tyr Ala Ser Ala Val Gly Gln Ile Pro Ala Gly Trp Ser Phe His
                165                 170                 175

Thr Ile Trp Gln Tyr Asn Ala Lys Tyr Pro Glu Gly Gly Asp Ser Asp
            180                 185                 190

Ile Phe Asn Gly Asp Glu Thr Arg Leu Lys Ala Leu Ala Ser Gly Ala
        195                 200                 205

<210> SEQ ID NO 135
<211> LENGTH: 669
<212> TYPE: DNA
<213> ORGANISM: Simplicillium obclavatum
<220> FEATURE:
<221> NAME/KEY: CDS
<222> LOCATION: (1)..(666)
<220> FEATURE:
<221> NAME/KEY: sig_peptide
<222> LOCATION: (1)..(57)
<220> FEATURE:
<221> NAME/KEY: mat_peptide
<222> LOCATION: (58)..(666)

<400> SEQUENCE: 135 atg aag ctt gcc acc gtg cta aac gtt ctt gca ctt gct gtt tct agc        48
Met Lys Leu Ala Thr Val Leu Asn Val Leu Ala Leu Ala Val Ser Ser
                -15                 -10                 -5 gtt atc ggc gca ccg aaa ggg att gac gtc agc cat tgg cag gga tcc        96
Val Ile Gly Ala Pro Lys Gly Ile Asp Val Ser His Trp Gln Gly Ser
        -1  1               5                   10

```
atc aac tgg ggt gca gtg aag gcg aac ggt atc gaa tgg gca tac atc      144
Ile Asn Trp Gly Ala Val Lys Ala Asn Gly Ile Glu Trp Ala Tyr Ile
         15                  20                  25 aaa gcc aca gaa tcc acg aac tac aaa gac cca aac ttc aat gca aac      192
Lys Ala Thr Glu Ser Thr Asn Tyr Lys Asp Pro Asn Phe Asn Ala Asn
 30                  35                  40                  45 tac gtt ggt gct acc aat gcg ggg ctc atc cgc ggc gca tac cat ttt      240
Tyr Val Gly Ala Thr Asn Ala Gly Leu Ile Arg Gly Ala Tyr His Phe
                     50                  55                  60 gct aga ccc ggc gat tct tca ggt gcg gcc cag gca aat tat ttt gct      288
Ala Arg Pro Gly Asp Ser Ser Gly Ala Ala Gln Ala Asn Tyr Phe Ala
             65                  70                  75 agc aac ggc ggc ggt tgg tca gca gac ggc ata act ctg cct ggt gcc      336
Ser Asn Gly Gly Gly Trp Ser Ala Asp Gly Ile Thr Leu Pro Gly Ala
                 80                  85                  90 gtt gat ctc gaa gca gga tgt tct gga ctg tcc cag tcc gca atg act      384
Val Asp Leu Glu Ala Gly Cys Ser Gly Leu Ser Gln Ser Ala Met Thr
         95                  100                 105 gct tgg ata aag gac ttc agc aac acc tat cac gcg cgc acc ggc cgg      432
Ala Trp Ile Lys Asp Phe Ser Asn Thr Tyr His Ala Arg Thr Gly Arg
110                 115                 120                 125 tac cca gct att tac acc acg agc tgg tgg aaa caa tgc act ggc          480
Tyr Pro Ala Ile Tyr Thr Thr Thr Ser Trp Trp Lys Gln Cys Thr Gly
                 130                 135                 140 aat gca tct ggt ttc caa aac aat aac ccg cta tgg att gct cgc tgg      528
Asn Ala Ser Gly Phe Gln Asn Asn Asn Pro Leu Trp Ile Ala Arg Trp
             145                 150                 155 gct tct tcc gta gga gag ttg cct gcg ggt tac agc tat cac aca ttt      576
Ala Ser Ser Val Gly Glu Leu Pro Ala Gly Tyr Ser Tyr His Thr Phe
                 160                 165                 170 tgg caa tat gcg gac cac gga ccg aac cca ggc gac cag gac gtt ttc      624
Trp Gln Tyr Ala Asp His Gly Pro Asn Pro Gly Asp Gln Asp Val Phe
         175                 180                 185 aat ggt gat tct gct ggc ctc aag agg atg gcc aag ggt agt tag          669
Asn Gly Asp Ser Ala Gly Leu Lys Arg Met Ala Lys Gly Ser
190                 195                 200

<210> SEQ ID NO 136
<211> LENGTH: 222
<212> TYPE: PRT
<213> ORGANISM: Simplicillium obclavatum

<400> SEQUENCE: 136

Met Lys Leu Ala Thr Val Leu Asn Val Leu Ala Leu Ala Val Ser Ser
                 -15                 -10                  -5

Val Ile Gly Ala Pro Lys Gly Ile Asp Val Ser His Trp Gln Gly Ser
         -1   1                   5                  10

Ile Asn Trp Gly Ala Val Lys Ala Asn Gly Ile Glu Trp Ala Tyr Ile
         15                  20                  25

Lys Ala Thr Glu Ser Thr Asn Tyr Lys Asp Pro Asn Phe Asn Ala Asn
 30                  35                  40                  45

Tyr Val Gly Ala Thr Asn Ala Gly Leu Ile Arg Gly Ala Tyr His Phe
                     50                  55                  60

Ala Arg Pro Gly Asp Ser Ser Gly Ala Ala Gln Ala Asn Tyr Phe Ala
             65                  70                  75

Ser Asn Gly Gly Gly Trp Ser Ala Asp Gly Ile Thr Leu Pro Gly Ala
                 80                  85                  90

Val Asp Leu Glu Ala Gly Cys Ser Gly Leu Ser Gln Ser Ala Met Thr
```

```
                    95                  100                 105
Ala Trp Ile Lys Asp Phe Ser Asn Thr Tyr His Ala Arg Thr Gly Arg
110                 115                 120                 125

Tyr Pro Ala Ile Tyr Thr Thr Thr Ser Trp Trp Lys Gln Cys Thr Gly
                    130                 135                 140

Asn Ala Ser Gly Phe Gln Asn Asn Pro Leu Trp Ile Ala Arg Trp
                145                 150                 155

Ala Ser Ser Val Gly Glu Leu Pro Ala Gly Tyr Ser Tyr His Thr Phe
                160                 165                 170

Trp Gln Tyr Ala Asp His Gly Pro Asn Pro Gly Asp Gln Asp Val Phe
            175                 180                 185

Asn Gly Asp Ser Ala Gly Leu Lys Arg Met Ala Lys Gly Ser
190                 195                 200

<210> SEQ ID NO 137
<211> LENGTH: 203
<212> TYPE: PRT
<213> ORGANISM: Simplicillium obclavatum
<220> FEATURE:
<221> NAME/KEY: mat_peptide
<222> LOCATION: (1)..(203)

<400> SEQUENCE: 137

Ala Pro Lys Gly Ile Asp Val Ser His Trp Gln Gly Ser Ile Asn Trp
1               5                   10                  15

Gly Ala Val Lys Ala Asn Gly Ile Glu Trp Ala Tyr Ile Lys Ala Thr
                20                  25                  30

Glu Ser Thr Asn Tyr Lys Asp Pro Asn Phe Asn Ala Asn Tyr Val Gly
            35                  40                  45

Ala Thr Asn Ala Gly Leu Ile Arg Gly Ala Tyr His Phe Ala Arg Pro
50                  55                  60

Gly Asp Ser Ser Gly Ala Ala Gln Ala Asn Tyr Phe Ala Ser Asn Gly
65                  70                  75                  80

Gly Gly Trp Ser Ala Asp Gly Ile Thr Leu Pro Gly Ala Val Asp Leu
                85                  90                  95

Glu Ala Gly Cys Ser Gly Leu Ser Gln Ser Ala Met Thr Ala Trp Ile
            100                 105                 110

Lys Asp Phe Ser Asn Thr Tyr His Ala Arg Thr Gly Arg Tyr Pro Ala
        115                 120                 125

Ile Tyr Thr Thr Thr Ser Trp Trp Lys Gln Cys Thr Gly Asn Ala Ser
    130                 135                 140

Gly Phe Gln Asn Asn Asn Pro Leu Trp Ile Ala Arg Trp Ala Ser Ser
145                 150                 155                 160

Val Gly Glu Leu Pro Ala Gly Tyr Ser Tyr His Thr Phe Trp Gln Tyr
                165                 170                 175

Ala Asp His Gly Pro Asn Pro Gly Asp Gln Asp Val Phe Asn Gly Asp
            180                 185                 190

Ser Ala Gly Leu Lys Arg Met Ala Lys Gly Ser
        195                 200

<210> SEQ ID NO 138
<211> LENGTH: 771
<212> TYPE: DNA
<213> ORGANISM: Aspergillus inflatus
<220> FEATURE:
<221> NAME/KEY: CDS
<222> LOCATION: (1)..(165)
<220> FEATURE:
```

<221> NAME/KEY: sig_peptide
<222> LOCATION: (1)..(51)
<220> FEATURE:
<221> NAME/KEY: mat_peptide
<222> LOCATION: (52)..(768)
<220> FEATURE:
<221> NAME/KEY: CDS
<222> LOCATION: (235)..(768)

<400> SEQUENCE: 138

```
atg aag ttc tct gcc att gct ctc ctg gct tct gcc tct gcc gtg gcc      48
Met Lys Phe Ser Ala Ile Ala Leu Leu Ala Ser Ala Ser Ala Val Ala
        -15                 -10                 -5 gcg gcc cct ctt gag gct cgt gcc aac act gtc cag ggg ttc gac atc      96
Ala Ala Pro Leu Glu Ala Arg Ala Asn Thr Val Gln Gly Phe Asp Ile
-1   1               5                  10                  15 tcc agc ttc cag ccc aat gtt gac ttt gcc gct gcc tac aag gcc ggt     144
Ser Ser Phe Gln Pro Asn Val Asp Phe Ala Ala Ala Tyr Lys Ala Gly
                20                  25                  30 gcc cgt ttt gtc atg atg aag gtcggtccca ttgaattcat cgacgcagat       195
Ala Arg Phe Val Met Met Lys
                35 atagatcaac cgaaatcact ggtactgact gcgcgctag gcc acc caa aac acc     249
                                                     Ala Thr Gln Asn Thr
                                                                    40 aac tac gtt gac aag acc ttt aac gca cac tac gag ggt gcc acc aag     297
Asn Tyr Val Asp Lys Thr Phe Asn Ala His Tyr Glu Gly Ala Thr Lys
    45                  50                  55 gct ggc ctc atc cgt ggt ggt tac cat ttc gcc att ccc aac ggc ccc     345
Ala Gly Leu Ile Arg Gly Gly Tyr His Phe Ala Ile Pro Asn Gly Pro
60                  65                  70                  75 tcc ggc gct gcc cag gcc gag tac ttc ctc gcc cat ggt ggc ggg tgg     393
Ser Gly Ala Ala Gln Ala Glu Tyr Phe Leu Ala His Gly Gly Gly Trp
                80                  85                  90 tcc gac gat ggc aag acc ctg ccc ggc atg atc gat ctt gag tac aac     441
Ser Asp Asp Gly Lys Thr Leu Pro Gly Met Ile Asp Leu Glu Tyr Asn
                95                 100                 105 ccc tat ggc caa acc tgc tac gac ctc tcc gcc gcg aag atg gtc gac     489
Pro Tyr Gly Gln Thr Cys Tyr Asp Leu Ser Ala Ala Lys Met Val Asp
            110                 115                 120 tgg atc aag gac ttc tcc aac acc tac cac gcc aag acc aag cgc tac     537
Trp Ile Lys Asp Phe Ser Asn Thr Tyr His Ala Lys Thr Lys Arg Tyr
125                 130                 135 ccc atg atc tac act acc gcc aac tgg tgg aag gag tgc act ggc gac     585
Pro Met Ile Tyr Thr Thr Ala Asn Trp Trp Lys Glu Cys Thr Gly Asp
140                 145                 150                 155 agc aaa gag ttc agc cag acc aac ccc ttg gtt ctg gct cgc tac tcc     633
Ser Lys Glu Phe Ser Gln Thr Asn Pro Leu Val Leu Ala Arg Tyr Ser
                160                 165                 170 agc tcc gcg ggc act gtc cct ggt ggc tgg ccc gcc tac tct ttc tgg     681
Ser Ser Ala Gly Thr Val Pro Gly Gly Trp Pro Ala Tyr Ser Phe Trp
            175                 180                 185 cag aac gcc gac aag tac aag ttc gga gga gac tct gac atc tgg aac     729
Gln Asn Ala Asp Lys Tyr Lys Phe Gly Gly Asp Ser Asp Ile Trp Asn
            190                 195                 200 ggc agt gag gac aac ctc aag aag ttt gcc aag ggt gct taa             771
Gly Ser Glu Asp Asn Leu Lys Lys Phe Ala Lys Gly Ala
205                 210                 215
```

<210> SEQ ID NO 139
<211> LENGTH: 233
<212> TYPE: PRT

<213> ORGANISM: Aspergillus inflatus

<400> SEQUENCE: 139

```
Met Lys Phe Ser Ala Ile Ala Leu Leu Ala Ser Ala Ser Val Ala
        -15                 -10                  -5
Ala Ala Pro Leu Glu Ala Arg Ala Asn Thr Val Gln Gly Phe Asp Ile
 -1   1           5                  10                  15
Ser Ser Phe Gln Pro Asn Val Asp Phe Ala Ala Tyr Lys Ala Gly
                 20                  25                  30
Ala Arg Phe Val Met Met Lys Ala Thr Gln Asn Thr Asn Tyr Val Asp
                 35                  40                  45
Lys Thr Phe Asn Ala His Tyr Glu Gly Ala Thr Lys Ala Gly Leu Ile
                 50                  55                  60
Arg Gly Gly Tyr His Phe Ala Ile Pro Asn Gly Pro Ser Gly Ala Ala
                 65                  70                  75
Gln Ala Glu Tyr Phe Leu Ala His Gly Gly Gly Trp Ser Asp Asp Gly
 80                  85                  90                  95
Lys Thr Leu Pro Gly Met Ile Asp Leu Glu Tyr Asn Pro Tyr Gly Gln
                100                 105                 110
Thr Cys Tyr Asp Leu Ser Ala Ala Lys Met Val Asp Trp Ile Lys Asp
                115                 120                 125
Phe Ser Asn Thr Tyr His Ala Lys Thr Lys Arg Tyr Pro Met Ile Tyr
                130                 135                 140
Thr Thr Ala Asn Trp Trp Lys Glu Cys Thr Gly Asp Ser Lys Glu Phe
                145                 150                 155
Ser Gln Thr Asn Pro Leu Val Leu Ala Arg Tyr Ser Ser Ser Ala Gly
160                 165                 170                 175
Thr Val Pro Gly Gly Trp Pro Ala Tyr Ser Phe Trp Gln Asn Ala Asp
                180                 185                 190
Lys Tyr Lys Phe Gly Gly Asp Ser Asp Ile Trp Asn Gly Ser Glu Asp
                195                 200                 205
Asn Leu Lys Lys Phe Ala Lys Gly Ala
                210                 215
```

<210> SEQ ID NO 140
<211> LENGTH: 216
<212> TYPE: PRT
<213> ORGANISM: Aspergillus inflatus
<220> FEATURE:
<221> NAME/KEY: mat_peptide
<222> LOCATION: (1)..(216)

<400> SEQUENCE: 140

```
Ala Pro Leu Glu Ala Arg Ala Asn Thr Val Gln Gly Phe Asp Ile Ser
 1               5                  10                  15
Ser Phe Gln Pro Asn Val Asp Phe Ala Ala Tyr Lys Ala Gly Ala
                 20                  25                  30
Arg Phe Val Met Met Lys Ala Thr Gln Asn Thr Asn Tyr Val Asp Lys
                 35                  40                  45
Thr Phe Asn Ala His Tyr Glu Gly Ala Thr Lys Ala Gly Leu Ile Arg
                 50                  55                  60
Gly Gly Tyr His Phe Ala Ile Pro Asn Gly Pro Ser Gly Ala Ala Gln
 65                  70                  75                  80
Ala Glu Tyr Phe Leu Ala His Gly Gly Gly Trp Ser Asp Asp Gly Lys
                 85                  90                  95
Thr Leu Pro Gly Met Ile Asp Leu Glu Tyr Asn Pro Tyr Gly Gln Thr
```

```
                    100             105                 110
Cys Tyr Asp Leu Ser Ala Ala Lys Met Val Asp Trp Ile Lys Asp Phe
            115                 120                 125

Ser Asn Thr Tyr His Ala Lys Thr Lys Arg Tyr Pro Met Ile Tyr Thr
        130                 135                 140

Thr Ala Asn Trp Trp Lys Glu Cys Thr Gly Asp Ser Lys Glu Phe Ser
145                 150                 155                 160

Gln Thr Asn Pro Leu Val Leu Ala Arg Tyr Ser Ser Ala Gly Thr
                165                 170                 175

Val Pro Gly Gly Trp Pro Ala Tyr Ser Phe Trp Gln Asn Ala Asp Lys
            180                 185                 190

Tyr Lys Phe Gly Gly Asp Ser Asp Ile Trp Asn Gly Ser Glu Asp Asn
        195                 200                 205

Leu Lys Lys Phe Ala Lys Gly Ala
        210                 215

<210> SEQ ID NO 141
<211> LENGTH: 738
<212> TYPE: DNA
<213> ORGANISM: Paracremonium inflatum
<220> FEATURE:
<221> NAME/KEY: CDS
<222> LOCATION: (1)..(153)
<220> FEATURE:
<221> NAME/KEY: sig_peptide
<222> LOCATION: (1)..(63)
<220> FEATURE:
<221> NAME/KEY: mat_peptide
<222> LOCATION: (64)..(735)
<220> FEATURE:
<221> NAME/KEY: CDS
<222> LOCATION: (205)..(735)

<400> SEQUENCE: 141 atg aaa act ttc ggc tat ttg ggc ctt ggc atg gtg tcc ctt gcg atc      48
Met Lys Thr Phe Gly Tyr Leu Gly Leu Gly Met Val Ser Leu Ala Ile
    -20             -15                 -10 acc tcg gtg tct gca aag gtg ttg ggt ttt gat att agt cat tac cag      96
Thr Ser Val Ser Ala Lys Val Leu Gly Phe Asp Ile Ser His Tyr Gln
 -5              -1  1               5                  10 gcc act gtt gac ttc aac gct gct aaa gac gcg gga gcc cga ttt gtg     144
Ala Thr Val Asp Phe Asn Ala Ala Lys Asp Ala Gly Ala Arg Phe Val
             15                  20                  25 atc atc aag gtagactacc tacccaacca gatggcgacg ttcccgagtt             193
Ile Ile Lys
         30 aataagacca g gcc aca gag gga aca acc tac aaa gac cca gcg ttc agc    243
             Ala Thr Glu Gly Thr Thr Tyr Lys Asp Pro Ala Phe Ser
                             35                  40 aaa cat tat acg ggg gcc aca aag gca ggc ctg atc cga ggc ggc tat     291
Lys His Tyr Thr Gly Ala Thr Lys Ala Gly Leu Ile Arg Gly Gly Tyr
 45                  50                  55 cac ttc gct cag cca gct tcc tcg tct ggc gct gct cag gcg act ttc     339
His Phe Ala Gln Pro Ala Ser Ser Ser Gly Ala Ala Gln Ala Thr Phe
 60                  65                  70                  75 ttc ctc gca cac ggc ggt ggt tgg tcg tct gat ggc ata aca ttg ccg     387
Phe Leu Ala His Gly Gly Gly Trp Ser Ser Asp Gly Ile Thr Leu Pro
                 80                  85                  90 ggc atg ctg gat tta gag tac aac ccc agt ggc tcg act tgc tac ggg     435
Gly Met Leu Asp Leu Glu Tyr Asn Pro Ser Gly Ser Thr Cys Tyr Gly
             95                 100                 105
```

```
ctg tca caa agc agc atg gtt cag tgg att tcc gac ttc atc gac aca    483
Leu Ser Gln Ser Ser Met Val Gln Trp Ile Ser Asp Phe Ile Asp Thr
    110             115                 120 tac cac tcc aaa aca ggg cga tat ccg ttg ata tat aca tct acc agc    531
Tyr His Ser Lys Thr Gly Arg Tyr Pro Leu Ile Tyr Thr Ser Thr Ser
    125             130                 135 tgg tgg aaa act tgc acg gga aac tca agc aag ttt gca gcg aac tgc    579
Trp Trp Lys Thr Cys Thr Gly Asn Ser Ser Lys Phe Ala Ala Asn Cys
140             145                 150                 155 ccg ctc gtc gtt gct cgc tac tcg agt tct gtc gga gag ctc cct gct    627
Pro Leu Val Val Ala Arg Tyr Ser Ser Ser Val Gly Glu Leu Pro Ala
                160                 165                 170 ggc tgg acg tat tac acg atc tgg caa aat tcg gat agc tat aaa tac    675
Gly Trp Thr Tyr Tyr Thr Ile Trp Gln Asn Ser Asp Ser Tyr Lys Tyr
            175                 180                 185 ggg ggt gat tcg gat atc ttc aat gga gac gag tcg caa ctc cag aaa    723
Gly Gly Asp Ser Asp Ile Phe Asn Gly Asp Glu Ser Gln Leu Gln Lys
        190                 195                 200 ctt gcc aag ggt taa                                                 738
Leu Ala Lys Gly
    205

<210> SEQ ID NO 142
<211> LENGTH: 228
<212> TYPE: PRT
<213> ORGANISM: Paracremonium inflatum

<400> SEQUENCE: 142

Met Lys Thr Phe Gly Tyr Leu Gly Leu Gly Met Val Ser Leu Ala Ile
    -20                 -15                 -10

Thr Ser Val Ser Ala Lys Val Leu Gly Phe Asp Ile Ser His Tyr Gln
-5              -1  1               5                   10

Ala Thr Val Asp Phe Asn Ala Ala Lys Asp Ala Gly Ala Arg Phe Val
                15                  20                  25

Ile Ile Lys Ala Thr Glu Gly Thr Tyr Lys Asp Pro Ala Phe Ser
            30                  35                  40

Lys His Tyr Thr Gly Ala Thr Lys Ala Gly Leu Ile Arg Gly Gly Tyr
        45                  50                  55

His Phe Ala Gln Pro Ala Ser Ser Gly Ala Ala Gln Ala Thr Phe
60                  65                  70                  75

Phe Leu Ala His Gly Gly Trp Ser Ser Asp Gly Ile Thr Leu Pro
                80                  85                  90

Gly Met Leu Asp Leu Glu Tyr Asn Pro Ser Gly Ser Thr Cys Tyr Gly
            95                  100                 105

Leu Ser Gln Ser Ser Met Val Gln Trp Ile Ser Asp Phe Ile Asp Thr
        110                 115                 120

Tyr His Ser Lys Thr Gly Arg Tyr Pro Leu Ile Tyr Thr Ser Thr Ser
    125                 130                 135

Trp Trp Lys Thr Cys Thr Gly Asn Ser Ser Lys Phe Ala Ala Asn Cys
140                 145                 150                 155

Pro Leu Val Val Ala Arg Tyr Ser Ser Ser Val Gly Glu Leu Pro Ala
                160                 165                 170

Gly Trp Thr Tyr Tyr Thr Ile Trp Gln Asn Ser Asp Ser Tyr Lys Tyr
            175                 180                 185

Gly Gly Asp Ser Asp Ile Phe Asn Gly Asp Glu Ser Gln Leu Gln Lys
        190                 195                 200

Leu Ala Lys Gly
```

<210> SEQ ID NO 143
<211> LENGTH: 207
<212> TYPE: PRT
<213> ORGANISM: Paracremonium inflatum
<220> FEATURE:
<221> NAME/KEY: mat_peptide
<222> LOCATION: (1)..(207)

<400> SEQUENCE: 143

Lys Val Leu Gly Phe Asp Ile Ser His Tyr Gln Ala Thr Val Asp Phe
1               5                   10                  15

Asn Ala Ala Lys Asp Ala Gly Ala Arg Phe Val Ile Ile Lys Ala Thr
            20                  25                  30

Glu Gly Thr Thr Tyr Lys Asp Pro Ala Phe Ser Lys His Tyr Thr Gly
        35                  40                  45

Ala Thr Lys Ala Gly Leu Ile Arg Gly Gly Tyr His Phe Ala Gln Pro
    50                  55                  60

Ala Ser Ser Ser Gly Ala Ala Gln Ala Thr Phe Phe Leu Ala His Gly
65                  70                  75                  80

Gly Gly Trp Ser Ser Asp Gly Ile Thr Leu Pro Gly Met Leu Asp Leu
                85                  90                  95

Glu Tyr Asn Pro Ser Gly Ser Thr Cys Tyr Gly Leu Ser Gln Ser Ser
            100                 105                 110

Met Val Gln Trp Ile Ser Asp Phe Ile Asp Thr Tyr His Ser Lys Thr
        115                 120                 125

Gly Arg Tyr Pro Leu Ile Tyr Thr Ser Thr Ser Trp Trp Lys Thr Cys
    130                 135                 140

Thr Gly Asn Ser Ser Lys Phe Ala Ala Asn Cys Pro Leu Val Val Ala
145                 150                 155                 160

Arg Tyr Ser Ser Ser Val Gly Glu Leu Pro Ala Gly Trp Thr Tyr Tyr
                165                 170                 175

Thr Ile Trp Gln Asn Ser Asp Ser Tyr Lys Tyr Gly Gly Asp Ser Asp
            180                 185                 190

Ile Phe Asn Gly Asp Glu Ser Gln Leu Gln Lys Leu Ala Lys Gly
        195                 200                 205

<210> SEQ ID NO 144
<211> LENGTH: 872
<212> TYPE: DNA
<213> ORGANISM: Westerdykella sp.
<220> FEATURE:
<221> NAME/KEY: CDS
<222> LOCATION: (1)..(144)
<220> FEATURE:
<221> NAME/KEY: sig_peptide
<222> LOCATION: (1)..(51)
<220> FEATURE:
<221> NAME/KEY: mat_peptide
<222> LOCATION: (52)..(869)
<220> FEATURE:
<221> NAME/KEY: CDS
<222> LOCATION: (199)..(259)
<220> FEATURE:
<221> NAME/KEY: CDS
<222> LOCATION: (342)..(765)
<220> FEATURE:
<221> NAME/KEY: CDS
<222> LOCATION: (824)..(869)

<400> SEQUENCE: 144 atg aag tct gta ctc gcc ctc ctc gcc gct ggc gcc cag ttt gcc agc        48

```
                Met Lys Ser Val Leu Ala Leu Leu Ala Ala Gly Ala Gln Phe Ala Ser
                    -15                 -10                  -5 gct gcc gtc tcc ggc atg gac atc tct cat tac caa ggc acg aac tac        96
Ala Ala Val Ser Gly Met Asp Ile Ser His Tyr Gln Gly Thr Asn Tyr
 -1   1               5                  10                  15 aac ttc gcc ggc gca tac tcg tct ggt gct cgt ttc gtc atc atc aag       144
Asn Phe Ala Gly Ala Tyr Ser Ser Gly Ala Arg Phe Val Ile Ile Lys
             20                  25                  30 gtacatattc gtcaacgcat aggacccaaa gtccagccat tgaacccatc ttag gca       201
                                                              Ala acc gaa ggg acc acc tac acg gat ccc caa ttt tct gct aac tat att       249
Thr Glu Gly Thr Thr Tyr Thr Asp Pro Gln Phe Ser Ala Asn Tyr Ile
         35                  40                  45 gcg gcc acc a gtacgtaata cctctatgtg ccgtcgactt tctgtgcccc             299
Ala Ala Thr
         50 aatcacgctg catgttcacg gacatcaact aacacctagc ag at  gcg ggc ttc        352
                                                  Asn Ala Gly Phe
                                                              55 atc agg ggg ggc tac cat ttc gcc cgc cct gcg gac tct acc ggc gcc       400
Ile Arg Gly Gly Tyr His Phe Ala Arg Pro Ala Asp Ser Thr Gly Ala
             60                  65                  70 gcc caa gcc aaa tac ttc gtc tcc cac ggc ggt ggc tgg tct tcc gat       448
Ala Gln Ala Lys Tyr Phe Val Ser His Gly Gly Gly Trp Ser Ser Asp
         75                  80                  85 ggt atc act ctc ccc gga atg ctc gac ctc gag tac ggc tca tcg tcc       496
Gly Ile Thr Leu Pro Gly Met Leu Asp Leu Glu Tyr Gly Ser Ser Ser
             90                  95                 100 gca tgc cac ggg ctt tcc gta tcg gcc atg aac aca tgg atc gcc tcg       544
Ala Cys His Gly Leu Ser Val Ser Ala Met Asn Thr Trp Ile Ala Ser
        105                 110                 115 ttc atc aac cag tat agg agc ttg acg ggc gcg tat ccc atg atc tac       592
Phe Ile Asn Gln Tyr Arg Ser Leu Thr Gly Ala Tyr Pro Met Ile Tyr
120                 125                 130                 135 act acg gcg gat tgg tgg aag acg tgc acc gga gat agc cag gct tgg       640
Thr Thr Ala Asp Trp Trp Lys Thr Cys Thr Gly Asp Ser Gln Ala Trp
                140                 145                 150 aac acc aag tgc cct ctg gta ttg gcc cgg tac tcc agc tct gtt ggg       688
Asn Thr Lys Cys Pro Leu Val Leu Ala Arg Tyr Ser Ser Ser Val Gly
            155                 160                 165 acg atc cca ggc ggc tgg cct tat cag act atc tgg cag ttc aac gat       736
Thr Ile Pro Gly Gly Trp Pro Tyr Gln Thr Ile Trp Gln Phe Asn Asp
        170                 175                 180 tcg tat aag tat ggc ggg gat tcg gac ac  gtgagttctc ccaaattgcg         785
Ser Tyr Lys Tyr Gly Gly Asp Ser Asp Thr
        185                 190 gagtcgccaa ttgatgaatg tgctgacgga acggatag a ttc aat ggt gac ttg       839
                                           Phe Asn Gly Asp Leu
                                                       195 gct ggc ttg aag agg ctc gcc aaa ggc agc tga                           872
Ala Gly Leu Lys Arg Leu Ala Lys Gly Ser
        200                 205

<210> SEQ ID NO 145
<211> LENGTH: 225
<212> TYPE: PRT
<213> ORGANISM: Westerdykella sp.

<400> SEQUENCE: 145

Met Lys Ser Val Leu Ala Leu Leu Ala Ala Gly Ala Gln Phe Ala Ser
```

```
                -15             -10              -5
Ala Ala Val Ser Gly Met Asp Ile Ser His Tyr Gln Gly Thr Asn Tyr
 -1   1           5                  10                      15

Asn Phe Ala Gly Ala Tyr Ser Ser Gly Ala Arg Phe Val Ile Ile Lys
             20                  25                  30

Ala Thr Glu Gly Thr Thr Tyr Thr Asp Pro Gln Phe Ser Ala Asn Tyr
             35                  40                  45

Ile Ala Ala Thr Asn Ala Gly Phe Ile Arg Gly Gly Tyr His Phe Ala
         50                  55                  60

Arg Pro Ala Asp Ser Thr Gly Ala Ala Gln Ala Lys Tyr Phe Val Ser
         65                  70                  75

His Gly Gly Gly Trp Ser Ser Asp Gly Ile Thr Leu Pro Gly Met Leu
 80                  85                  90                  95

Asp Leu Glu Tyr Gly Ser Ser Ala Cys His Gly Leu Ser Val Ser
                100                 105                 110

Ala Met Asn Thr Trp Ile Ala Ser Phe Ile Asn Gln Tyr Arg Ser Leu
             115                 120                 125

Thr Gly Ala Tyr Pro Met Ile Tyr Thr Thr Ala Asp Trp Trp Lys Thr
         130                 135                 140

Cys Thr Gly Asp Ser Gln Ala Trp Asn Thr Lys Cys Pro Leu Val Leu
         145                 150                 155

Ala Arg Tyr Ser Ser Val Gly Thr Ile Pro Gly Gly Trp Pro Tyr
160                 165                 170                 175

Gln Thr Ile Trp Gln Phe Asn Asp Ser Tyr Lys Tyr Gly Gly Asp Ser
                 180                 185                 190

Asp Thr Phe Asn Gly Asp Leu Ala Gly Leu Lys Arg Leu Ala Lys Gly
                 195                 200                 205

Ser

<210> SEQ ID NO 146
<211> LENGTH: 208
<212> TYPE: PRT
<213> ORGANISM: Westerdykella sp.
<220> FEATURE:
<221> NAME/KEY: mat_peptide
<222> LOCATION: (1)..(208)

<400> SEQUENCE: 146

Ala Val Ser Gly Met Asp Ile Ser His Tyr Gln Gly Thr Asn Tyr Asn
 1               5                  10                  15

Phe Ala Gly Ala Tyr Ser Ser Gly Ala Arg Phe Val Ile Ile Lys Ala
             20                  25                  30

Thr Glu Gly Thr Thr Tyr Thr Asp Pro Gln Phe Ser Ala Asn Tyr Ile
         35                  40                  45

Ala Ala Thr Asn Ala Gly Phe Ile Arg Gly Gly Tyr His Phe Ala Arg
     50                  55                  60

Pro Ala Asp Ser Thr Gly Ala Ala Gln Ala Lys Tyr Phe Val Ser His
 65                  70                  75                  80

Gly Gly Gly Trp Ser Ser Asp Gly Ile Thr Leu Pro Gly Met Leu Asp
                 85                  90                  95

Leu Glu Tyr Gly Ser Ser Ala Cys His Gly Leu Ser Val Ser Ala
             100                 105                 110

Met Asn Thr Trp Ile Ala Ser Phe Ile Asn Gln Tyr Arg Ser Leu Thr
         115                 120                 125

Gly Ala Tyr Pro Met Ile Tyr Thr Thr Ala Asp Trp Trp Lys Thr Cys
```

```
                130                 135                 140
Thr Gly Asp Ser Gln Ala Trp Asn Thr Lys Cys Pro Leu Val Leu Ala
145                 150                 155                 160

Arg Tyr Ser Ser Ser Val Gly Thr Ile Pro Gly Gly Trp Pro Tyr Gln
                165                 170                 175

Thr Ile Trp Gln Phe Asn Asp Ser Tyr Lys Tyr Gly Gly Asp Ser Asp
            180                 185                 190

Thr Phe Asn Gly Asp Leu Ala Gly Leu Lys Arg Leu Ala Lys Gly Ser
            195                 200                 205

<210> SEQ ID NO 147
<211> LENGTH: 909
<212> TYPE: DNA
<213> ORGANISM: Stropharia semiglobata
<220> FEATURE:
<221> NAME/KEY: CDS
<222> LOCATION: (1)..(393)
<220> FEATURE:
<221> NAME/KEY: sig_peptide
<222> LOCATION: (1)..(60)
<220> FEATURE:
<221> NAME/KEY: mat_peptide
<222> LOCATION: (61)..(906)
<220> FEATURE:
<221> NAME/KEY: CDS
<222> LOCATION: (447)..(545)
<220> FEATURE:
<221> NAME/KEY: CDS
<222> LOCATION: (608)..(691)
<220> FEATURE:
<221> NAME/KEY: CDS
<222> LOCATION: (744)..(772)
<220> FEATURE:
<221> NAME/KEY: CDS
<222> LOCATION: (831)..(906)

<400> SEQUENCE: 147 atg ttc tct ttc gtc aaa gcg ctc atc ctc ctc ccg gcc ctt gtg act      48
Met Phe Ser Phe Val Lys Ala Leu Ile Leu Leu Pro Ala Leu Val Thr
-20                 -15                 -10                 -5 tcc gcg tat gcc ctc gta tat ggc gta gac tcg tct acc ttg gtt tct      96
Ser Ala Tyr Ala Leu Val Tyr Gly Val Asp Ser Ser Thr Leu Val Ser
        -1  1               5                   10 act gca acc tac aag aaa gcc aag agc gag ggc ttc act aag gct atc     144
Thr Ala Thr Tyr Lys Lys Ala Lys Ser Glu Gly Phe Thr Lys Ala Ile
            15                  20                  25 atc cgc ggg tat cag gaa gca tgt ggc agt ggt gga cgc gtc gac ccc     192
Ile Arg Gly Tyr Gln Glu Ala Cys Gly Ser Gly Gly Arg Val Asp Pro
        30                  35                  40 aac ttc gtc gcg acc tac aag aat gca cgg gcc gcg ggt atc acc gat     240
Asn Phe Val Ala Thr Tyr Lys Asn Ala Arg Ala Ala Gly Ile Thr Asp
45                  50                  55                  60 atc gac atg tac tgg ttc cca tgc aac ggg tcc ggt aac tca tgc aag     288
Ile Asp Met Tyr Trp Phe Pro Cys Asn Gly Ser Gly Asn Ser Cys Lys
                65                  70                  75 tcg tac gct aag cag ctc tcc gag atc gcg aat gtc ttc agt gcg aat     336
Ser Tyr Ala Lys Gln Leu Ser Glu Ile Ala Asn Val Phe Ser Ala Asn
            80                  85                  90 agc atg aaa att ggg aca att tgg att gat ttt gag aag gat tct ggt     384
Ser Met Lys Ile Gly Thr Ile Trp Ile Asp Phe Glu Lys Asp Ser Gly
        95                  100                 105 tgc aac aac gtgagtttca tggacattat gtccttcata ataaatgac              433
Cys Asn Asn
    110
```

```
ggattttatc aag tgg aac tac ggc acc acg ggt aat ctc aac cat gca        482
           Trp Asn Tyr Gly Thr Thr Gly Asn Leu Asn His Ala
               115                 120 aag gca ctc atc tcc gcg att aaa gcg act ggg ttt aaa ttc ggt atc      530
Lys Ala Leu Ile Ser Ala Ile Lys Ala Thr Gly Phe Lys Phe Gly Ile
    125                 130                 135 tac agc tca cct ggc gtaaggcttt ttacctttcg tatccgcttc atcaagttaa      585
Tyr Ser Ser Pro Gly
140 cttagtccgc gactcgtttt ag gaa tgg ggt acc ctg ttt ggg tcc acc ggg      637
                         Glu Trp Gly Thr Leu Phe Gly Ser Thr Gly
                                     145                 150 gta gta ctc gat agc tcg gcc ccc ctt tgg ttc gct acg tgg aac aat      685
Val Val Leu Asp Ser Ser Ala Pro Leu Trp Phe Ala Thr Trp Asn Asn
155                 160                 165                 170 gta aag gtatgtgacc ccgcctacta cagaaataac atctctcaaa gtttaaccat ag    743
Val Lys act ctt acc ttg gga acg cat ttc ggg gg  gtaagtgcaa tatatataca        792
Thr Leu Thr Leu Gly Thr His Phe Gly Gly
        175                 180 tcgaaatatg ggatattgaa tactgacgtt gcttgaag g tgg act aaa gcc gtt     846
                                           Trp Thr Lys Ala Val
                                                       185 ggc cac cag tat aca gat gtg tcc gcc tct ggc caa ttc gac ctc aat      894
Gly His Gln Tyr Thr Asp Val Ser Ala Ser Gly Gln Phe Asp Leu Asn
        190                 195                 200 gtc ttt gca aat taa                                                  909
Val Phe Ala Asn
    205

<210> SEQ ID NO 148
<211> LENGTH: 227
<212> TYPE: PRT
<213> ORGANISM: Stropharia semiglobata

<400> SEQUENCE: 148

Met Phe Ser Phe Val Lys Ala Leu Ile Leu Leu Pro Ala Leu Val Thr
-20                 -15                 -10                 -5

Ser Ala Tyr Ala Leu Val Tyr Gly Val Asp Ser Ser Thr Leu Val Ser
            -1  1                 5                  10

Thr Ala Thr Tyr Lys Lys Ala Lys Ser Glu Gly Phe Thr Lys Ala Ile
        15                  20                  25

Ile Arg Gly Tyr Gln Glu Ala Cys Gly Ser Gly Arg Val Asp Pro
    30                  35                  40

Asn Phe Val Ala Thr Tyr Lys Asn Ala Arg Ala Ala Gly Ile Thr Asp
45                  50                  55                  60

Ile Asp Met Tyr Trp Phe Pro Cys Asn Gly Ser Gly Asn Ser Cys Lys
            65                  70                  75

Ser Tyr Ala Lys Gln Leu Ser Glu Ile Ala Asn Val Phe Ser Ala Asn
            80                  85                  90

Ser Met Lys Ile Gly Thr Ile Trp Ile Asp Phe Glu Lys Asp Ser Gly
        95                  100                 105

Cys Asn Asn Trp Asn Tyr Gly Thr Thr Gly Asn Leu Asn His Ala Lys
    110                 115                 120

Ala Leu Ile Ser Ala Ile Lys Ala Thr Gly Phe Lys Phe Gly Ile Tyr
125                 130                 135                 140

Ser Ser Pro Gly Glu Trp Gly Thr Leu Phe Gly Ser Thr Gly Val Val
            145                 150                 155
```

Leu Asp Ser Ser Ala Pro Leu Trp Phe Ala Thr Trp Asn Asn Val Lys
        160                 165                 170

Thr Leu Thr Leu Gly Thr His Phe Gly Gly Trp Thr Lys Ala Val Gly
        175                 180                 185

His Gln Tyr Thr Asp Val Ser Ala Ser Gly Gln Phe Asp Leu Asn Val
        190                 195                 200

Phe Ala Asn
205

<210> SEQ ID NO 149
<211> LENGTH: 207
<212> TYPE: PRT
<213> ORGANISM: Stropharia semiglobata
<220> FEATURE:
<221> NAME/KEY: mat_peptide
<222> LOCATION: (1)..(207)

<400> SEQUENCE: 149

Leu Val Tyr Gly Val Asp Ser Ser Thr Leu Val Ser Thr Ala Thr Tyr
1               5                   10                  15

Lys Lys Ala Lys Ser Glu Gly Phe Thr Lys Ala Ile Ile Arg Gly Tyr
            20                  25                  30

Gln Glu Ala Cys Gly Ser Gly Gly Arg Val Asp Pro Asn Phe Val Ala
        35                  40                  45

Thr Tyr Lys Asn Ala Arg Ala Ala Gly Ile Thr Asp Ile Asp Met Tyr
    50                  55                  60

Trp Phe Pro Cys Asn Gly Ser Gly Asn Ser Cys Lys Ser Tyr Ala Lys
65                  70                  75                  80

Gln Leu Ser Glu Ile Ala Asn Val Phe Ser Ala Asn Ser Met Lys Ile
                85                  90                  95

Gly Thr Ile Trp Ile Asp Phe Glu Lys Asp Ser Gly Cys Asn Asn Trp
            100                 105                 110

Asn Tyr Gly Thr Thr Gly Asn Leu Asn His Ala Lys Ala Leu Ile Ser
        115                 120                 125

Ala Ile Lys Ala Thr Gly Phe Lys Phe Gly Ile Tyr Ser Ser Pro Gly
    130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Asn Val Lys Thr Leu Thr Leu
                165                 170                 175

Gly Thr His Phe Gly Gly Trp Thr Lys Ala Val Gly His Gln Tyr Thr
            180                 185                 190

Asp Val Ser Ala Ser Gly Gln Phe Asp Leu Asn Val Phe Ala Asn
        195                 200                 205

<210> SEQ ID NO 150
<211> LENGTH: 909
<212> TYPE: DNA
<213> ORGANISM: Stropharia semiglobata
<220> FEATURE:
<221> NAME/KEY: CDS
<222> LOCATION: (1)..(393)
<220> FEATURE:
<221> NAME/KEY: sig_peptide
<222> LOCATION: (1)..(60)
<220> FEATURE:
<221> NAME/KEY: mat_peptide
<222> LOCATION: (61)..(906)
<220> FEATURE:
<221> NAME/KEY: CDS

```
<222> LOCATION: (447)..(545)
<220> FEATURE:
<221> NAME/KEY: CDS
<222> LOCATION: (608)..(691)
<220> FEATURE:
<221> NAME/KEY: CDS
<222> LOCATION: (743)..(771)
<220> FEATURE:
<221> NAME/KEY: CDS
<222> LOCATION: (831)..(906)

<400> SEQUENCE: 150 atg ttc cct ttc gtc aaa acg ctc ata cta ctc ccg acc ctt gtg acc      48
Met Phe Pro Phe Val Lys Thr Leu Ile Leu Leu Pro Thr Leu Val Thr
-20             -15                 -10                 -5 tcc gca tac gcc ctt gta tat ggc gta gac tcg tcc act cta gtc tct      96
Ser Ala Tyr Ala Leu Val Tyr Gly Val Asp Ser Ser Thr Leu Val Ser
            -1  1               5                   10 act gca acg tac agt aaa gcc aag agc gag ggc ttc act aag gct atc     144
Thr Ala Thr Tyr Ser Lys Ala Lys Ser Glu Gly Phe Thr Lys Ala Ile
        15                  20                  25 atc cgc ggg tat cag gaa gca tgt ggc agt ggt gga cgc gtc gac ccc     192
Ile Arg Gly Tyr Gln Glu Ala Cys Gly Ser Gly Gly Arg Val Asp Pro
    30                  35                  40 aac ttc gtc gcg acc tac aag aat gca cgg gcc gcg ggc atc acc gat     240
Asn Phe Val Ala Thr Tyr Lys Asn Ala Arg Ala Ala Gly Ile Thr Asp
45                  50                  55                  60 atc gac atg tac tgg ttc cca tgc aac ggg tcc ggt aac tct tgc aag     288
Ile Asp Met Tyr Trp Phe Pro Cys Asn Gly Ser Gly Asn Ser Cys Lys
                65                  70                  75 tcg tac gct aca cag ctc tcc gag atc gcg aat gcg ttc agt gcg aat     336
Ser Tyr Ala Thr Gln Leu Ser Glu Ile Ala Asn Ala Phe Ser Ala Asn
            80                  85                  90 agc atg aaa att ggg aca att tgg att gat ttt gag aag gat tct acc     384
Ser Met Lys Ile Gly Thr Ile Trp Ile Asp Phe Glu Lys Asp Ser Thr
        95                 100                 105 tgc aac aac gtgagtttca tggacattat gtccttcata ataaattgac             433
Cys Asn Asn
110 ggattttatc aag tgg aac tac ggc acc acg ggt aat ctc aac cat gca      482
            Trp Asn Tyr Gly Thr Thr Gly Asn Leu Asn His Ala
                115                 120 aag gca ctc atc tcc gcg att aaa gcg act ggg ttt aaa ttc ggt atc     530
Lys Ala Leu Ile Ser Ala Ile Lys Ala Thr Gly Phe Lys Phe Gly Ile
    125                 130                 135 tac agc tca cct ggc gtaaggcttt ttacctttcg tatccgcttc atcaagttaa     585
Tyr Ser Ser Pro Gly
140 cttagtccgc gactcgtttt ag gaa tgg ggt acc ctg ttt ggg tcc acc ggg    637
                        Glu Trp Gly Thr Leu Phe Gly Ser Thr Gly
                                145                 150 gta gta ctc gat agc tcg gcc ccc ctt tgg ttc gct acg tgg aac aat     685
Val Val Leu Asp Ser Ser Ala Pro Leu Trp Phe Ala Thr Trp Asn Asn
155                 160                 165                 170 gta aag gtatgtgacc ccgcctacta cagaaataac atctctcaaa gtttaacata g    742
Val Lys act ctt acc ttg gga acg cat ttc ggg gg gtaagtgcaa tatatataca        791
Thr Leu Thr Leu Gly Thr His Phe Gly Gly
        175                 180 tcgaaagatg gaataattaa atactgatct cgcttaaag g tgg act aca gcc gcg    846
                                            Trp Thr Thr Ala Ala
                                                185
```

```
ggt cac cag tac aca gac gtg tct tcc tct ggc caa ttc gac ctc aat    894
Gly His Gln Tyr Thr Asp Val Ser Ser Ser Gly Gln Phe Asp Leu Asn
        190                 195                 200 gtg ttt gca aat taa                                                909
Val Phe Ala Asn
    205
```

<210> SEQ ID NO 151
<211> LENGTH: 227
<212> TYPE: PRT
<213> ORGANISM: Stropharia semiglobata

<400> SEQUENCE: 151

```
Met Phe Pro Phe Val Lys Thr Leu Ile Leu Leu Pro Thr Leu Val Thr
-20             -15                 -10                 -5

Ser Ala Tyr Ala Leu Val Tyr Gly Val Asp Ser Ser Thr Leu Val Ser
            -1  1               5                   10

Thr Ala Thr Tyr Ser Lys Ala Lys Ser Glu Gly Phe Thr Lys Ala Ile
            15                  20                  25

Ile Arg Gly Tyr Gln Glu Ala Cys Gly Ser Gly Gly Arg Val Asp Pro
            30                  35                  40

Asn Phe Val Ala Thr Tyr Lys Asn Ala Arg Ala Ala Gly Ile Thr Asp
45                  50                  55                  60

Ile Asp Met Tyr Trp Phe Pro Cys Asn Gly Ser Gly Asn Ser Cys Lys
                65                  70                  75

Ser Tyr Ala Thr Gln Leu Ser Glu Ile Ala Asn Ala Phe Ser Ala Asn
                80                  85                  90

Ser Met Lys Ile Gly Thr Ile Trp Ile Asp Phe Glu Lys Asp Ser Thr
                95                  100                 105

Cys Asn Asn Trp Asn Tyr Gly Thr Thr Gly Asn Leu Asn His Ala Lys
            110                 115                 120

Ala Leu Ile Ser Ala Ile Lys Ala Thr Gly Phe Lys Phe Gly Ile Tyr
125                 130                 135                 140

Ser Ser Pro Gly Glu Trp Gly Thr Leu Phe Gly Ser Thr Gly Val Val
                145                 150                 155

Leu Asp Ser Ser Ala Pro Leu Trp Phe Ala Thr Trp Asn Asn Val Lys
                160                 165                 170

Thr Leu Thr Leu Gly Thr His Phe Gly Gly Trp Thr Thr Ala Ala Gly
                175                 180                 185

His Gln Tyr Thr Asp Val Ser Ser Ser Gly Gln Phe Asp Leu Asn Val
            190                 195                 200

Phe Ala Asn
205
```

<210> SEQ ID NO 152
<211> LENGTH: 207
<212> TYPE: PRT
<213> ORGANISM: Stropharia semiglobata
<220> FEATURE:
<221> NAME/KEY: mat_peptide
<222> LOCATION: (1)..(207)

<400> SEQUENCE: 152

```
Leu Val Tyr Gly Val Asp Ser Ser Thr Leu Val Ser Thr Ala Thr Tyr
1               5                   10                  15

Ser Lys Ala Lys Ser Glu Gly Phe Thr Lys Ala Ile Ile Arg Gly Tyr
            20                  25                  30
```

```
Gln Glu Ala Cys Gly Ser Gly Gly Arg Val Asp Pro Asn Phe Val Ala
         35                  40                  45

Thr Tyr Lys Asn Ala Arg Ala Gly Ile Thr Asp Ile Asp Met Tyr
 50                  55                  60

Trp Phe Pro Cys Asn Gly Ser Gly Asn Ser Cys Lys Ser Tyr Ala Thr
 65                  70                  75                  80

Gln Leu Ser Glu Ile Ala Asn Ala Phe Ser Ala Asn Ser Met Lys Ile
             85                  90                  95

Gly Thr Ile Trp Ile Asp Phe Glu Lys Asp Ser Thr Cys Asn Asn Trp
                100                 105                 110

Asn Tyr Gly Thr Thr Gly Asn Leu Asn His Ala Lys Ala Leu Ile Ser
            115                 120                 125

Ala Ile Lys Ala Thr Gly Phe Lys Phe Gly Ile Tyr Ser Ser Pro Gly
130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Val Lys Thr Leu Thr Leu
                165                 170                 175

Gly Thr His Phe Gly Gly Trp Thr Thr Ala Ala Gly His Gln Tyr Thr
                180                 185                 190

Asp Val Ser Ser Ser Gly Gln Phe Asp Leu Asn Val Phe Ala Asn
            195                 200                 205

<210> SEQ ID NO 153
<211> LENGTH: 917
<212> TYPE: DNA
<213> ORGANISM: Stropharia semiglobata
<220> FEATURE:
<221> NAME/KEY: CDS
<222> LOCATION: (1)..(393)
<220> FEATURE:
<221> NAME/KEY: sig_peptide
<222> LOCATION: (1)..(57)
<220> FEATURE:
<221> NAME/KEY: mat_peptide
<222> LOCATION: (58)..(914)
<220> FEATURE:
<221> NAME/KEY: CDS
<222> LOCATION: (464)..(562)
<220> FEATURE:
<221> NAME/KEY: CDS
<222> LOCATION: (617)..(700)
<220> FEATURE:
<221> NAME/KEY: CDS
<222> LOCATION: (757)..(785)
<220> FEATURE:
<221> NAME/KEY: CDS
<222> LOCATION: (842)..(914)

<400> SEQUENCE: 153 atg gtc aaa atc ttg agc ctt cta gcc ctc ctt ccc ctg ctc acg cag      48
Met Val Lys Ile Leu Ser Leu Leu Ala Leu Leu Pro Leu Leu Thr Gln
            -15                 -10                  -5 tcc tat gcg ctc acg tac gcc gtg gac tcg tcc acg ctc gtc tcg gtc      96
Ser Tyr Ala Leu Thr Tyr Ala Val Asp Ser Ser Thr Leu Val Ser Val
     -1   1               5                  10 gcg acg tac acc aag gca aag agc cag ggc ttc acc aag gcc att atc     144
Ala Thr Tyr Thr Lys Ala Lys Ser Gln Gly Phe Thr Lys Ala Ile Ile
         15                  20                  25 cgc ggc tac cag gag gcg tgc ggc tcc ggg ggg gca gtc gat ccc aac     192
Arg Gly Tyr Gln Glu Ala Cys Gly Ser Gly Gly Ala Val Asp Pro Asn
 30                  35                  40                  45 ttc gtc caa act tac aag aac gcg cgc gca gca ggc tac acc gac atc     240
Phe Val Gln Thr Tyr Lys Asn Ala Arg Ala Ala Gly Tyr Thr Asp Ile
```

```
                                                                    Phe Val Gln Thr Tyr Lys Asn Ala Arg Ala Ala Gly Tyr Thr Asp Ile
                                                                                     50                  55                  60 gac atg tac tgg ttc cca tgc aac ggg tcc acg cac aac tgc aag tcg       288
Asp Met Tyr Trp Phe Pro Cys Asn Gly Ser Thr His Asn Cys Lys Ser
             65                  70                  75 tac gcg acg cag att gcc gct ata gcc gcg acg ttc agc gcg aac tcg       336
Tyr Ala Thr Gln Ile Ala Ala Ile Ala Ala Thr Phe Ser Ala Asn Ser
         80                  85                  90 atg aag atc ggc agg atc tgg atc gac atc gag aag gac gct gcc gtc       384
Met Lys Ile Gly Arg Ile Trp Ile Asp Ile Glu Lys Asp Ala Ala Val
     95                 100                 105 tgc aat aac gtacgtgctg tggtgtactg actggggagt gagcgcactg              433
Cys Asn Asn
110 atgacacgcg aatgacgcct cggtttgcag tgg aat tat ggc acg gcc ggt aat      487
                                 Trp Asn Tyr Gly Thr Ala Gly Asn
                                             115                 120 cta tcc cag gcg aaa gca ctg atc tcg gcc att aag gct tcg ggt ttc       535
Leu Ser Gln Ala Lys Ala Leu Ile Ser Ala Ile Lys Ala Ser Gly Phe
                 125                 130                 135 gtg tac ggc atc tac agc agt cct ggg gtatgtttct ttttttatcg             582
Val Tyr Gly Ile Tyr Ser Ser Pro Gly
         140                 145 ttttttttag ggtactcacc gttaaatttt gtag gaa tgg ggc aat atc ttc ggt     637
                                      Glu Trp Gly Asn Ile Phe Gly
                                                          150 tcc aca agc gtc gtt gtt gac aac tct gcc cca ctc tgg ttt gct aca       685
Ser Thr Ser Val Val Val Asp Asn Ser Ala Pro Leu Trp Phe Ala Thr
             155                 160                 165 tgg aac aac gtt cag gtacctaaat tcacaatcat ttttgcttct ccactgtttc       740
Trp Asn Asn Val Gln
    170 tgatgataat tctcag act ctg act atg gga acc aag ttt gga gg              785
               Thr Leu Thr Met Gly Thr Lys Phe Gly Gly
                       175                 180 gtgtgtatcc ctgtactttt tattattgtt tcactcaata acgacgcgtt cttcag g       842 tgg act tcg gca atg ggc cat caa tac acg gac gtc tct gcc tct gga       890
Trp Thr Ser Ala Met Gly His Gln Tyr Thr Asp Val Ser Ala Ser Gly
         185                 190                 195 caa ttc gac ctg agc gta ttc gca tag                                   917
Gln Phe Asp Leu Ser Val Phe Ala
200                 205

<210> SEQ ID NO 154
<211> LENGTH: 226
<212> TYPE: PRT
<213> ORGANISM: Stropharia semiglobata

<400> SEQUENCE: 154

Met Val Lys Ile Leu Ser Leu Leu Ala Leu Leu Pro Leu Leu Thr Gln
                -15                 -10                  -5

Ser Tyr Ala Leu Thr Tyr Ala Val Asp Ser Ser Thr Leu Val Ser Val
        -1   1               5                  10

Ala Thr Tyr Thr Lys Ala Lys Ser Gln Gly Phe Thr Lys Ala Ile Ile
         15                  20                  25

Arg Gly Tyr Gln Glu Ala Cys Gly Ser Gly Ala Val Asp Pro Asn
 30                  35                  40                  45

Phe Val Gln Thr Tyr Lys Asn Ala Arg Ala Ala Gly Tyr Thr Asp Ile
                 50                  55                  60
```

```
Asp Met Tyr Trp Phe Pro Cys Asn Gly Ser Thr His Asn Cys Lys Ser
            65                  70                  75

Tyr Ala Thr Gln Ile Ala Ala Ile Ala Ala Thr Phe Ser Ala Asn Ser
        80                  85                  90

Met Lys Ile Gly Arg Ile Trp Ile Asp Ile Glu Lys Asp Ala Ala Val
95                  100                 105

Cys Asn Asn Trp Asn Tyr Gly Thr Ala Gly Asn Leu Ser Gln Ala Lys
110                 115                 120                 125

Ala Leu Ile Ser Ala Ile Lys Ala Ser Gly Phe Val Tyr Gly Ile Tyr
            130                 135                 140

Ser Ser Pro Gly Glu Trp Gly Asn Ile Phe Gly Ser Thr Ser Val Val
            145                 150                 155

Val Asp Asn Ser Ala Pro Leu Trp Phe Ala Thr Trp Asn Asn Val Gln
            160                 165                 170

Thr Leu Thr Met Gly Thr Lys Phe Gly Gly Trp Thr Ser Ala Met Gly
        175                 180                 185

His Gln Tyr Thr Asp Val Ser Ala Ser Gly Gln Phe Asp Leu Ser Val
190                 195                 200                 205

Phe Ala

<210> SEQ ID NO 155
<211> LENGTH: 207
<212> TYPE: PRT
<213> ORGANISM: Stropharia semiglobata
<220> FEATURE:
<221> NAME/KEY: mat_peptide
<222> LOCATION: (1)..(207)

<400> SEQUENCE: 155

Leu Thr Tyr Ala Val Asp Ser Ser Thr Leu Val Ser Val Ala Thr Tyr
1               5                   10                  15

Thr Lys Ala Lys Ser Gln Gly Phe Thr Lys Ala Ile Ile Arg Gly Tyr
            20                  25                  30

Gln Glu Ala Cys Gly Ser Gly Gly Ala Val Asp Pro Asn Phe Val Gln
        35                  40                  45

Thr Tyr Lys Asn Ala Arg Ala Ala Gly Tyr Thr Asp Ile Asp Met Tyr
50                  55                  60

Trp Phe Pro Cys Asn Gly Ser Thr His Asn Cys Lys Ser Tyr Ala Thr
65                  70                  75                  80

Gln Ile Ala Ala Ile Ala Ala Thr Phe Ser Ala Asn Ser Met Lys Ile
            85                  90                  95

Gly Arg Ile Trp Ile Asp Ile Glu Lys Asp Ala Ala Val Cys Asn Asn
        100                 105                 110

Trp Asn Tyr Gly Thr Ala Gly Asn Leu Ser Gln Ala Lys Ala Leu Ile
        115                 120                 125

Ser Ala Ile Lys Ala Ser Gly Phe Val Tyr Gly Ile Tyr Ser Ser Pro
        130                 135                 140

Gly Glu Trp Gly Asn Ile Phe Gly Ser Thr Ser Val Val Val Asp Asn
145                 150                 155                 160

Ser Ala Pro Leu Trp Phe Ala Thr Trp Asn Asn Val Gln Thr Leu Thr
                165                 170                 175

Met Gly Thr Lys Phe Gly Gly Trp Thr Ser Ala Met Gly His Gln Tyr
            180                 185                 190

Thr Asp Val Ser Ala Ser Gly Gln Phe Asp Leu Ser Val Phe Ala
        195                 200                 205
```

<210> SEQ ID NO 156
<211> LENGTH: 765
<212> TYPE: DNA
<213> ORGANISM: Gelasinospora cratophora
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(762)
<220> FEATURE:
<221> NAME/KEY: CDS
<222> LOCATION: (229)..(762)

<400> SEQUENCE: 156

```
atg aag tcc ttc gtc ctc acg gcc ttc gcc ggc ctc atc ggc gct gct      48
Met Lys Ser Phe Val Leu Thr Ala Phe Ala Gly Leu Ile Gly Ala Ala
        -15                 -10                  -5 cag gct acc gtc cag ggc ttc gat atc tcc cac tac cag agc agc gtc      96
Gln Ala Thr Val Gln Gly Phe Asp Ile Ser His Tyr Gln Ser Ser Val
 -1   1                   5                  10 aac ttt gcc ggc gct tac tct tcc ggt gcc cgc ttc gtc atc atc aag     144
Asn Phe Ala Gly Ala Tyr Ser Ser Gly Ala Arg Phe Val Ile Ile Lys
 15                  20                  25                  30 gtgcgtcttt tcttgtctca gagcaagccc catatcttca caggacctcc atccatccat   204
actaacccac gaccccgctc acag gcc acc gaa gga acc acc tac atc gac      255
                          Ala Thr Glu Gly Thr Thr Tyr Ile Asp
                                               35 tcc tcg ttc tcc tcc cac tac acc ggc gcc acc tcc gcc ggc ctg atc     303
Ser Ser Phe Ser Ser His Tyr Thr Gly Ala Thr Ser Ala Gly Leu Ile
 40                  45                  50                  55 cgc ggc ggc tac cac ttc gcg cac ccg gac tcc tcc acc ggc gcc gct     351
Arg Gly Gly Tyr His Phe Ala His Pro Asp Ser Ser Thr Gly Ala Ala
                 60                  65                  70 cag gcc gac tac ttc ctc gcg cac ggc ggc tgg tcc gcc gac ggc         399
Gln Ala Asp Tyr Phe Leu Ala His Gly Gly Trp Ser Ala Asp Gly
             75                  80                  85 atc acc ttg ccc ggc atg atc gac ctg gag tcc gtc tcg ggc aaa gcc     447
Ile Thr Leu Pro Gly Met Ile Asp Leu Glu Ser Val Ser Gly Lys Ala
             90                  95                 100 act tgc ttc ggc ctg tcg act tcg gcc atg gtc tcg tgg atc aag tcc     495
Thr Cys Phe Gly Leu Ser Thr Ser Ala Met Val Ser Trp Ile Lys Ser
105                 110                 115 ttc tcg gat cgc tac tac gcc aag acg ggc cgc tac ccc atg atc tac     543
Phe Ser Asp Arg Tyr Tyr Ala Lys Thr Gly Arg Tyr Pro Met Ile Tyr
120                 125                 130                 135 acc aac tac tcg tgg tgg aac cag tgc acg ggt aac tct gcc agc ttt     591
Thr Asn Tyr Ser Trp Trp Asn Gln Cys Thr Gly Asn Ser Ala Ser Phe
                140                 145                 150 gcc gcg acc aac ccg ctg gtg ctg gcg agg tgg tcg agc acg gtg ggc     639
Ala Ala Thr Asn Pro Leu Val Leu Ala Arg Trp Ser Ser Thr Val Gly
                155                 160                 165 acc ctg ccg ggg ggt tgg agt gtt cag act att tgg cag aat gcg gat     687
Thr Leu Pro Gly Gly Trp Ser Val Gln Thr Ile Trp Gln Asn Ala Asp
            170                 175                 180 acg tat act tat ggt ggt gac tcg gat gtt ttt aac ggt agc ctt gat     735
Thr Tyr Thr Tyr Gly Gly Asp Ser Asp Val Phe Asn Gly Ser Leu Asp
            185                 190                 195
```

```
cgc ctt aag gct ctt gct aag gga tct taa                                     765
Arg Leu Lys Ala Leu Ala Lys Gly Ser
200             205
```

<210> SEQ ID NO 157
<211> LENGTH: 226
<212> TYPE: PRT
<213> ORGANISM: Gelasinospora cratophora

<400> SEQUENCE: 157

```
Met Lys Ser Phe Val Leu Thr Ala Phe Ala Gly Leu Ile Gly Ala Ala
            -15                 -10                 -5
Gln Ala Thr Val Gln Gly Phe Asp Ile Ser His Tyr Gln Ser Ser Val
    -1  1               5                   10
Asn Phe Ala Gly Ala Tyr Ser Ser Gly Ala Arg Phe Val Ile Ile Lys
 15              20                  25                  30
Ala Thr Glu Gly Thr Thr Tyr Ile Asp Ser Ser Phe Ser Ser His Tyr
                35                  40                  45
Thr Gly Ala Thr Ser Ala Gly Leu Ile Arg Gly Tyr His Phe Ala
                50                  55                  60
His Pro Asp Ser Ser Thr Gly Ala Ala Gln Ala Asp Tyr Phe Leu Ala
                65                  70                  75
His Gly Gly Trp Ser Ala Asp Gly Ile Thr Leu Pro Gly Met Ile
 80                  85                  90
Asp Leu Glu Ser Val Ser Gly Lys Ala Thr Cys Phe Gly Leu Ser Thr
 95                 100                 105                 110
Ser Ala Met Val Ser Trp Ile Lys Ser Phe Ser Asp Arg Tyr Tyr Ala
                115                 120                 125
Lys Thr Gly Arg Tyr Pro Met Ile Tyr Thr Asn Tyr Ser Trp Trp Asn
                130                 135                 140
Gln Cys Thr Gly Asn Ser Ala Ser Phe Ala Ala Thr Asn Pro Leu Val
                145                 150                 155
Leu Ala Arg Trp Ser Ser Thr Val Gly Thr Leu Pro Gly Gly Trp Ser
                160                 165                 170
Val Gln Thr Ile Trp Gln Asn Ala Asp Thr Tyr Thr Tyr Gly Gly Asp
175                 180                 185                 190
Ser Asp Val Phe Asn Gly Ser Leu Asp Arg Leu Lys Ala Leu Ala Lys
                195                 200                 205
Gly Ser
```

<210> SEQ ID NO 158
<211> LENGTH: 208
<212> TYPE: PRT
<213> ORGANISM: Gelasinospora cratophora
<220> FEATURE:
<221> NAME/KEY: mat_peptide
<222> LOCATION: (1)..(208)

<400> SEQUENCE: 158

```
Thr Val Gln Gly Phe Asp Ile Ser His Tyr Gln Ser Ser Val Asn Phe
 1               5                   10                  15
Ala Gly Ala Tyr Ser Ser Gly Ala Arg Phe Val Ile Ile Lys Ala Thr
                20                  25                  30
Glu Gly Thr Thr Tyr Ile Asp Ser Ser Phe Ser Ser His Tyr Thr Gly
                35                  40                  45
Ala Thr Ser Ala Gly Leu Ile Arg Gly Gly Tyr His Phe Ala His Pro
 50                  55                  60
```

```
Asp Ser Ser Thr Gly Ala Ala Gln Ala Asp Tyr Phe Leu Ala His Gly
65                  70                  75                  80

Gly Gly Trp Ser Ala Asp Gly Ile Thr Leu Pro Gly Met Ile Asp Leu
                85                  90                  95

Glu Ser Val Ser Gly Lys Ala Thr Cys Phe Gly Leu Ser Thr Ser Ala
            100                 105                 110

Met Val Ser Trp Ile Lys Ser Phe Ser Asp Arg Tyr Tyr Ala Lys Thr
        115                 120                 125

Gly Arg Tyr Pro Met Ile Tyr Thr Asn Tyr Ser Trp Trp Asn Gln Cys
    130                 135                 140

Thr Gly Asn Ser Ala Ser Phe Ala Ala Thr Asn Pro Leu Val Leu Ala
145                 150                 155                 160

Arg Trp Ser Ser Thr Val Gly Thr Leu Pro Gly Gly Trp Ser Val Gln
                165                 170                 175

Thr Ile Trp Gln Asn Ala Asp Thr Tyr Thr Tyr Gly Gly Asp Ser Asp
            180                 185                 190

Val Phe Asn Gly Ser Leu Asp Arg Leu Lys Ala Leu Ala Lys Gly Ser
        195                 200                 205
```

```
<210> SEQ ID NO 159
<211> LENGTH: 208
<212> TYPE: PRT
<213> ORGANISM: Acremonium alcalophilum
<220> FEATURE:
<221> NAME/KEY: mat_peptide
<222> LOCATION: (1)..(208)

<400> SEQUENCE: 159
```

```
Arg Ile Pro Gly Phe Asp Ile Ser Gly Trp Gln Pro Thr Thr Asp Phe
1               5                   10                  15

Ala Arg Ala Tyr Ala Asn Gly Asp Arg Phe Val Tyr Ile Lys Ala Thr
                20                  25                  30

Glu Gly Thr Thr Phe Lys Ser Ser Ala Phe Ser Arg Gln Tyr Thr Gly
            35                  40                  45

Ala Thr Gln Asn Gly Phe Ile Arg Gly Ala Tyr His Phe Ala Gln Pro
        50                  55                  60

Ala Ala Ser Ser Gly Ala Ala Gln Ala Arg Tyr Phe Ala Ser Asn Gly
65                  70                  75                  80

Gly Gly Trp Ser Lys Asp Gly Ile Thr Leu Pro Gly Ala Leu Asp Ile
                85                  90                  95

Glu Tyr Asn Pro Asn Gly Ala Thr Cys Tyr Gly Leu Ser Gln Ser Ala
            100                 105                 110

Met Val Asn Trp Ile Glu Asp Phe Val Thr Thr Tyr His Gly Ile Thr
        115                 120                 125

Ser Arg Trp Pro Val Ile Tyr Thr Thr Thr Asp Trp Trp Thr Gln Cys
    130                 135                 140

Thr Gly Asn Ser Asn Arg Phe Ala Asn Arg Cys Pro Leu Trp Ile Ala
145                 150                 155                 160

Arg Tyr Ala Ser Ser Val Gly Thr Leu Pro Asn Gly Trp Gly Phe Tyr
                165                 170                 175

Thr Phe Trp Gln Tyr Asn Asp Lys Tyr Pro Gln Gly Gly Asp Ser Asn
            180                 185                 190

Trp Phe Asn Gly Asp Ala Ser Arg Leu Arg Ala Leu Ala Asn Gly Asp
        195                 200                 205
```

```
<210> SEQ ID NO 160
```

```
<211> LENGTH: 4
<212> TYPE: PRT
<213> ORGANISM: Artificial Sequence
<220> FEATURE:
<223> OTHER INFORMATION: Conserved motif YKNA

<400> SEQUENCE: 160

Tyr Lys Asn Ala
1

<210> SEQ ID NO 161
<211> LENGTH: 5
<212> TYPE: PRT
<213> ORGANISM: Artificial Sequence
<220> FEATURE:
<223> OTHER INFORMATION: Conserved motif FGGW[S/T].
<220> FEATURE:
<221> NAME/KEY: MISC_FEATURE
<222> LOCATION: (5)..(5)
<223> OTHER INFORMATION: The amino acid in position 1 of the conserved
      motif is either serine (Ser, S) or threonine (T, Thr).

<400> SEQUENCE: 161

Phe Gly Gly Trp Xaa
1               5

<210> SEQ ID NO 162
<211> LENGTH: 52
<212> TYPE: DNA
<213> ORGANISM: Artificial Sequence
<220> FEATURE:
<223> OTHER INFORMATION: Primer

<400> SEQUENCE: 162
acacaactgg ggatccacca tgttgaaaac aattatctat accacccttg cc          52

<210> SEQ ID NO 163
<211> LENGTH: 41
<212> TYPE: DNA
<213> ORGANISM: Artificial Sequence
<220> FEATURE:
<223> OTHER INFORMATION: Primer

<400> SEQUENCE: 163
agatctcgag aagcttagcc ctttgcaaat cgttgcaatc c                      41

<210> SEQ ID NO 164
<211> LENGTH: 40
<212> TYPE: DNA
<213> ORGANISM: Artificial sequence
<220> FEATURE:
<223> OTHER INFORMATION: Primer

<400> SEQUENCE: 164
acacaactgg ggatccacca tgaagttcgc atccgtcgcc                        40

<210> SEQ ID NO 165
<211> LENGTH: 38
<212> TYPE: DNA
<213> ORGANISM: Artificial sequence
<220> FEATURE:
<223> OTHER INFORMATION: Primer

<400> SEQUENCE: 165
agatctcgag aagcttaacc ggcgttggca atcttctt                          38

<210> SEQ ID NO 166
```

```
<211> LENGTH: 41
<212> TYPE: DNA
<213> ORGANISM: Artificial sequence
<220> FEATURE:
<223> OTHER INFORMATION: Primer

<400> SEQUENCE: 166
acacaactgg ggatccacca tgcgcccctc cgtcatattg c                    41

<210> SEQ ID NO 167
<211> LENGTH: 50
<212> TYPE: DNA
<213> ORGANISM: Artificial sequence
<220> FEATURE:
<223> OTHER INFORMATION: Primer

<400> SEQUENCE: 167
agatctcgag aagcttaagc agaaaacacg ttcaaatcaa acttcttact            50

<210> SEQ ID NO 168
<211> LENGTH: 46
<212> TYPE: DNA
<213> ORGANISM: Artificial sequence
<220> FEATURE:
<223> OTHER INFORMATION: Primer

<400> SEQUENCE: 168
acacaactgg ggatccacca tgaagctcac ctttgcctct ctaact               46

<210> SEQ ID NO 169
<211> LENGTH: 40
<212> TYPE: DNA
<213> ORGANISM: Artificial sequence
<220> FEATURE:
<223> OTHER INFORMATION: Primer

<400> SEQUENCE: 169
agatctcgag aagcttaggc tcctttggcc atcctagaca                      40

<210> SEQ ID NO 170
<211> LENGTH: 42
<212> TYPE: DNA
<213> ORGANISM: Artificial sequence
<220> FEATURE:
<223> OTHER INFORMATION: Primer

<400> SEQUENCE: 170
acacaactgg ggatccacca tgcgcgcctt tattccagtc tt                   42

<210> SEQ ID NO 171
<211> LENGTH: 48
<212> TYPE: DNA
<213> ORGANISM: Artificial sequence
<220> FEATURE:
<223> OTHER INFORMATION: Primer

<400> SEQUENCE: 171
agatctcgag aagcttaggc agagaaaacg ttgagatcaa atttcttg             48

<210> SEQ ID NO 172
<211> LENGTH: 48
<212> TYPE: DNA
<213> ORGANISM: Artificial sequence
<220> FEATURE:
<223> OTHER INFORMATION: Primer

<400> SEQUENCE: 172
```
acacaactgg ggatccacca tgaagctgtc tctcctcctt attgttgc    48

<210> SEQ ID NO 173
<211> LENGTH: 41
<212> TYPE: DNA
<213> ORGANISM: Artificial sequence
<220> FEATURE:
<223> OTHER INFORMATION: Primer

<400> SEQUENCE: 173
agatctcgag aagcttaacc tagggccatt ctcttcaacc c    41

<210> SEQ ID NO 174
<211> LENGTH: 48
<212> TYPE: DNA
<213> ORGANISM: Artificial sequence
<220> FEATURE:
<223> OTHER INFORMATION: Primer

<400> SEQUENCE: 174
acacaactgg ggatccacca tgaagtcttt tggtgttatt gctaccgg    48

<210> SEQ ID NO 175
<211> LENGTH: 39
<212> TYPE: DNA
<213> ORGANISM: Artificial sequence
<220> FEATURE:
<223> OTHER INFORMATION: Primer

<400> SEQUENCE: 175
agatctcgag aagcttagcc tctggcgatt ctctgaagc    39

<210> SEQ ID NO 176
<211> LENGTH: 48
<212> TYPE: DNA
<213> ORGANISM: Artificial sequence
<220> FEATURE:
<223> OTHER INFORMATION: Primer

<400> SEQUENCE: 176
ctatatacac aactggggat ccaccatgaa gtccttcgtc ctcacggc    48

<210> SEQ ID NO 177
<211> LENGTH: 55
<212> TYPE: DNA
<213> ORGANISM: Artificial sequence
<220> FEATURE:
<223> OTHER INFORMATION: Primer

<400> SEQUENCE: 177
tagagtcgac ccagccgcgc cggccattaa gatcccttag caagagcctt aaggc    55

<210> SEQ ID NO 178
<211> LENGTH: 54
<212> TYPE: DNA
<213> ORGANISM: Artificial sequence
<220> FEATURE:
<223> OTHER INFORMATION: Primer

<400> SEQUENCE: 178
ctatatacac aactggggat ccaccatgaa gtctgttact ttcatcgcca gtct    54

<210> SEQ ID NO 179
<211> LENGTH: 54
<212> TYPE: DNA

```
<213> ORGANISM: Artificial sequence
<220> FEATURE:
<223> OTHER INFORMATION: Primer

<400> SEQUENCE: 179
tagagtcgac ccagccgcgc cggccattac gaagcgttag caatacgctt aagc         54

<210> SEQ ID NO 180
<211> LENGTH: 50
<212> TYPE: DNA
<213> ORGANISM: Artificial sequence
<220> FEATURE:
<223> OTHER INFORMATION: Primer

<400> SEQUENCE: 180
ctatatacac aactggggat ccaccatgaa ggcttcttcc atcctctccc              50

<210> SEQ ID NO 181
<211> LENGTH: 51
<212> TYPE: DNA
<213> ORGANISM: Artificial sequence
<220> FEATURE:
<223> OTHER INFORMATION: Primer

<400> SEQUENCE: 181
tagagtcgac ccagccgcgc cggccatcat ccactcgcca acttcttcaa c            51

<210> SEQ ID NO 182
<211> LENGTH: 50
<212> TYPE: DNA
<213> ORGANISM: Artificial sequence
<220> FEATURE:
<223> OTHER INFORMATION: Primer

<400> SEQUENCE: 182
ctatatacac aactggggat ccaccatgtt ctctttcgtc aaagcgctca              50

<210> SEQ ID NO 183
<211> LENGTH: 58
<212> TYPE: DNA
<213> ORGANISM: Artificial sequence
<220> FEATURE:
<223> OTHER INFORMATION: Primer

<400> SEQUENCE: 183
tagagtcgac ccagccgcgc cggccattaa tttgcaaaga cattgaggtc gaattggc     58

<210> SEQ ID NO 184
<211> LENGTH: 50
<212> TYPE: DNA
<213> ORGANISM: Artificial sequence
<220> FEATURE:
<223> OTHER INFORMATION: Primer

<400> SEQUENCE: 184
ctatatacac aactggggat ccaccatgtt ccctttcgtc aaaacgctca              50

<210> SEQ ID NO 185
<211> LENGTH: 57
<212> TYPE: DNA
<213> ORGANISM: Artificial sequence
<220> FEATURE:
<223> OTHER INFORMATION: Primer

<400> SEQUENCE: 185
tagagtcgac ccagccgcgc cggccattaa tttgcaaaca cattgaggtc gaattgg      57
```

<210> SEQ ID NO 186
<211> LENGTH: 52
<212> TYPE: DNA
<213> ORGANISM: Artificial sequence
<220> FEATURE:
<223> OTHER INFORMATION: Primer

<400> SEQUENCE: 186
ctatatacac aactggggat ccaccatggt caaaatcttg agccttctag cc        52

<210> SEQ ID NO 187
<211> LENGTH: 53
<212> TYPE: DNA
<213> ORGANISM: Artificial sequence
<220> FEATURE:
<223> OTHER INFORMATION: Primer

<400> SEQUENCE: 187
tagagtcgac ccagccgcgc cggccactat gcgaatacgc tcaggtcgaa ttg       53

<210> SEQ ID NO 188
<211> LENGTH: 37
<212> TYPE: DNA
<213> ORGANISM: Artificial sequence
<220> FEATURE:
<223> OTHER INFORMATION: Primer

<400> SEQUENCE: 188
acacaactgg ggatccacca tgaagactac gggtgtc                         37

<210> SEQ ID NO 189
<211> LENGTH: 35
<212> TYPE: DNA
<213> ORGANISM: Artificial sequence
<220> FEATURE:
<223> OTHER INFORMATION: Primer

<400> SEQUENCE: 189
ccctctagat ctcgagttaa gaaccttgg caaag                            35

<210> SEQ ID NO 190
<211> LENGTH: 39
<212> TYPE: DNA
<213> ORGANISM: Artificial sequence
<220> FEATURE:
<223> OTHER INFORMATION: Primer

<400> SEQUENCE: 190
acacaactgg ggatccacca tgaagttcac taccattgc                       39

<210> SEQ ID NO 191
<211> LENGTH: 34
<212> TYPE: DNA
<213> ORGANISM: Artificial sequence
<220> FEATURE:
<223> OTHER INFORMATION: Primer

<400> SEQUENCE: 191
ccctctagat ctcgagctac ccctcgacaa tctt                            34

<210> SEQ ID NO 192
<211> LENGTH: 38
<212> TYPE: DNA
<213> ORGANISM: Artificial sequence
<220> FEATURE:

```
<223> OTHER INFORMATION: Primer

<400> SEQUENCE: 192
acacaactgg ggatccacca tgaagtctgt tgctgtct                             38

<210> SEQ ID NO 193
<211> LENGTH: 36
<212> TYPE: DNA
<213> ORGANISM: Artificial sequence
<220> FEATURE:
<223> OTHER INFORMATION: Primer

<400> SEQUENCE: 193
ccctctagat ctcgagctaa gaagcattcg caatgc                              36

<210> SEQ ID NO 194
<211> LENGTH: 37
<212> TYPE: DNA
<213> ORGANISM: Artificial sequence
<220> FEATURE:
<223> OTHER INFORMATION: Primer

<400> SEQUENCE: 194
acacaactgg ggatccacca tgaagctcac gagtgtg                             37

<210> SEQ ID NO 195
<211> LENGTH: 35
<212> TYPE: DNA
<213> ORGANISM: Artificial sequence
<220> FEATURE:
<223> OTHER INFORMATION: Primer

<400> SEQUENCE: 195
ccctctagat ctcgagttac gaacctctag caagc                               35

<210> SEQ ID NO 196
<211> LENGTH: 40
<212> TYPE: DNA
<213> ORGANISM: Artificial sequence
<220> FEATURE:
<223> OTHER INFORMATION: Primer

<400> SEQUENCE: 196
acacaactgg ggatccacca tgaagtctta catcgccccc                          40

<210> SEQ ID NO 197
<211> LENGTH: 39
<212> TYPE: DNA
<213> ORGANISM: Artificial sequence
<220> FEATURE:
<223> OTHER INFORMATION: Primer

<400> SEQUENCE: 197
gtgcggccgc aagcttaatc agaggcttcc tcccatagg                           39

<210> SEQ ID NO 198
<211> LENGTH: 43
<212> TYPE: DNA
<213> ORGANISM: Artificial sequence
<220> FEATURE:
<223> OTHER INFORMATION: Primer

<400> SEQUENCE: 198
acacaactgg ggatccacca tgaagtatct cgttcccctt ttg                      43
```

-continued

```
<210> SEQ ID NO 199
<211> LENGTH: 38
<212> TYPE: DNA
<213> ORGANISM: Artificial sequence
<220> FEATURE:
<223> OTHER INFORMATION: Primer

<400> SEQUENCE: 199
agatctcgag aagcttatta gcccttagcc agtctctt                      38

<210> SEQ ID NO 200
<211> LENGTH: 43
<212> TYPE: DNA
<213> ORGANISM: Artificial sequence
<220> FEATURE:
<223> OTHER INFORMATION: Primer

<400> SEQUENCE: 200
acacaactgg ggatccacca tgaagctcac cacttttatc acg                43

<210> SEQ ID NO 201
<211> LENGTH: 38
<212> TYPE: DNA
<213> ORGANISM: Artificial sequence
<220> FEATURE:
<223> OTHER INFORMATION: Primer

<400> SEQUENCE: 201
ctagatctcg agaagctttt aagtcccctt ggcaagcg                      38

<210> SEQ ID NO 202
<211> LENGTH: 44
<212> TYPE: DNA
<213> ORGANISM: Artificial sequence
<220> FEATURE:
<223> OTHER INFORMATION: Primer

<400> SEQUENCE: 202
acacaactgg ggatccacca tgaagtttgc actcctagta tctg               44

<210> SEQ ID NO 203
<211> LENGTH: 42
<212> TYPE: DNA
<213> ORGANISM: Artificial sequence
<220> FEATURE:
<223> OTHER INFORMATION: Primer

<400> SEQUENCE: 203
ctagatctcg agaagctttt agccatagta gttcttgtcc ca                 42

<210> SEQ ID NO 204
<211> LENGTH: 37
<212> TYPE: DNA
<213> ORGANISM: Artificial sequence
<220> FEATURE:
<223> OTHER INFORMATION: Primer

<400> SEQUENCE: 204
acacaactgg ggatccacca tggcaaagct cctcaag                       37

<210> SEQ ID NO 205
<211> LENGTH: 35
<212> TYPE: DNA
<213> ORGANISM: Artificial sequence
<220> FEATURE:
<223> OTHER INFORMATION: Primer
```

<400> SEQUENCE: 205
agatctcgag aagcttatta gtgggcgaag acgtt    35

<210> SEQ ID NO 206
<211> LENGTH: 39
<212> TYPE: DNA
<213> ORGANISM: Artificial sequence
<220> FEATURE:
<223> OTHER INFORMATION: Primer

<400> SEQUENCE: 206
acacaactgg ggatccacca tgaagcttct ttccgccct    39

<210> SEQ ID NO 207
<211> LENGTH: 38
<212> TYPE: DNA
<213> ORGANISM: Artificial sequence
<220> FEATURE:
<223> OTHER INFORMATION: Primer

<400> SEQUENCE: 207
agatctcgag aagcttatca ctgagaggca aacttgac    38

<210> SEQ ID NO 208
<211> LENGTH: 39
<212> TYPE: DNA
<213> ORGANISM: Artificial sequence
<220> FEATURE:
<223> OTHER INFORMATION: Primer

<400> SEQUENCE: 208
acacaactgg ggatccacca tggcttccag actgaccct    39

<210> SEQ ID NO 209
<211> LENGTH: 38
<212> TYPE: DNA
<213> ORGANISM: Artificial sequence
<220> FEATURE:
<223> OTHER INFORMATION: Primer

<400> SEQUENCE: 209
ctagatctcg agaagctttt aagctgccac gcactggg    38

<210> SEQ ID NO 210
<211> LENGTH: 27
<212> TYPE: DNA
<213> ORGANISM: Artificial sequence
<220> FEATURE:
<223> OTHER INFORMATION: Primer

<400> SEQUENCE: 210
gaattcgagc tcggtacctt gaagttc    27

<210> SEQ ID NO 211
<211> LENGTH: 31
<212> TYPE: DNA
<213> ORGANISM: Artificial sequence
<220> FEATURE:
<223> OTHER INFORMATION: Primer

<400> SEQUENCE: 211
ggtggatccc cagttgtgta tatagaggat t    31

<210> SEQ ID NO 212
<211> LENGTH: 26

```
<212> TYPE: DNA
<213> ORGANISM: Artificial sequence
<220> FEATURE:
<223> OTHER INFORMATION: Primer

<400> SEQUENCE: 212
tgcgcggcgc ggctgggtcg actcta                                          26

<210> SEQ ID NO 213
<211> LENGTH: 27
<212> TYPE: DNA
<213> ORGANISM: Artificial sequence
<220> FEATURE:
<223> OTHER INFORMATION: Primer

<400> SEQUENCE: 213
ttcacacagg aaacagctat gaccatg                                         27

<210> SEQ ID NO 214
<211> LENGTH: 25
<212> TYPE: DNA
<213> ORGANISM: Artificial sequence
<220> FEATURE:
<223> OTHER INFORMATION: Primer

<400> SEQUENCE: 214
ctatatacac aactggggat ccacc                                           25

<210> SEQ ID NO 215
<211> LENGTH: 26
<212> TYPE: DNA
<213> ORGANISM: Artificial sequence
<220> FEATURE:
<223> OTHER INFORMATION: Primer

<400> SEQUENCE: 215
tagagtcgac ccagccgcgc cggcca                                          26

<210> SEQ ID NO 216
<211> LENGTH: 10767
<212> TYPE: DNA
<213> ORGANISM: Artificial Sequence
<220> FEATURE:
<223> OTHER INFORMATION: Synthetic DNA construct of plasmid pDAu770.

<400> SEQUENCE: 216
taggcgtatc acgaggccct ttcgtctcgc gcgtttcggt gatgacggtg aaaacctctg     60
acacatgcag ctcccggaga cggtcacagc ttgtctgtaa gcggatgccg ggagcagaca    120
agcccgtcag ggcgcgtcag cgggtgttgg cgggtgtcgg ggctggctta actatgcggc    180
atcagagcag attgtactga gagtgcacca tatgcggtgt gaaataccgc acagatgcgt    240
aaggagaaaa taccgcatca ggcgccattc gccattcagg ctgcgcaact gttgggaagg    300
gcgatcggtg cgggcctctt cgctattacg ccagctggcg aaagggggat gtgctgcaag    360
gcgattaagt tgggtaacgc cagggttttc ccagtcacga cgttgtaaaa cgacggccag    420
tgaattggcc tccatggccg cggccgcgct ttgctaaaac tttggttgat ggaaggtatc    480
tggcgataaa ctccgacgac gtctagaagc aacaatctta tgcaaacgct cattggttct    540
tttcgaccgc aacatccatc atgaaactgg tattttgtct gtgtcagcag tctagaaccc    600
cttgccgggt attttagcat ttcattttc tataaaaagg taccagcatg tatgatcgt     660 atcttccgta ccgtggttat taaatcccag cagaggccga taggcttaag aagtgaacat    720
```

-continued

| | |
|---|---|
| ggcatggtta aggaagaagc cattactgag tatatatggc tagaataatc gctgggaaag | 780 |
| atttatgctt ccaagaggcg taggacggta taccatacag tacggtattt atgaacaatt | 840 |
| cgataatacc actccccaaa gcgggagata ggacacccgc ctcaggcacc aaccacaccc | 900 |
| tttttcaact gtcagtggtg cacgtttcca tcgagcataa gcttggtacc ctaaggatag | 960 |
| gccctaatct tatctacatg tgactgcatc gatgtgtttg gtcaaaatga ggcatgtggc | 1020 |
| tcacccaca ggcggagaaa cgtgtggcta gtgcatgaca gtcccctcca tagattcaat | 1080 |
| ttaatttttc gcggcaattg tcgtgcagtt tgtatctaca tttcattcca tatatcaaga | 1140 |
| gttagtagtt ggacatcctg attattttgt ctaattactg aaaactcgaa gtactaaccct | 1200 |
| actaataagc cagtttcaac cactaagtgc tcatttatac aatatttgca gaaccccgcg | 1260 |
| ctaccctcc atcgccaaca tgtcttccaa gtcgcaattg acctacagcg cacgcgctag | 1320 |
| caagcacccc aatgcgctcg taaagaagct cttcgaggtt gccgaggcca agaaaaccaa | 1380 |
| tgtcaccgtt ccgccgacg tgacaaccac caaagagctg ctggatttgg ctgaccgtat | 1440 |
| gcgcaccggg gttgaagttc ctattccgag ttcctattct tcaaatagta taggaacttc | 1500 |
| attagtttaa acgtacgatt ttgacatttg ctccattgtc gaggatggat ggaacgagcg | 1560 |
| gcgtgcgcca cgaaagtgag gctattgcct atcagctctt tgctacattc cggaaacaaa | 1620 |
| catccctttt tgtgaattat ctacgcaact tagatggcgt gaacgcatct tcaaagtctt | 1680 |
| tcggcaggtc cggcacgact tttgcatcca gagaagcgcc tacatgtgta ttcgaccacc | 1740 |
| tcctagcgcg cttggatatg aggaaatatt actgagagtc gaaacaagc tccaccgcac | 1800 |
| cagctcttct tggagttta tattaaagaa tattcccagc tcgttgtatt attcttttc | 1860 |
| taccgtgcta atgtatcaag actttggta cctattaacg ttattattcg tgtgctattc | 1920 |
| ccaaacataa ccctgtatat gtttcgaacg ccgttatgac ccatgtctta catactcatt | 1980 |
| aagtcattcc cttggataat ctcgactcag atgcggcggt tgatgtagga ggagaggtaa | 2040 |
| tcgaggacct cctgggagat gatgccgttc caggcgggga gcggatgga gccctcggcg | 2100 |
| gagcccttga gctgctcgat atgctgccac tcctcgatgg ggttggtctc atccttgagg | 2160 |
| gcgatcatct ccttggagat gggatcgtag gcgtagtagc gggagactag tgcgaagtaa | 2220 |
| tgatcgggga tggcggtgat ctgatgggtg taggtggtgc gggcgacggc ggaggcgcgc | 2280 |
| ttatcggacc agttgccgac gacgttggtg agctcggtga ggcccttcat ggagaggaag | 2340 |
| gaggtcatga gatggcggcc gatatgggac ttggggccgt tcttgatggc gaagatggag | 2400 |
| taggggggcgt tcttcttgag ggccttgttg taggagcgga cgaggttatc cttgaggagc | 2460 |
| tggtactcct gcttgttgga ggaggagttg ccggtgcggt tgacgcgctt gaggacgggc | 2520 |
| tcggagttgc ggaggaactc atcgaggtag acgaggggat cgatgcggcc gcggcggag | 2580 |
| aagaagtaga tatggcggga gacggaggtc ttggtctcgg tgacgaggca ctggatgatg | 2640 |
| acgccgaggt acttgttctg gacgagcttg aaggacttgg gatcgacgtt cttgatatcg | 2700 |
| gagaagcggc cgcagttgat gaaggtggcg aggaagagga actggtagag ggtcttggtc | 2760 |
| ttggtgaagc gggaggtgta ctcgaaggag ttgaggatct tctcggtgat ctcccagatg | 2820 |
| gactcgccct cggagaggag ggccttgagc atcttcttgg aatgggagtt gcccttatcg | 2880 |
| gcctcctcgg aggactcgaa ctggagctgg agggaggaga cgatatcggt gatatcggac | 2940 |
| tgatgcttct ggccgtagta ggggatgatg gtgaactccc aggcggggat gagcttcttg | 3000 |
| agggaggcct ccaggatggt ggccttctgg gtcttgtact tgaactggag ggacttgttg | 3060 |
| acgatatcga aggagaggga gttggagatg atggtgttgt aggacatgaa ggtggcgcgc | 3120 |

```
ttgatggcgg tgccgttatg ggtgatcatc cagcagaggt aggtgagctc ggcggcgcag    3180
agggcgatct tctcgccgga ggggcgctcg aagcgctcga cgaactggcg gacgaggacc    3240
ttgggggggg tcttgcagag gatatcgaac tggggcatgg tgctcagata ctacggctga    3300
tcgcgtagag gtactgagca aaacagatgt cagtaaggag aagagttgaa tgaatggaag    3360
aagagtagga aaggaggtat gggggaaaga tatacgtact gatgcggacg aagagagaaa    3420
gaaggaaaaa agttgtggga ggggaaggag ggggaatcct tatatggagg ggcaagcgag    3480
aaggcgaatt agtgggcggg cttaagccct cgaccgccgc ccttatcatt ggacatggag    3540
gggtaatgcc cccaccacgc atgtgcggga ccgacgcaga atctgcacgg cggagtctct    3600
tccagactgt tgacttttgg gcgatgactc ttgttgctgc ggccttttgg gtacaccaac    3660
ctcgttgatc ttgtttcctt ggttctcttt cgctcggaga cccgaccatg accccaccat    3720
cagtcactat cctgcctcgt cgataaaaat tttttcttcc ctctgattgt tacatagtat    3780
gtttccacct ttccggtgga tttcggacag tcaaactggg catcaacgca gtggtgggct    3840
gcttcgtttg ctgcgtgttg tacttgtttg catttgaacc ccgcggtcgt tcgagtcctt    3900
aattggtccg ctcccggtca cacccaagc agctgtggcc cggccgagtg gcgcctgtct    3960
ggtccacagt taattaaagg agagagttga acctggacgc cgcgcaaaaa gcaaagacgc    4020
gcctcgtggg cggtggatca atgatcggat ttagtggcag atggcatcac aggcggccaa    4080
tgaccaccgg gccaactggc cccgacattc cagcaatact gcctaattga ctccaccatg    4140
catctcggct attattgaac tgggtttgat ggatggggac cctcttggaa ttgtcaaaga    4200
ttttgaagcg aagacgatct attggacggt agagatatac tcttgattta gtcgttggga    4260
ggcccctggg gaaagcaatg atggggaatg ttgctgctcc actgtggacc tcggctatgg    4320
aattacgtgc ttggatctaa gatgagctca tggctatgca ttgaatgaca gtgatatcag    4380
cagagcaagc agagaaggat ggaatgctaa ttttctagtg cttgtgcaa gggtaaatca    4440 gggactgtct gtctggtctt ctacacgaag gaaagaccat ggctttcacg gtgtctgtat    4500
ttccggatat cctcaattcc gtcggtcgat tacaatcaca tgacttggct tccatttcac    4560
tactattatg cacacccact acatacatga tcatataacc aattgccctc atccccatcc    4620
tttaactata gcgaaatgga ttgattgtct accgccaggt gtcagtcacc ctctagatct    4680
cgagctcgct agagtcgacc tatggagtca ccacatttcc cagcaacttc cccacttcct    4740
ctgcaatcgc caacgtcctc tcttcactga gtctccgtcc gataacctgc actgcaaccg    4800
gtgccccatg gtacgcctcc ggatcatact cttcctgcac gagggcatca agctcactaa    4860
ccgccttgaa actctcattc ttcttatcga tgttcttatc cgcaaaggta accggaacaa    4920
ccacgctcgt gaaatccagc aggttgatca cagaggcata cccatagtac cggaactggt    4980
catgccgtac cgcagcggta ggcgtaatcg gcgcgatgat ggcgtccagt tccttcccgg    5040
ccttttcttc agcctcccgc catttctcaa ggtactccat ctggtaattc acttctggaa    5100
gatgcgtgtc ccagagctcg ttcatgttaa cagctttgat gttcgggttc agtaggtctt    5160
tgatatttgg aatcgccggc tcgccggatg cactgatatc gcgcattacg tcggcgctgc    5220
cgtcagccgc gtagatatgg gagatgagat cgtggccgaa atcgtgcttg tatggcgtcc    5280
acggggtcac ggtgtgaccg gctttggcga gtgcggcgac ggtggtttcc acgccgcgca    5340
ggataggagg gtgtggaagg acattgccgt cgaagttgta gtagccgata ttgagcccgc    5400
cgttcttgat cttggaggca ataatgtccg actcggactg gcgccagggc atgggatga    5460
```

```
ccttggagtc gtatttccat ggctcctgac cgaggacgga tttggtgaag aggcggaggt    5520
ctaacatact tcatcagtga ctgccggtct cgtatatagt ataaaaagca agaaaggagg    5580
acagtggagg cctggtatag agcaggaaaa gaaggaagag gcgaaggact caccctcaac    5640
agagtgcgta atcggcccga caacgctgtg caccgtctcc tgaccctcca tgctgttcgc    5700
catctttgca tacggcagcc gcccatgact cggccttaga ccgtacagga agttgaacgc    5760
ggccggcact cgaatcgagc caccgatatc cgttcctaca ccgatgacgc caccacgaat    5820
cccaacgatc gcaccctcac caccagaact gccgccgcac gaccagttct tgttgcgtgg    5880
gttgacggtg cgcccgatga tgttgttgac tgtctcgcag accatcaggg tctgcgggac    5940
agaggtcttg acgtagaaga cggcaccggc tttgcggagc atggttgtca gaaccgagtc    6000
cccttcgtcg tacttgttta gccatgagat gtagcccatt gatgtttcgt agccctggtg    6060
gcatatgtta gctgacaaaa agggacatct aacgacttag gggcaacggt gtaccttgac    6120
tcgaagctgg tctttgagag agatggggag gccatggagt ggaccaacgg gtctcttgtg    6180
ctttgcgtag tattcatcga gttcccttgc ctgcgcgaga gcggcgtcag ggaagaactc    6240
gtgggcgcag tttgtctgca cagaagccag cgtcagcttg atagtcccat aaggtggcgt    6300
tgttacatct ccctgagagg tagaggggac cctactaact gctgggcgat tgctgcccgt    6360
ttacagaatg ctagcgtaac ttccaccgag gtcaactctc cggccgccag cttggacaca    6420
agatctgcag cggaggcctc tgtgatcttc agttcggcct ctgaaaggat caccgatttc    6480
tttgggaaat caataacgct gtcttccgca ggcagcgtct ggactttcca ttcatcaggg    6540 atggttttg cgaggcggc gcgcttatca gcggccagtt cttcccagga ttgaggcatg    6600
tgcatgcaat gtgtgtttat gtggaagtaa gatacgacga gtttgattga gaaaagacag    6660
ggtgattgtc aagttcagta tggaagaaag agtagaagaa gatcagacga cagggaagag    6720
cgatgacata aaaggtggaa gacggaagaa aaacgaacca aatcaatccc actctatggc    6780
gggggttgga ctgcctgagg ccggcactgg tggggcttat cgataagttc tcgtcaccgg    6840
atgcaatgcg ctgtcaactg ctgacttggc cctgaacatc ctgtcctcta cagatccata    6900
ctatacaatg atcccagtta tagtgcggta aggtgcatat catatctcat tctcatgact    6960
cattcgactt ttttttagag aaagtacata cgtggaacat acactaaacg caacaggtcg    7020
cgacaacact ggtatacaaa acggtccccg gtgaatgacg ttattagtgt ctatccccca    7080
ctcacacccg aaaagaataa tagaaactaa cagaaaaagc ggcccgagga taagaggaac    7140
attcaaacag aaggggaatc ataaaaaccg aaaaatgcaa ggaaaagaga actcaaatca    7200
ataattttca taatactgtc gagagtaata cggaccagcg tctctcaggg acatgcgtcg    7260
gcgcaaggca tcatccaatc tctcatctaa cacatccagc attcgtgttc gatagtctaa    7320
ctgcttctct cggcgctcaa gtcttgcttc ccgatcatcg agttaattaa gaagttccta    7380
tactttctag agaataggaa ctcggaatag gaacttcaag gtaccgagct ctatcctcaa    7440
taccctattt tccacgattc cattgtcata tccaattccg ttttcttttc ttgttttccc    7500
ctcatccaat cccgtccatc atttactcct ttttcttgtg aatgcaagtg gcactaagaa    7560 atccaaccc cagacaaatt ttcctactca ggaaacacaa aacctcgttt ctgctccctt    7620
ctcgtacttc attcctatcg tctcggaatt tcctcaacaa cccttccga ctttgcgaca    7680 gcgtcgcgat tccagactta tgtgttctcg ttcctactgt cgttaccagt ctatttattc    7740
cgaaacctct gatcgctgaa tttcacacac aacaccccc cgttgatgct ggtggagaat    7800
ccgtagcgtc aagagttgaa ttcactccat gttgtaacga agtccacgaa ttgagacgat    7860
```

```
tgatgattac aaccccgcga tcgcctatcg acgattcgac gagatgccat tctcatcctc    7920
ctcatcctcc tccaccccg aggtgtctac caccccgctc gcagattact tctggatcgc     7980
aggtgtcgat ggcgcggaaa tcttagagac tttccaaaga ctcggcgacg aatacagggc    8040
aaacagtgcc accgctcctg gccccgctct tgcggacacg atcgaggaag atgcggacgc    8100
ggaggaggca cacgaccccc gtctggactc cctctctcga cccaattcca tggctggggg    8160
ccgcaattcc ttccagcggt tctcaatgcg ctcaggagac tccagtgagt ccagtgggaa    8220
tggtaccagc agcaaccgga gcagtctgac catcaagggt aatcagtcgc ccagagggtc    8280
gtcgtttcta aagatttcg actttgacaa ggccctgttc aagtttgcaa acgagcggga     8340
gtcgttcctg tcggatctga gtctcagtgc cggagcaatc actcccacct cccgtcctag    8400
gtccaggtta cgtacacaga agattgtctc cgaggaaagt ccctcccagc catccagctt    8460
gcttcgatca ggcattggta gtgtgcggcg tcatatggca ttcagagaca tgaatagtat    8520
gaaacggcag ccgtcagttg ctcgtcgcgg ccgcagcttg gcgtaatcat ggtcatagct    8580
gtttcctgtg tgaaattgtt atccgctcac aattccacac aacatacgag ccggaagcat    8640
aaagtgtaaa gcctgggtg cctaatgagt gagctaactc acattaattg cgttgcgctc      8700
actgcccgct ttccagtcgg gaaacctgtc gtgccagctg cattaatgaa tcggccaacg     8760
cgcggggaga ggcggtttgc gtattgggcg ctcttccgct tcctcgctca ctgactcgct     8820
gcgctcggtc gttcggctgc ggcgagcggt atcagctcac tcaaaggcgg taatacggtt     8880
atccacagaa tcaggggata acgcaggaaa gaacatgtga gcaaaaggcc agcaaaaggc     8940
caggaaccgt aaaaaggccg cgttgctggc gttttccat aggctccgcc cccctgacga     9000
gcatcacaaa aatcgacgct caagtcagag gtggcgaaac ccgacaggac tataaagata    9060
ccaggcgttt ccccctggaa gctccctcgt gcgctctcct gttccgaccc tgccgcttac    9120
cggatacctg tccgccttt tcccttcggg aagcgtggcg ctttctcata gctcacgctg      9180
taggtatctc agttcggtgt aggtcgttcg ctccaagctg ggctgtgtgc acgaaccccc    9240
cgttcagccc gaccgctgcg ccttatccgg taactatcgt cttgagtcca acccggtaag    9300
acacgactta tcgccactgg cagcagccac tggtaacagg attagcagag cgaggtatgt    9360
aggcggtgct acagagttct tgaagtggtg gcctaactac ggctacacta agaacagt      9420 atttggtatc tgcgctctgc tgaagccagt taccttcgga aaaagagttg gtagctcttg    9480
atccggcaaa caaaccaccg ctggtagcgg tggtttttt gtttgcaagc agcagattac      9540
gcgcagaaaa aaaggatctc aagaagatcc tttgatcttt tctacggggt ctgacgctca    9600
gtggaacgaa aactcacgtt aagggatttt ggtcatgaga ttatcaaaaa ggatcttcac    9660
ctagatcctt ttaaattaaa aatgaagttt taaatcaatc taaagtatat atgagtaaac    9720
ttggtctgac agttaccaat gcttaatcag tgaggcacct atctcagcga tctgtctatt    9780
tcgttcatcc atagttgcct gactccccgt cgtgtagata actacgatac gggagggctt    9840
accatctggc cccagtgctg caatgatacc gcgagaccca cgctcaccgg ctccagattt    9900
atcagcaata aaccagccag ccggaagggc cgagcgcaga agtggtcctg caactttatc    9960
cgcctccatc cagtctatta attgttgccg ggaagctaga gtaagtagtt cgccagttaa    10020
tagtttgcgc aacgttgttg ccattgctac aggcatcgtg gtgtcacgct cgtcgtttgg    10080
tatggcttca ttcagctccg gttcccaacg atcaaggcga gttacatgat cccccatgtt    10140
gtgcaaaaaa gcggttagct ccttcggtcc tccgatcgtt gtcagaagta agttggccgc    10200
```

-continued

```
agtgttatca ctcatggtta tgcagcact gcataattct cttactgtca tgccatccgt    10260
aagatgcttt tctgtgactg gtgagtactc aaccaagtca ttctgagaat agtgtatgcg    10320
gcgaccgagt tgctcttgcc cggcgtcaat acgggataat accgcgccac atagcagaac    10380
tttaaaagtg ctcatcattg gaaaacgttc ttcggggcga aaactctcaa ggatcttacc    10440
gctgttgaga tccagttcga tgtaacccac tcgtgcaccc aactgatctt cagcatcttt    10500
tactttcacc agcgtttctg ggtgagcaaa aacaggaagg caaaatgccg caaaaagggg    10560
aataagggcg acacggaaat gttgaatact catactcttc cttttcaat attattgaag     10620 catttatcag ggttattgtc tcatgagcgg atacatattt gaatgtattt agaaaaataa    10680 acaaatagggg gttccgcgca catttccccg aaaagtgcca cctgacgtct aagaaaccat    10740
tattatcatg acattaacct ataaaaa                                        10767
```

<210> SEQ ID NO 217
<211> LENGTH: 1052
<212> TYPE: DNA
<213> ORGANISM: Flammulina velutipes
<220> FEATURE:
<221> NAME/KEY: CDS
<222> LOCATION: (1)..(157)
<220> FEATURE:
<221> NAME/KEY: sig_peptide
<222> LOCATION: (1)..(51)
<220> FEATURE:
<221> NAME/KEY: mat_peptide
<222> LOCATION: (52)..(1049)
<220> FEATURE:
<221> NAME/KEY: CDS
<222> LOCATION: (213)..(347)
<220> FEATURE:
<221> NAME/KEY: CDS
<222> LOCATION: (401)..(451)
<220> FEATURE:
<221> NAME/KEY: CDS
<222> LOCATION: (504)..(600)
<220> FEATURE:
<221> NAME/KEY: CDS
<222> LOCATION: (659)..(666)
<220> FEATURE:
<221> NAME/KEY: CDS
<222> LOCATION: (715)..(838)
<220> FEATURE:
<221> NAME/KEY: CDS
<222> LOCATION: (895)..(981)
<220> FEATURE:
<221> NAME/KEY: CDS
<222> LOCATION: (1037)..(1049)

<400> SEQUENCE: 217

```
atg cgc atc tta ctc ttc atc gct gtg acc att gca ctc ggc gtc cat      48
Met Arg Ile Leu Leu Phe Ile Ala Val Thr Ile Ala Leu Gly Val His
    -15                 -10                 -5 gct cgt ctc aat ggc atc gac gtt tcc ggg tat cag ccg aac gtc aac      96
Ala Arg Leu Asn Gly Ile Asp Val Ser Gly Tyr Gln Pro Asn Val Asn
-1   1               5                  10                  15 tgg gcc act gtc aag gct aat ggc gtc tca ttc gcg tat atc aag gcc     144
Trp Ala Thr Val Lys Ala Asn Gly Val Ser Phe Ala Tyr Ile Lys Ala
                 20                  25                  30 acc gaa ggc act a gtaagttcac ttcctatatc cttttggtcc agtgctgata        197
Thr Glu Gly Thr
             35 tcatcgacaa cccag ct  tat acg aac ccg tcg ttc tca tcg caa tac acc    247
                    Thr Tyr Thr Asn Pro Ser Phe Ser Ser Gln Tyr Thr
                                     40                  45 gga gct acc aaa gct gga ctc att cga gga tcg tac cat ttt gcg cac     295
```

``` cca agt agt agc acg ggc gct gca cag gcc aga tac ttt gtc gcg cat    343
Pro Ser Ser Thr Gly Ala Ala Gln Ala Arg Tyr Phe Val Ala His
 65                  70                  75 ggc g gtaggaattg atccatcttg tgtggcgtcc cccattgaca caatccttga tag  400
Gly
 80 gt  ggc tgg tcg gga gac gga atc act ctg cct ggg gcg ctg gat ata   447
Gly Gly Trp Ser Gly Asp Gly Ile Thr Leu Pro Gly Ala Leu Asp Ile
             85                  90                  95 gaa t gtaatgatca gtcagatcta ttacgttttg agtcacattg acaacttctt ag   503
Glu ac  aat cca agt ggc gca act tgc tac ggc ctg agt acc tca tca atg   550
Tyr Asn Pro Ser Gly Ala Thr Cys Tyr Gly Leu Ser Thr Ser Ser Met
            100                 105                 110 gtc aat tgg att gcc gac ttc tct aac act tac cat tcc ctc act gga   598
Val Asn Trp Ile Ala Asp Phe Ser Asn Thr Tyr His Ser Leu Thr Gly
        115                 120                 125 ag  gttaggcttc gtaaacacaa gccatgtact gccgtagtaa cgctaatctc        650
Arg
130 catttcag a tac cct g gtacaccaat cccacaatca ttttgagtct gctcatctcc  706
           Tyr Pro cctgacag ta  att tac acc acc gca gac tgg tgg agg aca tgt act ggt 755
             Ile Tyr Thr Thr Ala Asp Trp Trp Arg Thr Cys Thr Gly
              135                 140                 145 aac agt gca tcc ttt gcc aac aac agt cct ctc tgg att gcg aga tat  803
Asn Ser Ala Ser Phe Ala Asn Asn Ser Pro Leu Trp Ile Ala Arg Tyr
            150                 155                 160 gcc agt acc atc ggt aca ctc cct gct gga tgg ag  gtgcgaccct       848
Ala Ser Thr Ile Gly Thr Leu Pro Ala Gly Trp Ser
            165                 170 tctacttatt cgatgactct gttctgaacc aagtgttcat tctaag c tac gcc aca 904
                                                    Tyr Ala Thr
                                                            175 ttc tgg cag tac gct gac tcg ggt agt aat ccc gga gat cag gat tat  952
Phe Trp Gln Tyr Ala Asp Ser Gly Ser Asn Pro Gly Asp Gln Asp Tyr
        180                 185                 190 ttc aac ggg gat gct gca ggt ctc aaa cg  gtaaattgat atctttttat    1001
Phe Asn Gly Asp Ala Ala Gly Leu Lys Arg
        195                 200 atatcttcac ctgcgagact aatccatgtt tatag g ctt gcc acc agt tga     1052
                                        Leu Ala Thr Ser
                                                205

<210> SEQ ID NO 218
<211> LENGTH: 224
<212> TYPE: PRT
<213> ORGANISM: Flammulina velutipes

<400> SEQUENCE: 218

Met Arg Ile Leu Leu Phe Ile Ala Val Thr Ile Ala Leu Gly Val His
            -15                 -10                 -5

Ala Arg Leu Asn Gly Ile Asp Val Ser Gly Tyr Gln Pro Asn Val Asn
 -1   1              5                  10                  15

Trp Ala Thr Val Lys Ala Asn Gly Val Ser Phe Ala Tyr Ile Lys Ala
             20                  25                  30

Thr Glu Gly Thr Thr Tyr Thr Asn Pro Ser Phe Ser Ser Gln Tyr Thr
```

```
                     35                  40                  45
Gly Ala Thr Lys Ala Gly Leu Ile Arg Gly Ser Tyr His Phe Ala His
                50                  55                  60

Pro Ser Ser Ser Thr Gly Ala Ala Gln Ala Arg Tyr Phe Val Ala His
            65                  70                  75

Gly Gly Gly Trp Ser Gly Asp Gly Ile Thr Leu Pro Gly Ala Leu Asp
80                  85                  90                  95

Ile Glu Tyr Asn Pro Ser Gly Ala Thr Cys Tyr Gly Leu Ser Thr Ser
                100                 105                 110

Ser Met Val Asn Trp Ile Ala Asp Phe Ser Asn Thr Tyr His Ser Leu
            115                 120                 125

Thr Gly Arg Tyr Pro Val Ile Tyr Thr Thr Ala Asp Trp Trp Arg Thr
        130                 135                 140

Cys Thr Gly Asn Ser Ala Ser Phe Ala Asn Asn Ser Pro Leu Trp Ile
    145                 150                 155

Ala Arg Tyr Ala Ser Thr Ile Gly Thr Leu Pro Ala Gly Trp Ser Tyr
160                 165                 170                 175

Ala Thr Phe Trp Gln Tyr Ala Asp Ser Gly Ser Asn Pro Gly Asp Gln
                180                 185                 190

Asp Tyr Phe Asn Gly Asp Ala Ala Gly Leu Lys Arg Leu Ala Thr Ser
            195                 200                 205

<210> SEQ ID NO 219
<211> LENGTH: 711
<212> TYPE: DNA
<213> ORGANISM: Artificial Sequence
<220> FEATURE:
<223> OTHER INFORMATION: Codon optimised sequence
<220> FEATURE:
<221> NAME/KEY: CDS
<222> LOCATION: (20)..(691)
<220> FEATURE:
<221> NAME/KEY: sig_peptide
<222> LOCATION: (20)..(70)
<220> FEATURE:
<221> NAME/KEY: mat_peptide
<222> LOCATION: (71)..(691)

<400> SEQUENCE: 219
acacaactgg ggatccacc atg cga atc ctc ttg ttc atc gca gtc aca atc       52
                    Met Arg Ile Leu Leu Phe Ile Ala Val Thr Ile
                        -15                 -10 gcg ttg gga gtc cat gcc agg ctc aac ggc atc gat gtc tcg gga tac      100
Ala Leu Gly Val His Ala Arg Leu Asn Gly Ile Asp Val Ser Gly Tyr
    -5                  -1  1               5                  10 cag ccg aac gtc aac tgg gcc acg gtc aaa gcg aac ggc gtg tcc ttc      148
Gln Pro Asn Val Asn Trp Ala Thr Val Lys Ala Asn Gly Val Ser Phe
                15                  20                  25 gcg tac atc aag gca acc gag ggc acc acg tat aca aac ccc tcg ttc      196
Ala Tyr Ile Lys Ala Thr Glu Gly Thr Thr Tyr Thr Asn Pro Ser Phe
            30                  35                  40 tcc tcc cag tac acc gga gca aca aaa gcc gga ttg atc agg ggc tcc      244
Ser Ser Gln Tyr Thr Gly Ala Thr Lys Ala Gly Leu Ile Arg Gly Ser
        45                  50                  55 tac cat ttc gcg cat cct tcg tcg tcc aca ggc gca gca cag gca cga      292
Tyr His Phe Ala His Pro Ser Ser Ser Thr Gly Ala Ala Gln Ala Arg
    60                  65                  70 tac ttc gtg gca cat ggc ggt ggt tgg tcc ggt gat ggt atc acc ttg      340
Tyr Phe Val Ala His Gly Gly Gly Trp Ser Gly Asp Gly Ile Thr Leu
75                  80                  85                  90
```

```
cct ggt gcg ctc gat atc gag tat aac cct tcg ggt gcg aca tgt tac       388
Pro Gly Ala Leu Asp Ile Glu Tyr Asn Pro Ser Gly Ala Thr Cys Tyr
                 95                 100                 105 ggc ctc tcg acc tcg tcc atg gtg aac tgg atc gcc gat ttc tcc aac       436
Gly Leu Ser Thr Ser Ser Met Val Asn Trp Ile Ala Asp Phe Ser Asn
         110                 115                 120 act tat cac tcg ctc aca ggc agg tac ccc gtc att tac acc act gcc       484
Thr Tyr His Ser Leu Thr Gly Arg Tyr Pro Val Ile Tyr Thr Thr Ala
         125                 130                 135 gat tgg tgg cga acc tgt acc ggc aac tcc gca tcc ttc gca aac aac       532
Asp Trp Trp Arg Thr Cys Thr Gly Asn Ser Ala Ser Phe Ala Asn Asn
         140                 145                 150 tcg cct ctc tgg att gcg cgt tac gcg tcg act atc ggt acg ctc cct       580
Ser Pro Leu Trp Ile Ala Arg Tyr Ala Ser Thr Ile Gly Thr Leu Pro
155                 160                 165                 170 gcc gga tgg tcg tac gcg acc ttc tgg cag tat gcg gat tcg ggc tcc       628
Ala Gly Trp Ser Tyr Ala Thr Phe Trp Gln Tyr Ala Asp Ser Gly Ser
                 175                 180                 185 aac cct ggc gat cag gat tac ttc aac ggt gac gca gcg ggt ctc aag       676
Asn Pro Gly Asp Gln Asp Tyr Phe Asn Gly Asp Ala Ala Gly Leu Lys
         190                 195                 200 cgt ctc gcg aca tcg taataagctt ctcgagatct                             711
Arg Leu Ala Thr Ser
         205

<210> SEQ ID NO 220
<211> LENGTH: 224
<212> TYPE: PRT
<213> ORGANISM: Artificial Sequence
<220> FEATURE:
<223> OTHER INFORMATION: Synthetic Construct

<400> SEQUENCE: 220

Met Arg Ile Leu Leu Phe Ile Ala Val Thr Ile Ala Leu Gly Val His
         -15                 -10                 -5

Ala Arg Leu Asn Gly Ile Asp Val Ser Gly Tyr Gln Pro Asn Val Asn
-1  1                5                  10                  15

Trp Ala Thr Val Lys Ala Asn Gly Val Ser Phe Ala Tyr Ile Lys Ala
                 20                  25                  30

Thr Glu Gly Thr Thr Tyr Thr Asn Pro Ser Phe Ser Ser Gln Tyr Thr
             35                  40                  45

Gly Ala Thr Lys Ala Gly Leu Ile Arg Gly Ser Tyr His Phe Ala His
         50                  55                  60

Pro Ser Ser Ser Thr Gly Ala Ala Gln Ala Arg Tyr Phe Val Ala His
65                  70                  75

Gly Gly Gly Trp Ser Gly Asp Gly Ile Thr Leu Pro Gly Ala Leu Asp
80                  85                  90                  95

Ile Glu Tyr Asn Pro Ser Gly Ala Thr Cys Tyr Gly Leu Ser Thr Ser
                 100                 105                 110

Ser Met Val Asn Trp Ile Ala Asp Phe Ser Asn Thr Tyr His Ser Leu
             115                 120                 125

Thr Gly Arg Tyr Pro Val Ile Tyr Thr Thr Ala Asp Trp Trp Arg Thr
         130                 135                 140

Cys Thr Gly Asn Ser Ala Ser Phe Ala Asn Asn Ser Pro Leu Trp Ile
         145                 150                 155

Ala Arg Tyr Ala Ser Thr Ile Gly Thr Leu Pro Ala Gly Trp Ser Tyr
160                 165                 170                 175

Ala Thr Phe Trp Gln Tyr Ala Asp Ser Gly Ser Asn Pro Gly Asp Gln
```

```
                    180                 185                 190

Asp Tyr Phe Asn Gly Asp Ala Ala Gly Leu Lys Arg Leu Ala Thr Ser
            195                 200                 205

<210> SEQ ID NO 221
<211> LENGTH: 207
<212> TYPE: PRT
<213> ORGANISM: Flammulina velutipes
<220> FEATURE:
<221> NAME/KEY: mat_peptide
<222> LOCATION: (1)..(207)

<400> SEQUENCE: 221

Arg Leu Asn Gly Ile Asp Val Ser Gly Tyr Gln Pro Asn Val Asn Trp
1               5                   10                  15

Ala Thr Val Lys Ala Asn Gly Val Ser Phe Ala Tyr Ile Lys Ala Thr
            20                  25                  30

Glu Gly Thr Thr Tyr Thr Asn Pro Ser Phe Ser Ser Gln Tyr Thr Gly
        35                  40                  45

Ala Thr Lys Ala Gly Leu Ile Arg Gly Ser Tyr His Phe Ala His Pro
    50                  55                  60

Ser Ser Ser Thr Gly Ala Ala Gln Ala Arg Tyr Phe Val Ala His Gly
65                  70                  75                  80

Gly Gly Trp Ser Gly Asp Gly Ile Thr Leu Pro Gly Ala Leu Asp Ile
                85                  90                  95

Glu Tyr Asn Pro Ser Gly Ala Thr Cys Tyr Gly Leu Ser Thr Ser Ser
            100                 105                 110

Met Val Asn Trp Ile Ala Asp Phe Ser Asn Thr Tyr His Ser Leu Thr
        115                 120                 125

Gly Arg Tyr Pro Val Ile Tyr Thr Thr Ala Asp Trp Trp Arg Thr Cys
    130                 135                 140

Thr Gly Asn Ser Ala Ser Phe Ala Asn Asn Ser Pro Leu Trp Ile Ala
145                 150                 155                 160

Arg Tyr Ala Ser Thr Ile Gly Thr Leu Pro Ala Gly Trp Ser Tyr Ala
                165                 170                 175

Thr Phe Trp Gln Tyr Ala Asp Ser Gly Ser Asn Pro Gly Asp Gln Asp
            180                 185                 190

Tyr Phe Asn Gly Asp Ala Ala Gly Leu Lys Arg Leu Ala Thr Ser
        195                 200                 205

<210> SEQ ID NO 222
<211> LENGTH: 921
<212> TYPE: DNA
<213> ORGANISM: Deconica coprophila
<220> FEATURE:
<221> NAME/KEY: CDS
<222> LOCATION: (1)..(390)
<220> FEATURE:
<221> NAME/KEY: sig_peptide
<222> LOCATION: (1)..(57)
<220> FEATURE:
<221> NAME/KEY: mat_peptide
<222> LOCATION: (58)..(918)
<220> FEATURE:
<221> NAME/KEY: CDS
<222> LOCATION: (449)..(547)
<220> FEATURE:
<221> NAME/KEY: CDS
<222> LOCATION: (600)..(683)
<220> FEATURE:
<221> NAME/KEY: CDS
<222> LOCATION: (751)..(779)
<220> FEATURE:
```

<221> NAME/KEY: CDS
<222> LOCATION: (843)..(918)

<400> SEQUENCE: 222

| | | |
|---|---|---|
| atg ctt ttc gca acc ttt ctt tgt ctt gcg agc tac gcg ttt gga tcg<br>Met Leu Phe Ala Thr Phe Leu Cys Leu Ala Ser Tyr Ala Phe Gly Ser<br>              -15                  -10                        -5 | | 48 |
| gcc tat gca ctc gtg cat gcc gta gac tct tct tcc ctc gtc tcc acc<br>Ala Tyr Ala Leu Val His Ala Val Asp Ser Ser Ser Leu Val Ser Thr<br>    -1  1                   5                              10 | | 96 |
| gcc act ttc tcc aag gca aag tct gaa ggc ttt acc aag gca gtc atc<br>Ala Thr Phe Ser Lys Ala Lys Ser Glu Gly Phe Thr Lys Ala Val Ile<br>        15                  20                      25 | | 144 |
| cgc ggg tac cag gag gct tgc gga agt ggt gga cgc gtc gac ccc aac<br>Arg Gly Tyr Gln Glu Ala Cys Gly Ser Gly Gly Arg Val Asp Pro Asn<br>30                      35                      40                      45 | | 192 |
| ttt gtt cag aca tac aag aac gca agg gcc gca gga att acc aac atc<br>Phe Val Gln Thr Tyr Lys Asn Ala Arg Ala Ala Gly Ile Thr Asn Ile<br>              50                      55                      60 | | 240 |
| gac acc tac tgg tat cca tgc aat gga tcc ggc aac agc tgc aag tcc<br>Asp Thr Tyr Trp Tyr Pro Cys Asn Gly Ser Gly Asn Ser Cys Lys Ser<br>        65                  70                      75 | | 288 |
| tac gca aag caa att gcg ggt atc agc gcc acg ttc aac gcg cat tcc<br>Tyr Ala Lys Gln Ile Ala Gly Ile Ser Ala Thr Phe Asn Ala His Ser<br>        80                  85                      90 | | 336 |
| atg aag atc ggc agg att tgg atc gac atc gag aaa gat tct att tgc<br>Met Lys Ile Gly Arg Ile Trp Ile Asp Ile Glu Lys Asp Ser Ile Cys<br>    95                    100                      105 | | 384 |
| aac aac gtaagtgggg ttgtcatact tttatctacc cacctctaaa aactgcgtta<br>Asn Asn<br>110 | | 440 |
| ccactcag tgg aac tac ggc act tct gga aat agg gac cat gcc aag aag<br>        Trp Asn Tyr Gly Thr Ser Gly Asn Arg Asp His Ala Lys Lys<br>              115                      120                      125 | | 490 |
| ttg att acc gcc atc aag aac tcc ggc ttc aaa tat gga atc tac agc<br>Leu Ile Thr Ala Ile Lys Asn Ser Gly Phe Lys Tyr Gly Ile Tyr Ser<br>        130                    135                    140 | | 538 |
| tct cct ggg gtaagtgcat ccatgccctg gaacgcgacc gacacagtaa<br>Ser Pro Gly | | 587 |
| ctccctatac ag gaa tgg agc act atc ttc ggc tcc gag agc ttc gac ctc<br>              Glu Trp Ser Thr Ile Phe Gly Ser Glu Ser Phe Asp Leu<br>                  145                      150                    155 | | 638 |
| gat agc ggg gcg cca ctg tgg ttt gcg aca tgg aac aac gtt cag<br>Asp Ser Gly Ala Pro Leu Trp Phe Ala Thr Trp Asn Asn Val Gln<br>        160                    165                    170 | | 683 |
| gtacgcaggt tatgactcgt aactctagga ggtggaatca ctcatacgat atattatgca | | 743 |
| tacacag act ctg aca ctc ggc acg cac ttt gga gg gtaagtctct<br>        Thr Leu Thr Leu Gly Thr His Phe Gly Gly<br>            175                      180 | | 789 |
| aggtttaaag ggttcgatat agatccatag actaatccac gttactctaa tag g tgg<br>                                                                                                                                                                                                     Trp | | 846 |
| aca agc gct cat gga cac cag tac acg gat aag tca gcc tcg ggt caa<br>Thr Ser Ala His Gly His Gln Tyr Thr Asp Lys Ser Ala Ser Gly Gln<br>        185                    190                    195 | | 894 |
| ttt gac ctc aac gtc ttt tcc tcg taa<br>Phe Asp Leu Asn Val Phe Ser Ser<br>200                    205 | | 921 |

<210> SEQ ID NO 223

```
<211> LENGTH: 226
<212> TYPE: PRT
<213> ORGANISM: Deconica coprophila

<400> SEQUENCE: 223

Met Leu Phe Ala Thr Phe Leu Cys Leu Ala Ser Tyr Ala Phe Gly Ser
                -15                 -10                  -5

Ala Tyr Ala Leu Val His Ala Val Asp Ser Ser Leu Val Ser Thr
        -1  1              5                  10

Ala Thr Phe Ser Lys Ala Lys Ser Glu Gly Phe Thr Lys Ala Val Ile
            15                  20                  25

Arg Gly Tyr Gln Glu Ala Cys Gly Ser Gly Gly Arg Val Asp Pro Asn
 30                  35                  40                  45

Phe Val Gln Thr Tyr Lys Asn Ala Arg Ala Ala Gly Ile Thr Asn Ile
                50                  55                  60

Asp Thr Tyr Trp Tyr Pro Cys Asn Gly Ser Gly Asn Ser Cys Lys Ser
                65                  70                  75

Tyr Ala Lys Gln Ile Ala Gly Ile Ser Ala Thr Phe Asn Ala His Ser
            80                  85                  90

Met Lys Ile Gly Arg Ile Trp Ile Asp Ile Glu Lys Asp Ser Ile Cys
 95                 100                 105

Asn Asn Trp Asn Tyr Gly Thr Ser Gly Asn Arg Asp His Ala Lys Lys
110                 115                 120                 125

Leu Ile Thr Ala Ile Lys Asn Ser Gly Phe Lys Tyr Gly Ile Tyr Ser
                130                 135                 140

Ser Pro Gly Glu Trp Ser Thr Ile Phe Gly Ser Glu Ser Phe Asp Leu
            145                 150                 155

Asp Ser Gly Ala Pro Leu Trp Phe Ala Thr Trp Asn Asn Val Gln Thr
            160                 165                 170

Leu Thr Leu Gly Thr His Phe Gly Gly Trp Thr Ser Ala His Gly His
    175                 180                 185

Gln Tyr Thr Asp Lys Ser Ala Ser Gly Gln Phe Asp Leu Asn Val Phe
190                 195                 200                 205

Ser Ser

<210> SEQ ID NO 224
<211> LENGTH: 207
<212> TYPE: PRT
<213> ORGANISM: Deconica coprophila
<220> FEATURE:
<221> NAME/KEY: mat_peptide
<222> LOCATION: (1)..(207)

<400> SEQUENCE: 224

Leu Val His Ala Val Asp Ser Ser Leu Val Ser Thr Ala Thr Phe
 1               5                  10                  15

Ser Lys Ala Lys Ser Glu Gly Phe Thr Lys Ala Val Ile Arg Gly Tyr
            20                  25                  30

Gln Glu Ala Cys Gly Ser Gly Gly Arg Val Asp Pro Asn Phe Val Gln
            35                  40                  45

Thr Tyr Lys Asn Ala Arg Ala Ala Gly Ile Thr Asn Ile Asp Thr Tyr
        50                  55                  60

Trp Tyr Pro Cys Asn Gly Ser Gly Asn Ser Cys Lys Ser Tyr Ala Lys
 65                  70                  75                  80

Gln Ile Ala Gly Ile Ser Ala Thr Phe Asn Ala His Ser Met Lys Ile
                85                  90                  95
```

```
Gly Arg Ile Trp Ile Asp Ile Glu Lys Asp Ser Ile Cys Asn Asn Trp
            100                 105                 110

Asn Tyr Gly Thr Ser Gly Asn Arg Asp His Ala Lys Lys Leu Ile Thr
        115                 120                 125

Ala Ile Lys Asn Ser Gly Phe Lys Tyr Gly Ile Tyr Ser Ser Pro Gly
    130                 135                 140

Glu Trp Ser Thr Ile Phe Gly Ser Glu Ser Phe Asp Leu Asp Ser Gly
145                 150                 155                 160

Ala Pro Leu Trp Phe Ala Thr Trp Asn Asn Val Gln Thr Leu Thr Leu
                165                 170                 175

Gly Thr His Phe Gly Gly Trp Thr Ser Ala His Gly His Gln Tyr Thr
            180                 185                 190

Asp Lys Ser Ala Ser Gly Gln Phe Asp Leu Asn Val Phe Ser Ser
            195                 200                 205

<210> SEQ ID NO 225
<211> LENGTH: 944
<212> TYPE: DNA
<213> ORGANISM: Rhizomucor pusillus
<220> FEATURE:
<221> NAME/KEY: CDS
<222> LOCATION: (1)..(181)
<220> FEATURE:
<221> NAME/KEY: sig_peptide
<222> LOCATION: (1)..(60)
<220> FEATURE:
<221> NAME/KEY: mat_peptide
<222> LOCATION: (61)..(941)
<220> FEATURE:
<221> NAME/KEY: CDS
<222> LOCATION: (242)..(484)
<220> FEATURE:
<221> NAME/KEY: CDS
<222> LOCATION: (555)..(688)
<220> FEATURE:
<221> NAME/KEY: CDS
<222> LOCATION: (757)..(825)
<220> FEATURE:
<221> NAME/KEY: CDS
<222> LOCATION: (885)..(941)

<400> SEQUENCE: 225 atg aag ttt gca ctc cta gta tct gct atc gca ggc ctt gca gca acc         48
Met Lys Phe Ala Leu Leu Val Ser Ala Ile Ala Gly Leu Ala Ala Thr
-20             -15                 -10                  -5 gcc gtc caa gcc tac gaa act ggc gtt gat gtc tct gcc ttg act tcc         96
Ala Val Gln Ala Tyr Glu Thr Gly Val Asp Val Ser Ala Leu Thr Ser
         -1  1               5                  10 acc tcc gcc tgg agc tgt gca aag aaa ctc ggt tac gat cac gct att        144
Thr Ser Ala Trp Ser Cys Ala Lys Lys Leu Gly Tyr Asp His Ala Ile
            15                  20                  25 gtc cgc tgc tac att gag gca tac gga ggc aac cct g caagtatcat          191
Val Arg Cys Tyr Ile Glu Ala Tyr Gly Gly Asn Pro
        30                  35              40 gcatcagaga agacgactac tacgttctag cgtgctaaca atgtactagg gt  ggt         246
                                                         Gly Gly aaa att gac agc aac tgc ttc cag aac tac aag aac gcc aaa gca ggt        294
Lys Ile Asp Ser Asn Cys Phe Gln Asn Tyr Lys Asn Ala Lys Ala Gly
         45                  50                  55 gga ttc acc agc gtt gac att tac atg ttc ccc tgc act ggc cgc tcc        342
Gly Phe Thr Ser Val Asp Ile Tyr Met Phe Pro Cys Thr Gly Arg Ser
 60                  65                  70 aca tgc aag tcg ccc gct gct cag gtc aag gag gtt gtt gac tac gtt        390
Thr Cys Lys Ser Pro Ala Ala Gln Val Lys Glu Val Val Asp Tyr Val
```

```
                  75                  80                  85                  90
ggc tcc aac aag atg act gtt gga cgt ctc tgg ctc gac gtc gaa atc          438
Gly Ser Asn Lys Met Thr Val Gly Arg Leu Trp Leu Asp Val Glu Ile
                 95                 100                 105 gat cct tct gct aac aac tgg cca tcc gcc agt agc gct cgc agc a            484
Asp Pro Ser Ala Asn Asn Trp Pro Ser Ala Ser Ser Ala Arg Ser
        110                 115                 120 gtaagaaaga ggacaagaaa ccaattcagg atgctacaa tgttgctaac attttttatt         544
acttgttaag cc  ttg aag tcc ttc aag tct gct ctt gac tcg act ggc           592
               Leu Lys Ser Phe Lys Ser Ala Leu Asp Ser Thr Gly
                        125                 130 tgg aaa tac ggt atc tat tct tct gct tcc caa tgg tcg cag atc acc          640
Trp Lys Tyr Gly Ile Tyr Ser Ser Ala Ser Gln Trp Ser Gln Ile Thr
135                 140                 145                 150 gga tcc tcc tcc tgg gag ctt gat tcc tcg ttg cca ctt tgg tac gct          688
Gly Ser Ser Ser Trp Glu Leu Asp Ser Ser Leu Pro Leu Trp Tyr Ala
                155                 160                 165 gtaagtagct ctcacgttat tccgtatatt gtgggagaac gtggctgatc tgaatttatt        748 accacaag cac tac gac gct tct ctc agc ttc agc gac ttt tcg cca ttt         798
         His Tyr Asp Ala Ser Leu Ser Phe Ser Asp Phe Ser Pro Phe
                170                 175                 180 ggt ggc tgg act aag cct acc atc aag gtaaatattc aggtcatccg                845
Gly Gly Trp Thr Lys Pro Thr Ile Lys
                185 gtgcttgacg catatgtact caattaaatt gccatttag caa tat gct ggc tct           899
                                           Gln Tyr Ala Gly Ser
                                                       190 gta agc ttc tgc tcc gct ggc tgg gac aag aac tac tat ggc taa              944
Val Ser Phe Cys Ser Ala Gly Trp Asp Lys Asn Tyr Tyr Gly
195                 200                 205
```

<210> SEQ ID NO 226
<211> LENGTH: 228
<212> TYPE: PRT
<213> ORGANISM: Rhizomucor pusillus

<400> SEQUENCE: 226

```
Met Lys Phe Ala Leu Leu Val Ser Ala Ile Ala Gly Leu Ala Ala Thr
-20                 -15                 -10                  -5

Ala Val Gln Ala Tyr Glu Thr Gly Val Asp Val Ser Ala Leu Thr Ser
        -1   1                   5                  10

Thr Ser Ala Trp Ser Cys Ala Lys Lys Leu Gly Tyr Asp His Ala Ile
            15                  20                  25

Val Arg Cys Tyr Ile Glu Ala Tyr Gly Gly Asn Pro Gly Gly Lys Ile
30                  35                  40

Asp Ser Asn Cys Phe Gln Asn Tyr Lys Asn Lys Ala Gly Gly Phe
45                  50                  55                  60

Thr Ser Val Asp Ile Tyr Met Phe Pro Cys Thr Gly Arg Ser Thr Cys
                65                  70                  75

Lys Ser Pro Ala Ala Gln Val Lys Glu Val Asp Tyr Val Gly Ser
            80                  85                  90

Asn Lys Met Thr Val Gly Arg Leu Trp Leu Asp Val Glu Ile Asp Pro
        95                 100                 105

Ser Ala Asn Asn Trp Pro Ser Ala Ser Ser Ala Arg Ser Thr Leu Lys
    110                 115                 120

Ser Phe Lys Ser Ala Leu Asp Ser Thr Gly Trp Lys Tyr Gly Ile Tyr
125                 130                 135                 140
```

```
Ser Ser Ala Ser Gln Trp Ser Gln Ile Thr Gly Ser Ser Ser Trp Glu
            145                 150                 155

Leu Asp Ser Ser Leu Pro Leu Trp Tyr Ala His Tyr Asp Ala Ser Leu
        160                 165                 170

Ser Phe Ser Asp Phe Ser Pro Phe Gly Gly Trp Thr Lys Pro Thr Ile
    175                 180                 185

Lys Gln Tyr Ala Gly Ser Val Ser Phe Cys Ser Ala Gly Trp Asp Lys
190                 195                 200

Asn Tyr Tyr Gly
205

<210> SEQ ID NO 227
<211> LENGTH: 208
<212> TYPE: PRT
<213> ORGANISM: Rhizomucor pusillus
<220> FEATURE:
<221> NAME/KEY: mat_peptide
<222> LOCATION: (1)..(208)

<400> SEQUENCE: 227

Tyr Glu Thr Gly Val Asp Val Ser Ala Leu Thr Ser Thr Ser Ala Trp
1               5                   10                  15

Ser Cys Ala Lys Lys Leu Gly Tyr Asp His Ala Ile Val Arg Cys Tyr
            20                  25                  30

Ile Glu Ala Tyr Gly Gly Asn Pro Gly Gly Lys Ile Asp Ser Asn Cys
        35                  40                  45

Phe Gln Asn Tyr Lys Asn Ala Lys Ala Gly Gly Phe Thr Ser Val Asp
    50                  55                  60

Ile Tyr Met Phe Pro Cys Thr Gly Arg Ser Thr Cys Lys Ser Pro Ala
65                  70                  75                  80

Ala Gln Val Lys Glu Val Val Asp Tyr Val Gly Ser Asn Lys Met Thr
                85                  90                  95

Val Gly Arg Leu Trp Leu Asp Val Glu Ile Asp Pro Ser Ala Asn Asn
            100                 105                 110

Trp Pro Ser Ala Ser Ser Ala Arg Ser Thr Leu Lys Ser Phe Lys Ser
        115                 120                 125

Ala Leu Asp Ser Thr Gly Trp Lys Tyr Gly Ile Tyr Ser Ser Ala Ser
    130                 135                 140

Gln Trp Ser Gln Ile Thr Gly Ser Ser Ser Trp Glu Leu Asp Ser Ser
145                 150                 155                 160

Leu Pro Leu Trp Tyr Ala His Tyr Asp Ala Ser Leu Ser Phe Ser Asp
                165                 170                 175

Phe Ser Pro Phe Gly Gly Trp Thr Lys Pro Thr Ile Lys Gln Tyr Ala
            180                 185                 190

Gly Ser Val Ser Phe Cys Ser Ala Gly Trp Asp Lys Asn Tyr Tyr Gly
        195                 200                 205

<210> SEQ ID NO 228
<211> LENGTH: 909
<212> TYPE: DNA
<213> ORGANISM: Stropharia semiglobata
<220> FEATURE:
<221> NAME/KEY: CDS
<222> LOCATION: (1)..(393)
<220> FEATURE:
<221> NAME/KEY: sig_peptide
<222> LOCATION: (1)..(60)
<220> FEATURE:
<221> NAME/KEY: mat_peptide
```

```
<222> LOCATION: (61)..(906)
<220> FEATURE:
<221> NAME/KEY: CDS
<222> LOCATION: (447)..(545)
<220> FEATURE:
<221> NAME/KEY: CDS
<222> LOCATION: (608)..(691)
<220> FEATURE:
<221> NAME/KEY: CDS
<222> LOCATION: (744)..(772)
<220> FEATURE:
<221> NAME/KEY: CDS
<222> LOCATION: (831)..(906)

<400> SEQUENCE: 228 atg ttc tct ttc gtc aaa gcg ctc ata cta ctc ccg acc ctt gtg acc       48
Met Phe Ser Phe Val Lys Ala Leu Ile Leu Leu Pro Thr Leu Val Thr
-20                 -15                 -10                  -5 tcc gca tac gcc ctt gta tat ggc gta gac tcg tcc act cta gtc tct       96
Ser Ala Tyr Ala Leu Val Tyr Gly Val Asp Ser Ser Thr Leu Val Ser
         -1   1               5                  10 act gca acg tac agt aaa gcc aag agc gag ggc ttc act aag gct atc      144
Thr Ala Thr Tyr Ser Lys Ala Lys Ser Glu Gly Phe Thr Lys Ala Ile
             15                  20                  25 atc cgc ggg tat cag gaa gca tgt ggc agt ggt gga cgc gtc gac ccc      192
Ile Arg Gly Tyr Gln Glu Ala Cys Gly Ser Gly Gly Arg Val Asp Pro
 30                  35                  40 aac ttc gtc gcg acc tac aag aat gca cgg gcc gcg ggt atc acc gat      240
Asn Phe Val Ala Thr Tyr Lys Asn Ala Arg Ala Ala Gly Ile Thr Asp
 45                  50                  55                  60 atc gac atg tac tgg ttc cca tgc aac ggg tcc ggt aac tca tgc aag      288
Ile Asp Met Tyr Trp Phe Pro Cys Asn Gly Ser Gly Asn Ser Cys Lys
                 65                  70                  75 tcg tac gct aag cag ctc tcc gag atc gcg aat gtc ttc agt gcg aat      336
Ser Tyr Ala Lys Gln Leu Ser Glu Ile Ala Asn Val Phe Ser Ala Asn
             80                  85                  90 agc atg aaa att ggg aca att tgg att gat ttt gag aag gat tct ggt      384
Ser Met Lys Ile Gly Thr Ile Trp Ile Asp Phe Glu Lys Asp Ser Gly
         95                 100                 105 tgc aac aac gtgagtttca tggacattat gtccttcata ataaattgac              433
Cys Asn Asn
        110 ggattttatc aag tgg aac tac ggc acc acg ggt aat ctc aac cat gca       482
                Trp Asn Tyr Gly Thr Thr Gly Asn Leu Asn His Ala
                                115                 120 aag gca ctc atc tcc gcg att aaa gcg act ggg ttt aaa ttc ggt atc      530
Lys Ala Leu Ile Ser Ala Ile Lys Ala Thr Gly Phe Lys Phe Gly Ile
                125                 130                 135 tac agc tca cct ggc gtaaggcttt ttacctttcg tatccgcttc atcaagtaa       585
Tyr Ser Ser Pro Gly
140 cttagtccgc gactcgtttt ag gaa tgg ggt acc ctg ttt ggg tcc acc ggg     637
                        Glu Trp Gly Thr Leu Phe Gly Ser Thr Gly
                                145                 150 gta gta ctc gat agc tcg gcc ccc ctt tgg ttc gct acg tgg aac aat      685
Val Val Leu Asp Ser Ser Ala Pro Leu Trp Phe Ala Thr Trp Asn Asn
155                 160                 165                 170 gta aag gtatgtgacc ccgcctacta cagaaataac atctctcaaa gtttaaccat ag    743
Val Lys act ctt acc ttg gga acg cat ttc ggg gg gtaagtgcaa tatatataca         792
Thr Leu Thr Leu Gly Thr His Phe Gly Gly
            175                 180
```

-continued

```
tcgaaatatg ggatattgaa tactgacgtt gcttgaag g tgg act aaa gcc gtt          846
                                            Trp Thr Lys Ala Val
                                                185 ggc cac cag tat aca gat gtg tcc gcc tct ggc caa ttc gac ctc aat          894
Gly His Gln Tyr Thr Asp Val Ser Ala Ser Gly Gln Phe Asp Leu Asn
        190                 195                 200 gtc ttt gca aat taa                                                      909
Val Phe Ala Asn
    205
```

<210> SEQ ID NO 229
<211> LENGTH: 227
<212> TYPE: PRT
<213> ORGANISM: Stropharia semiglobata

<400> SEQUENCE: 229

Met Phe Ser Phe Val Lys Ala Leu Ile Leu Leu Pro Thr Leu Val Thr
-20                 -15                 -10                  -5

Ser Ala Tyr Ala Leu Val Tyr Gly Val Asp Ser Ser Thr Leu Val Ser
            -1   1               5                  10

Thr Ala Thr Tyr Ser Lys Ala Lys Ser Glu Gly Phe Thr Lys Ala Ile
        15                  20                  25

Ile Arg Gly Tyr Gln Glu Ala Cys Gly Ser Gly Gly Arg Val Asp Pro
    30                  35                  40

Asn Phe Val Ala Thr Tyr Lys Asn Ala Arg Ala Ala Gly Ile Thr Asp
45                  50                  55                  60

Ile Asp Met Tyr Trp Phe Pro Cys Asn Gly Ser Gly Asn Ser Cys Lys
                65                  70                  75

Ser Tyr Ala Lys Gln Leu Ser Glu Ile Ala Asn Val Phe Ser Ala Asn
            80                  85                  90

Ser Met Lys Ile Gly Thr Ile Trp Ile Asp Phe Glu Lys Asp Ser Gly
        95                  100                 105

Cys Asn Asn Trp Asn Tyr Gly Thr Thr Gly Asn Leu Asn His Ala Lys
    110                 115                 120

Ala Leu Ile Ser Ala Ile Lys Ala Thr Gly Phe Lys Phe Gly Ile Tyr
125                 130                 135                 140

Ser Ser Pro Gly Glu Trp Gly Thr Leu Phe Gly Ser Thr Gly Val Val
                145                 150                 155

Leu Asp Ser Ser Ala Pro Leu Trp Phe Ala Thr Trp Asn Asn Val Lys
            160                 165                 170

Thr Leu Thr Leu Gly Thr His Phe Gly Gly Trp Thr Lys Ala Val Gly
        175                 180                 185

His Gln Tyr Thr Asp Val Ser Ala Ser Gly Gln Phe Asp Leu Asn Val
    190                 195                 200

Phe Ala Asn
205

<210> SEQ ID NO 230
<211> LENGTH: 207
<212> TYPE: PRT
<213> ORGANISM: Stropharia semiglobata
<220> FEATURE:
<221> NAME/KEY: mat_peptide
<222> LOCATION: (1)..(207)

<400> SEQUENCE: 230

Leu Val Tyr Gly Val Asp Ser Ser Thr Leu Val Ser Thr Ala Thr Tyr
1               5                   10                  15

```
Ser Lys Ala Lys Ser Glu Gly Phe Thr Lys Ala Ile Ile Arg Gly Tyr
         20                  25                  30

Gln Glu Ala Cys Gly Ser Gly Gly Arg Val Asp Pro Asn Phe Val Ala
         35                  40                  45

Thr Tyr Lys Asn Ala Arg Ala Ala Gly Ile Thr Asp Ile Asp Met Tyr
 50                  55                  60

Trp Phe Pro Cys Asn Gly Ser Gly Asn Ser Cys Lys Ser Tyr Ala Lys
 65                  70                  75                  80

Gln Leu Ser Glu Ile Ala Asn Val Phe Ser Ala Asn Ser Met Lys Ile
             85                  90                  95

Gly Thr Ile Trp Ile Asp Phe Glu Lys Asp Ser Gly Cys Asn Asn Trp
            100                 105                 110

Asn Tyr Gly Thr Thr Gly Asn Leu Asn His Ala Lys Ala Leu Ile Ser
        115                 120                 125

Ala Ile Lys Ala Thr Gly Phe Lys Phe Gly Ile Tyr Ser Ser Pro Gly
    130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Val Lys Thr Leu Thr Leu
                165                 170                 175

Gly Thr His Phe Gly Gly Trp Thr Lys Ala Val Gly His Gln Tyr Thr
            180                 185                 190

Asp Val Ser Ala Ser Gly Gln Phe Asp Leu Asn Val Phe Ala Asn
        195                 200                 205

<210> SEQ ID NO 231
<211> LENGTH: 910
<212> TYPE: DNA
<213> ORGANISM: Stropharia semiglobata
<220> FEATURE:
<221> NAME/KEY: CDS
<222> LOCATION: (1)..(393)
<220> FEATURE:
<221> NAME/KEY: sig_peptide
<222> LOCATION: (1)..(60)
<220> FEATURE:
<221> NAME/KEY: mat_peptide
<222> LOCATION: (61)..(907)
<220> FEATURE:
<221> NAME/KEY: CDS
<222> LOCATION: (447)..(545)
<220> FEATURE:
<221> NAME/KEY: CDS
<222> LOCATION: (608)..(691)
<220> FEATURE:
<221> NAME/KEY: CDS
<222> LOCATION: (744)..(772)
<220> FEATURE:
<221> NAME/KEY: CDS
<222> LOCATION: (832)..(907)

<400> SEQUENCE: 231 atg ttc cct ttc gtc aaa acg ctc atc ctc ctc ccg gcc ctt gtg act     48
Met Phe Pro Phe Val Lys Thr Leu Ile Leu Leu Pro Ala Leu Val Thr
-20                 -15                 -10                  -5 tcc gcg tat gcc ctc gta tat ggc gta gac tcg tct acc ttg gtt tct     96
Ser Ala Tyr Ala Leu Val Tyr Gly Val Asp Ser Ser Thr Leu Val Ser
         -1   1                   5                  10 act gca acc tac aag aaa gcc aag agc gag ggc ttc act aag gct atc    144
Thr Ala Thr Tyr Lys Lys Ala Lys Ser Glu Gly Phe Thr Lys Ala Ile
                 15                  20                  25 atc cgc ggg tat cag gaa gca tgt ggc agt ggt gga cgc gtc gac ccc    192
Ile Arg Gly Tyr Gln Glu Ala Cys Gly Ser Gly Gly Arg Val Asp Pro
```

```
                  30                  35                  40
aac ttc gtc gcg acc tac aag aat gca cgg gcc gcg ggt atc acc gat         240
Asn Phe Val Ala Thr Tyr Lys Asn Ala Arg Ala Ala Gly Ile Thr Asp
 45                  50                  55                  60 atc gac atg tac tgg ttc cca tgc aac ggg tcc ggt aac tca tgc aag         288
Ile Asp Met Tyr Trp Phe Pro Cys Asn Gly Ser Gly Asn Ser Cys Lys
                 65                  70                  75 tcg tac gct aag cag ctc tcc gag atc gcg aat gtc ttc agt gcg aat         336
Ser Tyr Ala Lys Gln Leu Ser Glu Ile Ala Asn Val Phe Ser Ala Asn
             80                  85                  90 agc atg aaa att ggg aca att tgg att gat ttt gag aag gat tct ggt         384
Ser Met Lys Ile Gly Thr Ile Trp Ile Asp Phe Glu Lys Asp Ser Gly
         95                 100                 105 tgc aac aac gtgagtttca tggacattat gtccttcata ataaaatgac                 433
Cys Asn Asn
    110 ggattttatc aag tgg aac tac ggc acc acg ggt aat ctc aac cat gca         482
           Trp Asn Tyr Gly Thr Thr Gly Asn Leu Asn His Ala
                       115                 120 aag gca ctc atc tcc gcg att aaa gcg act ggg ttt aaa ttc ggt atc         530
Lys Ala Leu Ile Ser Ala Ile Lys Ala Thr Gly Phe Lys Phe Gly Ile
         125                 130                 135 tac agc tca cct ggc gtaaggcttt ttaccttcg tatccgcttc atcaagttaa         585
Tyr Ser Ser Pro Gly
140 cttagtccgc gactcgtttt ag gaa tgg ggt acc ctg ttt ggg tcc acc ggg       637
                        Glu Trp Gly Thr Leu Phe Gly Ser Thr Gly
                                    145                 150 gta gta ctc gat agc tcg gcc ccc ctt tgg ttc gct acg tgg aac aat        685
Val Val Leu Asp Ser Ser Ala Pro Leu Trp Phe Ala Thr Trp Asn Asn
155                 160                 165                 170 gta aag gtatgtgacc ccgcctacta cagaaataac atctctcaaa gtttaaccat ag      743
Val Lys act ctt acc ttg gga acg cat ttc ggg gg  gtaagtgcaa tatatataca         792
Thr Leu Thr Leu Gly Thr His Phe Gly Gly
         175                 180 tcgaaagatg gaataattaa atactgatct cgcttaaag g tgg act aca gcc gcg     847
                                            Trp Thr Thr Ala Ala
                                                            185 ggt cac cag tac aca gac gtg tct tcc tct ggc caa ttc gac ctc aat         895
Gly His Gln Tyr Thr Asp Val Ser Ser Ser Gly Gln Phe Asp Leu Asn
            190                 195                 200 gtg ttt gca aat taa                                                     910
Val Phe Ala Asn
    205

<210> SEQ ID NO 232
<211> LENGTH: 227
<212> TYPE: PRT
<213> ORGANISM: Stropharia semiglobata

<400> SEQUENCE: 232

Met Phe Pro Phe Val Lys Thr Leu Ile Leu Leu Pro Ala Leu Val Thr
-20                 -15                 -10                  -5

Ser Ala Tyr Ala Leu Val Tyr Gly Val Asp Ser Ser Thr Leu Val Ser
             -1  1                   5                  10

Thr Ala Thr Tyr Lys Lys Ala Lys Ser Glu Gly Phe Thr Lys Ala Ile
         15                  20                  25

Ile Arg Gly Tyr Gln Glu Ala Cys Gly Ser Gly Gly Arg Val Asp Pro
```

```
            30                  35                  40
Asn Phe Val Ala Thr Tyr Lys Asn Ala Arg Ala Ala Gly Ile Thr Asp
 45                  50                  55                  60

Ile Asp Met Tyr Trp Phe Pro Cys Asn Gly Ser Gly Asn Ser Cys Lys
                 65                  70                  75

Ser Tyr Ala Lys Gln Leu Ser Glu Ile Ala Asn Val Phe Ser Ala Asn
                 80                  85                  90

Ser Met Lys Ile Gly Thr Ile Trp Ile Asp Phe Glu Lys Asp Ser Gly
                 95                 100                 105

Cys Asn Asn Trp Asn Tyr Gly Thr Thr Gly Asn Leu Asn His Ala Lys
            110                 115                 120

Ala Leu Ile Ser Ala Ile Lys Ala Thr Gly Phe Lys Phe Gly Ile Tyr
125                 130                 135                 140

Ser Ser Pro Gly Glu Trp Gly Thr Leu Phe Gly Ser Thr Gly Val Val
                145                 150                 155

Leu Asp Ser Ser Ala Pro Leu Trp Phe Ala Thr Trp Asn Asn Val Lys
                160                 165                 170

Thr Leu Thr Leu Gly Thr His Phe Gly Gly Trp Thr Thr Ala Ala Gly
                175                 180                 185

His Gln Tyr Thr Asp Val Ser Ser Gly Gln Phe Asp Leu Asn Val
            190                 195                 200

Phe Ala Asn
205

<210> SEQ ID NO 233
<211> LENGTH: 207
<212> TYPE: PRT
<213> ORGANISM: Stropharia semiglobata
<220> FEATURE:
<221> NAME/KEY: mat_peptide
<222> LOCATION: (1)..(207)

<400> SEQUENCE: 233

Leu Val Tyr Gly Val Asp Ser Ser Thr Leu Val Ser Thr Ala Thr Tyr
 1               5                  10                  15

Lys Lys Ala Lys Ser Glu Gly Phe Thr Lys Ala Ile Ile Arg Gly Tyr
                 20                  25                  30

Gln Glu Ala Cys Gly Ser Gly Gly Arg Val Asp Pro Asn Phe Val Ala
                 35                  40                  45

Thr Tyr Lys Asn Ala Arg Ala Ala Gly Ile Thr Asp Ile Asp Met Tyr
             50                  55                  60

Trp Phe Pro Cys Asn Gly Ser Gly Asn Ser Cys Lys Ser Tyr Ala Lys
65                  70                  75                  80

Gln Leu Ser Glu Ile Ala Asn Val Phe Ser Ala Asn Ser Met Lys Ile
                 85                  90                  95

Gly Thr Ile Trp Ile Asp Phe Glu Lys Asp Ser Gly Cys Asn Asn Trp
                100                 105                 110

Asn Tyr Gly Thr Thr Gly Asn Leu Asn His Ala Lys Ala Leu Ile Ser
            115                 120                 125

Ala Ile Lys Ala Thr Gly Phe Lys Phe Gly Ile Tyr Ser Ser Pro Gly
130                 135                 140

Glu Trp Gly Thr Leu Phe Gly Ser Thr Gly Val Val Leu Asp Ser Ser
145                 150                 155                 160

Ala Pro Leu Trp Phe Ala Thr Trp Asn Asn Val Lys Thr Leu Thr Leu
                165                 170                 175
```

-continued

```
Gly Thr His Phe Gly Gly Trp Thr Thr Ala Ala Gly His Gln Tyr Thr
            180                 185                 190

Asp Val Ser Ser Ser Gly Gln Phe Asp Leu Asn Val Phe Ala Asn
        195                 200                 205

<210> SEQ ID NO 234
<211> LENGTH: 47
<212> TYPE: DNA
<213> ORGANISM: Artificial Sequence
<220> FEATURE:
<223> OTHER INFORMATION: SEQ ID NO: 225 is the forward primer C8VSE-F.

<400> SEQUENCE: 234
acacaactgg ggatccacca tgcttttcgc aacctttctt tgtcttg                47

<210> SEQ ID NO 235
<211> LENGTH: 45
<212> TYPE: DNA
<213> ORGANISM: Artificial Sequence
<220> FEATURE:
<223> OTHER INFORMATION: SEQ ID NO: 226 is the reverse primer C8VSE-R.

<400> SEQUENCE: 235
agatctcgag aagcttacga ggaaaagacg ttgaggtcaa attga                  45
```

POLYPEPTIDES HAVING LYSOZYME ACTIVITY, POLYNUCLEOTIDES ENCODING SAME AND USES AND COMPOSITIONS THEREOF

CROSS-REFERENCE TO RELATED APPLICATIONS

This application is a 35 U.S.C. 371 national application of international application No. PCT/CN2017/117765 filed Dec. 21, 2017, which claims priority or the benefit under 35 U.S.C. 119 of international application Nos. PCT/CN2016/111317 and PCT/CN2017/075978 filed Dec. 21, 2016 and Mar. 8, 2017, respectively. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates animal feed or animal feed additives comprising one or more polypeptides having lysozyme activity. The invention also relates to polypeptides having lysozyme activity, polynucleotides encoding the polypeptides nucleic acid constructs, vectors, and host cells comprising the polynucleotides as well as methods of producing and using the polypeptides.

BACKGROUND OF THE INVENTION

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of unbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have recently been identified in fungi. The lysozyme family GH25 has been found to be structurally unrelated to the other lysozyme families.

Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", J Food Prot. 65(12):1916-23).

Antimicrobial growth promoters (AGP's) have traditionally been used for growth promotion in animals, and probably work by preventing low level infections by pathogens such as *Clostridium perfringens*. However, AGP's are increasingly being banned worldwide and therefore new solutions to promote animal growth but which are not AGP's are of interest.

WO2013/076253 and WO2005/080559 disclose GH25 lysozymes for use in animal feed. However, said lysozymes are not highly active in degrading the cell wall from *Micrococcus lysodeikticus* (a typical lysozyme activity assay) and more active lysozymes would be desired. The object of the present invention is to provide new and more active lysozymes which could be suitable for animal health.

SUMMARY OF THE INVENTION

The invention relates to polypeptides which have improved lysozyme activity against the peptidoglycans found in the cell walls of *Micrococcus lysodeikticus*. The lysozymes of the invention are all GH25 lysozymes and all have improved ability to lyse bacterial cell walls of *Micrococcus lysodeikticus*, thereby rendering them suitable for use in animal feed to improve the animal health. The lysozymes of the invention have improved activity compared to the lysozyme described in WO2013/076253 (it is described herein as SEQ ID NO 159). A large subset of the GH25 lysozymes have surprisingly been found to furthermore have lysozyme activity against *Lactobacillus johnsonii*. *Lactobacillus johnsonii* is an important bacterium of the intestinal flora of animals. Without being bound to a particular theory, it is believed that removal of dead *Lactobacillus johnsonii* cells from the intestinal flora, by means of enzymatic lyses of the partially degraded bacterial cell wall, to be an important contributor to intestinal health of an animal.

An aspect of the invention is directed to an isolated GH25 polypeptide having lysozyme activity selected from the group consisting of:

(a) a polypeptide having at least 80% sequence identity to the polypeptide of SEQ ID NO: 3;
(b) a polypeptide having at least 84% sequence identity to the polypeptide of SEQ ID NO: 6;
(c) a polypeptide having at least 80% sequence identity to the polypeptide of SEQ ID NO: 9;
(d) a polypeptide having at least 80% sequence identity to the polypeptide of SEQ ID NO: 12;
(e) a polypeptide having at least 80% sequence identity to the polypeptide of SEQ ID NO: 15;
(f) a polypeptide having at least 80% sequence identity to the polypeptide of SEQ ID NO: 18;
(g) a polypeptide having at least 80% sequence identity to the polypeptide of SEQ ID NO: 21;
(h) a polypeptide having at least 80% sequence identity to the polypeptide of SEQ ID NO: 24;
(i) a polypeptide having at least 80% sequence identity to the polypeptide of SEQ ID NO: 27;
(j) a polypeptide having at least 84% sequence identity to the polypeptide of SEQ ID NO: 30;
(k) a polypeptide having at least 80% sequence identity to the polypeptide of SEQ ID NO: 33;
(l) a polypeptide having at least 80% sequence identity to the polypeptide of SEQ ID NO: 36;
(m) a polypeptide having at least 84% sequence identity to the polypeptide of SEQ ID NO: 39;

(n) a polypeptide having at least 80% sequence identity to the polypeptide of SEQ ID NO: 42;
(o) a polypeptide having at least 80% sequence identity to the polypeptide of SEQ ID NO: 45;
(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

A further aspect of the invention is directed to an isolated GH25 polypeptide having lysozyme activity selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(ac) a polypeptide having at least 90% sequence identity to the polypeptide of SEQ ID NO: 89;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(aq) a polypeptide having at least 90% sequence identity to the polypeptide of SEQ ID NO: 131;
(as) a polypeptide having at least 90% sequence identity to the polypeptide of SEQ ID NO: 137;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(ba) a polypeptide having at least 90% sequence identity to the polypeptide of SEQ ID NO: 221;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

As stated, the polypeptides of the invention have improved lysozyme activity. An interesting embodiment of the invention relates to the polypeptides of the invention having improved lysozyme activity a) compared to the lysozyme activity of hen eggwhite lysozyme (HEWL) or b) compared to the lysozyme activity of SEQ ID NO: 159 as determined by any one of i) Method for the Determination of Lysozyme Activity Against *Micrococcus lysodeikticus* and ii) Method for the Determination of Lysozyme Activity Against *Lactobacillus johnsonii*.

A further aspect of the invention is directed to a method of hydrolysing peptidoglycan in bacterial cell walls comprising treating bacterial cells with one or more GH25 polypeptides having lysozyme activity, wherein the polypeptide is as defined above.

The invention is furthermore directed to a method of increasing the digestibility of peptidoglycans in animal feed comprising the use of a polypeptide as described herein and to an animal feed additive or animal feed comprising the polypeptide as defined herein. A related aspect of the invention is directed to a zootechnical additive for use in feed for poultry or swine, said additive comprising the polypeptide as defined herein.

An aspect of the invention is directed to a method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide as defined by the invention.

An aspect of the invention is directed to a method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

An aspect of the invention is directed to a method of promoting the elimination of dead *Lactobacillus johnsonii* cells, or cell wall debris therefrom, from the digestive tract of an animal comprising feeding said animal a polypeptide or source of a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119 or a polypeptide or source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

The invention also relates to a granule comprising one or more GH25 polypeptides as described above. The invention further relates to an isolated polypeptide having lysozyme activity as described in the claims.

The invention further relates to compositions comprising the polypeptide of the invention, such as animal feed additives or animal feed; use of the polypeptide of the invention in animal feed, in animal feed additives, in the preparation of a composition for use in animal feed, for improving one or more performance parameters in an animal; and isolated polynucleotides encoding the polypeptides of the invention, recombinant host cells and method of producing the polypeptide of the invention.

Overview of Sequence Listing

SEQ ID NO: 1 is the cDNA sequence of a GH25 lysozyme as isolated from *Sporormia fimetaria*.

SEQ ID NO: 2 is the amino acid sequence as deduced from SEQ ID NO: 1.

SEQ ID NO: 3 is the amino acid sequence of the mature GH25 lysozyme from *Sporormia fimetaria*.

SEQ ID NO: 4 is the cDNA sequence of a GH25 lysozyme as isolated from *Poronia punctata*.

SEQ ID NO: 5 is the amino acid sequence as deduced from SEQ ID NO: 4.

SEQ ID NO: 6 is the amino acid sequence of the mature GH25 lysozyme from *Poronia punctata*.

SEQ ID NO: 7 is the cDNA sequence of a GH25 lysozyme as isolated from *Poronia punctata*.

SEQ ID NO: 8 is the amino acid sequence as deduced from SEQ ID NO: 7.

SEQ ID NO: 9 is the amino acid sequence of the mature GH25 lysozyme from *Poronia punctata*.

SEQ ID NO: 10 is the cDNA sequence of a GH25 lysozyme as isolated from *Lecanicillium* sp. WMM742.

SEQ ID NO: 11 is the amino acid sequence as deduced from SEQ ID NO: 10.

SEQ ID NO: 12 is the amino acid sequence of the mature GH25 lysozyme from *Lecanicillium* sp. WMM742.

SEQ ID NO: 13 is the cDNA sequence of a GH25 lysozyme as isolated from *Lecanicillium* sp. WMM742.

SEQ ID NO: 14 is the amino acid sequence as deduced from SEQ ID NO: 13.

SEQ ID NO: 15 is the amino acid sequence of the mature GH25 lysozyme from *Lecanicillium* sp. WMM742.

SEQ ID NO: 16 is the cDNA sequence of a GH25 lysozyme as isolated from *Onygena equina*.

SEQ ID NO: 17 is the amino acid sequence as deduced from SEQ ID NO: 16.

SEQ ID NO: 18 is the amino acid sequence of the mature GH25 lysozyme from *Onygena equina*.

SEQ ID NO: 19 is the cDNA sequence of a GH25 lysozyme as isolated from *Purpureocillium lilacinum*.

SEQ ID NO: 20 is the amino acid sequence as deduced from SEQ ID NO: 19.

SEQ ID NO: 21 is the amino acid sequence of the mature GH25 lysozyme from *Purpureocillium lilacinum*.

SEQ ID NO: 22 is the cDNA sequence of a GH25 lysozyme as isolated from *Trichobolus zukalii*.

SEQ ID NO: 23 is the amino acid sequence as deduced from SEQ ID NO: 22.

SEQ ID NO: 24 is the amino acid sequence of the mature GH25 lysozyme from *Trichobolus zukalii*.

SEQ ID NO: 25 is the cDNA sequence of a GH25 lysozyme as isolated from *Penicillium citrinum*.

SEQ ID NO: 26 is the amino acid sequence as deduced from SEQ ID NO: 25.

SEQ ID NO: 27 is the amino acid sequence of the mature GH25 lysozyme from *Penicillium citrinum*.

SEQ ID NO: 28 is the cDNA sequence of a GH25 lysozyme as isolated from *Cladorrhinum bulbillosum*.

SEQ ID NO: 29 is the amino acid sequence as deduced from SEQ ID NO: 28.

SEQ ID NO: 30 is the amino acid sequence of the mature GH25 lysozyme from *Cladorrhinum bulbillosum*.

SEQ ID NO: 31 is the cDNA sequence of a GH25 lysozyme as isolated from *Umbelopsis westeae*.

SEQ ID NO: 32 is the amino acid sequence as deduced from SEQ ID NO: 31.

SEQ ID NO: 33 is the amino acid sequence of the mature GH25 lysozyme from *Umbelopsis westeae*.

SEQ ID NO: 34 is the cDNA sequence of a GH25 lysozyme as isolated from *Zygomycetes* sp. XZ2655.

SEQ ID NO: 35 is the amino acid sequence as deduced from SEQ ID NO: 34.

SEQ ID NO: 36 is the amino acid sequence of the mature GH25 lysozyme from *Zygomycetes* sp. XZ2655.

SEQ ID NO: 37 is the cDNA sequence of a GH25 lysozyme as isolated from *Chaetomium cupreum*.

SEQ ID NO: 38 is the amino acid sequence as deduced from SEQ ID NO: 37.

SEQ ID NO: 39 is the amino acid sequence of the mature GH25 lysozyme from *Chaetomium cupreum*.

SEQ ID NO: 40 is the cDNA sequence of a GH25 lysozyme as isolated from *Cordyceps cardinalis*.

SEQ ID NO: 41 is the amino acid sequence as deduced from SEQ ID NO: 40.

SEQ ID NO: 42 is the amino acid sequence of the mature GH25 lysozyme from *Cordyceps cardinalis*.

SEQ ID NO: 43 is the cDNA sequence of a GH25 lysozyme as isolated from *Penicillium* sp. 'qii'.

SEQ ID NO: 44 is the amino acid sequence as deduced from SEQ ID NO: 43.

SEQ ID NO: 45 is the amino acid sequence of the mature GH25 lysozyme from *Penicillium* sp. 'qii'.

SEQ ID NO: 46 is the cDNA sequence of a GH25 lysozyme as isolated from *Aspergillus* sp. nov. XZ2609.

SEQ ID NO: 47 is the amino acid sequence as deduced from SEQ ID NO: 46.

SEQ ID NO: 48 is the amino acid sequence of the mature GH25 lysozyme from *Aspergillus* sp. nov. XZ2609.

SEQ ID NO: 49 is the cDNA sequence of a GH25 lysozyme as isolated from *Paecilomyces* sp. XZ2658.

SEQ ID NO: 50 is the amino acid sequence as deduced from SEQ ID NO: 49.

SEQ ID NO: 51 is the amino acid sequence of the mature GH25 lysozyme from *Paecilomyces* sp. XZ2658.

SEQ ID NO: 52 is the cDNA sequence of a GH25 lysozyme as isolated from *Paecilomyces* sp. XZ2658.

SEQ ID NO: 53 is the amino acid sequence as deduced from SEQ ID NO: 52.

SEQ ID NO: 54 is the amino acid sequence of the mature GH25 lysozyme from *Paecilomyces* sp. XZ2658.

SEQ ID NO: 55 is the cDNA sequence of a GH25 lysozyme as isolated from *Rhizomucor pusillus*.

SEQ ID NO: 56 is the amino acid sequence as deduced from SEQ ID NO: 55.

SEQ ID NO: 57 is the amino acid sequence of the mature GH25 lysozyme from *Rhizomucor pusillus*.

SEQ ID NO: 58 is the cDNA sequence of a GH25 lysozyme as isolated from *Pycnidiophora* cf. *dispera*.

SEQ ID NO: 59 is the amino acid sequence as deduced from SEQ ID NO: 58.

SEQ ID NO: 60 is the amino acid sequence of the mature GH25 lysozyme from *Pycnidiophora* cf. *dispera*.

SEQ ID NO: 61 is the cDNA sequence of a GH25 lysozyme as isolated from *Thermomucor indicae-seudaticae*.

SEQ ID NO: 62 is the amino acid sequence as deduced from SEQ ID NO: 61.

SEQ ID NO: 63 is the amino acid sequence of the mature GH25 lysozyme from *Thermomucor indicae-seudaticae*.

SEQ ID NO: 64 is the cDNA sequence of a GH25 lysozyme as isolated from *Isaria farinosa*.

SEQ ID NO: 65 is the amino acid sequence as deduced from SEQ ID NO: 64.

SEQ ID NO: 66 is the amino acid sequence of the mature GH25 lysozyme from *Isaria farinosa*.

SEQ ID NO: 67 is the cDNA sequence of a GH25 lysozyme as isolated from *Lecanicillium* sp. WMM742.

SEQ ID NO: 68 is the amino acid sequence as deduced from SEQ ID NO: 67.

SEQ ID NO: 69 is the amino acid sequence of the mature GH25 lysozyme from *Lecanicillium* sp. WMM742.

SEQ ID NO: 70 is the cDNA sequence of a GH25 lysozyme as isolated from *Zopfiella* sp. t180-6.

SEQ ID NO: 71 is the amino acid sequence as deduced from SEQ ID NO: 70.

SEQ ID NO: 72 is the amino acid sequence of the mature GH25 lysozyme from *Zopfiella* sp. t180-6.

SEQ ID NO: 73 is the cDNA sequence of a GH25 lysozyme as isolated from *Malbranchea flava*.

SEQ ID NO: 74 is the amino acid sequence as deduced from SEQ ID NO: 73.

SEQ ID NO: 75 is the amino acid sequence of the mature GH25 lysozyme from *Malbranchea flava*.

SEQ ID NO: 76 is the cDNA sequence of a GH25 lysozyme as isolated from *Hypholoma polytrichi*.

SEQ ID NO: 77 is the amino acid sequence as deduced from SEQ ID NO: 76.

SEQ ID NO: 78 is the codon optimised DNA the GH25 lysozyme as isolated from *Hypholoma polytrichi*.

SEQ ID NO: 79 is the amino acid sequence as deduced from SEQ ID NO: 78.

SEQ ID NO: 80 is the amino acid sequence of the mature GH25 lysozyme from *Hypholoma polytrichi*.

SEQ ID NO: 81 is the cDNA sequence of a GH25 lysozyme as isolated from *Aspergillus deflectus*.

SEQ ID NO: 82 is the amino acid sequence as deduced from SEQ ID NO: 81.

SEQ ID NO: 83 is the amino acid sequence of the mature GH25 lysozyme from *Aspergillus deflectus*.

SEQ ID NO: 84 is the cDNA sequence of a GH25 lysozyme as isolated from *Ascobolus stictoideus*.

SEQ ID NO: 85 is the amino acid sequence as deduced from SEQ ID NO: 84.

SEQ ID NO: 86 is the amino acid sequence of the mature GH25 lysozyme from *Ascobolus stictoideus*.

SEQ ID NO: 87 is the cDNA sequence of a GH25 lysozyme as isolated from *Coniochaeta* sp.

SEQ ID NO: 88 is the amino acid sequence as deduced from SEQ ID NO: 87.

SEQ ID NO: 89 is the amino acid sequence of the mature GH25 lysozyme from *Coniochaeta* sp.

SEQ ID NO: 90 is the cDNA sequence of a GH25 lysozyme as isolated from *Daldinia fissa*.

SEQ ID NO: 91 is the amino acid sequence as deduced from SEQ ID NO: 90.

SEQ ID NO: 92 is the amino acid sequence of the mature GH25 lysozyme from *Daldinia fissa*.

SEQ ID NO: 93 is the cDNA sequence of a GH25 lysozyme as isolated from *Rosellinia* sp.

SEQ ID NO: 94 is the amino acid sequence as deduced from SEQ ID NO: 93.

SEQ ID NO: 95 is the amino acid sequence of the mature GH25 lysozyme from *Rosellinia* sp.

SEQ ID NO: 96 is the cDNA sequence of a GH25 lysozyme as isolated from *Ascobolus* sp. ZY179.

SEQ ID NO: 97 is the amino acid sequence as deduced from SEQ ID NO: 96.

SEQ ID NO: 98 is the amino acid sequence of the mature GH25 lysozyme from *Ascobolus* sp. ZY179.

SEQ ID NO: 99 is the cDNA sequence of a GH25 lysozyme as isolated from *Curreya* sp. XZ2623.

SEQ ID NO: 100 is the amino acid sequence as deduced from SEQ ID NO: 99.

SEQ ID NO: 101 is the amino acid sequence of the mature GH25 lysozyme from *Curreya* sp. XZ2623.

SEQ ID NO: 102 is the cDNA sequence of a GH25 lysozyme as isolated from *Coniothyrium* sp.

SEQ ID NO: 103 is the amino acid sequence as deduced from SEQ ID NO: 102.

SEQ ID NO: 104 is the amino acid sequence of the mature GH25 lysozyme from *Coniothyrium* sp.

SEQ ID NO: 105 is the cDNA sequence of a GH25 lysozyme as isolated from *Hypoxylon* sp.

SEQ ID NO: 106 is the amino acid sequence as deduced from SEQ ID NO: 105.

SEQ ID NO: 107 is the amino acid sequence of the mature GH25 lysozyme from *Hypoxylon* sp.

SEQ ID NO: 108 is the cDNA sequence of a GH25 lysozyme as isolated from *Xylariaceae* sp. 1653h.

SEQ ID NO: 109 is the amino acid sequence as deduced from SEQ ID NO: 108.

SEQ ID NO: 110 is the amino acid sequence of the mature GH25 lysozyme from *Xylariaceae* sp. 1653h.

SEQ ID NO: 111 is the cDNA sequence of a GH25 lysozyme as isolated from *Hypoxylon* sp.

SEQ ID NO: 112 is the amino acid sequence as deduced from SEQ ID NO: 111.

SEQ ID NO: 113 is the amino acid sequence of the mature GH25 lysozyme from *Hypoxylon* sp.

SEQ ID NO: 114 is the cDNA sequence of a GH25 lysozyme as isolated from *Yunnania penicillata*.

SEQ ID NO: 115 is the amino acid sequence as deduced from SEQ ID NO: 114.

SEQ ID NO: 116 is the amino acid sequence of the mature GH25 lysozyme from *Yunnania penicillata*.

SEQ ID NO: 117 is the cDNA sequence of a GH25 lysozyme as isolated from *Engyodontium album*.

SEQ ID NO: 118 is the amino acid sequence as deduced from SEQ ID NO: 117.

SEQ ID NO: 119 is the amino acid sequence of the mature GH25 lysozyme from *Engyodontium album*.

SEQ ID NO: 120 is the cDNA sequence of a GH25 lysozyme as isolated from *Metapochonia bulbillosa*.

SEQ ID NO: 121 is the amino acid sequence as deduced from SEQ ID NO: 120.

SEQ ID NO: 122 is the amino acid sequence of the mature GH25 lysozyme from *Metapochonia bulbillosa*.

SEQ ID NO: 123 is the cDNA sequence of a GH25 lysozyme as isolated from *Hamigera paravellanea*.

SEQ ID NO: 124 is the amino acid sequence as deduced from SEQ ID NO: 123.

SEQ ID NO: 125 is the amino acid sequence of the mature GH25 lysozyme from *Hamigera paravellanea*.

SEQ ID NO: 126 is the cDNA sequence of a GH25 lysozyme as isolated from *Metarhizium iadini*.

SEQ ID NO: 127 is the amino acid sequence as deduced from SEQ ID NO: 126.

SEQ ID NO: 128 is the amino acid sequence of the mature GH25 lysozyme from *Metarhizium iadini*.

SEQ ID NO: 129 is the cDNA sequence of a GH25 lysozyme as isolated from *Thermoascus aurantiacus*.

SEQ ID NO: 130 is the amino acid sequence as deduced from SEQ ID NO: 129.

SEQ ID NO: 131 is the amino acid sequence of the mature GH25 lysozyme from *Thermoascus aurantiacus*.

SEQ ID NO: 132 is the cDNA sequence of a GH25 lysozyme as isolated from *Clonostachys rossmaniae*.

SEQ ID NO: 133 is the amino acid sequence as deduced from SEQ ID NO: 132.

SEQ ID NO: 134 is the amino acid sequence of the mature GH25 lysozyme from *Clonostachys rossmaniae*.

SEQ ID NO: 135 is the cDNA sequence of a GH25 lysozyme as isolated from *Simplicillium obclavatum*.

SEQ ID NO: 136 is the amino acid sequence as deduced from SEQ ID NO: 135.

SEQ ID NO: 137 is the amino acid sequence of the mature GH25 lysozyme from *Simplicillium obclavatum*.

SEQ ID NO: 138 is the cDNA sequence of a GH25 lysozyme as isolated from *Aspergillus inflatus*.

SEQ ID NO: 139 is the amino acid sequence as deduced from SEQ ID NO: 138.

SEQ ID NO: 140 is the amino acid sequence of the mature GH25 lysozyme from *Aspergillus inflatus*.

SEQ ID NO: 141 is the cDNA sequence of a GH25 lysozyme as isolated from *Paracremonium inflatum*.

SEQ ID NO: 142 is the amino acid sequence as deduced from SEQ ID NO: 141.

SEQ ID NO: 143 is the amino acid sequence of the mature GH25 lysozyme from *Paracremonium inflatum*.

SEQ ID NO: 144 is the cDNA sequence of a GH25 lysozyme as isolated from *Westerdykella* sp.

SEQ ID NO: 145 is the amino acid sequence as deduced from SEQ ID NO: 144.

SEQ ID NO: 146 is the amino acid sequence of the mature GH25 lysozyme from *Westerdykella* sp.

SEQ ID NO: 147 is the cDNA sequence of a GH25 lysozyme as isolated from *Stropharia semiglobata*.

SEQ ID NO: 148 is the amino acid sequence as deduced from SEQ ID NO: 147.

SEQ ID NO: 149 is the amino acid sequence of the mature GH25 lysozyme from *Stropharia semiglobata*.

SEQ ID NO: 150 is the cDNA sequence of a GH25 lysozyme as isolated from *Stropharia semiglobata*.

SEQ ID NO: 151 is the amino acid sequence as deduced from SEQ ID NO: 150.

SEQ ID NO: 152 is the amino acid sequence of the mature GH25 lysozyme from *Stropharia semiglobata*.

SEQ ID NO: 153 is the cDNA sequence of a GH25 lysozyme as isolated from *Stropharia semiglobata*.

SEQ ID NO: 154 is the amino acid sequence as deduced from SEQ ID NO: 153.

SEQ ID NO: 155 is the amino acid sequence of the mature GH25 lysozyme from *Stropharia semiglobata*.

SEQ ID NO: 156 is the cDNA sequence of a GH25 lysozyme as isolated from *Gelasinospora cratophora*.

SEQ ID NO: 157 is the amino acid sequence as deduced from SEQ ID NO: 156.

SEQ ID NO: 158 is the amino acid sequence of the mature GH25 lysozyme from *Gelasinospora cratophora*.

SEQ ID NO: 159 is the mature amino acid sequence of a wild type GH25 lysozyme from *Acremonium alcalophilum* as described in WO 2013/076253.

SEQ ID NO: 160 is the conserved motif YKNA.

SEQ ID NO: 161 is the conserved motif FGGW[S/T].

SEQ ID NO: 162 is the forward primer C8VRJ-F.

SEQ ID NO: 163 is the reverse primer C8VRJ-R.

SEQ ID NO: 164 is the forward primer C8VRQ-F.

SEQ ID NO: 165 is the reverse primer C8VRQ-R.

SEQ ID NO: 166 is the forward primer C8VS9-F.

SEQ ID NO: 167 is the reverse primer C8VS9-R.

SEQ ID NO: 168 is the forward primer C8VSA-F.

SEQ ID NO: 169 is the reverse primer C8VSA-R.

SEQ ID NO: 170 is the forward primer C8VSC-F.

SEQ ID NO: 171 is the reverse primer C8VSC-R.

SEQ ID NO: 172 is the forward primer C8VRT-F.

SEQ ID NO: 173 is the reverse primer C8VRT-R.

SEQ ID NO: 174 is the forward primer C8VS8-F.

SEQ ID NO: 175 is the reverse primer C8VS8-R.

SEQ ID NO: 176 is the forward primer C122P5-F.

SEQ ID NO: 177 is the reverse primer C122P5-R.

SEQ ID NO: 178 is the forward primer C6ZGC-F.

SEQ ID NO: 179 is the reverse primer C6ZGC-R.

SEQ ID NO: 180 is the forward primer C6ZG7-FF.

SEQ ID NO: 181 is the reverse primer C6ZG7-R.

SEQ ID NO: 182 is the forward primer C122PC-F.

SEQ ID NO: 183 is the reverse primer C122PC-R.

SEQ ID NO: 184 is the forward primer C122PA-F.

SEQ ID NO: 185 is the reverse primer C122PA-R.

SEQ ID NO: 186 is the forward primer C122P9-F.

SEQ ID NO: 187 is the reverse primer C122P9-R.

SEQ ID NO: 188 is the forward primer WIN1054-F.

SEQ ID NO: 189 is the reverse primer WIN1054-R.

SEQ ID NO: 190 is the forward primer WIN1065-F.

SEQ ID NO: 191 is the reverse primer WIN1065-R.

SEQ ID NO: 192 is the forward primer WIN1057-F.

SEQ ID NO: 193 is the reverse primer WIN1057-R.

SEQ ID NO: 194 is the forward primer WIN1058-F.

SEQ ID NO: 195 is the reverse primer WIN1058-R.

SEQ ID NO: 196 is the forward primer KKSCO132-F.
SEQ ID NO: 197 is the reverse primer KKSC0132-R.
SEQ ID NO: 198 is the forward primer KKSCO133-F.
SEQ ID NO: 199 is the reverse primer KKSC0133-R.
SEQ ID NO: 200 is the forward primer KKSC0311-F.
SEQ ID NO: 201 is the reverse primer KKSC0311-R.
SEQ ID NO: 202 is the forward primer KKSC0314-F.
SEQ ID NO: 203 is the reverse primer KKSC0314-R.
SEQ ID NO: 204 is the forward primer KKSC0862-F.
SEQ ID NO: 205 is the reverse primer KKSC0862-R.
SEQ ID NO: 206 is the forward primer KKSC0819-F.
SEQ ID NO: 207 is the reverse primer KKSC0819-R.
SEQ ID NO: 208 is the forward primer KKSC0317-F.
SEQ ID NO: 209 is the reverse primer KKSC0317-F.
SEQ ID NO: 210 is forward primer F1.
SEQ ID NO: 211 is reverse primer F1.
SEQ ID NO: 212 is forward primer F3.
SEQ ID NO: 213 is reverse primer F3.
SEQ ID NO: 214 is primer bind forward.
SEQ ID NO: 215 is primer bind reverse.
SEQ ID NO: 216 is the synthetic DNA construct of plasmid pDAu770.
SEQ ID NO: 217 is the cDNA sequence of a GH25 lysozyme as isolated from *Flammulina velutipes*.
SEQ ID NO: 218 is the amino acid sequence as deduced from SEQ ID NO: 217.
SEQ ID NO: 219 is the codon optimised DNA the GH25 lysozyme as isolated from *Flammulina velutipes*.
SEQ ID NO: 220 is the amino acid sequence as deduced from SEQ ID NO: 219.
SEQ ID NO: 221 is the amino acid sequence of the mature GH25 lysozyme from *Flammulina velutipes*.
SEQ ID NO: 222 is the cDNA sequence of a GH25 lysozyme as isolated from *Deconica coprophila*.
SEQ ID NO: 223 is the amino acid sequence as deduced from SEQ ID NO: 222.
SEQ ID NO: 224 is the amino acid sequence of the mature GH25 lysozyme from *Deconica coprophila*.
SEQ ID NO: 225 is the cDNA sequence of a GH25 lysozyme as isolated from *Rhizomucor pusillus*.
SEQ ID NO: 226 is the amino acid sequence as deduced from SEQ ID NO: 225.
SEQ ID NO: 227 is the amino acid sequence of the mature GH25 lysozyme from *Rhizomucor pusillus*.
SEQ ID NO: 228 is the cDNA sequence of a GH25 lysozyme as isolated from *Stropharia semiglobata*.
SEQ ID NO: 229 is the amino acid sequence as deduced from SEQ ID NO: 228.
SEQ ID NO: 230 is the amino acid sequence of the mature GH25 lysozyme from *Stropharia semiglobata*.
SEQ ID NO: 231 is the cDNA sequence of a GH25 lysozyme as isolated from *Stropharia semiglobata*.
SEQ ID NO: 232 is the amino acid sequence as deduced from SEQ ID NO: 231.
SEQ ID NO: 233 is the amino acid sequence of the mature GH25 lysozyme from *Stropharia semiglobata*.
SEQ ID NO: 234 is the forward primer C8VSE-F.
SEQ ID NO: 235 is the reverse primer C8VSE-R.

The top panel represents the locus amy2 with the integration of the FLP landing pad composed of FRT-F and FRT-F3 the FLPase recognition site, as well as the amdS (acetamide) selection marker and the FLPase expression cassette. A split PyrG marker has been used and at the amy2 locus the 5' end of the pyrG marker is inserted.

The middle panel represents the transforming DNA, in particular the region that is integrated at the FLP landing pad by site specific recombination mediated by FLPase. The plasmid or PCR product must contain FRT-F and F3 sites as well as the remaining 3' part of the pyrG marker.

The bottom panel represents the resulting amy2 locus after site specific integration of the transformaing DNA between the FRT sites. The amdS and FLP cassettes have been exchanged with the GOI expression cassette and the 3' part of the pyrG marker reconstituting a fully functional selection marker.

Figure 3:
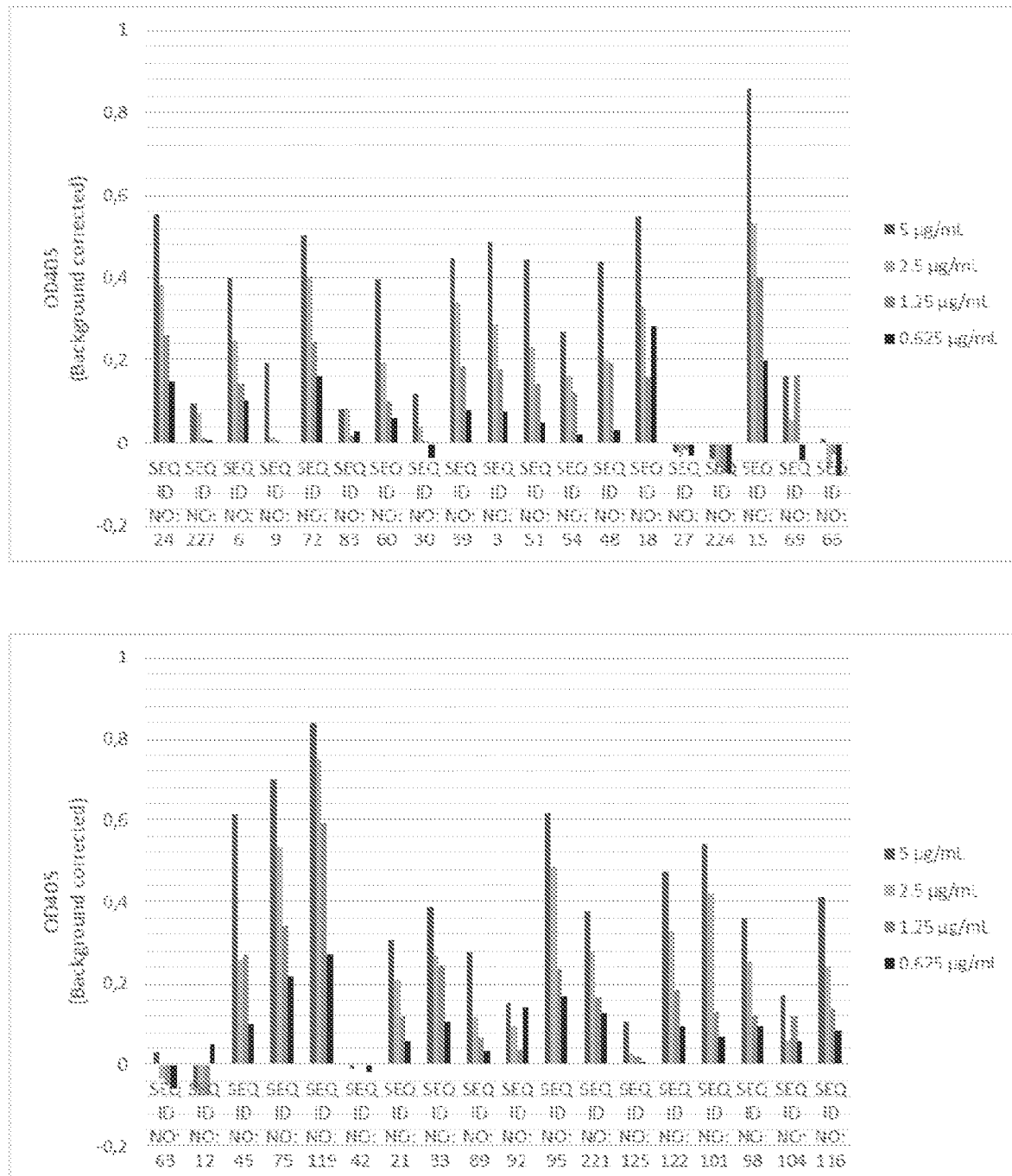
Figure 4:
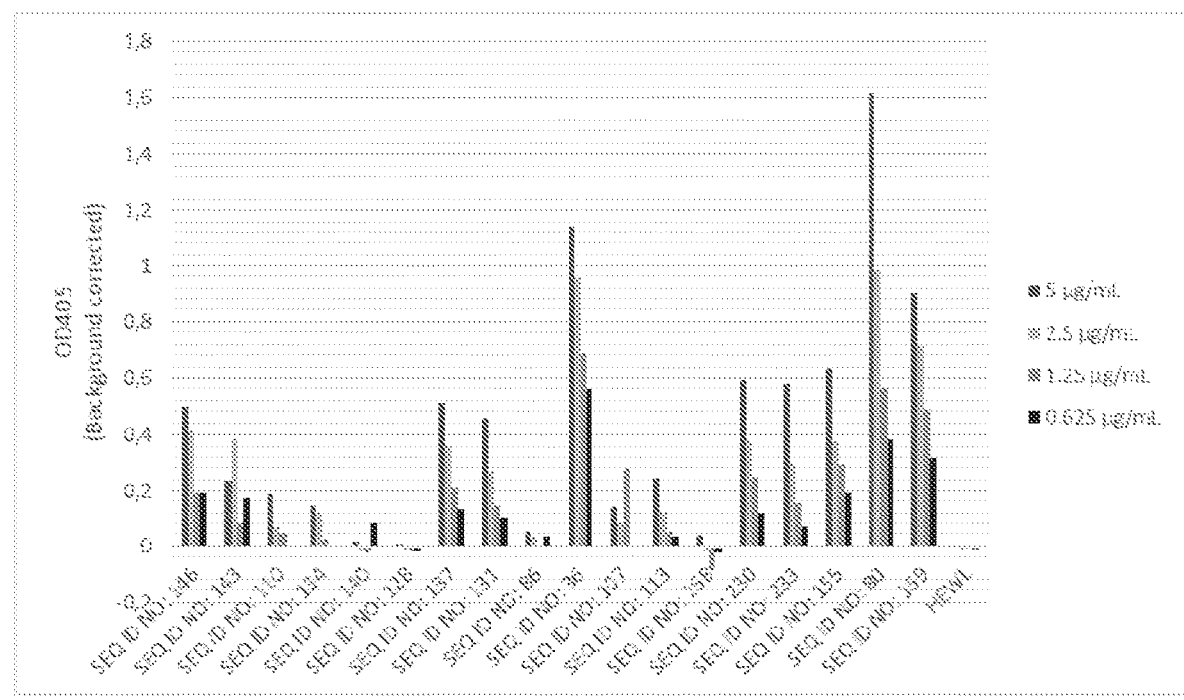

FIGS. 3 and 4 are a series of panels each illustrating the results of Example 56: Method for the Determination of Lysozyme Activity (OD405) Against *Lactobacillus johnsonii* at concentrations of the enzymes of 0.625 ppm, 1.25 ppm, 2.5 ppm and 5 ppm. Each OD measurement represents the difference after the original (background) reading was subtracted and represents the average of two OD measurements.

The Figures illustrate that a number of the enzymes that have improved lysozyme activity against the peptidoglycans found in the cell walls of *Micrococcus lysodeikticus* also have excellent lysozyme activity against the peptidoglycans found in the cell walls of *Lactobacillus johnsonii* even at very low doses.

Figure 5:
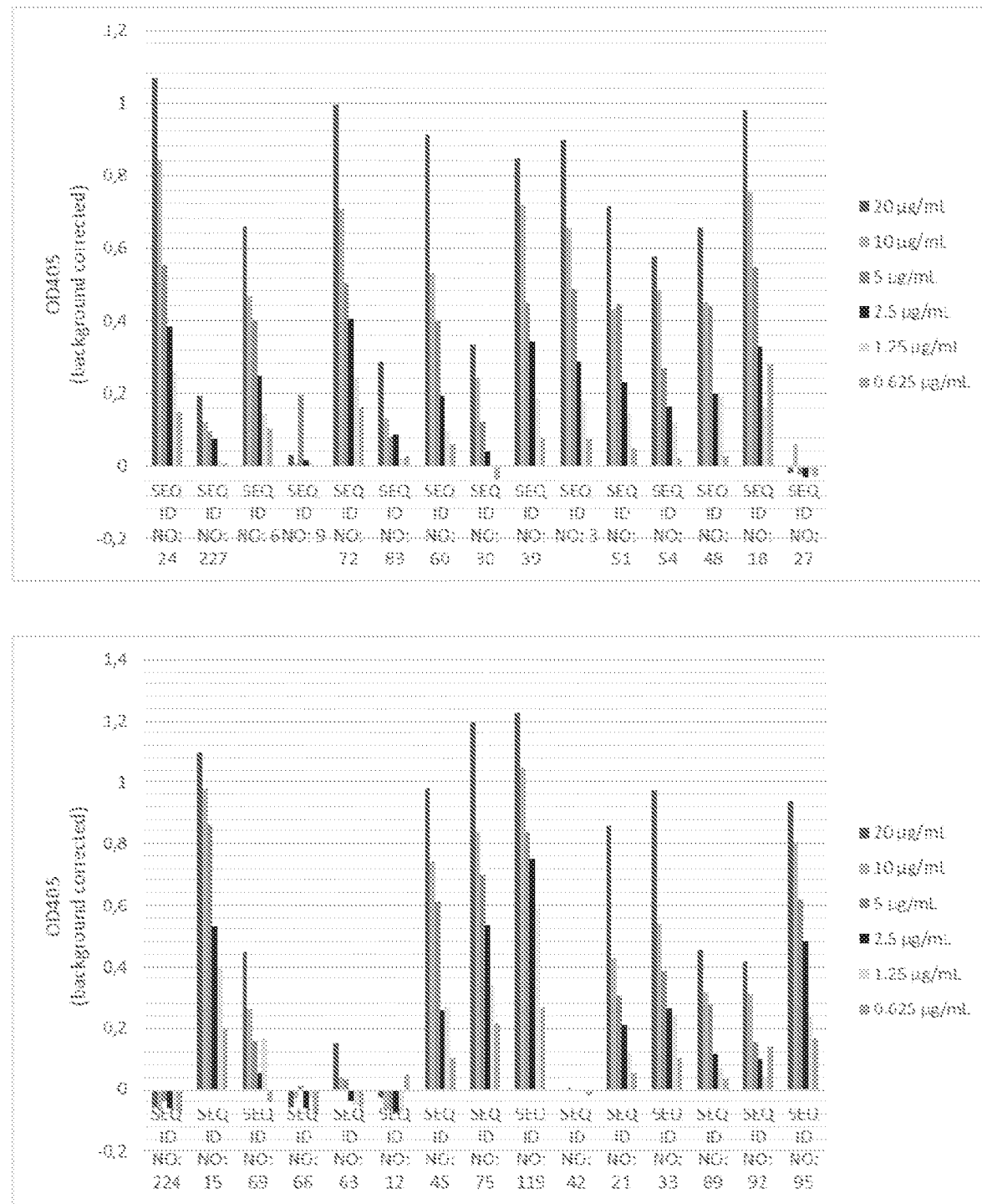
Figure 6:
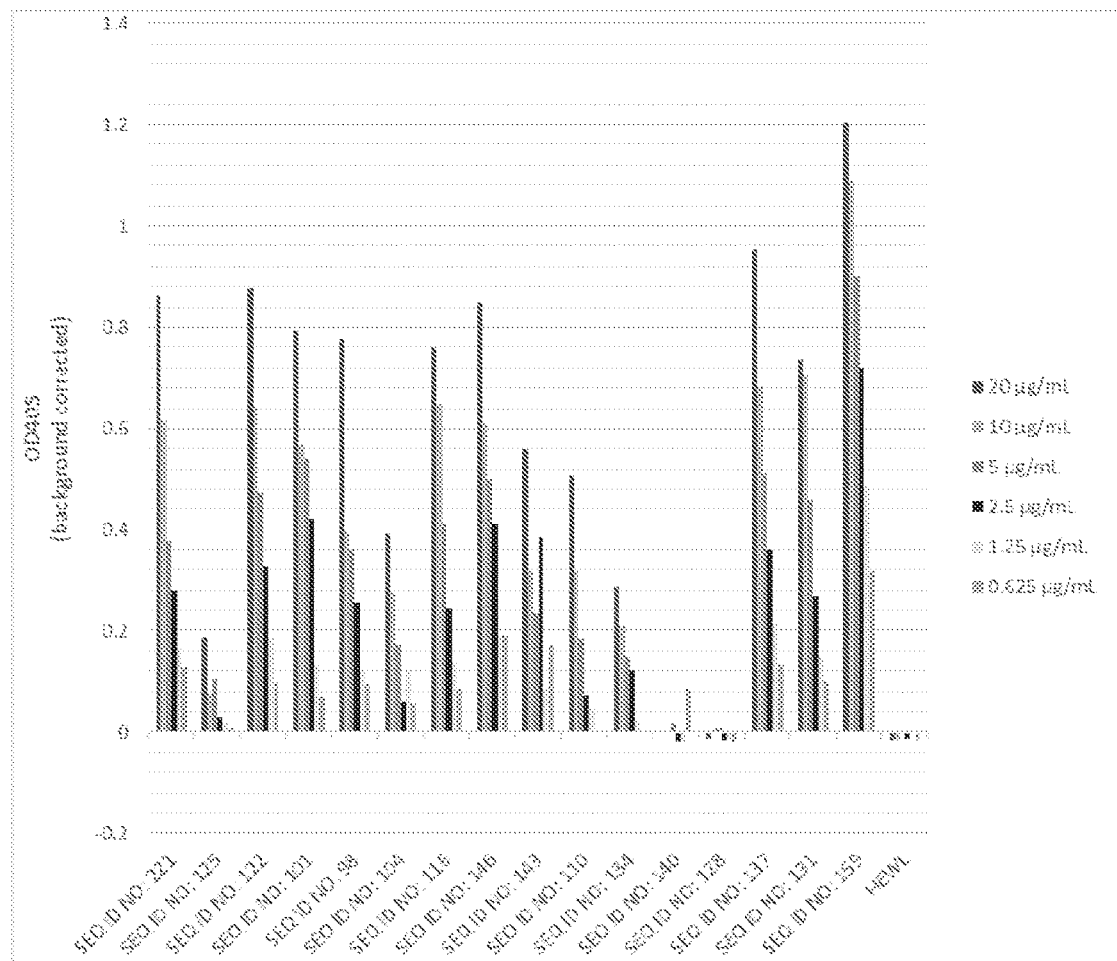

FIGS. 5 and 6 represents a series of panels each illustrating the results of Example 56: Method for the Determination of Lysozyme Activity (OD405) Against *Lactobacillus johnsonii* at concentrations of the enzymes of 0.625 ppm, 1.25 ppm, 2.5 ppm, 5 ppm, 10 and 20 ppm. Each OD measurement represents the difference after the original (background) reading was subtracted and represents the average of two OD measurements.

The Figures illustrate that a number of the enzymes that have improved lysozyme activity against the peptidoglycans found in the cell walls of *Micrococcus lysodeikticus* also have excellent lysozyme activity against the peptidoglycans found in the cell walls of *Lactobacillus johnsonii*, even at very low doses.

DETAILED DESCRIPTION OF THE INVENTION

Animal: The term "animal" refers to any animal except humans. Examples of animals are monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Antimicrobial activity: The term "antimicrobial activity" is defined herein as an activity that kills or inhibits the growth of microorganisms, such as, algae, archea, bacteria, fungi and/or protozoans. The antimicrobial activity can, for example, be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

European Production Efficacy Factor (EPEF): The "European Production Efficacy Factor" is a way of comparing the performance of animals. This single-figure facilitates comparison of performance within and among farms and can be used to assess environmental, climatic and managemental variables. The EPEF is calculated as [(liveability (%)× Liveweight (kg))/(Age at depletion (days)×FCR)]×100, wherein livability is the percentage of animals alive at slaughter, Liveweight is the average weight of the animals at slaughter, age of depletion is the age of the animals at slaughter and FCR is the feed conversion ratio at slaughter.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. A FCR improvement of 2% means that the FCR was reduced by 2%.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g. kale, rapeseed (canola), rutabaga (swede), turnip), clover (e.g. alsike clover, red clover, subterranean clover, white clover), grass (e.g.

Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide having one or more (e.g., several) amino acids absent from the amino and/or carboxyl terminus of a mature polypeptide or domain; wherein the fragment has lysozyme activity.

In one aspect, the fragment comprises at least 90% of the length of the mature polypeptide, such as at least 186 amino acids of SEQ ID NO: 2, at least 186 amino acids of SEQ ID NO: 3, at least 180 amino acids of SEQ ID NO: 5, at least 180 amino acids of SEQ ID NO: 6, at least 180 amino acids of SEQ ID NO: 8, at least 180 amino acids of SEQ ID NO: 9, at least 182 amino acids of SEQ ID NO: 11, at least 182 amino acids of SEQ ID NO: 12, at least 187 amino acids of SEQ ID NO: 14, at least 187 amino acids of SEQ ID NO: 15, at least 186 amino acids of SEQ ID NO: 17, at least 186 amino acids of SEQ ID NO: 18, at least 187 amino acids of SEQ ID NO: 20, at least 187 amino acids of SEQ ID NO: 21, at least 186 amino acids of SEQ ID NO: 23, at least 186 amino acids of SEQ ID NO: 24, at least 186 amino acids of SEQ ID NO: 26, at least 186 amino acids of SEQ ID NO: 27, at least 186 amino acids of SEQ ID NO: 29, at least 186 amino acids of SEQ ID NO: 30, at least 187 amino acids of SEQ ID NO: 32, at least 187 amino acids of SEQ ID NO: 33, at least 187 amino acids of SEQ ID NO: 35, at least 187 amino acids of SEQ ID NO: 36, at least 185 amino acids of SEQ ID NO: 38, at least 185 amino acids of SEQ ID NO: 39, at least 186 amino acids of SEQ ID NO: 41, at least 186 amino acids of SEQ ID NO: 42, at least 194 amino acids of SEQ ID NO: 44, at least 194 amino acids of SEQ ID NO: 45, at least 196 amino acids of SEQ ID NO: 47, at least 196 amino acids of SEQ ID NO: 48, at least 183 amino acids of SEQ ID NO: 50, at least 183 amino acids of SEQ ID NO: 51, at least 182 amino acids of SEQ ID NO: 53, at least 182 amino acids of SEQ ID NO: 54, at least 188 amino acids of SEQ ID NO: 56, at least 188 amino acids of SEQ ID NO: 57, at least 187 amino acids of SEQ ID NO: 59, at least 187 amino acids of SEQ ID NO: 60, at least 189 amino acids of SEQ ID NO: 62, at least 189 amino acids of SEQ ID NO: 63, at least 186 amino acids of SEQ ID NO: 65, at least 186 amino acids of SEQ ID NO: 66, at least 186 amino acids of SEQ ID NO: 68, at least 186 amino acids of SEQ ID NO: 69, at least 187 amino acids of SEQ ID NO: 71, at least 187 amino acids of SEQ ID NO: 72, at least 195 amino acids of SEQ ID NO: 74, at least 195 amino acids of SEQ ID NO: 75, at least 187 amino acids of SEQ ID NO: 77, at least 187 amino acids of SEQ ID NO: 79, at least 187 amino acids of SEQ ID NO: 80, at least 180 amino acids of SEQ ID NO: 82, at least 180 amino acids of SEQ ID NO: 83, at least 181 amino acids of SEQ ID NO: 85, at least 181 amino acids of SEQ ID NO: 86, at least 186 amino acids of SEQ ID NO: 88, at least 186 amino acids of SEQ ID NO: 89, at least 181 amino acids of SEQ ID NO: 91, at least 181 amino acids of SEQ ID NO: 92, at least 180 amino acids of SEQ ID NO: 94, at least 180 amino acids of SEQ ID NO: 95, at least 181 amino acids of SEQ ID NO: 97, at least 181 amino acids of SEQ ID NO: 98, at least 185 amino acids of SEQ ID NO: 100, at least 185 amino acids of SEQ ID NO: 101, at least 181 amino acids of SEQ ID NO: 103, at least 181 amino acids of SEQ ID NO: 104, at least 181 amino acids of SEQ ID NO: 106, at least 181 amino acids of SEQ ID NO: 107, at least 181 amino acids of SEQ ID NO: 109, at least 181 amino acids of SEQ ID NO: 110, at least 181 amino acids of SEQ ID NO: 112, at least 181 amino acids of SEQ ID NO: 113, at least 185 amino acids of SEQ ID NO: 115, at least 185 amino acids of SEQ ID NO: 116, at least 186 amino acids of SEQ ID NO: 118, at least 186 amino acids of SEQ ID NO: 119, at least 187 amino acids of SEQ ID NO: 121, at least 187 amino acids of SEQ ID NO: 122, at least 193 amino acids of SEQ ID NO: 124, at least 193 amino acids of SEQ ID NO: 125, at least 195 amino acids of SEQ ID NO: 127, at least 195 amino acids of SEQ ID NO: 128, at least 192 amino acids of SEQ ID NO: 130, at least 192 amino acids of SEQ ID NO: 131, at least 187 amino acids of SEQ ID NO: 133, at least 187 amino acids of SEQ ID NO: 134, at least 182 amino acids of SEQ ID NO: 136, at least 182 amino acids of SEQ ID NO: 137, at least 194 amino acids of SEQ ID NO: 139, at least 194 amino acids of SEQ ID NO: 140, at least 186 amino acids of SEQ ID NO: 142, at least 186 amino acids of SEQ ID NO: 143, at least 187 amino acids of SEQ ID NO: 145, at least 187 amino acids of SEQ ID NO: 146, at least 186 amino acids of SEQ ID NO: 148, at least 186 amino acids of SEQ ID NO: 149, at least 186 amino acids of SEQ ID NO: 151, at least 186 amino acids of SEQ ID NO: 152, at least 186 amino acids of SEQ ID NO: 154, at least 186 amino acids of SEQ ID NO: 155, at least 187 amino acids of SEQ ID NO: 157, at least 187 amino acids of SEQ ID NO: 158, at least 186 amino acids of SEQ ID NO: 218, at least 186 amino acids of SEQ ID NO: 220, at least 186 amino acids of SEQ ID NO: 221, at least 186 amino acids of SEQ ID NO: 223, at least 186 amino acids of SEQ ID NO: 224, at least 187 amino acids of SEQ ID NO: 226, at least 187 amino acids of SEQ ID NO: 227, at least 186 amino acids of SEQ ID NO: 229, at least 186 amino acids of SEQ ID NO: 230, at least 186 amino acids of SEQ ID NO: 232, or at least 186 amino acids of SEQ ID NO: 233.

In one aspect, the fragment comprises at least 92% of the length of the mature polypeptide, such as at least 190 amino acids of SEQ ID NO: 2, at least 190 amino acids of SEQ ID NO: 3, at least 184 amino acids of SEQ ID NO: 5, at least 184 amino acids of SEQ ID NO: 6, at least 184 amino acids of SEQ ID NO: 8, at least 184 amino acids of SEQ ID NO: 9, at least 186 amino acids of SEQ ID NO: 11, at least 186 amino acids of SEQ ID NO: 12, at least 191 amino acids of SEQ ID NO: 14, at least 191 amino acids of SEQ ID NO: 15, at least 190 amino acids of SEQ ID NO: 17, at least 190 amino acids of SEQ ID NO: 18, at least 191 amino acids of SEQ ID NO: 20, at least 191 amino acids of SEQ ID NO: 21, at least 190 amino acids of SEQ ID NO: 23, at least 190 amino acids of SEQ ID NO: 24, at least 190 amino acids of SEQ ID NO: 26, at least 190 amino acids of SEQ ID NO: 27, at least 190 amino acids of SEQ ID NO: 29, at least 190 amino acids of SEQ ID NO: 30, at least 191 amino acids of SEQ ID NO: 32, at least 191 amino acids of SEQ ID NO: 33, at least 191 amino acids of SEQ ID NO: 35, at least 191 amino acids of SEQ ID NO: 36, at least 189 amino acids of SEQ ID NO: 38, at least 189 amino acids of SEQ ID NO: 39, at least 190 amino acids of SEQ ID NO: 41, at least 190 amino acids of SEQ ID NO: 42, at least 198 amino acids of SEQ ID NO: 44, at least 198 amino acids of SEQ ID NO: 45, at least 200 amino acids of SEQ ID NO: 47, at least 200 amino acids of SEQ ID NO: 48, at least 187 amino acids of SEQ ID NO: 50, at least 187 amino acids of SEQ ID NO: 51, at least 186 amino acids of SEQ ID NO: 53, at least 186 amino acids of SEQ ID NO: 54, at least 192 amino acids of SEQ ID NO: 56, at least 192 amino acids of SEQ ID NO: 57, at least 191 amino acids of SEQ ID NO: 59, at least 191 amino acids of SEQ ID NO: 60, at least 193 amino acids of SEQ ID NO: 62, at least 193 amino acids of SEQ ID NO: 63, at least 190 amino acids of SEQ ID NO: 65, at least 190 amino acids of SEQ ID NO: 66, at least 190 amino acids of SEQ ID NO: 68, at least 190 amino acids of SEQ ID NO: 69, at least 191 amino acids of SEQ ID NO: 71, at least 191 amino acids of SEQ ID NO: 72, at least 199 amino acids of SEQ ID NO: 74, at least 199 amino acids of SEQ ID NO: 75, at least 191 amino acids of SEQ ID NO: 77, at least 191 amino acids of SEQ ID NO: 79, at least 191 amino acids of SEQ ID NO: 80, at least 184 amino acids of SEQ ID NO: 82, at least 184 amino acids of SEQ ID NO: 83, at least 185 amino acids of SEQ ID NO: 85, at least 185 amino acids of SEQ ID NO: 86, at least 190 amino acids of SEQ ID NO: 88, at least 190 amino acids of SEQ ID NO: 89, at least 185 amino acids of SEQ ID NO: 91, at least 185 amino acids of SEQ ID NO: 92, at least 184 amino acids of SEQ ID NO: 94, at least 184 amino acids of SEQ ID NO: 95, at least 185 amino acids of SEQ ID NO: 97, at least 185 amino acids of SEQ ID NO: 98, at least 189 amino acids of SEQ ID NO: 100, at least 189 amino acids of SEQ ID NO: 101, at least 185 amino acids of SEQ ID NO: 103, at least 185 amino acids of SEQ ID NO: 104, at least 185 amino acids of SEQ ID NO: 106, at least 185 amino acids of SEQ ID NO: 107, at least 185 amino acids of SEQ ID NO: 109, at least 185 amino acids of SEQ ID NO: 110, at least 185 amino acids of SEQ ID NO: 112, at least 185 amino acids of SEQ ID NO: 113, at least 189 amino acids of SEQ ID NO: 115, at least 189 amino acids of SEQ ID NO: 116, at least 190 amino acids of SEQ ID NO: 118, at least 190 amino acids of SEQ ID NO: 119, at least 191 amino acids of SEQ ID NO: 121, at least 191 amino acids of SEQ ID NO: 122, at least 197 amino acids of SEQ ID NO: 124, at least 197 amino acids of SEQ ID NO: 125, at least 199 amino acids of SEQ ID NO: 127, at least 199 amino acids of SEQ ID NO: 128, at least 196 amino acids of SEQ ID NO: 130, at least 196 amino acids of SEQ ID NO: 131, at least 191 amino acids of SEQ ID NO: 133, at least 191 amino acids of SEQ ID NO: 134, at least 186 amino acids of SEQ ID NO: 136, at least 186 amino acids of SEQ ID NO: 137, at least 198 amino acids of SEQ ID NO: 139, at least 198 amino acids of SEQ ID NO: 140, at least 190 amino acids of SEQ ID NO: 142, at least 190 amino acids of SEQ ID NO: 143, at least 191 amino acids of SEQ ID NO: 145, at least 191 amino acids of SEQ ID NO: 146, at least 190 amino acids of SEQ ID NO: 148, at least 190 amino acids of SEQ ID NO: 149, at least 190 amino acids of SEQ ID NO: 151, at least 190 amino acids of SEQ ID NO: 152, at least 190 amino acids of SEQ ID NO: 154, at least 190 amino acids of SEQ ID NO: 155, at least 191 amino acids of SEQ ID NO: 157, at least 191 amino acids of SEQ ID NO: 158, at least 190 amino acids of SEQ ID NO: 218, at least 190 amino acids of SEQ ID NO: 220, at least 190 amino acids of SEQ ID NO: 221, at least 190 amino acids of SEQ ID NO: 223, at least 190 amino acids of SEQ ID NO: 224, at least 191 amino acids of SEQ ID NO: 226, at least 191 amino acids of SEQ ID NO: 227, at least 190 amino acids of SEQ ID NO: 229, at least 190 amino acids of SEQ ID NO: 230, at least 190 amino acids of SEQ ID NO: 232, or at least 190 amino acids of SEQ ID NO: 233.

In one aspect, the fragment comprises at least 94% of the length of the mature polypeptide, such as at least 194 amino acids of SEQ ID NO: 2, at least 194 amino acids of SEQ ID NO: 3, at least 188 amino acids of SEQ ID NO: 5, at least 188 amino acids of SEQ ID NO: 6, at least 188 amino acids of SEQ ID NO: 8, at least 188 amino acids of SEQ ID NO: 9, at least 190 amino acids of SEQ ID NO: 11, at least 190 amino acids of SEQ ID NO: 12, at least 195 amino acids of SEQ ID NO: 14, at least 195 amino acids of SEQ ID NO: 15, at least 194 amino acids of SEQ ID NO: 17, at least 194 amino acids of SEQ ID NO: 18, at least 195 amino acids of SEQ ID NO: 20, at least 195 amino acids of SEQ ID NO: 21, at least 194 amino acids of SEQ ID NO: 23, at least 194 amino acids of SEQ ID NO: 24, at least 194 amino acids of SEQ ID NO: 26, at least 194 amino acids of SEQ ID NO: 27, at least 194 amino acids of SEQ ID NO: 29, at least 194 amino acids of SEQ ID NO: 30, at least 195 amino acids of SEQ ID NO: 32, at least 195 amino acids of SEQ ID NO: 33, at least 195 amino acids of SEQ ID NO: 35, at least 195 amino acids of SEQ ID NO: 36, at least 193 amino acids of SEQ ID NO: 38, at least 193 amino acids of SEQ ID NO: 39, at least 194 amino acids of SEQ ID NO: 41, at least 194 amino acids of SEQ ID NO: 42, at least 203 amino acids of SEQ ID NO: 44, at least 203 amino acids of SEQ ID NO: 45, at least 204 amino acids of SEQ ID NO: 47, at least 204 amino acids of SEQ ID NO: 48, at least 191 amino acids of SEQ ID NO: 50, at least 191 amino acids of SEQ ID NO: 51, at least 190 amino acids of SEQ ID NO: 53, at least 190 amino acids of SEQ ID NO: 54, at least 196 amino acids of SEQ ID NO: 56, at least 196 amino acids of SEQ ID NO: 57, at least 195 amino acids of SEQ ID NO: 59, at least 195 amino acids of SEQ ID NO: 60, at least 197 amino acids of SEQ ID NO: 62, at least 197 amino acids of SEQ ID NO: 63, at least 194 amino acids of SEQ ID NO: 65, at least 194 amino acids of SEQ ID NO: 66, at least 194 amino acids of SEQ ID NO: 68, at least 194 amino acids of SEQ ID NO: 69, at least 195 amino acids of SEQ ID NO: 71, at least 195 amino acids of SEQ ID NO: 72, at least 203 amino acids of SEQ ID NO: 74, at least 203 amino acids of SEQ ID NO: 75, at least 195 amino acids of SEQ ID NO: 77, at least 195 amino acids of SEQ ID NO: 79, at least 195 amino acids of SEQ ID NO: 80, at least 188 amino acids of SEQ ID NO: 82, at least 188 amino acids of SEQ ID NO: 83, at least 189 amino acids of SEQ ID NO: 85, at least 189 amino acids of SEQ ID NO: 86, at least 194 amino acids of SEQ ID NO: 88, at least 194 amino acids of SEQ ID NO: 89, at least 189 amino acids of SEQ ID NO: 91, at least 189 amino acids of SEQ ID NO: 92, at least 188 amino acids of SEQ ID NO: 94, at least 188 amino acids of SEQ ID NO: 95, at least 189 amino acids of SEQ ID NO: 97, at least 189 amino acids of SEQ ID NO: 98, at least 193 amino acids of SEQ ID NO: 100, at least 193 amino acids of SEQ ID NO: 101, at least 189 amino acids of SEQ ID NO: 103, at least 189 amino acids of SEQ ID NO: 104, at least 189 amino acids of SEQ ID NO: 106, at least 189 amino acids of SEQ ID NO: 107, at least 189 amino acids of SEQ ID NO: 109, at least 189 amino acids of SEQ ID NO: 110, at least 189 amino acids of SEQ ID NO: 112, at least 189 amino acids of SEQ ID NO: 113, at least 193 amino acids of SEQ ID NO: 115, at least 193 amino acids of SEQ ID NO: 116, at least 194 amino acids of SEQ ID NO: 118, at least 194 amino acids of SEQ ID NO: 119, at least 195 amino acids of SEQ ID NO: 121, at least 195 amino acids of SEQ ID NO: 122, at least 202 amino acids of SEQ ID NO: 124, at least 202 amino acids of SEQ ID NO: 125, at least 203 amino acids of SEQ ID NO: 127, at least 203 amino acids of SEQ ID NO: 128, at least 201 amino acids of SEQ ID NO: 130, at least 201 amino acids of SEQ ID NO: 131, at least 195 amino acids of SEQ ID NO: 133, at least 195 amino acids of SEQ ID NO: 134, at least 190 amino acids of SEQ ID NO: 136, at least 190 amino acids of SEQ ID NO: 137, at least 203 amino acids of SEQ ID NO: 139, at least 203 amino acids of SEQ ID NO: 140, at least 194 amino acids of SEQ ID NO: 142, at least 194 amino acids of SEQ ID NO: 143, at least 195 amino acids of SEQ ID NO: 145, at least 195 amino acids of SEQ ID NO: 146, at least 194 amino acids of SEQ ID NO: 148, at least 194 amino acids of SEQ ID NO: 149, at least 194 amino acids of SEQ ID NO: 151, at least 194 amino acids of SEQ ID NO: 152, at least 194 amino acids of SEQ ID NO: 154, at least 194 amino acids of SEQ ID NO: 155, at least 195 amino acids of SEQ ID NO: 157, at least 195 amino acids of SEQ ID NO: 158, at least 194 amino acids of SEQ ID NO: 218, at least 194 amino acids of SEQ ID NO: 220, at least 194 amino acids of SEQ ID NO: 221, at least 194 amino acids of SEQ ID NO: 223, at least 194 amino acids of SEQ ID NO: 224, at least 195 amino acids of SEQ ID NO: 226, at least 195 amino acids of SEQ ID NO: 227, at least 194 amino acids of SEQ ID NO: 229, at least 194 amino acids of SEQ ID NO: 230, at least 194 amino acids of SEQ ID NO: 232, or at least 194 amino acids of SEQ ID NO: 233.

In one aspect, the fragment comprises at least 96% of the length of the mature polypeptide, such as at least 198 amino acids of SEQ ID NO: 2, at least 198 amino acids of SEQ ID NO: 3, at least 192 amino acids of SEQ ID NO: 5, at least 192 amino acids of SEQ ID NO: 6, at least 192 amino acids of SEQ ID NO: 8, at least 192 amino acids of SEQ ID NO: 9, at least 194 amino acids of SEQ ID NO: 11, at least 194 amino acids of SEQ ID NO: 12, at least 199 amino acids of SEQ ID NO: 14, at least 199 amino acids of SEQ ID NO: 15, at least 198 amino acids of SEQ ID NO: 17, at least 198 amino acids of SEQ ID NO: 18, at least 199 amino acids of SEQ ID NO: 20, at least 199 amino acids of SEQ ID NO: 21, at least 198 amino acids of SEQ ID NO: 23, at least 198 amino acids of SEQ ID NO: 24, at least 198 amino acids of SEQ ID NO: 26, at least 198 amino acids of SEQ ID NO: 27, at least 198 amino acids of SEQ ID NO: 29, at least 198 amino acids of SEQ ID NO: 30, at least 199 amino acids of SEQ ID NO: 32, at least 199 amino acids of SEQ ID NO: 33, at least 199 amino acids of SEQ ID NO: 35, at least 199 amino acids of SEQ ID NO: 36, at least 197 amino acids of SEQ ID NO: 38, at least 197 amino acids of SEQ ID NO: 39, at least 198 amino acids of SEQ ID NO: 41, at least 198 amino acids of SEQ ID NO: 42, at least 207 amino acids of SEQ ID NO: 44, at least 207 amino acids of SEQ ID NO: 45, at least 209 amino acids of SEQ ID NO: 47, at least 209 amino acids of SEQ ID NO: 48, at least 195 amino acids of SEQ ID NO: 50, at least 195 amino acids of SEQ ID NO: 51, at least 194 amino acids of SEQ ID NO: 53, at least 194 amino acids of SEQ ID NO: 54, at least 200 amino acids of SEQ ID NO: 56, at least 200 amino acids of SEQ ID NO: 57, at least 199 amino acids of SEQ ID NO: 59, at least 199 amino acids of SEQ ID NO: 60, at least 201 amino acids of SEQ ID NO: 62, at least 201 amino acids of SEQ ID NO: 63, at least 198 amino acids of SEQ ID NO: 65, at least 198 amino acids of SEQ ID NO: 66, at least 198 amino acids of SEQ ID NO: 68, at least 198 amino acids of SEQ ID NO: 69, at least 199 amino acids of SEQ ID NO: 71, at least 199 amino acids of SEQ ID NO: 72, at least 208 amino acids of SEQ ID NO: 74, at least 208 amino acids of SEQ ID NO: 75, at least 199 amino acids of SEQ ID NO: 77, at least 199 amino acids of SEQ ID NO: 79, at least 199 amino acids of SEQ ID NO: 80, at least 192 amino acids of SEQ ID NO: 82, at least 192 amino acids of SEQ ID NO: 83, at least 193 amino acids of SEQ ID NO: 85, at least 193 amino acids of SEQ ID NO: 86, at least 198 amino acids of SEQ ID NO: 88, at least 198 amino acids of SEQ ID NO: 89, at least 193 amino acids of SEQ ID NO: 91, at least 193 amino acids of SEQ ID NO: 92, at least 192 amino acids of SEQ ID NO: 94, at least 192 amino acids of SEQ ID NO: 95, at least 193 amino acids of SEQ ID NO: 97, at least 193 amino acids of SEQ ID NO: 98, at least 197 amino acids of SEQ ID NO: 100, at least 197 amino acids of SEQ ID NO: 101, at least 193 amino acids of SEQ ID NO: 103, at least 193 amino acids of SEQ ID NO: 104, at least 193 amino acids of SEQ ID NO: 106, at least 193 amino acids of SEQ ID NO: 107, at least 193 amino acids of SEQ ID NO: 109, at least 193 amino acids of SEQ ID NO: 110, at least 193 amino acids of SEQ ID NO: 112, at least 193 amino acids of SEQ ID NO: 113, at least 197 amino acids of SEQ ID NO: 115, at least 197 amino acids of SEQ ID NO: 116, at least 198 amino acids of SEQ ID NO: 118, at least 198 amino acids of SEQ ID NO: 119, at least 199 amino acids of SEQ ID NO: 121, at least 199 amino acids of SEQ ID NO: 122, at least 206 amino acids of SEQ ID NO: 124, at least 206 amino acids of SEQ ID NO: 125, at least 208 amino acids of SEQ ID NO: 127, at least 208 amino acids of SEQ ID NO: 128, at least 205 amino acids of SEQ ID NO: 130, at least 205 amino acids of SEQ ID NO: 131, at least 199 amino acids of SEQ ID NO: 133, at least 199 amino acids of SEQ ID NO: 134, at least 194 amino acids of SEQ ID NO: 136, at least 194 amino acids of SEQ ID NO: 137, at least 207 amino acids of SEQ ID NO: 139, at least 207 amino acids of SEQ ID NO: 140, at least 198 amino acids of SEQ ID NO: 142, at least 198 amino acids of SEQ ID NO: 143, at least 199 amino acids of SEQ ID NO: 145, at least 199 amino acids of SEQ ID NO: 146, at least 198 amino acids of SEQ ID NO: 148, at least 198 amino acids of SEQ ID NO: 149, at least 198 amino acids of SEQ ID NO: 151, at least 198 amino acids of SEQ ID NO: 152, at least 198 amino acids of SEQ ID NO: 154, at least 198 amino acids of SEQ ID NO: 155, at least 199 amino acids of SEQ ID NO: 157, at least 199 amino acids of SEQ ID NO: 158, at least 198 amino acids of SEQ ID NO: 218, at least 198 amino acids of SEQ ID NO: 220, at least 198 amino acids of SEQ ID NO: 221, at least 198 amino acids of SEQ ID NO: 223, at least 198 amino acids of SEQ ID NO: 224, at least 199 amino acids of SEQ ID NO: 226, at least 199 amino acids of SEQ ID NO: 227, at least 198 amino acids of SEQ ID NO: 229, at least 198 amino acids of SEQ ID NO: 230, at least 198 amino acids of SEQ ID NO: 232, or at least 198 amino acids of SEQ ID NO: 233.

In one aspect, the fragment comprises at least 98% of the length of the mature polypeptide, such as at least 202 amino acids of SEQ ID NO: 2, at least 202 amino acids of SEQ ID NO: 3, at least 196 amino acids of SEQ ID NO: 5, at least 196 amino acids of SEQ ID NO: 6, at least 196 amino acids of SEQ ID NO: 8, at least 196 amino acids of SEQ ID NO: 9, at least 198 amino acids of SEQ ID NO: 11, at least 198 amino acids of SEQ ID NO: 12, at least 203 amino acids of SEQ ID NO: 14, at least 203 amino acids of SEQ ID NO: 15, at least 202 amino acids of SEQ ID NO: 17, at least 202 amino acids of SEQ ID NO: 18, at least 203 amino acids of SEQ ID NO: 20, at least 203 amino acids of SEQ ID NO: 21, at least 202 amino acids of SEQ ID NO: 23, at least 202 amino acids of SEQ ID NO: 24, at least 202 amino acids of SEQ ID NO: 26, at least 202 amino acids of SEQ ID NO: 27, at least 202 amino acids of SEQ ID NO: 29, at least 202 amino acids of SEQ ID NO: 30, at least 203 amino acids of SEQ ID NO: 32, at least 203 amino acids of SEQ ID NO: 33, at least 203 amino acids of SEQ ID NO: 35, at least 203 amino acids of SEQ ID NO: 36, at least 201 amino acids of SEQ ID NO: 38, at least 201 amino acids of SEQ ID NO: 39, at least 202 amino acids of SEQ ID NO: 41, at least 202 amino acids of SEQ ID NO: 42, at least 211 amino acids of SEQ ID NO: 44, at least 211 amino acids of SEQ ID NO: 45, at least 213 amino acids of SEQ ID NO: 47, at least 213 amino acids of SEQ ID NO: 48, at least 199 amino acids of SEQ ID NO: 50, at least 199 amino acids of SEQ ID NO: 51, at least 198 amino acids of SEQ ID NO: 53, at least 198 amino acids of SEQ ID NO: 54, at least 204 amino acids of SEQ ID NO: 56, at least 204 amino acids of SEQ ID NO: 57, at least 203 amino acids of SEQ ID NO: 59, at least 203 amino acids of SEQ ID NO: 60, at least 205 amino acids of SEQ ID NO: 62, at least 205 amino acids of SEQ ID NO: 63, at least 202 amino acids of SEQ ID NO: 65, at least 202 amino acids of SEQ ID NO: 66, at least 202 amino acids of SEQ ID NO: 68, at least 202 amino acids of SEQ ID NO: 69, at least 203 amino acids of SEQ ID NO: 71, at least 203 amino acids of SEQ ID NO: 72, at least 212 amino acids of SEQ ID NO: 74, at least 212 amino acids of SEQ ID NO: 75, at least 203 amino acids of SEQ ID NO: 77, at least 203 amino acids of SEQ ID NO: 79, at least 203 amino acids of SEQ ID NO: 80, at least 196 amino acids of SEQ ID NO: 82, at least 196 amino acids of SEQ ID NO: 83, at least 197 amino acids of SEQ ID NO: 85, at least 197 amino acids of SEQ ID NO: 86, at least 202 amino acids of SEQ ID NO: 88, at least 202 amino acids of SEQ ID NO: 89, at least 197 amino acids of SEQ ID NO: 91, at least 197 amino acids of SEQ ID NO: 92, at least 196 amino acids of SEQ ID NO: 94, at least 196 amino acids of SEQ ID NO: 95, at least 197 amino acids of SEQ ID NO: 97, at least 197 amino acids of SEQ ID NO: 98, at least 201 amino acids of SEQ ID NO: 100, at least 201 amino acids of SEQ ID NO: 101, at least 197 amino acids of SEQ ID NO: 103, at least 197 amino acids of SEQ ID NO: 104, at least 197 amino acids of SEQ ID NO: 106, at least 197 amino acids of SEQ ID NO: 107, at least 197 amino acids of SEQ ID NO: 109, at least 197 amino acids of SEQ ID NO: 110, at least 197 amino acids of SEQ ID NO: 112, at least 197 amino acids of SEQ ID NO: 113, at least 201 amino acids of SEQ ID NO: 115, at least 201 amino acids of SEQ ID NO: 116, at least 202 amino acids of SEQ ID NO: 118, at least 202 amino acids of SEQ ID NO: 119, at least 203 amino acids of SEQ ID NO: 121, at least 203 amino acids of SEQ ID NO: 122, at least 210 amino acids of SEQ ID NO: 124, at least 210 amino acids of SEQ ID NO: 125, at least 212 amino acids of SEQ ID NO: 127, at least 212 amino acids of SEQ ID NO: 128, at least 209 amino acids of SEQ ID NO: 130, at least 209 amino acids of SEQ ID NO: 131, at least 203 amino acids of SEQ ID NO: 133, at least 203 amino acids of SEQ ID NO: 134, at least 198 amino acids of SEQ ID NO: 136, at least 198 amino acids of SEQ ID NO: 137, at least 211 amino acids of SEQ ID NO: 139, at least 211 amino acids of SEQ ID NO: 140, at least 202 amino acids of SEQ ID NO: 142, at least 202 amino acids of SEQ ID NO: 143, at least 203 amino acids of SEQ ID NO: 145, at least 203 amino acids of SEQ ID NO: 146, at least 202 amino acids of SEQ ID NO: 148, at least 202 amino acids of SEQ ID NO: 149, at least 202 amino acids of SEQ ID NO: 151, at least 202 amino acids of SEQ ID NO: 152, at least 202 amino acids of SEQ ID NO: 154, at least 202 amino acids of SEQ ID NO: 155, at least 203 amino acids of SEQ ID NO: 157, at least 203 amino acids of SEQ ID NO: 158, at least 202 amino acids of SEQ ID NO: 218, at least 202 amino acids of SEQ ID NO: 220, at least 202 amino acids of SEQ ID NO: 221, at least 202 amino acids of SEQ ID NO: 223, at least 202 amino acids of SEQ ID NO: 224, at least 203 amino acids of SEQ ID NO: 226, at least 203 amino acids of SEQ ID NO: 227, at least 202 amino acids of SEQ ID NO: 229, at least 202 amino acids of SEQ ID NO: 230, at least 202 amino acids of SEQ ID NO: 232, or at least 202 amino acids of SEQ ID NO: 233.

In one aspect, the fragment comprises at least 99% of the length of the mature polypeptide, such as at least 204 amino acids of SEQ ID NO: 2, at least 204 amino acids of SEQ ID NO: 3, at least 198 amino acids of SEQ ID NO: 5, at least 198 amino acids of SEQ ID NO: 6, at least 198 amino acids of SEQ ID NO: 8, at least 198 amino acids of SEQ ID NO: 9, at least 200 amino acids of SEQ ID NO: 11, at least 200 amino acids of SEQ ID NO: 12, at least 205 amino acids of SEQ ID NO: 14, at least 205 amino acids of SEQ ID NO: 15, at least 204 amino acids of SEQ ID NO: 17, at least 204 amino acids of SEQ ID NO: 18, at least 205 amino acids of SEQ ID NO: 20, at least 205 amino acids of SEQ ID NO: 21, at least 204 amino acids of SEQ ID NO: 23, at least 204 amino acids of SEQ ID NO: 24, at least 204 amino acids of SEQ ID NO: 26, at least 204 amino acids of SEQ ID NO: 27, at least 204 amino acids of SEQ ID NO: 29, at least 204 amino acids of SEQ ID NO: 30, at least 205 amino acids of SEQ ID NO: 32, at least 205 amino acids of SEQ ID NO: 33, at least 205 amino acids of SEQ ID NO: 35, at least 205 amino acids of SEQ ID NO: 36, at least 203 amino acids of SEQ ID NO: 38, at least 203 amino acids of SEQ ID NO: 39, at least 204 amino acids of SEQ ID NO: 41, at least 204 amino acids of SEQ ID NO: 42, at least 213 amino acids of SEQ ID NO: 44, at least 213 amino acids of SEQ ID NO: 45, at least 215 amino acids of SEQ ID NO: 47, at least 215 amino acids of SEQ ID NO: 48, at least 201 amino acids of SEQ ID NO: 50, at least 201 amino acids of SEQ ID NO: 51, at least 200 amino acids of SEQ ID NO: 53, at least 200 amino acids of SEQ ID NO: 54, at least 206 amino acids of SEQ ID NO: 56, at least 206 amino acids of SEQ ID NO: 57, at least 205 amino acids of SEQ ID NO: 59, at least 205 amino acids of SEQ ID NO: 60, at least 207 amino acids of SEQ ID NO: 62, at least 207 amino acids of SEQ ID NO: 63, at least 204 amino acids of SEQ ID NO: 65, at least 204 amino acids of SEQ ID NO: 66, at least 204 amino acids of SEQ ID NO: 68, at least 204 amino acids of SEQ ID NO: 69, at least 205 amino acids of SEQ ID NO: 71, at least 205 amino acids of SEQ ID NO: 72, at least 214 amino acids of SEQ ID NO: 74, at least 214 amino acids of SEQ ID NO: 75, at least 205 amino acids of SEQ ID NO: 77, at least 205 amino acids of SEQ ID NO: 79, at least 205 amino acids of SEQ ID NO: 80, at least 198 amino acids of SEQ ID NO: 82, at least 198 amino acids of SEQ ID NO: 83, at least 199 amino acids of SEQ ID NO: 85, at least 199 amino acids of SEQ ID NO: 86, at least 204 amino acids of SEQ ID NO: 88, at least 204 amino acids of SEQ ID NO: 89, at least 199 amino acids of SEQ ID NO: 91, at least 199 amino acids of SEQ ID NO: 92, at least 198 amino acids of SEQ ID NO: 94, at least 198 amino acids of SEQ ID NO: 95, at least 199 amino acids of SEQ ID NO: 97, at least 199 amino acids of SEQ ID NO: 98, at least 203 amino acids of SEQ ID NO: 100, at least 203 amino acids of SEQ ID NO: 101, at least 199 amino acids of SEQ ID NO: 103, at least 199 amino acids of SEQ ID NO: 104, at least 199 amino acids of SEQ ID NO: 106, at least 199 amino acids of SEQ ID NO: 107, at least 199 amino acids of SEQ ID NO: 109, at least 199 amino acids of SEQ ID NO: 110, at least 199 amino acids of SEQ ID NO: 112, at least 199 amino acids of SEQ ID NO: 113, at least 203 amino acids of SEQ ID NO: 115, at least 203 amino acids of SEQ ID NO: 116, at least 204 amino acids of SEQ ID NO: 118, at least 204 amino acids of SEQ ID NO: 119, at least 205 amino acids of SEQ ID NO: 121, at least 205 amino acids of SEQ ID NO: 122, at least 212 amino acids of SEQ ID NO: 124, at least 212 amino acids of SEQ ID NO: 125, at least 214 amino acids of SEQ ID NO: 127, at least 214 amino acids of SEQ ID NO: 128, at least 211 amino acids of SEQ ID NO: 130, at least 211 amino acids of SEQ ID NO: 131, at least 205 amino acids of SEQ ID NO: 133, at least 205 amino acids of SEQ ID NO: 134, at least 200 amino acids of SEQ ID NO: 136, at least 200 amino acids of SEQ ID NO: 137, at least 213 amino acids of SEQ ID NO: 139, at least 213 amino acids of SEQ ID NO: 140, at least 204 amino acids of SEQ ID NO: 142, at least 204 amino acids of SEQ ID NO: 143, at least 205 amino acids of SEQ ID NO: 145, at least 205 amino acids of SEQ ID NO: 146, at least 204 amino acids of SEQ ID NO: 148, at least 204 amino acids of SEQ ID NO: 149, at least 204 amino acids of SEQ ID NO: 151, at least 204 amino acids of SEQ ID NO: 152, at least 204 amino acids of SEQ ID NO: 154, at least 204 amino acids of SEQ ID NO: 155, at least 205 amino acids of SEQ ID NO: 157, at least 205 amino acids of SEQ ID NO: 158, at least 204 amino acids of SEQ ID NO: 218, at least 204 amino acids of SEQ ID NO: 220, at least 204 amino acids of SEQ ID NO: 221, at least 204 amino acids of SEQ ID NO: 223, at least 204 amino acids of SEQ ID NO: 224, at least 205 amino acids of SEQ ID NO: 226, at least 205 amino acids of SEQ ID NO: 227, at least 204 amino acids of SEQ ID NO: 229, at least 204 amino acids of SEQ ID NO: 230, at least 204 amino acids of SEQ ID NO: 232, or at least 204 amino acids of SEQ ID NO: 233.

Fusion polypeptide: The term "fusion polypeptide" is a polypeptide in which one polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, Science 266: 776-779). A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, J. Biotechnol. 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Hybrid polypeptide: The term "hybrid polypeptide" means a polypeptide comprising domains from two or more polypeptides, e.g., a binding domain from one polypeptide and a catalytic domain from another polypeptide. The domains may be fused at the N-terminus or the C-terminus.

Isolated: The term "isolated" means a substance in a form that does not occur in nature or in an environment in which the substance does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Lysozyme activity: The term "lysozyme activity" means the hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis. Lysozyme belongs to the enzyme class EC 3.2.1.17. Lysozyme activity is typically measured by the lytic action of the lysozyme on *Micrococcus luteus* ATCC 4698. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the reducing-ends assay described in example 1 ("Determination of Lysozyme Activity"). The polypeptide has lysozyme activity if it shows activity against *Micrococcus luteus* ATCC 4698, and specifically the lysozymes of the invention exhibit improved activity compared to the prior art lysozyme of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 207 of SEQ ID NO: 2 and amino acids −17 to −1 of SEQ ID NO: 2 are a signal peptide. In another aspect, the mature polypeptide is amino acids 1 to 207 of SEQ ID NO: 3.

In one aspect, the mature polypeptide is amino acids 1 to 201 of SEQ ID NO: 5 and amino acids −17 to −1 of SEQ ID NO: 5 are a signal peptide. In another aspect, the mature polypeptide is amino acids 1 to 201 of SEQ ID NO: 6.

In one aspect, the mature polypeptide is amino acids 1 to 201 of SEQ ID NO: 8 and amino acids −16 to −1 of SEQ ID NO: 8 are a signal peptide. In another aspect, the mature polypeptide is amino acids 1 to 201 of SEQ ID NO: 9.

In one aspect, the mature polypeptide is amino acids 1 to 203 of SEQ ID NO: 11 and amino acids −21 to −1 of SEQ ID NO: 11 are a signal peptide. In another aspect, the mature polypeptide is amino acids 1 to 203 of SEQ ID NO: 12.

In one aspect, the mature polypeptide is amino acids 1 to 208 of SEQ ID NO: 14 and amino acids −20 to −1 of SEQ ID NO: 14 are a signal peptide. In another aspect, the mature polypeptide is amino acids 1 to 208 of SEQ ID NO: 15.

In one aspect, the mature polypeptide is amino acids 1 to 207 of SEQ ID NO: 17 and amino acids −18 to −1 of SEQ ID NO: 17 are a signal peptide. In another aspect, the mature polypeptide is amino acids 1 to 207 of SEQ ID NO: 18.

In one aspect, the mature polypeptide is amino acids 1 to 208 of SEQ ID NO: 20 and amino acids −19 to −1 of SEQ ID NO: 20 are a signal peptide. In another aspect, the mature polypeptide is amino acids 1 to 208 of SEQ ID NO: 21.

In one aspect, the mature polypeptide is amino acids 1 to 207 of SEQ ID NO: 23 and amino acids −18 to −1 of SEQ ID NO: 23 are a signal peptide. In another aspect, the mature polypeptide is amino acids 1 to 207 of SEQ ID NO: 24.

In one aspect, the mature polypeptide is amino acids 1 to 207 of SEQ ID NO: 26 and amino acids −16 to −1 of SEQ ID NO: 26 are a signal peptide. In another aspect, the mature polypeptide is amino acids 1 to 207 of SEQ ID NO: 27.

In one aspect, the mature polypeptide is amino acids 1 to 207 of SEQ ID NO: 29 and amino acids −22 to −1 of SEQ ID NO: 29 are a signal peptide. In another aspect, the mature polypeptide is amino acids 1 to 207 of SEQ ID NO: 30.

In one aspect, the mature polypeptide is amino acids 1 to 208 of SEQ ID NO: 32 and amino acids −20 to −1 of SEQ ID NO: 32 are a signal peptide. In another aspect, the mature polypeptide is amino acids 1 to 208 of SEQ ID NO: 33.

In one aspect, the mature polypeptide is amino acids 1 to 208 of SEQ ID NO: 35 and amino acids −19 to −1 of SEQ ID NO: 35 are a signal peptide. In another aspect, the mature polypeptide is amino acids 1 to 208 of SEQ ID NO: 36.

In one aspect, the mature polypeptide is amino acids 1 to 206 of SEQ ID NO: 38 and amino acids −17 to −1 of SEQ ID NO: 38 are a signal peptide. In another aspect, the mature polypeptide is amino acids 1 to 206 of SEQ ID NO: 39.

In one aspect, the mature polypeptide is amino acids 1 to 207 of SEQ ID NO: 41 and amino acids −17 to −1 of SEQ ID NO: 41 are a signal peptide. In another aspect, the mature polypeptide is amino acids 1 to 207 of SEQ ID NO: 42.

In one aspect, the mature polypeptide is amino acids 1 to 216 of SEQ ID NO: 44 and amino acids −17 to −1 of SEQ ID NO: 44 are a signal peptide. In another aspect, the mature polypeptide is amino acids 1 to 216 of SEQ ID NO: 45.

In one aspect, the mature polypeptide is amino acids 1 to 218 of SEQ ID NO: 47 and amino acids −18 to −1 of SEQ ID NO: 47 are a signal peptide. In another aspect, the mature polypeptide is amino acids 1 to 218 of SEQ ID NO: 48.

In one aspect, the mature polypeptide is amino acids 1 to 204 of SEQ ID NO: 50 and amino acids −19 to −1 of SEQ ID NO: 50 are a signal peptide. In another aspect, the mature polypeptide is amino acids 1 to 204 of SEQ ID NO: 51.

In one aspect, the mature polypeptide is amino acids 1 to 203 of SEQ ID NO: 53 and amino acids −19 to −1 of SEQ ID NO: 53 are a signal peptide. In another aspect, the mature polypeptide is amino acids 1 to 203 of SEQ ID NO: 54.

In one aspect, the mature polypeptide is amino acids 1 to 209 of SEQ ID NO: 56 and amino acids −20 to −1 of SEQ ID NO: 56 are a signal peptide. In another aspect, the mature polypeptide is amino acids 1 to 209 of SEQ ID NO: 57.

In one aspect, the mature polypeptide is amino acids 1 to 208 of SEQ ID NO: 59 and amino acids −17 to −1 of SEQ ID NO: 59 are a signal peptide. In another aspect, the mature polypeptide is amino acids 1 to 208 of SEQ ID NO: 60.

In one aspect, the mature polypeptide is amino acids 1 to 210 of SEQ ID NO: 62 and amino acids −22 to −1 of SEQ ID NO: 62 are a signal peptide. In another aspect, the mature polypeptide is amino acids 1 to 210 of SEQ ID NO: 63.

In one aspect, the mature polypeptide is amino acids 1 to 207 of SEQ ID NO: 65 and amino acids −17 to −1 of SEQ ID NO: 65 are a signal peptide. In another aspect, the mature polypeptide is amino acids 1 to 207 of SEQ ID NO: 66.

In one aspect, the mature polypeptide is amino acids 1 to 207 of SEQ ID NO: 68 and amino acids −19 to −1 of SEQ ID NO: 68 are a signal peptide. In another aspect, the mature polypeptide is amino acids 1 to 207 of SEQ ID NO: 69.

In one aspect, the mature polypeptide is amino acids 1 to 208 of SEQ ID NO: 71 and amino acids −17 to −1 of SEQ ID NO: 71 are a signal peptide. In another aspect, the mature polypeptide is amino acids 1 to 208 of SEQ ID NO: 72.

In one aspect, the mature polypeptide is amino acids 1 to 217 of SEQ ID NO: 74 and amino acids −18 to −1 of SEQ ID NO: 74 are a signal peptide. In another aspect, the mature polypeptide is amino acids 1 to 217 of SEQ ID NO: 75.

In one aspect, the mature polypeptide is amino acids 1 to 208 of SEQ ID NO: 77 and amino acids −20 to −1 of SEQ ID NO: 77 are a signal peptide. In another aspect, the mature polypeptide is amino acids 1 to 208 of SEQ ID NO: 80.

In one aspect, the mature polypeptide is amino acids 1 to 201 of SEQ ID NO: 82 and amino acids −15 to −1 of SEQ ID NO: 82 are a signal peptide. In another aspect, the mature polypeptide is amino acids 1 to 201 of SEQ ID NO: 83.

In one aspect, the mature polypeptide is amino acids 1 to 202 of SEQ ID NO: 85 and amino acids −16 to −1 of SEQ ID NO: 85 are a signal peptide. In another aspect, the mature polypeptide is amino acids 1 to 202 of SEQ ID NO: 86.

In one aspect, the mature polypeptide is amino acids 1 to 207 of SEQ ID NO: 88 and amino acids −17 to −1 of SEQ ID NO: 88 are a signal peptide. In another aspect, the mature polypeptide is amino acids 1 to 207 of SEQ ID NO: 89.

In one aspect, the mature polypeptide is amino acids 1 to 202 of SEQ ID NO: 91 and amino acids −20 to −1 of SEQ ID NO: 91 are a signal peptide. In another aspect, the mature polypeptide is amino acids 1 to 202 of SEQ ID NO: 92.

In one aspect, the mature polypeptide is amino acids 1 to 201 of SEQ ID NO: 94 and amino acids −17 to −1 of SEQ ID NO: 94 are a signal peptide. In another aspect, the mature polypeptide is amino acids 1 to 201 of SEQ ID NO: 95.

In one aspect, the mature polypeptide is amino acids 1 to 202 of SEQ ID NO: 97 and amino acids −16 to −1 of SEQ ID NO: 97 are a signal peptide. In another aspect, the mature polypeptide is amino acids 1 to 202 of SEQ ID NO: 98.

In one aspect, the mature polypeptide is amino acids 1 to 206 of SEQ ID NO: 100 and amino acids −18 to −1 of SEQ ID NO: 100 are a signal peptide. In another aspect, the mature polypeptide is amino acids 1 to 206 of SEQ ID NO: 101.

In one aspect, the mature polypeptide is amino acids 1 to 202 of SEQ ID NO: 103 and amino acids −16 to −1 of SEQ ID NO: 103 are a signal peptide. In another aspect, the mature polypeptide is amino acids 1 to 202 of SEQ ID NO: 104.

In one aspect, the mature polypeptide is amino acids 1 to 202 of SEQ ID NO: 106 and amino acids −17 to −1 of SEQ ID NO: 106 are a signal peptide. In another aspect, the mature polypeptide is amino acids 1 to 202 of SEQ ID NO: 107.

In one aspect, the mature polypeptide is amino acids 1 to 202 of SEQ ID NO: 109 and amino acids −17 to −1 of SEQ ID NO: 109 are a signal peptide. In another aspect, the mature polypeptide is amino acids 1 to 202 of SEQ ID NO: 110.

In one aspect, the mature polypeptide is amino acids 1 to 202 of SEQ ID NO: 112 and amino acids −17 to −1 of SEQ ID NO: 112 are a signal peptide. In another aspect, the mature polypeptide is amino acids 1 to 202 of SEQ ID NO: 113.

In one aspect, the mature polypeptide is amino acids 1 to 206 of SEQ ID NO: 115 and amino acids −18 to −1 of SEQ ID NO: 115 are a signal peptide. In another aspect, the mature polypeptide is amino acids 1 to 206 of SEQ ID NO: 116.

In one aspect, the mature polypeptide is amino acids 1 to 207 of SEQ ID NO: 118 and amino acids −20 to −1 of SEQ ID NO: 118 are a signal peptide. In another aspect, the mature polypeptide is amino acids 1 to 207 of SEQ ID NO: 119.

In one aspect, the mature polypeptide is amino acids 1 to 208 of SEQ ID NO: 121 and amino acids −19 to −1 of SEQ ID NO: 121 are a signal peptide. In another aspect, the mature polypeptide is amino acids 1 to 208 of SEQ ID NO: 122.

In one aspect, the mature polypeptide is amino acids 1 to 215 of SEQ ID NO: 124 and amino acids −18 to −1 of SEQ ID NO: 124 are a signal peptide. In another aspect, the mature polypeptide is amino acids 1 to 215 of SEQ ID NO: 125.

In one aspect, the mature polypeptide is amino acids 1 to 217 of SEQ ID NO: 127 and amino acids −20 to −1 of SEQ ID NO: 127 are a signal peptide. In another aspect, the mature polypeptide is amino acids 1 to 217 of SEQ ID NO: 128.

In one aspect, the mature polypeptide is amino acids 1 to 214 of SEQ ID NO: 130 and amino acids −16 to −1 of SEQ ID NO: 130 are a signal peptide. In another aspect, the mature polypeptide is amino acids 1 to 214 of SEQ ID NO: 131.

In one aspect, the mature polypeptide is amino acids 1 to 208 of SEQ ID NO: 133 and amino acids −18 to −1 of SEQ ID NO: 133 are a signal peptide. In another aspect, the mature polypeptide is amino acids 1 to 208 of SEQ ID NO: 134.

In one aspect, the mature polypeptide is amino acids 1 to 203 of SEQ ID NO: 136 and amino acids −19 to −1 of SEQ ID NO: 136 are a signal peptide. In another aspect, the mature polypeptide is amino acids 1 to 203 of SEQ ID NO: 137.

In one aspect, the mature polypeptide is amino acids 1 to 216 of SEQ ID NO: 139 and amino acids −17 to −1 of SEQ ID NO: 139 are a signal peptide. In another aspect, the mature polypeptide is amino acids 1 to 216 of SEQ ID NO: 140.

In one aspect, the mature polypeptide is amino acids 1 to 207 of SEQ ID NO: 142 and amino acids −21 to −1 of SEQ ID NO: 142 are a signal peptide. In another aspect, the mature polypeptide is amino acids 1 to 207 of SEQ ID NO: 143.

In one aspect, the mature polypeptide is amino acids 1 to 208 of SEQ ID NO: 145 and amino acids −17 to −1 of SEQ ID NO: 145 are a signal peptide. In another aspect, the mature polypeptide is amino acids 1 to 208 of SEQ ID NO: 146.

In one aspect, the mature polypeptide is amino acids 1 to 207 of SEQ ID NO: 148 and amino acids −20 to −1 of SEQ ID NO: 148 are a signal peptide. In another aspect, the mature polypeptide is amino acids 1 to 207 of SEQ ID NO: 149.

In one aspect, the mature polypeptide is amino acids 1 to 207 of SEQ ID NO: 151 and amino acids −20 to −1 of SEQ ID NO: 151 are a signal peptide. In another aspect, the mature polypeptide is amino acids 1 to 207 of SEQ ID NO: 152.

In one aspect, the mature polypeptide is amino acids 1 to 207 of SEQ ID NO: 154 and amino acids −19 to −1 of SEQ ID NO: 154 are a signal peptide. In another aspect, the mature polypeptide is amino acids 1 to 207 of SEQ ID NO: 155.

In one aspect, the mature polypeptide is amino acids 1 to 208 of SEQ ID NO: 157 and amino acids −18 to −1 of SEQ ID NO: 157 are a signal peptide. In another aspect, the mature polypeptide is amino acids 1 to 208 of SEQ ID NO: 158.

In one aspect, the mature polypeptide is amino acids 1 to 207 of SEQ ID NO: 218 and amino acids −17 to −1 of SEQ ID NO: 218 are a signal peptide. In another aspect, the mature polypeptide is amino acids 1 to 207 of SEQ ID NO: 221.

In one aspect, the mature polypeptide is amino acids 1 to 207 of SEQ ID NO: 223 and amino acids −19 to −1 of SEQ ID NO: 223 are a signal peptide. In another aspect, the mature polypeptide is amino acids 1 to 207 of SEQ ID NO: 224.

In one aspect, the mature polypeptide is amino acids 1 to 208 of SEQ ID NO: 226 and amino acids −20 to −1 of SEQ ID NO: 226 are a signal peptide. In another aspect, the mature polypeptide is amino acids 1 to 208 of SEQ ID NO: 227.

In one aspect, the mature polypeptide is amino acids 1 to 207 of SEQ ID NO: 229 and amino acids −20 to −1 of SEQ ID NO: 229 are a signal peptide. In another aspect, the mature polypeptide is amino acids 1 to 207 of SEQ ID NO: 230.

In one aspect, the mature polypeptide is amino acids 1 to 207 of SEQ ID NO: 232 and amino acids −20 to −1 of SEQ ID NO: 232 are a signal peptide. In another aspect, the mature polypeptide is amino acids 1 to 207 of SEQ ID NO: 233.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having lysozyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operably linked: The term "operably linked" means a configuration in which a control sequence is placed at an appropriate position relative to the coding sequence of a polynucleotide such that the control sequence directs expression of the coding sequence.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labelled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having lysozyme activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 150%, e.g., at least 175%, at least 200%, at least 225%, at least 250%, at least 275%, at least 300%, at least 350%, or at least 400% of the lysozyme activity of SEQ ID NO: 159.

In one aspect, the variant of the present invention has at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the variant of the present invention has at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

Nomenclature

For purposes of the present invention, the nomenclature [E/Q] means that the amino acid at this position may be a glutamic acid (Glu, E) or a glutamine (Gln, Q). Likewise the nomenclature [V/G/A/l] means that the amino acid at this position may be a valine (Val, V), glycine (Gly, G), alanine (Ala, A) or isoleucine (lie, I), and so forth for other combinations as described herein. Unless otherwise limited further, the amino acid X is defined such that it may be any of the 20 natural amino acids.

Methods of Hydrolysing Peptidoglycan in Bacterial Cell Walls

In the first aspect, the invention relates to a method of hydrolysing peptidoglycan in bacterial cell walls comprising treating bacterial cells with one or more GH25 polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;
(b) a polypeptide having at least 84%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;
(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;

(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

Granules Comprising Polypeptides Having Lysozyme Activity

In a second aspect, the invention relates to a granule comprising one or more GH25 polypeptides having lysozyme activity, wherein the polypeptide is selected from the group consisting of:
(a) a polypeptide having at least 80%, such as at least 85%, at least 90% or at least 95% sequence identity to the polypeptide of SEQ ID NO: 3;
(b) a polypeptide having at least 84%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;
(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;

(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 μL of 0.7 μg/mL lysozyme in phosphate buffer (5 mM citrate, 5 mM $K_2HPO_4$, 0.01% TritonX-100, pH 5.0)) is mixed with *Micrococcus lysodeikticus* solution (450 μL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 μL) is mixed with HCl (50 μL 3.2M) and incubated at 95° C. for 80 min; NaOH (50 μL, 3.5 M) is added and 150 μL of the sample is added to 4-hydroxybenzhydrazide in K—Na tartrate/NaOH buffer (75 μL of 50 g/L K—Na tartrate+20 g/L NaOH); the mixture is incubated at 95° C. for 10 min; and the optical density is measured at 405 nm.

In one embodiment of the second aspect, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1, 2-propylene glycol, 1, 3-propylene glycol, sodium sulfate, dextrin, cellulose, sodium thiosulfate, kaolin and calcium carbonate.

In a further embodiment to any part of the second aspect, the granule comprises a core particle and one or more coatings. In a preferred embodiment, the coating comprises salt and/or wax and/or flour.

In one embodiment, the granule comprises one or more additional enzymes. The one or more additional enzymes is preferably selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

In one embodiment, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediocosus acidilactici, Pediococcus* sp., *Propionibacterium thoenii, Propionibacterium* sp. and *Streptococcus* sp. or any combination thereof.

Polypeptides Having Lysozyme Activity

In a third aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 2.

In a continuation of the third aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 3. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 3.

In one embodiment, the invention relates to polypeptides having lysozyme activity and having a sequence identity to SEQ ID NO: 3 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 3 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 2. In one embodiment, the polypeptide preferably comprises or consists of the amino acid sequence of SEQ ID NO: 3; comprises the amino acid sequence of SEQ ID NO: 3 and a N-terminal and/or C-terminal His-tag and/or HQ-tag; comprises the amino acid sequence of SEQ ID NO: 3 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 3. In one embodiment, the polypeptide comprises or consists of amino acids 1 to 207 of SEQ ID NO: 3. In an embodiment, the polypeptide has been isolated.

In a continuation of the third aspect, the invention relates to a polypeptide having lysozyme activity encoded by a polynucleotide having a sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the third aspect, the invention relates to variants of SEQ ID NO: 3 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In one embodiment, the number of substitutions and/or deletions and/or insertions in SEQ ID NO: 3 is not more than 10, e.g., 1, 2, 3, 4, 5, 6, 7, 8, 9 or 10. In a further embodiment, the number of substitutions, preferably conservative substitutions, in SEQ ID NO: 3 is not more than 10, e.g., 1, 2, 3, 4, 5, 6, 7, 8, 9 or 10.

In an embodiment of the third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide or a fusion polypeptide.

In a fourth aspect the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 5. In one embodiment, the polypeptides differ by up to 22 amino acids, e.g., 1, 2, 3, 4, 5, 6, 7, 8, 9, 10, 11, 12, 13, 14, 15, 16, 17, 18, 19, 20, 21 or 22 amino acids from the mature polypeptide of SEQ ID NO: 5.

In a continuation of the fourth aspect, the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to SEQ ID NO: 6. In one embodiment, the polypeptides differ by up to 22 amino acids, e.g., 1, 2, 3, 4, 5, 6, 7, 8, 9, 10, 11, 12, 13, 14, 15, 16, 17, 18, 19, 20, 21 or 22 amino acids from the mature polypeptide of SEQ ID NO: 6.

In one embodiment, the invention relates to polypeptides having lysozyme activity and having a sequence identity to SEQ ID NO: 6 of at least 89% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 6 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 6 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 5. In one embodiment, the polypeptide preferably comprises or consists of the amino acid sequence of SEQ ID NO: 6; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 6. In one embodiment, the polypeptide comprises or consists of amino acids 1 to 201 of SEQ ID NO: 6. In an embodiment, the polypeptide has been isolated.

In a continuation of the fourth aspect, the invention relates to a polypeptide having lysozyme activity encoded by a polynucleotide having a sequence identity to the mature polypeptide coding sequence of SEQ ID NO: 4 of at least 89%, e.g., at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fourth aspect, the invention relates to variants of SEQ ID NO: 6 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 6 is not more than 22, e.g., 1, 2, 3, 4, 5, 6, 7, 8, 9, 10, 11, 12, 13, 14, 15, 16, 17, 18, 19, 20, 21 or 22. In an embodiment, the number of positions comprising one or more amino acid substitutions, and/or one or more amino acid deletions, and/or one or more amino acid insertions or any combination thereof in SEQ ID NO: 6 is not more than 10, e.g., 1, 2, 3, 4, 5, 6, 7, 8, 9 or 10. In one embodiment, the number of substitutions and/or deletions and/or insertions in SEQ ID NO: 6 is not more than 10, e.g., 1, 2, 3, 4, 5, 6, 7, 8, 9 or 10. In a further embodiment, the number of substitutions, preferably conservative substitutions, in SEQ ID NO: 6 is not more than 10, e.g., 1, 2, 3, 4, 5, 6, 7, 8, 9 or 10. Examples of amino acid changes and conservative substitutions are described in the third aspect of the invention.

In an embodiment of the fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 acids from the mature polypeptide of SEQ ID NO: 8.

In a continuation of the fifth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 9.

In one embodiment, the invention relates to polypeptides having lysozyme activity and having a sequence identity to SEQ ID NO: 9 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 9 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 8. In one embodiment, the polypeptide preferably comprises or consists of the amino acid sequence of SEQ ID NO: 9; comprises the amino acid sequence of SEQ ID NO: 9 and a N-terminal and/or C-terminal His-tag and/or HQ-tag; comprises the amino acid sequence of SEQ ID NO: 9 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 9. In one embodiment, the polypeptide comprises or consists of amino acids 1 to 201 of SEQ ID NO: 9. In an embodiment, the polypeptide has been isolated.

In a continuation of the fifth aspect, the invention relates to a polypeptide having lysozyme activity encoded by a polynucleotide having a sequence identity to the mature polypeptide coding sequence of SEQ ID NO: 7 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifth aspect, the invention relates to variants of SEQ ID NO: 9 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 9 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In one embodiment, the number of substitutions and/or deletions and/or insertions in SEQ ID NO: 9 is not more than 10, e.g., 1, 2, 3, 4, 5, 6, 7, 8, 9 or 10. In a further embodiment, the number of substitutions, preferably conservative substitutions, in SEQ ID NO: 9 is not more than 10, e.g., 1, 2, 3, 4, 5, 6, 7, 8, 9 or 10. Examples of amino acid changes and conservative substitutions are described in the third aspect of the invention.

In an embodiment of the fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 11. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 11.

In a continuation of the sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 12.

In one embodiment, the invention relates to polypeptides having lysozyme activity and having a sequence identity to SEQ ID NO: 12 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 12 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 11. In one embodiment, the polypeptide preferably comprises or consists of the amino acid sequence of SEQ ID NO: 12; comprises the amino acid sequence of SEQ ID NO: 12 and a N-terminal and/or C-terminal His-tag and/or HQ-tag; comprises the amino acid sequence of SEQ ID NO: 12 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 12. In one embodiment, the polypeptide comprises or consists of amino acids 1 to 203 of SEQ ID NO: 12. In an embodiment, the polypeptide has been isolated.

In a continuation of the sixth aspect, the invention relates to a polypeptide having lysozyme activity encoded by a polynucleotide having a sequence identity to the mature polypeptide coding sequence of SEQ ID NO: 10 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the sixth aspect, the invention relates to variants of SEQ ID NO: 12 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 12 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In one embodiment, the number of substitutions and/or deletions and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. Examples of amino acid changes and conservative substitutions are described in the third aspect of the invention.

In an embodiment of the sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the sixth aspect comprises the motif YKNA (SEQ ID NO: 160) and/or the motif FGGW[S/T] (SEQ ID NO: 161).

In a seventh aspect the invention relates to polypeptides having lysozyme activity having at least 97%, e.g., at least 97.5%, at least 98%, at least 98.5%, at least 99%, at least 99.5%, or 100% sequence identity to the mature polypeptide of SEQ ID NO: 14. In one embodiment, the polypeptides differ by up to 6 amino acids, e.g., 1, 2, 3, 4, 5 or 6 amino acids from the mature polypeptide of SEQ ID NO: 14.

In a continuation of the seventh aspect, the invention relates to polypeptides having lysozyme activity having at least 97%, e.g., at least 97.5%, at least 98%, at least 98.5%, at least 99%, at least 99.5%, or 100% sequence identity to SEQ ID NO: 15. In one embodiment, the polypeptides differ by up to 6 amino acids, e.g., 1, 2, 3, 4, 5 or 6 amino acids from the mature polypeptide of SEQ ID NO: 15.

In one embodiment, the invention relates to polypeptides having lysozyme activity and having a sequence identity to SEQ ID NO: 15 of at least 97% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 15 of at least 98% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 15 of at least 99% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 14. In one embodiment, the polypeptide preferably comprises or consists of the amino acid sequence of SEQ ID NO: 15; comprises the amino acid sequence of SEQ ID NO: 15 and a N-terminal and/or C-terminal His-tag and/or HQ-tag; comprises the amino acid sequence of SEQ ID NO: 15 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 15. In one embodiment, the polypeptide comprises or consists of amino acids 1 to 208 of SEQ ID NO: 15. In an embodiment, the polypeptide has been isolated.

In a continuation of the seventh aspect, the invention relates to a polypeptide having lysozyme activity encoded by a polynucleotide having a sequence identity to the mature polypeptide coding sequence of SEQ ID NO: 13 of at least 97%, e.g., at least 97.5%, at least 98%, at least 98.5%, at least 99%, at least 99.5%, or 100%. In a further embodiment, the polypeptide has been isolated.

In an embodiment of the seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the seventh aspect, the invention relates to variants of SEQ ID NO: 15 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 6, e.g., 1, 2, 3, 4, 5 or 6. In an embodiment, the number of positions comprising one or more amino acid substitutions, and/or one or more amino acid deletions, and/or one or more amino acid insertions or any combination thereof in SEQ ID NO: 15 is not more than 6, e.g., 1, 2, 3, 4, 5 or 6. In one embodiment, the number of substitutions and/or deletions and/or insertions in SEQ ID NO: 15 is not more than 6, e.g., 1, 2, 3, 4, 5 or 6. In a further embodiment, the number of substitutions, preferably conservative substitutions, in SEQ ID NO: 15 is not more than 6, e.g., 1, 2, 3, 4, 5 or 6. Examples of amino acid changes and conservative substitutions are described in the third aspect of the invention.

In an embodiment of the seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a eighth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 17. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 17.

In a continuation of the eighth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 18.

In one embodiment, the invention relates to polypeptides having lysozyme activity and having a sequence identity to SEQ ID NO: 18 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 18 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 18 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 18 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 17. In one embodiment, the polypeptide preferably comprises or consists of the amino acid sequence of SEQ ID NO: 18; comprises the amino acid sequence of SEQ ID NO: 18 and a N-terminal and/or C-terminal His-tag and/or HQ-tag; comprises the amino acid sequence of SEQ ID NO: 18 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 18. In one embodiment, the polypeptide comprises or consists of amino acids 1 to 207 of SEQ ID NO: 18. In an embodiment, the polypeptide has been isolated.

In a continuation of the eighth aspect, the invention relates to a polypeptide having lysozyme activity encoded by a polynucleotide having a sequence identity to the mature polypeptide coding sequence of SEQ ID NO: 16 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eighth aspect, the invention relates to variants of SEQ ID NO: 18 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 18 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In one embodiment, the number of substitutions and/or deletions and/or insertions in SEQ ID NO: 18 is not more than 10, e.g., 1, 2, 3, 4, 5, 6, 7, 8, 9 or 10. In a further embodiment, the number of substitutions, preferably conservative substitutions, in SEQ ID NO: 18 is not more than 10, e.g., 1, 2, 3, 4, 5, 6, 7, 8, 9 or 10. Examples of amino acid changes and conservative substitutions are described in the third aspect of the invention.

In an embodiment of the eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 23. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 23.

In a continuation of the ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 24.

In one embodiment, the invention relates to polypeptides having lysozyme activity and having a sequence identity to SEQ ID NO: 24 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 24 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 23. In one embodiment, the polypeptide preferably comprises or consists of the amino acid sequence of SEQ ID NO: 24; comprises the amino acid sequence of SEQ ID NO: 24 and a N-terminal and/or C-terminal His-tag and/or HQ-tag; comprises the amino acid sequence of SEQ ID NO: 24 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 24. In one embodiment, the polypeptide comprises or consists of amino acids 1 to 207 of SEQ ID NO: 24. In an embodiment, the polypeptide has been isolated.

In a continuation of the ninth aspect, the invention relates to a polypeptide having lysozyme activity encoded by a polynucleotide having a sequence identity to the mature polypeptide coding sequence of SEQ ID NO: 22 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the ninth aspect, the invention relates to variants of SEQ ID NO: 24 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 24 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 24 is not more than 10, e.g., 1, 2, 3, 4, 5, 6, 7, 8, 9 or 10. In one embodiment, the number of substitutions and/or deletions and/or insertions in SEQ ID NO: 24 is not more than 10, e.g., 1, 2, 3, 4, 5, 6, 7, 8, 9 or 10. In a further embodiment, the number of substitutions, preferably conservative substitutions, in SEQ ID NO: 24 is not more than 10, e.g., 1, 2, 3, 4, 5, 6, 7, 8, 9 or 10. Examples of amino acid changes and conservative substitutions are described in the third aspect of the invention.

In an embodiment of the ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a tenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 26. In one embodiment, the polypeptides differ by up to 40 amino acids, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 26.

In a continuation of the tenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 27.

In one embodiment, the invention relates to polypeptides having lysozyme activity and having a sequence identity to SEQ ID NO: 27 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 27 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 26. In one embodiment, the polypeptide preferably comprises or consists of the amino acid sequence of SEQ ID NO: 27; comprises the amino acid sequence of SEQ ID NO: 27 and a N-terminal and/or C-terminal His-tag and/or HQ-tag; comprises the amino acid sequence of SEQ ID NO: 27 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 27. In one embodiment, the polypeptide comprises or consists of amino acids 1 to 207 of SEQ ID NO: 27. In an embodiment, the polypeptide has been isolated.

In a continuation of the tenth aspect, the invention relates to a polypeptide having lysozyme activity encoded by a polynucleotide having a sequence identity to the mature polypeptide coding sequence of SEQ ID NO: 25 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the tenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the tenth aspect, the invention relates to variants of SEQ ID NO: 27 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In one embodiment, the number of substitutions and/or deletions and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10. Examples of amino acid changes and conservative substitutions are described in the third aspect of the invention.

In an embodiment of the tenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the tenth aspect comprises the motif YKNA (SEQ ID NO: 160) and/or the motif FGGW[S/T] (SEQ ID NO: 161).

In an eleventh aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 29. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 29.

In a continuation of the eleventh aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 30.

In one embodiment, the invention relates to polypeptides having lysozyme activity and having a sequence identity to SEQ ID NO: 30 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 30 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 29. In one embodiment, the polypeptide preferably comprises or consists of the amino acid sequence of SEQ ID NO: 30; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 30. In one embodiment, the polypeptide comprises or consists of amino acids 1 to 207 of SEQ ID NO: 30. In an embodiment, the polypeptide has been isolated.

In a continuation of the eleventh aspect, the invention relates to a polypeptide having lysozyme activity encoded by a polynucleotide having a sequence identity to the mature polypeptide coding sequence of SEQ ID NO: 28 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the eleventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eleventh aspect, the invention relates to variants of SEQ ID NO: 30 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 30 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 30 is not more than 10, e.g., 1, 2, 3, 4, 5, 6, 7, 8, 9 or 10. In one embodiment, the number of substitutions and/or deletions and/or insertions in SEQ ID NO: 30 is not more than 10, e.g., 1, 2, 3, 4, 5, 6, 7, 8, 9 or 10. In a further embodiment, the number of substitutions, preferably conservative substitutions, in SEQ ID NO: 30 is not more than 10, e.g., 1, 2, 3, 4, 5, 6, 7, 8, 9 or 10. Examples of amino acid changes and conservative substitutions are described in the third aspect of the invention.

In an embodiment of the eleventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twelfth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 32. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 32.

In a continuation of the twelfth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 33. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 33.

In one embodiment, the invention relates to polypeptides having lysozyme activity and having a sequence identity to SEQ ID NO: 33 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 33 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 32. In one embodiment, the polypeptide preferably comprises or consists of the amino acid sequence of SEQ ID NO: 33; comprises the amino acid sequence of SEQ ID NO: 33 and a N-terminal and/or C-terminal His-tag and/or HQ-tag; comprises the amino acid sequence of SEQ ID NO: 33 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 33. In one embodiment, the polypeptide comprises or consists of amino acids 1 to 208 of SEQ ID NO: 33. In an embodiment, the polypeptide has been isolated.

In a continuation of the twelfth aspect, the invention relates to a polypeptide having lysozyme activity encoded by a polynucleotide having a sequence identity to the mature polypeptide coding sequence of SEQ ID NO: 31 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twelfth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twelfth aspect, the invention relates to variants of SEQ ID NO: 33 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 33 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 33 is not more than 10, e.g., 1, 2, 3, 4, 5, 6, 7, 8, 9 or 10. In one embodiment, the number of substitutions and/or deletions and/or insertions in SEQ ID NO: 33 is not more than 10, e.g., 1, 2, 3, 4, 5, 6, 7, 8, 9 or 10. In a further embodiment, the number of substitutions, preferably conservative substitutions, in SEQ ID NO: 33 is not more than 10, e.g., 1, 2, 3, 4, 5, 6, 7, 8, 9 or 10. Examples of amino acid changes and conservative substitutions are described in the third aspect of the invention.

In an embodiment of the twelfth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirteenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 35. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 35.

In a continuation of the thirteenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 36. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 36.

In one embodiment, the invention relates to polypeptides having lysozyme activity and having a sequence identity to SEQ ID NO: 36 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 90% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 36 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 35. In one embodiment, the polypeptide preferably comprises or consists of the amino acid sequence of SEQ ID NO: 36; comprises the amino acid sequence of SEQ ID NO: 36 and a N-terminal and/or C-terminal His-tag and/or HQ-tag; comprises the amino acid sequence of SEQ ID NO: 36 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 36. In one embodiment, the polypeptide comprises or consists of amino acids 1 to 208 of SEQ ID NO: 36. In an embodiment, the polypeptide has been isolated.

In a continuation of the thirteenth aspect, the invention relates to a polypeptide having lysozyme activity encoded by a polynucleotide having a sequence identity to the mature polypeptide coding sequence of SEQ ID NO: 34 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirteenth aspect, the invention relates to variants of SEQ ID NO: 36 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 36 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 36 is not more than 10, e.g., 1, 2, 3, 4, 5, 6, 7, 8, 9 or 10. In one embodiment, the number of substitutions and/or deletions and/or insertions in SEQ ID NO: 36 is not more than 10, e.g., 1, 2, 3, 4, 5, 6, 7, 8, 9 or 10. In a further embodiment, the number of substitutions, preferably conservative substitutions, in SEQ ID NO: 36 is not more than 10, e.g., 1, 2, 3, 4, 5, 6, 7, 8, 9 or 10. Examples of amino acid changes and conservative substitutions are described in the third aspect of the invention.

In an embodiment of the thirteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fourteenth aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 38. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 38.

In a continuation of the fourteenth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 39. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 39.

In one embodiment, the invention relates to polypeptides having lysozyme activity and having a sequence identity to SEQ ID NO: 39 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 39 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 38. In one embodiment, the polypeptide preferably comprises or consists of the amino acid sequence of SEQ ID NO: 39; comprises the amino acid sequence of SEQ ID NO: 39 and a N-terminal and/or C-terminal His-tag and/or HQ-tag; comprises the amino acid sequence of SEQ ID NO: 39 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 39. In one embodiment, the polypeptide comprises or consists of amino acids 1 to 206 of SEQ ID NO: 39. In an embodiment, the polypeptide has been isolated.

In a continuation of the fourteenth aspect, the invention relates to a polypeptide having lysozyme activity encoded by a polynucleotide having a sequence identity to the mature polypeptide coding sequence of SEQ ID NO: 37 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fourteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fourteenth aspect, the invention relates to variants of SEQ ID NO: 39 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 39 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 39 is not more than 10, e.g., 1, 2, 3, 4, 5, 6, 7, 8, 9 or 10. In one embodiment, the number of substitutions and/or deletions and/or insertions in SEQ ID NO: 39 is not more than 10, e.g., 1, 2, 3, 4, 5, 6, 7, 8, 9 or 10. In a further embodiment, the number of substitutions, preferably conservative substitutions, in SEQ ID NO: 39 is not more than 10, e.g., 1, 2, 3, 4, 5, 6, 7, 8, 9 or 10. Examples of amino acid changes and conservative substitutions are described in the third aspect of the invention.

In an embodiment of the fourteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifteenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 41. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 41.

In a continuation of the fifteenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 42. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 42.

In one embodiment, the invention relates to polypeptides having lysozyme activity and having a sequence identity to SEQ ID NO: 42 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 42 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 41. In one embodiment, the polypeptide preferably comprises or consists of the amino acid sequence of SEQ ID NO: 42; comprises the amino acid sequence of SEQ ID NO: 42 and a N-terminal and/or C-terminal His-tag and/or HQ-tag; comprises the amino acid sequence of SEQ ID NO: 42 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 42. In one embodiment, the polypeptide comprises or consists of amino acids 1 to 207 of SEQ ID NO: 42. In an embodiment, the polypeptide has been isolated.

In a continuation of the fifteenth aspect, the invention relates to a polypeptide having lysozyme activity encoded by a polynucleotide having a sequence identity to the mature polypeptide coding sequence of SEQ ID NO: 40 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifteenth aspect, the invention relates to variants of SEQ ID NO: 42 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 42 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 42 is not more than 10, e.g., 1, 2, 3, 4, 5, 6, 7, 8, 9 or 10. In one embodiment, the number of substitutions and/or deletions and/or insertions in SEQ ID NO: 42 is not more than 10, e.g., 1, 2, 3, 4, 5, 6, 7, 8, 9 or 10. In a further embodiment, the number of substitutions, preferably conservative substitutions, in SEQ ID NO: 42 is not more than 10, e.g., 1, 2, 3, 4, 5, 6, 7, 8, 9 or 10. Examples of amino acid changes and conservative substitutions are described in the third aspect of the invention.

In an embodiment of the fifteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifteenth aspect comprises the motif YKNA (SEQ ID NO: 160) and/or the motif FGGW[S/T] (SEQ ID NO: 161).

In a sixteenth aspect the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 44. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 44.

In a continuation of the sixteenth aspect, the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 45. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 45.

In one embodiment, the invention relates to polypeptides having lysozyme activity and having a sequence identity to SEQ ID NO: 45 of at least 86% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 45 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 45 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 44. In one embodiment, the polypeptide preferably comprises or consists of the amino acid sequence of SEQ ID NO: 45; comprises the amino acid sequence of SEQ ID NO: 45 and a N-terminal and/or C-terminal His-tag and/or HQ-tag; comprises the amino acid sequence of SEQ ID NO: 45 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 45. In one embodiment, the polypeptide comprises or consists of amino acids 1 to 216 of SEQ ID NO: 45. In an embodiment, the polypeptide has been isolated.

In a continuation of the sixteenth aspect, the invention relates to a polypeptide having lysozyme activity encoded by a polynucleotide having a sequence identity to the mature polypeptide coding sequence of SEQ ID NO: 43 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the sixteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the sixteenth aspect, the invention relates to variants of SEQ ID NO: 45 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 45 is not more than 30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In an embodiment, the number of positions comprising one or more amino acid substitutions, and/or one or more amino acid deletions, and/or one or more amino acid insertions or any combination thereof in SEQ ID NO: 45 is not more than 10, e.g., 1, 2, 3, 4, 5, 6, 7, 8, 9 or 10. In one embodiment, the number of substitutions and/or deletions and/or insertions in SEQ ID NO: 45 is not more than 10, e.g., 1, 2, 3, 4, 5, 6, 7, 8, 9 or 10. In a further embodiment, the number of substitutions, preferably conservative substitutions, in SEQ ID NO: 45 is not more than 10, e.g., 1, 2, 3, 4, 5, 6, 7, 8, 9 or 10. Examples of amino acid changes and conservative substitutions are described in the third aspect of the invention.

In an embodiment of the sixteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a seventeenth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 47. In one embodiment, the polypeptides differ by up to 40 amino acids, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 47.

In a continuation of the seventeenth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 48. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 48.

In one embodiment, the invention relates to polypeptides having lysozyme activity and having a sequence identity to SEQ ID NO: 48 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 48 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 47. In one embodiment, the polypeptide preferably comprises or consists of the amino acid sequence of SEQ ID NO: 48; comprises the amino acid sequence of SEQ ID NO: 48 and a N-terminal and/or C-terminal His-tag and/or HQ-tag; comprises the amino acid sequence of SEQ ID NO: 48 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 48. In one embodiment, the polypeptide comprises or consists of amino acids 1 to 218 of SEQ ID NO: 48. In an embodiment, the polypeptide has been isolated.

In a continuation of the seventeenth aspect, the invention relates to a polypeptide having lysozyme activity encoded by a polynucleotide having a sequence identity to the mature polypeptide coding sequence of SEQ ID NO: 46 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the seventeenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the seventeenth aspect, the invention relates to variants of SEQ ID NO: 48 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 48 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 48 is not more than 10, e.g., 1, 2, 3, 4, 5, 6, 7, 8, 9 or 10. In one embodiment, the number of substitutions and/or deletions and/or insertions in SEQ ID NO: 48 is not more than 10, e.g., 1, 2, 3, 4, 5, 6, 7, 8, 9 or 10. In a further embodiment, the number of substitutions, preferably conservative substitutions, in SEQ ID NO: 48 is not more than 10, e.g., 1, 2, 3, 4, 5, 6, 7, 8, 9 or 10. Examples of amino acid changes and conservative substitutions are described in the third aspect of the invention.

In an embodiment of the seventeenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an eighteenth aspect, the invention relates to polypeptides having lysozyme activity having at least 92%, e.g., at least 93%, at least 94%, at least 95%, at least 96%, at least 97%, at least 98%, at least 99%, or 100% sequence identity to the mature polypeptide of SEQ ID NO: 50. In one embodiment, the polypeptides differ by up to 16 amino acids, e.g., 1, 2, 3, 4, 5, 6, 7, 8, 9, 10, 11, 12, 13, 14, 15 or 16 amino acids from the mature polypeptide of SEQ ID NO: 50.

In a continuation of the eighteenth aspect, the invention relates to polypeptides having lysozyme activity having at least 92%, e.g., at least 93%, at least 94%, at least 95%, at least 96%, at least 97%, at least 98%, at least 99%, or 100% sequence identity to SEQ ID NO: 51. In one embodiment, the polypeptides differ by up to 16 amino acids, e.g., 1, 2, 3, 4, 5, 6, 7, 8, 9, 10, 11, 12, 13, 14, 15 or 16 amino acids from the mature polypeptide of SEQ ID NO: 51.

In one embodiment, the invention relates to polypeptides having lysozyme activity and having a sequence identity to SEQ ID NO: 51 of at least 92% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 51 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 50. In one embodiment, the polypeptide preferably comprises or consists of the amino acid sequence of SEQ ID NO: 51; comprises the amino acid sequence of SEQ ID NO: 51 and a N-terminal and/or C-terminal His-tag and/or HQ-tag; comprises the amino acid sequence of SEQ ID NO: 51 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 51. In one embodiment, the polypeptide comprises or consists of amino acids 1 to 204 of SEQ ID NO: 51. In an embodiment, the polypeptide has been isolated.

In a continuation of the eighteenth aspect, the invention relates to a polypeptide having lysozyme activity encoded by a polynucleotide having a sequence identity to the mature polypeptide coding sequence of SEQ ID NO: 49 of at least 92%, e.g., at least 93%, at least 94%, at least 95%, at least 96%, at least 97%, at least 98%, at least 99%, or 100%. In a further embodiment, the polypeptide has been isolated.

In an embodiment of the eighteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the eighteenth aspect, the invention relates to variants of SEQ ID NO: 51 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 51 is not more than 16, e.g., 1, 2, 3, 4, 5, 6, 7, 8, 9, 10, 11, 12, 13, 14, 15 or 16. In an embodiment, the number of positions comprising one or more amino acid substitutions, and/or one or more amino acid deletions, and/or one or more amino acid insertions or any combination thereof in SEQ ID NO: 51 is not more than 10, e.g., 1, 2, 3, 4, 5, 6, 7, 8, 9 or 10. In one embodiment, the number of substitutions and/or deletions and/or insertions in SEQ ID NO: 51 is not more than 10, e.g., 1, 2, 3, 4, 5, 6, 7, 8, 9 or 10. In a further embodiment, the number of substitutions, preferably conservative substitutions, in SEQ ID NO: 51 is not more than 10, e.g., 1, 2, 3, 4, 5, 6, 7, 8, 9 or 10. Examples of amino acid changes and conservative substitutions are described in the third aspect of the invention.

In an embodiment of the eighteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a nineteenth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 53. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 53.

In a continuation of the nineteenth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 54. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 54.

In one embodiment, the invention relates to polypeptides having lysozyme activity and having a sequence identity to SEQ ID NO: 54 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 54 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 53. In one embodiment, the polypeptide preferably comprises or consists of the amino acid sequence of SEQ ID NO: 54; comprises the amino acid sequence of SEQ ID NO: 54 and a N-terminal and/or C-terminal His-tag and/or HQ-tag; comprises the amino acid sequence of SEQ ID NO: 54 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 54. In one embodiment, the polypeptide comprises or consists of amino acids 1 to 203 of SEQ ID NO: 54. In an embodiment, the polypeptide has been isolated.

In a continuation of the nineteenth aspect, the invention relates to a polypeptide having lysozyme activity encoded by a polynucleotide having a sequence identity to the mature polypeptide coding sequence of SEQ ID NO: 52 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the nineteenth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the nineteenth aspect, the invention relates to variants of SEQ ID NO: 54 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 54 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 54 is not more than 10, e.g., 1, 2, 3, 4, 5, 6, 7, 8, 9 or 10. In one embodiment, the number of substitutions and/or deletions and/or insertions in SEQ ID NO: 54 is not more than 10, e.g., 1, 2, 3, 4, 5, 6, 7, 8, 9 or 10. In a further embodiment, the number of substitutions, preferably conservative substitutions, in SEQ ID NO: 54 is not more than 10, e.g., 1, 2, 3, 4, 5, 6, 7, 8, 9 or 10. Examples of amino acid changes and conservative substitutions are described in the third aspect of the invention.

In an embodiment of the nineteenth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twentieth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 56. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 56.

In a continuation of the twentieth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 57. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 57.

In one embodiment, the invention relates to polypeptides having lysozyme activity and having a sequence identity to SEQ ID NO: 57 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 57 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 56. In one embodiment, the polypeptide preferably comprises or consists of the amino acid sequence of SEQ ID NO: 57; comprises the amino acid sequence of SEQ ID NO: 57 and a N-terminal and/or C-terminal His-tag and/or HQ-tag; comprises the amino acid sequence of SEQ ID NO: 57 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 57. In one embodiment, the polypeptide comprises or consists of amino acids 1 to 209 of SEQ ID NO: 57. In an embodiment, the polypeptide has been isolated.

In a continuation of the twentieth aspect, the invention relates to a polypeptide having lysozyme activity encoded by a polynucleotide having a sequence identity to the mature polypeptide coding sequence of SEQ ID NO: 55 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twentieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twentieth aspect, the invention relates to variants of SEQ ID NO: 57 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 57 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 57 is not more than 10, e.g., 1, 2, 3, 4, 5, 6, 7, 8, 9 or 10. In one embodiment, the number of substitutions and/or deletions and/or insertions in SEQ ID NO: 57 is not more than 10, e.g., 1, 2, 3, 4, 5, 6, 7, 8, 9 or 10. In a further embodiment, the number of substitutions, preferably conservative substitutions, in SEQ ID NO: 57 is not more than 10, e.g., 1, 2, 3, 4, 5, 6, 7, 8, 9 or 10. Examples of amino acid changes and conservative substitutions are described in the third aspect of the invention.

In an embodiment of the twentieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twentieth aspect comprises the motif YKNA (SEQ ID NO: 160) and/or the motif FGGW[S/T] (SEQ ID NO: 161).

In a twenty-first aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 59. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 59.

In a continuation of the twenty-first aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 60. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 60.

In one embodiment, the invention relates to polypeptides having lysozyme activity and having a sequence identity to SEQ ID NO: 60 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 60 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 59. In one embodiment, the polypeptide preferably comprises or consists of the amino acid sequence of SEQ ID NO: 60; comprises the amino acid sequence of SEQ ID NO: 60 and a N-terminal and/or C-terminal His-tag and/or HQ-tag; comprises the amino acid sequence of SEQ ID NO: 60 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 60. In one embodiment, the polypeptide comprises or consists of amino acids 1 to 208 of SEQ ID NO: 60. In an embodiment, the polypeptide has been isolated.

In a continuation of the twenty-first aspect, the invention relates to a polypeptide having lysozyme activity encoded by a polynucleotide having a sequence identity to the mature polypeptide coding sequence of SEQ ID NO: 58 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-first aspect, the invention relates to variants of SEQ ID NO: 60 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 60 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 60 is not more than 10, e.g., 1, 2, 3, 4, 5, 6, 7, 8, 9 or 10. In one embodiment, the number of substitutions and/or deletions and/or insertions in SEQ ID NO: 60 is not more than 10, e.g., 1, 2, 3, 4, 5, 6, 7, 8, 9 or 10. In a further embodiment, the number of substitutions, preferably conservative substitutions, in SEQ ID NO: 60 is not more than 10, e.g., 1, 2, 3, 4, 5, 6, 7, 8, 9 or 10. Examples of amino acid changes and conservative substitutions are described in the third aspect of the invention.

In an embodiment of the twenty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-second aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 62. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 62.

In a continuation of the twenty-second aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 63. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 63.

In one embodiment, the invention relates to polypeptides having lysozyme activity and having a sequence identity to SEQ ID NO: 63 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 63 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 62. In one embodiment, the polypeptide preferably comprises or consists of the amino acid sequence of SEQ ID NO: 63; comprises the amino acid sequence of SEQ ID NO: 63 and a N-terminal and/or C-terminal His-tag and/or HQ-tag; comprises the amino acid sequence of SEQ ID NO: 63 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 63. In one embodiment, the polypeptide comprises or consists of amino acids 1 to 210 of SEQ ID NO: 63. In an embodiment, the polypeptide has been isolated.

In a continuation of the twenty-second aspect, the invention relates to a polypeptide having lysozyme activity encoded by a polynucleotide having a sequence identity to the mature polypeptide coding sequence of SEQ ID NO: 61 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-second aspect, the invention relates to variants of SEQ ID NO: 63 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 63 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 63 is not more than 10, e.g., 1, 2, 3, 4, 5, 6, 7, 8, 9 or 10. In one embodiment, the number of substitutions and/or deletions and/or insertions in SEQ ID NO: 63 is not more than 10, e.g., 1, 2, 3, 4, 5, 6, 7, 8, 9 or 10. In a further embodiment, the number of substitutions, preferably conservative substitutions, in SEQ ID NO: 63 is not more than 10, e.g., 1, 2, 3, 4, 5, 6, 7, 8, 9 or 10. Examples of amino acid changes and conservative substitutions are described in the third aspect of the invention.

In an embodiment of the twenty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-second aspect comprises the motif YKNA (SEQ ID NO: 160) and/or the motif FGGW[S/T] (SEQ ID NO: 161).

In a twenty-third aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 65. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 65.

In a continuation of the twenty-third aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 66. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 66.

In one embodiment, the invention relates to polypeptides having lysozyme activity and having a sequence identity to SEQ ID NO: 66 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 66 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 65. In one embodiment, the polypeptide preferably comprises or consists of the amino acid sequence of SEQ ID NO: 66; comprises the amino acid sequence of SEQ ID NO: 66 and a N-terminal and/or C-terminal His-tag and/or HQ-tag; comprises the amino acid sequence of SEQ ID NO: 66 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 66. In one embodiment, the polypeptide comprises or consists of amino acids 1 to 207 of SEQ ID NO: 66. In an embodiment, the polypeptide has been isolated.

In a continuation of the twenty-third aspect, the invention relates to a polypeptide having lysozyme activity encoded by a polynucleotide having a sequence identity to the mature polypeptide coding sequence of SEQ ID NO: 64 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-third aspect, the invention relates to variants of SEQ ID NO: 66 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 66 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 66 is not more than 10, e.g., 1, 2, 3, 4, 5, 6, 7, 8, 9 or 10. In one embodiment, the number of substitutions and/or deletions and/or insertions in SEQ ID NO: 66 is not more than 10, e.g., 1, 2, 3, 4, 5, 6, 7, 8, 9 or 10. In a further embodiment, the number of substitutions, preferably conservative substitutions, in SEQ ID NO: 66 is not more than 10, e.g., 1, 2, 3, 4, 5, 6, 7, 8, 9 or 10. Examples of amino acid changes and conservative substitutions are described in the third aspect of the invention.

In an embodiment of the twenty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-third aspect comprises the motif YKNA (SEQ ID NO: 160) and/or the motif FGGW[S/T] (SEQ ID NO: 161).

In a twenty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 68. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 68.

In a continuation of the twenty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 69. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 69.

In one embodiment, the invention relates to polypeptides having lysozyme activity and having a sequence identity to SEQ ID NO: 69 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 69 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 69 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 69 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 68. In one embodiment, the polypeptide preferably comprises or consists of the amino acid sequence of SEQ ID NO: 69; comprises the amino acid sequence of SEQ ID NO: 69 and a N-terminal and/or C-terminal His-tag and/or HQ-tag; comprises the amino acid sequence of SEQ ID NO: 69 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 69. In one embodiment, the polypeptide comprises or consists of amino acids 1 to 207 of SEQ ID NO: 69. In an embodiment, the polypeptide has been isolated.

In a continuation of the twenty-fourth aspect, the invention relates to a polypeptide having lysozyme activity encoded by a polynucleotide having a sequence identity to the mature polypeptide coding sequence of SEQ ID NO: 67 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-fourth aspect, the invention relates to variants of SEQ ID NO: 69 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 69 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 69 is not more than 10, e.g., 1, 2, 3, 4, 5, 6, 7, 8, 9 or 10. In one embodiment, the number of substitutions and/or deletions and/or insertions in SEQ ID NO: 69 is not more than 10, e.g., 1, 2, 3, 4, 5, 6, 7, 8, 9 or 10. In a further embodiment, the number of substitutions, preferably conservative substitutions, in SEQ ID NO: 69 is not more than 10, e.g., 1, 2, 3, 4, 5, 6, 7, 8, 9 or 10. Examples of amino acid changes and conservative substitutions are described in the third aspect of the invention.

In an embodiment of the twenty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-fifth aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 71. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 71.

In a continuation of the twenty-fifth aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 72. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 72.

In one embodiment, the invention relates to polypeptides having lysozyme activity and having a sequence identity to SEQ ID NO: 72 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 72 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 71. In one embodiment, the polypeptide preferably comprises or consists of the amino acid sequence of SEQ ID NO: 72; comprises the amino acid sequence of SEQ ID NO: 72 and a N-terminal and/or C-terminal His-tag and/or HQ-tag; comprises the amino acid sequence of SEQ ID NO: 72 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 72. In one embodiment, the polypeptide comprises or consists of amino acids 1 to 208 of SEQ ID NO: 72. In an embodiment, the polypeptide has been isolated.

In a continuation of the twenty-fifth aspect, the invention relates to a polypeptide having lysozyme activity encoded by a polynucleotide having a sequence identity to the mature polypeptide coding sequence of SEQ ID NO: 70 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-fifth aspect, the invention relates to variants of SEQ ID NO: 72 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 72 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 72 is not more than 10, e.g., 1, 2, 3, 4, 5, 6, 7, 8, 9 or 10. In one embodiment, the number of substitutions and/or deletions and/or insertions in SEQ ID NO: 72 is not more than 10, e.g., 1, 2, 3, 4, 5, 6, 7, 8, 9 or 10. In a further embodiment, the number of substitutions, preferably conservative substitutions, in SEQ ID NO: 72 is not more than 10, e.g., 1, 2, 3, 4, 5, 6, 7, 8, 9 or 10. Examples of amino acid changes and conservative substitutions are described in the third aspect of the invention.

In an embodiment of the twenty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 74. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 74.

In a continuation of the twenty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 75. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 75.

In one embodiment, the invention relates to polypeptides having lysozyme activity and having a sequence identity to SEQ ID NO: 75 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 75 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 74. In one embodiment, the polypeptide preferably comprises or consists of the amino acid sequence of SEQ ID NO: 75; comprises the amino acid sequence of SEQ ID NO: 75 and a N-terminal and/or C-terminal His-tag and/or HQ-tag; comprises the amino acid sequence of SEQ ID NO: 75 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 75. In one embodiment, the polypeptide comprises or consists of amino acids 1 to 217 of SEQ ID NO: 75. In an embodiment, the polypeptide has been isolated.

In a continuation of the twenty-sixth aspect, the invention relates to a polypeptide having lysozyme activity encoded by a polynucleotide having a sequence identity to the mature polypeptide coding sequence of SEQ ID NO: 73 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-sixth aspect, the invention relates to variants of SEQ ID NO: 75 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 75 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 75 is not more than 10, e.g., 1, 2, 3, 4, 5, 6, 7, 8, 9 or 10. In one embodiment, the number of substitutions and/or deletions and/or insertions in SEQ ID NO: 75 is not more than 10, e.g., 1, 2, 3, 4, 5, 6, 7, 8, 9 or 10. In a further embodiment, the number of substitutions, preferably conservative substitutions, in SEQ ID NO: 75 is not more than 10, e.g., 1, 2, 3, 4, 5, 6, 7, 8, 9 or 10. Examples of amino acid changes and conservative substitutions are described in the third aspect of the invention.

In an embodiment of the twenty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-seventh aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 77. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 77.

In a continuation of the twenty-seventh aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 79. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 79.

In a continuation of the twenty-seventh aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 80. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from SEQ ID NO: 80.

In one embodiment, the invention relates to polypeptides having lysozyme activity and having a sequence identity to SEQ ID NO: 80 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 80 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 77. In one embodiment, the polypeptide comprises or consists of the mature polypeptide of SEQ ID NO: 79. In one embodiment, the polypeptide preferably comprises or consists of the amino acid sequence of SEQ ID NO: 80; comprises the amino acid sequence of SEQ ID NO: 80 and a N-terminal and/or C-terminal His-tag and/or HQ-tag; comprises the amino acid sequence of SEQ ID NO: 80 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 80. In one embodiment, the polypeptide comprises or consists of amino acids 1 to 208 of SEQ ID NO: 80. In an embodiment, the polypeptide has been isolated.

In a continuation of the twenty-seventh aspect, the invention relates to a polypeptide having lysozyme activity encoded by a polynucleotide having a sequence identity to the mature polypeptide coding sequence of SEQ ID NO: 76 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-seventh aspect, the invention relates to variants of SEQ ID NO: 80 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 80 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 80 is not more than 10, e.g., 1, 2, 3, 4, 5, 6, 7, 8, 9 or 10. In one embodiment, the number of substitutions and/or deletions and/or insertions in SEQ ID NO: 80 is not more than 10, e.g., 1, 2, 3, 4, 5, 6, 7, 8, 9 or 10. In a further embodiment, the number of substitutions, preferably conservative substitutions, in SEQ ID NO: 80 is not more than 10, e.g., 1, 2, 3, 4, 5, 6, 7, 8, 9 or 10. Examples of amino acid changes and conservative substitutions are described in the third aspect of the invention.

In an embodiment of the twenty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the twenty-seventh aspect comprises the motif YKNA (SEQ ID NO: 160) and/or the motif FGGW[S/T] (SEQ ID NO: 161).

In a twenty-eighth aspect the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 82. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 82.

In a continuation of the twenty-eighth aspect, the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 83. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 83.

In one embodiment, the invention relates to polypeptides having lysozyme activity and having a sequence identity to SEQ ID NO: 83 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 83 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 82. In one embodiment, the polypeptide preferably comprises or consists of the amino acid sequence of SEQ ID NO: 83; comprises the amino acid sequence of SEQ ID NO: 83 and a N-terminal and/or C-terminal His-tag and/or HQ-tag; comprises the amino acid sequence of SEQ ID NO: 83 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 83. In one embodiment, the polypeptide comprises or consists of amino acids 1 to 201 of SEQ ID NO: 83. In an embodiment, the polypeptide has been isolated.

In a continuation of the twenty-eighth aspect, the invention relates to a polypeptide having lysozyme activity encoded by a polynucleotide having a sequence identity to the mature polypeptide coding sequence of SEQ ID NO: 81 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-eighth aspect, the invention relates to variants of SEQ ID NO: 83 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 83 is not more than 36 e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. In an embodiment, the number of positions comprising one or more amino acid substitutions, and/or one or more amino acid deletions, and/or one or more amino acid insertions or any combination thereof in SEQ ID NO: 83 is not more than 10, e.g., 1, 2, 3, 4, 5, 6, 7, 8, 9 or 10. In one embodiment, the number of substitutions and/or deletions and/or insertions in SEQ ID NO: 83 is not more than 10, e.g., 1, 2, 3, 4, 5, 6, 7, 8, 9 or 10. In a further embodiment, the number of substitutions, preferably conservative substitutions, in SEQ ID NO: 83 is not more than 10, e.g., 1, 2, 3, 4, 5, 6, 7, 8, 9 or 10. Examples of amino acid changes and conservative substitutions are described in the third aspect of the invention.

In an embodiment of the twenty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a twenty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 85. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 85.

In a continuation of the twenty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 86. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 86.

In one embodiment, the invention relates to polypeptides having lysozyme activity and having a sequence identity to SEQ ID NO: 86 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 86 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 85. In one embodiment, the polypeptide preferably comprises or consists of the amino acid sequence of SEQ ID NO: 86; comprises the amino acid sequence of SEQ ID NO: 86 and a N-terminal and/or C-terminal His-tag and/or HQ-tag; comprises the amino acid sequence of SEQ ID NO: 86 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 86. In one embodiment, the polypeptide comprises or consists of amino acids 1 to 202 of SEQ ID NO: 86. In an embodiment, the polypeptide has been isolated.

In a continuation of the twenty-ninth aspect, the invention relates to a polypeptide having lysozyme activity encoded by a polynucleotide having a sequence identity to the mature polypeptide coding sequence of SEQ ID NO: 84 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the twenty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the twenty-ninth aspect, the invention relates to variants of SEQ ID NO: 86 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 86 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 86 is not more than 10, e.g., 1, 2, 3, 4, 5, 6, 7, 8, 9 or 10. In one embodiment, the number of substitutions and/or deletions and/or insertions in SEQ ID NO: 86 is not more than 10, e.g., 1, 2, 3, 4, 5, 6, 7, 8, 9 or 10. In a further embodiment, the number of substitutions, preferably conservative substitutions, in SEQ ID NO: 86 is not more than 10, e.g., 1, 2, 3, 4, 5, 6, 7, 8, 9 or 10. Examples of amino acid changes and conservative substitutions are described in the third aspect of the invention.

In an embodiment of the twenty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirtieth aspect the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 88. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 88.

In a continuation of the thirtieth aspect, the invention relates to polypeptides having lysozyme activity having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 89. In one embodiment, the polypeptides differ by up to 28 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27 or 28 amino acids from the mature polypeptide of SEQ ID NO: 89.

In one embodiment, the invention relates to polypeptides having lysozyme activity and having a sequence identity to SEQ ID NO: 89 of at least 86% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 89 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 89 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 88. In one embodiment, the polypeptide preferably comprises or consists of the amino acid sequence of SEQ ID NO: 89; comprises the amino acid sequence of SEQ ID NO: 89 and a N-terminal and/or C-terminal His-tag and/or HQ-tag; comprises the amino acid sequence of SEQ ID NO: 89 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 89. In one embodiment, the polypeptide comprises or consists of amino acids 1 to 207 of SEQ ID NO: 89. In an embodiment, the polypeptide has been isolated.

In a continuation of the thirtieth aspect, the invention relates to a polypeptide having lysozyme activity encoded by a polynucleotide having a sequence identity to the mature polypeptide coding sequence of SEQ ID NO: 87 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirtieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirtieth aspect, the invention relates to variants of SEQ ID NO: 89 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 89 is not more than 28, e.g., 1, 2, 3, 4, 5, 6, 7, 8, 9, 10, 11, 12, 13, 14, 15, 16, 17, 18, 19, 20, 21, 22, 23, 24, 25, 26, 27 or 28. In an embodiment, the number of positions comprising one or more amino acid substitutions, and/or one or more amino acid deletions, and/or one or more amino acid insertions or any combination thereof in SEQ ID NO: 89 is not more than 10, e.g., 1, 2, 3, 4, 5, 6, 7, 8, 9 or 10. In one embodiment, the number of substitutions and/or deletions and/or insertions in SEQ ID NO: 89 is not more than 10, e.g., 1, 2, 3, 4, 5, 6, 7, 8, 9 or 10. In a further embodiment, the number of substitutions, preferably conservative substitutions, in SEQ ID NO: 89 is not more than 10, e.g., 1, 2, 3, 4, 5, 6, 7, 8, 9 or 10. Examples of amino acid changes and conservative substitutions are described in the third aspect of the invention.

In an embodiment of the thirtieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-first aspect the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 91. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 91.

In a continuation of the thirty-first aspect, the invention relates to polypeptides having lysozyme activity having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 92. In one embodiment, the polypeptides differ by up to 36 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 amino acids from the mature polypeptide of SEQ ID NO: 92.

In one embodiment, the invention relates to polypeptides having lysozyme activity and having a sequence identity to SEQ ID NO: 92 of at least 82% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 92 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 91. In one embodiment, the polypeptide preferably comprises or consists of the amino acid sequence of SEQ ID NO: 92; comprises the amino acid sequence of SEQ ID NO: 92 and a N-terminal and/or C-terminal His-tag and/or HQ-tag; comprises the amino acid sequence of SEQ ID NO: 92 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 92. In one embodiment, the polypeptide comprises or consists of amino acids 1 to 202 of SEQ ID NO: 92. In an embodiment, the polypeptide has been isolated.

In a continuation of the thirty-first aspect, the invention relates to a polypeptide having lysozyme activity encoded by a polynucleotide having a sequence identity to the mature polypeptide coding sequence of SEQ ID NO: 90 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-first aspect, the invention relates to variants of SEQ ID NO: 92 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 92 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. In an embodiment, the number of positions comprising one or more amino acid substitutions, and/or one or more amino acid deletions, and/or one or more amino acid insertions or any combination thereof in SEQ ID NO: 92 is not more than 10, e.g., 1, 2, 3, 4, 5, 6, 7, 8, 9 or 10. In one embodiment, the number of substitutions and/or deletions and/or insertions in SEQ ID NO: 92 is not more than 10, e.g., 1, 2, 3, 4, 5, 6, 7, 8, 9 or 10. In a further embodiment, the number of substitutions, preferably conservative substitutions, in SEQ ID NO: 92 is not more than 10, e.g., 1, 2, 3, 4, 5, 6, 7, 8, 9 or 10. Examples of amino acid changes and conservative substitutions are described in the third aspect of the invention.

In an embodiment of the thirty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-second aspect the invention relates to polypeptides having lysozyme activity having at least 94%, e.g., at least 95%, at least 96%, at least 97%, at least 98%, at least 99%, or 100% sequence identity to the mature polypeptide of SEQ ID NO: 94. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 94.

In a continuation of the thirty-second aspect, the invention relates to polypeptides having lysozyme activity having at least 94%, e.g., at least 95%, at least 96%, at least 97%, at least 98%, at least 99%, or 100% sequence identity to SEQ ID NO: 95. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 95.

In one embodiment, the invention relates to polypeptides having lysozyme activity and having a sequence identity to SEQ ID NO: 95 of at least 94% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 95 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 94. In one embodiment, the polypeptide preferably comprises or consists of the amino acid sequence of SEQ ID NO: 95; comprises the amino acid sequence of SEQ ID NO: 95 and a N-terminal and/or C-terminal His-tag and/or HQ-tag; comprises the amino acid sequence of SEQ ID NO: 95 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 95. In one embodiment, the polypeptide comprises or consists of amino acids 1 to 201 of SEQ ID NO: 95. In an embodiment, the polypeptide has been isolated.

In a continuation of the thirty-second aspect, the invention relates to a polypeptide having lysozyme activity encoded by a polynucleotide having a sequence identity to the mature polypeptide coding sequence of SEQ ID NO: 93 of at least 94%, e.g., at least 95%, at least 96%, at least 97%, at least 98%, at least 99%, or 100%. In a further embodiment, the polypeptide has been isolated.

In an embodiment of the thirty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-second aspect, the invention relates to variants of SEQ ID NO: 95 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 95 is not more than 12, e.g., 1, 2, 3, 4, 5, 6, 7, 8, 9, 10, 11 or 12. In an embodiment, the number of positions comprising one or more amino acid substitutions, and/or one or more amino acid deletions, and/or one or more amino acid insertions or any combination thereof in SEQ ID NO: 95 is not more than 10, e.g., 1, 2, 3, 4, 5, 6, 7, 8, 9 or 10. In one embodiment, the number of substitutions and/or deletions and/or insertions in SEQ ID NO: 95 is not more than 10, e.g., 1, 2, 3, 4, 5, 6, 7, 8, 9 or 10. In a further embodiment, the number of substitutions, preferably conservative substitutions, in SEQ ID NO: 95 is not more than 10, e.g., 1, 2, 3, 4, 5, 6, 7, 8, 9 or 10. Examples of amino acid changes and conservative substitutions are described in the third aspect of the invention.

In an embodiment of the thirty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-third aspect the invention relates to polypeptides having lysozyme activity having at least 94%, e.g., at least 95%, at least 96%, at least 97%, at least 98%, at least 99%, or 100% sequence identity to the mature polypeptide of SEQ ID NO: 97. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 97.

In a continuation of the thirty-third aspect, the invention relates to polypeptides having lysozyme activity having at least 94%, e.g., at least 95%, at least 96%, at least 97%, at least 98%, at least 99%, or 100% sequence identity to SEQ ID NO: 98. In one embodiment, the polypeptides differ by up to 12 amino acids, e.g., 1, 2, 3, 4, 5, 6, 7, 8, 9, 10, 11 or 12 amino acids from the mature polypeptide of SEQ ID NO: 98.

In one embodiment, the invention relates to polypeptides having lysozyme activity and having a sequence identity to SEQ ID NO: 98 of at least 94% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 98 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 97. In one embodiment, the polypeptide preferably comprises or consists of the amino acid sequence of SEQ ID NO: 98; comprises the amino acid sequence of SEQ ID NO: 98 and a N-terminal and/or C-terminal His-tag and/or HQ-tag; comprises the amino acid sequence of SEQ ID NO: 98 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 98. In one embodiment, the polypeptide comprises or consists of amino acids 1 to 202 of SEQ ID NO: 98. In an embodiment, the polypeptide has been isolated.

In a continuation of the thirty-third aspect, the invention relates to a polypeptide having lysozyme activity encoded by a polynucleotide having a sequence identity to the mature polypeptide coding sequence of SEQ ID NO: 96 of at least 94%, e.g., at least 95%, at least 96%, at least 97%, at least 98%, at least 99%, or 100%. In a further embodiment, the polypeptide has been isolated.

In an embodiment of the thirty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-third aspect, the invention relates to variants of SEQ ID NO: 98 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 98 is not more than 12, e.g., 1, 2, 3, 4, 5, 6, 7, 8, 9, 10, 11 or 12. In an embodiment, the number of positions comprising one or more amino acid substitutions, and/or one or more amino acid deletions, and/or one or more amino acid insertions or any combination thereof in SEQ ID NO: 98 is not more than 10, e.g., 1, 2, 3, 4, 5, 6, 7, 8, 9 or 10. In one embodiment, the number of substitutions and/or deletions and/or insertions in SEQ ID NO: 98 is not more than 10, e.g., 1, 2, 3, 4, 5, 6, 7, 8, 9 or 10. In a further embodiment, the number of substitutions, preferably conservative substitutions, in SEQ ID NO: 98 is not more than 10, e.g., 1, 2, 3, 4, 5, 6, 7, 8, 9 or 10. Examples of amino acid changes and conservative substitutions are described in the third aspect of the invention.

In an embodiment of the thirty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 100. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 100.

In a continuation of the thirty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 101. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 101.

In one embodiment, the invention relates to polypeptides having lysozyme activity and having a sequence identity to SEQ ID NO: 101 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 101 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 100. In one embodiment, the polypeptide preferably comprises or consists of the amino acid sequence of SEQ ID NO: 101; comprises the amino acid sequence of SEQ ID NO: 101 and a N-terminal and/or C-terminal His-tag and/or HQ-tag; comprises the amino acid sequence of SEQ ID NO: 101 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 101. In one embodiment, the polypeptide comprises or consists of amino acids 1 to 206 of SEQ ID NO: 101. In an embodiment, the polypeptide has been isolated.

In a continuation of the thirty-fourth aspect, the invention relates to a polypeptide having lysozyme activity encoded by a polynucleotide having a sequence identity to the mature polypeptide coding sequence of SEQ ID NO: 99 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-fourth aspect, the invention relates to variants of SEQ ID NO: 101 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 101 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 101 is not more than 10, e.g., 1, 2, 3, 4, 5, 6, 7, 8, 9 or 10. In one embodiment, the number of substitutions and/or deletions and/or insertions in SEQ ID NO: 101 is not more than 10, e.g., 1, 2, 3, 4, 5, 6, 7, 8, 9 or 10. In a further embodiment, the number of substitutions, preferably conservative substitutions, in SEQ ID NO: 101 is not more than 10, e.g., 1, 2, 3, 4, 5, 6, 7, 8, 9 or 10. Examples of amino acid changes and conservative substitutions are described in the third aspect of the invention.

In an embodiment of the thirty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-fifth aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 103. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 103.

In a continuation of the thirty-fifth aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 104. In one embodiment, the polypeptides differ by up to 38 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 104.

In one embodiment, the invention relates to polypeptides having lysozyme activity and having a sequence identity to SEQ ID NO: 104 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 104 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 103. In one embodiment, the polypeptide preferably comprises or consists of the amino acid sequence of SEQ ID NO: 104; comprises the amino acid sequence of SEQ ID NO: 104 and a N-terminal and/or C-terminal His-tag and/or HQ-tag; comprises the amino acid sequence of SEQ ID NO: 104 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 104. In one embodiment, the polypeptide comprises or consists of amino acids 1 to 202 of SEQ ID NO: 104. In an embodiment, the polypeptide has been isolated.

In a continuation of the thirty-fifth aspect, the invention relates to a polypeptide having lysozyme activity encoded by a polynucleotide having a sequence identity to the mature polypeptide coding sequence of SEQ ID NO: 102 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-fifth aspect, the invention relates to variants of SEQ ID NO: 104 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 104 is not more than 38, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38. In an embodiment, the number of positions comprising one or more amino acid substitutions, and/or one or more amino acid deletions, and/or one or more amino acid insertions or any combination thereof in SEQ ID NO: 104 is not more than 10, e.g., 1, 2, 3, 4, 5, 6, 7, 8, 9 or 10. In one embodiment, the number of substitutions and/or deletions and/or insertions in SEQ ID NO: 104 is not more than 10, e.g., 1, 2, 3, 4, 5, 6, 7, 8, 9 or 10. In a further embodiment, the number of substitutions, preferably conservative substitutions, in SEQ ID NO: 104 is not more than 10, e.g., 1, 2, 3, 4, 5, 6, 7, 8, 9 or 10.

Examples of amino acid changes and conservative substitutions are described in the third aspect of the invention.

In an embodiment of the thirty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 106. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 106.

In a continuation of the thirty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 107. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 107.

In one embodiment, the invention relates to polypeptides having lysozyme activity and having a sequence identity to SEQ ID NO: 107 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 107 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 106. In one embodiment, the polypeptide preferably comprises or consists of the amino acid sequence of SEQ ID NO: 107; comprises the amino acid sequence of SEQ ID NO: 107 and a N-terminal and/or C-terminal His-tag and/or HQ-tag; comprises the amino acid sequence of SEQ ID NO: 107 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 107. In one embodiment, the polypeptide comprises or consists of amino acids 1 to 202 of SEQ ID NO: 107. In an embodiment, the polypeptide has been isolated.

In a continuation of the thirty-sixth aspect, the invention relates to a polypeptide having lysozyme activity encoded by a polynucleotide having a sequence identity to the mature polypeptide coding sequence of SEQ ID NO: 105 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-sixth aspect, the invention relates to variants of SEQ ID NO: 107 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 107 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 107 is not more than 10, e.g., 1, 2, 3, 4, 5, 6, 7, 8, 9 or 10. In one embodiment, the number of substitutions and/or deletions and/or insertions in SEQ ID NO: 107 is not more than 10, e.g., 1, 2, 3, 4, 5, 6, 7, 8, 9 or 10. In a further embodiment, the number of substitutions, preferably conservative substitutions, in SEQ ID NO: 107 is not more than 10, e.g., 1, 2, 3, 4, 5, 6, 7, 8, 9 or 10. Examples of amino acid changes and conservative substitutions are described in the third aspect of the invention.

In an embodiment of the thirty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-seventh aspect the invention relates to polypeptides having lysozyme activity having at least 88%, e.g., at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 109. In one embodiment, the polypeptides differ by up to 24 amino acids, e.g., 1, 2, 3, 4, 5, 6, 7, 8, 9, 10, 11, 12, 13, 14, 15, 16, 17, 18, 19, 20, 21, 22, 23 or 24 amino acids from the mature polypeptide of SEQ ID NO: 109.

In a continuation of the thirty-seventh aspect, the invention relates to polypeptides having lysozyme activity having at least 88%, e.g., at least 89%, at least 90%, at least 91%, at least 92%, at least 93%, at least 94%, at least 95%, at least 96%, at least 97%, at least 98%, at least 99%, or 100% sequence identity to SEQ ID NO: 110. In one embodiment, the polypeptides differ by up to 24 amino acids, e.g., 1, 2, 3, 4, 5, 6, 7, 8, 9, 10, 11, 12, 13, 14, 15, 16, 17, 18, 19, 20, 21, 22, 23 or 24 amino acids from the mature polypeptide of SEQ ID NO: 110.

In one embodiment, the invention relates to polypeptides having lysozyme activity and having a sequence identity to SEQ ID NO: 110 of at least 88% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 110 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 110 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 109. In one embodiment, the polypeptide preferably comprises or consists of the amino acid sequence of SEQ ID NO: 110; comprises the amino acid sequence of SEQ ID NO: 110 and a N-terminal and/or C-terminal His-tag and/or HQ-tag; comprises the amino acid sequence of SEQ ID NO: 110 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 110. In one embodiment, the polypeptide comprises or consists of amino acids 1 to 202 of SEQ ID NO: 110. In an embodiment, the polypeptide has been isolated.

In a continuation of the thirty-seventh aspect, the invention relates to a polypeptide having lysozyme activity encoded by a polynucleotide having a sequence identity to the mature polypeptide coding sequence of SEQ ID NO: 108 of at least 88%, e.g., at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-seventh aspect, the invention relates to variants of SEQ ID NO: 110 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 110 is not more than 24, e.g., 1, 2, 3, 4, 5, 6, 7, 8, 9, 10, 11, 12, 13, 14, 15, 16, 17, 18, 19, 20, 21, 22, 23 or 24. In an embodiment, the number of positions comprising one or more amino acid substitutions, and/or one or more amino acid deletions, and/or one or more amino acid insertions or any combination thereof in SEQ ID NO: 110 is not more than 10, e.g., 1, 2, 3, 4, 5, 6, 7, 8, 9 or 10. In one embodiment, the number of substitutions and/or deletions and/or insertions in SEQ ID NO: 110 is not more than 10, e.g., 1, 2, 3, 4, 5, 6, 7, 8, 9 or 10. In a further embodiment, the number of substitutions, preferably conservative substitutions, in SEQ ID NO: 110 is not more than 10, e.g., 1, 2, 3, 4, 5, 6, 7, 8, 9 or 10. Examples of amino acid changes and conservative substitutions are described in the third aspect of the invention.

In an embodiment of the thirty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-eighth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 112. In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 112.

In a continuation of the thirty-eighth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 113.

In one embodiment, the polypeptides differ by up to 30 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids from the mature polypeptide of SEQ ID NO: 113.

In one embodiment, the invention relates to polypeptides having lysozyme activity and having a sequence identity to SEQ ID NO: 113 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 113 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 113 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 112. In one embodiment, the polypeptide preferably comprises or consists of the amino acid sequence of SEQ ID NO: 113; comprises the amino acid sequence of SEQ ID NO: 113 and a N-terminal and/or C-terminal His-tag and/or HQ-tag; comprises the amino acid sequence of SEQ ID NO: 113 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 113. In one embodiment, the polypeptide comprises or consists of amino acids 1 to 202 of SEQ ID NO: 113. In an embodiment, the polypeptide has been isolated.

In a continuation of the thirty-eighth aspect, the invention relates to a polypeptide having lysozyme activity encoded by a polynucleotide having a sequence identity to the mature polypeptide coding sequence of SEQ ID NO: 111 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-eighth aspect, the invention relates to variants of SEQ ID NO: 113 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 113 is not more than 30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In an embodiment, the number of positions comprising one or more amino acid substitutions, and/or one or more amino acid deletions, and/or one or more amino acid insertions or any combination thereof in SEQ ID NO: 113 is not more than 10, e.g., 1, 2, 3, 4, 5, 6, 7, 8, 9 or 10. In one embodiment, the number of substitutions and/or deletions and/or insertions in SEQ ID NO: 113 is not more than 10, e.g., 1, 2, 3, 4, 5, 6, 7, 8, 9 or 10. In a further embodiment, the number of substitutions, preferably conservative substitutions, in SEQ ID NO: 113 is not more than 10, e.g., 1, 2, 3, 4, 5, 6, 7, 8, 9 or 10. Examples of amino acid changes and conservative substitutions are described in the third aspect of the invention.

In an embodiment of the thirty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a thirty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 115. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 115.

In a continuation of the thirty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 116. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 116.

In one embodiment, the invention relates to polypeptides having lysozyme activity and having a sequence identity to SEQ ID NO: 116 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 116 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 115. In one embodiment, the polypeptide preferably comprises or consists of the amino acid sequence of SEQ ID NO: 116; comprises the amino acid sequence of SEQ ID NO: 116 and a N-terminal and/or C-terminal His-tag and/or HQ-tag; comprises the amino acid sequence of SEQ ID NO: 116 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 116. In one embodiment, the polypeptide comprises or consists of amino acids 1 to 206 of SEQ ID NO: 116. In an embodiment, the polypeptide has been isolated.

In a continuation of the thirty-ninth aspect, the invention relates to a polypeptide having lysozyme activity encoded by a polynucleotide having a sequence identity to the mature polypeptide coding sequence of SEQ ID NO: 114 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the thirty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the thirty-ninth aspect, the invention relates to variants of SEQ ID NO: 116 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 116 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 116 is not more than 10, e.g., 1, 2, 3, 4, 5, 6, 7, 8, 9 or 10. In one embodiment, the number of substitutions and/or deletions and/or insertions in SEQ ID NO: 116 is not more than 10, e.g., 1, 2, 3, 4, 5, 6, 7, 8, 9 or 10. In a further embodiment, the number of substitutions, preferably conservative substitutions, in SEQ ID NO: 116 is not more than 10, e.g., 1, 2, 3, 4, 5, 6, 7, 8, 9 or 10. Examples of amino acid changes and conservative substitutions are described in the third aspect of the invention.

In an embodiment of the thirty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fortieth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 118. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 118.

In a continuation of the fortieth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 119. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 119.

In one embodiment, the invention relates to polypeptides having lysozyme activity and having a sequence identity to SEQ ID NO: 119 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 119 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 118. In one embodiment, the polypeptide preferably comprises or consists of the amino acid sequence of SEQ ID NO: 119; comprises the amino acid sequence of SEQ ID NO: 119 and a N-terminal and/or C-terminal His-tag and/or HQ-tag; comprises the amino acid sequence of SEQ ID NO: 119 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 119. In one embodiment, the polypeptide comprises or consists of amino acids 1 to 207 of SEQ ID NO: 119. In an embodiment, the polypeptide has been isolated.

In a continuation of the fortieth aspect, the invention relates to a polypeptide having lysozyme activity encoded by a polynucleotide having a sequence identity to the mature polypeptide coding sequence of SEQ ID NO: 117 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fortieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fortieth aspect, the invention relates to variants of SEQ ID NO: 119 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 119 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 119 is not more than 10, e.g., 1, 2, 3, 4, 5, 6, 7, 8, 9 or 10. In one embodiment, the number of substitutions and/or deletions and/or insertions in SEQ ID NO: 119 is not more than 10, e.g., 1, 2, 3, 4, 5, 6, 7, 8, 9 or 10. In a further embodiment, the number of substitutions, preferably conservative substitutions, in SEQ ID NO: 119 is not more than 10, e.g., 1, 2, 3, 4, 5, 6, 7, 8, 9 or 10. Examples of amino acid changes and conservative substitutions are described in the third aspect of the invention.

In an embodiment of the fortieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-first aspect the invention relates to polypeptides having lysozyme activity having at least 96.5%, e.g., at least 97%, at least 97.5%, at least 98%, at least 98.5%, at least 99%, at least 99.5%, or 100% sequence identity to the mature polypeptide of SEQ ID NO: 121.

In one embodiment, the polypeptides differ by up to 7 amino acids, e.g., 1, 2, 3, 4, 5, 6 or 7 amino acids from the mature polypeptide of SEQ ID NO: 121.

In a continuation of the forty-first aspect, the invention relates to polypeptides having lysozyme activity having at least 96.5%, e.g., at least 97%, at least 97.5%, at least 98%, at least 98.5%, at least 99%, at least 99.5%, or 100% sequence identity to SEQ ID NO: 122. In one embodiment, the polypeptides differ by up to 7 amino acids, e.g., 1, 2, 3, 4, 5, 6 or 7 amino acids from the mature polypeptide of SEQ ID NO: 122.

In one embodiment, the invention relates to polypeptides having lysozyme activity and having a sequence identity to SEQ ID NO: 122 of at least 96.5% and wherein the polypeptide has at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 121. In one embodiment, the polypeptide preferably comprises or consists of the amino acid sequence of SEQ ID NO: 122; comprises the amino acid sequence of SEQ ID NO: 122 and a N-terminal and/or C-terminal His-tag and/or HQ-tag; comprises the amino acid sequence of SEQ ID NO: 122 and a N-terminal and/or C-terminal extension of up to 10 amino acids, e.g., 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 122. In one embodiment, the polypeptide comprises or consists of amino acids 1 to 208 of SEQ ID NO: 122. In an embodiment, the polypeptide has been isolated.

In a continuation of the forty-first aspect, the invention relates to a polypeptide having lysozyme activity encoded by a polynucleotide having a sequence identity to the mature polypeptide coding sequence of SEQ ID NO: 120 of at least 96.5%, e.g., at least 97%, at least 97.5%, at least 98%, at least 98.5%, at least 99%, at least 99.5%, or 100%. In a further embodiment, the polypeptide has been isolated.

In an embodiment of the forty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-first aspect, the invention relates to variants of SEQ ID NO: 122 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 122 is not more than 7, e.g., 1, 2, 3, 4, 5, 6 or 7. In one embodiment, the number of substitutions and/or deletions and/or insertions in SEQ ID NO: 122 is not more than 7, e.g., 1, 2, 3, 4, 5, 6 or 7. In a further embodiment, the number of substitutions, preferably conservative substitutions, in SEQ ID NO: 122 is not more than 7, e.g., 1, 2, 3, 4, 5, 6 or 7. Examples of amino acid changes and conservative substitutions are described in the third aspect of the invention.

In an embodiment of the forty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-second aspect the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 124. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 124.

In a continuation of the forty-second aspect, the invention relates to polypeptides having lysozyme activity having at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 125. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 125.

In one embodiment, the invention relates to polypeptides having lysozyme activity and having a sequence identity to SEQ ID NO: 125 of at least 81% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 125 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 124. In one embodiment, the polypeptide preferably comprises or consists of the amino acid sequence of SEQ ID NO: 125; comprises the amino acid sequence of SEQ ID NO: 125 and a N-terminal and/or C-terminal His-tag and/or HQ-tag; comprises the amino acid sequence of SEQ ID NO: 125 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 125. In one embodiment, the polypeptide comprises or consists of amino acids 1 to 215 of SEQ ID NO: 125. In an embodiment, the polypeptide has been isolated.

In a continuation of the forty-second aspect, the invention relates to a polypeptide having lysozyme activity encoded by a polynucleotide having a sequence identity to the mature polypeptide coding sequence of SEQ ID NO: 123 of at least 81%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-second aspect, the invention relates to variants of SEQ ID NO: 125 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 125 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 125 is not more than 10, e.g., 1, 2, 3, 4, 5, 6, 7, 8, 9 or 10. In one embodiment, the number of substitutions and/or deletions and/or insertions in SEQ ID NO: 125 is not more than 10, e.g., 1, 2, 3, 4, 5, 6, 7, 8, 9 or 10. In a further embodiment, the number of substitutions, preferably conservative substitutions, in SEQ ID NO: 125 is not more than 10, e.g., 1, 2, 3, 4, 5, 6, 7, 8, 9 or 10. Examples of amino acid changes and conservative substitutions are described in the third aspect of the invention.

In an embodiment of the forty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-third aspect the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to the mature polypeptide of SEQ ID NO: 127. In one embodiment, the polypeptides differ by up to 23 amino acids, e.g., 1, 2, 3, 4, 5, 6, 7, 8, 9, 10, 11, 12, 13, 14, 15, 16, 17, 18, 19, 20, 21, 22 or 23 amino acids from the mature polypeptide of SEQ ID NO: 127.

In a continuation of the forty-third aspect, the invention relates to polypeptides having lysozyme activity having at least 89%, e.g., at least 90%, at least 91%, at least 92%, at least 93%, at least 94%, at least 95%, at least 96%, at least 97%, at least 98%, at least 99%, or 100% sequence identity to SEQ ID NO: 128. In one embodiment, the polypeptides differ by up to 23 amino acids, e.g., 1, 2, 3, 4, 5, 6, 7, 8, 9, 10, 11, 12, 13, 14, 15, 16, 17, 18, 19, 20, 21, 22 or 23 amino acids from the mature polypeptide of SEQ ID NO: 128.

In one embodiment, the invention relates to polypeptides having lysozyme activity and having a sequence identity to SEQ ID NO: 128 of at least 89% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 128 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 128 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 127. In one embodiment, the polypeptide preferably comprises or consists of the amino acid sequence of SEQ ID NO: 128;

comprises the amino acid sequence of SEQ ID NO: 128 and a N-terminal and/or C-terminal His-tag and/or HQ-tag; comprises the amino acid sequence of SEQ ID NO: 128 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 128. In one embodiment, the polypeptide comprises or consists of amino acids 1 to 217 of SEQ ID NO: 128. In an embodiment, the polypeptide has been isolated.

In a continuation of the forty-third aspect, the invention relates to a polypeptide having lysozyme activity encoded by a polynucleotide having a sequence identity to the mature polypeptide coding sequence of SEQ ID NO: 126 of at least 89%, e.g., at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-third aspect, the invention relates to variants of SEQ ID NO: 128 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 128 is not more than 23, e.g., 1, 2, 3, 4, 5, 6, 7, 8, 9, 10, 11, 12, 13, 14, 15, 16, 17, 18, 19, 20, 21, 22 or 23. In an embodiment, the number of positions comprising one or more amino acid substitutions, and/or one or more amino acid deletions, and/or one or more amino acid insertions or any combination thereof in SEQ ID NO: 128 is not more than 10, e.g., 1, 2, 3, 4, 5, 6, 7, 8, 9 or 10. In one embodiment, the number of substitutions and/or deletions and/or insertions in SEQ ID NO: 128 is not more than 10, e.g., 1, 2, 3, 4, 5, 6, 7, 8, 9 or 10. In a further embodiment, the number of substitutions, preferably conservative substitutions, in SEQ ID NO: 128 is not more than 10, e.g., 1, 2, 3, 4, 5, 6, 7, 8, 9 or 10. Examples of amino acid changes and conservative substitutions are described in the third aspect of the invention.

In an embodiment of the forty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-fourth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 130. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 130.

In a continuation of the forty-fourth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 131. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 131.

In one embodiment, the invention relates to polypeptides having lysozyme activity and having a sequence identity to SEQ ID NO: 131 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 131 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 130. In one embodiment, the polypeptide preferably comprises or consists of the amino acid sequence of SEQ ID NO: 131; comprises the amino acid sequence of SEQ ID NO: 131 and a N-terminal and/or C-terminal His-tag and/or HQ-tag; comprises the amino acid sequence of SEQ ID NO: 131 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 131. In one embodiment, the polypeptide comprises or consists of amino acids 1 to 214 of SEQ ID NO: 131. In an embodiment, the polypeptide has been isolated.

In a continuation of the forty-fourth aspect, the invention relates to a polypeptide having lysozyme activity encoded by a polynucleotide having a sequence identity to the mature polypeptide coding sequence of SEQ ID NO: 129 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-fourth aspect, the invention relates to variants of SEQ ID NO: 131 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 131 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 131 is not more than 10, e.g., 1, 2, 3, 4, 5, 6, 7, 8, 9 or 10. In one embodiment, the number of substitutions and/or deletions and/or insertions in SEQ ID NO: 131 is not more than 10, e.g., 1, 2, 3, 4, 5, 6, 7, 8, 9 or 10. In a further embodiment, the number of substitutions, preferably conservative substitutions, in SEQ ID NO: 131 is not more than 10, e.g., 1, 2, 3, 4, 5, 6, 7, 8, 9 or 10. Examples of amino acid changes and conservative substitutions are described in the third aspect of the invention.

In an embodiment of the forty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-fifth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 133. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 133.

In a continuation of the forty-fifth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 134. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 134.

In one embodiment, the invention relates to polypeptides having lysozyme activity and having a sequence identity to SEQ ID NO: 134 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 134 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 133. In one embodiment, the polypeptide preferably comprises or consists of the amino acid sequence of SEQ ID NO: 134; comprises the amino acid sequence of SEQ ID NO: 134 and a N-terminal and/or C-terminal His-tag and/or HQ-tag; comprises the amino acid sequence of SEQ ID NO: 134 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 134. In one embodiment, the polypeptide comprises or consists of amino acids 1 to 208 of SEQ ID NO: 134. In an embodiment, the polypeptide has been isolated.

In a continuation of the forty-fifth aspect, the invention relates to a polypeptide having lysozyme activity encoded by a polynucleotide having a sequence identity to the mature polypeptide coding sequence of SEQ ID NO: 132 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-fifth aspect, the invention relates to variants of SEQ ID NO: 134 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 134 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 134 is not more than 10, e.g., 1, 2, 3, 4, 5, 6, 7, 8, 9 or 10. In one embodiment, the number of substitutions and/or deletions and/or insertions in SEQ ID NO: 134 is not more than 10, e.g., 1, 2, 3, 4, 5, 6, 7, 8, 9 or 10. In a further embodiment, the number of substitutions, preferably conservative substitutions, in SEQ ID NO: 134 is not more than 10, e.g., 1, 2, 3, 4, 5, 6, 7, 8, 9 or 10. Examples of amino acid changes and conservative substitutions are described in the third aspect of the invention.

In an embodiment of the forty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-sixth aspect the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 136. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 136.

In a continuation of the forty-sixth aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to SEQ ID NO: 137. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 137.

In one embodiment, the invention relates to polypeptides having lysozyme activity and having a sequence identity to SEQ ID NO: 137 of at least 90% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 137 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 136. In one embodiment, the polypeptide preferably comprises or consists of the amino acid sequence of SEQ ID NO: 137; comprises the amino acid sequence of SEQ ID NO: 137 and a N-terminal and/or C-terminal His-tag and/or HQ-tag; comprises the amino acid sequence of SEQ ID NO: 137 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 137. In one embodiment, the polypeptide comprises or consists of amino acids 1 to 203 of SEQ ID NO: 137. In an embodiment, the polypeptide has been isolated.

In a continuation of the forty-sixth aspect, the invention relates to a polypeptide having lysozyme activity encoded by a polynucleotide having a sequence identity to the mature polypeptide coding sequence of SEQ ID NO: 135 of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-sixth aspect, the invention relates to variants of SEQ ID NO: 137 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 137 is not more than 20, e.g., 1, 2, 3, 4, 5, 6, 7, 8, 9, 10, 11, 12, 13, 14, 15, 16, 17, 18, 19 or 20. In an embodiment, the number of positions comprising one or more amino acid substitutions, and/or one or more amino acid deletions, and/or one or more amino acid insertions or any combination thereof in SEQ ID NO: 137 is not more than 10, e.g., 1, 2, 3, 4, 5, 6, 7, 8, 9 or 10. In one embodiment, the number of substitutions and/or deletions and/or insertions in SEQ ID NO: 137 is not more than 10, e.g., 1, 2, 3, 4, 5, 6, 7, 8, 9 or 10. In a further embodiment, the number of substitutions, preferably conservative substitutions, in SEQ ID NO: 137 is not more than 10, e.g., 1, 2, 3, 4, 5, 6, 7, 8, 9 or 10. Examples of amino acid changes and conservative substitutions are described in the third aspect of the invention.

In an embodiment of the forty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-seventh aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 139. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 139.

In a continuation of the forty-seventh aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 140. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 140.

In one embodiment, the invention relates to polypeptides having lysozyme activity and having a sequence identity to SEQ ID NO: 140 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 140 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 139. In one embodiment, the polypeptide preferably comprises or consists of the amino acid sequence of SEQ ID NO: 140; comprises the amino acid sequence of SEQ ID NO: 140 and a N-terminal and/or C-terminal His-tag and/or HQ-tag; comprises the amino acid sequence of SEQ ID NO: 140 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 140. In one embodiment, the polypeptide comprises or consists of amino acids 1 to 216 of SEQ ID NO: 140. In an embodiment, the polypeptide has been isolated.

In a continuation of the forty-seventh aspect, the invention relates to a polypeptide having lysozyme activity encoded by a polynucleotide having a sequence identity to the mature polypeptide coding sequence of SEQ ID NO: 138 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-seventh aspect, the invention relates to variants of SEQ ID NO: 140 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 140 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 140 is not more than 10, e.g., 1, 2, 3, 4, 5, 6, 7, 8, 9 or 10. In one embodiment, the number of substitutions and/or deletions and/or insertions in SEQ ID NO: 140 is not more than 10, e.g., 1, 2, 3, 4, 5, 6, 7, 8, 9 or 10. In a further embodiment, the number of substitutions, preferably conservative substitutions, in SEQ ID NO: 140 is not more than 10, e.g., 1, 2, 3, 4, 5, 6, 7, 8, 9 or 10. Examples of amino acid changes and conservative substitutions are described in the third aspect of the invention.

In an embodiment of the forty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-eighth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 142. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 142.

In a continuation of the forty-eighth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 143. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 143.

In one embodiment, the invention relates to polypeptides having lysozyme activity and having a sequence identity to SEQ ID NO: 143 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 143 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 142. In one embodiment, the polypeptide preferably comprises or consists of the amino acid sequence of SEQ ID NO: 143; comprises the amino acid sequence of SEQ ID NO: 143 and a N-terminal and/or C-terminal His-tag and/or HQ-tag; comprises the amino acid sequence of SEQ ID NO: 143 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 143. In one embodiment, the polypeptide comprises or consists of amino acids 1 to 207 of SEQ ID NO: 143. In an embodiment, the polypeptide has been isolated.

In a continuation of the forty-eighth aspect, the invention relates to a polypeptide having lysozyme activity encoded by a polynucleotide having a sequence identity to the mature polypeptide coding sequence of SEQ ID NO: 141 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-eighth aspect, the invention relates to variants of SEQ ID NO: 143 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 143 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 143 is not more than 10, e.g., 1, 2, 3, 4, 5, 6, 7, 8, 9 or 10. In one embodiment, the number of substitutions and/or deletions and/or insertions in SEQ ID NO: 143 is not more than 10, e.g., 1, 2, 3, 4, 5, 6, 7, 8, 9 or 10. In a further embodiment, the number of substitutions, preferably conservative substitutions, in SEQ ID NO: 143 is not more than 10, e.g., 1, 2, 3, 4, 5, 6, 7, 8, 9 or 10. Examples of amino acid changes and conservative substitutions are described in the third aspect of the invention.

In an embodiment of the forty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-ninth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 145. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 145.

In a continuation of the forty-ninth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 146. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 146.

In one embodiment, the invention relates to polypeptides having lysozyme activity and having a sequence identity to SEQ ID NO: 146 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 146 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 145. In one embodiment, the polypeptide preferably comprises or consists of the amino acid sequence of SEQ ID NO: 146; comprises the amino acid sequence of SEQ ID NO: 146 and a N-terminal and/or C-terminal His-tag and/or HQ-tag; comprises the amino acid sequence of SEQ ID NO: 146 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 146. In one embodiment, the polypeptide comprises or consists of amino acids 1 to 208 of SEQ ID NO: 146. In an embodiment, the polypeptide has been isolated.

In a continuation of the forty-ninth aspect, the invention relates to a polypeptide having lysozyme activity encoded by a polynucleotide having a sequence identity to the mature polypeptide coding sequence of SEQ ID NO: 144 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-ninth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-ninth aspect, the invention relates to variants of SEQ ID NO: 146 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 146 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 146 is not more than 10, e.g., 1, 2, 3, 4, 5, 6, 7, 8, 9 or 10. In one embodiment, the number of substitutions and/or deletions and/or insertions in SEQ ID NO: 146 is not more than 10, e.g., 1, 2, 3, 4, 5, 6, 7, 8, 9 or 10. In a further embodiment, the number of substitutions, preferably conservative substitutions, in SEQ ID NO: 146 is not more than 10, e.g., 1, 2, 3, 4, 5, 6, 7, 8, 9 or 10. Examples of amino acid changes and conservative substitutions are described in the third aspect of the invention.

In an embodiment of the forty-ninth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fiftieth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 148. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 148.

In a continuation of the fiftieth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 149.

In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 149.

In one embodiment, the invention relates to polypeptides having lysozyme activity and having a sequence identity to SEQ ID NO: 149 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 149 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 149 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 148. In one embodiment, the polypeptide preferably comprises or consists of the amino acid sequence of SEQ ID NO: 149; comprises the amino acid sequence of SEQ ID NO: 149 and a N-terminal and/or C-terminal His-tag and/or HQ-tag; comprises the amino acid sequence of SEQ ID NO: 149 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 149. In one embodiment, the polypeptide comprises or consists of amino acids 1 to 207 of SEQ ID NO: 149. In an embodiment, the polypeptide has been isolated.

In a continuation of the fiftieth aspect, the invention relates to a polypeptide having lysozyme activity encoded by a polynucleotide having a sequence identity to the mature polypeptide coding sequence of SEQ ID NO: 147 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fiftieth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fiftieth aspect, the invention relates to variants of SEQ ID NO: 149 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 149 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 149 is not more than 10, e.g., 1, 2, 3, 4, 5, 6, 7, 8, 9 or 10. In one embodiment, the number of substitutions and/or deletions and/or insertions in SEQ ID NO: 149 is not more than 10, e.g., 1, 2, 3, 4, 5, 6, 7, 8, 9 or 10. In a further embodiment, the number of substitutions, preferably conservative substitutions, in SEQ ID NO: 149 is not more than 10, e.g., 1, 2, 3, 4, 5, 6, 7, 8, 9 or 10. Examples of amino acid changes and conservative substitutions are described in the third aspect of the invention.

In an embodiment of the fiftieth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fiftieth aspect comprises the motif YKNA (SEQ ID NO: 160) and/or the motif FGGW[S/T] (SEQ ID NO: 161).

In a fifty-first aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 151. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 151.

In a continuation of the fifty-first aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 152.

In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 152.

In one embodiment, the invention relates to polypeptides having lysozyme activity and having a sequence identity to SEQ ID NO: 152 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 152 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 152 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 151. In one embodiment, the polypeptide preferably comprises or consists of the amino acid sequence of SEQ ID NO: 152; comprises the amino acid sequence of SEQ ID NO: 152 and a N-terminal and/or C-terminal His-tag and/or HQ-tag; comprises the amino acid sequence of SEQ ID NO: 152 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 152. In one embodiment, the polypeptide comprises or consists of amino acids 1 to 207 of SEQ ID NO: 152. In an embodiment, the polypeptide has been isolated.

In a continuation of the fifty-first aspect, the invention relates to a polypeptide having lysozyme activity encoded by a polynucleotide having a sequence identity to the mature polypeptide coding sequence of SEQ ID NO: 150 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-first aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-first aspect, the invention relates to variants of SEQ ID NO: 152 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 152 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 152 is not more than 10, e.g., 1, 2, 3, 4, 5, 6, 7, 8, 9 or 10. In one embodiment, the number of substitutions and/or deletions and/or insertions in SEQ ID NO: 152 is not more than 10, e.g., 1, 2, 3, 4, 5, 6, 7, 8, 9 or 10. In a further embodiment, the number of substitutions, preferably conservative substitutions, in SEQ ID NO: 152 is not more than 10, e.g., 1, 2, 3, 4, 5, 6, 7, 8, 9 or 10. Examples of amino acid changes and conservative substitutions are described in the third aspect of the invention.

In an embodiment of the fifty-first aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-first aspect comprises the motif YKNA (SEQ ID NO: 160) and/or the motif FGGW[S/T] (SEQ ID NO: 161).

In a fifty-second aspect the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 154. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 154.

In a continuation of the fifty-second aspect, the invention relates to polypeptides having lysozyme activity having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 155. In one embodiment, the polypeptides differ by up to 33 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 amino acids from the mature polypeptide of SEQ ID NO: 155.

In one embodiment, the invention relates to polypeptides having lysozyme activity and having a sequence identity to SEQ ID NO: 155 of at least 84% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 155 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 155 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 155 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 154. In one embodiment, the polypeptide preferably comprises or consists of the amino acid sequence of SEQ ID NO: 155; comprises the amino acid sequence of SEQ ID NO: 155 and a N-terminal and/or C-terminal His-tag and/or HQ-tag; comprises the amino acid sequence of SEQ ID NO: 155 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 155. In one embodiment, the polypeptide comprises or consists of amino acids 1 to 207 of SEQ ID NO: 155. In an embodiment, the polypeptide has been isolated.

In a continuation of the fifty-second aspect, the invention relates to a polypeptide having lysozyme activity encoded by a polynucleotide having a sequence identity to the mature polypeptide coding sequence of SEQ ID NO: 153 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-second aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-second aspect, the invention relates to variants of SEQ ID NO: 155 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 155 is not more than 33, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33. In an embodiment, the number of positions comprising one or more amino acid substitutions, and/or one or more amino acid deletions, and/or one or more amino acid insertions or any combination thereof in SEQ ID NO: 155 is not more than 10, e.g., 1, 2, 3, 4, 5, 6, 7, 8, 9 or 10. In one embodiment, the number of substitutions and/or deletions and/or insertions in SEQ ID NO: 155 is not more than 10, e.g., 1, 2, 3, 4, 5, 6, 7, 8, 9 or 10. In a further embodiment, the number of substitutions, preferably conservative substitutions, in SEQ ID NO: 155 is not more than 10, e.g., 1, 2, 3, 4, 5, 6, 7, 8, 9 or 10. Examples of amino acid changes and conservative substitutions are described in the third aspect of the invention.

In an embodiment of the fifty-second aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-second aspect comprises the motif YKNA (SEQ ID NO: 160) and/or the motif FGGW[S/T] (SEQ ID NO: 161).

In a fifty-third aspect the invention relates to polypeptides having lysozyme activity having at least 95%, e.g., at least 96%, at least 97%, at least 98%, at least 99%, or 100% sequence identity to the mature polypeptide of SEQ ID NO: 157. In one embodiment, the polypeptides differ by up to 10 amino acids, e.g., 1, 2, 3, 4, 5, 6, 7, 8, 9 or 10 amino acids from the mature polypeptide of SEQ ID NO: 157.

In a continuation of the fifty-third aspect, the invention relates to polypeptides having lysozyme activity having at least 95%, e.g., at least 96%, at least 97%, at least 98%, at least 99%, or 100% sequence identity to SEQ ID NO: 158. In one embodiment, the polypeptides differ by up to 10 amino acids, e.g., 1, 2, 3, 4, 5, 6, 7, 8, 9 or 10 amino acids from the mature polypeptide of SEQ ID NO: 158.

In one embodiment, the invention relates to polypeptides having lysozyme activity and having a sequence identity to SEQ ID NO: 158 of at least 95% and wherein the polypeptide has at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 157. In one embodiment, the polypeptide preferably comprises or consists of the amino acid sequence of SEQ ID NO: 158; comprises the amino acid sequence of SEQ ID NO: 158 and a N-terminal and/or C-terminal His-tag and/or HQ-tag; comprises the amino acid sequence of SEQ ID NO: 158 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 158. In one embodiment, the polypeptide comprises or consists of amino acids 1 to 208 of SEQ ID NO: 158. In an embodiment, the polypeptide has been isolated.

In a continuation of the fifty-third aspect, the invention relates to a polypeptide having lysozyme activity encoded by a polynucleotide having a sequence identity to the mature polypeptide coding sequence of SEQ ID NO: 156 of at least 95%, e.g., at least 96%, at least 97%, at least 98%, at least 99%, or 100%. In a further embodiment, the polypeptide has been isolated.

In an embodiment of the fifty-third aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-third aspect, the invention relates to variants of SEQ ID NO: 158 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 158 is not more than 10, e.g., 1, 2, 3, 4, 5, 6, 7, 8, 9 or 10. In one embodiment, the number of substitutions and/or deletions and/or insertions in SEQ ID NO: 158 is not more than 10, e.g., 1, 2, 3, 4, 5, 6, 7, 8, 9 or 10. In a further embodiment, the number of substitutions, preferably conservative substitutions, in SEQ ID NO: 158 is not more than 10, e.g., 1, 2, 3, 4, 5, 6, 7, 8, 9 or 10. Examples of amino acid changes and conservative substitutions are described in the third aspect of the invention.

In an embodiment of the fifty-third aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifty-fourth aspect the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 218. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 218.

In a continuation of the fifty-fourth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 220. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from the mature polypeptide of SEQ ID NO: 220.

In a continuation of the fifty-fourth aspect, the invention relates to polypeptides having lysozyme activity having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 221. In one embodiment, the polypeptides differ by up to 35 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 amino acids from SEQ ID NO: 221.

In one embodiment, the invention relates to polypeptides having lysozyme activity and having a sequence identity to SEQ ID NO: 221 of at least 83% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 221 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 218. In one embodiment, the polypeptide comprises or consists of the mature polypeptide of SEQ ID NO: 220. In one embodiment, the polypeptide preferably comprises or consists of the amino acid sequence of SEQ ID NO: 221; comprises the amino acid sequence of SEQ ID NO: 221 and a N-terminal and/or C-terminal His-tag and/or HQ-tag; comprises the amino acid sequence of SEQ ID NO: 221 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 221. In one embodiment, the polypeptide comprises or consists of amino acids 1 to 207 of SEQ ID NO: 221. In an embodiment, the polypeptide has been isolated.

In a continuation of the fifty-fourth aspect, the invention relates to a polypeptide having lysozyme activity encoded by a polynucleotide having a sequence identity to the mature polypeptide coding sequence of SEQ ID NO: 217 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-fourth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-fourth aspect, the invention relates to variants of SEQ ID NO: 221 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 221 is not more than 35, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35. In an embodiment, the number of positions comprising one or more amino acid substitutions, and/or one or more amino acid deletions, and/or one or more amino acid insertions or any combination thereof in SEQ ID NO: 221 is not more than 10, e.g., 1, 2, 3, 4, 5, 6, 7, 8, 9 or 10. In one embodiment, the number of substitutions and/or deletions and/or insertions in SEQ ID NO: 221 is not more than 10, e.g., 1, 2, 3, 4, 5, 6, 7, 8, 9 or 10. In a further embodiment, the number of substitutions, preferably conservative substitutions, in SEQ ID NO: 221 is not more than 10, e.g., 1, 2, 3, 4, 5, 6, 7, 8, 9 or 10. Examples of amino acid changes and conservative substitutions are described in the third aspect of the invention.

In an embodiment of the fifty-fourth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a forty-sixth aspect the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to the mature polypeptide of SEQ ID NO: 136. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 136.

In a continuation of the forty-sixth aspect, the invention relates to polypeptides having lysozyme activity having at least 90%, e.g., at least 91%, at least 92%, at least 93%, at least 94%, at least 95%, at least 96%, at least 97%, at least 98%, at least 99%, or 100% sequence identity to SEQ ID NO: 137. In one embodiment, the polypeptides differ by up to 20 amino acids, e.g., 1, 2, 3, 4, 5, 6, 7, 8, 9, 10, 11, 12, 13, 14, 15, 16, 17, 18, 19 or 20 amino acids from the mature polypeptide of SEQ ID NO: 137.

In one embodiment, the invention relates to polypeptides having lysozyme activity and having a sequence identity to SEQ ID NO: 137 of at least 90% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 137 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 136. In one embodiment, the polypeptide preferably comprises or consists of the amino acid sequence of SEQ ID NO: 137; comprises the amino acid sequence of SEQ ID NO: 137 and a N-terminal and/or C-terminal His-tag and/or HQ-tag; comprises the amino acid sequence of SEQ ID NO: 137 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 137. In one embodiment, the polypeptide comprises or consists of amino acids 1 to 203 of SEQ ID NO: 137. In an embodiment, the polypeptide has been isolated.

In a continuation of the forty-sixth aspect, the invention relates to a polypeptide having lysozyme activity encoded by a polynucleotide having a sequence identity to the mature polypeptide coding sequence of SEQ ID NO: 135 of at least 90%, e.g., at least 91%, at least 92%, at least 93%, at least 94%, at least 95%, at least 96%, at least 97%, at least 98%, at least 99%, or 100%. In a further embodiment, the polypeptide has been isolated.

In an embodiment of the forty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the forty-sixth aspect, the invention relates to variants of SEQ ID NO: 137 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 137 is not more than 20, e.g., 1, 2, 3, 4, 5, 6, 7, 8, 9, 10, 11, 12, 13, 14, 15, 16, 17, 18, 19 or 20. In an embodiment, the number of positions comprising one or more amino acid substitutions, and/or one or more amino acid deletions, and/or one or more amino acid insertions or any combination thereof in SEQ ID NO: 137 is not more than 10, e.g., 1, 2, 3, 4, 5, 6, 7, 8, 9 or 10. In one embodiment, the number of substitutions and/or deletions and/or insertions in SEQ ID NO: 137 is not more than 10, e.g., 1, 2, 3, 4, 5, 6, 7, 8, 9 or 10. In a further embodiment, the number of substitutions, preferably conservative substitutions, in SEQ ID NO: 137 is not more than 10, e.g., 1, 2, 3, 4, 5, 6, 7, 8, 9 or 10. Examples of amino acid changes and conservative substitutions are described in the third aspect of the invention.

In an embodiment of the forty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a fifty-fifth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 223. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 223.

In a continuation of the fifty-fifth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 224. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 224.

In one embodiment, the invention relates to polypeptides having lysozyme activity and having a sequence identity to SEQ ID NO: 224 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 224 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 224 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 224 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 223. In one embodiment, the polypeptide preferably comprises or consists of the amino acid sequence of SEQ ID NO: 224; comprises the amino acid sequence of SEQ ID NO: 224 and a N-terminal and/or C-terminal His-tag and/or HQ-tag; comprises the amino acid sequence of SEQ ID NO: 224 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 224. In one embodiment, the polypeptide comprises or consists of amino acids 1 to 207 of SEQ ID NO: 224. In an embodiment, the polypeptide has been isolated.

In a continuation of the fifty-fifth aspect, the invention relates to a polypeptide having lysozyme activity encoded by a polynucleotide having a sequence identity to the mature polypeptide coding sequence of SEQ ID NO: 222 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-fifth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-fifth aspect, the invention relates to variants of SEQ ID NO: 224 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 224 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 224 is not more than 10, e.g., 1, 2, 3, 4, 5, 6, 7, 8, 9 or 10. In one embodiment, the number of substitutions and/or deletions and/or insertions in SEQ ID NO: 224 is not more than 10, e.g., 1, 2, 3, 4, 5, 6, 7, 8, 9 or 10. In a further embodiment, the number of substitutions, preferably conservative substitutions, in SEQ ID NO: 224 is not more than 10, e.g., 1, 2, 3, 4, 5, 6, 7, 8, 9 or 10. Examples of amino acid changes and conservative substitutions are described in the third aspect of the invention.

In an embodiment of the fifty-fifth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-fifth aspect comprises the motif YKNA (SEQ ID NO: 160) and/or the motif FGGW[S/T] (SEQ ID NO: 161).

In a fifty-sixth aspect the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 226. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 226.

In a continuation of the fifty-sixth aspect, the invention relates to polypeptides having lysozyme activity having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 227. In one embodiment, the polypeptides differ by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acids from the mature polypeptide of SEQ ID NO: 227.

In one embodiment, the invention relates to polypeptides having lysozyme activity and having a sequence identity to SEQ ID NO: 227 of at least 80% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 227 of at least 85% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 227 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 227 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 226. In one embodiment, the polypeptide preferably comprises or consists of the amino acid sequence of SEQ ID NO: 227; comprises the amino acid sequence of SEQ ID NO: 227 and a N-terminal and/or C-terminal His-tag and/or HQ-tag; comprises the amino acid sequence of SEQ ID NO: 227 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 227. In one embodiment, the polypeptide comprises or consists of amino acids 1 to 208 of SEQ ID NO: 227. In an embodiment, the polypeptide has been isolated.

In a continuation of the fifty-sixth aspect, the invention relates to a polypeptide having lysozyme activity encoded by a polynucleotide having a sequence identity to the mature polypeptide coding sequence of SEQ ID NO: 225 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-sixth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-sixth aspect, the invention relates to variants of SEQ ID NO: 227 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 227 is not more than 40, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. In an embodiment, the number of positions comprising one or more amino acid substitutions, and/or one or more amino acid deletions, and/or one or more amino acid insertions or any combination thereof in SEQ ID NO: 227 is not more than 10, e.g., 1, 2, 3, 4, 5, 6, 7, 8, 9 or 10. In one embodiment, the number of substitutions and/or deletions and/or insertions in SEQ ID NO: 227 is not more than 10, e.g., 1, 2, 3, 4, 5, 6, 7, 8, 9 or 10. In a further embodiment, the number of substitutions, preferably conservative substitutions, in SEQ ID NO: 227 is not more than 10, e.g., 1, 2, 3, 4, 5, 6, 7, 8, 9 or 10. Examples of amino acid changes and conservative substitutions are described in the third aspect of the invention.

In an embodiment of the fifty-sixth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-sixth aspect comprises the motif YKNA (SEQ ID NO: 160) and/or the motif FGGW[S/T] (SEQ ID NO: 161).

In a fifty-seventh aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 229. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 229.

In a continuation of the fifty-seventh aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 230.

In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 230.

In one embodiment, the invention relates to polypeptides having lysozyme activity and having a sequence identity to SEQ ID NO: 230 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 230 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 230 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 229. In one embodiment, the polypeptide preferably comprises or consists of the amino acid sequence of SEQ ID NO: 230; comprises the amino acid sequence of SEQ ID NO: 230 and a N-terminal and/or C-terminal His-tag and/or HQ-tag; comprises the amino acid sequence of SEQ ID NO: 230 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 230. In one embodiment, the polypeptide comprises or consists of amino acids 1 to 207 of SEQ ID NO: 230. In an embodiment, the polypeptide has been isolated.

In a continuation of the fifty-seventh aspect, the invention relates to a polypeptide having lysozyme activity encoded by a polynucleotide having a sequence identity to the mature polypeptide coding sequence of SEQ ID NO: 228 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-seventh aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-seventh aspect, the invention relates to variants of SEQ ID NO: 230 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 230 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 230 is not more than 10, e.g., 1, 2, 3, 4, 5, 6, 7, 8, 9 or 10. In one embodiment, the number of substitutions and/or deletions and/or insertions in SEQ ID NO: 230 is not more than 10, e.g., 1, 2, 3, 4, 5, 6, 7, 8, 9 or 10. In a further embodiment, the number of substitutions, preferably conservative substitutions, in SEQ ID NO: 230 is not more than 10, e.g., 1, 2, 3, 4, 5, 6, 7, 8, 9 or 10. Examples of amino acid changes and conservative substitutions are described in the third aspect of the invention.

In an embodiment of the fifty-seventh aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-seventh aspect comprises the motif YKNA (SEQ ID NO: 160) and/or the motif FGGW[S/T] (SEQ ID NO: 161).

In a fifty-eighth aspect the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 232. In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 232.

In a continuation of the fifty-eighth aspect, the invention relates to polypeptides having lysozyme activity having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 233.

In one embodiment, the polypeptides differ by up to 31 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 amino acids from the mature polypeptide of SEQ ID NO: 233.

In one embodiment, the invention relates to polypeptides having lysozyme activity and having a sequence identity to SEQ ID NO: 233 of at least 85% and wherein the polypeptide has at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 233 of at least 90% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159. In one embodiment, the invention relates to polypeptides having lysozyme activity and having a sequence identity to SEQ ID NO: 233 of at least 95% and wherein the polypeptide has at least at least 150%, such as at least 175%, at least 200%, at least 225%, at least 250%, at least 275%, at least 300%, at least 350%, or at least 400% of the lysozyme activity of SEQ ID NO: 159.

In one embodiment, the polypeptide comprises or consists of the mature polypeptide of SEQ ID NO: 232. In one embodiment, the polypeptide preferably comprises or consists of the amino acid sequence of SEQ ID NO: 233; comprises the amino acid sequence of SEQ ID NO: 233 and a N-terminal and/or C-terminal His-tag and/or HQ-tag; comprises the amino acid sequence of SEQ ID NO: 233 and a N-terminal and/or C-terminal extension of up to 10 amino acids, e.g. 1, 2, 3, 4, 5, 6, 7, 8, 9 or 10 amino acids; or is a fragment thereof having lysozyme activity and having at least 90% such as at least 91%, at least 92%, at least 93%, at least 94%, at least 95%, at least 96%, at least 97%, at least 98% or at least 99% of the length of SEQ ID NO: 233. In one embodiment, the polypeptide comprises or consists of amino acids 1 to 207 of SEQ ID NO: 233. In an embodiment, the polypeptide has been isolated.

In a continuation of the fifty-eighth aspect, the invention relates to a polypeptide having lysozyme activity encoded by a polynucleotide having a sequence identity to the mature polypeptide coding sequence of SEQ ID NO: 231 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In an embodiment of the fifty-eighth aspect, the polypeptide has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In a continuation of the fifty-eighth aspect, the invention relates to variants of SEQ ID NO: 233 having lysozyme activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 233 is not more than 31, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31. In an embodiment, the number of positions comprising one or more amino acid substitutions, and/or one or more amino acid deletions, and/or one or more amino acid insertions or any combination thereof in SEQ ID NO: 233 is not more than 10, e.g., 1, 2, 3, 4, 5, 6, 7, 8, 9 or 10. In one embodiment, the number of substitutions and/or deletions and/or insertions in SEQ ID NO: 233 is not more than 10, e.g., 1, 2, 3, 4, 5, 6, 7, 8, 9 or 10. In a further embodiment, the number of substitutions, preferably conservative substitutions, in SEQ ID NO: 233 is not more than 10, e.g., 1, 2, 3, 4, 5, 6, 7, 8, 9 or 10. Examples of amino acid changes and conservative substitutions are described in the third aspect of the invention.

In an embodiment of the fifty-eighth aspect, the variant has at least at least 150%, such as at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In an embodiment, the polypeptide of the fifty-eighth aspect comprises the motif YKNA (SEQ ID NO: 160) and/or the motif FGGW[S/T] (SEQ ID NO: 161).

Taxonoimic and Structural Families

In one embodiment, the GH25 polypeptide comprises the motif YKNA (SEQ ID NO: 160) and/or the motif FGGW [S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In one embodiment, the GH25 polypeptide is obtained or is obtainable from the taxonomic order Agaricales and is preferably is selected from the group selected from SEQ ID NO: 80, SEQ ID NO: 149, SEQ ID NO:152, SEQ ID NO: 155, SEQ ID NO: 221, SEQ ID NO: 224, SEQ ID NO: 230 and SEQ ID NO: 233.

In one embodiment, the GH25 polypeptide is obtained or is obtainable from the taxonomic order Agaricales, preferably the taxonomic family Strophariaceae. In one embodiment, the GH25 polypeptide is obtained or is obtainable from the taxonomic family Strophariaceae and is selected from the group selected from SEQ ID NO: 80, SEQ ID NO: 155, SEQ ID NO: 224, SEQ ID NO: 230 and SEQ ID NO: 233.

In one embodiment, the GH25 polypeptide is obtained or is obtainable from the taxonomic class Dothideomycetes, preferably the taxonomic order Pleosporales. In one embodiment, the GH25 polypeptide is obtained or is obtainable from the taxonomic class Dothideomycetes, preferably the taxonomic order Pleosporales and is selected from the group selected from SEQ ID NO: 3, SEQ ID NO: 60, SEQ ID NO: 95, SEQ ID NO:101, SEQ ID NO:104 and SEQ ID NO: 146.

In one embodiment, the GH25 polypeptide is obtained or is obtainable from the taxonomic class Eurotiomycetes but not from the taxonomic genus *Aspergillus fumigatus*. In one embodiment, the GH25 polypeptide is obtained or is obtainable from the taxonomic class Eurotiomycetes but not from the taxonomic genus *Aspergillus fumigatus* and is selected from the group selected from SEQ ID NO: 18, SEQ ID NO: 27, SEQ ID NO: 45, SEQ ID NO: 48, SEQ ID NO: 75, SEQ ID NO: 82, SEQ ID NO: 125, SEQ ID NO: 131 and SEQ ID NO: 140.

In one embodiment, the GH25 polypeptide is obtained or is obtainable from the taxonomic order Eurotiales but not from the taxonomic genus *Aspergillus fumigatus*. In one embodiment, the GH25 polypeptide is obtained or is obtainable from the taxonomic order Eurotiales but not from the taxonomic genus *Aspergillus fumigatus* and is selected from the group selected from SEQ ID NO: 27, SEQ ID NO: 45, SEQ ID NO: 48, SEQ ID NO: 82, SEQ ID NO: 125, SEQ ID NO: 131 and SEQ ID NO: 140.

In one embodiment, the GH25 polypeptide is obtained or is obtainable from the taxonomic family Aspergillaceae but not from the taxonomic genus *Aspergillus fumigatus*. In one embodiment, the GH25 polypeptide is obtained or is obtainable from the taxonomic family Aspergillaceae but not from the taxonomic genus *Aspergillus fumigatus* and is selected from the group selected from SEQ ID NO: 27, SEQ ID NO: 45, SEQ ID NO: 48, SEQ ID NO: 82, SEQ ID NO: 125 and SEQ ID NO: 140.

In one embodiment, the GH25 polypeptide is obtained or is obtainable from the taxonomic class Pezizomycetes, preferably the taxonomic order Pezizales, more preferably the taxonomic family Ascobolaceae. In one embodiment, the GH25 polypeptide is obtained or is obtainable from the taxonomic class Pezizomycetes, preferably the taxonomic order Pezizales, more preferably the taxonomic family Ascobolaceae and is selected from the group selected from SEQ ID NO: 86 and SEQ ID NO: 98.

In one embodiment, the GH25 polypeptide is obtained or is obtainable from the taxonomic order Coniochaetales. In one embodiment, the GH25 polypeptide is obtained or is obtainable from the taxonomic order Coniochaetales and is selected from the group selected from SEQ ID NO: 89.

In one embodiment, the GH25 polypeptide is obtained or is obtainable from the taxonomic order Hypocreales but not from the taxonomic genus *Trichoderma reesei*. In one embodiment, the GH25 polypeptide is obtained or is obtainable from the taxonomic order Hypocreales but not from the taxonomic genus *Trichoderma reesei* and is selected from the group selected from SEQ ID NO: 12, SEQ ID NO: 15, SEQ ID NO: 21, SEQ ID NO: 42, SEQ ID NO: 51, SEQ ID NO: 54, SEQ ID NO: 66, SEQ ID NO: 69, SEQ ID NO: 122, SEQ ID NO: 128, SEQ ID NO: 134, SEQ ID NO: 137 and SEQ ID NO: 143.

In one embodiment, the GH25 polypeptide is obtained or is obtainable from the taxonomic family Clavicipitaceae. In one embodiment, the GH25 polypeptide is obtained or is obtainable from the taxonomic family Clavicipitaceae and is selected from the group selected from SEQ ID NO: 51, SEQ ID NO: 54, SEQ ID NO: 122 and SEQ ID NO: 128.

In one embodiment, the GH25 polypeptide is obtained or is obtainable from the taxonomic family Cordycipitaceae. In one embodiment, the GH25 polypeptide is obtained or is obtainable from the taxonomic family Cordycipitaceae and is selected from the group selected from SEQ ID NO: 12, SEQ ID NO: 15, SEQ ID NO: 42, SEQ ID NO: 66, SEQ ID NO: 69 and SEQ ID NO: 137.

In one embodiment, the GH25 polypeptide is obtained or is obtainable from the taxonomic order Microascales. In one embodiment, the GH25 polypeptide is obtained or is obtainable from the taxonomic order Microascales and is selected from the group selected from SEQ ID NO: 16.

In one embodiment, the GH25 polypeptide is obtained or is obtainable from the taxonomic order Sordariales. In one embodiment, the GH25 polypeptide is obtained or is obtainable from the taxonomic order Sordarialesand is selected from the group selected from SEQ ID NO: 30, SEQ ID NO: 39, SEQ ID NO: 7, and SEQ ID NO: 158.

In one embodiment, the GH25 polypeptide is obtained or is obtainable from the taxonomic order Sordariales. In one embodiment, the GH25 polypeptide is obtained or is obtainable from the taxonomic order Sordariales and is selected from the group selected from SEQ ID NO: 30, SEQ ID NO: 39, SEQ ID NO: 7, and SEQ ID NO: 158.

In one embodiment, the GH25 polypeptide is obtained or is obtainable from the taxonomic order Xylariales. In one embodiment, the GH25 polypeptide is obtained or is obtainable from the taxonomic order Xylariales and is selected from the group selected from SEQ ID NO: 6, SEQ ID NO: 9, SEQ ID NO: 92, SEQ ID NO: 107, SEQ ID NO: 110 and SEQ ID NO: 113.

Sources of Polypeptides Having Lysozyme Activity

A polypeptide having lysozyme activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus* or from the species *Aspergillus* sp. nov. XZ2609.

In another aspect, the polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Chaetomium* or from the species *Chaetomium cupreum*.

In another aspect, the polypeptide may be a fungal polypeptide. In one aspect, the polypeptide is a polypeptide having lysozyme activity from a fungus of the class Sordariomycetes, such as from the order Sordariales, or from the family Lasiosphaeriaceae, or from the genus *Cladorrhinum* or from the species *Cladorrhinum bulbillosum*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Cordyceps* or from the species *Cordyceps cardinalis*.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Hypholoma* or from the species *Hypholoma polytrichi*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Isaria* or from the species *Isaria farinosa*.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Lecanicillium* or from the species *Lecanicillium* sp. WMM742.

In another aspect, the polypeptide may be a fungal polypeptide. In one aspect, the polypeptide is a polypeptide having lysozyme activity from a fungus of the class Eurotiomycetes, such as from the order Onygenales, or from the genus *Malbranchea* or from the species *Malbranchea flava*.

In another aspect, the polypeptide may be a fungal polypeptide. In one aspect, the polypeptide is a polypeptide having lysozyme activity from a fungus of the class Eurotiomycetes, such as from the order Onygenales, or from the family Onygenaceae, or from the genus *Onygena* or from the species *Onygena equina*.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Paecilomyces* or from the species *Paecilomyces* sp. XZ2658.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium* or from the species *Penicillium citrinum*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Penicillium* or from the species *Penicillium citrinum* or *Penicillium* sp. 'qii'.

In another aspect, the polypeptide may be a fungal polypeptide. In one aspect, the polypeptide is a polypeptide having lysozyme activity from a fungus of the class Sordariomycetes, such as from the order Xylariales, or from the family Xylariaceae, or from the genus *Poronia* or from the species *Poronia punctata*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Pycnidiophora* or from the species *Pycnidiophora* cf. *dispera*.

In another aspect, the polypeptide may be a fungal polypeptide. In one aspect, the polypeptide is a polypeptide having lysozyme activity from a fungus of the order Mucorales, such as from the family Lichtheimiaceae, or from the genus *Rhizomucor* or from the species *Rhizomucor pusillus*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Sporormia* or from the species *Sporormia fimetaria*.

In another aspect, the polypeptide may be a fungal polypeptide. In one aspect, the polypeptide is a polypeptide having lysozyme activity from a fungus of the order Mucorales, such as from the family Lichtheimiaceae, or from the genus Thermomucor or from the species *Thermomucor indicae-seudaticae*.

In another aspect, the polypeptide may be a fungal polypeptide. In one aspect, the polypeptide is a polypeptide having lysozyme activity from a fungus of the genus *Trichobolus* or from the species *Trichobolus zukalii*.

In another aspect, the polypeptide may be a fungal polypeptide. In one aspect, the polypeptide is a polypeptide having lysozyme activity from a fungus of the order Mucorales, such as from the family Umbelopsidaceae, or from the genus *Umbelopsis* or from the species *Umbelopsis westeae*.

In another aspect, the polypeptide may be a fungal polypeptide. In one aspect, the polypeptide is a polypeptide having lysozyme activity from a fungus of the class Sordariomycetes, such as from the order Sordariales, or from the family Chaetomiaceae, or from the genus *Zopfiella* or from the species *Zopfiella* sp. t180-6.

In another aspect, the polypeptide may be a fungal polypeptide. In one aspect, the polypeptide is a polypeptide having lysozyme activity from a fungus of the genus *Zygomycetes* or from the species *Zygomycetes* sp. XZ2655.

In another aspect, the polypeptide may be a fungal polypeptide. In one aspect, the polypeptide is a polypeptide having lysozyme activity from a fungus of the class Sordariomycetes, such as from the order Sordariales, or from the family Sordariaceae, or from the genus *Gelasinospora*, or from the species *Gelasinospora cratophora*.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Stropharia*, or from the species *Stropharia semiglobata*.

In another aspect, the polypeptide may be a fungal polypeptide. In one aspect, the polypeptide is a polypeptide having lysozyme activity from a fungus of the class Sordariomycetes, such as from the order Hypocreales, or from the family Bionectriaceae, or from the genus *Clonostachys*, or from the species *Clonostachys rossmaniae*.

In another aspect, the polypeptide may be a fungal polypeptide. In one aspect, the polypeptide is a polypeptide having lysozyme activity from a fungus of the class Sordariomycetes, such as from the order Hypocreales, or from the family Nectriaceae, or from the genus *Paracremonium*, or from the species *Paracremonium inflatum*.

In another aspect, the polypeptide may be a fungal polypeptide. In one aspect, the polypeptide is a polypeptide having lysozyme activity from a fungus of the class Dothideomycetes, such as from the order Pleosporales, or from the family Cucurbitariaceae, or from the genus *Curreya*, or from the species *Curreya* sp. XZ2623.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Metapochonia*, or from the species *Metapochonia bulbillosa*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus inflatus*.

In another aspect, the polypeptide may be a fungal polypeptide. In one aspect, the polypeptide is a polypeptide having lysozyme activity from a fungus of the class Pezizomycetes, such as from the order Pezizales, or from the family Ascobolaceae, or from the genus *Ascobolus*, or from the species *Ascobolus* sp. ZY179.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Daldinia*, or from the species *Daldinia fissa*.

In another aspect, the polypeptide may be a fungal polypeptide. In one aspect, the polypeptide is a polypeptide having lysozyme activity from a fungus of the class Sordariomycetes, such as from the order Coniochaetales, or from the family Coniochaetaceae, or from the genus *Coniochaeta*, or from the species *Coniochaeta* sp.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Aspergillus*, or from the species *Aspergillus deflectus*.

In another aspect, the polypeptide may be a fungal polypeptide. In one aspect, the polypeptide is a polypeptide having lysozyme activity from a fungus of the class Dothideomycetes, such as from the order Pleosporales, or from the family Delitschiaceae, or from the genus *Delitschia*, or from the species *Delitschia* sp.

In another aspect, the polypeptide may be a fungal polypeptide. In one aspect, the polypeptide is a polypeptide having lysozyme activity from a fungus of the class Sordariomycetes, such as from the order Hypocreales, or from the family Clavicipitaceae, or from the genus *Metarhizium*, or from the species *Metarhizium iadini*.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Hypoxylon*, or from the species *Hypoxylon* sp.

In another aspect, the polypeptide may be a fungal polypeptide. In one aspect, the polypeptide is a polypeptide having lysozyme activity from a fungus of the class Sordariomycetes, such as from the order Xylariales, or from the family *Xylariaceae*, or from the genus *Hypoxylon*, or from the species *Hypoxylon* sp.

In another aspect, the polypeptide may be a fungal polypeptide. In one aspect, the polypeptide is a polypeptide having lysozyme activity from a fungus of the class Sordariomycetes, such as from the order Hypocreales, or from the family Cordycipitaceae, or from the genus *Simplicillium*, or from the species *Simplicillium obclavatum*.

In another aspect, the polypeptide may be a fungal polypeptide. In one aspect, the polypeptide is a polypeptide having lysozyme activity from a fungus of the class Sordariomycetes, such as from the order Microascales, or from the family Microascaceae, or from the genus *Yunnania*, or from the species *Yunnania penicillata*.

In another aspect, the polypeptide may be a fungal polypeptide. In one aspect, the polypeptide is a polypeptide having lysozyme activity from a fungus of the class Dothideomycetes, such as from the order Pleosporales, or from the family Sporormiaceae, or from the genus *Westerdykella*, or from the species *Westerdykella* sp.

In another aspect, the polypeptide may be a fungal polypeptide. In one aspect, the polypeptide is a polypeptide having lysozyme activity from a fungus of the class Eurotiomycetes, such as from the order Eurotiales, or from the family Thermoascaceae, or from the genus *Thermoascus*, or from the species *Thermoascus aurantiacus*.

In another aspect, the polypeptide may be a fungal polypeptide. In one aspect, the polypeptide is a polypeptide having lysozyme activity from a fungus of the class Dothideomycetes, such as from the order Pleosporales, or from the family Coniothyriaceae, or from the genus *Coniothyrium*, or from the species *Coniothyrium* sp.

In another aspect, the polypeptide may be a fungal polypeptide. In one aspect, the polypeptide is a polypeptide having lysozyme activity from a fungus of the class Pezizomycetes, such as from the order Pezizales, or from the family Ascobolaceae, or from the genus *Ascobolus*, or from the species *Ascobolus stictoideus*.

In another aspect, the polypeptide may be a fungal polypeptide. In one aspect, the polypeptide is a polypeptide having lysozyme activity from a fungus of the class Eurotiomycetes, such as from the order Eurotiales, or from the family Aspergillaceae, or from the genus *Hamigera*, or from the species *Hamigera paravellanea*.

In another aspect, the polypeptide may be a fungal polypeptide. In one aspect, the polypeptide is a polypeptide having lysozyme activity from a fungus of the phylum Ascomycota, such as from the genus *Engyodontium*, or from the species *Engyodontium album*.

In another aspect, the polypeptide may be a fungal polypeptide. In one aspect, the polypeptide is a polypeptide having lysozyme activity from a fungus of the class Sordariomycetes, such as from the order Xylariales, or from the genus *Xylariaceae*, or from the species *Xylariaceae* sp. 1653h.

In another aspect, the polypeptide may be a fungal polypeptide. In one aspect, the polypeptide is a polypeptide having lysozyme activity from a fungus of the class Agaricomycetes, such as from the order Agaricales, or from the family Strophariaceae, or from the genus *Deconica* or from the species *Deconica coprophila*.

In another aspect, the polypeptide may be a fungal polypeptide. In one aspect, the polypeptide is a polypeptide having lysozyme activity from a fungus of the class Agaricomycetes, such as from the order Agaricales, or from the family Physalacriaceae, or from the genus *Flammulina* or from the species *Flammulina velutipes*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applications*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichophaea* or a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIII/A gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase I, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase,

*Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

In some embodiments, the polypeptide is heterologous to the recombinant host cell.

In some embodiments, at least one of the one or more control sequences is heterologous to the polynucleotide encoding the polypeptide.

In some embodiments, the recombinant host cell comprises at least two copies, e.g., three, four, or five, of the polynucleotide of the present invention.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In,

*Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is an *Aspergillus* sp. nov. XZ2609 cell. In one aspect, the cell is a *Chaetomium cupreum* cell. In one aspect, the cell is a *Cladorrhinum bulbillosum* cell. In one aspect, the cell is a *Cordyceps cardinalis* cell. In one aspect, the cell is a *Hypholoma polytrichi* cell. In one aspect, the cell is *Isaria farinosa* cell. In one aspect, the cell is a *Lecanicillium* sp. WMM742 cell. In one aspect, the cell is a *Malbranchea flava* cell. In one aspect, the cell is a *Onygena equina* cell. In one aspect, the cell is a *Paecilomyces* sp. XZ2658 cell. In one aspect, the cell is a *Penicillium citrinum* cell. In one aspect, the cell is a *Penicillium* sp. 'qii' cell. In one aspect, the cell is a *Poronia punctata* cell. In one aspect, the cell is a *Pycnidiophora* cf. *dispera* cell. In one aspect, the cell is a *Rhizomucor pusillus* cell. In one aspect, the cell is a *Sporormia fimetaria* cell. In one aspect, the cell is a *Thermomucor indicae-seudaticae* cell. In one aspect, the cell is a *Trichobolus zukalii* cell. In one aspect, the cell is a *Umbelopsis westeae* cell. In one aspect, the cell is a *Zopfiella* sp. t180-6 cell. In one aspect, the cell is a *Zygomycetes* sp. XZ2655 cell.

In one aspect, the cell is a *Gelasinospora cratophora* cell. In one aspect, the cell is a *Stropharia semiglobata* cell. In one aspect, the cell is a *Clonostachys rossmaniae* cell. In one aspect, the cell is a *Paracremonium inflatum* cell. In one aspect, the cell is a *Curreya* sp. XZ2623 cell. In one aspect, the cell is a *Metapochonia bulbillosa* cell. In one aspect, the cell is a *Aspergillus inflatus* cell. In one aspect, the cell is a *Ascobolus* sp. ZY179 cell. In one aspect, the cell is a *Daldinia fissa* cell. In one aspect, the cell is a *Coniochaeta* sp. cell. In one aspect, the cell is a *Aspergillus deflectus* cell. In one aspect, the cell is a *Delitschia* sp. cell. In one aspect, the cell is a *Metarhizium iadini* cell. In one aspect, the cell is a *Hypoxylon* sp. cell. In one aspect, the cell is a *Hypoxylon* sp. cell. In one aspect, the cell is a *Simplicillium obclavatum* cell. In one aspect, the cell is a *Yunnania penicillata* cell. In one aspect, the cell is a *Westerdykella* sp. cell. In one aspect, the cell is a *Thermoascus aurantiacus* cell. In one aspect, the cell is a *Coniothyrium* sp. cell. In one aspect, the cell is a *Ascobolus stictoideus* cell. In one aspect, the cell is a *Hamigera paravellanea* cell. In one aspect, the cell is a *Engyodontium album* cell. In one aspect, the cell is a *Xylariaceae* sp. 1653h cell. In one aspect, the cell is a *Deconica coprophila* cell. In one aspect, the cell is a *Flammulina velutipes* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the fermentation medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In some embodiments, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In some embodiments, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in the polypeptide of the invention. The term "enriched" indicates that the lysozyme activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In a preferred embodiment, the composition comprises one or more lysozymes selected from the list consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the composition comprises the polypeptide of the invention and one or more formulating agents, as described below.

The compositions may further comprise multiple enzymatic activities, such as one or more (e.g., several) enzymes selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

The compositions may further comprise one or more probiotics. In an embodiment, the probiotic is selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococsus acidilactici*, *Pediococcus* sp., *Propionibacterium thoenii*, *Propionibacterium* sp. and *Streptococcus* sp. or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the lysozyme of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93,0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the lysozyme of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:
(a) a core comprising a lysozyme according to the invention, and
(b) a coating consisting of one or more layer(s) surrounding the core.

In one embodiment, the coating comprises a salt coating as described herein. In one embodiment, the coating comprises a wax coating as described herein. In one embodiment, the coating comprises a salt coating followed by a wax coating as described herein.

Animal Feed Additives

The present invention also relates to animal feed additives comprising one or more lysozymes of the invention. Thus in one embodiment, the invention relates to an animal feed additive comprising one or more GH25 polypeptides having lysozyme activity, wherein the polypeptide is selected from the group consisting of:
(a) a polypeptide having at least 80%, such as at least 85%, at least 90% or at least 95% sequence identity to the polypeptide of SEQ ID NO: 3;
(b) a polypeptide having at least 84%, such as at least 85%, at least 90% or at least 95% sequence identity to the polypeptide of SEQ ID NO: 6;
(c) a polypeptide having at least 80%, such as at least 85%, at least 90% or at least 95% sequence identity to the polypeptide of SEQ ID NO: 9;
(d) a polypeptide having at least 80%, such as at least 85%, at least 90% or at least 95% sequence identity to the polypeptide of SEQ ID NO: 12;
(e) a polypeptide having at least 80%, such as at least 85%, at least 90% or at least 95% sequence identity to the polypeptide of SEQ ID NO: 15;
(f) a polypeptide having at least 80%, such as at least 85%, at least 90% or at least 95% sequence identity to the polypeptide of SEQ ID NO: 18;
(g) a polypeptide having at least 80%, such as at least 85%, at least 90% or at least 95% sequence identity to the polypeptide of SEQ ID NO: 21;
(h) a polypeptide having at least 80%, such as at least 85%, at least 90% or at least 95% sequence identity to the polypeptide of SEQ ID NO: 24;
(i) a polypeptide having at least 80%, such as at least 85%, at least 90% or at least 95% sequence identity to the polypeptide of SEQ ID NO: 27;
(j) a polypeptide having at least 84%, such as at least 85%, at least 90% or at least 95% sequence identity to the polypeptide of SEQ ID NO: 30;
(k) a polypeptide having at least 80%, such as at least 85%, at least 90% or at least 95% sequence identity to the polypeptide of SEQ ID NO: 33;
(l) a polypeptide having at least 80%, such as at least 85%, at least 90% or at least 95% sequence identity to the polypeptide of SEQ ID NO: 36;
(m) a polypeptide having at least 84%, such as at least 85%, at least 90% or at least 95% sequence identity to the polypeptide of SEQ ID NO: 39;
(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;

(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM K$_2$HPO$_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

In an embodiment, the animal feed additive comprises one or more formulating agents, preferably as described herein above.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

Animal Feed

The present invention also relates to animal feed compositions comprising one or more lysozymes of the invention. In one embodiment, the invention relates to an animal feed comprising the granule as described herein and plant based material. In one embodiment, the invention relates to an animal feed comprising the animal feed additive as described herein and plant based material.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one lysozyme as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w).

Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) lysozyme/enzyme preparation may also be added before or during the feed ingredient step. Typically a liquid lysozyme/enzyme preparation comprises the lysozyme of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the lysozyme can be prepared by freezing a mixture of liquid enzyme solution with a bulking agent such as ground soybean meal, and then lyophilizing the mixture.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet.

It is at present contemplated that the enzyme is administered in one or more of the following amounts (dosage ranges): 0.01-200; 0.05-100; 0.1-50; 0.2-20; 0.1-1; 0.2-2; 0.5-5; or 1-10;—all these ranges being in mg lysozyme protein per kg feed (ppm).

For determining mg lysozyme protein per kg feed, the lysozyme is purified from the feed composition, and the specific activity of the purified lysozyme is determined using a relevant assay (see under lysozyme activity). The lysozyme activity of the feed composition as such is also determined using the same assay, and on the basis of these two determinations, the dosage in mg lysozyme protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed).

This is so in particular for premixes.

The same principles apply for determining mg lysozyme protein in feed additives. Of course, if a sample is available of the lysozyme used for preparing the feed additive or the feed, the specific activity is determined from this sample (no need to purify the lysozyme from the feed composition or the additive).

Thus in a further aspect, the present invention also relates to an animal feed comprising one or more lysozymes of the invention and plant based material. In another aspect, the present invention also relates to an animal feed comprising the animal feed additive of the invention (as described herein above) and plant based material.

Thus in one embodiment, the invention relates to an animal feed additive comprising plant based material and one or more GH25 polypeptides having lysozyme activity, wherein the polypeptide is selected from the group consisting of:

(a) a polypeptide having at least 80%, such as at least 85%, at least 90% or at least 95% sequence identity to the polypeptide of SEQ ID NO: 3;

(b) a polypeptide having at least 84%, such as at least 85%, at least 90% or at least 95% sequence identity to the polypeptide of SEQ ID NO: 6;

(c) a polypeptide having at least 80%, such as at least 85%, at least 90% or at least 95% sequence identity to the polypeptide of SEQ ID NO: 9;

(d) a polypeptide having at least 80%, such as at least 85%, at least 90% or at least 95% sequence identity to the polypeptide of SEQ ID NO: 12;

(e) a polypeptide having at least 80%, such as at least 85%, at least 90% or at least 95% sequence identity to the polypeptide of SEQ ID NO: 15;

(f) a polypeptide having at least 80%, such as at least 85%, at least 90% or at least 95% sequence identity to the polypeptide of SEQ ID NO: 18;

(g) a polypeptide having at least 80%, such as at least 85%, at least 90% or at least 95% sequence identity to the polypeptide of SEQ ID NO: 21;

(h) a polypeptide having at least 80%, such as at least 85%, at least 90% or at least 95% sequence identity to the polypeptide of SEQ ID NO: 24;

(i) a polypeptide having at least 80%, such as at least 85%, at least 90% or at least 95% sequence identity to the polypeptide of SEQ ID NO: 27;

(j) a polypeptide having at least 84%, such as at least 85%, at least 90% or at least 95% sequence identity to the polypeptide of SEQ ID NO: 30;

(k) a polypeptide having at least 80%, such as at least 85%, at least 90% or at least 95% sequence identity to the polypeptide of SEQ ID NO: 33;

(l) a polypeptide having at least 80%, such as at least 85%, at least 90% or at least 95% sequence identity to the polypeptide of SEQ ID NO: 36;

(m) a polypeptide having at least 84%, such as at least 85%, at least 90% or at least 95% sequence identity to the polypeptide of SEQ ID NO: 39;

(n) a polypeptide having at least 80%, such as at least 85%, at least 90% or at least 95% sequence identity to the polypeptide of SEQ ID NO: 42;
(o) a polypeptide having at least 80%, such as at least 85%, at least 90% or at least 95% sequence identity to the polypeptide of SEQ ID NO: 45;
(p) a polypeptide having at least 80%, such as at least 85%, at least 90% or at least 95% sequence identity to the polypeptide of SEQ ID NO: 48;
(q) a polypeptide having at least 80%, such as at least 85%, at least 90% or at least 95% sequence identity to the polypeptide of SEQ ID NO: 51;
(r) a polypeptide having at least 80%, such as at least 85%, at least 90% or at least 95% sequence identity to the polypeptide of SEQ ID NO: 54;
(s) a polypeptide having at least 80%, such as at least 85%, at least 90% or at least 95% sequence identity to the polypeptide of SEQ ID NO: 57;
(t) a polypeptide having at least 80%, such as at least 85%, at least 90% or at least 95% sequence identity to the polypeptide of SEQ ID NO: 60;
(u) a polypeptide having at least 80%, such as at least 85%, at least 90% or at least 95% sequence identity to the polypeptide of SEQ ID NO: 63;
(v) a polypeptide having at least 80%, such as at least 85%, at least 90% or at least 95% sequence identity to the polypeptide of SEQ ID NO: 66;
(w) a polypeptide having at least 80%, such as at least 85%, at least 90% or at least 95% sequence identity to the polypeptide of SEQ ID NO: 69;
(x) a polypeptide having at least 84%, such as at least 85%, at least 90% or at least 95% sequence identity to the polypeptide of SEQ ID NO: 72;
(y) a polypeptide having at least 80%, such as at least 85%, at least 90% or at least 95% sequence identity to the polypeptide of SEQ ID NO: 75;
(z) a polypeptide having at least 80%, such as at least 85%, at least 90% or at least 95% sequence identity to the polypeptide of SEQ ID NO: 80;
(aa) a polypeptide having at least 80%, such as at least 85%, at least 90% or at least 95% sequence identity to the polypeptide of SEQ ID NO: 83;
(ab) a polypeptide having at least 80%, such as at least 85%, at least 90% or at least 95% sequence identity to the polypeptide of SEQ ID NO: 86;
(ac) a polypeptide having at least 86%, such as at least 90% or at least 95% sequence identity to the polypeptide of SEQ ID NO: 89;
(ad) a polypeptide having at least 82%, such as at least 85%, at least 90% or at least 95% sequence identity to the polypeptide of SEQ ID NO: 92;
(ae) a polypeptide having at least 82%, such as at least 85%, at least 90% or at least 95% sequence identity to the polypeptide of SEQ ID NO: 95;
(af) a polypeptide having at least 80%, such as at least 85%, at least 90% or at least 95% sequence identity to the polypeptide of SEQ ID NO: 98;
(ag) a polypeptide having at least 80%, such as at least 85%, at least 90% or at least 95% sequence identity to the polypeptide of SEQ ID NO: 101;
(ah) a polypeptide having at least 80%, such as at least 85%, at least 90% or at least 95% sequence identity to the polypeptide of SEQ ID NO: 104;
(ai) a polypeptide having at least 80%, such as at least 85%, at least 90% or at least 95% sequence identity to the polypeptide of SEQ ID NO: 107;
(aj) a polypeptide having at least 82%, such as at least 85%, at least 90% or at least 95% sequence identity to the polypeptide of SEQ ID NO: 110;
(ak) a polypeptide having at least 81%, such as at least 85%, at least 90% or at least 95% sequence identity to the polypeptide of SEQ ID NO: 113;
(al) a polypeptide having at least 80%, such as at least 85%, at least 90% or at least 95% sequence identity to the polypeptide of SEQ ID NO: 116;
(am) a polypeptide having at least 80%, such as at least 85%, at least 90% or at least 95% sequence identity to the polypeptide of SEQ ID NO: 119;
(an) a polypeptide having at least 80%, such as at least 85%, at least 90% or at least 95% sequence identity to the polypeptide of SEQ ID NO: 122;
(ao) a polypeptide having at least 80%, such as at least 85%, at least 90% or at least 95% sequence identity to the polypeptide of SEQ ID NO: 125;
(ap) a polypeptide having at least 80%, such as at least 85%, at least 90% or at least 95% sequence identity to the polypeptide of SEQ ID NO: 128;
(aq) a polypeptide having at least 80%, such as at least 85%, at least 90% or at least 95% sequence identity to the polypeptide of SEQ ID NO: 131;
(ar) a polypeptide having at least 80%, such as at least 85%, at least 90% or at least 95% sequence identity to the polypeptide of SEQ ID NO: 134;
(as) a polypeptide having at least 80%, such as at least 85%, at least 90% or at least 95% sequence identity to the polypeptide of SEQ ID NO: 137;
(at) a polypeptide having at least 80%, such as at least 85%, at least 90% or at least 95% sequence identity to the polypeptide of SEQ ID NO: 140;
(au) a polypeptide having at least 80%, such as at least 85%, at least 90% or at least 95% sequence identity to the polypeptide of SEQ ID NO: 143;
(av) a polypeptide having at least 80%, such as at least 85%, at least 90% or at least 95% sequence identity to the polypeptide of SEQ ID NO: 146;
(aw) a polypeptide having at least 80%, such as at least 85%, at least 90% or at least 95% sequence identity to the polypeptide of SEQ ID NO: 149;
(ax) a polypeptide having at least 80%, such as at least 85%, at least 90% or at least 95% sequence identity to the polypeptide of SEQ ID NO: 152;
(ay) a polypeptide having at least 80%, such as at least 85%, at least 90% or at least 95% sequence identity to the polypeptide of SEQ ID NO: 155;
(az) a polypeptide having at least 80%, such as at least 85%, at least 90% or at least 95% sequence identity to the polypeptide of SEQ ID NO: 158;
(ba) a polypeptide having at least 80%, such as at least 85%, at least 90% or at least 95% sequence identity to the polypeptide of SEQ ID NO: 221;
(bb) a polypeptide having at least 80%, such as at least 85%, at least 90% or at least 95% sequence identity to the polypeptide of SEQ ID NO: 224;
(bc) a polypeptide having at least 80%, such as at least 85%, at least 90% or at least 95% sequence identity to the polypeptide of SEQ ID NO: 227;
(bd) a polypeptide having at least 80%, such as at least 85%, at least 90% or at least 95% sequence identity to the polypeptide of SEQ ID NO: 230;
(be) a polypeptide having at least 80%, such as at least 85%, at least 90% or at least 95% sequence identity to the polypeptide of SEQ ID NO: 233;

(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;

(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;

(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and (bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

In an embodiment, the one or more GH25 polypeptides comprises the motif YKNA (SEQ ID NO: 160) and/or the motif FGGW[S/T] (SEQ ID NO: 161), and preferably is selected from the group selected from SEQ ID NO: 12, SEQ ID NO: 27, SEQ ID NO: 42, SEQ ID NO: 57, SEQ ID NO: 63, SEQ ID NO: 66, SEQ ID NO: 80, SEQ ID NO: 149, SEQ ID NO:152, SEQ ID NO: 155, SEQ ID NO: 224, SEQ ID NO: 227, SEQ ID NO: 230 and SEQ ID NO: 233.

In an embodiment, the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

In a preferred embodiment, the polypeptide has at least 150%, such as at least 175%, at least 200%, at least 225%, at least 250%, at least 275%, at least 300%, at least 350%, or at least 400% of the lysozyme activity of SEQ ID NO: 159. In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

In one aspect, the polypeptides of the present invention have at least 150% (i.e. 1.5 times higher), e.g., at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

In a further embodiment, the animal feed has been pelleted.

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediocosus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^3$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™, Biacid™, ProHacid™ Classic and ProHacid™ Advance™ (all Promivi/Cargill) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate). Examples of commercial products are VevoVitall® (DSM Nutritional Products), Amasil®, Luprisil®, Lupro-Grain®, Lupro-Cid®, Lupro-Mix® (BASF), n-Butyric Acid AF (OXEA) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin C, vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, iodine, selenium and zinc.

Non-limiting examples of macro minerals include calcium, magnesium, phosphorus, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet |
| --- | --- |
| Vitamin A | 10,000-15,000 IU/kg feed |
| Vitamin D3 | 1800-2000 IU/kg feed |
| Vitamin E | 60-100 mg/kg feed |
| Vitamin K3 | 2-4 mg/kg feed |
| Vitamin B1 | 2-4 mg/kg feed |
| Vitamin B2 | 6-10 mg/kg feed |
| Vitamin B6 | 4-8 mg/kg feed |
| Vitamin B12 | 0.03-0.05 mg/kg feed |
| Niacin (Vitamin B3) | 30-50 mg/kg feed |
| Pantothenic acid | 20-40 mg/kg feed |
| Folic acid | 1-2 mg/kg feed |
| Biotin | 0.15-0.4 mg/kg feed |
| Choline chloride | 200-400 mg/kg feed |

| Vitamin | Broiler diet |
| --- | --- |
| Vitamin A | 8-12,500 IU/kg feed |
| Vitamin D3 | 3000-5000 IU/kg feed |
| Vitamin E | 150-240 mg/kg feed |
| Vitamin K3 | 2-4 mg/kg feed |
| Vitamin B1 | 2-3 mg/kg feed |
| Vitamin B2 | 7-9 mg/kg feed |
| Vitamin B6 | 3-6 mg/kg feed |
| Vitamin B12 | 0.015-0.04 mg/kg feed |
| Niacin (Vitamin B3) | 50-80 mg/kg feed |
| Pantothenic acid | 10-18 mg/kg feed |
| Folic acid | 1-2 mg/kg feed |
| Biotin | 0.15-0.3 mg/kg feed |
| Choline chloride | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in nmegative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Uses

Use in Animal Feed

A lysozyme of the invention may also be used in animal feed, wherein the term "animal" refers to all animals except humans. Examples of animals are mono-gastric animals, e.g. pigs or swine (including, but not limited to, piglets, growing pigs, and sows); poultry (including but not limited to poultry, turkey, duck, quail, guinea fowl, goose, pigeon, squab, chicken, broiler, layer, pullet and chick); fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

In the use according to the invention the lysozymes can be fed to the animal before, after, or simultaneously with the diet. The latter is preferred.

In a particular embodiment, the lysozyme, in the form in which it is added to the feed, or when being included in a feed additive, is well-defined. Well-defined means that the lysozyme preparation is at least 50% pure as determined by Size-exclusion chromatography (see Example 12 of WO 01/58275). In other particular embodiments the lysozyme preparation is at least 60, 70, 80, 85, 88, 90, 92, 94, or at least 95% pure as determined by this method.

A well-defined lysozyme preparation is advantageous. For instance, it is much easier to dose correctly to the feed a lysozyme that is essentially free from interfering or contaminating other lysozymes. The term dose correctly refers in particular to the objective of obtaining consistent and constant results, and the capability of optimizing dosage based upon the desired effect.

For the use in animal feed, however, the lysozyme need not be pure; it may e.g. include other enzymes, in which case it could be termed a lysozyme preparation.

The lysozyme preparation can be (a) added directly to the feed, or (b) it can be used in the production of one or more intermediate compositions such as feed additives or premixes that is subsequently added to the feed (or used in a treatment process). The degree of purity described above refers to the purity of the original lysozyme preparation, whether used according to (a) or (b) above.

The lysozyme of the present invention could also be used in the treatment of necrotic enteritis and/or *Clostridium perfringens*.

Methods of Improving Animal Performance

In an embodiment, the present invention also relates to a method of improving the performance of an animal comprising administering to the animal the animal feed or the animal feed additive of the invention.

In a preferred embodiment, the method of improving the performance of an animal comprises administering to the animal the animal feed or the animal feed additive comprising the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the present invention also relates to the use of the animal feed or an animal feed additive of the invention for improving the performance of an animal. In another embodiment, the invention relates to the use of one or more lysozymes of the invention for improving the performance of an animal.

In one embodiment, 'improving the performance of an animal' means that there is an increase in body weight gain. In another embodiment, 'improving the performance of an animal' means that there is an improved feed conversion ratio. In a further embodiment, 'improving the performance of an animal' means that there is an increased feed efficiency. In a further embodiment, 'improving the performance of an animal' means that there is an increase in body weight gain and/or an improved feed conversion ratio and/or an increased feed efficiency.

In an embodiment, the animal feed comprises plant based material selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.

Methods of Preparing an Animal Feed

In an embodiment, the present invention provides a method for preparing an animal feed comprising adding one or more lysozymes of the present invention to one or more animal feed ingredients. Animal feed ingredients include, but are not limited to concentrates (as defined herein), forage (as defined herein), enzymes, probiotic, vitamins, minerals and amino acids.

In a preferred embodiment, the method of preparing an animal feed comprises mixing plant based material with the lysozyme selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233.

In an embodiment, the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.

Embodiments

Herein follows a list of embodiments of the invention.

1. A method of hydrolysing peptidoglycan in bacterial cell walls comprising treating bacterial cells with one or more GH25 polypeptides having lysozyme activity, wherein the polypeptide is selected from the group consisting of:
    (a) a polypeptide having at least 80% sequence identity to the polypeptide of SEQ ID NO: 3;
    (b) a polypeptide having at least 84% sequence identity to the polypeptide of SEQ ID NO: 6;
    (c) a polypeptide having at least 80% sequence identity to the polypeptide of SEQ ID NO: 9;
    (d) a polypeptide having at least 80% sequence identity to the polypeptide of SEQ ID NO: 12;
    (e) a polypeptide having at least 80% sequence identity to the polypeptide of SEQ ID NO: 15;
    (f) a polypeptide having at least 80% sequence identity to the polypeptide of SEQ ID NO: 18;
    (g) a polypeptide having at least 80% sequence identity to the polypeptide of SEQ ID NO: 21;
    (h) a polypeptide having at least 80% sequence identity to the polypeptide of SEQ ID NO: 24;
    (i) a polypeptide having at least 80% sequence identity to the polypeptide of SEQ ID NO: 27;
    (j) a polypeptide having at least 84% sequence identity to the polypeptide of SEQ ID NO: 30;
    (k) a polypeptide having at least 80% sequence identity to the polypeptide of SEQ ID NO: 33;
    (l) a polypeptide having at least 80% sequence identity to the polypeptide of SEQ ID NO: 36;
    (m) a polypeptide having at least 84% sequence identity to the polypeptide of SEQ ID NO: 39;
    (n) a polypeptide having at least 80% sequence identity to the polypeptide of SEQ ID NO: 42;
    (o) a polypeptide having at least 80% sequence identity to the polypeptide of SEQ ID NO: 45;

(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

2. The method of item 1, wherein the polypeptide is selected from the group consisting of: (a) a polypeptide having at least 85% sequence identity to the polypeptide of SEQ ID NO: 3;
(b) a polypeptide having at least 85% sequence identity to the polypeptide of SEQ ID NO: 6;
(c) a polypeptide having at least 85% sequence identity to the polypeptide of SEQ ID NO: 9;
(d) a polypeptide having at least 85% sequence identity to the polypeptide of SEQ ID NO: 12;
(e) a polypeptide having at least 85% sequence identity to the polypeptide of SEQ ID NO: 15;
(f) a polypeptide having at least 85% sequence identity to the polypeptide of SEQ ID NO: 18;
(g) a polypeptide having at least 85% sequence identity to the polypeptide of SEQ ID NO: 21;
(h) a polypeptide having at least 85% sequence identity to the polypeptide of SEQ ID NO: 24;
(i) a polypeptide having at least 85% sequence identity to the polypeptide of SEQ ID NO: 27;
(j) a polypeptide having at least 85% sequence identity to the polypeptide of SEQ ID NO: 30;
(k) a polypeptide having at least 85% sequence identity to the polypeptide of SEQ ID NO: 33;
(l) a polypeptide having at least 85% sequence identity to the polypeptide of SEQ ID NO: 36;
(m) a polypeptide having at least 85% sequence identity to the polypeptide of SEQ ID NO: 39;
(n) a polypeptide having at least 85% sequence identity to the polypeptide of SEQ ID NO: 42;
(o) a polypeptide having at least 85% sequence identity to the polypeptide of SEQ ID NO: 45;
(p) a polypeptide having at least 85% sequence identity to the polypeptide of SEQ ID NO: 48;
(q) a polypeptide having at least 85% sequence identity to the polypeptide of SEQ ID NO: 51;
(r) a polypeptide having at least 85% sequence identity to the polypeptide of SEQ ID NO: 54;
(s) a polypeptide having at least 85% sequence identity to the polypeptide of SEQ ID NO: 57;
(t) a polypeptide having at least 85% sequence identity to the polypeptide of SEQ ID NO: 60;
(u) a polypeptide having at least 85% sequence identity to the polypeptide of SEQ ID NO: 63;
(v) a polypeptide having at least 85% sequence identity to the polypeptide of SEQ ID NO: 66;
(w) a polypeptide having at least 85% sequence identity to the polypeptide of SEQ ID NO: 69;
(x) a polypeptide having at least 85% sequence identity to the polypeptide of SEQ ID NO: 72;
(y) a polypeptide having at least 85% sequence identity to the polypeptide of SEQ ID NO: 75;
(z) a polypeptide having at least 85% sequence identity to the polypeptide of SEQ ID NO: 80;
(aa) a polypeptide having at least 85% sequence identity to the polypeptide of SEQ ID NO: 83;
(ab) a polypeptide having at least 85% sequence identity to the polypeptide of SEQ ID NO: 86;
(ac) a polypeptide having at least 86% sequence identity to the polypeptide of SEQ ID NO: 89;
(ad) a polypeptide having at least 85% sequence identity to the polypeptide of SEQ ID NO: 92;
(ae) a polypeptide having at least 85% sequence identity to the polypeptide of SEQ ID NO: 95;
(af) a polypeptide having at least 85% sequence identity to the polypeptide of SEQ ID NO: 98;
(ag) a polypeptide having at least 85% sequence identity to the polypeptide of SEQ ID NO: 101;
(ah) a polypeptide having at least 85% sequence identity to the polypeptide of SEQ ID NO: 104;
(ai) a polypeptide having at least 85% sequence identity to the polypeptide of SEQ ID NO: 107;
(aj) a polypeptide having at least 85% sequence identity to the polypeptide of SEQ ID NO: 110;
(ak) a polypeptide having at least 85% sequence identity to the polypeptide of SEQ ID NO: 113;
(al) a polypeptide having at least 85% sequence identity to the polypeptide of SEQ ID NO: 116;
(am) a polypeptide having at least 85% sequence identity to the polypeptide of SEQ ID NO: 119;
(an) a polypeptide having at least 85% sequence identity to the polypeptide of SEQ ID NO: 122;
(ao) a polypeptide having at least 85% sequence identity to the polypeptide of SEQ ID NO: 125;
(ap) a polypeptide having at least 85% sequence identity to the polypeptide of SEQ ID NO: 128;
(aq) a polypeptide having at least 85% sequence identity to the polypeptide of SEQ ID NO: 131;
(ar) a polypeptide having at least 85% sequence identity to the polypeptide of SEQ ID NO: 134;
(as) a polypeptide having at least 85% sequence identity to the polypeptide of SEQ ID NO: 137;
(at) a polypeptide having at least 85% sequence identity to the polypeptide of SEQ ID NO: 140;
(au) a polypeptide having at least 85% sequence identity to the polypeptide of SEQ ID NO: 143;
(av) a polypeptide having at least 85% sequence identity to the polypeptide of SEQ ID NO: 146;
(aw) a polypeptide having at least 85% sequence identity to the polypeptide of SEQ ID NO: 149;
(ax) a polypeptide having at least 85% sequence identity to the polypeptide of SEQ ID NO: 152;
(ay) a polypeptide having at least 85% sequence identity to the polypeptide of SEQ ID NO: 155;
(az) a polypeptide having at least 85% sequence identity to the polypeptide of SEQ ID NO: 158;
(ba) a polypeptide having at least 85% sequence identity to the polypeptide of SEQ ID NO: 221;
(bb) a polypeptide having at least 85% sequence identity to the polypeptide of SEQ ID NO: 224;
(bc) a polypeptide having at least 85% sequence identity to the polypeptide of SEQ ID NO: 227;
(bd) a polypeptide having at least 85% sequence identity to the polypeptide of SEQ ID NO: 230; and
(be) a polypeptide having at least 85% sequence identity to the polypeptide of SEQ ID NO: 233.

3. The method of item 1, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;

(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(u) a polypeptide having at least 90% sequence identity to the polypeptide of SEQ ID NO: 63;
(v) a polypeptide having at least 90% sequence identity to the polypeptide of SEQ ID NO: 66;
(w) a polypeptide having at least 90% sequence identity to the polypeptide of SEQ ID NO: 69;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(aa) a polypeptide having at least 90% sequence identity to the polypeptide of SEQ ID NO: 83;
(ab) a polypeptide having at least 90% sequence identity to the polypeptide of SEQ ID NO: 86;
(ac) a polypeptide having at least 90% sequence identity to the polypeptide of SEQ ID NO: 89;
(ad) a polypeptide having at least 90% sequence identity to the polypeptide of SEQ ID NO: 92;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ah) a polypeptide having at least 90% sequence identity to the polypeptide of SEQ ID NO: 104;
(ai) a polypeptide having at least 90% sequence identity to the polypeptide of SEQ ID NO: 107;
(aj) a polypeptide having at least 90% sequence identity to the polypeptide of SEQ ID NO: 110;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(ao) a polypeptide having at least 90% sequence identity to the polypeptide of SEQ ID NO: 125;
(ap) a polypeptide having at least 90% sequence identity to the polypeptide of SEQ ID NO: 128;
(aq) a polypeptide having at least 90% sequence identity to the polypeptide of SEQ ID NO: 131;
(ar) a polypeptide having at least 90% sequence identity to the polypeptide of SEQ ID NO: 134;
(as) a polypeptide having at least 90% sequence identity to the polypeptide of SEQ ID NO: 137;
(at) a polypeptide having at least 90% sequence identity to the polypeptide of SEQ ID NO: 140;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(az) a polypeptide having at least 90% sequence identity to the polypeptide of SEQ ID NO: 158;
(ba) a polypeptide having at least 90% sequence identity to the polypeptide of SEQ ID NO: 221;
(bb) a polypeptide having at least 90% sequence identity to the polypeptide of SEQ ID NO: 224;
(bc) a polypeptide having at least 90% sequence identity to the polypeptide of SEQ ID NO: 227;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

4. The method of item 1, wherein the polypeptide is selected from the group consisting of:
(a) a polypeptide having at least 95% sequence identity to the polypeptide of SEQ ID NO: 3;

(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;
(n) a polypeptide having at least 95% sequence identity to the polypeptide of SEQ ID NO: 42;
(o) a polypeptide having at least 95% sequence identity to the polypeptide of SEQ ID NO: 45;
(p) a polypeptide having at least 95% sequence identity to the polypeptide of SEQ ID NO: 48;
(q) a polypeptide having at least 95% sequence identity to the polypeptide of SEQ ID NO: 51;
(r) a polypeptide having at least 95% sequence identity to the polypeptide of SEQ ID NO: 54;
(s) a polypeptide having at least 95% sequence identity to the polypeptide of SEQ ID NO: 57;
(t) a polypeptide having at least 95% sequence identity to the polypeptide of SEQ ID NO: 60;
(u) a polypeptide having at least 95% sequence identity to the polypeptide of SEQ ID NO: 63;
(v) a polypeptide having at least 95% sequence identity to the polypeptide of SEQ ID NO: 66;
(w) a polypeptide having at least 95% sequence identity to the polypeptide of SEQ ID NO: 69;
(x) a polypeptide having at least 95% sequence identity to the polypeptide of SEQ ID NO: 72;
(y) a polypeptide having at least 95% sequence identity to the polypeptide of SEQ ID NO: 75;
(z) a polypeptide having at least 95% sequence identity to the polypeptide of SEQ ID NO: 80;
(aa) a polypeptide having at least 95% sequence identity to the polypeptide of SEQ ID NO: 83;
(ab) a polypeptide having at least 95% sequence identity to the polypeptide of SEQ ID NO: 86;
(ac) a polypeptide having at least 95% sequence identity to the polypeptide of SEQ ID NO: 89;
(ad) a polypeptide having at least 95% sequence identity to the polypeptide of SEQ ID NO: 92;
(ae) a polypeptide having at least 95% sequence identity to the polypeptide of SEQ ID NO: 95;
(af) a polypeptide having at least 95% sequence identity to the polypeptide of SEQ ID NO: 98;
(ag) a polypeptide having at least 95% sequence identity to the polypeptide of SEQ ID NO: 101;
(ah) a polypeptide having at least 95% sequence identity to the polypeptide of SEQ ID NO: 104;
(ai) a polypeptide having at least 95% sequence identity to the polypeptide of SEQ ID NO: 107;
(aj) a polypeptide having at least 95% sequence identity to the polypeptide of SEQ ID NO: 110;
(ak) a polypeptide having at least 95% sequence identity to the polypeptide of SEQ ID NO: 113;
(al) a polypeptide having at least 95% sequence identity to the polypeptide of SEQ ID NO: 116;
(am) a polypeptide having at least 95% sequence identity to the polypeptide of SEQ ID NO: 119;
(an) a polypeptide having at least 95% sequence identity to the polypeptide of SEQ ID NO: 122;
(ao) a polypeptide having at least 95% sequence identity to the polypeptide of SEQ ID NO: 125;
(ap) a polypeptide having at least 95% sequence identity to the polypeptide of SEQ ID NO: 128;
(aq) a polypeptide having at least 95% sequence identity to the polypeptide of SEQ ID NO: 131;
(ar) a polypeptide having at least 95% sequence identity to the polypeptide of SEQ ID NO: 134;
(as) a polypeptide having at least 95% sequence identity to the polypeptide of SEQ ID NO: 137;
(at) a polypeptide having at least 95% sequence identity to the polypeptide of SEQ ID NO: 140;
(au) a polypeptide having at least 95% sequence identity to the polypeptide of SEQ ID NO: 143;
(av) a polypeptide having at least 95% sequence identity to the polypeptide of SEQ ID NO: 146;
(aw) a polypeptide having at least 95% sequence identity to the polypeptide of SEQ ID NO: 149;
(ax) a polypeptide having at least 95% sequence identity to the polypeptide of SEQ ID NO: 152;
(ay) a polypeptide having at least 95% sequence identity to the polypeptide of SEQ ID NO: 155;
(az) a polypeptide having at least 95% sequence identity to the polypeptide of SEQ ID NO: 158;
(ba) a polypeptide having at least 95% sequence identity to the polypeptide of SEQ ID NO: 221;
(bb) a polypeptide having at least 95% sequence identity to the polypeptide of SEQ ID NO: 224;
(bc) a polypeptide having at least 95% sequence identity to the polypeptide of SEQ ID NO: 227;
(bd) a polypeptide having at least 95% sequence identity to the polypeptide of SEQ ID NO: 230;
(be) a polypeptide having at least 95% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions.

5. The method of item 1, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

6. The method of any of items 1 to 5, wherein the polypeptide has at least 150%, at least 175%, at least 200%, at least 225%, at least 250%, at least 275%, at least 300%, at least 350%, or at least 400% of the lysozyme activity of SEQ ID NO: 159.

7. The method of item 6, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

8. The method of item 6, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

9. A granule comprising one or more GH25 polypeptides having lysozyme activity, wherein the polypeptide is selected from the group consisting of:
   (a) a polypeptide having at least 80% sequence identity to the polypeptide of SEQ ID NO: 3;
   (b) a polypeptide having at least 84% sequence identity to the polypeptide of SEQ ID NO: 6;
   (c) a polypeptide having at least 80% sequence identity to the polypeptide of SEQ ID NO: 9;
   (d) a polypeptide having at least 80% sequence identity to the polypeptide of SEQ ID NO: 12;
   (e) a polypeptide having at least 80% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 21;
   (h) a polypeptide having at least 80% sequence identity to the polypeptide of SEQ ID NO: 24;
   (i) a polypeptide having at least 80% sequence identity to the polypeptide of SEQ ID NO: 27;
   (j) a polypeptide having at least 84% sequence identity to the polypeptide of SEQ ID NO: 30;
   (k) a polypeptide having at least 80% sequence identity to the polypeptide of SEQ ID NO: 33;
   (l) a polypeptide having at least 80% sequence identity to the polypeptide of SEQ ID NO: 36;
   (m) a polypeptide having at least 84% sequence identity to the polypeptide of SEQ ID NO: 39;
   (n) a polypeptide having at least 80% sequence identity to the polypeptide of SEQ ID NO: 42;
   (o) a polypeptide having at least 80% sequence identity to the polypeptide of SEQ ID NO: 45;
   (p) a polypeptide having at least 80% sequence identity to the polypeptide of SEQ ID NO: 48;
   (q) a polypeptide having at least 80% sequence identity to the polypeptide of SEQ ID NO: 51;
   (r) a polypeptide having at least 80% sequence identity to the polypeptide of SEQ ID NO: 54;
   (s) a polypeptide having at least 80% sequence identity to the polypeptide of SEQ ID NO: 57;
   (t) a polypeptide having at least 80% sequence identity to the polypeptide of SEQ ID NO: 60;
   (u) a polypeptide having at least 80% sequence identity to the polypeptide of SEQ ID NO: 63;
   (v) a polypeptide having at least 80% sequence identity to the polypeptide of SEQ ID NO: 66;
   (w) a polypeptide having at least 80% sequence identity to the polypeptide of SEQ ID NO: 69;
   (x) a polypeptide having at least 84% sequence identity to the polypeptide of SEQ ID NO: 72;
   (y) a polypeptide having at least 80% sequence identity to the polypeptide of SEQ ID NO: 75;
   (z) a polypeptide having at least 80% sequence identity to the polypeptide of SEQ ID NO: 80;

(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

10. The granule of item 9, wherein the polypeptide is selected from the group consisting of:
(a) a polypeptide having at least 85% sequence identity to the polypeptide of SEQ ID NO: 3;
(b) a polypeptide having at least 85% sequence identity to the polypeptide of SEQ ID NO: 6;
(c) a polypeptide having at least 85% sequence identity to the polypeptide of SEQ ID NO: 9;
(d) a polypeptide having at least 85% sequence identity to the polypeptide of SEQ ID NO: 12;
(e) a polypeptide having at least 85% sequence identity to the polypeptide of SEQ ID NO: 15;
(f) a polypeptide having at least 85% sequence identity to the polypeptide of SEQ ID NO: 18;
(g) a polypeptide having at least 85% sequence identity to the polypeptide of SEQ ID NO: 21;
(h) a polypeptide having at least 85% sequence identity to the polypeptide of SEQ ID NO: 24;
(i) a polypeptide having at least 85% sequence identity to the polypeptide of SEQ ID NO: 27;
(j) a polypeptide having at least 85% sequence identity to the polypeptide of SEQ ID NO: 30;

(k) a polypeptide having at least 85% sequence identity to the polypeptide of SEQ ID NO: 33;
(l) a polypeptide having at least 85% sequence identity to the polypeptide of SEQ ID NO: 36;
(m) a polypeptide having at least 85% sequence identity to the polypeptide of SEQ ID NO: 39;
(n) a polypeptide having at least 85% sequence identity to the polypeptide of SEQ ID NO: 42;
(o) a polypeptide having at least 85% sequence identity to the polypeptide of SEQ ID NO: 45;
(p) a polypeptide having at least 85% sequence identity to the polypeptide of SEQ ID NO: 48;
(q) a polypeptide having at least 85% sequence identity to the polypeptide of SEQ ID NO: 51;
(r) a polypeptide having at least 85% sequence identity to the polypeptide of SEQ ID NO: 54;
(s) a polypeptide having at least 85% sequence identity to the polypeptide of SEQ ID NO: 57;
(t) a polypeptide having at least 85% sequence identity to the polypeptide of SEQ ID NO: 60;
(u) a polypeptide having at least 85% sequence identity to the polypeptide of SEQ ID NO: 63;
(v) a polypeptide having at least 85% sequence identity to the polypeptide of SEQ ID NO: 66;
(w) a polypeptide having at least 85% sequence identity to the polypeptide of SEQ ID NO: 69;
(x) a polypeptide having at least 85% sequence identity to the polypeptide of SEQ ID NO: 72;
(y) a polypeptide having at least 85% sequence identity to the polypeptide of SEQ ID NO: 75;
(z) a polypeptide having at least 85% sequence identity to the polypeptide of SEQ ID NO: 80;
(aa) a polypeptide having at least 85% sequence identity to the polypeptide of SEQ ID NO: 83;
(ab) a polypeptide having at least 85% sequence identity to the polypeptide of SEQ ID NO: 86;
(ac) a polypeptide having at least 86% sequence identity to the polypeptide of SEQ ID NO: 89;
(ad) a polypeptide having at least 85% sequence identity to the polypeptide of SEQ ID NO: 92;
(ae) a polypeptide having at least 85% sequence identity to the polypeptide of SEQ ID NO: 95;
(af) a polypeptide having at least 85% sequence identity to the polypeptide of SEQ ID NO: 98;
(ag) a polypeptide having at least 85% sequence identity to the polypeptide of SEQ ID NO: 101;
(ah) a polypeptide having at least 85% sequence identity to the polypeptide of SEQ ID NO: 104;
(ai) a polypeptide having at least 85% sequence identity to the polypeptide of SEQ ID NO: 107;
(aj) a polypeptide having at least 85% sequence identity to the polypeptide of SEQ ID NO: 110;
(ak) a polypeptide having at least 85% sequence identity to the polypeptide of SEQ ID NO: 113;
(al) a polypeptide having at least 85% sequence identity to the polypeptide of SEQ ID NO: 116;
(am) a polypeptide having at least 85% sequence identity to the polypeptide of SEQ ID NO: 119;
(an) a polypeptide having at least 85% sequence identity to the polypeptide of SEQ ID NO: 122;
(ao) a polypeptide having at least 85% sequence identity to the polypeptide of SEQ ID NO: 125;
(ap) a polypeptide having at least 85% sequence identity to the polypeptide of SEQ ID NO: 128;
(aq) a polypeptide having at least 85% sequence identity to the polypeptide of SEQ ID NO: 131;
(ar) a polypeptide having at least 85% sequence identity to the polypeptide of SEQ ID NO: 134;
(as) a polypeptide having at least 85% sequence identity to the polypeptide of SEQ ID NO: 137;
(at) a polypeptide having at least 85% sequence identity to the polypeptide of SEQ ID NO: 140;
(au) a polypeptide having at least 85% sequence identity to the polypeptide of SEQ ID NO: 143;
(av) a polypeptide having at least 85% sequence identity to the polypeptide of SEQ ID NO: 146;
(aw) a polypeptide having at least 85% sequence identity to the polypeptide of SEQ ID NO: 149;
(ax) a polypeptide having at least 85% sequence identity to the polypeptide of SEQ ID NO: 152;
(ay) a polypeptide having at least 85% sequence identity to the polypeptide of SEQ ID NO: 155;
(az) a polypeptide having at least 85% sequence identity to the polypeptide of SEQ ID NO: 158;
(ba) a polypeptide having at least 85% sequence identity to the polypeptide of SEQ ID NO: 221;
(bb) a polypeptide having at least 85% sequence identity to the polypeptide of SEQ ID NO: 224;
(bc) a polypeptide having at least 85% sequence identity to the polypeptide of SEQ ID NO: 227;
(bd) a polypeptide having at least 85% sequence identity to the polypeptide of SEQ ID NO: 230; and
(be) a polypeptide having at least 85% sequence identity to the polypeptide of SEQ ID NO: 233.

11. The granule of item 9, wherein the polypeptide is selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(c) a polypeptide having at least 90% sequence identity to the polypeptide of SEQ ID NO: 9;
(d) a polypeptide having at least 90% sequence identity to the polypeptide of SEQ ID NO: 12;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(i) a polypeptide having at least 90% sequence identity to the polypeptide of SEQ ID NO: 27;
(j) a polypeptide having at least 90% sequence identity to the polypeptide of SEQ ID NO: 30;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(n) a polypeptide having at least 90% sequence identity to the polypeptide of SEQ ID NO: 42;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;

(s) a polypeptide having at least 90% sequence identity to the polypeptide of SEQ ID NO: 57;
(t) a polypeptide having at least 90% sequence identity to the polypeptide of SEQ ID NO: 60;
(u) a polypeptide having at least 90% sequence identity to the polypeptide of SEQ ID NO: 63;
(v) a polypeptide having at least 90% sequence identity to the polypeptide of SEQ ID NO: 66;
(w) a polypeptide having at least 90% sequence identity to the polypeptide of SEQ ID NO: 69;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(aa) a polypeptide having at least 90% sequence identity to the polypeptide of SEQ ID NO: 83;
(ab) a polypeptide having at least 90% sequence identity to the polypeptide of SEQ ID NO: 86;
(ac) a polypeptide having at least 90% sequence identity to the polypeptide of SEQ ID NO: 89;
(ad) a polypeptide having at least 90% sequence identity to the polypeptide of SEQ ID NO: 92;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ah) a polypeptide having at least 90% sequence identity to the polypeptide of SEQ ID NO: 104;
(ai) a polypeptide having at least 90% sequence identity to the polypeptide of SEQ ID NO: 107;
(aj) a polypeptide having at least 90% sequence identity to the polypeptide of SEQ ID NO: 110;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(ao) a polypeptide having at least 90% sequence identity to the polypeptide of SEQ ID NO: 125;
(ap) a polypeptide having at least 90% sequence identity to the polypeptide of SEQ ID NO: 128;
(aq) a polypeptide having at least 90% sequence identity to the polypeptide of SEQ ID NO: 131;
(ar) a polypeptide having at least 90% sequence identity to the polypeptide of SEQ ID NO: 134;
(as) a polypeptide having at least 90% sequence identity to the polypeptide of SEQ ID NO: 137;
(at) a polypeptide having at least 90% sequence identity to the polypeptide of SEQ ID NO: 140;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(az) a polypeptide having at least 90% sequence identity to the polypeptide of SEQ ID NO: 158;
(ba) a polypeptide having at least 90% sequence identity to the polypeptide of SEQ ID NO: 221;
(bb) a polypeptide having at least 90% sequence identity to the polypeptide of SEQ ID NO: 224;
(bc) a polypeptide having at least 90% sequence identity to the polypeptide of SEQ ID NO: 227;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

12. The granule of item 9, wherein the polypeptide is selected from the group consisting of:
(a) a polypeptide having at least 95% sequence identity to the polypeptide of SEQ ID NO: 3;
(b) a polypeptide having at least 95% sequence identity to the polypeptide of SEQ ID NO: 6;
(c) a polypeptide having at least 95% sequence identity to the polypeptide of SEQ ID NO: 9;
(d) a polypeptide having at least 95% sequence identity to the polypeptide of SEQ ID NO: 12;
(e) a polypeptide having at least 95% sequence identity to the polypeptide of SEQ ID NO: 15;
(f) a polypeptide having at least 95% sequence identity to the polypeptide of SEQ ID NO: 18;
(g) a polypeptide having at least 95% sequence identity to the polypeptide of SEQ ID NO: 21;
(h) a polypeptide having at least 95% sequence identity to the polypeptide of SEQ ID NO: 24;
(i) a polypeptide having at least 95% sequence identity to the polypeptide of SEQ ID NO: 27;
(j) a polypeptide having at least 95% sequence identity to the polypeptide of SEQ ID NO: 30;
(k) a polypeptide having at least 95% sequence identity to the polypeptide of SEQ ID NO: 33;
(l) a polypeptide having at least 95% sequence identity to the polypeptide of SEQ ID NO: 36;
(m) a polypeptide having at least 95% sequence identity to the polypeptide of SEQ ID NO: 39;

(n) a polypeptide having at least 95% sequence identity to the polypeptide of SEQ ID NO: 42;
(o) a polypeptide having at least 95% sequence identity to the polypeptide of SEQ ID NO: 45;
(p) a polypeptide having at least 95% sequence identity to the polypeptide of SEQ ID NO: 48;
(q) a polypeptide having at least 95% sequence identity to the polypeptide of SEQ ID NO: 51;
(r) a polypeptide having at least 95% sequence identity to the polypeptide of SEQ ID NO: 54;
(s) a polypeptide having at least 95% sequence identity to the polypeptide of SEQ ID NO: 57;
(t) a polypeptide having at least 95% sequence identity to the polypeptide of SEQ ID NO: 60;
(u) a polypeptide having at least 95% sequence identity to the polypeptide of SEQ ID NO: 63;
(v) a polypeptide having at least 95% sequence identity to the polypeptide of SEQ ID NO: 66;
(w) a polypeptide having at least 95% sequence identity to the polypeptide of SEQ ID NO: 69;
(x) a polypeptide having at least 95% sequence identity to the polypeptide of SEQ ID NO: 72;
(y) a polypeptide having at least 95% sequence identity to the polypeptide of SEQ ID NO: 75;
(z) a polypeptide having at least 95% sequence identity to the polypeptide of SEQ ID NO: 80;
(aa) a polypeptide having at least 95% sequence identity to the polypeptide of SEQ ID NO: 83;
(ab) a polypeptide having at least 95% sequence identity to the polypeptide of SEQ ID NO: 86;
(ac) a polypeptide having at least 95% sequence identity to the polypeptide of SEQ ID NO: 89;
(ad) a polypeptide having at least 95% sequence identity to the polypeptide of SEQ ID NO: 92;
(ae) a polypeptide having at least 95% sequence identity to the polypeptide of SEQ ID NO: 95;
(af) a polypeptide having at least 95% sequence identity to the polypeptide of SEQ ID NO: 98;
(ag) a polypeptide having at least 95% sequence identity to the polypeptide of SEQ ID NO: 101;
(ah) a polypeptide having at least 95% sequence identity to the polypeptide of SEQ ID NO: 104;
(ai) a polypeptide having at least 95% sequence identity to the polypeptide of SEQ ID NO: 107;
(aj) a polypeptide having at least 95% sequence identity to the polypeptide of SEQ ID NO: 110;
(ak) a polypeptide having at least 95% sequence identity to the polypeptide of SEQ ID NO: 113;
(al) a polypeptide having at least 95% sequence identity to the polypeptide of SEQ ID NO: 116;
(am) a polypeptide having at least 95% sequence identity to the polypeptide of SEQ ID NO: 119;
(an) a polypeptide having at least 95% sequence identity to the polypeptide of SEQ ID NO: 122;
(ao) a polypeptide having at least 95% sequence identity to the polypeptide of SEQ ID NO: 125;
(ap) a polypeptide having at least 95% sequence identity to the polypeptide of SEQ ID NO: 128;
(aq) a polypeptide having at least 95% sequence identity to the polypeptide of SEQ ID NO: 131;
(ar) a polypeptide having at least 95% sequence identity to the polypeptide of SEQ ID NO: 134;
(as) a polypeptide having at least 95% sequence identity to the polypeptide of SEQ ID NO: 137;
(at) a polypeptide having at least 95% sequence identity to the polypeptide of SEQ ID NO: 140;
(au) a polypeptide having at least 95% sequence identity to the polypeptide of SEQ ID NO: 143;
(av) a polypeptide having at least 95% sequence identity to the polypeptide of SEQ ID NO: 146;
(aw) a polypeptide having at least 95% sequence identity to the polypeptide of SEQ ID NO: 149;
(ax) a polypeptide having at least 95% sequence identity to the polypeptide of SEQ ID NO: 152;
(ay) a polypeptide having at least 95% sequence identity to the polypeptide of SEQ ID NO: 155;
(az) a polypeptide having at least 95% sequence identity to the polypeptide of SEQ ID NO: 158;
(ba) a polypeptide having at least 95% sequence identity to the polypeptide of SEQ ID NO: 221;
(bb) a polypeptide having at least 95% sequence identity to the polypeptide of SEQ ID NO: 224;
(bc) a polypeptide having at least 95% sequence identity to the polypeptide of SEQ ID NO: 227;
(bd) a polypeptide having at least 95% sequence identity to the polypeptide of SEQ ID NO: 230;
(be) a polypeptide having at least 95% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions.

13. The granule of item 9, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

14. The granule of any of items 9 to 13, wherein the polypeptide has at least 150%, at least 175%, at least 200%, at least 225%, at least 250%, at least 275%, at least 300%, at least 350%, or at least 400% of the lysozyme activity of SEQ ID NO: 159.

15. The granule of item 14, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

16. The granule of item 14, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

17. The granule of any of items 9 to 16, wherein the granule comprises one or more formulating agents.

18. The granule of item 17, wherein the formulating agent is selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose, preferably selected from the list consisting of 1, 2-propylene glycol, 1, 3-propylene glycol, sodium sulfate, dextrin, cellulose, sodium thiosulfate, kaolin and calcium carbonate.

19. The granule of any of items 9 to 18, wherein the granule comprises a core particle and one or more coatings.

20. The granule of item 19, wherein the coating comprises salt and/or wax and/or flour.

21. The granule of any of items 9 to 20 further comprising one or more additional enzymes.

22. The granule of item 21, wherein the one or more additional enzymes is selected from the group consisting of phytase, xylanase, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

23. The granule of any of items 9 to 22 further comprising one or more probiotics.

24. The granule of item 23, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococus acidilactici, Pediococcus* sp., *Propionibacterium thoenii, Propionibacterium* sp. and *Streptococcus* sp. or any combination thereof.

25. An isolated polypeptide having lysozyme activity, selected from the group consisting of:
   (a) a polypeptide having at least 80% sequence identity to the polypeptide of SEQ ID NO: 3;
   (b) a polypeptide having at least 89% sequence identity to the polypeptide of SEQ ID NO: 6;
   (c) a polypeptide having at least 81% sequence identity to the polypeptide of SEQ ID NO: 9;
   (d) a polypeptide having at least 80% sequence identity to the polypeptide of SEQ ID NO: 12;
   (e) a polypeptide having at least 97% sequence identity to the polypeptide of SEQ ID NO: 15;
   (f) a polypeptide having at least 80% sequence identity to the polypeptide of SEQ ID NO: 18;
   (g) a polypeptide having at least 80% sequence identity to the polypeptide of SEQ ID NO: 24;
   (h) a polypeptide having at least 80% sequence identity to the polypeptide of SEQ ID NO: 27;
   (i) a polypeptide having at least 83% sequence identity to the polypeptide of SEQ ID NO: 30;
   (j) a polypeptide having at least 80% sequence identity to the polypeptide of SEQ ID NO: 33;
   (k) a polypeptide having at least 80% sequence identity to the polypeptide of SEQ ID NO: 36;
   (l) a polypeptide having at least 83% sequence identity to the polypeptide of SEQ ID NO: 39;
   (m) a polypeptide having at least 80% sequence identity to the polypeptide of SEQ ID NO: 42;
   (n) a polypeptide having at least 86% sequence identity to the polypeptide of SEQ ID NO: 45;
   (o) a polypeptide having at least 80% sequence identity to the polypeptide of SEQ ID NO: 48;
   (p) a polypeptide having at least 92% sequence identity to the polypeptide of SEQ ID NO: 51;

(q) a polypeptide having at least 81% sequence identity to the polypeptide of SEQ ID NO: 54;
(r) a polypeptide having at least 80% sequence identity to the polypeptide of SEQ ID NO: 57;
(s) a polypeptide having at least 80% sequence identity to the polypeptide of SEQ ID NO: 60;
(t) a polypeptide having at least 80% sequence identity to the polypeptide of SEQ ID NO: 63;
(u) a polypeptide having at least 80% sequence identity to the polypeptide of SEQ ID NO: 66;
(v) a polypeptide having at least 80% sequence identity to the polypeptide of SEQ ID NO: 69;
(w) a polypeptide having at least 84% sequence identity to the polypeptide of SEQ ID NO: 72;
(x) a polypeptide having at least 80% sequence identity to the polypeptide of SEQ ID NO: 75;
(y) a polypeptide having at least 84% sequence identity to the polypeptide of SEQ ID NO: 80;
(z) a polypeptide having at least 82% sequence identity to the polypeptide of SEQ ID NO: 83;
(aa) a polypeptide having at least 80% sequence identity to the polypeptide of SEQ ID NO: 86;
(ab) a polypeptide having at least 86% sequence identity to the polypeptide of SEQ ID NO: 89;
(ac) a polypeptide having at least 82% sequence identity to the polypeptide of SEQ ID NO: 92;
(ad) a polypeptide having at least 94% sequence identity to the polypeptide of SEQ ID NO: 95;
(ae) a polypeptide having at least 94% sequence identity to the polypeptide of SEQ ID NO: 98;
(af) a polypeptide having at least 80% sequence identity to the polypeptide of SEQ ID NO: 101;
(ag) a polypeptide having at least 81% sequence identity to the polypeptide of SEQ ID NO: 104;
(ah) a polypeptide having at least 80% sequence identity to the polypeptide of SEQ ID NO: 107;
(ai) a polypeptide having at least 88% sequence identity to the polypeptide of SEQ ID NO: 110;
(aj) a polypeptide having at least 85% sequence identity to the polypeptide of SEQ ID NO: 113;
(ak) a polypeptide having at least 80% sequence identity to the polypeptide of SEQ ID NO: 116;
(al) a polypeptide having at least 80% sequence identity to the polypeptide of SEQ ID NO: 119;
(am) a polypeptide having at least 96.5% sequence identity to the polypeptide of SEQ ID NO: 122;
(an) a polypeptide having at least 81% sequence identity to the polypeptide of SEQ ID NO: 125;
(ao) a polypeptide having at least 89% sequence identity to the polypeptide of SEQ ID NO: 128;
(ap) a polypeptide having at least 80% sequence identity to the polypeptide of SEQ ID NO: 131;
(aq) a polypeptide having at least 80% sequence identity to the polypeptide of SEQ ID NO: 134;
(ar) a polypeptide having at least 90% sequence identity to the polypeptide of SEQ ID NO: 137;
(as) a polypeptide having at least 80% sequence identity to the polypeptide of SEQ ID NO: 140;
(at) a polypeptide having at least 80% sequence identity to the polypeptide of SEQ ID NO: 143;
(au) a polypeptide having at least 80% sequence identity to the polypeptide of SEQ ID NO: 146;
(av) a polypeptide having at least 85% sequence identity to the polypeptide of SEQ ID NO: 149;
(aw) a polypeptide having at least 85% sequence identity to the polypeptide of SEQ ID NO: 152;
(ax) a polypeptide having at least 84% sequence identity to the polypeptide of SEQ ID NO: 155;
(ay) a polypeptide having at least 95% sequence identity to the polypeptide of SEQ ID NO: 158;
(az) a polypeptide having at least 80% sequence identity to the polypeptide of SEQ ID NO: 221;
(ba) a polypeptide having at least 80% sequence identity to the polypeptide of SEQ ID NO: 224;
(bb) a polypeptide having at least 80% sequence identity to the polypeptide of SEQ ID NO: 227;
(bc) a polypeptide having at least 85% sequence identity to the polypeptide of SEQ ID NO: 230;
(bd) a polypeptide having at least 85% sequence identity to the polypeptide of SEQ ID NO: 233;
(be) a variant of the polypeptide selected from the group consisting of SEQ ID NO: 3, SEQ ID NO: 12, SEQ ID NO: 18, SEQ ID NO: 24 SEQ ID NO: 27, SEQ ID NO: 33, SEQ ID NO: 36, SEQ ID NO: 42, SEQ ID NO: 48, SEQ ID NO: 57, SEQ ID NO: 60, SEQ ID NO: 63, SEQ ID NO: 66, SEQ ID NO: 69, SEQ ID NO: 75, SEQ ID NO: 86, SEQ ID NO:101, SEQ ID NO: 107, SEQ ID NO: 116, SEQ ID NO: 119, SEQ ID NO: 125, SEQ ID NO: 131, SEQ ID NO: 134, SEQ ID NO: 140, SEQ ID NO: 143, SEQ ID NO: 146, SEQ ID NO: 221, SEQ ID NO: 224 and SEQ ID NO: 227, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 positions;
(bf) a variant of the polypeptide selected from the group consisting of SEQ ID NO: 9, SEQ ID NO: 54 and SEQ ID NO: 104, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 positions;
(bg) a variant of the polypeptide selected from the group consisting of SEQ ID NO: 83 and SEQ ID NO: 92, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 positions;
(bh) a variant of the polypeptide selected from the group consisting of SEQ ID NO: 30 and SEQ ID NO: 39, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 positions;
(bi) a variant of the polypeptide selected from the group consisting of SEQ ID NO: 72, SEQ ID NO: 80 and SEQ ID NO: 155, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 positions;
(bj) a variant of the polypeptide selected from the group consisting of SEQ ID NO: 149, SEQ ID NO: 152, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 positions;
(bk) a variant of the polypeptide selected from the group consisting of SEQ ID NO: 45 and SEQ ID NO: 113, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 positions;
(bl) a variant of SEQ ID NO: 89, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bm) a variant of SEQ ID NO: 110, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23 or 24 positions;
(bn) a variant of SEQ ID NO: 128, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22 or 23 positions;
(bo) a variant of SEQ ID NO: 6, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21 or 22 positions;
(bp) a variant of SEQ ID NO: 137, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions;
(bq) a variant of SEQ ID NO: 51, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15 or 16 positions;
(br) a variant of the polypeptide selected from the group consisting of SEQ ID NO: 95 and SEQ ID NO: 98, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11 or 12 positions;
(bs) a variant of SEQ ID NO: 158, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9 or 10 positions;
(bt) a variant of SEQ ID NO: 122, wherein the variant has lysozyme activity and comprises one or more amino acid substitutions, and/or one or more amino acid deletions, and/or one or more amino acid insertions or any combination thereof in 1, 2, 3, 4, 5, 6 or 7 positions;
(bu) a variant of SEQ ID NO: 15, wherein the variant has lysozyme activity and comprises one or more amino acid substitutions, and/or one or more amino acid deletions, and/or one or more amino acid insertions or any combination thereof in 1, 2, 3, 4, 5 or 6 positions;
(bv) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) and a N-terminal and/or C-terminal His-tag and/or HQ-tag;
(bw) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) and a N-terminal and/or C-terminal extension of up to 10 amino acids, e.g. 1, 2, 3, 4, 5, 6, 7, 8, 9 or 10 amino acids; and
(bx) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be), (bf), (bg), (bh), (bi), (bj), (bk), (bl), (bm), (bn), (bo), (bp), (bq), (br), (bs), (bt) or (bu) having lysozyme activity and having at least 90% of the length of the mature polypeptide.

26. The polypeptide of item 25, wherein the polypeptide comprises or consists of amino acids 1 to 207 of SEQ ID NO: 3, amino acids 1 to 201 of SEQ ID NO: 6, amino acids 1 to 201 of SEQ ID NO: 9, amino acids 1 to 203 of SEQ ID NO: 12, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 27, amino acids 1 to 207 of SEQ ID NO: 30, amino acids 1 to 208 of SEQ ID NO: 33, amino acids 1 to 208 of SEQ ID NO: 36, amino acids 1 to 206 of SEQ ID NO: 39, amino acids 1 to 207 of SEQ ID NO: 42, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 209 of SEQ ID NO: 57, amino acids 1 to 208 of SEQ ID NO: 60, amino acids 1 to 210 of SEQ ID NO: 63, amino acids 1 to 207 of SEQ ID NO: 66, amino acids 1 to 207 of SEQ ID NO: 69, amino acids 1 to 208 of SEQ ID NO: 72, amino acids 1 to 217 of SEQ ID NO: 75, amino acids 1 to 208 of SEQ ID NO: 80, amino acids 1 to 201 of SEQ ID NO: 83, amino acids 1 to 202 of SEQ ID NO: 86, amino acids 1 to 207 of SEQ ID NO: 89, amino acids 1 to 202 of SEQ ID NO: 92, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 104, amino acids 1 to 202 of SEQ ID NO: 107, amino acids 1 to 202 of SEQ ID NO: 110, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 208 of SEQ ID NO: 134, amino acids 1 to 203 of SEQ ID NO: 137, amino acids 1 to 216 of SEQ ID NO: 140, amino acids 1 to 207 of SEQ ID NO: 143, amino acids 1 to 208 of SEQ ID NO: 146, amino acids 1 to 207 of SEQ ID NO: 149, amino acids 1 to 207 of SEQ ID NO: 152, amino acids 1 to 207 of SEQ ID NO: 155, amino acids 1 to 208 of SEQ ID NO: 158, amino acids 1 to 207 of SEQ ID NO: 221, amino acids 1 to 207 of SEQ ID NO: 224, amino acids 1 to 208 of SEQ ID NO: 227, amino acids 1 to 207 of SEQ ID NO: 230 or amino acids 1 to 207 of SEQ ID NO: 233.

27. The polypeptide of any of items 25 to 26, wherein the polypeptide has at least 150%, at least 175%, at least 200%, at least 225%, at least 250%, at least 275%, at least 300%, at least 350%, or at least 400% of the lysozyme activity of SEQ ID NO: 159.

28. The polypeptide of any of items 25 to 27, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as described in example 1.

29. The polypeptide of item 28, wherein the polypeptide has at least 150%, at least 175%, at least 200%, at least 225%, at least 250%, at least 275%, at least 300%, at least 350%, or at least 400% of the lysozyme activity of SEQ ID NO: 159 wherein lysozyme activity is determined as follows: lysozyme (50 µL of 0.7 µg/mL lysozyme in phosphate buffer (5 mM citrate, 5 mM $K_2HPO_4$, 0.01% TritonX-100, pH 5.0)) is mixed with *Micrococcus lysodeikticus* solution (450 µL of 1% lyophilized *Micrococcus lysodeikticus* ATCC No. 4698 in milli-Q water) and incubated at 40° C. with shaking (500 rpm) for 45 min; the sample is centrifuged (4000 g, 5 min); supernatant (100 µL) is mixed with HCl (50 µL 3.2M) and incubated at 95° C. for 80 min; NaOH (50 µL, 3.5 M) is added and 150 µL of the sample is added to 4-hydroxybenzhydrazide in K—Na tartrate/NaOH buffer (75 µL of 50 g/L K—Na tartrate+20 g/L NaOH); the mixture is incubated at 95° C. for 10 min; and the optical density is measured at 405 nm.

30. A composition comprising the polypeptide of any of items 25 to 29.

31. The composition of item 30 further comprising one or more formulating agents.

32. The composition of item 31 wherein the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

33. An animal feed additive comprising the lysozyme as disclosed in any of items 1 to 8, the granule of any of items 9 to 24, the polypeptide of any of items 25 to 29 or the composition of any of items 30 to 32.

34. The animal feed additive of item 33 further comprising one or more components selected from the list consisting of:
   one or more vitamins;
   one or more minerals;
   one or more amino acids;
   one or more prebiotics;
   one or more organic acids; and one or more other feed ingredients.

35. The animal feed additive of any of items 33 to 34 further comprising one or more additional enzymes.

36. The animal feed additive of item 35, wherein the one or more additional enzymes is selected from the group consisting of phytase, lysozyme, galactanase, alpha-galactosidase, beta-galactosidase, protease, phospholipase A1, phospholipase A2, lysophospholipase, phospholipase C, phospholipase D, amylase, lysozyme, arabinofuranosidase, beta-xylosidase, acetyl xylan esterase, feruloyl esterase, cellulase, cellobiohydrolases, beta-glucosidase, pullulanase, and beta-glucanase or any combination thereof.

37. The animal feed additive of any of items 33 to 36 further comprising one or more probiotics.

38. The animal feed additive of item 37, wherein the one or more probiotics is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococsus acidilactici, Pediococcus sp., Propionibacterium thoenii, Propionibacterium sp.* and *Streptococcus sp.* or any combination thereof.

39. The animal feed additive of any of items 33 to 38 further comprising one or more phytogenics.

40. The animal feed additive of item 39, wherein the phytogenic is selected from the group consisting of rosemary, sage, oregano, thyme, clove, lemongrass, essential oils, thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and *curcuma* extract or any combination thereof.

41. An animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.

42. The animal feed of item 41, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
43. A pelleted animal feed comprising the lysozyme as disclosed in any of items 1 to 8, the granule of any of items 9 to 24, the polypeptide of any of items 25 to 29, the composition of any of items 30 to 32 or the animal feed additive of any of items 33 to 40 and plant based material.
44. The pelleted animal feed of item 43, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.
45. A method of improving one or more performance parameters of an animal comprising administering to one or more animals the lysozyme as disclosed in any of items 1 to 8, the granule of any of items 9 to 24, the polypeptide of any of items 25 to 29, the composition of any of items 30 to 32, the animal feed additive of any of items 33 to 40, the animal feed of any of items 41 to 42 or the pelleted animal feed of any of items 43 to 44.
46. The method of item 45, wherein improving the performance of an animal means improved body weight gain, improved European Production Efficiency Factor (EPEF) and/or improved FCR.
47. A method of preparing an animal feed comprising mixing the lysozyme as disclosed in any of items 1 to 8, the granule of any of items 9 to 24, the polypeptide of any of items 25 to 29, the composition of any of items 30 to 32 or the animal feed additive of any of items 33 to 40 with plant based material.
48. The method of item 47, wherein the plant based material is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, quinoa, or pea, in a processed form thereof (such as soybean meal, rapeseed meal) or any combination thereof.
49. A method for improving the nutritional value of an animal feed, comprising adding to the feed the lysozyme as disclosed in any of items 1 to 8, the granule of any of items 9 to 24, the polypeptide of any of items 25 to 29, the composition of any of items 30 to 32 or the animal feed additive of any of items 33 to 40.
50. The method of item 49, wherein the feed is selected from the group consisting of legumes, cereals, oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape), rice, beet, cabbage, sugar beet, spinach, *quinoa*, or pea, in a processed form thereof (such as soybean meal, rapeseed meal) or any combination thereof.
51. A polynucleotide encoding the polypeptide of any of items 25 to 29.
52. A nucleic acid construct or expression vector comprising the polynucleotide of item 51 operably linked to one or more control sequences that direct the production of the polypeptide in an expression host.
53. A recombinant host cell comprising the polynucleotide of item 51 operably linked to one or more control sequences that direct the production of the polypeptide.
54. A method of producing the polypeptide of any of items 25 to 29, comprising:
    (a) cultivating a cell, which in its wild-type form produces the polypeptide, under conditions conductive for production of the polypeptide; and
    (b) recovering the polypeptide.
55. A method of producing the polypeptide of any of items 25 to 29, comprising:
    (a) cultivating a host cell of item 53 under conditions conducive for production of the polypeptide; and
    (b) recovering the polypeptide.
56. A transgenic plant, plant part or plant cell transformed with a polynucleotide encoding the polypeptide of any of items 25 to 29.
57. A whole broth formulation or cell culture composition comprising a polypeptide of any of items 25 to 29.
58. Use of the lysozyme as disclosed in any of any of items 1 to 8, the granule of any of items 9 to 24, the polypeptide of any of items 25 to 29, the composition of any of items 30 to 32 or the animal feed additive of any of items 33 to 40:
    in animal feed;
    in animal feed additives;
    in the preparation of a composition for use in animal feed;
    for improving the nutritional value of an animal feed; and/or
    for improving one or more performance parameters in an animal.
59. An isolated GH25 polypeptide having lysozyme activity selected from the group consisting of:
    (a) a polypeptide having at least 80% sequence identity to the polypeptide of SEQ ID NO: 3;
    (b) a polypeptide having at least 84% sequence identity to the polypeptide of SEQ ID NO: 6;
    (c) a polypeptide having at least 80% sequence identity to the polypeptide of SEQ ID NO: 9;
    (d) a polypeptide having at least 80% sequence identity to the polypeptide of SEQ ID NO: 12;
    (e) a polypeptide having at least 80% sequence identity to the polypeptide of SEQ ID NO: 15;
    (f) a polypeptide having at least 80% sequence identity to the polypeptide of SEQ ID NO: 18;
    (g) a polypeptide having at least 80% sequence identity to the polypeptide of SEQ ID NO: 21;
    (h) a polypeptide having at least 80% sequence identity to the polypeptide of SEQ ID NO: 24;
    (i) a polypeptide having at least 80% sequence identity to the polypeptide of SEQ ID NO: 27;
    (j) a polypeptide having at least 84% sequence identity to the polypeptide of SEQ ID NO: 30;
    (k) a polypeptide having at least 80% sequence identity to the polypeptide of SEQ ID NO: 33;
    (l) a polypeptide having at least 80% sequence identity to the polypeptide of SEQ ID NO: 36;
    (m) a polypeptide having at least 84% sequence identity to the polypeptide of SEQ ID NO: 39;
    (n) a polypeptide having at least 80% sequence identity to the polypeptide of SEQ ID NO: 42;
    (o) a polypeptide having at least 80% sequence identity to the polypeptide of SEQ ID NO: 45;

(p) a polypeptide having at least 80% sequence identity to the polypeptide of SEQ ID NO: 48;
(q) a polypeptide having at least 80% sequence identity to the polypeptide of SEQ ID NO: 51;
(r) a polypeptide having at least 80% sequence identity to the polypeptide of SEQ ID NO: 54;
(s) a polypeptide having at least 80% sequence identity to the polypeptide of SEQ ID NO: 57;
(t) a polypeptide having at least 80% sequence identity to the polypeptide of SEQ ID NO: 60;
(u) a polypeptide having at least 80% sequence identity to the polypeptide of SEQ ID NO: 63;
(v) a polypeptide having at least 80% sequence identity to the polypeptide of SEQ ID NO: 66;
(w) a polypeptide having at least 80% sequence identity to the polypeptide of SEQ ID NO: 69;
(x) a polypeptide having at least 84% sequence identity to the polypeptide of SEQ ID NO: 72;
(y) a polypeptide having at least 80% sequence identity to the polypeptide of SEQ ID NO: 75;
(z) a polypeptide having at least 80% sequence identity to the polypeptide of SEQ ID NO: 80;
(aa) a polypeptide having at least 80% sequence identity to the polypeptide of SEQ ID NO: 83;
(ab) a polypeptide having at least 80% sequence identity to the polypeptide of SEQ ID NO: 86;
(ac) a polypeptide having at least 86% sequence identity to the polypeptide of SEQ ID NO: 89;
(ad) a polypeptide having at least 82% sequence identity to the polypeptide of SEQ ID NO: 92;
(ae) a polypeptide having at least 82% sequence identity to the polypeptide of SEQ ID NO: 95;
(af) a polypeptide having at least 80% sequence identity to the polypeptide of SEQ ID NO: 98;
(ag) a polypeptide having at least 80% sequence identity to the polypeptide of SEQ ID NO: 101;
(ah) a polypeptide having at least 80% sequence identity to the polypeptide of SEQ ID NO: 104;
(ai) a polypeptide having at least 80% sequence identity to the polypeptide of SEQ ID NO: 107;
(aj) a polypeptide having at least 82% sequence identity to the polypeptide of SEQ ID NO: 110;
(ak) a polypeptide having at least 81% sequence identity to the polypeptide of SEQ ID NO: 113;
(al) a polypeptide having at least 80% sequence identity to the polypeptide of SEQ ID NO: 116;
(am) a polypeptide having at least 80% sequence identity to the polypeptide of SEQ ID NO: 119;
(an) a polypeptide having at least 80% sequence identity to the polypeptide of SEQ ID NO: 122;
(ao) a polypeptide having at least 80% sequence identity to the polypeptide of SEQ ID NO: 125;
(ap) a polypeptide having at least 80% sequence identity to the polypeptide of SEQ ID NO: 128;
(aq) a polypeptide having at least 80% sequence identity to the polypeptide of SEQ ID NO: 131;
(ar) a polypeptide having at least 80% sequence identity to the polypeptide of SEQ ID NO: 134;
(as) a polypeptide having at least 80% sequence identity to the polypeptide of SEQ ID NO: 137;
(at) a polypeptide having at least 80% sequence identity to the polypeptide of SEQ ID NO: 140;
(au) a polypeptide having at least 80% sequence identity to the polypeptide of SEQ ID NO: 143;
(av) a polypeptide having at least 80% sequence identity to the polypeptide of SEQ ID NO: 146;
(aw) a polypeptide having at least 80% sequence identity to the polypeptide of SEQ ID NO: 149;
(ax) a polypeptide having at least 80% sequence identity to the polypeptide of SEQ ID NO: 152;
(ay) a polypeptide having at least 80% sequence identity to the polypeptide of SEQ ID NO: 155;
(az) a polypeptide having at least 80% sequence identity to the polypeptide of SEQ ID NO: 158;
(ba) a polypeptide having at least 80% sequence identity to the polypeptide of SEQ ID NO: 221;
(bb) a polypeptide having at least 80% sequence identity to the polypeptide of SEQ ID NO: 224;
(bc) a polypeptide having at least 80% sequence identity to the polypeptide of SEQ ID NO: 227;
(bd) a polypeptide having at least 80% sequence identity to the polypeptide of SEQ ID NO: 230;
(be) a polypeptide having at least 80% sequence identity to the polypeptide of SEQ ID NO: 233;
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27 or 28 positions;
(bg) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal His-tag and/or HQ-tag;
(bh) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) and a N-terminal and/or C-terminal extension of up to 10 amino acids, e.g. 1, 2, 3, 4, 5, 6, 7, 8, 9 or 10 amino acids; and
(bi) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad), (ae), (af), (ag), (ah), (ai), (aj), (ak), (al), (am), (an), (ao), (ap), (aq), (ar), (as), (at), (au), (av), (aw), (ax), (ay), (az), (ba), (bb), (bc), (bd), (be) or (bf) having lysozyme activity and having at least 90% of the length of the mature polypeptide.

60. The polypeptide according to embodiment 59, wherein the polypeptide is selected from the group consisting of:
    (a) a polypeptide having at least 90% sequence identity to the polypeptide of SEQ ID NO: 3;
    (b) a polypeptide having at least 90% sequence identity to the polypeptide of SEQ ID NO: 6;
    (c) a polypeptide having at least 90% sequence identity to the polypeptide of SEQ ID NO: 9;
    (d) a polypeptide having at least 90% sequence identity to the polypeptide of SEQ ID NO: 12;
    (e) a polypeptide having at least 90% sequence identity to the polypeptide of SEQ ID NO: 15;
    (f) a polypeptide having at least 90% sequence identity to the polypeptide of SEQ ID NO: 18;
    (g) a polypeptide having at least 90% sequence identity to the polypeptide of SEQ ID NO: 21;
    (h) a polypeptide having at least 90% sequence identity to the polypeptide of SEQ ID NO: 24;
    (i) a polypeptide having at least 90% sequence identity to the polypeptide of SEQ ID NO: 27;
    (j) a polypeptide having at least 90% sequence identity to the polypeptide of SEQ ID NO: 30;
    (k) a polypeptide having at least 90% sequence identity to the polypeptide of SEQ ID NO: 33;
    (l) a polypeptide having at least 90% sequence identity to the polypeptide of SEQ ID NO: 36;
    (m) a polypeptide having at least 90% sequence identity to the polypeptide of SEQ ID NO: 39;
    (n) a polypeptide having at least 90% sequence identity to the polypeptide of SEQ ID NO: 42;
    (o) a polypeptide having at least 90% sequence identity to the polypeptide of SEQ ID NO: 45;
    (p) a polypeptide having at least 90% sequence identity to the polypeptide of SEQ ID NO: 48;
    (q) a polypeptide having at least 90% sequence identity to the polypeptide of SEQ ID NO: 51;
    (r) a polypeptide having at least 90% sequence identity to the polypeptide of SEQ ID NO: 54;
    (s) a polypeptide having at least 90% sequence identity to the polypeptide of SEQ ID NO: 57;
    (t) a polypeptide having at least 90% sequence identity to the polypeptide of SEQ ID NO: 60;
    (u) a polypeptide having at least 90% sequence identity to the polypeptide of SEQ ID NO: 63;
    (v) a polypeptide having at least 90% sequence identity to the polypeptide of SEQ ID NO: 66;
    (w) a polypeptide having at least 90% sequence identity to the polypeptide of SEQ ID NO: 69;
    (x) a polypeptide having at least 90% sequence identity to the polypeptide of SEQ ID NO: 72;
    (y) a polypeptide having at least 90% sequence identity to the polypeptide of SEQ ID NO: 75;
    (z) a polypeptide having at least 90% sequence identity to the polypeptide of SEQ ID NO: 80;
    (aa) a polypeptide having at least 90% sequence identity to the polypeptide of SEQ ID NO: 83;
    (ab) a polypeptide having at least 90% sequence identity to the polypeptide of SEQ ID NO: 86;
    (ac) a polypeptide having at least 90% sequence identity to the polypeptide of SEQ ID NO: 89;
    (ad) a polypeptide having at least 90% sequence identity to the polypeptide of SEQ ID NO: 92;
    (ae) a polypeptide having at least 90% sequence identity to the polypeptide of SEQ ID NO: 95;
    (af) a polypeptide having at least 90% sequence identity to the polypeptide of SEQ ID NO: 98;
    (ag) a polypeptide having at least 90% sequence identity to the polypeptide of SEQ ID NO: 101;
    (ah) a polypeptide having at least 90% sequence identity to the polypeptide of SEQ ID NO: 104;
    (ai) a polypeptide having at least 90% sequence identity to the polypeptide of SEQ ID NO: 107;
    (aj) a polypeptide having at least 90% sequence identity to the polypeptide of SEQ ID NO: 110;
    (ak) a polypeptide having at least 90% sequence identity to the polypeptide of SEQ ID NO: 113;
    (al) a polypeptide having at least 90% sequence identity to the polypeptide of SEQ ID NO: 116;
    (am) a polypeptide having at least 90% sequence identity to the polypeptide of SEQ ID NO: 119;
    (an) a polypeptide having at least 90% sequence identity to the polypeptide of SEQ ID NO: 122;
    (ao) a polypeptide having at least 90% sequence identity to the polypeptide of SEQ ID NO: 125;
    (ap) a polypeptide having at least 90% sequence identity to the polypeptide of SEQ ID NO: 128;
    (aq) a polypeptide having at least 90% sequence identity to the polypeptide of SEQ ID NO: 131;
    (ar) a polypeptide having at least 90% sequence identity to the polypeptide of SEQ ID NO: 134;
    (as) a polypeptide having at least 90% sequence identity to the polypeptide of SEQ ID NO: 137;
    (at) a polypeptide having at least 90% sequence identity to the polypeptide of SEQ ID NO: 140;
    (au) a polypeptide having at least 90% sequence identity to the polypeptide of SEQ ID NO: 143;
    (av) a polypeptide having at least 90% sequence identity to the polypeptide of SEQ ID NO: 146;
    (aw) a polypeptide having at least 90% sequence identity to the polypeptide of SEQ ID NO: 149;
    (ax) a polypeptide having at least 90% sequence identity to the polypeptide of SEQ ID NO: 152;
    (ay) a polypeptide having at least 90% sequence identity to the polypeptide of SEQ ID NO: 155;
    (az) a polypeptide having at least 90% sequence identity to the polypeptide of SEQ ID NO: 158;
    (ba) a polypeptide having at least 90% sequence identity to the polypeptide of SEQ ID NO: 221;
    (bb) a polypeptide having at least 90% sequence identity to the polypeptide of SEQ ID NO: 224;
    (bc) a polypeptide having at least 90% sequence identity to the polypeptide of SEQ ID NO: 227;
    (bd) a polypeptide having at least 90% sequence identity to the polypeptide of SEQ ID NO: 230;
    (be) a polypeptide having at least 90% sequence identity to the polypeptide of SEQ ID NO: 233; and
    (bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

61. An isolated GH25 polypeptide having lysozyme activity selected from the group consisting of:
(a) a polypeptide having at least 90% sequence identity to the polypeptide of SEQ ID NO: 3;
(b) a polypeptide having at least 90% sequence identity to the polypeptide of SEQ ID NO: 6;
(e) a polypeptide having at least 90% sequence identity to the polypeptide of SEQ ID NO: 15;
(f) a polypeptide having at least 90% sequence identity to the polypeptide of SEQ ID NO: 18;
(g) a polypeptide having at least 90% sequence identity to the polypeptide of SEQ ID NO: 21;
(h) a polypeptide having at least 90% sequence identity to the polypeptide of SEQ ID NO: 24;
(k) a polypeptide having at least 90% sequence identity to the polypeptide of SEQ ID NO: 33;
(l) a polypeptide having at least 90% sequence identity to the polypeptide of SEQ ID NO: 36;
(m) a polypeptide having at least 90% sequence identity to the polypeptide of SEQ ID NO: 39;
(o) a polypeptide having at least 90% sequence identity to the polypeptide of SEQ ID NO: 45;
(p) a polypeptide having at least 90% sequence identity to the polypeptide of SEQ ID NO: 48;
(q) a polypeptide having at least 90% sequence identity to the polypeptide of SEQ ID NO: 51;
(r) a polypeptide having at least 90% sequence identity to the polypeptide of SEQ ID NO: 54;
(s) a polypeptide having at least 90% sequence identity to the polypeptide of SEQ ID NO: 57;
(t) a polypeptide having at least 90% sequence identity to the polypeptide of SEQ ID NO: 60;
(x) a polypeptide having at least 90% sequence identity to the polypeptide of SEQ ID NO: 72;
(y) a polypeptide having at least 90% sequence identity to the polypeptide of SEQ ID NO: 75;
(z) a polypeptide having at least 90% sequence identity to the polypeptide of SEQ ID NO: 80;
(ac) a polypeptide having at least 90% sequence identity to the polypeptide of SEQ ID NO: 89;
(ae) a polypeptide having at least 90% sequence identity to the polypeptide of SEQ ID NO: 95;
(af) a polypeptide having at least 90% sequence identity to the polypeptide of SEQ ID NO: 98;
(ag) a polypeptide having at least 90% sequence identity to the polypeptide of SEQ ID NO: 101;
(ak) a polypeptide having at least 90% sequence identity to the polypeptide of SEQ ID NO: 113;
(al) a polypeptide having at least 90% sequence identity to the polypeptide of SEQ ID NO: 116;
(am) a polypeptide having at least 90% sequence identity to the polypeptide of SEQ ID NO: 119;
(an) a polypeptide having at least 90% sequence identity to the polypeptide of SEQ ID NO: 122;
(aq) a polypeptide having at least 90% sequence identity to the polypeptide of SEQ ID NO: 131;
(as) a polypeptide having at least 90% sequence identity to the polypeptide of SEQ ID NO: 137;
(au) a polypeptide having at least 90% sequence identity to the polypeptide of SEQ ID NO: 143;
(av) a polypeptide having at least 90% sequence identity to the polypeptide of SEQ ID NO: 146;
(aw) a polypeptide having at least 90% sequence identity to the polypeptide of SEQ ID NO: 149;
(ax) a polypeptide having at least 90% sequence identity to the polypeptide of SEQ ID NO: 152;
(ay) a polypeptide having at least 90% sequence identity to the polypeptide of SEQ ID NO: 155;
(ba) a polypeptide having at least 90% sequence identity to the polypeptide of SEQ ID NO: 221;
(bd) a polypeptide having at least 90% sequence identity to the polypeptide of SEQ ID NO: 230;
(be) a polypeptide having at least 90% sequence identity to the polypeptide of SEQ ID NO: 233; and
(bf) a variant of the polypeptide selected from the group consisting of SEQ ID NO: 3, SEQ ID NO: 6, SEQ ID NO: 9, SEQ ID NO: 12, SEQ ID NO: 15, SEQ ID NO: 18, SEQ ID NO: 24, SEQ ID NO: 27, SEQ ID NO: 30, SEQ ID NO: 33, SEQ ID NO: 36, SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 221, SEQ ID NO: 224, SEQ ID NO: 227, SEQ ID NO: 230 and SEQ ID NO: 233, wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19 or 20 positions.

62. The polypeptide according to embodiments 59 to 61 having improved lysozyme activity a) compared to the lysozyme activity of hen eggwhite lysozyme (HEWL) or b) compared to the lysozyme activity of SEQ ID NO: 39 as determined by the Method for the Determination of Lysozyme Activity Against *Micrococcus lysodeikticus*.

63. The polypeptide according to embodiment 59 to 61 having improved lysozyme activity a) compared to the lysozyme activity of hen eggwhite lysozyme (HEWL) and/or b) compared to the lysozyme activity of SEQ ID NO: 39 as determined by any one of i) Method for the Determination of Lysozyme Activity Against *Micrococcus lysodeikticus* and ii) Method for the Determination of Lysozyme Activity Against *Lactobacillus johnsonii*.

64. The peptide according any of embodiment 59 to 63, wherein the polypeptide comprises or consists of amino acids 1 to 207 of SEQ ID NO: 3, amino acids 1 to 201 of SEQ ID NO: 6, amino acids 1 to 208 of SEQ ID NO: 15, amino acids 1 to 207 of SEQ ID NO: 18, amino acids 1 to 208 of SEQ ID NO: 21, amino acids 1 to 207 of SEQ ID NO: 24, amino acids 1 to 208 of SEQ ID NO: 33, amino acids 1 to 208 of SEQ ID NO: 36, amino acids 1 to 206 of SEQ ID NO: 39, amino acids 1 to 216 of SEQ ID NO: 45, amino acids 1 to 218 of SEQ ID NO: 48, amino acids 1 to 204 of SEQ ID NO: 51, amino acids 1 to 203 of SEQ ID NO: 54, amino acids 1 to 208 of SEQ ID NO: 60, amino acids 1 to 208 of SEQ ID NO: 72, amino acids 1 to 217 of SEQ ID NO: 75, amino acids 1 to 208 of SEQ ID NO: 80, amino acids 1 to 207 of SEQ ID NO: 89, amino acids 1 to 201 of SEQ ID NO: 95, amino acids 1 to 202 of SEQ ID NO: 98, amino acids 1 to 206 of SEQ ID NO: 101, amino acids 1 to 202 of SEQ ID NO: 113, amino acids 1 to 206 of SEQ ID NO: 116, amino acids 1 to 207 of SEQ ID NO: 119, amino acids 1 to 208 of SEQ ID NO: 122, amino acids 1 to 215 of SEQ ID NO: 125, amino acids 1 to 217 of SEQ ID NO: 128, amino acids 1 to 214 of SEQ ID NO: 131, amino acids 1 to 203 of SEQ ID NO: 137, amino acids 1 to 207 of SEQ ID NO: 143, amino acids 1 to 208 of SEQ ID NO: 146, amino acids 1 to 207 of SEQ ID NO: 155, amino acids 1 to 207 of SEQ ID NO: 221, amino acids 1 to 207 of SEQ ID NO: 230 or amino acids 1 to 207 of SEQ ID NO: 233.

65. The polypeptide according to embodiment 59 to 63, wherein the polypeptide is selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119.

66. A method of hydrolysing peptidoglycan in bacterial cell walls comprising treating bacterial cells with one or more GH25 polypeptides having lysozyme activity, wherein the polypeptide is as defined in any one of embodiment 59 to 63.

67. A method of increasing the digestibility of peptidoglycans in animal feed comprising the use of a peptide as defined in any of embodiment 59 to 63.

68. An animal feed additive comprising the polypeptide as defined in any of embodiment 59 to 63.

68. An animal feed additive according to embodiment 67 further comprising one or more components selected from the list consisting of:
one or more vitamins;
one or more minerals;
one or more amino acids;
one or more prebiotics;
one or more organic acids;
one or more other feed ingredients;
one or more additional enzymes;
one or more probiotics; and one or more phytogenics 69. An animal feed comprising the polypeptide as defined in any of embodiment 59 to 63.

70. An animal feed according to embodiment 69 further comprising plant based material.

71. A composition comprising the polypeptide of any of embodiment 59 to 63.

72. A polynucleotide encoding the polypeptide of any of embodiment 59 to 63.

73. A recombinant host cell comprising the polynucleotide of embodiment 72 operably linked to one or more control sequences that direct the production of the polypeptide.

74. A method of producing the polypeptide of any of embodiment 59 to 63 comprising:
(a) cultivating a host cell of claim 16 under conditions conducive for production of the polypeptide; and
(b) recovering the polypeptide.

75. Use of the polypeptide as disclosed in any of embodiment 59 to 63:
in animal feed;
in animal feed additives;
in the preparation of a composition for use in animal feed; and/or for improving the intestinal health in an animal.

76. A zootechnical additive for use in feed for poultry or swine, said additive comprising the polypeptide as defined in any of embodiment 59 to 63.

77. A method of improving the intestinal health in an animal comprising reducing the amount of dead *Lactobacillus johnsonii* cells in the digestive tract of said animal, comprising feeding the animal with a feed or feed additive comprising a polypeptide as defined in any of embodiments 59 to 63.

78. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119, preferably selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 80, and a polypeptide having at least 90% sequence identity to the polypeptide of SEQ ID NO: 119, more preferably a polypeptide having at least 90% sequence identity to the polypeptide of SEQ ID NO: 36 and a polypeptide having at least 90% sequence identity to the polypeptide of SEQ ID NO: 80.

79. A method of improving the intestinal health in an animal comprising reducing the amount of dead *Lactobacillus johnsonii* cells, or cell wall debris therefrom, in the digestive tract of said animal, comprising feeding the animal with a feed or feed additive comprising a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

80. A method of promoting the elimination of dead *Lactobacillus johnsonii* cells, or cell wall debris therefrom, from the digestive tract of an animal comprising feeding said animal a source of a polypeptide as defined in any of embodiment 61 to 63.

81. A method of promoting the elimination of dead *Lactobacillus johnsonii* cells, or cell wall debris therefrom, from the digestive tract of an animal comprising feeding said animal a source of a polypeptide selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 75, a polypeptide having at least 90% sequence identity to the polypeptide of SEQ ID NO: 80, and a polypeptide having at least 90% sequence identity to the polypeptide of SEQ ID NO: 119, preferably selected from the group consisting of a polypeptide having at least 90% sequence identity to the polypeptide of SEQ ID NO: 15, a polypeptide having at least 90% sequence identity to the polypeptide of SEQ ID NO: 36, a polypeptide having at least 90% sequence identity to the polypeptide of SEQ ID NO: 80, and a polypeptide having at least 90% sequence identity to the polypeptide of SEQ ID NO: 119, more preferably a polypeptide having at least 90% sequence identity to the polypeptide of SEQ ID NO: 36 and a polypeptide having at least 90% sequence identity to the polypeptide of SEQ ID NO: 80.

82. A method of promoting the elimination of dead *Lactobacillus johnsonii* cells, or cell wall debris therefrom, from the digestive tract of an animal comprising feeding said animal a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO 159.

83. The method according to any one of embodiments 77 to 82 wherein the polypeptide has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

The present invention is further described by the following examples that should not be construed as limiting the scope of the invention.

EXAMPLES

Strains

*Escherichia coli* Top-10 strain was purchased from Invitrogen (Life Technologies, Carlsbad, Calif., USA) and was used to propagate the expression vectors encoding for lysozyme polypeptides.

*Aspergillus oryzae* strain MT3568 was used for heterologous expression of the lysozyme polypeptide encoding sequences. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene.

*Aspergillus niger* MBin118 is disclosed in WO 2004/090155.

The fungal strain NN047801 was isolated from litter samples collected from China, in 2003 by the dilution plate method with PDA medium, 25 C. It was then purified by transferring a single conidium onto a PDA agar plate. The strain NN047801 was identified as *Sporormia fimetaria*, based on both morphological characteristics and ITS rDNA sequence.

Strain *Poronia punctata* NN009607 was isolated from Sweden. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN054002 was isolated from soil samples collected from Tibet, China, in 2011 by the dilution plate method with PDA medium, 10 C. It was then purified by transferring a single conidium onto a PDA agar plate. The strain NN054002 was identified as *Lecanicillium* sp., based on both morphological characteristics and ITS rDNA sequence.

Strain *Onygena equina* NN056731 was isolated on Gotland, Sweden. The strain was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Trichobolus zukalii* CBS720.69 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Penicillium citrinum* NN070248 was isolated from *Antarctica*. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 6 days at 26° C. with shaking at 100 rpm.

The fungal strain NN057876 was from Professor Cai Lei in Institude of Microbiology, CAS. The strain was collected from a compost sample from China, in 2014 by the dilution plate method with PDA medium, 37 C. It was then purified by transferring a single conidium onto a PDA agar plate. The strain NN047801 was identified as *Cladorrhinum bulbillosum*, based on both morphological characteristics and ITS rDNA sequence.

Strain *Umbelopsis westeae* CBS871.85 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

The fungal strain NN058098 was isolated from soil samples collected from Guizhou Province, China, in 2014 by the dilution plate method with PDA medium pH3, 25 C. It was then purified by transferring a single conidium onto a PDA agar plate. The strain NN058098 was identified as *Zygomycetes* sp., based on both morphological characteristics and ITS rDNA sequence.

The fungal strain NN058297 was isolated from litter samples collected from Guizhou Province, China, in 2014 by the dilution plate method with PDA medium, 25 C. It was then purified by transferring a single conidium onto a PDA agar plate. The strain NN058297 was identified as *Chaetomium cupreum*, based on both morphological characteristics and ITS rDNA sequence.

*Cordyceps cardinalis* CBS113411 was purchased from CBS-KNAW Fungal Biodiversity Centre, Uppsalalaan 8, 3584 CT, Utrecht, The Netherlands and inoculated onto a PDA plate and incubated for 8 days at 26° C. in the darkness. Several mycelia-PDA plugs were inoculated into 500 ml shake flasks containing 100 mls of YPG medium. The flasks were incubated for 5 days at 26° C. with shaking at 100 rpm.

The fungal strain NN044232 was isolated from soil samples collected from China, in 1998 by the dilution plate method with PDA medium, pH7, 25 C. It was then purified by transferring a single conidium onto a PDA agar plate. The strain NN044232 was identified as *Penicillium* sp. 'qii', based on both morphological characteristics and ITS rDNA sequence.

The fungal strain NN058292 was isolated from soil samples collected from Guizhou Province, China, in 2014 by the dilution plate method with PDA medium pH3. It was then purified by transferring a single conidium onto a PDA agar plate. The strain NN058292 was identified as *Aspergillus* sp. nov. XZ2609, based on both morphological characteristics and ITS rDNA sequence.

The fungal strain NN058101 was isolated from soil samples collected from Guizhou Province, China, in 2014 by the dilution plate method with PDA medium pH3, 25 C. It was then purified by transferring a single conidium onto a PDA agar plate. The strain NN058101 was identified as *Paecilomyces* sp. XZ2658, based on both morphological characteristics and ITS rDNA sequence.

The fungal strain NN046782 was isolated from soil samples collected from China, in 1998 by the dilution plate method with YG medium, pH7, 45 C. It was then purified by transferring a single conidium onto another YG plate. The strain NN046782 was identified as *Rhizomucor pusillus* T185-2, based on both morphological characteristics and ITS rDNA sequence.

The fungal strain NN051201 was isolated from litter samples collected from China, in 2008 by the dilution plate method with PDA medium, 25 C. It was then purified by transferring a single conidium onto a PDA agar plate. The strain NN051201 was identified as *Pycnidiophora* cf. *dispera*, based on both morphological characteristics and ITS rDNA sequence.

The fungal strain NN000400 was from CBS with access number as CBS104.75. The strain NN000400 was identified as *Thermomucor indicae-seudaticae*, based on both morphological characteristics and ITS rDNA sequence.

The fungal strain NN054449 was isolated from dead insect samples collected from Tibet, China, in 2012 by the dilution plate method with Horikoshi medium, pH10, 15 C. It was then purified by transferring a single conidium onto a PDA agar plate. The strain NN054449 was identified as *Isaria farinosa*, based on both morphological characteristics and ITS rDNA sequence.

The fungal strain NN046871 was isolated from soil samples collected from China, in 2000 by the dilution plate method with YG medium, 37 C. It was then purified by transferring a single conidium onto a PDA agar plate. The strain NN046871 was identified as *Zopfiella* sp., based on both morphological characteristics and ITS rDNA sequence.

Strain *Malbranchea flava* CBS132.77 was purchased CBS-KNAW Fungal Biodiversity Centre, and inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Hypholoma polytrichi* NN057040 was isolated from the Utsjoki region at the northernmost tip of Finland (69° 45' N, 27° 01' E). The strain was inoculated onto a PDA plate and incubated for 10 days at 26° C. in the darkness. Mycelia and spores from the plate were inoculated into 500 ml shake flasks containing 100 mls of YPG medium. The flasks were incubated for 15 days at 26° C. with shaking at 100 rpm.

Strain *Aspergillus deflectus* NN051662 was isolated from Jilin province in China. Please consult NZ China for propagation and DNA isolation conditions otherwise, the following would work: The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Ascobolus stictoideus* NN007614 (original code A4-1.1) an isolate from Denmark was purchased from the Institut for Sporeplanter, University of Copenhagen. The strain was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN053834 was isolated from soil samples collected from China with a collaboration with the Institute of Microbiology, CAS, in 2011, by the dilution plate method with PDA medium, pH7, 10 C. It was then purified by transferring a single conidium onto a PDA agar plate. The strain NN053834 was identified as *Coniochaeta* sp., based on both morphological characteristics and ITS rDNA sequence.

The fungal strain NN054033 was isolated from soil samples collected from China with a collaboration with the Institute of Microbiology, CAS, in 2011, by the dilution plate method with PDA medium, pH7, 10 C. It was then purified by transferring a single conidium onto a PDA agar plate. The strain NN054033 was identified as *Daldinia fissa*, based on both morphological characteristics and ITS rDNA sequence.

The fungal strain NN051542 was isolated from rotten corn stover samples collected from China, in 2007 by the dilution plate method with PDA medium, pH7, 25 C. It was then purified by transferring a single conidium onto a PDA agar plate. The strain NN051542 was identified as *Rosellinia* sp., based on both morphological characteristics and ITS rDNA sequence.

The fungal strain NN057909 was obtained through a collaboration with Professor Cai Lei in Institute of Microbiology, CAS, in 2014. The strain was collected from China. It was identified as *Ascobolus* sp., based on both morphological characteristics and ITS rDNA sequence.

The fungal strain NN058306 was isolated from soil samples collected from Guizhou Province, China, in 2014 by the dilution plate method with PDA medium pH3. It was then purified by transferring a single conidium onto a PDA agar plate. The strain NN058306 was identified as *Curreya* sp., based on both morphological characteristics and ITS rDNA sequence.

The fungal strain NN043614 was isolated from soil samples collected from, China, in 1998 by the dilution plate method with PDA medium, pH7, 25 C. It was then purified by transferring a single conidium onto a PDA agar plate. The strain NN043614 was identified as *Coniothyrium* sp., based on both morphological characteristics and ITS rDNA sequence.

The fungal strain NN047189 was isolated from soil samples collected from, China, in 1998 by the dilution plate method with PDA medium, pH7, 25 C. It was then purified by transferring a single conidium onto a PDA agar plate. The strain NN047189 was identified as *Hypoxylon* sp., based on both morphological characteristics and ITS rDNA sequence.

The fungal strain NN043914 was isolated from soil samples collected from, China, in 1998 by the dilution plate method with PDA medium, pH7, 25 C. It was then purified by transferring a single conidium onto a PDA agar plate. The strain NN043914 was identified as *Xylariaceae* sp., based on both morphological characteristics and ITS rDNA sequence.

The fungal strain NN046688 was isolated from soil samples collected from China, in 1998 by the dilution plate method with YG medium, pH7, 45 C. It was then purified by transferring a single conidium onto another YG plate. The strain NN046688 was identified as *Hypoxylon* sp., based on both morphological characteristics and ITS rDNA sequence.

The fungal strain NN046158 was isolated from soil samples collected from China, in 1998 by the dilution plate method with PDA medium, pH10, 25 C. It was then purified by transferring a single conidium onto a PDA agar plate. The strain NN046158 was identified as *Yunnania penicillata*, based on both morphological characteristics and ITS rDNA sequence.

Strain *Engyodontium album* NN042720 was isolated in Denmark. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metapochonia bulbillosa* XZ2653 NN058096 was isolated from a soil sample from Guizhou China. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Hamigera paravellanea* A3661 NN102174 was isolated in Japan. The strain was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

The fungal strain NN047633 was isolated from dead insect samples collected from China, in 2002 by the dilution plate method with PDA medium, pH7, 25 C. It was then purified by transferring a single conidium onto a PDA agar plate. The strain NN047633 was identified as *Metarhizium iadini*, based on both morphological characteristics and ITS rDNA sequence.

The fungal strain NN044936 was isolated from soil samples collected from China, in 1998 by the dilution plate method with YG medium, pH7, 45 C. It was then purified by transferring a single conidium onto another YG agar plate. The strain NN044936 was identified as *Thermoascus aurantiacus*, based on both morphological characteristics and ITS rDNA sequence.

The fungal strain NN071248 was isolated from soil samples collected from Shandong Province, China, in 2015 by the dilution plate method with Horikoshi medium, pH10, 25 C. It was then purified by transferring a single conidium onto another Horikoshi plate. The strain NN071248 was identified as *Clonostachys rossmaniae*, based on both morphological characteristics and ITS rDNA sequence.

The fungal strain NN046572 was isolated from soil samples collected from China, in 1998 by the dilution plate method with PDA medium, pH7, 25 C. It was then purified by transferring a single conidium onto a PDA agar plate. The strain NN046572 was identified as *Simpliciliium obclavatum*, based on both morphological characteristics and ITS rDNA sequence.

The fungal strain NN058092 was isolated from soil samples collected from Guizhou Province, China, in 2014 by the dilution plate method with PDA medium pH3, 25 C. It was then purified by transferring a single conidium onto a PDA agar plate. The strain NN058092 was identified as *Aspergillus inflatus*, based on both morphological characteristics and ITS rDNA sequence.

The fungal strain NN071247 was isolated from soil samples collected from Shandong Province, China, in 2015 by the dilution plate method with Horikoshi medium, pH10, 25 C. It was then purified by transferring a single conidium onto another Horikoshi agar plate. The strain NN071247 was identified as *Paracremonium inflatum*, based on both morphological characteristics and ITS rDNA sequence.

The fungal strain NN046156 was isolated from soil samples collected from China, in 1998 by the dilution plate method with Horikoshi medium, pH10, 25 C. It was then purified by transferring a single conidium onto another Horikoshi agar plate. The strain NN046156 was identified as *Westerdykella* sp., based on both morphological characteristics and ITS rDNA sequence.

Strain *Stropharia semiglobata* NN070885 was isolated in Kongstrup Bakker in Denmark. The strain was inoculated onto a PDA plate and incubated for 32 days at 26° C. in the darkness. Mycelia and spores from the plate were inoculated into 500 ml shake flasks containing 100 mls of YPG medium. The flasks were incubated for 14 days at 26° C. with shaking at 100 rpm.

Strain *Gelasinospora cratophora* NN070952 was isolated from a soil sample in Denmark. The strain was inoculated onto a PDA plate and incubated for 2 days at 26° C. in the darkness. Mycelia and spores from the plate were inoculated into 500 ml shake flasks containing 100 mls of YPG medium. The flasks were incubated for 4 days at 26° C. with shaking at 100 rpm.

Strain *Deconica coprophila* MS02928 was isolated from the Denmark. The strain was inoculated onto a half strength PDA plate and incubated for 10 days at 20° C. in the darkness. Mycelia and spores from the plate were inoculated into 500 ml shake flasks containing 100 mls of YPG medium. The flasks were incubated for 15 days at 26° C. with shaking at 100 rpm.

Media and Solutions

DAP4C-1 medium was composed of 0.5 g yeast extract, 10 g maltose, 20 g dextrose, 11 g magnesium sulphate heptahydrate, 1 g dipotassium phosphate, 2 g citric acid monohydrate, 5.2 g potassium phosphate tribasic monohydrate, 1 mL Dowfax 63N10 (antifoaming agent), 2.5 g calcium carbonate, supplemented with 1 mL KU6 metal solution, and deionised water to 1000 mL.

KU6 metal solution was composed of 6.8 g $ZnCl_2$, 2.5 g $CuSO_4 \cdot 5H_2O$, 0.13 g $NiCl_2$, 13.9 g $FeSO_4 \cdot 7H_2O$, 8.45 g $MnSO_4 \cdot H_2O$, 3 g $C_6H_8O_7 \cdot H_2O$, and deionised water to 1000 mL.

YP 2% glucose medium was composed of 10 g yeast extract, 20 g Bacto-peptone, 20 g glucose, and deionised water to 1000 mL.

LB plates were composed of 10 g of Bacto-tryptone, 5 g of yeast extract, 10 g of sodium chloride, 15 g of Bacto-agar, and deionised water to 1000 mL.

LB medium was composed of 10 g of Bacto-tryptone, 5 g of yeast extract, and 10 g of sodium chloride, and deionised water to 1000 mL.

COVE-Sucrose-T plates were composed of 342 g of sucrose, 20 g of agar powder, 20 mL of COVE salt solution, and deionised water to 1000 mL. The medium was sterilized by autoclaving at 15 psi for 15 minutes (Bacteriological Analytical Manual, 8th Edition, Revision A, 1998). The medium was cooled to 60° C. and 10 mM acetamide, Triton X-100 (50 µL/500 mL) were added.

COVE-N-Agar tubes were composed of 218 g Sorbitol, 10 g Dextrose, 2.02 g $KNO_3$, 25 g agar, 50 mL Cove salt solution, and deionised water up to 1000 mL.

COVE salt solution was composed of 26 g of $MgSO_4 \cdot 7H_2O$, 26 g of KCL, 26 g of $KH_2PO_4$, 50 mL of COVE trace metal solution, and deionised water to 1000 mL.

COVE trace metal solution was composed of 0.04 g of $Na_2B4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_4 \cdot 2H_2O$, 10 g of $ZnSO_4 \cdot 7H_2O$, and deionised water to 1000 mL.

YPM medium contained 1% of Yeast extract, 2% of Peptone and 2% of Maltose.

Hen eggwhite lysozyme (HEWL) was obtained from Sigma-Aldrich #62972

Example 1: Method for the Determination of Lysozyme Activity Against *Micrococcus Lysodeikticus* (Reducing End Method)

The lysozyme was diluted in phosphate buffer (5 mM citrate, 5 mM $K_2HPO_4$, 0.01% TritonX-100, pH 5.0) to 50 µg/mL in polypropylene tubes. The diluted lysozyme was further diluted in a 96-well polypropylene microtiter plate to a concentration of 0.7 µg/mL in phosphate buffer (5 mM citrate, 5 mM $K_2HPO_4$, 0.01% TritonX-100, pH 5.0). In a polypropylene deepwell plate 50 µL of the lysozyme dilution was mixed with 450 µL 1% *Micrococcus lysodeikticus* solution (lyophilized *Micrococcus lysodeikticus* ATCC No. 4698 (Sigma M3770) in milli-Q water) and incubated at 40° C. with shaking (500 rpm) for 45 min. After incubation the deepwell plate was centrifuged (4000 g, 5 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide solution in K—Na tartrate/NaOH buffer (50 g/L K—Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water). The OD measurement values represent the difference after the original (background) reading was subtracted. The average OD measurement for hen eggwhite lysozyme by the present method is 0.55 at 0.9 ppm and the average OD measurement for SEQ ID NO 159 is 0.34 at 0.9 ppm (data not shown).

Example 2: Genomic DNA Extraction from Strains of *Sporormia fimetaria* (SEQ ID NO: 1), *Poronia punctata* (SEQ ID NO: 4 and 7), *Lecanicillium* sp. (SEQ ID NO: 10, 13 and 67), *Onygena equina* (SEQ ID NO: 16), *Purpureocillium lilacinum* (SEQ ID NO: 19), *Trichobolus zukalii* (SEQ ID NO: 22), *Penicillium citrinum* (SEQ ID NO: 25), *Cladorrhinum bulbillosum* (SEQ ID NO: 28), *Umbelopsis westeae* (SEQ ID NO: 31), *Zygomycetes* sp. (SEQ ID NO: 34), *Chaetomium cupreum* (SEQ ID NO: 37), *Cordyceps cardinalis* (SEQ ID NO: 40), *Penicillium* sp. 'qii' (SEQ ID NO: 43), *Aspergillus* sp. nov. XZ2609 (SEQ ID NO: 46), *Paecilomyces* sp. XZ2658 (SEQ ID NO: 49 and 52), *Pycnidiophora* cf. *dispera* (SEQ ID NO: 58), *Isaria farinosa* (SEQ ID NO: 64), *Zopfiella* sp. (SEQ ID NO: 70), *Malbranchea flava* (SEQ ID NO: 73), *Hypholoma polytrichi* (SEQ ID NO: 76), *Aspergillus deflectus* (SEQ ID NO: 81), *Ascobolus stictoideus* (SEQ ID NO: 84), *Coniochaeta* sp. (SEQ ID NO: 87), *Ascobolus* sp. ZY179 (SEQ ID NO: 96), *Curreya* sp. XZ2623 (SEQ ID NO: 99), *Coniothyrium* sp. (SEQ ID NO: 102), *Hypoxylon* sp. (105 and 111), *Xylariaceae* sp. 1653h (SEQ ID NO: 108), *Engyodontium album* (SEQ ID NO: 117), *Metapochonia bulbillosa* XZ2653 (SEQ ID NO: 120), *Hamigera paravellanea* A3661 (SEQ ID NO: 123), *Metarhizium iadini* (SEQ ID NO: 126), *Clonostachys rossmaniae* (SEQ ID NO: 132), *Aspergillus inflatus* (SEQ ID NO: 138), *Paracremonium inflatum* (SEQ ID NO: 141), *Westerdykella* sp. (SEQ ID NO: 144), *Stropharia semiglobata* (SEQ ID NO: 228, 231 and 153), and *Gelasinospora cratophora* (SEQ ID NO: 156)

*Sporormia fimetaria* strain NN047801 was inoculated onto a PDA plate and incubated for 7 days at 28° C. in the darkness. Several mycelia-PDA plugs were inoculated into 500 ml shake flasks containing 100 ml of YPG medium. The flasks were incubated for 3 days at 28° C. with shaking at 160 rpm.

Strain *Poronia punctata* NN009607 was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

*Lecanicillium* sp. strain NN054002 was inoculated onto a PDA plate and incubated for 7 days at 15° C. in the darkness. Several mycelia-PDA plugs were inoculated into 500 ml shake flasks containing 100 ml of YPG medium. The flasks were incubated for 5 days at 20° C. with shaking at 160 rpm.

Strain *Onygena equina* NN056731 was inoculated onto a PDA plate and incubated for 18 days at 20° C. in the darkness. Mycelia and spores from the plate were inoculated into 500 ml shake flasks containing 100 mls of YPG medium. The flasks were incubated for 18 days at 20° C. with shaking at 100 rpm.

Strain *Purpureocillium lilacinum* NN070261 was isolated from a soil sample from the United States, and inoculated onto a PDA plate and incubated for 8 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Trichobolus zukalii* CBS720.69 was purchased CBS-KNAW Fungal Biodiversity Centre, and inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

Strain *Penicillium citrinum* NN070248 was inoculated onto a PDA plate and incubated for 7 days at 26° C. in the darkness. Mycelia and spores from the plate were inoculated into 500 ml shake flasks containing 100 mls of YPG medium. The flasks were incubated for 6 days at 26° C. with shaking at 100 rpm.

*Cladorrhinum bulbillosum* strain NN057876 was inoculated onto a PDA plate and incubated for 7 days at 37° C. in the darkness. Several mycelia-PDA plugs were inoculated into 500 ml shake flasks containing 100 ml of YPG medium. The flasks were incubated for 3 days at 37° C. with shaking at 160 rpm.

Strain *Umbelopsis westeae* NN070463 was inoculated onto a PDA plate and incubated for 7 days at 26° C. in the darkness. Mycelia and spores from the plate were inoculated into 500 ml shake flasks containing 100 mls of YPG medium. The flasks were incubated for 3 days at 26° C. with shaking at 100 rpm.

*Zygomycetes* sp. Strain NN058098, *Chaetomium cupreum* strain NN058297 and *Pycnidiophora* cf *dispera* strain NN051201 were inoculated onto a PDA plate and incubated for 7 days at 25° C. in the darkness. Several mycelia-PDA plugs were inoculated into 500 ml shake flasks containing 100 ml of YPG medium. The flasks were incubated for 3 days at 25° C. with shaking at 160 rpm.

*Cordyceps cardinalis* NN070475 was inoculated onto a PDA plate and incubated for 8 days at 26° C. in the darkness. Several mycelia-PDA plugs were inoculated into 500 ml shake flasks containing 100 mls of YPG medium. The flasks were incubated for 5 days at 26° C. with shaking at 100 rpm.

Strain *Penicillium* sp. 'qii' NN044232 was inoculated onto a PDA plate and incubated for 5 days at 25° C. in the darkness. Mycelia and spores from the plate were inoculated into 500 ml shake flasks containing 100 ml of YPG medium. The flasks were incubated for 4 days at 25° C. with shaking at 100 rpm.

Strain *Aspergillus* sp. nov. XZ2609 NN058292 was inoculated onto a PDA plate and incubated for 5 days at 25° C. in the darkness. Mycelia and spores from the plate were inoculated into 500 ml shake flasks containing 100 ml of YPG medium. The flasks were incubated for 7 days at 25° C. with shaking at 100 rpm.

Strain *Paecilomyces* sp. XZ2658 NN058101 was inoculated onto a PDA plate and incubated for 5 days at 25° C. in the darkness. Mycelia and spores from the plate were inoculated into 500 ml shake flasks containing 100 mls of YPG medium. The flasks were incubated for 5 days at 25° C. with shaking at 100 rpm.

*Isaria farinosa* strain NN054449 was inoculated onto a PDA plate and incubated for 7 days at 15° C. in the darkness. Several mycelia-PDA plugs were inoculated into 500 ml shake flasks containing 100 ml of YPG medium. The flasks were incubated for 4 days at 25° C. with shaking at 160 rpm.

*Zopfiella* sp. strain NN046871 was inoculated onto a PDA plate and incubated for 7 days at 37° C. in the darkness. Several mycelia-PDA plugs were inoculated into 500 ml shake flasks containing 100 ml of YPG medium. The flasks were incubated for 2 days at 37° C. with shaking at 160 rpm.

Strain *Malbranchea flava* NN070411 was inoculated onto a PDA plate and incubated for 14 days at 26° C. in the darkness. Mycelia and spores from the plate were inoculated into 500 ml shake flasks containing 100 mls of YPG medium. The flasks were incubated for 20 days at 26° C. with shaking at 100 rpm.

Strain *Hypholoma polytrichi* NN057040 was inoculated onto a PDA plate and incubated for 10 days at 26° C. in the darkness. Mycelia and spores from the plate were inoculated into 500 ml shake flasks containing 100 mls of YPG medium. The flasks were incubated for 15 days at 26° C. with shaking at 100 rpm.

Strain *Aspergillus deflectus* NN051662 was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Ascobolus stictoideus* NN007614 was inoculated onto a PDA plate and incubated for 7 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Coniochaeta* sp. NN053834 were inoculated onto a PDA plate and incubated for 7 days at 20° C. in the darkness. Several mycelia-PDA plugs were inoculated into 500 ml shake flasks containing 100 ml of YPG medium. The flasks were incubated for 4 days at 20° C. with shaking at 160 rpm.

Strain *Ascobolus* sp. ZY179 NN057909 were inoculated onto a PDA plate and incubated for 7 days at 37° C. in the darkness. Several mycelia-PDA plugs were inoculated into 500 ml shake flasks containing 100 ml of YPG medium. The flasks were incubated for 5 days at 37° C. with shaking at 160 rpm.

Strain *Curreya* sp. XZ2623 NN058306 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Coniothyrium* sp. NN043614 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Hypoxylon* sp. NN047189 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Xylariaceae* sp. 1653h NN043914 were inoculated onto a PDA plate and incubated for 7 days at 37° C. in the darkness. Several mycelia-PDA plugs were inoculated into 500 ml shake flasks containing 100 ml of YPG medium. The flasks were incubated for 5 days at 37° C. with shaking at 160 rpm.

Strain *Hypoxylon* sp. NN046688 were inoculated onto a PDA plate and incubated for 7 days at 37° C. in the darkness. Several mycelia-PDA plugs were inoculated into 500 ml shake flasks containing 100 ml of YPG medium. The flasks were incubated for 4 days at 37° C. with shaking at 160 rpm.

Strain *Engyodontium album* NN042720 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metapochonia bulbillosa* XZ2653 NN058096 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Hamigera paravellanea* A3661 NN102174 was inoculated onto a PDA plate and incubated for 5 days at 26° C. in the darkness. Mycelia and spores from the plate were inoculated into 500 ml shake flasks containing 100 mls of YPG medium. The flasks were incubated for 5 days at 26° C. with shaking at 100 rpm.

Strain *Metarhizium iadini* NN047633 were inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

Strain *Clonostachys rossmaniae* NN071248 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Aspergillus inflatus* NN058092 were inoculated onto a PDA plate and incubated for 7 days at 25° C. in the darkness. Several mycelia-PDA plugs were inoculated into 500 ml shake flasks containing 100 ml of YPG medium. The flasks were incubated for 5 days at 25° C. with shaking at 160 rpm.

Strain *Paracremonium inflatum* NN071247 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Westerdykella* sp. NN046156 were inoculated onto a PDA plate and incubated for 7 days at 25° C. in the darkness. Several mycelia-PDA plugs were inoculated into 500 ml shake flasks containing 100 ml of YPG medium. The flasks were incubated for 7 days at 25° C. with shaking at 160 rpm.

Strain *Stropharia semiglobata* NN070885 was inoculated onto a PDA plate and incubated for 32 days at 26° C. in the darkness. Mycelia and spores from the plate were inoculated into 500 ml shake flasks containing 100 mls of YPG medium. The flasks were incubated for 14 days at 26° C. with shaking at 100 rpm.

Strain *Gelasinospora cratophora* NN070952 was inoculated onto a PDA plate and incubated for 2 days at 26° C. in the darkness. Mycelia and spores from the plate were inoculated into 500 ml shake flasks containing 100 mls of YPG medium. The flasks were incubated for 4 days at 26° C. with shaking at 100 rpm.

Strain *Deconica coprophila* MS02928 was inoculated onto a half strength PDA plate and incubated for 10 days at 20° C. in the darkness. Mycelia and spores from the plate were inoculated into 500 ml shake flasks containing 100 mls of YPG medium. The flasks were incubated for 15 days at 26° C. with shaking at 100 rpm.

In all cases, the mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using DNeasy Plant Maxi Kit (24) (QIAGEN GmbH, Hilden, Germany) following the manufacturer's instructions.

Example 3: Genomic DNA Extraction from *Rhizomucor pusillus* T185-2 (SEQ ID NO: 225) and *Thermomucor indicae-Seudaticae* (SEQ ID NO: 61)

*Rhizomucor pusillus* T185-2 NN046782 was inoculated onto a PDA plate and incubated for 3 days at 45° C. in the darkness. Mycelia and spores from the plate were inoculated into 500 ml shake flasks containing 100 mls of FG4 medium. The flasks were incubated for 3 days at 45° C. with shaking at 100 rpm.

*Thermomucor indicae-seudaticae* strain NN000400 was inoculated onto a PDA plate and incubated for 7 days at 45° C. in the darkness. Several mycelia-PDA plugs were inoculated into 500 ml shake flasks containing 100 ml of YPG medium. The flasks were incubated for 3 days at 45° C. with shaking at 160 rpm.

In all cases, the mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using a method developed by Scott O. Rogers & Arnold J. Bendich (Plant Molecular Biology 5: 69-76, 1985).

Example 4: Genomic DNA Extraction from *Daldinia fissa* (SEQ ID NO: 90)

Strain *Daldinia fissa* NN054033 were inoculated onto a PDA plate and incubated for 15 days at 15° C. in the darkness.

The mycelia were collected by scraping from agar plate with the sterilized scalpel and frozen under liquid nitrogen. Frozen mycelia were ground, by a mortar and a pestle, to a fine powder, and genomic DNA was isolated using FastDNA spin kit for soil (MP Biomedicals, Santa Ana, Calif., USA) following the manufacturer's instruction.

Example 5: Genomic DNA Extraction from *Rosellinia* sp-51542 (SEQ ID NO: 93), *Yunnania penicillata* (SEQ ID NO: 114) and *Simplicillium obclavatum* (SEQ ID NO: 135)

Strain *Rosellinia* sp-51542 NN051542 were inoculated onto a PDA plate and incubated for 7 days at 37° C. in the darkness. Several mycelia-PDA plugs were inoculated into 500 ml shake flasks containing 100 ml of YPG medium. The flasks were incubated for 4 days at 37° C. with shaking at 160 rpm.

Strain *Yunnania penicillata* NN046158 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

Strain *Simplicillium obclavatum* NN046572 were inoculated onto a PDA plate and incubated for 7 days at 25° C. in the darkness. Several mycelia-PDA plugs were inoculated into 500 ml shake flasks containing 100 ml of YPG medium. The flasks were incubated for 4 days at 25° C. with shaking at 160 rpm.

In all cases, the mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using MP Faster DNA spin Kit (MP Biomedicals, Santa Ana, Calif., USA) following the manufacturer's instruction.

Example 6: Genomic DNA Extraction from *Thermoascus aurantiacus* (SEQ ID NO: 129)

Strain *Thermoascus aurantiacus* NN044936 were inoculated onto a PDA plate and incubated for 7 days at 45° C. in the darkness. Several mycelia-PDA plugs were inoculated into 500 ml shake flasks containing 100 ml of YPG medium. The flasks were incubated for 3 days at 45° C. with shaking at 160 rpm.

The mycelia were collected by filtration through MIRACLOTH® (Calbiochem, La Jolla, Calif., USA) and frozen under liquid nitrogen. Frozen mycelia were ground, by a mortar and a pestle, to a fine powder, and genomic DNA was isolated using Large-Scale Column Fungal DNAout (Win Honor Bioscience Limited, Beijing, China) following the manufacturer's instruction.

Example 7: Genome Sequencing, Assembly and Annotation of *Sporormia fimetaria* (SEQ ID NO: 1), *Thermomucor indicae-seudaticae* (SEQ ID NO: 61), *Thermoascus aurantiacus* (SEQ ID NO: 129)

The extracted genomic DNA samples of *Thermoascus aurantiacus*, *Sporormia fimetaria* and *Thermomucor indicae-seudaticae* were delivered to Beijing Genome Institute (BGI, Shenzhen, China) for genome sequencing using an ILLUMINA® GA2 System (Illumina, Inc., San Diego, Calif., USA). The raw reads were assembled at BGI using program SOAPdenovo (Li et al., 2010, *Genome Research*, 20: 265-72). The assembled sequences were analyzed using standard bioinformatics methods for gene identification and functional prediction. GeneMark-ES fungal version (Ter-Hovhannisyan V et al., 2008, *Genome Research*, 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 8: Genome Sequencing, Assembly and Annotation of *Cladorrhinum bulbillosum* (SEQ ID NO: 28), *Zygomycetes* sp. (SEQ ID NO: 34), *Chaetomium cupreum* (SEQ ID NO: 37), *Ascobolus* sp. ZY179 (SEQ ID NO: 96), *Curreya* sp. XZ2623 (SEQ ID NO: 99), *Hypoxylon* sp. (105 and 111), *Xylariaceae* sp. 1653h (SEQ ID NO: 108), *Metarhizium iadini* (SEQ ID NO: 126), *Clonostachys rossmaniae* (SEQ ID NO: 132), *Simplicillium obclavatum* (SEQ ID NO: 135), *Paracremonium inflatum* (SEQ ID NO: 141) and *Westerdykella* sp. (SEQ ID NO: 144)

The extracted genomic DNA samples of *Cladorrhinum bulbillosum*, *Zygomycetes* sp. *Ascobolus* sp. ZY179, *Curreya* sp. XZ2623, *Coniothyrium* sp., *Hypoxylon* sp., *Xylariaceae* sp. 1653h, *Metarhizium iadini*, *Clonostachys rossmaniae*, *Simplicillium obclavatum*, *Paracremonium inflatum*, *Westerdykella* sp. and *Chaetomium cupreum* were delivered to Novozymes Davis (USA) for genome sequencing using an ILLUMINA® MiSeq System. The raw reads were assembled at Novozymes Denmark using program Spades (Anton Bankevich et al., 2012, *Journal of Computational Biology*, 19(5): 455-477). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 9: Genome Sequencing, Assembly and Annotation of *Lecanicillium* sp. (SEQ ID NO: 10, 13 and 67), *Pycnidiophora* cf. *dispera* (SEQ ID NO: 58), *Isaria farinosa* (SEQ ID NO: 64), *Zopfiella* sp. (SEQ ID NO: 70), *Coniochaeta* sp. (SEQ ID NO: 87), *Daldinia fissa* (SEQ ID NO: 90), *Rosellinia* sp-51542 (SEQ ID NO: 93), *Coniothyrium* sp. (SEQ ID NO: 102) and *Yunnania penicillata* (SEQ ID NO: 114)

The extracted genomic DNA samples of *Coniochaeta* sp., *Daldinia fissa*, *Rosellinia* sp., *Yunnania penicillata*, *Lecanicillium* sp., *Isaria farinosa*, *Pycnidiophora* cf *dispera* and *Zopfiella* sp. were delivered to Fasteris (Switzerland) for genome sequencing using an ILLUMINA® HiSeq 2000 System (Illumina, Inc., San Diego, Calif., USA). The raw reads were assembled at Novozymes Denmark using program Idba (Peng, Yu et al., 2010, *Research in Computational Molecular Biology*, 6044:426-440. Springer Berlin Heidelberg.). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 10: Genome Sequencing, Assembly and Annotation of *Aspergillus inflatus* (SEQ ID NO: 138)

The extracted genomic DNA samples of *Aspergillus inflatus* were delivered to Exiqon A/S (Denmark) for genome sequencing using an ILLUMINA® MiSeq System (Illumina, Inc., San Diego, Calif., USA). The raw reads were assembled at Novozymes Denmark using program Spades (Anton Bankevich et al., 2012, *Journal of Computational Biology*, 19(5): 455-477). The assembled sequences were analyzed using standard bioinformatics methods for gene identification and function prediction. GeneMark-ES fungal version (Ter-Hovhannisyan V et al., 2008, *Genome Research* 18(12): 1979-1990) was used for gene prediction. Blastall version 2.2.10 (Altschul et al., 1990, *Journal of Molecular Biology*, 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozymes were identified directly by analysis of the Blast results. The Agene program (Munch and Krogh, 2006, *BMC Bioinformatics*, 7:263) and SignalP program (Nielsen et al., 1997, *Protein Engineering*, 10: 1-6) were used to identify start codons. SignalP program was further used to predict signal peptides. Pepstats (Rice et al., 2000, *Trends Genet*, 16(6): 276-277) was used to predict isoelectric points and molecular weights.

Example 11: Genome Sequencing, Assembly and Annotation of *Poronia punctata* (SEQ ID NO: 4 and 7), *Onygena equina* (SEQ ID NO: 16), *Purpureocillium lilacinum* (SEQ ID NO: 19), *Trichobolus zukalii* (SEQ ID NO: 22), *Penicillium citrinum* (SEQ ID NO: 25), *Umbelopsis westeae* (SEQ ID NO: 31), *Cordyceps cardinalis* (SEQ ID NO: 40), *Penicillium* sp. 'qii' (SEQ ID NO: 43), *Aspergillus* sp. nov. XZ2609 (SEQ ID NO: 46), *Paecilomyces* sp. XZ2658 (SEQ ID NO: 49 and 52), *Rhizomucor pusillus* T185-2 (SEQ ID NO: 225), *Malbranchea flava* (SEQ ID NO: 73), *Hypholoma* polytrichi (SEQ ID NO: 76), *Aspergillus deflectus* (SEQ ID NO: 81), *Ascobolus stictoideus* (SEQ ID NO: 84), *Engyodontium album* (SEQ ID NO: 117), *Metapochonia bulbillosa* XZ2653 (SEQ ID NO: 120), *Hamigera paravellanea* A3661 (SEQ ID NO: 123), *Stropharia semiglobata* (SEQ ID NO: 228, 231 and 153) and *Gelasinospora cratophora* (SEQ ID NO: 156)

The extracted genomic DNA samples of *Cordyceps cardinalis, Malbranchea flava, Poronia punctata, Gelasinospora cratophora, Penicillium* sp. 'qii', *Paecilomyces* sp. XZ2658 *Aspergillus* sp. nov. XZ2609, *Metapochonia bulbillosa* XZ2653, *Stropharia semiglobata, Hamigera paravellanea, Rhizomucor pusillus* T185-2, *Umbelopsis westeae, Hypholoma polytrichi, Trichobolus zukalii, Purpureocillium lilacinum, Penicillium citrinum, Ascobolus stictoideus, Engyodontium album, Onygena equina* and *Aspergillus deflectus* were genome sequenced using an ILLUMINA® HiSeq 2000 System (Illumina, Inc., San Diego, Calif., USA).

The raw reads of *Cordyceps cardinalis, Malbranchea flava, Poronia punctata, Gelasinospora cratophora, Penicillium* sp. 'qii', *Paecilomyces* sp. XZ2658 *Aspergillus* sp. nov. XZ2609, *Metapochonia bulbillosa* XZ2653, *Stropharia semiglobata* and *Umbelopsis westeae* were assembled using program Spades (Anton Bankevich et al., 2012, *Journal of Computational Biology*, 19(5): 455-477). *Hypholoma polytrichi, Trichobolus zukalii, Purpureocillium lilacinum, Penicillium citrinum, Ascobolus stictoideus, Engyodontium album, Onygena equina, Hamigera paravellanea, Rhizomucor pusillus* T185-2 and *Aspergillus deflectus* were assembled using program Idba (Peng Yu et al., 2010, Research in Computational Molecular Biology. 6044:426-440. Springer Berlin Heidelberg.) The assembled sequences were analyzed using standard bioinformatics methods for gene identification and function prediction. GeneMark-ES fungal version (Ter-Hovhannisyan V et al., 2008, Genome Research 18(12): 1979-1990) was used for gene prediction. Blastall version 2.2.10 (Altschul et al., 1990, Journal of Molecular Biology. 215(3): 403-410, ftp://ftp.ncbi.nlm.nih.gov/blast/executables/release/2.2.10/) and HMMER version 2.1.1 (National Center for Biotechnology Information (NCBI), Bethesda, Md., USA) were used to predict function based on structural homology. The GH25 family lysozyme polypeptides were identified directly by analysis of the Blast results. The Agene program (Munch and Krogh, 2006, BMC Bioinformatics 7: 263) and SignalP program (Nielsen et al., 1997, Protein Engineering 10: 1-6) were used to identify start codons. SignalP program was further used to predict signal peptides. Pepstats (Rice et al., 2000, Trends in Genetics. 16(6): 276-277) was used to predict isoelectric points and molecular weights.

Example 12: Cloning and Expression of GH25 Lysozymes (SEQ ID NO: 1, 10, 13, 28, 34, 37, 58, 61, 64, 67 and 70)

Eleven fungal GH25 lysozyme wild type sequences were cloned from *Sporormia fimetaria* (SEQ ID NO: 1), *Lecanicillium* sp. WMM742 (SEQ ID NO: 10, 13, 67), *Cladorrhinum bulbillosum* (SEQ ID NO: 28), *Zygomycetes* sp. (SEQ ID NO: 34), *Chaetomium cupreum* (SEQ ID NO: 37), *Pycnidiophora* cf. *dispera* (SEQ ID NO: 58), *Thermomucor indicae-seudaticae* (SEQ ID NO:61), *Isaria farinosa* (SEQ ID NO: 64) and *Zopfiella* sp. (SEQ ID NO: 70).

The fungal GH25 lysozymes were cloned into an *Aspergillus oryzae* expression vector pCaHj505 as described in WO2013029496. The transcription of the GH25 lysozyme coding sequence with the native secretion signal was under the control of an *Aspergillus oryzae* alpha-amylase gene promoter.

The final expression plasmids were individually transformed into an *Aspergillus oryzae* expression host. The GH25 lysozyme genes were integrated by homologous recombination into the *Aspergillus oryzae* host genome upon transformation. Four transformants of each transformation were selected from the selective media agar plate and inoculated to 3 ml of YPM medium in 24-well plate and incubated at 30° C., 150 rpm. After 3 days incubation, 20 μl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all 11 genes were expressed with 1 or 2 protein bands each detected at 20 KD, 25 KD, 25 KD, 20 KD, 20 KD, 20 KD, 20 KD, 18 & 22 KD, 25 KD, 25 KD and 20 KD respectively. The recombinant *Aspergillus oryzae* strain with the strongest protein band were selected for shaking flask culturing and were inoculated on slant made of slant medium and incubated at 37 C for 6-7 days. When strains were well grown to fully sporulated, they were inoculated to 2 L shaking flasks each containing 400 ml of YPM and 4-8 flasks for each strain. Flasks were shaking at 80 rpm, 30 C. Cultures were harvested on day 3 and filtered using a 0.45 μm DURAPORE Membrane and were purified as described in Examples 20 to 30 respectively.

Example 13: Cloning and Expression of GH25 Lysozymes (SEQ ID NO: 87, 90, 93, 96, 99, 102, 105, 108, 111, 114, 126, 129, 132, 135, 138, 141 and 144)

Seventeen fungal GH25 lysozyme wild type sequences were cloned from *Coniochaeta* sp. (SEQ ID NO: 87), *Daldinia fissa* (SEQ ID NO: 90), *Rosellinia* sp. (SEQ ID NO: 93), *Ascobolus* sp. (SEQ ID NO: 96), *Curreya* sp. (SEQ ID NO: 99), *Coniothyrium* sp. (SEQ ID NO: 102), *Hypoxylon* sp. (SEQ ID NO:105), *Xylariaceae* sp. (SEQ ID NO: 108), *Hypoxylon* sp. (SEQ ID NO: 111), *Yunnania penicillata* (SEQ ID NO: 114), *Metarhizium iadini* (SEQ ID NO: 126), *Thermoascus aurantiacus* (SEQ ID NO: 129), *Clonostachys rossmaniae* (SEQ ID NO: 132), *Simplicillium obclavatum* (SEQ ID NO: 135), *Aspergillus inflatus* (SEQ ID NO: 138), *Paracremonium inflatum* (SEQ ID NO: 141), and *Westerdykella* sp. (SEQ ID NO: 144). The fungal GH25 lysozymes were cloned into an *Aspergillus oryzae* expression vector pCaHj505 as described in WO2013029496. The transcription of the GH25 lysozyme coding sequence with the native secretion signal was under the control of an *Aspergillus oryzae* alpha-amylase gene promoter.

The final expression plasmids were individually transformed into an *Aspergillus oryzae* expression host. The GH25 lysozyme genes were integrated by homologous recombination into the *Aspergillus oryzae* host genome upon transformation. Four transformants of each transformation were selected from the selective media agar plate and inoculated to 3 ml of YPM or Dap4C medium in 24-well plate and incubated at 30° C., 150 rpm. After 3 days incubation, 20 μl of supernatant from each transformant were analyzed on NuPAGE Novex 4-12% Bis-Tris Gel w/MES according to the manufacturer's instructions. The resulting gel was stained with Instant Blue. SDS-PAGE profiles of the cultures showed that all 17 genes were expressed with 1 or 2 protein bands each detected at 20 KD, 20 KD, 20 KD, 20 KD, 20 KD, 20 KD, 20 KD, 20 KD, 20 KD, 20 KD, 25 & 28 KD, 25 KD, 26 KD, 24 KD, 26 KD, 26 KD and 20 KD respectively. The recombinant *Aspergillus oryzae* strain with the strongest protein band were selected for shaking flask culturing and were inoculated on slant made of slant medium and incubated at 37 C for 6-7 days. When strains were well grown to fully sporulated, they were inoculated to 2 L shaking flasks each containing 400 ml of Dap4C and 2-6 flasks for each strain. Flasks were shaking at 80 rpm, 30 C. Cultures were harvested on day 3 and filtered using a 0.45 μm DURAPORE Membrane and were purified as described in Examples 31 to 47 respectively.

Example 13: Construction of the Improved Split-Marker *Aspergillus oryzae* Host (DAU)

Figure 1:
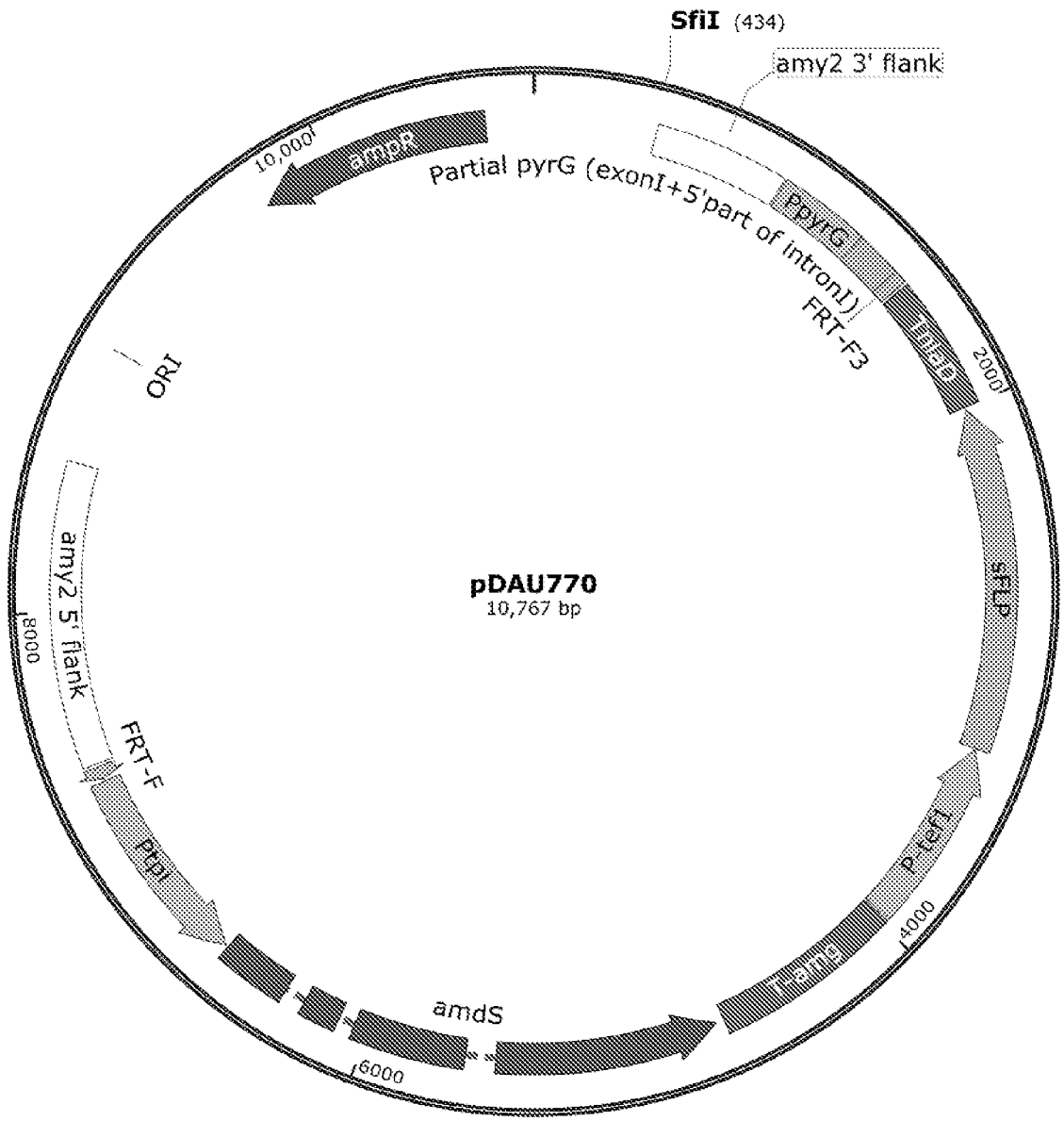
FIG. 1 represents the map of the different DNA features included on the plasmid pDAu770. The amy2 locus flanking regions (3' and 5') are indicated by white boxes. Promoter regions are indicated by green boxes for the promoter region of the pyrG, tef1 and tpi gene. The purple boxes indicate the selection cassette (ampR for ampicillin resistance and amdS for acetamide selection). The terminator regions are indicated by blue boxes for the terminator region of the niaD and amg genes. The coding region of the FLPase (sFLP) and the first exon of the pyrG gene are indicated in orange. The 5' region of the pyrG intron is indicated in grey. The origin of replication of the plasmid is indicated by ORI.
Figure 2:
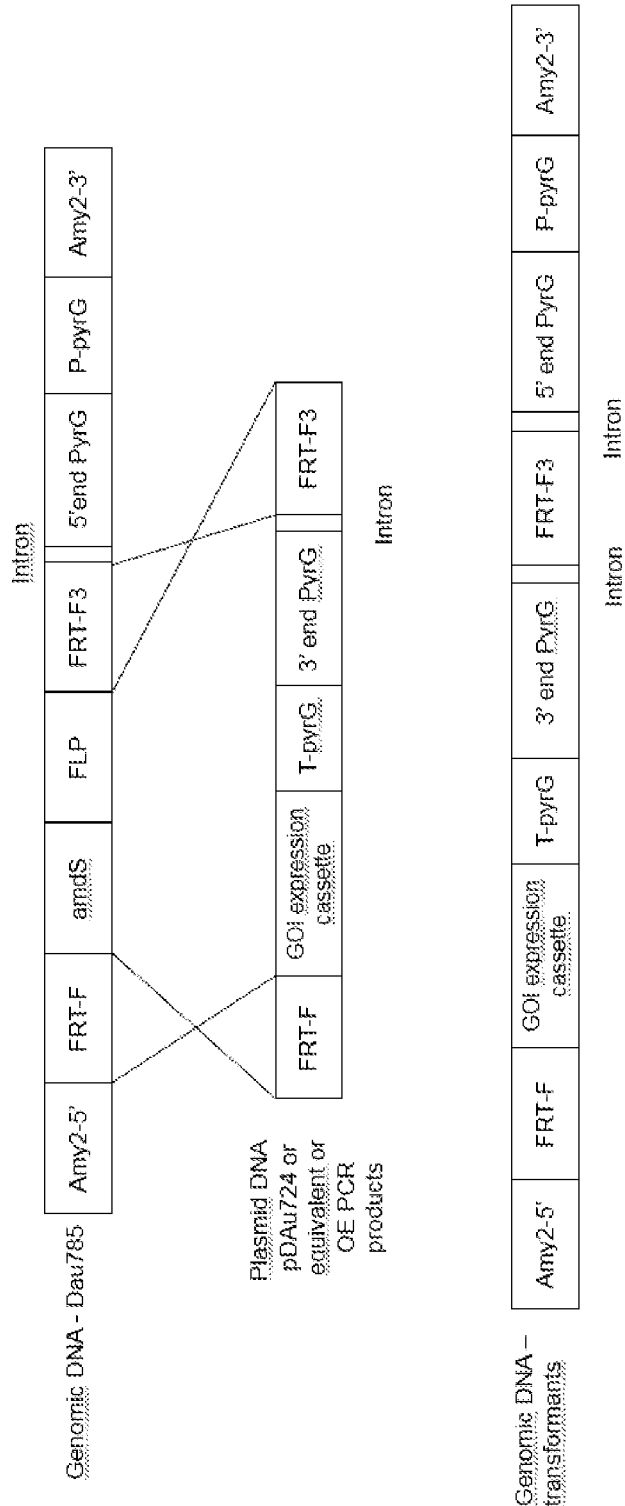
FIG. 2 is the schematic representation of transformation of the host strain DAu785 by the transforming DNA (either plasmid pDAu724 or derivatives or OverlapExtension PCR products.

An improved *Aspergillus oryzae* host/vector system comparable to the one described in example 5 disclosed in WO 2016026938A1 was constructed. The improvement was made to reduce the size of the transforming DNA by moving the FLPase expression cassette located on PART-II of the plasmid pDAu724 (see page 34 in WO 2016026938A1, FIG. 7 and SEQ ID NO: 30) to the integration locus amy2 in the genome of the host strain. The cloning of the FLPase expression cassette into pDAu703 (WO 2016026938A1 page 32 and FIG. 6 and SEQ ID NO: 29) was done by amplification of the FLPase expression cassette from pDAu724 and cloning in between FRT-F3 and the amdS selection marker of pDAu703 to give the plasmid pDAu770 (FIG. 1, SEQ ID NO: 216). The same protocol as described in WO 2016026938A1 page 33 was used to transform the linearized plasmid pDAu770 into protoplasts of *A. oryzae* strain Jal1338 (disclosed in WO2012/160097). Transformants were selected on AmdS selection plates to obtain strain DAu785. The resulting recombinant host strain DAu785 has a modified amy2 locus comparable to the one in DAU716 (WO2016/026938) with the addition of the FLPase expression cassette (FIG. 2, top panel). The host strain DAu785 is now constitutively expressing the FLPase site specific recombinase allowing the integration at the FRT sites of the transforming DNA in this case the PCR fragments obtained by Overlap Extension PCR reaction (FIG. 2, middle and bottom panels) and described in Example 17 below.

Example 14: PCR Amplification and InFusion Cloning of Lysozyme Encoding Sequences SEQ ID NO: 16, 19, 25, 31, 40, 73 and 117

Based on the lysozyme gene sequences identified by genome mining in *Onygena equina, Purpureocillium lilacinum, Malbranchea flava, Engyodontium album, Penicillium citrinum, Umbelopsis westeae*, and *Cordyceps cardinalis*, InFusion cloning primers were designed and ordered (Sigma Aldrich, Darmstadt, Germany) (see list in table 2 below).

TABLE 2

| | | | |
|---|---|---|---|
| InFusion cloning primers | | | |
| Primer* | Primer SEQ ID NO: | Primer to lysozyme SEQ ID NO: | Sequence |
| C8VRJ-F | 162 | 16 | ACACAACTGGGGATCCACCATGTTGAAAA CAATTATCTATACCACCCTTGCC |
| C8VRJ-R | 163 | 16 | AGATCTCGAGAAGCTTAGCCCTTTGCAAA TCGTTGCAATCC |

TABLE 2-continued

InFusion cloning primers

| Primer* | Primer SEQ ID NO: | Primer to lysozyme SEQ ID NO: | Sequence |
|---|---|---|---|
| C8VRQ-F | 164 | 19 | ACACAACTGGGGATCCACCATGAAGTTCG CATCCGTCGCC |
| C8VRQ-R | 165 | 19 | AGATCTCGAGAAGCTTAACCGGCGTTGGC AATCTTCTT |
| C8VS9-F | 166 | 25 | ACACAACTGGGGATCCACCATGCGCCCCT CCGTCATATTGC |
| C8VS9-R | 167 | 25 | AGATCTCGAGAAGCTTAAGCAGAAAACAC GTTCAAATCAAACTTCTTACT |
| C8VSA-F | 168 | 31 | ACACAACTGGGGATCCACCATGAAGCTCA CCTTTGCCTCTCTAACT |
| C8VSA-R | 169 | 31 | AGATCTCGAGAAGCTTAGGCTCCTTTGGC CATCCTAGACA |
| C8VSC-F | 170 | 40 | ACACAACTGGGGATCCACCATGCGCGCCT TTATTCCAGTCTT |
| C8VSC-R | 171 | 40 | AGATCTCGAGAAGCTTAGGCAGAGAAAAC GTTGAGATCAAATTTCTTG |
| C8VRT-F | 172 | 73 | ACACAACTGGGGATCCACCATGAAGCTGT CTCTCCTCCTTATTGTTGC |
| C8VRT-R | 173 | 73 | AGATCTCGAGAAGCTTAACCTAGGGCCAT TCTCTTCAACCC |
| C8VS8-F | 174 | 117 | ACACAACTGGGGATCCACCATGAAGTCTT TTGGTGTTATTGCTACCGG |
| C8VS8-R | 175 | 117 | AGATCTCGAGAAGCTTAGCCTCTGGCGAT TCTCTGAAGC |

*-F - forward primer; -R - reverse primer

PCR amplifications of SEQ ID NO: 16, 19, 25, 31, 40, 73 and 117 encoding for lysozyme polypeptides were carried out using Phusion High-Fidelity DNA polymerase (New England Biolabs, BioNordika Denmark A/S, Herlev, Denmark) in a 50 μL volume reaction. The PCR reaction mixes were consisting of 10 μL Phusion reaction buffer HF (5×); 1 μL of PCR nucleotide Mix (10 mM); 2 μL forward cloning primers (2.5 mM); 2 μL reverse cloning primers (2.5 mM); 1 μL Phusion High-Fidelity DNA Polymerase #M0530L (2000 U/mL); and PCR grade water up to 50 μL. PCR reactions were incubated on a thermocycler T100 (Biorad, Hercules, Calif., USA) using the following program: initial denaturation of 2 min at 98° C. followed by 30 cycles of 10 sec at 98° C., 2 min at 72° C. and ending up by a final elongation of 10 min at 72° C. PCR amplicons were purified using AMPure XP beads system kit (Agencourt, Beverly, Mass., USA) adapted on a Biomek FXp Liquid handler (Beckman Coulter, Brea, Calif., USA).

InFusion cloning was made using InFusion HD Plus EcoDry Cloning system kit (Takara, Kusatsu, Japan) in expression vector pDAu109 (WO 2005042735) previously digested with BamHI and HindIII restriction enzymes and following manufacturer's instructions.

A 2.5 μL volume of the five time diluted ligation mixtures was used to transform E. coli TOP10 (see strain chapter) chemically competent cells (Life Technologies, Carlsbad, Calif., USA). Three colonies were selected from LB agar plates containing 100 μg of ampicillin per ml and cultivated overnight in 3 mL of LB medium supplemented with 100 μg of ampicillin per ml. Plasmids DNA were purified using a Qiagen Spin Miniprep kit (Cat. 27106) (QIAGEN GmbH, Hilden, Germany) according to the manufacturer's instructions.

Lysozyme sequences cloned by InFusion were scrutinized for errors by Sanger DNA sequencing.

Forward and reverse oligonucleotide primers shown below were designed to PCR amplify the GH25 open reading frame from the genomic DNA samples. An IN-FUSION™ Cloning Kit (Clontech, Mountain View, Calif., USA) was used to clone the fragment directly into the expression vector pDau109 (WO 2005/042735).

Example 15: PCR Amplification and InFusion Cloning of Lysozyme Encoding Sequences SEQ ID NO: 43, 46, 49 and 52

BamHI-XhoI based cloning from *Penicillium* sp. 'qii' (SEQ ID NO: 43), *Paecilomyces* sp. XZ2658 (SEQ ID NO: 46 and 49) and *Aspergillus* sp. nov. XZ2609 (SEQ ID NO: 52).

The forward and reverse PCR primers shown in table 3 were used to generate an EcoRI-XhoI flanked cloning cassette from the genomic DNA prepared above for the following samples:

TABLE 3

PCR primers

| Primer* | Primer SEQ ID NO: | Primer to lysozyme SEQ ID NO: | Sequence |
|---|---|---|---|
| WIN1054-F | 188 | 43 | 5'-ACACAACTGGGGATCCACCATGAAG ACTACGGGTGTC |
| WIN1054-R | 189 | 43 | 5'-CCCTCTAGATCTCGAGTTAAGAACC CTTGGCAAAG |
| WIN1065-F | 190 | 46 | 5'-ACACAACTGGGGATCCACCATGAAG TTCACTACCATTGC |
| WIN1065-R | 191 | 46 | 5'-CCCTCTAGATCTCGAGCTACCCCTC GACAATCTT |
| WIN1057-F | 192 | 49 | 5'-ACACAACTGGGGATCCACCATGAAG TCTGTTGCTGTCT |
| WIN1057-R | 193 | 49 | 5'-CCCTCTAGATCTCGAGCTAAGAAGC ATTCGCAATGC |
| WIN1058-F | 194 | 52 | 5'-ACACAACTGGGGATCCACCATGAAG CTCACGAGTGTG |
| WIN1058-R | 195 | 52 | 5'-CCCTCTAGATCTCGAGTTACGAACC TCTAGCAAGC |

*-F - forward primer; -R - reverse primer

Bold letters represent coding sequence. The underlined sequence is homologous to the insertion sites of pDau109.

The PCR reaction (25 µl) was composed of 12.5 µl of 2×IPROOF™ HF Master Mix, 0.5 µl of appropriate forward primer (100 µM), 0.5 µl of the appropriate reverse primer (100 µM), 0.5 µl of genomic (100 ng/µl), and 11 µl of deionized water. The PCR reaction was incubated in a DYAD® Dual-Block Thermal Cycler (MJ Research Inc., Waltham, Mass., USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five µl of the PCR reaction were analyzed by 1% agarose gel electrophoresis using TAE buffer where an DNA band of the appropriate size was observed. In the case of WIN1054 for example, an approximately 700 base pair band was observed. The remaining PCR reactions were purified using an ILLUSTRA™ GFX™ PCR DNA and Gel Band Purification Kit according to the manufacturer's instructions.

The fragments were then cloned into BamHI and XhoI digested pDau109 using an INFUSION™ Cloning Kit resulting in plasmids containing the inserts. Cloning of the GH25 lysozyme PCR inserts into Bam HI-XhoI digested pDau109 resulted in the transcription of the cloned genes under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase. Isolated plasmids were sequenced with vector primers in order to determine a representative plasmid expression clone that was free of PCR errors.

Example 16: PCR Amplification and InFusion Cloning of Lysozyme Encoding Sequences SEQ ID NO: 4, 7, 22, 225, 76, 81 and 84

BamHI-HindIII based cloning of *Hypholoma polytrichi* (SEQ ID NO: 76), *Aspergillus deflectus* (SEQ ID NO: 81), *Trichobolus zukalii* (SEQ ID NO: 22), *Rhizomucor pusillus* (SEQ ID NO: 225), *Poronia punctata* (SEQ ID NO: 4 and 7) and *Ascobolus stictoideus* (SEQ ID NO: 84).

The forward and reverse PCR primers shown in table 4 were used to generate an BamHI-HindIII flanked cloning cassette from the genomic DNA prepared above for the following samples:

TABLE 4

PCR primers

| Primer* | Primer SEQ ID NO: | Primer to lysozyme SEQ ID NO: | Sequence |
|---|---|---|---|
| KKSC0132-F | 196 | 4 | 5'-ACACAACTGGGGATCCACCATGAA GTCTTACATCGCCCCC |
| KKSC0132-R | 197 | 4 | 5'-GTGCGGCCGCAAGCTTAATCAGAG GCTTCCTCCCATAGG |

TABLE 4-continued

PCR primers

| Primer* | Primer SEQ ID NO: | Primer to lysozyme SEQ ID NO: | Sequence |
|---|---|---|---|
| KKSC0133-F | 198 | 7 | 5'-ACACAACTGGGGATCCACCATGAA GTATCTCGTTCCCCTTTTG |
| KKSC0133-R | 199 | 7 | 5'-AGATCTCGAGAAGCTTATTAGCCC TTAGCCAGTCTCTT |
| KKSC0311-F | 200 | 22 | 5'-ACACAACTGGGGATCCACCATGAA GCTCACCACTTTTATCACG |
| KKSC0311-R | 201 | 22 | 5'-CTAGATCTCGAGAAGCTTTTAAGT CCCCTTGGCAAGCG |
| KKSC0314-F | 202 | 225 | 5'-ACACAACTGGGGATCCACCATGAA GTTTGCACTCCTAGTATCTG |
| KKSC0314-R | 203 | 225 | 5'-CTAGATCTCGAGAAGCTTTTAGCC ATAGTAGTTCTTGTCCCA |
| KKSC0862-F | 204 | 76 | 5'-ACACAACTGGGGATCCACCATGGC AAAGCTCCTCAAG |
| KKSC0862-R | 205 | 76 | 5'-AGATCTCGAGAAGCTTATTAGTGG GCGAAGACGTT |
| KKSC0819-F | 206 | 81 | 5-ACACAACTGGGGATCCACCATGAAG CTTCTTTCCGCCCT |
| KKSC0819-R | 207 | 81 | 5'-AGATCTCGAGAAGCTTATCACTGA GAGGCAAACTTGAC |
| KKSC0317-F | 208 | 84 | 5'-ACACAACTGGGGATCCACCATGGC TTCCAGACTGACCCT |
| KKSC0317-F | 209 | 84 | 5'-CTAGATCTCGAGAAGCTTTTAAGC TGCCACGCACTGGG |

*-F - forward primer; -R - reverse primer

Bold letters represent coding sequence. The underlined sequence is homologous to the insertion sites of pDau109.

The PCR reaction (25 µl) was composed of 12.5 µl of 2×IPROOF™ HF Master Mix, 0.5 µl of appropriate forward primer (100 µM), 0.5 µl of the appropriate reverse primer (100 µM), 0.5 µl of genomic (100 ng/µl), and 11 µl of deionized water. The PCR reaction was incubated in a DYAD® Dual-Block Thermal Cycler (MJ Research Inc., Waltham, Mass., USA) programmed for 1 cycle at 98° C. for 30 seconds; 30 cycles each at 98° C. for 10 seconds, 55° C. for 10 seconds, and 72° C. for 60 seconds; and 1 cycle at 72° C. for 10 minutes. Samples were cooled to 10° C. before removal and further processing.

Five µl of the PCR reaction were analyzed by 1% agarose gel electrophoresis using TAE buffer where an DNA band of the appropriate size was observed. In the case of KKSC0317 for example, an approximately 860 base pair band was observed. The remaining PCR reactions were purified using an ILLUSTRA™ GFX™ PCR DNA and Gel Band Purification Kit according to the manufacturer's instructions.

The fragments were then cloned into BamHI and HindIII digested pDau109 using an INFUSION™ HD Plus EcoDry Cloning system kit (Takara, Kusatsu, Japan). Cloning of the GH25 lysozyme PCR inserts into BamHI-HindIII digested pDau109 resulted in the transcription of the cloned genes under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase. Isolated plasmids were sequenced with vector primers in order to determine a representative plasmid expression clone that was free of PCR errors.

Example 17: Overlap Extension PCR Cloning
(SEQ ID NO: 120, 123, 228, 231, 153 and 156)

pDAu724 plasmid was used as DNA template to amplify two PCR products (F1 and F3) in reactions composed of 10 µL of KAPA polymerase buffer 5×, 1 µL 10 mM KAPA PCR Nucleotide Mix, 1 µL of 10 µM of the appropriate forward primers (SEQ ID NO: 210 for F1 and SEQ ID NO: 212 for F3), 1 µL of 10 µM of the appropriate reverse primers (SEQ ID NO: 211 for F1 and SEQ ID NO: 213 for F3), 1 to 10 ng of pDAu724 plasmid, 1 µL of KAPA Biosystems polymerase KK2502 (1unit) and PCR-grade water up to 50 µL.

PCR amplification reactions were carried out on a DYAD® Dual-Block Thermal Cycler (MJ Research Inc., Waltham, Mass., USA) programmed for 2 min. at 98° C. and followed by 35 cycles of 10 sec. at 98° C. and 2 min. at 72° C. and one final cycle of 10 min. at 72° C.

Five µl of the PCR reaction were analyzed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

Forward primer F1:
SEQ ID NO: 210: GAATTCGAGCTCGGTACCTTGAAGTTC

Reverse primer F1:
SEQ ID NO: 211: GGTGGATCCCCAGTTGTGTATATAGAGGATT

Forward primer F3:
SEQ ID NO: 212: TGCGCGGCGCGGCTGGGTCGACTCTA

Reverse primer F3:
SEQ ID NO: 213: TTCACACAGGAAACAGCTATGACCATG

Overlap Extension PCR reaction for cloning lysozyme genes amplified from *Gelasinospora cratophora*, *Metapochonia bulbillosa*, *Hamigera paravellanea*, and *Stropharia semiglobata* (3 sequences) gDNAs were composed of 10 µL KAPA polymerase buffer (5×), 1 µL 10 mM KAPA PCR Nucleotide Mix, 50 ng of PCR fragment F1 and equimolar amounts of PCR fragment F3 and lysozyme genes encoding for SEQ ID NO: 120, 123, 228, 231, 153 and 156, 1 µl KAPA Biosystems polymerase KK2502 (1unit) and PCR-grade water up to 48 µL. Reaction were incubated on a DYAD® Dual-Block Thermal Cycler (MJ Research Inc., Waltham, Mass., USA) using a program composed of 2 min. at 98° C.; followed by 5 cycles each composed of 10 sec. at 98° C., 30 sec. at 68° C., and 5 min. at 72° C. and completed by a final extension of 8 min. at 72° C.

During the OE PCR reactions, annealing between fragment F1 and lysozyme genes encoding for SEQ ID NO: 120, 123, 228, 231, 153 and 156 respectively were ensured by overlap SEQ ID NO: 214 included in the forward cloning primers (C6ZGC-F; C6ZG7-F; C122PC-F; C122PA-F; C122P9-F and C122P5-F respectively, table 4a) and annealing between fragment F3 and the lysozyme genes encoding for SEQ ID NO: 120, 123, 228, 231, 153 and 156 respectively were ensured by the overlapping SEQ ID NO: 215 included in the reverse cloning primers (C6ZGC-R; C6ZG7-R; C122PC-R; C122PA-R; C122P9-R and C122P5-R respectively, table 4a).

TABLE 4a

Cloning primers

| Primer* | Primer SEQ ID NO: | Primer to lysozyme SEQ ID NO: | Sequence |
| --- | --- | --- | --- |
| C122P5-F | 176 | 156 | CTATATACACAACTGGGGATCCACCATGAAGTCCTTCGTCCTCACGGC |
| C122P5-R | 177 | 156 | TAGAGTCGACCCAGCCGCGCCGGCCATTAAGATCCCTTAGCAAGAGCCTTAAGGC |
| C6ZGC-F | 178 | 120 | CTATATACACAACTGGGGATCCACCATGAAGTCTGTTACTTTCATCGCCAGTCT |
| C6ZGC-R | 179 | 120 | TAGAGTCGACCCAGCCGCGCCGGCCATTACGAAGCGTTAGCAATACGCTTAAGC |
| C6ZG7-F | 180 | 123 | CTATATACACAACTGGGGATCCACCATGAAGGCTTCTTCCATCCTCTCCC |
| C6ZG7-R | 181 | 123 | TAGAGTCGACCCAGCCGCGCCGGCCATCATCCACTCGCCAACTTCTTCAAC |
| C122PC-F | 182 | 228 | CTATATACACAACTGGGGATCCACCATGTTCTCTTTCGTCAAAGCGCTCA |
| C122PC-R | 183 | 228 | TAGAGTCGACCCAGCCGCGCCGGCCATTAATTTGCAAAGACATTGAGGTCGAATTGGC |
| C122PA-F | 184 | 231 | CTATATACACAACTGGGGATCCACCATGTTCCCTTTCGTCAAAACGCTCA |
| C122PA-R | 185 | 231 | TAGAGTCGACCCAGCCGCGCCGGCCATTAATTTGCAAACACATTGAGGTCGAATTGG |
| C122P9-F | 186 | 153 | CTATATACACAACTGGGGATCCACCATGGTCAAAATCTTGAGCCTTCTAGCC |
| C122P9-R | 187 | 153 | TAGAGTCGACCCAGCCGCGCCGGCCACTATGCGAATACGCTCAGGTCGAATTG |

One µL of 10 µM primer SEQ1 and 1 µL of 10 µM primer SEQ4 were added to the OE PCR reactions and the reactions were incubated a second time on a DYAD® Dual-Block Thermal Cycler (MJ Research Inc., Waltham, Mass., USA) using a program composed of 2 min at 98° C.; followed by 25 cycles each composed of 10 sec. at 98° C., and 4 min. at 72° C. and completed by a final extension of 10 min. at 72° C.

Five µl of the PCR reactions were analyzed by 1% agarose gel electrophoresis using TAE buffer where an DNA bands of the appropriate size were observed. The remaining PCR reactions were up-concentrated to 20 µL by heating the tubes at 60° C. 10 µL of those reactions were used for *Aspergillus oryzae* DAu785 protoplasts transformation.

Primer bind forward SEQ ID NO: 214:
CTATATACACAACTGGGGATCCACC

-continued

Primer bind reverse SEQ ID NO: 215:
TAGAGTCGACCCAGCCGCGCCGGCCA

Example 18: Preparation and Expression of Aspergillus Protoplasts (SEQ ID NO: 16, 19, 25, 31, 40, 73, 117, 120, 123, 228, 231, 153 and 156)

Protoplasts of Aspergillus oryzae MT3568 were prepared according to WO 95/002043. One hundred µl of protoplasts were mixed with 1-3 µg of the Aspergillus expression vectors or OE PCRs (for SEQ ID NO: 16, 19, 25, 31, 40, 73, 117, 120, 123, 228, 231, 153 and 156) and 250 µL of 60% PEG 4000 (Applichem, Darmstadt, Germany) (polyethylene glycol, molecular weight 4,000), 10 mM CaCl$_2$, and 10 mM Tris-HCl pH 7.5 and gently mixed. The mixtures were incubated at 37° C. for 30 minutes and the protoplasts were spread onto COVE plates for selection. After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

Spores of the best transformants for each transformation were spread onto COVE plates containing 0.01% TRITON® X-100 in order to isolate single colonies. The spreading was repeated twice in total on COVE plates containing 10 mM sodium nitrate. Spores were then inoculated into 500 mL shake flasks containing 100 mL of YP+2% glucose and incubated for 4 days at 30° C. with shaking at 100 rpm.

Previously selected strains were inoculated in 250 mL shake flasks with baffle containing 100 to 150 mL of DAP4C-1 supplemented lactic acid and with diammonium phosphate or YP2% glucose medium and fermented during 4 days at a temperature of 30° C. under 150 rpm agitation. Culture broths were harvested by filtration using a 0.2 µm filter device.

The culture broths can be purified as described in Example 48.

Example 19: Expression of GH25 Lysozymes in Aspergillus oryzae (SEQ ID NO: 4, 7, 22, 43, 46, 49, 52, 225, 76, 81 and 84)

Protoplasts of Aspergillus oryzae MT3568 were prepared according to WO 95/002043. One hundred µl of protoplasts were mixed with 1-3 µg of one of the following Aspergil/us expression vectors: SEQ ID NO: 4, 7, 22, 43, 46, 49, 52, 225, 76, 81 and 84.

Six ul containing about 3.0 µg total DNA was used for the transformation. The DNA was gently added to 100 µl of A. oryzae MT3568 protoplasts and 250 µl of 60% PEG 4000 (Sigma-Aldrich cat. No. 95904). The 60% (W/V) PEG 4000 was prepared in the following manner: PEG 4000 powder was dissolved in double distilled H2O and then heated for 10-20 seconds in a microwave oven at 800 watt until dissolved. The dissolved solution was cooled down to room temperature and then then adjusted with CaCl$_2$ solution and Tris-HCl solution (pH 7.5) for a final concentration of 10 mM of each. After adding the 60% PEG 4000 solution, the tube was gently mixed and incubated at 37° C. for 30 minutes. The mix was added to 6 ml of top agar with 10 mM acetamide and plated onto COVE-sorbitol plates with 10 mM acetamide.

The plates were incubated at 37° C. for 3 or more days and then moved to 26° C. for two days. Spores from 4 to 8 individual colonies were picked by first dipping a white 10 µl inoculation pin (Nunc A/S, Denmark) in a 0.1% TWEEN® 80 solution, contacting the sporulating colony on the selection plate, and restreaking with the pin onto fresh COVE sorbitol plates containing 10 mM acetamide. After 5 days at 26° C., spores from the restreaked colonies were used to inoculate a 96 well deep dish plate (NUNC, cat. no. 260251, Thermoscientific, USA). The wells of the deep dish plate contained 500 uls of either YP+2% glucose or DAP4C media. The inoculated plate was sealed with gas permeable tape (89009-656, VWR.com). Plates were incubated stationary at 30 C for 5 days. Expression was verified by analysis of 20 uls of harvested culture fluid on SDS-PAGE using a NUPAGE® 10% Bis-Tris gel (Invitrogen, Carlsbad, Calif., USA) and Coomassie blue staining. One transformant for each transformation experiment was selected for further work.

Spores of each designated transformant were inoculated into both YP+2% glucose medium and DAP-4C-1 medium (100 mls in 500 ml Erlenmeyer shake flask with baffles). The cultures were incubated at 26° C. and 150 rpm, 3 days and if necessary 4 days. An SDS gel was run as above to test protein amount.

After incubation for 4-7 days at 37° C. spores of four transformants were inoculated into 0.2 mL of YP+2% glucose or DAP4C-1 medium in 96 well microtiter plates. After 4 days cultivation at 30° C., the culture broths were analysed by SDS-PAGE to identify transformants producing the highest amounts of lysozyme enzymes.

The culture broths were purified as described in Example 48.

Example 20: Purification of SEQ ID NO: 3

The culture supernatant of O23CD8 was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM NaAc at pH5.0 with 1.5M (NH$_4$)$_2$SO$_4$ added. A gradient decrease of (NH$_4$)$_2$SO$_4$ concentration was applied as elution buffer from 1.5M to zero, and then elution fractions and flow-through fraction were collected to detect lysozyme activity. The fractions with lysozyme activity were analyzed by SDS-PAGE, and then concentrated, changed buffer by 20 mM PBS at pH6.0 for further evaluation. The protein concentration was determined by Qubit® Protein Assay Kit (Invitrogen, cat Q33212).

Example 21: Purification of SEQ ID NO: 12

The culture supernatant of O23T24 was firstly precipitated with ammonium sulfate (80% saturation), then dialyzed with 20 mM NaAc at pH5.5. The solution was filtered with 0.45 um filter and then loaded into SP Fast Flow column (GE Healthcare) equilibrated with 20 mM NaAc at pH5.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled and concentrated for further evaluation. The protein concentration was determined by Qubit® Protein Assay Kit (Invitrogen, cat Q33212).

Example 22: Purification of SEQ ID NO: 15

The culture supernatant of O23T22 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled together.

Since the purified sample has more than two bands, the conductivity of sample was adjusted to 140 mS/cm, and then loaded into a Phenyl HP column (GE Healthcare), which was equilibrated by 20 mM PBS at pH6.0 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, and then pooled and concentrated. The buffer of sample was changed by 20 mM PBS at pH6.0 for further evaluation. The protein concentration was determined by Qubit® Protein Assay Kit (Invitrogen, cat Q33212).

Example 23: Purification of SEQ ID NO: 30

The culture supernatant of O233Q7 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, and then pooled and concentrated for further evaluation. The protein concentration was determined by Qubit® Protein Assay Kit (Invitrogen, cat Q33212).

Example 24: Purification of SEQ ID NO: 36

The culture supernatant of O23CD9 was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH7.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, and then concentrated, changed buffer by 20 mM PBS at pH6.0 for further evaluation. The protein concentration was determined by Qubit® Protein Assay Kit (Invitrogen, cat Q33212).

Example 25: Purification of SEQ ID NO: 39

The culture supernatant of O233Q9 was firstly precipitated with ammonium sulfate (80% saturation), then the precipitation was added water to adjust conductance to about 190 mS/cm. The solution was filtered with 0.45 um filter and then loaded into Phenyl Sepharose 6 Fast Flow column (GE Healthcare) equilibrated with 20 mM PBS at pH6.5 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM PBS at pH6.0 for further evaluation. The protein concentration was determined by Qubit® Protein Assay Kit (Invitrogen, cat Q33212).

Example 26: Purification of SEQ ID NO: 60

The culture supernatant of O234A2 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 27: Purification of SEQ ID NO: 63

The culture supernatant of O241RS was firstly precipitated with ammonium sulfate (80% saturation), then the precipitation was added water to adjust conductance to about 160 mS/cm. The solution was filtered with 0.45 um filter and then loaded into Phenyl Sepharose 6 Fast Flow column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity.

Since most lysozyme activity was kept in flow-through fraction, the conductivity of sample was adjusted to 180 mS/cm and loaded again into Phenyl Sepharose 6 Fast Flow column (GE Healthcare) equilibrated with 20 mM NaAc at pH4.5 with 1.8M $(NH_4)_2SO_4$ added. A gradient decrease of $(NH_4)_2SO_4$ concentration was applied as elution buffer from 1.8M to zero, and then elution fractions and flow-through fraction were collected to detect lysozyme activity. The fractions with lysozyme activity were analyzed by SDS-PAGE, but two major protein bands were found.

The fractions with lysozyme activity were pooled together and dialyzed with 20 mM NaAc at pH4.5. The sample was loaded into Capto SP column (GE Healthcare) equilibrated with 20 mM NaAc at pH4.5. A concentration gradient of NaCl was applied as elution buffer from zero to 1M, and then elution fractions and flow-through fraction were collected to detect lysozyme activity. The fractions with lysozyme activity were analyzed by SDS-PAGE and two bands also were found. The fractions were pooled together and loaded into SP High Performance column (GE Healthcare) for further purification, but the two bands still could not be separated. Finally, the fractions were pooled together, and then concentrated. The protein concentration was determined by Qubit® Protein Assay Kit (Invitrogen, cat Q33212).

Example 28: Purification of SEQ ID NO: 66

The culture supernatant of O23T25 was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 29: Purification of SEQ ID NO: 69

The culture supernatant of O23T23 was firstly precipitated with ammonium sulfate (80% saturation), then the precipitation was added water to adjust conductance to about 160 mS/cm. The solution was filtered with 0.45 um filter and then loaded into Phenyl Sepharose 6 Fast Flow column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 30: Purification of SEQ ID NO: 72

The culture supernatant of O14PP6 was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 31: Purification of SEQ ID NO: 89

The culture supernatant of O24KKU was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM NaAc at pH5.0 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 32: Purification of SEQ ID NO: 92

The culture supernatant of O24KKV was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM NaAc at pH4.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 33: Purification of SEQ ID NO: 95

The culture supernatant of O24KKX was firstly precipitated with ammonium sulfate (80% saturation), then the precipitation was added water to adjust conductance to about 140 mS/cm. The solution was filtered with 0.45 um filter and then loaded into Phenyl Sepharose High Performance column (GE Healthcare) equilibrated with 20 mM NaAc at pH4.5 with 1.2M $(NH_4)_2SO_4$ added. A gradient decrease of $(NH_4)_2SO_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH4.5 for further evaluation. The protein concentration was determined by Qubit® Protein Assay Kit (Invitrogen, cat Q33212).

Example 34: Purification of SEQ ID NO: 98

The culture supernatant of O33DRM was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM Bis-Tris at pH6.5 with 1.5M $(NH_4)_2SO_4$ added. A gradient decrease of $(NH_4)_2SO_4$ concentration was applied as elution buffer from 1.5M to zero, and then elution fractions and flow-through fraction were collected to detect lysozyme activity. The fractions with lysozyme activity were analyzed by SDS-PAGE.

The fractions with lysozyme activity were pooled together and dialyzed with 20 mM Bis-Tris at pH6.5. The sample was loaded into Capto SP column (GE Healthcare) equilibrated with 20 mM Bis-Tris at pH6.5. A concentration gradient of NaCl was applied as elution buffer from zero to 1M, and then elution fractions and flow-through fraction were collected to detect lysozyme activity. The fractions with lysozyme activity were analyzed by SDS-PAGE. Finally, the fractions were pooled together, and then concentrated. The protein concentration was determined by Qubit® Protein Assay Kit (Invitrogen, cat Q33212).

Example 35: Purification of SEQ ID NO: 101

The culture supernatant of O33DRQ was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM PBS at pH7.0 with 1.5M (NH$_4$)$_2$SO$_4$ added. A gradient decrease of (NH$_4$)$_2$SO$_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 36: Purification of SEQ ID NO: 104

The culture supernatant of O33DRN was firstly precipitated with ammonium sulfate (80% saturation), then the precipitation was added water to adjust conductance to about 140 mS/cm. The solution was filtered with 0.45 um filter and then loaded into Phenyl Sepharose High Performance column (GE Healthcare) equilibrated with 20 mM NaAc at pH5.5 with 1.2M (NH$_4$)$_2$SO$_4$ added. A gradient decrease of (NH$_4$)$_2$SO$_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 37: Purification of SEQ ID NO: 107

The culture supernatant of O33DRS was firstly precipitated with ammonium sulfate (80% saturation), then the precipitation was added water to adjust conductance to about 170 mS/cm. The solution was filtered with 0.45 um filter and then loaded into Phenyl Sepharose High Performance column (GE Healthcare) equilibrated with 20 mM PBS at pH7.0 with 1.5M (NH$_4$)$_2$SO$_4$ added. A gradient decrease of (NH$_4$)$_2$SO$_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 38: Purification of SEQ ID NO: 110

The culture supernatant of O33DRT was firstly precipitated with ammonium sulfate (80% saturation), then the precipitation was added water to adjust conductance to about 150 mS/cm. The solution was filtered with 0.45 um filter and then loaded into Phenyl Sepharose High Performance column (GE Healthcare) equilibrated with 20 mM NaAc at pH5.0 with 3M NaCl added. A gradient decrease of (NH$_4$)$_2$SO$_4$ concentration was applied as elution buffer from 1.2M to zero, and then elution fractions and flow-through fraction were collected to detect lysozyme activity. The fractions with lysozyme activity were analyzed by SDS-PAGE, pooled together, and then concentrated. The protein concentration was determined by Qubit® Protein Assay Kit (Invitrogen, cat Q33212).

Example 39: Purification of SEQ ID NO: 113

The culture supernatant of O33DRU was firstly precipitated with ammonium sulfate (80% saturation), then the precipitation was added water to adjust conductance to about 185 mS/cm. The solution was filtered with 0.45 um filter and then loaded into Phenyl Sepharose 6 Fast Flow column (GE Healthcare) equilibrated with 20 mM NaAc at pH5.0 with 1.8M (NH$_4$)$_2$SO$_4$ added. A gradient decrease of (NH$_4$)$_2$SO$_4$ concentration was applied as elution buffer from 1.8M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 40: Purification of SEQ ID NO: 116

The culture supernatant of O33V2R was firstly precipitated with ammonium sulfate (80% saturation), then the precipitation was added water to adjust conductance to about 170 mS/cm. The solution was filtered with 0.45 um filter and then loaded into Phenyl Sepharose 6 Fast Flow column (GE Healthcare) equilibrated with 20 mM NaAc at pH5.0 with 1.5M (NH$_4$)$_2$SO$_4$ added. A gradient decrease of (NH$_4$)$_2$SO$_4$ concentration was applied as elution buffer from 1.5M to zero, and then elution fractions and flow-through fraction were collected to detect lysozyme activity. The fractions with lysozyme activity were analyzed by SDS-PAGE, pooled together, and then concentrated. The buffer of final sample was changed by 20 mM NaAc at pH5.0 for further evaluation. The protein concentration was determined by Qubit® Protein Assay Kit (Invitrogen, cat Q33212).

Example 41: Purification of SEQ ID NO: 128

The culture supernatant of O34A3R was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5.

A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 42: Purification of SEQ ID NO: 131

The culture supernatant of O34A3S was firstly precipitated with ammonium sulfate (80% saturation), then dialyzed with 20 mM NaAc at pH5.0. The solution was filtered with 0.45 um filter and then loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 43: Purification of SEQ ID NO: 134

The culture supernatant of O34A3T was firstly precipitated with ammonium sulfate (80% saturation), then dialyzed with 20 mM NaAc at pH5.5. The solution was filtered with 0.45 um filter and then loaded into Capto SP column (GE Healthcare) equilibrated with 20 mM NaAc at pH5.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 44: Purification of SEQ ID NO: 137

The culture supernatant of O34A3V was firstly precipitated with ammonium sulfate (80% saturation), then dialyzed with 20 mM NaAc at pH5.0. The solution was filtered with 0.45 um filter and then loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, but two bands were found.

The fractions with lysozyme activity were pooled together and adjusted pH to 4.5, then loaded into SP High Performance column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE. Two bands with lysozyme activity were collected separately, then concentrated for further evaluation with two different purification IDs. The protein concentration was determined by Qubit® Protein Assay Kit (Invitrogen, cat Q33212).

Example 45: Purification of SEQ ID NO: 140

The culture supernatant of O34A3W was firstly precipitated with ammonium sulfate (80% saturation), then dialyzed with 20 mM NaAc at pH4.5. The solution was filtered with 0.45 um filter and then loaded into SP Fast Flow column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 46: Purification of SEQ ID NO: 143

The culture supernatant of O34A3x was firstly precipitated with ammonium sulfate (80% saturation), then the precipitation was added water to adjust conductance to about 200 mS/cm. The solution was filtered with 0.45 um filter and then loaded into Phenyl Sepharose High Performance column (GE Healthcare) equilibrated with 20 mM PBS at pH6.0 with 2.0M $(NH_4)_2SO_4$ added. A gradient decrease of $(NH_4)_2SO_4$ concentration was applied as elution buffer from 2.0M to zero, and then elution fractions and flow-through fraction were collected to detect lysozyme activity and analyzed by SDS-PAGE. The fractions with lysozyme activity were pooled together and then dialyzed with 20 mM NaAc at pH5.0. The sample was loaded into Capto SP column (GE Healthcare) equilibrated with 20 mM NaAc at pH5.0. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated. The protein concentration was determined by Qubit® Protein Assay Kit (Invitrogen, cat Q33212).

Example 47: Purification of SEQ ID NO: 146

The culture supernatant of O33X6Z was firstly precipitated with ammonium sulfate (80% saturation), then dialyzed with 20 mM NaAc at pH4.5. The solution was filtered with 0.45 um filter and then loaded into Capto SP column (GE Healthcare) equilibrated with 20 mM NaAc at pH4.5. A gradient increase of NaCl concentration was applied as elution buffer from zero to 1M, and then elution fractions and flow-through fraction were collected to detect lysozyme activity. The fractions with lysozyme activity were analyzed by SDS-PAGE, pooled together, and then concentrated for further evaluation. The protein concentration was determined by Qubit® Protein Assay Kit (Invitrogen, cat Q33212).

Example 48: Purification of GH25 Lysozymes

General Purification Procedure

The fermentation supernatant with the lysozyme was filtered through a Fast PES Bottle top filter with a 0.22 μm cut-off. pH was adjusted to 4.5 with 10% acetic acid. After the pH-adjustment the solution became a little cloudy and this was removed by filtration through a Fast PES Bottle top filter with a 0.22 μm cut-off.

After pretreatment about 650 ml of the lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5. The fractions from the column were pooled based on the chromatogram (absorption at 280 and 254 nm) and SDS-PAGE analysis. The pooled fractions were buffer-changed into 50 mM Na-acetate, pH 5.5 and concentrated using Amicon spin filters with a 10 kDa cut-off.

Purification of SEQ ID NO: 45, 48, 51 and 54

The fermentation broth biomass was separated by centrifugation. The sample filtration was then carried out by tangential flow filtration using hollow fiber 0.2 μcartridges mounted on a QuixStand® system and then loaded into a Hydrophobic column (TOYOPEARL® Phenyl-650M) equilibrated with 50 mM HEPES pH 8+1.5M Ammonium Sulphate at pH8.0. Step gradient decrease of ammonium sulphate concentration was applied as elution buffer from 1.5M to zero. The pooled elution peak fractions, wash and flow-through were collected and analysed on SDS gel. The peak with lysozyme band on gel was then buffer exchanged by 50 mM HEPES pH 8 and the protein concentration was determined by spectrophotometer (Agilent 8453 UV-visible Spectroscopy System).

Purification of SEQ ID NO: 6, 18, 21, 24, 27, 33, 42, 227, 75, 86, 119, 122, 230, 233 and 155

The fermentation supernatant with the lysozyme was filtered through a Fast PES Bottle top filter with a 0.22 μm cut-off.

Pretreatment of the filtered broth may be necessary if the expression level is low and/or conductivity is high (in general >10 S/m). Pretreatment can be performed using ultrafiltration on a 3-5 kDa cutoff membrane, buffer exchange on a G25 gel filtration column or dialysis. SEQ ID NO: 33, 42, 75 and 122 were pretreated using a G25 gel filtration column using 50 mM acetate pH4.5 whilst SEQ ID NO: 18, 21 and 27 were pretreated in a dialysis membrane (6-8 KDa) overnight in 50 mM acetate 4.5.

pH was adjusted to 4.5. If the solution became cloudy after the pH-adjustment, this was removed by filtration through a Fast PES Bottle top filter with a 0.22 µm cut-off. The lysozyme containing solution was purified by chromatography on SP Sepharose, approximately 50 ml in a XK26 column, using as buffer A 50 mM Na-acetate pH 4.5, and as buffer B 50 mM Na-acetate+1 M NaCl pH 4.5 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 9

The fermentation supernatant with the lysozyme was filtered through a Fast PES Bottle top filter with a 0.22 µm cut-off.

The pH adjusted to 7.5 and the sample was filtered through a Fast PES Bottle top filter with a 0.22 µm cut-off. The lysozyme containing solution was purified by chromatography on Q-Sepharose, approximately 70 ml in a XK26 column, using as buffer A 50 mM Tris pH 7.5 and as buffer B 50 mM Tris+1 M NaCl pH 7.5 and a 0-100% gradient over ca. 5 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 78

The fermentation supernatant with the lysozyme was filtered through a Fast PES Bottle top filter with a 0.22 µm cut-off.

The sample was concentrated on a vivacelle (cut off 5000 kd). The sample was diluted 3× with Milli-Q water and pH adjusted to 7.5. The lysozyme containing solution was purified by chromatography on Q-Sepharose, approximately 30 ml in a XK26 column, using as buffer A 50 mM Hepes pH 7.5 and as buffer B 50 mM Hepes+1 M NaCl pH 7.5 and a 0-50% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 83

The fermentation supernatant with the lysozyme was filtered through a Fast PES Bottle top filter with a 0.22 µm cut-off.

The sample was ultrafiltreted and diafiltrated on Sartorius UF-system 10 kDa. If the solution became cloudy after the pH-adjustment, this was removed by filtration through a Fast PES Bottle top filter with a 0.22 µm cut-off. The lysozyme containing solution was purified by chromatography on Q-Sepharose, approximately 50 ml in a XK26 column, using as buffer A 50 mM Hepes pH 7.0 and as buffer B 50 mM Hepes+1 M NaCl pH 7.0 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 125

The fermentation supernatant with the lysozyme was filtered through a Fast PES Bottle top filter with a 0.22 µm cut-off.

The sample was pretreated using a G25 gel filtration column using 50 mM Na-acetate pH and the elutant was purified by chromatography on Q-Sepharose, approximately 50 ml in a XK26 column, using as buffer A 50 mM Tris pH 8.0 and as buffer B 50 mM Tris+2 M NaCl pH 8.0 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Purification of SEQ ID NO: 158

The fermentation supernatant with the lysozyme was filtered through a Fast PES Bottle top filter with a 0.22 µm cut-off.

The sample was diluted 50% with milli-Q water and the pH was adjusted to pH 4.5. The sample was purified by chromatography on Capto S, approximately 50 ml in a XK26 column, using as buffer A 50 mM acetate pH 9.0 and as buffer B 50 mM acetate+2 M NaCl pH 9.0. The fractions from the column were pooled based on the chromatogram (absorption at 280 and 254 nm) and SDS-PAGE analysis.

The molecular weight was estimated from SDS-PAGE and the purity was >90%.

Example 49: Determination of Lysozyme Activity

Method for the Determination of Lysozyme Activity Against *Micrococcus lysodeikticus*.

The lysozymes of the application were tested according to Example 1 in the same plate as a prior art lysozyme (a GH25 lysozyme from *Acremonium alcalophilum* as described in WO 2013/076253, herein denoted SEQ ID NO: 159). The ratio of OD measurements of the lysozyme of the invention to the lysozyme of SEQ ID NO: 159 was calculated and is shown in tables 5 to 32 below.

TABLE 5

| OD Meaurement of SEQ ID NO: 24 and 227 | | |
|---|---|---|
| Lysozyme | OD Measurement | Ratio |
| SEQ ID NO: 159 | 0.41 | — |
| SEQ ID NO: 227 | 1.34 | 3.3 |
| SEQ ID NO: 24 | 1.99 | 4.9 |

TABLE 6

| OD Measurement of SEQ ID NO: 6 and 9 | | |
|---|---|---|
| Lysozyme | OD Measurement | Ratio |
| SEQ ID NO: 159 | 0.37 | — |
| SEQ ID NO: 9 | 0.85 | 2.3 |
| SEQ ID NO: 6 | 1.78 | 4.8 |

TABLE 7

| OD Measurement of SEQ ID NO: 72 and 83 | | |
|---|---|---|
| Lysozyme | OD Measurement | Ratio |
| SEQ ID NO: 159 | 0.49 | — |
| SEQ ID NO: 83 | 0.99 | 2.0 |
| SEQ ID NO: 72 | 2.22 | 4.5 |

TABLE 8

OD Measurement of SEQ ID NO: 86

| Lysozyme | OD Measurement | Ratio |
|---|---|---|
| SEQ ID NO: 159 | 0.65 | — |
| SEQ ID NO: 86 | 1.34 | 2.1 |

TABLE 9

OD Measurement of SEQ ID NO: 30 and 60

| Lysozyme | OD Measurement | Ratio |
|---|---|---|
| SEQ ID NO: 159 | 0.61 | — |
| SEQ ID NO: 60 | 2.32 | 3.5 |
| SEQ ID NO: 30 | 2.14 | 3.2 |

TABLE 10

OD Measurement of SEQ ID NO: 3, 36 and 39

| Lysozyme | OD Measurement | Ratio |
|---|---|---|
| SEQ ID NO: 159 | 0.52 | — |
| SEQ ID NO: 36 | 2.52 | 4.8 |
| SEQ ID NO: 3 | 2.60 | 5.0 |
| SEQ ID NO: 39 | 1.71 | 3.3 |

TABLE 11

OD Measurement of SEQ ID NO: 27 and 80

| Lysozyme | OD Measurement | Ratio |
|---|---|---|
| SEQ ID NO: 159 | 0.62 | — |
| SEQ ID NO: 80 | 1.86 | 3.0 |
| SEQ ID NO: 27 | 1.20 | 2.0 |

TABLE 12

OD Measurement of SEQ ID NO: 18 and 21

| Lysozyme | OD Measurement | Ratio |
|---|---|---|
| SEQ ID NO: 159 | 0.69 | — |
| SEQ ID NO: 18 | 1.76 | 2.6 |
| SEQ ID NO: 21 | 2.62 | 3.8 |

TABLE 13

OD Measurement of SEQ ID NO: 63, 66 and 69

| Lysozyme | OD Measurement | Ratio |
|---|---|---|
| SEQ ID NO: 159 | 0.63 | — |
| SEQ ID NO: 63 | 1.38 | 2.2 |
| SEQ ID NO: 66 | 1.72 | 2.7 |
| SEQ ID NO: 69 | 2.03 | 3.2 |

TABLE 14

OD Measurement of SEQ ID NO: 12 and 15

| Lysozyme | OD Measurement | Ratio |
|---|---|---|
| SEQ ID NO: 159 | 0.71 | — |
| SEQ ID NO: 15 | 1.79 | 2.5 |
| SEQ ID NO: 12 | 1.47 | 2.1 |

TABLE 15

OD Measurement of SEQ ID NO: 45, 51 and 54

| Lysozyme | OD Measurement | Ratio |
|---|---|---|
| SEQ ID NO: 159 | 0.50 | — |
| SEQ ID NO: 51 | 2.06 | 4.2 |
| SEQ ID NO: 54 | 1.98 | 4.0 |
| SEQ ID NO: 45 | 2.07 | 4.2 |

TABLE 16

OD Measurement of SEQ ID NO: 48

| Lysozyme | OD Measurement | Ratio |
|---|---|---|
| SEQ ID NO: 159 | 0.44 | — |
| SEQ ID NO: 48 | 0.93 | 2.1 |

TABLE 17

OD Measurement of SEQ ID NO: 33 and 75

| Lysozyme | OD Measurement | Ratio |
|---|---|---|
| SEQ ID NO: 159 | 0.56 | — |
| SEQ ID NO: 75 | 1.56 | 2.8 |
| SEQ ID NO: 33 | 2.33 | 4.2 |

TABLE 18

OD Measurement of SEQ ID NO: 21 and 42

| Lysozyme | OD Measurement | Ratio |
|---|---|---|
| SEQ ID NO: 159 | 0.72 | — |
| SEQ ID NO: 21 | 3.13 | 4.4 |
| SEQ ID NO: 42 | 1.94 | 2.7 |

TABLE 19

OD Measurement of SEQ ID NO: 24 and 125

| Lysozyme | OD Measurement | Ratio |
|---|---|---|
| SEQ ID NO: 159 | 0.44 | — |
| SEQ ID NO: 24 | 1.97 | 4.5 |
| SEQ ID NO: 125 | 1.74 | 2.9 |

TABLE 20

OD Measurement of SEQ ID NO: 98

| Lysozyme | OD Measurement | Ratio |
|---|---|---|
| SEQ ID NO: 159 | 0.55 | — |
| SEQ ID NO: 98 | 1.79 | 3.3 |

TABLE 21

OD Measurement of SEQ ID NO: 104 and 122

| Lysozyme | OD Measurement | Ratio |
|---|---|---|
| SEQ ID NO: 159 | 0.44 | — |
| SEQ ID NO: 122 | 2.09 | 4.8 |
| SEQ ID NO: 104 | 1.23 | 2.8 |

TABLE 22

OD Measurement of SEQ ID NO: 89

| Lysozyme | OD Measurement | Ratio |
|---|---|---|
| SEQ ID NO: 159 | 0.63 | — |
| SEQ ID NO: 89 | 2.11 | 3.4 |

TABLE 23

OD Measurement of SEQ ID NO: 92, 95, 128, 134 and 143

| Lysozyme | OD Measurement | Ratio |
|---|---|---|
| SEQ ID NO: 159 | 0.49 | — |
| SEQ ID NO: 92 | 1.30 | 2.6 |
| SEQ ID NO: 95 | 1.59 | 3.2 |
| SEQ ID NO: 128 | 2.38 | 4.8 |
| SEQ ID NO: 134 | 1.24 | 2.5 |
| SEQ ID NO: 143 | 2.59 | 5.2 |

TABLE 24

OD Measurement of SEQ ID NO: 146

| Lysozyme | OD Measurement | Ratio |
|---|---|---|
| SEQ ID NO: 159 | 0.38 | — |
| SEQ ID NO: 146 | 1.94 | 5.1 |

TABLE 25

OD Measurement of SEQ ID NO: 110 and 116

| Lysozyme | OD Measurement | Ratio |
|---|---|---|
| SEQ ID NO: 159 | 0.46 | — |
| SEQ ID NO: 110 | 1.53 | 3.3 |
| SEQ ID NO: 116 | 1.28 | 2.8 |

TABLE 26

OD Measurement of SEQ ID NO: 131

| Lysozyme | OD Measurement | Ratio |
|---|---|---|
| SEQ ID NO: 159 | 0.30 | — |
| SEQ ID NO: 131 | 2.35 | 7.8 |

TABLE 27

OD Measurement of SEQ ID NO: 110, 128 and 137

| Lysozyme | OD Measurement | Ratio |
|---|---|---|
| SEQ ID NO: 159 | 0.34 | — |
| SEQ ID NO: 137 | 1.87 | 5.5 |
| SEQ ID NO: 137 | 1.48 | 4.4 |
| SEQ ID NO: 128 | 2.09 | 6.2 |
| SEQ ID NO: 110 | 1.50 | 4.5 |

TABLE 28

OD Measurement of SEQ ID NO: 131

| Lysozyme | OD Measurement | Ratio |
|---|---|---|
| SEQ ID NO: 159 | 0.40 | — |
| SEQ ID NO: 131 | 2.42 | 6.0 |

TABLE 29

OD Measurement of SEQ ID NO: 140

| Lysozyme | OD Measurement | Ratio |
|---|---|---|
| SEQ ID NO: 159 | 0.61 | — |
| SEQ ID NO: 140 | 2.03 | 3.3 |

TABLE 30

OD Measurement of SEQ ID NO: 158

| Lysozyme | OD Measurement | Ratio |
|---|---|---|
| SEQ ID NO: 159 | 0.56 | — |
| SEQ ID NO: 158 | 1.65 | 3.0 |

TABLE 31

OD Measurement of SEQ ID NO: 230, 233 and 155

| Lysozyme | OD Measurement | Ratio |
|---|---|---|
| SEQ ID NO: 159 | 0.48 | — |
| SEQ ID NO: 230 | 1.34 | 2.8 |
| SEQ ID NO: 233 | 1.52 | 3.2 |
| SEQ ID NO: 155 | 1.01 | 2.1 |

TABLE 32

OD Measurement of SEQ ID NO: 101, 107, 113 and 119

| Lysozyme | OD Measurement | Ratio |
|---|---|---|
| SEQ ID NO: 159 | 0.53 | — |
| SEQ ID NO: 113 | 1.77 | 3.4 |
| SEQ ID NO: 101 | 1.91 | 3.6 |
| SEQ ID NO: 107 | 1.50 | 2.9 |
| SEQ ID NO: 119 | 2.40 | 4.6 |

The results show that the lysozymes of the invention have increased activity compared to this prior art lysozyme.

Example 50: Animal Feed and Animal Feed Additives Comprising a Lysozyme of the Invention Animal Feed Additive A formulation of a lysozyme of the invention (e.g. SEQ ID NO: 3, 6, 9, 12, 15, 18, 21, 24, 27, 30, 33, 36, 39, 42, 45, 48, 51, 54, 57, 60, 63, 66, 69, 72, 75, 80, 83, 86, 89, 92, 95, 98, 101, 104, 107, 110, 113, 116, 119, 122, 125, 128, 131, 134, 137, 140, 143, 146, 149, 152, 155, 158, 221, 224, 227, 230 or 233) containing 0.01 g to 10 g enzyme protein is added to the following premix (per kilo of premix):

| | |
|---|---|
| 5000000 IE | Vitamin A |
| 1000000 IE | Vitamin D3 |
| 13333 mg | Vitamin E |
| 1000 mg | Vitamin K3 |
| 750 mg | Vitamin B1 |
| 2500 mg | Vitamin B2 |
| 1500 mg | Vitamin B6 |
| 7666 mcg | Vitamin B12 |
| 12333 mg | Niacin |
| 33333 mcg | Biotin |
| 300 mg | Folic Acid |
| 3000 mg | Ca-D-Panthothenate |
| 1666 mg | Cu |
| 16666 mg | Fe |
| 16666 mg | Zn |
| 23333 mg | Mn |
| 133 mg | Co |
| 66 mg | — |
| 66 mg | Se |
| 5.8% | Calcium |
| 25% | Sodium |

Animal Feed

This is an example of an animal feed (broiler feed) comprising the animal feed additive as described above:
- 62.55% Maize
- 33.8% Soybean meal (50% crude protein)
- 1.0% Soybean oil
- 0.2% DL-Methionine
- 0.22% DCP (dicalcium phosphate)
- 0.76% CaCO$_3$ (calcium carbonate)
- 0.32% Sand
- 0.15% NaCl (sodium chloride)
- 1% of the above Premix The ingredients are mixed, and the feed is pelleted at the desired temperature, e.g. 60, 65, 75, 80, 85, 90 or even 95° C.

Example 51: Cloning and Expression of Flammulina velutipes (SEQ ID NO: 221)

A GH25 lysozyme was identified from the downloaded genomic DNA assembly from the following project: Park Y J et al., "Whole genome and global gene expression analyses of the model mushroom *Flammulina velutipes* reveal a high capacity for lignocellulose degradation.", *PLoS One*, 2014 Apr. 8; 9(4):e93560.

A codon optimized, intronless version of the *Flammulina velutipes* GH25 lysozyme (SEQ ID NO: 217) was ordered from GeneArt, Invitrogen having SEQ ID NO: 219.

SEQ ID NO: 219

```
ACACAACTGGGGATCCACCATGCGAATCCTCTTGTTCATCGCAGTCACAATCGCGT

TGGGAGTCCATGCCAGGCTCAACGGCATCGATGTCTCGGGATACCAGCCGAACGTC

AACTGGGCCACGGTCAAAGCGAACGGCGTGTCCTTCGCGTACATCAAGGCAACCGA

GGGCACCACGTATACAAACCCCTCGTTCTCCTCCCAGTACACCGGAGCAACAAAAG

CCGGATTGATCAGGGGCTCCTACCATTTCGCGCATCCTTCGTCGTCCACAGGCGCA

GCACAGGCACGATACTTCGTGGCACATGGCGGTGGTTGGTCCGGTGATGGTATCAC

CTTGCCTGGTGCGCTCGATATCGAGTATAACCCTTCGGGTGCGACATGTTACGGCC

TCTCGACCTCGTCCATGGTGAACTGGATCGCCGATTTCTCCAACACTTATCACTCG

CTCACAGGCAGGTACCCCGTCATTTACACCACTGCCGATTGGTGGCGAACCTGTAC

CGGCAACTCCGCATCCTTCGCAAACAACTCGCCTCTCTGGATTGCGCGTTACGCGT

CGACTATCGGTACGCTCCCTGCCGGATGGTCGTACGCGACCTTCTGGCAGTATGCG

GATTCGGGCTCCAACCCTGGCGATCAGGATTACTTCAACGGTGACGCAGCGGGTCT

CAAGCGTCTCGCGACATCGTAATAAGCTTCTCGAGATCT
```
the underlined portions are restriction enzymes used for cloning intop Dau109.

The synthetic gene was cloned directly into pDau109 as described in the Example 16 as a ligation into the BamHI-HindIII site of the vector. The GH25 lysozyme having SEQ ID NO: 221 was expressed as described in Example 19 and purified as described in Example 52.

Example 52: Purification of the GH25 Lysozyme from Flammulina velutipes (SEQ ID NO: 221)

The fermentation supernatant with the lysozyme was filtered through a Fast PES Bottle top filter with a 0.22 µm cut-off.

The sample was pretreated using a G25 gel filtration column using 50 mM acetate pH4.5 and the elutant was purified by chromatography on SP Sepharose, approximately 50 ml in a XK26 column, using as buffer A 50 mM Na-acetate pH 4.5, and as buffer B 50 mM Na-acetate+2 M NaCl pH 4.5 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Example 53: PCR Amplification and InFusion Cloning of Lysozyme Encoding Sequences SEQ ID NO: 222

The InFusion cloning primers given in table 33 were used to generate an BamHI-HindIII flanked cloning cassette from the genomic DNA as described in Example 16.

TABLE 33

InFusion cloning primers

| Primer* | Primer SEQ ID NO: | Primer to lysozyme SEQ ID NO: | Sequence |
|---|---|---|---|
| C8VSE-F | 225 | 222 | 5'-ACACAACTGGGGATCCACCATGCTTTT CGCAACCTTTCTTTGTCTTG |
| C8VSE-R | 226 | 222 | 5'-AGATCTCGAGAAGCTTACGAGGAAAAG ACGTTGAGGTCAAATTGA |

*-F - forward primer; -R - reverse primer

Bold letters represent coding sequence. The underlined sequence is homologous to the insertion sites of pDau109.

The GH25 lysozymes were expressed in *Aspergillus oryzae* as described in Example 19 and purified as described in Example 54.

Example 54: Purification of the GH25 Lysozyme from *Deconica coprophila* (SEQ ID NO: 222)

The fermentation supernatant with the lysozyme was filtered through a Fast PES Bottle top filter with a 0.22 μm cut-off.

The sample was pretreated using a G25 gel filtration column using 50 mM acetate pH4.5 and the elutant was purified by chromatography on SP Sepharose, approximately 50 ml in a XK26 column, using as buffer A 50 mM Na-acetate pH 4.5, and as buffer B 50 mM Na-acetate+2 M NaCl pH 4.5 and a 0-100% gradient over ca. 10 CV. The fractions from the column were pooled based on the chromatogram (absorption at 280 and 254 nm) and SDS-PAGE analysis.

The molecular weight was estimated from SDS-PAGE and the purity was >90%.

Example 55: Determination of Lysozyme Activity

The lysozymes of the application were tested according to Example 1 in the same plate as a prior art lysozyme (a GH25 lysozyme from *Acremonium alcalophilum* as described in WO 2013/076253, herein denoted SEQ ID NO: 159). The ratio of OD measurement of the lysozyme of the invention to the lysozyme of SEQ ID NO: 159 was calculated and is shown in Table 34 below.

TABLE 34

OD Measurement of SEQ ID NO: 221 and 224

| Lysozyme | OD Measurement | Ratio |
|---|---|---|
| SEQ ID NO: 159 | 0.51 | — |
| SEQ ID NO: 221 | 1.74 | 3.4 |
| SEQ ID NO: 224 | 1.80 | 3.5 |

The results show that the lysozymes of the invention have increased activity compared to this prior art lysozyme.

Example 56 Method for the Determination of Lysozyme Activity Against *Lactobacillus johnsonii*

Pgn Extraction:
Cultivation of *Lactobacillus johnsonii:*
Materials
  MRS broth, product number BD 288130, pH 6.3-6.7.
  MRS agar plates, BD 288130; Agar Oxoid LP0011; pH 6.3-6.7.
  0.9% NaCl, Merck 106404, Cas no. 7647145
  jars, supplier Merck 116387, Anaerocult anaerobic jar 2.5 L
  Anaerogen 2.5 L, ThermoScientific, catalogue no. AN0025A *Lactobacillus johnsonii*, DSM10533

Procedure

*L. johnsonii* was streaked from freeze stock to MRS agar plate and incubated under anaerobic conditions for 2 days, anaerobic jar with Anaerogen 2.5 L, 30° C. Some colonies were inoculated into 500 mLMRS broth in a 500 mL blue cap bottle and placed in an anaerobic jar with Anaerogen 2.5 L for 72 hours at 30° C.

The culture was spun down (6000 rpm, 10 minutes) and the supernatant was poured off before another round of centrifugation was performed. The pellet was washed in 100 mL 0.9% NaCl and the suspension was mixed well and centrifuged at 6000 rpm for 10 minutes. The supernatant was poured off and the washing procedure in 0.9% NaCl was repeated to a total of three washes. Approximately 40 mL 0.9% NaCl was added to the pellet and the solution was transferred to a 50 mL falcon tube. The solution was centrifuged at 6000 rpm for 10 minutes and the supernatant was poured off. The pellet was stored at −18° C. until the extraction of the peptidoglycan was conducted.

Extraction Procedure:

Materials
  Protease from *Streptomyces griseus*, Sigma-Aldrich P5147, CAS 9036-06-0
  PBS pH 7.3:
  NaCl: 8 g, Sigma-Aldrich 31434, CAS 7647-14-5
  KCl: 0.2 g, Sigma-Aldrich P9333, CAS 7447-40-7
  $KH_2PO_4$: 0.24 g, Sigma-Aldrich P5655, CAS 7778-77-0
  $Na_2HPO_4 \cdot 2\ H_2O$: 1.44 g, Sigma-Aldrich 30412, CAS 10028-24-7
  Add Milli-Q water to 1000 mL
  1% Triton-X 100 solution:
  1 mL Triton X100, Sigma-Aldrich X100, CAS 9002-93-1
  Add Milli Q water to 100 mL 500 mM sodium carbonate buffer, pH 9.3:
500 mM sodium carbonate is made from 21 g Na$_2$CO$_3$ (Sigma-Aldrich S7795, CAS 497-19-8) in 500 mL MQ water
500 mM sodium bicarbonate is made from 72 g NaHCO$_3$ (Sigma-Aldrich S6014, CAS 144-55-8) in 500 mL MW water
The pH 9.3 buffer is made from 320 mL NaHCO$_3$ and 80 mL Na$_2$CO$_3$ and adjusting pH with HCl Phenol solution with 10 mM Tris HCl, pH 8.0, 1 mM EDTA, Sigma-Aldrich P4557, CAS 108-95-2

Acetone, Sigma-Aldrich 32201-M, CAS 67-64-1

Ethanol, 96%, CCS Healthcare 1680643, CAS 64-17-5

Procedure

*L. johnsonii* cell material was freeze dried. The freeze dried material (525 mg) was suspended in PBS (40 mL) in a 50 mL Falcon tube. The suspension was shaken for 2 h @ 700 rpm in a thermoshaker at room temperature. *Streptomyces griseus* protease (55 mg) was then added and the suspension was incubated 6 h @ 37 C in the thermoshaker. It was then centrifuged 20 min @ 1900 g at room temperature, and the supernatant was decanted. The pellet was re-suspended in 1% Triton X-100 (40 mL) and shaken overnight @ 37 C. After another centrifugation and decantation, the pellet was re-suspended in PBS (40 mL) and protease (55 mg) added again. The suspension was again incubated 6 h @ 37 C, centrifuged and decanted. The pellet was re-suspended in PBS (40 mL) and shaken overnight @ 37 C. This washing procedure was repeated once more with PBS (40 mL, 30 min agitation), then with 50% ethanol/water (40 mL, 30 min agitation). The pellet was then split into two Falcon tubes. To each tube was added phenol solution (15 mL) pre-heated to 40 C. The suspensions were shaken 10 min @ 40 C, and then added 96% ethanol (25 mL to each tube), centrifuged and decanted. The pellets were further washed with acetone (40 mL in each tube) and 96% ethanol (40 mL in each tube), before being freeze dried. Combining the pellets from the two tubes yielded 80 mg purified peptidoglycan as a white powder.

Reducing End Assay

The lysozyme was diluted in phosphate dilution buffer (5 mM citrate, 5 mM K$_2$HPO$_4$, 0.01% TritonX-100, pH 5.0) to 200 or 50 µg/mL in polypropylene tubes, dependent on the strength of available stock solutions. The diluted lysozyme was further diluted in a 96-well polypropylene microtiter plate by preparing a two-fold dilution series down to a concentration of 6.3 µg/mL in phosphate dilution buffer (5 mM citrate, 5 mM K$_2$HPO$_4$, 0.01% TritonX-100, pH 5.0). A 50 mg/ml stock solution of *L. johnsonii* substrate in MillQ was prepared and diluted in phosphate buffer (50 mM citrate, 50 mM K$_2$HPO$_4$, pH 5.0) to 250 µg/ml. In a polypropylene deepwell plate 50 µL of the lysozyme dilution was mixed with 450 µL *L. johnsonii* solution and incubated at 40° C. with shaking (500 rpm) for 45 min. After incubation, the deepwell plate was centrifuged (3200 rpm, 7 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide (PAHBAH) solution in K—Na tartrate/NaOH buffer (50 g/L K—Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water). The OD measurement values represent the difference after the original (background) reading was subtracted and represent the average of two OD measurement values. Results are shown in Table 35 and in FIGS. 3 and 4.

TABLE 35

Average OD405 measurements (background corrected) in Reducing End Assay

| | Concentration of lysozyme in µg/mL | | | | | |
|---|---|---|---|---|---|---|
| Lysozyme | 20 | 10 | 5 | 2.5 | 1.25 | 0.63 |
| SEQ ID NO: 24 | 1.07 | 0.85 | 0.56 | 0.39 | 0.26 | 0.15 |
| SEQ ID NO: 227 | 0.19 | 0.12 | 0.10 | 0.07 | 0.01 | 0.01 |
| SEQ ID NO: 6 | 0.66 | 0.47 | 0.40 | 0.25 | 0.14 | 0.10 |
| SEQ ID NO: 9 | 0.03 | 0.01 | 0.19 | 0.02 | 0.01 | 0.00 |
| SEQ ID NO: 72 | 1.00 | 0.71 | 0.50 | 0.40 | 0.24 | 0.16 |
| SEQ ID NO: 83 | 0.29 | 0.13 | 0.08 | 0.09 | 0.02 | 0.03 |
| SEQ ID NO: 60 | 0.91 | 0.53 | 0.40 | 0.19 | 0.10 | 0.06 |
| SEQ ID NO: 30 | 0.33 | 0.24 | 0.12 | 0.04 | 0.00 | −0.04 |
| SEQ ID NO: 39 | 0.85 | 0.72 | 0.45 | 0.34 | 0.19 | 0.08 |
| SEQ ID NO: 3 | 0.90 | 0.66 | 0.49 | 0.29 | 0.18 | 0.07 |
| SEQ ID NO: 51 | 0.71 | 0.43 | 0.45 | 0.23 | 0.14 | 0.05 |
| SEQ ID NO: 54 | 0.58 | 0.48 | 0.27 | 0.16 | 0.12 | 0.02 |
| SEQ ID NO: 48 | 0.66 | 0.45 | 0.44 | 0.20 | 0.19 | 0.03 |
| SEQ ID NO: 18 | 0.98 | 0.75 | 0.55 | 0.33 | 0.16 | 0.28 |
| SEQ ID NO: 27 | −0.02 | 0.06 | −0.02 | −0.03 | −0.02 | −0.03 |
| SEQ ID NO: 224 | −0.06 | −0.07 | −0.04 | −0.06 | −0.07 | −0.07 |
| SEQ ID NO: 15 | 1.10 | 0.98 | 0.86 | 0.53 | 0.40 | 0.20 |
| SEQ ID NO: 69 | 0.45 | 0.27 | 0.16 | 0.05 | 0.17 | −0.04 |
| SEQ ID NO: 66 | −0.06 | −0.03 | 0.01 | −0.06 | −0.03 | −0.08 |
| SEQ ID NO: 63 | 0.15 | 0.04 | 0.03 | −0.04 | −0.05 | −0.06 |
| SEQ ID NO: 12 | −0.03 | −0.07 | −0.06 | −0.07 | −0.08 | 0.05 |
| SEQ ID NO: 45 | 0.98 | 0.74 | 0.61 | 0.26 | 0.27 | 0.10 |
| SEQ ID NO: 75 | 1.20 | 0.84 | 0.70 | 0.53 | 0.34 | 0.22 |
| SEQ ID NO: 119 | 1.23 | 1.05 | 0.84 | 0.75 | 0.59 | 0.27 |
| SEQ ID NO: 42 | 0.00 | 0.01 | −0.01 | 0.00 | 0.00 | −0.02 |
| SEQ ID NO: 21 | 0.86 | 0.43 | 0.31 | 0.21 | 0.12 | 0.06 |
| SEQ ID NO: 33 | 0.97 | 0.54 | 0.39 | 0.27 | 0.24 | 0.10 |
| SEQ ID NO: 89 | 0.46 | 0.31 | 0.28 | 0.12 | 0.07 | 0.03 |
| SEQ ID NO: 92 | 0.42 | 0.31 | 0.15 | 0.10 | 0.04 | 0.14 |
| SEQ ID NO: 95 | 0.94 | 0.81 | 0.62 | 0.49 | 0.24 | 0.17 |
| SEQ ID NO: 221 | 0.86 | 0.62 | 0.38 | 0.28 | 0.17 | 0.13 |
| SEQ ID NO: 125 | 0.19 | 0.08 | 0.11 | 0.03 | 0.02 | 0.01 |
| SEQ ID NO: 122 | 0.88 | 0.64 | 0.47 | 0.33 | 0.18 | 0.10 |
| SEQ ID NO: 101 | 0.79 | 0.57 | 0.54 | 0.42 | 0.13 | 0.07 |
| SEQ ID NO: 98 | 0.78 | 0.40 | 0.36 | 0.26 | 0.12 | 0.09 |
| SEQ ID NO: 104 | 0.39 | 0.27 | 0.17 | 0.06 | 0.12 | 0.06 |
| SEQ ID NO: 116 | 0.76 | 0.65 | 0.41 | 0.24 | 0.14 | 0.09 |
| SEQ ID NO: 146 | 0.85 | 0.61 | 0.50 | 0.41 | 0.19 | 0.19 |
| SEQ ID NO: 143 | 0.56 | 0.32 | 0.24 | 0.38 | 0.08 | 0.17 |
| SEQ ID NO: 110 | 0.51 | 0.32 | 0.19 | 0.07 | 0.05 | 0.00 |
| SEQ ID NO: 134 | 0.28 | 0.21 | 0.15 | 0.12 | 0.02 | 0.00 |
| SEQ ID NO: 140 | 0.00 | 0.00 | 0.02 | −0.02 | −0.02 | 0.09 |
| SEQ ID NO: 128 | −0.01 | 0.01 | 0.01 | −0.02 | −0.02 | −0.02 |
| SEQ ID NO: 137 | 0.95 | 0.68 | 0.51 | 0.36 | 0.21 | 0.13 |
| SEQ ID NO: 131 | 0.74 | 0.71 | 0.46 | 0.27 | 0.15 | 0.10 |
| SEQ ID NO: 86 | ND | ND | 0.05 | 0.03 | −0.01 | 0.03 |
| SEQ ID NO: 36 | ND | ND | 1.14 | 0.96 | 0.69 | 0.56 |
| SEQ ID NO: 107 | ND | ND | 0.14 | 0.08 | 0.28 | 0.00 |
| SEQ ID NO: 113 | ND | ND | 0.25 | 0.13 | 0.05 | 0.03 |
| SEQ ID NO: 158 | ND | ND | 0.04 | −0.02 | −0.09 | −0.02 |
| SEQ ID NO: 230 | ND | ND | 0.59 | 0.38 | 0.25 | 0.12 |
| SEQ ID NO: 233 | ND | ND | 0.58 | 0.30 | 0.16 | 0.07 |
| SEQ ID NO: 155 | ND | ND | 0.63 | 0.37 | 0.29 | 0.19 |
| SEQ ID NO: 80 | ND | ND | 1.62 | 0.98 | 0.57 | 0.39 |
| SEQ ID NO: 159 | 1.21 | 1.09 | 0.90 | 0.72 | 0.49 | 0.32 |
| HEWL | −0.02 | −0.02 | 0.00 | −0.01 | 0.00 | −0.02 |

ND: not determinded due to low concentration of enzyme stock solution

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A recombinant host cell comprising a polynucleotide encoding a GH25 polypeptide having lysozyme activity, wherein the polypeptide has at least 80% sequence identity to SEQ ID NO: 9 and the polynucleotide is operably linked to one or more control sequences that direct the production of the polypeptide.

2. The recombinant host cell of claim 1, wherein the polypeptide has at least 85% sequence identity to SEQ ID NO: 9.

3. The recombinant host cell of claim 1, wherein the polypeptide has at least 90% sequence identity to SEQ ID NO: 9.

4. The recombinant host cell of claim 1, wherein the polypeptide has at least 95% sequence identity to SEQ ID NO: 9.

5. The recombinant host cell of claim 1, wherein the polypeptide has at least 97% sequence identity to SEQ ID NO: 9.

6. The recombinant host cell of claim 1, wherein the polypeptide comprises the amino acid sequence of SEQ ID NO: 9.

7. The recombinant host cell of claim 1, wherein the polypeptide is a fragment of SEQ ID NO: 9 and wherein the fragment comprises at least 180 amino acids.

8. The recombinant host cell of claim 4, which comprises more than one copy of the polynucleotide.

9. The recombinant host cell of claim 8, which comprises two, three, four, or five copies of the polynucleotide.

10. The recombinant host cell of claim 4, wherein at least one of the one or more control sequences is heterologous to the polynucleotide.

11. The recombinant host cell of claim 4, which is a yeast cell or a filamentous fungal cell.

12. The recombinant host cell of claim 11, which is an Acremonium, Aspergillus, Aureobasidium, Bjerkandera, Ceriporiopsis, Chrysosporium, Coprinus, Coriolus, Cryptococcus, Fihbasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

13. The recombinant host cell of claim 4, which is an Aspergillus awamori, Aspergillus foetidus, Aspergillus fumigatus, Aspergillus japonicus, Aspergillus nidulans, Aspergillus niger, Aspergillus oryzae, Trichoderma harzianum, Trichoderma koningii, Trichoderma longibrachiatum, Trichoderma reesei, or Trichoderma viride cell.

14. A method of producing a GH25 polypeptide having lysozyme activity, comprising
   (a) cultivating a host cell of claim 1 under conditions conducive for production of the polypeptide; and
   (b) recovering the polypeptide.

15. A method of producing a GH25 polypeptide having lysozyme activity, comprising
   (a) cultivating a host cell of claim 4 under conditions conducive for production of the polypeptide; and
   (b) recovering the polypeptide.

16. A method of producing a GH25 polypeptide having lysozyme activity, comprising
   (a) cultivating a host cell of claim 9 under conditions conducive for production of the polypeptide; and
   (b) recovering the polypeptide.

17. A method of producing a GH25 polypeptide having lysozyme activity, comprising
   (a) cultivating a host cell of claim 10 under conditions conducive for production of the polypeptide; and
   (b) recovering the polypeptide.

18. A method of producing a GH25 polypeptide having lysozyme activity, comprising
   (a) cultivating a host cell of claim 11 under conditions conducive for production of the polypeptide; and
   (b) recovering the polypeptide.

19. A method of producing a GH25 polypeptide having lysozyme activity, comprising (a) cultivating a host cell of claim 12 under conditions conducive for production of the polypeptide; and
(b) recovering the polypeptide.

20. A method of producing a GH25 polypeptide having lysozyme activity, comprising
(a) cultivating a host cell of claim 13 under conditions conducive for production of the polypeptide; and
(b) recovering the polypeptide.

\* \* \* \* \*